United States Patent
Mohammadi et al.

(10) Patent No.: US 9,926,355 B2
(45) Date of Patent: Mar. 27, 2018

(54) CHIMERIC FIBROBLAST GROWTH FACTOR 21 PROTEINS AND METHODS OF USE

(71) Applicant: New York University, New York, NY (US)

(72) Inventors: Moosa Mohammadi, Scarsdale, NY (US); Regina Goetz, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/289,447

(22) Filed: Oct. 10, 2016

(65) Prior Publication Data

US 2017/0029480 A1 Feb. 2, 2017

Related U.S. Application Data

(62) Division of application No. 13/837,880, filed on Mar. 15, 2013, now Pat. No. 9,464,126.

(60) Provisional application No. 61/658,778, filed on Jun. 7, 2012, provisional application No. 61/664,081, filed on Jun. 25, 2012.

(51) Int. Cl.
  *C07K 14/50* (2006.01)
  *A61K 38/18* (2006.01)
  *A61K 45/06* (2006.01)
  *A61K 31/00* (2006.01)

(52) U.S. Cl.
  CPC .............. *C07K 14/50* (2013.01); *A61K 31/00* (2013.01); *A61K 38/1825* (2013.01); *A61K 45/06* (2013.01); *C07K 14/501* (2013.01); *C07K 14/503* (2013.01); *C07K 2319/00* (2013.01); *G01N 2333/50* (2013.01); *G01N 2500/02* (2013.01); *G01N 2800/042* (2013.01)

(58) Field of Classification Search
  None
  See application file for complete search history.

(56) References Cited

U.S. PATENT DOCUMENTS

| | | | |
|---|---|---|---|
| 5,132,408 A | 7/1992 | Baird et al. | |
| 5,478,804 A | 12/1995 | Calabresi et al. | |
| 5,656,458 A * | 8/1997 | Barr .................... | C07K 14/501 435/254.2 |
| 6,326,484 B1 | 12/2001 | Gage et al. | |
| 6,982,170 B1 | 1/2006 | Maciag et al. | |
| 7,491,697 B2 | 2/2009 | Beals | |
| 7,582,607 B2 | 9/2009 | Frye et al. | |
| 7,622,445 B2 | 11/2009 | Frye et al. | |
| 7,655,627 B2 | 2/2010 | Frye et al. | |
| 7,956,033 B2 | 6/2011 | Cheng et al. | |
| 8,168,591 B2 | 5/2012 | Takada et al. | |
| 8,642,546 B2 | 2/2014 | Belouski et al. | |
| 8,889,426 B2 | 11/2014 | Mohammadi et al. | |
| 8,889,621 B2 | 11/2014 | Mohammadi et al. | |
| 8,906,854 B2 | 12/2014 | Jonker et al. | |
| 8,951,966 B2 | 2/2015 | Ling et al. | |
| 8,999,929 B2 | 4/2015 | Mohammadi et al. | |
| 9,072,708 B2 | 7/2015 | Jonker et al. | |
| 9,272,017 B2 | 3/2016 | Mohammadi et al. | |
| 9,464,126 B2 | 10/2016 | Mohammadi et al. | |
| 9,474,785 B2 | 10/2016 | Mohammadi et al. | |
| 9,475,856 B2 | 10/2016 | Mohammadi et al. | |
| 9,550,820 B2 | 1/2017 | Mohammadi et al. | |
| 9,657,075 B2 | 5/2017 | Mohammadi et al. | |
| 2004/0259780 A1 | 12/2004 | Glasebrook et al. | |
| 2007/0142278 A1 | 6/2007 | Beals et al. | |
| 2007/0237768 A1 | 10/2007 | Glaesner et al. | |
| 2007/0265200 A1 | 11/2007 | Glaesner et al. | |
| 2007/0293430 A1 | 12/2007 | Frye et al. | |
| 2007/0299007 A1 | 12/2007 | Frye et al. | |
| 2008/0103096 A1 | 5/2008 | Frye et al. | |
| 2008/0255045 A1 | 10/2008 | Cujec et al. | |
| 2008/0261875 A1 | 10/2008 | Etgen et al. | |
| 2009/0111742 A1 | 4/2009 | Kharitonenkov et al. | |

(Continued)

FOREIGN PATENT DOCUMENTS

EP 0 645 451 B1 8/2001
WO WO 2011/047267 A1 4/2011

(Continued)

OTHER PUBLICATIONS

DiGabriele et al., Nature, 393:812-17, Jun. 25, 1998.*
Yie et al., "FGF21 N- and C-Termini Play Different Roles in Receptor Interaction and Activation," FEBS Lett. 583:19-24 (2009).
Andrukhova et al., "FGF23 Acts Directly on Renal Proximal Tubules to Induce Phosphaturia Through Activation of the ERK1/2-SKG1 Signaling Pathway," Bone 51(3):621-8 (Jun. 12, 2012).
Beenken et al., "Plasticity in Interactions of Fibroblast Growth Factor 1 (FGF1) N Terminus With FGF Receptors Underlies Promiscuity of FGF1," J. Biol. Chem. 287(5):3067-3078 (Nov. 4, 2011).

(Continued)

*Primary Examiner* — Marianne P Allen
(74) *Attorney, Agent, or Firm* — LeClairRyan, a Professional Corporation

(57) ABSTRACT

The present invention relates to a chimeric protein that includes an N-terminus coupled to a C-terminus, where the N-terminus includes a portion of a paracrine fibroblast growth factor ("FGF") and the C-terminus includes a C-terminal portion of an FGF21 molecule. The portion of the paracrine FGF is modified to decrease binding affinity for heparin and/or heparan sulfate compared to the portion without the modification. The present invention also relates to pharmaceutical compositions including chimeric proteins according to the present invention, methods for treating a subject suffering from diabetes, obesity, or metabolic syndrome, and methods of screening for compounds with enhanced binding affinity for the βKlotho-FGF receptor complex involving the use of chimeric proteins of the present invention.

41 Claims, 13 Drawing Sheets

(56) References Cited

U.S. PATENT DOCUMENTS

| | | |
|---|---|---|
| 2009/0118190 A1 | 5/2009 | Beals et al. |
| 2009/0305986 A1 | 12/2009 | Belouski et al. |
| 2010/0062984 A1 | 3/2010 | Kumar et al. |
| 2010/0158914 A1 | 6/2010 | Desnoyers |
| 2010/0184665 A1 | 7/2010 | Suzuki et al. |
| 2010/0216715 A1 | 8/2010 | Tagmose et al. |
| 2010/0285131 A1 | 11/2010 | Belouski et al. |
| 2010/0286042 A1 | 11/2010 | Imamura et al. |
| 2010/0323954 A1 | 12/2010 | Li et al. |
| 2011/0053841 A1 | 3/2011 | Yayon et al. |
| 2011/0104152 A1 | 5/2011 | Sonoda |
| 2011/0150901 A1 | 6/2011 | Smith et al. |
| 2011/0172401 A1 | 7/2011 | Cujec et al. |
| 2011/0190207 A1 | 8/2011 | Mohammadi et al. |
| 2011/0195077 A1 | 8/2011 | Gass et al. |
| 2012/0052069 A1 | 3/2012 | Belouski et al. |
| 2012/0288886 A1 | 11/2012 | Mohammadi et al. |
| 2013/0023474 A1 | 1/2013 | Ling et al. |
| 2013/0058896 A1 | 3/2013 | Takada et al. |
| 2013/0116171 A1 | 5/2013 | Jonker et al. |
| 2013/0184211 A1 | 7/2013 | Mohammadi et al. |
| 2013/0231277 A1 | 9/2013 | Mohammadi et al. |
| 2013/0331316 A1 | 12/2013 | Mohammadi et al. |
| 2013/0331317 A1 | 12/2013 | Mohammadi et al. |
| 2013/0331325 A1 | 12/2013 | Mohammadi et al. |
| 2014/0094406 A1 | 4/2014 | Mohammadi et al. |
| 2014/0107022 A1 | 4/2014 | Mohammadi et al. |
| 2014/0155316 A1 | 6/2014 | Mohammadi et al. |
| 2014/0171361 A1 | 6/2014 | Jonker et al. |
| 2014/0243260 A1 | 8/2014 | Mohammadi et al. |
| 2015/0111821 A1 | 4/2015 | Suh et al. |
| 2015/0343022 A1 | 12/2015 | Jonker et al. |
| 2016/0206695 A1 | 7/2016 | Suh et al. |
| 2017/0096462 A1 | 4/2017 | Mohammadi et al. |
| 2017/0101449 A1 | 4/2017 | Mohammadi et al. |
| 2017/0226172 A1 | 8/2017 | Mohammadi et al. |

FOREIGN PATENT DOCUMENTS

| | | |
|---|---|---|
| WO | WO 2011/130729 A2 | 10/2011 |
| WO | WO 2013/184958 A1 | 12/2013 |
| WO | WO 2013/184960 A2 | 12/2013 |
| WO | WO 2013/184962 A1 | 12/2013 |
| WO | WO 2015/149069 A1 | 10/2015 |

OTHER PUBLICATIONS

Jonker et al., "A PPARgamma-FGF1 Axis Is Required for Adaptive Adipose Remodelling and Metabolic Homeostasis," Nature 485(7398):391-394 (Apr. 22, 2012).
Wu et al., "A Unique FGF23 With the Ability to Activate FGFR Signaling Through Both alphaKlotho and betaKlotho," J. Mol. Biol. 418:82-89 (2012).
Beenken & Mohammadi, "The Structural Biology of the FGF19 Subfamily," Adv. Exp. Med. Biol. 728:1-24 (2012).
Wu et al., "C-Terminal Tail of FGF19 Determines Its Specificity Toward Klotho Co-Receptors," J. Biol. Chem. 283(48):33304-33309 (2008).
Goetz et al., "Conversion of a Paracrine Fibroblast Growth Factor Into an Endocrine Fibrobalst Growth Factor," J. Biol. Chem. 287(34):29134-29146 (Jun. 25, 2012).
Goetz et al., "Klotho Coreceptors Inhibit Signaling by Paracrine Fibroblast Growth Factor 8 Subfamily Ligands," Mol. Cell. Biol. 32(10):1944-1954 (Mar. 26, 2012).
Olsen et al., "Insights Into the Molecular Basis for Fibroblast Growth Factor Receptor Autoinhibition and Ligand-Binding Promiscuity,"Proc. Nat'l. Acad. Sci. USA 101(4):935-940 (2004).
Wei et al., "Fibroblast Growth Factor 21 Promotes Bone Loss by Potentiating the Effects of Peroxisome Proliferator-Activated Receptor Gamma," Proc. Nat'l. Acad. Sci. USA 109(8):3143-3148 (Feb. 21, 2012).

Wu et al., "Separating Mitogenic and Metabolic Activities of Fibroblast Growth Factor 19 (FGF19)," Proc. Nat'l. Acad. Sci. USA 107(32):14158-14163 (2010).
Wu et al., "FGF19-Induced Hepatocyte Proliferation Is Mediated Through FGFR4 Activation," J. Biol. Chem. 285(8):5165-5170 (2009).
Zhang et al., "Receptor Specificity of the Fibroblast Growth Factor Family," J. Biol. Chem. 281(23):15694-15700 (2006).
Presta et al., "Structure-Function Relationship of Basic Fibroblast Growth Factor: Site-Directed Mutagenesis of a Putative Heparin-Binding and Receptor-Binding Region," Biochem. Biophys. Res. Commun. 185(3):1098-1107 (1992).
Zakrzewska et al., "Increased Protein Stability of FGF1 Can Compensate for Its Reduced Affinity for Heparin," J. Biol. Chem. 284(37):25388-403 (2009).
Motomura et al., "An FGF1:FGF2 Chimeric Growth Factor Exhibits Universal FGF Receptor Specificity, Enhanced Stability and Augmented Activity Useful for Epithelial Proliferation and Radioprotection," Biochim. Biophys. Acta 1780(12):1432-40 (2008).
Nakayama et al., "Post Treatment With an FGF Chimeric Growth Factor Enhances Epithelial Cell Proliferation to Improve Recovery From Radiation-Induced Intestinal Damage," Int. J. Radiat. Oncol. Biol. Phys. 78(3):860-7 (2010).
Kharitonenkov et al., "The Metabolic State of Diabetic Monkeys is Regulated by Fibroblast Growth Factor-21," Endocrinology 148(2):774-81 (2007).
Igarashi et al., "Characterization of Recombinant Human Fibroblast Growth Factor (FGF)-10 Reveals Functional Similarities With Keratinocyte Growth Factor (FGF-7)," J. Biol. Chem. 273(21):13230-5 (1998).
Goetz et al., "Molecular Insights Into the Klotho-Dependent, Endocrine Mode of Action of Fibroblast Growth Factor 19 Subfamily Members," Mol. Cell. Biol. 27(9):3417-3428 (2007).
Beenken, "Structural and Biochemical Studies of FGF-FGFR Complexes," Thesis (Sep. 2011).
Ge et al., "Characterization of a FGF19 Variant With Altered Receptor Specificity Revealed a Central Role for FGFR1c in the Regulation of Glucose Metabolism," PLoS One, 7(3):e33603 (Epub Mar. 23, 2012).
Wu et al., "FGF19 Regulates Cell Proliferation, Glucose and Bile Acid Metabolism Via FGFR4-Dependent and Independent Pathways," PLoS One 6(3):e17868 (Mar. 8, 2011).
Wu et al., "Selective Activation of FGFR4 by an FGF19 Variant Does Not Improve Glucose Metabolism in OB/OB Mice," Proc. Nat'l. Acad. Sci U.S.A. 106(34):14379-84 (2009).
Mohammadi et al., "Structural Basis for Fibroblast Growth Factor Receptor Activation," Cytokine & Growth Factor Reviews 16:107-137 (2005).
Hutley et al., "Fibroblast Growth Factor 1: A Key Regulator of Human Adipogenesis," Diabetes 53:3097-3106 (2004).
International Search Report and Written Opinion for PCT/US13/44594 (dated Nov. 13,2013).
Imamura et al., "Recovery of Mitogenic Activity of a Growth Factor Mutant with Nuclear Translocation Sequence," Science 249:1567-1570 (Sep. 28, 1990).
Goetz et al., "Isolated C-Terminal tail of FGF23 Alleviates Hypophosphatemia by Inhibiting FGF23-FGFR-Klotho Complex Formation," PNAS 107(1):407-412 (Epub Dec. 4, 2009).
Razzaque, "The FGF23-Klotho Axis: Endocrine Regulation of Phosphate Homeostasis," Nat. Rev. Endocrinol. 5(11):611-19 (2009).
Abraham et al., "Human Basic Fibroblast Growth Factor: Nucleotide Sequence and Genomic Organization," *EMBO J.* 10:2523-2528 (1986).
Esch et al., "Primary Structure of Bovine Pituitary Basic Fibroblast Growth Factor (FGF) and Comparison with the Amino-Terminal Sequence of Bovine Brain Acidic FGF," PNAS 82:6507-6511 (1985).
Kurosu et al., "The Klotho Gene Family as a Regulator of Endocrine Fibroblast Growth Factors," Mol Cel Endocrin. 299:72-78 (2009).

(56) References Cited

OTHER PUBLICATIONS

Ono et al., "Novel Regulation of Fibroblast Growth Factor 2 (FGF2)-Mediated Cell Growth by Polysialic Acid," J. Biol. Chem. 287(6):3710-3722 (2012).

Schlessinger et al., "Crystal Structure of a Ternary FGF-FGFR-Heparin Complex Reveals a Dual Role for Heparin in FGFR Binding and Dimerization," Molecular Cell 6:743-750 (2000).

Thompson et al., "Energetic Characterization of the Basic Fibroblast Growth Factor-Heparin Interaction: Identification of the Heparin Binding Domains," Biochemistry 33:3831-3840 (1994).

Suh et al., "Endocrinization of FGF1 Produces a Neomorphic and Potent Insulin Sensitizer," Author Manuscript, Nature 513(7518): 436-439 (2014).

Beenken et al., "The FGF Family: Biology, Pathophysiology and Therapy," Nat Rev Drug Discov. 8(3):235-53 (Mar. 2009).

Kurosu et al., "Tissue-specific Expression of βKlotho and Fibroblast Growth Factor (FGF) Receptor Isoforms Determines Metabolic Activity of FGF19 and FGF21," J. Biol. Chem. 282(37):26687-26695 (2007).

Micanovic et al., "Different Roles of N- and C- Termini in the Functional Activity of FGF21," J. Cell. Physiol. 219:227-234 (2009).

Kharitonenkov et al.,"FGF-21/FGF-21 Receptor Interaction and Activation is Determined by βKlotho," J. Cell. Physiol. 215:1-7 (2008).

Yao et al., "Expression and Pharmacological Evaluation of Fusion Protein FGF21-L-Fc," Acta Pharmaceutica Sinica 46(7):787-92 (2011) (Abstract in English).

Pellegrini et al., "Crystal Structure of Fibroblast Growth Factor Receptor Ectodomain Bound to Ligand and Heparin," Nature 407:1029-1034 (2000).

Pellegrini et al., Protein Data Bank, 1E0O, "Crystal Structure of a Ternary FGF1-FGFR2-Heparin Complex," (Released Oct. 23, 2000).

Second Office Action for Chinese Patent Application No. 201380039848.9 (dated Jun. 8, 2017).

Office Action in U.S. Appl. No. 15/289,544 (dated May 30, 2017).

Crumley et al., Genbank Accession No. 1605206A, acidic fibroblast growth factor (1996).

Unpublished U.S. Appl. No. 15/598,420, filed May 18, 2017.

\* cited by examiner

FIG. 2

```
FGF19 (169)  LPMV PEEPEDLRGH - - LESDMFSSPL ETDSMDPFGL VTGLEAVRSP SFEK - - - - - -
FGF21 (168)  PGLP PALPE - - - - - PPGILAPQRP DVGSSDPLSM V-GPSQGRSP SYAS - - - - - -
FGF23 (163)  - - - - PLI - HFNTP IPRRHTRSAE DDSERDPLN- VLKPRARMTP APASCSQELP

FGF19        - - - - - - - - - - - - - - - - - - - -
FGF21        - - - - - - - - - - - - - - - - - - - -
FGF23 (212)  SAEDNSPMAS DPLGVVRGGR VNTHAGGTGP EGCRPFAKFI
```

CHIMERIC FIBROBLAST GROWTH FACTOR 21 PROTEINS AND METHODS OF USE

This application is a divisional application of U.S. patent application Ser. No. 13/837,880, filed Mar. 15, 2013, which claims priority benefit of U.S. Provisional Patent Application No. 61/656,778, filed Jun. 7, 2012, and U.S. Provisional Patent Application No. 61/664,081, filed Jun. 25, 2012, each of which is hereby incorporated by reference in its entirety.

This invention was made with government support under grant numbers DE13686, DK077276, AG019712, DK091392, and DK067158 awarded by the U.S. National Institutes of Health. The government has certain rights in this invention.

FIELD OF THE INVENTION

The present invention relates to chimeric fibroblast growth factor ("FGF") proteins and uses thereof.

BACKGROUND OF THE INVENTION

Type 2 diabetes is a chronic progressive disorder, which results from end-organ resistance to the action of insulin in combination with insufficient insulin secretion from the pancreas. The metabolic abnormalities associated with insulin resistance and secretory defects, in particular the hyperglycemia, lead over the course of years to extensive irreversible damage to multiple organs including heart, blood vessels, kidney, and eye. Currently, nearly 200 million or 2.9% of the world population have type 2 diabetes (World Health Organization, Diabetes Fact Sheet N° 312, January 2011; Wild et al., "Global Prevalence of Diabetes: Estimates for the Year 2000 and Projections for 2030," *Diabetes Care* 27(5):1047-1053 (2004)), and its prevalence is rising at an alarmingly fast pace in parallel with the rise in the prevalence of overweight and obesity (World Health Organization, Obesity and Overweight Fact Sheet N° 311, January 2011). Until the end of the 20$^{th}$ century, type 2 diabetes was observed only in adults but what was once known as "adult-onset diabetes" is now also diagnosed in children and adolescents, and this growing incidence can be related to the increase in overweight and obesity among children and adolescents. The prevalence of pre-diabetes, an intermediate metabolic stage between normal glucose homeostasis and diabetes, is even greater than that of type 2 diabetes. Currently, nearly 80 million or 26% of the population in the United States alone have pre-diabetes (Center for Disease Control and Prevention, National Diabetes Fact Sheet 2011), and as such are at high risk for progressing to type 2 diabetes. Type 2 diabetes ranks among the ten leading causes of death worldwide, and the World Health Organization projects that mortality from diabetes (90% of which is type 2) will more than double within the next decade (World Health Organization, Diabetes Fact Sheet N° 312, January 2011). Type 2 diabetes also is a major cause of disability. As a consequence of diabetic retinopathy, about 10% of all patients with diabetes in the world develop severe visual impairment and 2% become blind 15 years into the disease (World Health Organization, Diabetes Fact Sheet N° 312, January 2011). Diabetic neuropathy, which affects up to half of all patients with diabetes worldwide (World Health Organization, Diabetes Fact Sheet N° 312, January 2011), accounts for the majority of nontraumatic lower-limb amputations. Indeed, in its recently published first worldwide report on non-infectious diseases, the World Health Organization considers diabetes, together with other chronic non-infectious diseases like cancer and heart disease, a global economic and social burden, which exceeds that imposed by infectious diseases such as HIV/AIDS.

The current drug therapy for type 2 diabetes is focused on correcting the hyperglycemia in the patients. Although a number of small molecules and biologics with different mechanisms of anti-hyperglycemic action are available for use as mono-therapy or combination therapy, most, if not all of these have limited efficacy, limited tolerability, and significant adverse effects (Moller, "New Drug Targets for Type 2 Diabetes and the Metabolic Syndrome," *Nature* 414 (6865):821-827 (2001)). For example, treatment with sulfonylureas, glinides, thiazolidinediones, or insulin has been associated with weight gain, which is an undesired effect since overweight is considered a driving force in the pathogenesis of type 2 diabetes. Some of these treatments have also been associated with increased risk of hypoglycemia. A limitation specific to the thiazolidinediones is the potential for adverse cardiovascular effects (DeSouza et al., "Therapeutic Targets to Reduce Cardiovascular Disease in Type 2 Diabetes," *Nat Rev Drug Discov* 8(5):361-367 (2009)). A meta-analysis of clinical data on the thiazolidinedione rosiglitazone (Avandia®), which was widely used for the treatment of type 2 diabetes, found that the drug increased the risk of myocardial infarction in patients with type 2 diabetes (Nissen et al., "Effect of Rosiglitazone on the Risk of Myocardial Infarction and Death from Cardiovascular Causes," *N Engl J Med* 356(24):2457-2471 (2007)). Of all diabetic complications, cardiovascular disease is the main cause of morbidity and mortality in patients with diabetes (World Health Organization, Diabetes Fact Sheet N° 312, January 2011; Center for Disease Control and Prevention, National Diabetes Fact Sheet 2011), and hence an aggravation of cardiovascular risk by drug treatment is absolutely unacceptable. In the wake of the debate about the cardiovascular safety of thiazolidinediones, the FDA issued a guidance on evaluating cardiovascular risk in new anti-diabetic therapies to treat type 2 diabetes (Opar A, "Diabetes Drugs Pass Cardiovascular Risk Check," *Nat Rev Drug Discov* 8(5):343-344 (2009)). Meanwhile, thiazolidinediones lost their popularity. Even for glucagon-like peptide-1 agonists, one of the latest class of drugs introduced for the treatment of type 2 diabetes, concerns about safety have been raised, namely the potential for carcinogenicity (Opar A, "Diabetes Drugs Pass Cardiovascular Risk Check," *Nat Rev Drug Discov* 8(5):343-344 (2009)). Therefore, novel therapies that are more effective and safer than existing drugs are needed. Since the currently available drugs do not directly target complications of advanced diabetic disease, especially cardiovascular disease, therapies that are not only effective in lowering blood glucose but also reduce cardiovascular risk factors such as dyslipidemia are particularly desired.

A search conducted by Eli Lilly & Co. for potential novel biotherapeutics to treat type 2 diabetes led to the discovery of fibroblast growth factor (FGF) 21 as a protein that stimulates glucose uptake into adipocytes in an insulin-independent fashion (Kharitonenkov et al., "FGF-21 as a Novel Metabolic Regulator," *J Clin Invest* 115(6): 1627-1635 (2005)). FGF21 has since emerged as a key endocrine regulator not only of glucose metabolism but also of lipid metabolism, and has become one of the most promising drug candidates for the treatment of type 2 diabetes, obesity, and metabolic syndrome. In mouse models of diabetes and obesity, pharmacologic doses of FGF21 lower plasma glucose and increase insulin sensitivity (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12): 6018-6027 (2008)). Concurrently, FGF21 lowers plasma triglyceride and cholesterol, enhances lipolysis and suppresses lipogenesis, and accelerates energy expenditure (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12):6018-6027 (2008)). In obese mice, FGF21 causes weight loss, in lean mice, it is weight neutral (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12):6018-6027 (2008)). Thus, FGF21 has some of the most desired characteristics of a drug for the treatment of type 2 diabetes; not only does it improve glycemic control, but also directly affects cardiovascular risk factors, such as hypertriglyceridemia, and reduces obesity, which is considered the single most important promoter of type 2 diabetes. Importantly, FGF21 does not induce hypoglycemia (Kharitonenkov et al., "FGF-21 as a Novel Metabolic Regulator," *J Clin Invest* 115(6): 1627-1635 (2005)), a side effect that can occur with several of the current anti-diabetic therapies, including insulin. Moreover, FGF21 does not exhibit any mitogenic activity in mice (Kharitonenkov et al., "FGF-21 as a Novel Metabolic Regulator," *J Clin Invest* 115(6): 1627-1635 (2005)), ruling out the possibility of a carcinogenic risk. The findings on FGF21 therapy in mouse models of diabetes have been reproduced in diabetic rhesus monkeys (Kharitonenkov et al., "The Metabolic State of Diabetic Monkeys is Regulated by Fibroblast Growth Factor-21*," Endocrinology* 148(2):774-781 (2007)), and are currently followed up with clinical trials in humans (Kharitonenkov et al., "FGF21 Reloaded: Challenges of a Rapidly Growing Field," *Trends Endocrinol Metab* 22(3):81-86 (2011)). However, there is a need for more effective FGF21 therapeutics.

The present invention overcomes these and other deficiencies in the art.

SUMMARY OF THE INVENTION

One aspect of the present invention relates to a chimeric protein. The chimeric protein includes an N-terminus coupled to a C-terminus, where the N-terminus includes a portion of a paracrine fibroblast growth factor ("FGF") and the C-terminus includes a C-terminal portion of an FGF21 molecule. The portion of the paracrine FGF is modified to decrease binding affinity for heparin and/or heparan sulfate compared to the portion without the modification.

Another aspect of the present invention relates to a method for treating a subject suffering from a disorder. This method involves selecting a subject suffering from the disorder and providing a chimeric FGF protein, where the chimeric FGF protein includes an N-terminus coupled to a C-terminus. The N-terminus includes a portion of a paracrine FGF and the C-terminus includes a C-terminal portion of FGF21. The portion of the paracrine FGF is modified to decrease binding affinity for heparin and/or heparan sulfate compared to the portion without the modification. This method also involves administering a therapeutically effective amount of the chimeric FGF protein to the selected subject under conditions effective to treat the disorder.

Another aspect of the present invention relates to a method of making a chimeric FGF protein possessing enhanced endocrine activity. This method involves introducing one or more modifications to an FGF protein, where the modification decreases the affinity of the FGF protein for heparin and/or heparan sulfate and coupling a Klotho co-receptor binding domain to the modified FGF protein's C-terminus, whereby a chimeric FGF protein possessing enhanced endocrine activity is made.

Yet another aspect of the present invention relates to a method of facilitating fibroblast growth factor receptor ("FGFR")-βKlotho co-receptor complex formation. This method involves providing a cell that includes a βKlotho co-receptor and an FGFR and providing a chimeric FGF protein. The chimeric FGF protein includes a C-terminal portion of FGF21 and a portion of a paracrine FGF, where the portion of the paracrine FGF is modified to decrease binding affinity for heparin and/or heparan sulfate compared to the portion without the modification. This method also involves contacting the cell and the chimeric FGF protein under conditions effective to cause FGFR-βKlotho co-receptor complex formation.

Yet a further aspect of the present invention relates to a method of screening for agents capable of facilitating FGFR-βKlotho complex formation in the treatment of a disorder. This method involves providing a chimeric FGF that includes an N-terminus coupled to a C-terminus, where the N-terminus includes a portion of a paracrine FGF and the C-terminus includes a C-terminal portion of FGF21. The portion of the paracrine FGF is modified to decrease binding affinity for heparin and/or heparan sulfate compared to the portion without the modification. This method also involves providing a binary βKlotho-FGFR complex and providing one or more candidate agents. This method further involves combining the chimeric FGF, the binary βKlotho-FGFR complex, and the one or more candidate agents under conditions permitting the formation of a ternary complex between the chimeric FGF and the binary βKlotho-FGFR complex in the absence of the one or more candidate agents. This method also involves identifying the one or more candidate agents that decrease ternary complex formation between the chimeric FGF and the binary βKlotho-FGFR complex compared to the ternary complex formation in the absence of the one or more candidate agents as suitable for treating the disorder.

Fibroblast growth factors (FGFs) 19, 21, and 23 are hormones that regulate in a Klotho co-receptor-dependent fashion major metabolic processes such as glucose and lipid metabolism (FGF21) and phosphate and vitamin D homeostasis (FGF23). The role of heparan sulfate glycosaminoglycan in the formation of the cell surface signaling complex of endocrine FGFs has remained unclear. To decipher the role of HS in endocrine FGF signaling, we generated FGF19 and FGF23 mutant ligands devoid of HS binding and compared their signaling capacity with that of wild-type ligands. The data presented herein show that the mutated ligands retain full metabolic activity demonstrating that HS does not participate in the formation of the endocrine FGF signaling complex. Here it is shown that heparan sulfate is not a component of the signal transduction unit of FGF19 and FGF23. A paracrine FGF is converted into an endocrine ligand by diminishing heparan sulfate binding affinity of the paracrine FGF and substituting its C-terminal tail for that of an endocrine FGF containing the Klotho co-receptor binding site in order to home the ligand into the target tissue. The ligand conversion provides a novel strategy for engineering endocrine FGF-like molecules for the treatment of metabolic disorders, including global epidemics such as type 2 diabetes and obesity.

BRIEF DESCRIPTION OF THE DRAWINGS

FIG. 1A shows interactions of FGF2 (schematic representation) with a heparin hexasaccharide (shown as sticks) as observed in the crystal structure of the 2:2 FGF2-FGFR1c dimer (PDB ID: 1FQ9; (Schlessinger et al., *Mol. Cell* 6:743-750 (2000), which is hereby incorporated by reference in its entirety)). The heparin hexasaccharide consists of three disaccharide units of 1→4 linked N-sulfated-6-O-sulfated D-glucosamine and 2-O-sulfated L-iduronic acid. Note that the heparin hexasaccharide interacts with both side chain and backbone atoms of residues in the HS-binding site of FGF2. Dashed lines denote hydrogen bonds. K128, R129, and K134, which make the majority of hydrogen bonds with the heparin hexasaccharide, are boxed. The β-strand nomenclature follows the original FGF1 and FGF2 crystal structures (Ago et al., *J. Biochem.* 110:360-363 (1991); Eriksson et al., *Proc. Nat'l. Acad. Sci. U.S.A.* 88:3441-3445 (1991); Zhang et al., *Proc. Nat'l. Acad. Sci. U.S.A.* 88:3446-3450 (1991); Zhu et al., *Science* 251:90-93 (1991), which are hereby incorporated by reference in their entirety). Please note that compared to the prototypical β-trefoil fold seen in soybean trypsin inhibitor (PDB ID: 1TIE; (Onesti et al., *J. Mol. Biol.* 217:153-176 (1991), which is hereby incorporated by reference in its entirety)) and interleukin 1β (PDB ID: 1I1B; (Finzel et al., *J. Mol. Biol.* 209:779-791 (1989), which is hereby incorporated by reference in its entirety)), the β10-β11 strand pairing in FGF2 and other paracrine FGFs is less well defined. FIGS. 1B and 1C show cartoon representation of the crystal structures of FGF19 (PDB ID: 2P23; (Goetz et al., *Mol. Cell Biol.* 27:3417-3428 (2007), which is hereby incorporated by reference in its entirety)) (FIG. 1B) and FGF23 (PDB ID: 2P39; (Goetz et al., *Mol. Cell Biol.* 27:3417-3428 (2007), which is hereby incorporated by reference in its entirety)) (FIG. 1C) shown in the same orientation as the FGF2 structure in FIG. 1A. Side chains of residues that map to the corresponding HS-binding sites of these ligands are shown as sticks. Residues selected for mutagenesis to knock out residual HS binding in FGF19 and FGF23 are boxed. NT and CT indicate N- and C-termini of the FGFs. FIG. 1D is a schematic of two working models for the endocrine FGF-FGFR-Klotho coreceptor signal transduction unit. A recent study on the ternary complex formation between FGF21, FGFR1c, and βKlotho supports the 1:2:1 model rather than the 2:2:2 model (Ming et al., *J. Biol. Chem.* 287:19997-20006 (2012), which is hereby incorporated by reference in its entirety). For comparison, a schematic of the paracrine FGF-FGFR-HS signaling unit is shown, which was made based on the crystal structure of the 2:2:2 FGF2-FGFR1c-HS complex (PDB ID: 1FQ9; (Schlessinger et al., *Mol. Cell* 6:743-750 (2000), which is hereby incorporated by reference in its entirety)). HS engages both paracrine FGF and receptor to enhance binding of FGF to its primary and secondary receptors thus promoting receptor dimerization. A question mark denotes whether or not HS is also a component of the endocrine FGF signaling complex.

FIG. 2 shows a sequence alignment of the endocrine FGFs, FGF1 and FGF2. The amino acid sequences of the mature human FGF19, FGF21, and FGF23 ligands are aligned. Also included in the alignment are the human sequences of FGF1 and FGF2, prototypical paracrine FGFs, which were used in the experiments described herein, in which FGF1 and FGF2 were converted into endocrine FGF ligands. Residue numbers corresponding to the human sequence of FGF1 (SEQ ID NO:1) (GenBank Accession No. AAH32697, which is hereby incorporated by reference in its entirety), FGF2 (SEQ ID NO: 121) (GenBank Accession No. EAX05222, which is hereby incorporated by reference in its entirety), FGF19 (SEQ ID NO: 337) (GenBank Accession No. NP_005108, which is hereby incorporated by reference in its entirety), FGF21 (SEQ ID NO: 233) (GenBank Accession No. NP_061986, which is hereby incorporated by reference in its entirety), and FGF23 (SEQ ID NO:351) (GenBank accession no. AAG09917, which is hereby incorporated by reference in its entirety) are in parenthesis to the left of the alignment. Secondary structure elements are labeled, and residues containing these elements for known secondary structures are boxed. Gaps (dashes) were introduced to optimize the sequence alignment. The β-trefoil core domain for known FGF crystal structures is shaded gray. Blue bars on top of the alignment indicate the location of the HS-binding regions. HS-binding residues selected for mutagenesis are shaded blue.

FIG. 3A shows an overlay of SPR sensorgrams illustrating heparin binding of FGF2, FGF19, FGF21, and FGF23 (left panel) and an exploded view of the binding responses for FGF19-, FGF21-, and FGF23-heparin interactions (right panel). Heparin was immobilized on a biosensor chip, and 400 nM of FGF2, FGF19, FGF21, or FGF23 were passed over the chip. Note that FGF19, FGF21, and FGF23 exhibit measurable, residual heparin binding and that differences in heparin binding exist between these three endocrine FGFs. FIGS. 3B-3D show overlays of SPR sensorgrams illustrating binding of FGF19 to heparin (FIG. 3B) and lack of interaction between the FGF19$^{K149A}$ mutant and heparin (FIG. 3C) and between the FGF19$^{K149A,\ R157A}$ mutant and heparin (FIG. 3D). Heparin was immobilized on a biosensor chip, and increasing concentrations of FGF19 were passed over the chip. Thereafter, FGF19$^{K149A}$ or FGF19$^{K149A,\ R157A}$ was injected over the heparin chip at the highest concentration tested for the wild-type ligand. FIGS. 3E-3G show overlays of SPR sensorgrams illustrating binding of FGF23 to heparin (FIG. 3E), poor interaction between the FGF23$^{R48A,\ N49A}$ mutant and heparin (FIG. 3F), and lack of interaction between the FGF23$^{R140A,\ R143A}$ mutant and heparin (FIG. 3G). Heparin was immobilized on a biosensor chip, and increasing concentrations of FGF23 were passed over the chip. FGF23$^{R48A,\ N49A}$ or FGF23$^{R140A,\ R143A}$ was then injected over the heparin chip at the highest concentration tested for the wild-type ligand.

FIG. 4A shows results of an immunoblot analysis of phosphorylation of FRS2α (pFRS2α) and 44/42 MAP kinase (p44/42 MAPK) in H4IIE hepatoma cells following stimulation with the FGF19$^{K149A}$ mutant, the FGF19$^{K149A,\ R157A}$ mutant, or wild-type FGF19. Numbers above the lanes give the amounts of protein added in ng ml$^{-1}$. Total 44/42 MAPK protein expression was used as a loading control. FIG. 4B shows results of an immunoblot analysis of phosphorylation of FRS2α (pFRS2α) and 44/42 MAP kinase (p44/42 MAPK) in a HEK293-αKlotho cell line following stimulation with the FGF23$^{R48A,\ N49A}$ mutant, the FGF23$^{R140A,\ R143A}$ mutant, or wild-type FGF23. Numbers above the lanes give the amounts of protein added in ng ml$^{-1}$. Total 44/42 MAPK and αKlotho protein expression were used as loading controls. FIG. 4C shows graphical results of a quantitative analysis of CYP7A1 and CYP8B1 mRNA expression in liver tissue from mice treated with $FGF19^{K149A}$, $FGF19^{K149A,\ R157A}$, FGF19, or vehicle. 1 mg of protein per kg of body weight was given. Data are presented as mean±SEM; ***, P<0.001 by Student's t test. FIG. 4D shows graphical results of analysis of serum phosphate concentrations (serum $P_i$) in mice before and 8 h after intraperitoneal injection of $FGF23^{R48A,\ N49A}$, $FGF23^{R140A,\ R143A}$, FGF23, or vehicle. Wild-type mice were given a single dose of protein (0.29 mg kg body weight$^{-1}$), whereas Fgf23 knockout mice received two doses of 0.71 mg kg body weight$^{-1}$ each. Data are presented as mean±SEM; *, P<0.05, and **, P<0.01 by ANOVA.

FIG. 5A is a schematic of human FGF2, FGF19, FGF21, FGF23, and engineered FGF2-FGF19, FGF2-FGF21, and FGF2-FGF23 chimeras. Amino acid boundaries of each ligand and of each component of the chimeras are labeled with residue letter and number. The β-trefoil core domain for the known ligand crystal structures is shaded gray. HS-binding residues mutated in the FGF2 portion of chimeras are labeled with residue letter and number. Also labeled are the arginine residues of the proteolytic cleavage site in the C-terminal region of FGF23 that were mutated to glutamine in both FGF23 and the FGF2-FGF23 chimeras. FIGS. 5B and 5C show overlays of SPR sensorgrams illustrating binding of $FGF2^{WTcore}$-$FGF21^{C-tail}$ (FIG. 5B) and $FGF2^{\Delta HBScore}$-$FGF21^{C-tail}$ (FIG. 5C) to heparin, and fitted saturation binding curves. Heparin was immobilized on a biosensor chip, and increasing concentrations of $FGF2^{WTcore}$-$FGF21^{C-tail}$ or $FGF2^{\Delta HBScore}$-$FGF21^{C-tail}$ were passed over the chip. Dissociation constants ($K_D$s) were derived from the saturation binding curves. FIGS. 5D and 5E show overlays of SPR sensorgrams illustrating binding of $FGF2^{WTcore}$-$FGF23^{C-tail}$ (FIG. 5D) and $FGF2^{\Delta HBScore}$-$FGF23^{C-tail}$ (FIG. 5E) to heparin. Increasing concentrations of $FGF2^{WTcore}$-$FGF23^{C-tail}$ or $FGF2^{\Delta HBScore}$-$FGF23^{C-tail}$ were passed over a chip containing immobilized heparin. FIGS. 5F and 5G show results of immunoblot analysis for Egr1 expression in HEK293 cells following stimulation with chimeras or native FGFs as denoted. Numbers above the lanes give the amounts of protein added in nanomolar. GAPDH protein expression was used as a loading control.

FIGS. 7A and 7B show overlays of SPR sensorgrams illustrating inhibition by $FGF2^{\Delta HBScore}$-$FGF23^{C-tail}$ (FIG. 7A) or FGF23 (FIG. 7B) of αKlotho-FGFR1c binding to FGF23 immobilized on a biosensor chip. Increasing concentrations of $FGF2^{\Delta HBScore}$-$FGF23^{C-tail}$ or FGF23 were mixed with a fixed concentration of αKlotho-FGFR1c complex, and the mixtures were passed over a FGF23 chip. FIG. 7C shows an overlay of SPR sensorgrams illustrating failure of FGF2 to inhibit αKlotho-FGFR1c binding to FGF23. FGF2 and αKlotho-FGFR1c complex were mixed at a molar ratio of 15:1, and the mixture was passed over a biosensor chip containing immobilized FGF23. FIGS. 7D and 7E show overlays of SPR sensorgrams illustrating no inhibition by $FGF2^{\Delta HBScore}$-$FGF23^{C-tail}$ (FIG. 7D) or FGF23 (FIG. 7E) of βKlotho-FGFR1c binding to FGF21. $FGF2^{\Delta HBScore}$-$FGF23^{C-tail}$ or FGF23 were mixed with βKlotho-FGFR1c complex at a molar ratio of 10:1, and the mixtures were passed over a biosensor chip containing immobilized FGF21. FIG. 7F shows analysis of serum phosphate concentrations (serum $P_i$) in mice before and 8 h after intraperitoneal injection of $FGF2^{\Delta HBScore}$-$FGF23^{C-tail}$, $FGF2^{WTcore}$-$FGF23^{C-tail}$, FGF23, or vehicle. Wild-type mice and αKlotho knockout mice were given 0.21 mg and 0.51 mg of protein, respectively, per kg of body weight. Data are presented as mean±SEM; , P<0.01; *, P<0.001 by ANOVA. FIG. 7G shows quantitative analysis of CYP27B1 mRNA expression in renal tissue from mice injected with $FGF2^{\Delta HBScore}$-$FGF23^{C-tail}$, $FGF2^{WTcore}$-$FGF23^{C-tail}$, FGF23, or vehicle. 0.21 mg of protein per kg of body weight were injected. Data are presented as mean±SEM; ***, P<0.001 by ANOVA.

FIGS. 8A-8B show overlays of SPR sensorgrams illustrating inhibition by $FGF2^{\Delta HBScore}$-$FGF21^{C-tail}$ (FIG. 8A) or FGF21 (FIG. 8B) of βKlotho-FGFR1c binding to FGF21 immobilized on a biosensor chip. Increasing concentrations of $FGF2^{\Delta HBScore}$-$FGF21^{C-tail}$ or FGF21 were mixed with a fixed concentration of βKlotho-FGFR1c complex, and the mixtures were passed over a FGF21 chip. FIG. 8C shows an overlay of SPR sensorgrams illustrating failure of FGF2 to inhibit βKlotho-FGFR1c binding to FGF21. FGF2 and βKlotho-FGFR1c complex were mixed at a molar ratio of 15:1, and the mixture was passed over a biosensor chip containing immobilized FGF21. FIGS. 8D-8E show overlays of SPR sensorgrams illustrating no inhibition by $FGF2^{\Delta HBScore}$-$FGF21^{C-tail}$ (FIG. 8D) or FGF21 (FIG. 8E) of αKlotho-FGFR1c binding to FGF23. $FGF2^{\Delta HBScore}$-$FGF21^{C-tail}$ or FGF21 were mixed with αKlotho-FGFR1c complex at a molar ratio of 10:1, and the mixtures were passed over a biosensor chip containing immobilized FGF23. FIG. 8F shows results of immunoblot analysis for Egr1 expression in HEK293-βKlotho cells stimulated with $FGF2^{\Delta HBScore}$-$FGF21^{C-tail}$ or FGF21. Numbers above the lanes give the amounts of protein added in ng ml$^{-1}$. GAPDH protein expression was used as a loading control. Note that the $FGF2^{\Delta HBScore}$-$FGF21^{C-tail}$ chimera is more potent than native FGF21 at inducing Egr1 expression suggesting that the chimera has agonistic property. This is expected since the core domain of FGF2 has inherently greater binding affinity for FGFR than the core domain of FGF21 (see FIGS. 10A and 10C). FIG. 8G shows graphical results of analysis of blood glucose concentrations in mice before and at the indicated time points after intraperitoneal injection of insulin alone, insulin plus $FGF2^{\Delta HBScore}$-$FGF21^{C-tail}$ chimera, insulin plus FGF21, or vehicle alone. 0.5 units of insulin per kg of body weight and 0.3 mg of FGF21 ligand per kg of body weight were injected. Blood glucose concentrations are expressed as percent of pre-injection values. Data are presented as mean±SEM.

FIG. 9A shows graphical results of analysis of blood glucose concentrations in ob/ob mice before and at the indicated time points after subcutaneous injection of FGF1 or FGF21.

FIG. 9B shows graphical results of analysis of blood glucose concentrations in ob/ob mice before and at the indicated time points after subcutaneous injection of FGF1, FGF1$^{\Delta NT}$, or FGF1$^{\Delta HBS}$. FIG. 9C shows graphical results of analysis of blood glucose concentrations in ob/ob mice before and at the indicated time points after subcutaneous injection of FGF1 or FGF1$^{\Delta HBScore}$-FGF21$^{C\text{-}tail}$ chimera. For the experiments shown in FIGS. 9A-9C, ob/ob mice were injected with a bolus of 0.5 mg of FGF protein per kg of body weight. Data are presented as mean±SD.

FIGS. 10A-10D show overlays of SPR sensorgrams illustrating binding of FGFR1c to FGF2 (FIG. 10A), FGF19 (FIG. 10B), FGF21 (FIG. 10C), and FGF23 (FIG. 10D), and fitted saturation binding curves. Increasing concentrations of FGFR1c ligand-binding domain were passed over a biosensor chip containing immobilized FGF2, FGF19, FGF21, or FGF23. FIG. 10E shows an overlay of SPR sensorgrams illustrating binding of αKlotho-FGFR1c complex to FGF23. Increasing concentrations of αKlotho-FGFR1c complex were passed over a biosensor chip containing immobilized FGF23. FIG. 10F shows an overlay of SPR sensorgrams showing lack of interaction between the C-terminal tail peptide of FGF23 and FGFR1c. FGF2$^{3C\text{-}tail}$ was immobilized on a biosensor chip and increasing concentrations of FGFR1c ligand-binding domain were passed over the chip. Dissociation constants ($_{K_D}$s) given in FIGS. 10A-10E were derived from the saturation binding curves.

FIG. 11 shows an alignment of the C-terminal tail sequences of human FGF19 (SEQ ID NO: 337) (GenBank Accession No. NP_005108, which is hereby incorporated by reference in its entirety), FGF21 (SEQ ID NO:233) (GenBank Accession No. NP_061986, which is hereby incorporated by reference in its entirety), and FGF23 (SEQ ID NO:351) (GenBank accession no. AAG09917, which is hereby incorporated by reference in its entirety). Residue numbers are in parenthesis to the left of the alignment. Gaps (dashes) were introduced to optimize the alignment. Residues that are identical between FGF19 and FGF21 are shaded gray. Note that 40% of these residues map to the most C-terminal sequence.

FIG. 12 shows an alignment of the C-terminal tail sequences of human FGF21 (SEQ ID NO:233) (GenBank Accession No. NP_061986, which is hereby incorporated by reference in its entirety), FGF19 (SEQ ID NO: 337) (GenBank Accession No. NP_005108, which is hereby incorporated by reference in its entirety), and variants of FGF21 harboring a single amino acid substitution or insertion for a residue unique to FGF19. Residue numbers for the sequences of native FGF21 and FGF19 are in parenthesis to the left of the alignment. Gaps (dashes) were introduced to optimize the alignment. In the sequence of native FGF19, residues unique to FGF19 are bold and boxed, and in the sequences of the variants of the FGF21 C-terminal tail, introduced FGF19 residues are highlighted in the same manner.

FIG. 13 shows an alignment of the C-terminal tail sequences of human FGF21 (SEQ ID NO:233) (GenBank Accession No. NP_061986, which is hereby incorporated by reference in its entirety), FGF19 (SEQ ID NO: 337) (GenBank Accession No. NP_005108, which is hereby incorporated by reference in its entirety), and variants of FGF21 in which residues unique to FGF19 progressively replace the corresponding residues of FGF21 or are inserted into the FGF21 sequence. Residue numbers for the sequences of native FGF21 and FGF19 are in parenthesis to the left of the alignment. Gaps (dashes) were introduced to optimize the alignment. In the sequence of native FGF19, residues unique to FGF19 are bold and boxed, and in the sequences of variants of the FGF21 C-terminal tail, introduced FGF19 residues are highlighted in the same manner.

DETAILED DESCRIPTION OF THE INVENTION

Figures 1A, 1B, 1C, 1D:
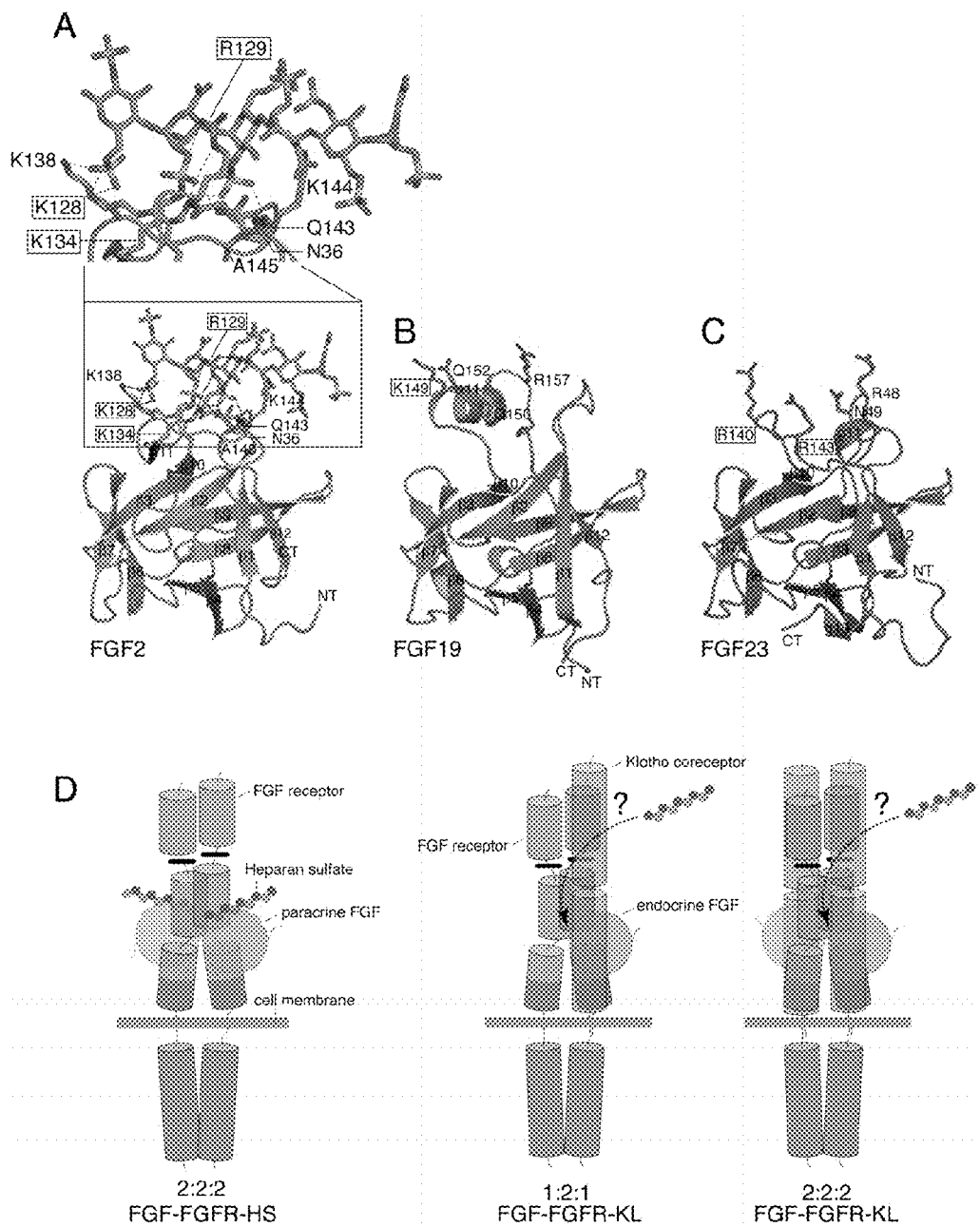
FIGS. 1A-1D are schematic diagrams showing side-by-side comparison of the HS-binding site of FGF2, FGF19, and FGF23, and two working models for the endocrine FGF signaling complex.
Figures 3A, 3B, 3C, 3D, 3E, 3F, 3G:
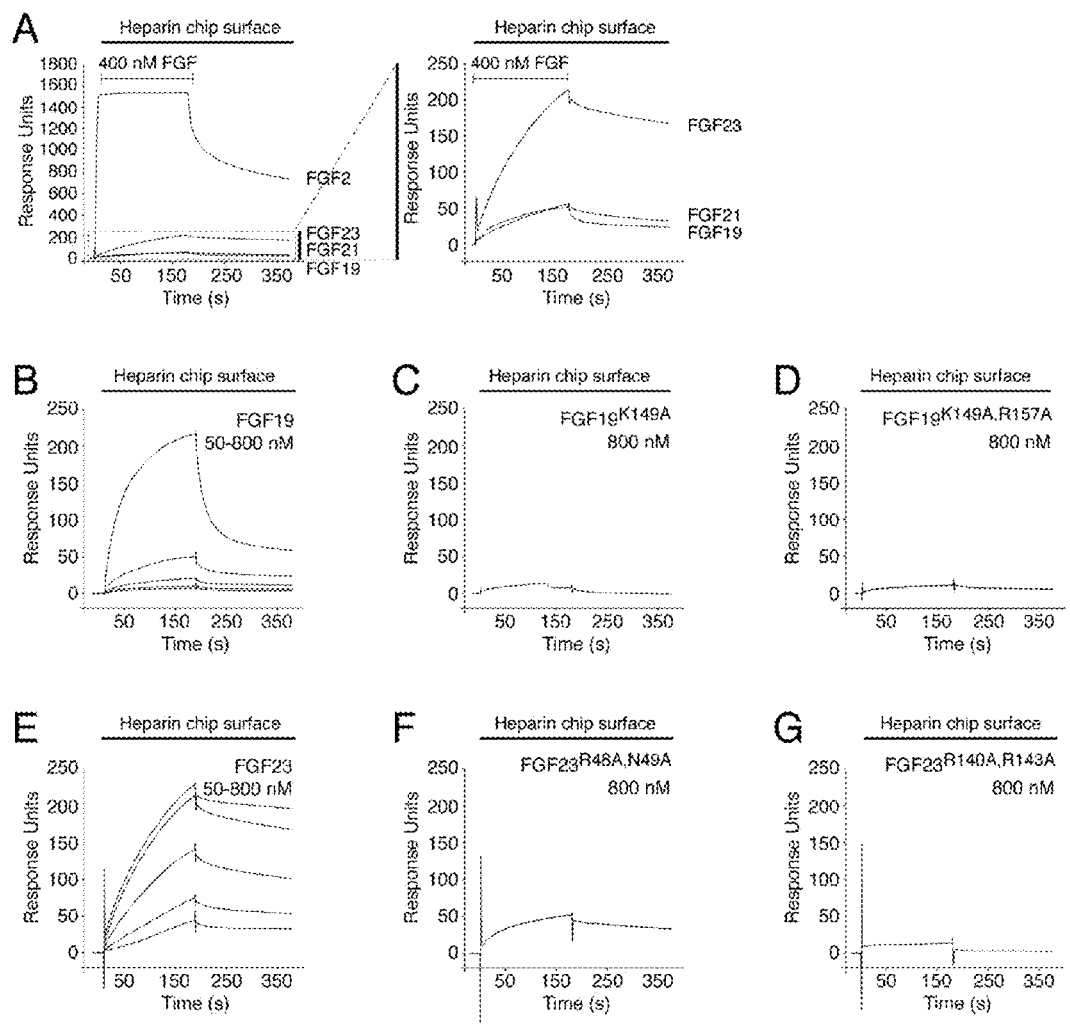
FIGS. 3A-3G show Surface plasmon resonance ("SPR") results relating to knockout of residual heparin binding in FGF19 and FGF23 by site-directed mutagenesis.

One aspect of the present invention relates to a chimeric protein. The chimeric protein includes an N-terminus coupled to a C-terminus, where the N-terminus includes a portion of a paracrine fibroblast growth factor ("FGF") and the C-terminus includes a C-terminal portion of an FGF21 molecule. The portion of the paracrine FGF is modified to decrease binding affinity for heparin and/or heparan sulfate compared to the portion without the modification.

As described by Goetz et al. (Goetz et al., "Molecular Insights into the Klotho-Dependent, Endocrine Mode of Action of Fibroblast Growth Factor 19 Subfamily Members," *Mol Cell Biol* 3417-3428 (2007), which is hereby incorporated by reference in its entirety), the mammalian fibroblast growth factor (FGF) family comprises 18 polypeptides (FGF1 to FGF10 and FGF16 to FGF23), which participate in a myriad of biological processes during embryogenesis, including but not limited to gastrulation, body plan formation, somitogenesis, and morphogenesis of essentially every tissue/organ such as limb, lung, brain, and kidney (Bottcher et al., "Fibroblast Growth Factor Signaling During Early Vertebrate Development," *Endocr Rev* 26:63-77 (2005), and Thisse et al., "Functions and Regulations of Fibroblast Growth Factor Signaling During Embryonic Development," *Dev Biol* 287:390-402 (2005), which are hereby incorporated by reference in their entirety).

FGFs execute their biological actions by binding to, dimerizing, and activating FGFR tyrosine kinases, which are encoded by four distinct genes (Fgfr1 to Fgfr4). Prototypical FGFRs consist of an extracellular domain composed of three immunoglobulin-like domains, a single-pass transmembrane domain, and an intracellular domain responsible for the tyrosine kinase activity (Mohammadi et al., "Structural Basis for Fibroblast Growth Factor Receptor Activation," *Cytokine Growth Factor Rev* 16:107-137 (2005), which is hereby incorporated by reference in its entirety).

The number of principal FGFRs is increased from four to seven due to a major tissue-specific alternative splicing event in the second half of the immunoglobulin-like domain 3 of FGFR1 to FGFR3, which creates epithelial lineage-specific "b" and mesenchymal lineage-specific "c" isoforms (Mohammadi et al., "Structural Basis for Fibroblast Growth Factor Receptor Activation," *Cytokine Growth Factor Rev* 16:107-137 (2005) and Ornitz et al., "Fibroblast Growth Factors," *Genome Biol* 2(3):reviews3005.1-reviews3005.12 (2001), which are hereby incorporated by reference in their entirety). Generally, the receptor-binding specificity of FGFs is divided along this major alternative splicing of receptors whereby FGFRb-interacting FGFs are produced by epithelial cells and FGFRc-interacting FGFs are produced by mesenchymal cells (Ornitz et al., "Fibroblast Growth Factors," *Genome Biol* 2(3):reviews3005.1-reviews3005.12 (2001), which is hereby incorporated by reference in its entirety). These reciprocal expression patterns of FGFs and FGFRs result in the establishment of specific paracrine FGF signaling loops between the epithelium and the mesenchyme, which is essential for proper organogenesis and patterning during embryonic development as well as tissue homeostasis in the adult organism.

Based on sequence homology and phylogenetic and structural considerations, the eighteen mammalian FGFs are grouped into six subfamilies (Itoh et al., "Fibroblast growth factors: from molecular evolution to roles in development, metabolism, and disease," *J Biochem* 149:121-130 (2011); Mohammadi et al., "Structural basis for fibroblast growth factor receptor activation," *Cytokine Growth Factor Rev* 16:107-137 (2005), which are hereby incorporated by reference in its entirety). The FGF core homology domain (approximately 120 amino acids long) is flanked by N- and C-terminal sequences that are highly variable in both length and primary sequence, particularly among different FGF subfamilies. The core region of FGF19 shares the highest sequence identity with FGF21 (38%) and FGF23 (36%), and therefore, these ligands are considered to form a subfamily.

Based on mode of action, the eighteen mammalian FGFs are grouped into paracrine-acting ligands (five FGF subfamilies) and endocrine-acting ligands (one FGF subfamily) comprising FGF19, FGF21 and FGF23 (Itoh and Ornitz, "Fibroblast Growth Factors: From Molecular Evolution to Roles in Development, Metabolism and Disease," *J. Biochem.* 149:121-130 (2011); Mohammadi et al., "Structural Basis for Fibroblast Growth Factor Receptor Activation," *Cytokine Growth Factor Rev.* 16:107-137 (2005), which are hereby incorporated by reference in their entirety).

Paracrine FGFs direct multiple processes during embryogenesis, including gastrulation, somitogenesis, organogenesis, and tissue patterning (Itoh and Ornitz, "Fibroblast Growth Factors: From Molecular Evolution to Roles in Development, Metabolism and Disease," *J. Biochem.* 149: 121-130 (2011); Bottcher and Niehrs, "Fibroblast Growth Factor Signaling During Early Vertebrate Development," *Endocr. Rev.* 26:63-77 (2005); Thisse et al., "Functions and Regulations of Fibroblast Growth Factor Signaling During Embryonic Development," *Dev. Biol.* 287:390-402 (2005), which are hereby incorporated by reference in their entirety), and also regulate tissue homeostasis in the adult (Hart et al., "Attenuation of FGF Signalling in Mouse Beta-cells Leads to Diabetes," *Nature* 408:864-868 (2000); Jonker et al., "A PPARγ-FGF1 Axis is Required for Adaptive Adipose Remodelling and Metabolic Homeostasis," *Nature* 485:391-394 (2012), which is hereby incorporated by reference in its entirety).

Endocrine FGFs control major metabolic processes such as bile acid homeostasis (Inagaki et al., "Fibroblast Growth Factor 15 Functions as an Enterohepatic Signal to Regulate Bile Acid Homeostasis," *Cell Metab.* 2:217-225 (2005), which is hereby incorporated by reference in its entirety), and hepatic glucose and protein metabolism (Kir et al., "FGF19 as a Postprandial, Insulin-Independent Activator of Hepatic Protein and Glycogen Synthesis," *Science* 331: 1621-1624 (2011); Potthoff et al., "FGF15/19 Regulates Hepatic Glucose Metabolism by Inhibiting the CREB-PGC-1α Pathway," *Cell Metab.* 13:729-738 (2011), which are hereby incorporated by reference in their entirety) (FGF19), glucose and lipid metabolism (Badman et al., "Hepatic Fibroblast Growth Factor 21 Is Regulated by PPARα and Is a Key Mediator of Hepatic Lipid Metabolism in Ketotic States," *Cell Metab.* 5:426-437 (2007); Inagaki et al., "Endocrine Regulation of the Fasting Response by PPARalpha-mediated Induction of Fibroblast Growth Factor 21," *Cell Metab.* 5:415-425 (2007); Kharitonenkov et al., "FGF-21 as a Novel Metabolic Regulator," *J. Clin. Invest.* 115: 1627-1635 (2005); Potthoff et al., "FGF21 Induces PGC-1alpha and Regulates Carbohydrate and Fatty Acid Metabolism During the Adaptive Starvation Response," *Proc. Nat'l. Acad. Sci. U.S.A.* 106:10853-10858 (2009), which are hereby incorporated by reference in their entirety) (FGF21), and phosphate and vitamin D homeostasis (White et al., "Autosomal Dominant Hypophosphataemic Rickets is Associated with Mutations in FGF23," *Nat. Genet.* 26:345-348 (2000); Shimada et al., "Targeted Ablation of Fgf23 Demonstrates an Essential Physiological Role of FGF23 in Phosphate and Vitamin D Metabolism," *J. Clin. Invest.* 113:561-568 (2004), which are hereby incorporated by reference in their entirety) (FGF23). Thus, these ligands have attracted much attention as potential drugs for the treatment of various inherited or acquired metabolic disorders (Beenken and Mohammadi, "The FGF Family: Biology, Pathophysiology and Therapy," *Nat. Rev. Drug Discov.* 8:235-253 (2009); Beenken and Mohammadi, "The Structural Biology of the FGF19 Subfamily," in *Endocrine FGFs and Klothos* (Kuro-o, M. ed.), Landes Bioscience. pp 1-24 (2012), which are hereby incorporated by reference in their entirety).

FGFs share a core homology region of about one hundred and twenty amino acids that fold into a β-trefoil (Ago et al., *J. Biochem.* 110:360-363 (1991); Eriksson et al., *Proc. Nat'l. Acad. Sci. U.S.A.* 88:3441-3445 (1991); Zhang et al., *Proc. Nat'l. Acad. Sci. U.S.A.* 88:3446-3450 (1991); Zhu et al., *Science* 251:90-93 (1991), which are hereby incorporated by reference in their entirety) consisting of twelve β strands in paracrine FGFs ((β1-β12) and eleven β strands in endocrine FGFs ((β1-β10 and β12) (Mohammadi et al., "Structural Basis for Fibroblast Growth Factor Receptor Activation," *Cytokine Growth Factor Rev.* 16:107-137 (2005); Goetz et al., *Mol. Cell Biol.* 27:3417-3428 (2007), which are hereby incorporated by reference in their entirety). The conserved core region is flanked by divergent N- and C-termini, which play a critical role in conferring distinct biological activity on FGFs (Mohammadi et al., "Structural Basis for Fibroblast Growth Factor Receptor Activation," *Cytokine Growth Factor Rev.* 16:107-137 (2005); Olsen et al., *Genes Dev.* 20:185-198 (2006), which are hereby incorporated by reference in their entirety).

All FGFs interact with pericellular heparan sulfate (HS) glycosaminoglycans albeit with different affinities (Asada et al., *Biochim. Biophys. Acta.* 1790:40-48 (2009), which is hereby incorporated by reference in its entirety). The HS-binding site of FGFs is comprised of the β1-β2 loop and the region between β10 and β12 strands (Mohammadi et al., "Structural Basis for Fibroblast Growth Factor Receptor Activation," *Cytokine Growth Factor Rev.* 16:107-137 (2005), which is hereby incorporated by reference in its entirety). HS interacts with both side chain and main chain atoms of the HS-binding site in paracrine FGFs (Schlessinger et al., *Mol. Cell* 6:743-750 (2000), which is hereby incorporated by reference in its entirety). The HS-binding site of endocrine FGFs deviates from the common conformation adopted by paracrine FGFs such that interaction of HS with backbone atoms of the HS-binding site is precluded (Goetz et al., *Mol. Cell Biol.* 27:3417-3428 (2007), which is hereby incorporated by reference in its entirety). As a result, compared to paracrine FGFs, endocrine FGFs exhibit poor affinity for HS (Beenken and Mohammadi, "The FGF Family: Biology, Pathophysiology and Therapy," *Nat. Rev. Drug Discov.* 8:235-253 (2009); Asada et al., *Biochim. Biophys. Acta.* 1790:40-48 (2009), which are hereby incorporated by reference in their entirety). The poor HS affinity enables these ligands to diffuse freely away from the site of their secretion and enter the blood circulation to reach their distant target organs (Goetz et al., *Mol. Cell Biol.* 27:3417-

3428 (2007); Asada et al., *Biochim. Biophys. Acta.* 1790: 40-48 (2009), which are hereby incorporated by reference in their entirety).

By contrast, owing to their high HS affinity (Asada et al., *Biochim. Biophys. Acta.* 1790:40-48 (2009), which is hereby incorporated by reference in its entirety), paracrine FGFs are mostly immobilized in the vicinity of the cells secreting these ligands, and hence can only act within the same organ. There is emerging evidence that differences in HS-binding affinity among paracrine FGFs translate into the formation of ligand-specific gradients in the pericellular matrix (Kalinina et al., *Mol. Cell Biol.* 29:4663-4678 (2009); Makarenkova et al., *Sci. Signal* 2:ra55 (2009), which are hereby incorporated by reference in their entirety), which contribute to the distinct functions of these ligands (Beenken and Mohammadi, "The FGF Family: Biology, Pathophysiology and Therapy," *Nat. Rev. Drug Discov.* 8:235-253 (2009); Itoh and Ornitz, "Fibroblast Growth Factors: From Molecular Evolution to Roles in Development, Metabolism and Disease," *J. Biochem.* 149:121-130 (2011), which are hereby incorporated by reference in their entirety).

Besides controlling ligand diffusion in the extracellular space, HS promotes the formation of the 2:2 paracrine FGF-FGFR signal transduction unit (Schlessinger et al., *Mol. Cell* 6:743-750 (2000); Mohammadi et al., *Curr. Opin. Struct. Biol.* 15:506-516 (2005), which are hereby incorporated by reference in their entirety). HS engages both ligand and receptor to enhance the binding affinity of FGF for receptor and promote dimerization of ligand-bound receptors. Owing to their poor HS-binding affinity, endocrine FGFs rely on Klotho co-receptors to bind their cognate FGFR (Kurosu et al., *J. Biol. Chem.* 282:26687-26695 (2007); Kurosu et al., *J. Biol. Chem.* 281:6120-6123 (2006); Ogawa et al., *Proc. Nat'l. Acad. Sci. U.S.A.* 104:7432-7437 (2007); Urakawa et al., *Nature* 444:770-774 (2006), which are hereby incorporated by reference in their entirety). Klotho co-receptors are single-pass transmembrane proteins with an extracellular domain composed of two type I β-glycosidase domains (Ito et al., *Mech. Dev.* 98:115-119 (2000); Kuro-o et al., *Nature* 390:45-51 (1997), which are hereby incorporated by reference in their entirety). Klotho co-receptors constitutively associate with FGFRs to enhance the binding affinity of endocrine FGFs for their cognate FGFRs in target tissues (Kurosu et al., *J. Biol. Chem.* 282:26687-26695 (2007); Kurosu et al., *J. Biol. Chem.* 281:6120-6123 (2006); Ogawa et al., *Proc. Nat'l. Acad. Sci. U.S.A.* 104:7432-7437 (2007); Urakawa et al., *Nature* 444: 770-774 (2006), which are hereby incorporated by reference in their entirety). αKlotho is the co-receptor for FGF23 (Kurosu et al., *J. Biol. Chem.* 281:6120-6123 (2006); Urakawa et al., *Nature* 444:770-774 (2006), which are hereby incorporated by reference in their entirety), and βKlotho is the co-receptor for both FGF19 and FGF21 (Kurosu et al., *J. Biol. Chem.* 282:26687-26695 (2007); Ogawa et al., *Proc. Nat'l. Acad. Sci. U.S.A.* 104:7432-7437 (2007), which are hereby incorporated by reference in their entirety). The C-terminal region of endocrine FGFs mediates binding of these ligands to the FGFR-α/βKlotho co-receptor complex (Goetz et al., *Mol. Cell Biol.* 27:3417-3428 (2007); Goetz et al., *Proc. Nat'l. Acad. Sci. U.S.A.* 107:407-412 (2010); Micanovic et al., *J. Cell Physiol.* 219:227-234 (2009); Wu et al., *J. Biol. Chem.* 283:33304-33309 (2008); Yie et al., *FEBS Lett,* 583:19-24 (2009); Goetz et al., *Mol. Cell Biol.* 32:1944-1954 (2012), which are hereby incorporated by reference in their entirety).

βKlotho promotes binding of FGF21 to its cognate FGFR by engaging ligand and receptor simultaneously through two distinct binding sites (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). βKlotho plays the same role in promoting binding of FGF19 to its cognate FGFR (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). The binding site for βKlotho was mapped on FGF21 and FGF19 to the C-terminal region of each ligand that follows the β-trefoil core domain (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). In the course of these studies, it was found that the C-terminal tail peptides of FGF21 and FGF19 share a common binding site on βKlotho, and that the C-terminal tail of FGF19 binds tighter than the C-terminal tail of FGF21 to this site (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety).

Endocrine FGFs still possess residual HS-binding affinity, and moreover, there are differences in this residual binding affinity among the endocrine FGFs (Goetz et al., *Mol. Cell Biol.* 27:3417-3428 (2007), which is hereby incorporated by reference in its entirety). These observations raise the possibility that HS may play a role in endocrine FGF signaling. Indeed, there are several reports showing that HS can promote endocrine FGF signaling in the presence as well as in the absence of Klotho co-receptor. It has been shown that HS augments the mitogenic signal elicited by endocrine FGFs in BaF3 cells over-expressing FGFR and Klotho co-receptor by at least two-fold (Suzuki et al., *Mol. Endocrinol.* 22:1006-1014 (2008), which is hereby incorporated by reference in its entirety). In addition, even in the absence of Klotho co-receptor, HS enables endocrine FGFs to induce proliferation of BaF3 cells over-expressing FGFR (Yu et al., *Endocrinology* 146:4647-4656 (2005); Zhang et al., *J. Biol. Chem.* 281:15694-15700 (2006), which are hereby incorporated by reference in their entirety). Compared to paracrine FGFs, however, significantly higher concentrations of both ligand and HS are needed, and the proliferative response of cells to endocrine FGFs still lags behind that of paracrine FGFs by about one order of magnitude (Zhang et al., *J. Biol. Chem.* 281:15694-15700 (2006), which is hereby incorporated by reference in its entirety).

As used herein, the terms "chimeric polypeptide" and "chimeric protein" encompass a polypeptide having a sequence that includes at least a portion of a full-length sequence of first polypeptide sequence and at least a portion of a full-length sequence of a second polypeptide sequence, where the first and second polypeptides are different polypeptides. A chimeric polypeptide also encompasses polypeptides that include two or more non-contiguous portions derived from the same polypeptide. A chimeric polypeptide or protein also encompasses polypeptides having at least one substitution, wherein the chimeric polypeptide includes a first polypeptide sequence in which a portion of the first polypeptide sequence has been substituted by a portion of a second polypeptide sequence.

As used herein, the term "N-terminal portion" of a given polypeptide sequence is a contiguous stretch of amino acids of the given polypeptide sequence that begins at or near the N-terminal residue of the given polypeptide sequence. An N-terminal portion of the given polypeptide can be defined by a contiguous stretch of amino acids (e.g., a number of amino acid residues). Similarly, the term "C-terminal portion" of a given polypeptide sequence is a contiguous length of the given polypeptide sequence that ends at or near the C-terminal residue of the given polypeptide sequence. A C-terminal portion of the given polypeptide can be defined by a contiguous stretch of amino acids (e.g., a number of amino acid residues).

The term "portion," when used herein with respect to a given polypeptide sequence, refers to a contiguous stretch of amino acids of the given polypeptide's sequence that is shorter than the given polypeptide's full-length sequence. A portion of a given polypeptide may be defined by its first position and its final position, in which the first and final positions each correspond to a position in the sequence of the given full-length polypeptide. The sequence position corresponding to the first position is situated N-terminal to the sequence position corresponding to the final position. The sequence of the portion is the contiguous amino acid sequence or stretch of amino acids in the given polypeptide that begins at the sequence position corresponding to the first position and ending at the sequence position corresponding to the final position. A portion may also be defined by reference to a position in the given polypeptide sequence and a length of residues relative to the referenced position, whereby the sequence of the portion is a contiguous amino acid sequence in the given full-length polypeptide that has the defined length and that is located in the given polypeptide in reference to the defined position.

As noted above, a chimeric protein according to the present invention may include an N-terminus coupled to a C-terminus. N-terminus and C-terminus are used herein to refer to the N-terminal region or portion and the C-terminal region or portion, respectively, of the chimeric protein of the present invention. In some embodiments of the present invention, the C-terminal portion and the N-terminal portion of the chimeric protein of the present invention are contiguously joined. In alternative embodiments, the C-terminal portion and the N-terminal portion of the chimeric protein of the present invention are coupled by an intervening spacer. In one embodiment, the spacer may be a polypeptide sequence of 1, 2, 3, 4, 5, 6, 7, 8, 9, 10, or more amino acid residues. In some embodiments, the C-terminal portion and/or the N-terminal portion of the chimeric protein of the present invention may include additional portion(s) coupled to the C-terminal residue and/or the N-terminal residue of the chimeric protein of the present invention, respectively. In some embodiments, the additional portion(s) may be a polypeptide sequence of 1, 2, 3, 4, 5, 6, 7, 8, 9, 10, or more amino acid residues. In some embodiments, the N-terminal portion and/or the C-terminal portion having such additional portion(s) will maintain the activity of the corresponding naturally occurring N-terminal portion and/or C-terminal portion, respectively. In some embodiments, the N-terminal portion and/or the C-terminal portion having such additional portion(s) will have enhanced and/or prolonged activity compared to the corresponding naturally occurring N-terminal portion and/or C-terminal portion, respectively. In other embodiments, the C-terminal portion and/or the N-terminal portion of the chimeric protein of the present invention do not include any additional portion(s) coupled to the C-terminal residue and/or the N-terminal residue of the chimeric protein of the present invention, respectively.

The portion of the paracrine FGF may be derived from any suitable paracrine FGF. Suitable paracrine FGFs in accordance with the present invention include FGF1, FGF2, and ligands of the FGF4 and FGF9 subfamilies. Certain embodiments of the present invention may include a full-length amino acid sequence of a paracrine FGF, rather than a portion of a paracrine FGF.

In one embodiment, the portion of the paracrine FGF is derived from a mammalian FGF. In one embodiment, the portion of the paracrine FGF is derived from a vertebrate FGF. In one embodiment, the portion of the paracrine FGF is derived from a human FGF. In one embodiment, the paracrine FGF is derived from a non-human mammalian FGF. In one embodiment, the portion of the paracrine FGF is derived from a non-human vertebrate FGF. In one embodiment, the paracrine FGF is derived from an ortholog of human FGF, or a polypeptide or protein obtained from one species that is the functional counterpart of a polypeptide or protein from a different species.

In one embodiment according to the present invention, the portion of the paracrine FGF of the chimeric protein includes an N-terminal portion of the paracrine FGF.

In one embodiment, the paracrine FGF is FGF1. In one embodiment, the portion of the FGF1 is from human FGF1 having the following amino acid sequence (GenBank Accession No. AAH32697, which is hereby incorporated by reference in its entirety) (SEQ ID NO: 1):

```
  1  MAEGEITTFT ALTEKFNLPP GNYKKPKLLY CSNGGHFLRI LPDGTVDGTR DRSDQHIQLQ
 61  LSAESVGEVY IKSTETGQYL AMDTDGLLYG SQTPNEECLF LERLEENHYN TYISKKHAEK
121  NWFVGLKKNG SCKRGPRTHY GQKAILFLPL PVSSD
```

In one embodiment, the portion of the paracrine FGF includes an amino acid sequence beginning at any one of residues 1 to 25 and ending at any one of residues 150 to 155 of SEQ ID NO: 1 (human FGF1). In one embodiment, the portion of the paracrine FGF includes amino acid residues 1-150, 1-151, 1-152, 1-153, 1-154, 1-155, 2-150, 2-151, 2-152, 2-153, 2-154, 2-155, 3-150, 3-151, 3-152, 3-153, 3-154, 3-155, 4-150, 4-151, 4-152, 4-153, 4-154, 4-155, 5-150, 5-151, 5-152, 5-153, 5-154, 5-155, 6-150, 6-151, 6-152, 6-153, 6-154, 6-155, 7-150, 7-151, 7-152, 7-153, 7-154, 7-155, 8-150, 8-151, 8-152, 8-153, 8-154, 8-155, 9-150, 9-151, 9-152, 9-153, 9-154, 9-155, 10-150, 10-151, 10-152, 10-153, 10-154, 10-155, 11-150, 11-151, 11-152, 11-153, 11-154, 11-155, 12-150, 12-151, 12-152, 12-153, 12-154, 12-155, 13-150, 13-151, 13-152, 13-153, 13-154, 13-155, 14-150, 14-151, 14-152, 14-153, 14-154, 14-155, 15-150, 15-151, 15-152, 15-153, 15-154, 15-155, 16-150, 16-151, 16-152, 16-153, 16-154, 16-155, 17-150, 17-151, 17-152, 17-153, 17-154, 17-155, 18-150, 18-151, 18-152, 18-153, 18-154, 18-155, 19-150, 19-151, 19-152, 19-153, 19-154, 19-155, 20-150, 20-151, 20-152, 20-153, 20-154, 20-155, 21-150, 21-151, 21-152, 21-153, 21-154, 21-155, 22-150, 22-151, 22-152, 22-153, 22-154, 22-155, 23-150, 23-151, 23-152, 23-153, 23-154, 23-155, 24-150, 24-151, 24-152, 24-153, 24-154, 24-155, 25-150, 25-151, 25-152, 25-153, 25-154, or 25-155 of FGF1 (SEQ ID NO: 1). In one embodiment, the portion of the paracrine FGF includes amino acid residues 1-150 or 25-150 of SEQ ID NO: 1.

In one embodiment, the portion of the paracrine FGF includes an amino acid sequence that has at least 80%, at least 85%, at least 90%, at least 95%, at least 97% or at least 99% amino acid sequence identity to an amino acid sequence beginning at any one of residues 1 to 25 and ending at any one of residues 150 to 155 of SEQ ID NO: 1 (human FGF1). In one embodiment, the portion of the paracrine FGF includes an amino acid sequence that has at least 80%, at least 85%, at least 90%, at least 95%, at least 97% or at least 99% amino acid sequence homology to an amino acid sequence beginning at any one of residues 1 to 25 and ending at any one of residues 150 to 155 of SEQ ID NO: 1 (human FGF1).

Percent (%) amino acid sequence identity with respect to a given polypeptide sequence identified herein is defined as the percentage of amino acid residues in a candidate sequence that are identical to the amino acid residues in the reference sequence, after aligning the sequences and introducing gaps, if necessary, to achieve the maximum percent sequence identity, and not considering any conservative substitutions as part of the sequence identity. Percent (%) amino acid sequence homology with respect to a given polypeptide sequence identified herein is the percentage of amino acid residues in a candidate sequence that are identical to or strongly similar to the amino acid residues in the reference sequence, after aligning the sequences and introducing gaps, if necessary, to achieve the maximum percent sequence homology. Strongly similar amino acid residues may include, for example, conservative amino acid substitutions known in the art. Alignment for purposes of determining percent amino acid sequence identity and/or homology can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

In one embodiment of the present invention, the portion of the paracrine FGF of the chimeric protein is derived from an ortholog of human FGF1. In one embodiment, the portion of FGF1 is derived from *Papio Anubis, Pongo abelii, Callithrix jacchus, Equus caballus, Pan troglodytes, Loxodonta Africana, Canis lupus familiaris, Ailuropoda melanoleuca, Saimiri boliviensis boliviensis, Sus scrofa, Otolemur garnettii, Rhinolophus ferrumequinum, Sorex araneus, Oryctolagus cuniculus, Cricetulus griseus, Sarcophilus harrisii, Mus musculus, Cavia porcellus, Monodelphis domestica, Desmodus rotundus, Bos taurus, Ornithorhynchus anatinus, Taeniopygia guttata, Dasypus novemcinctus, Xenopus Silurana tropicalis, Heterocephalus glaber, Pteropus alecto, Tupaia chinensis, Columba livia, Ovis aries, Gallus gallus, Vicugna pacos, Anolis carolinensis, Otolemur garnettii, Felis catus, Pelodiscus sinensis, Latimeria chalumnae, Tursiops truncates, Mustela putorius furo, Nomascus leucogenys, Gorilla gorilla, Erinaceus europaeus, Procavia capensis, Dipodomys ordii, Petromyzon marinus, Echinops telfairi, Macaca mulatta, Pteropus vampyrus, Myotis lucifugus, Microcebus murinus, Ochotona princeps, Rattus norvegicus, Choloepus hoffmanni, Ictidomys tridecemlineatus, Tarsius syrichta, Tupaia belangeri, Meleagris gallopavo, Macropus eugenii,* or *Danio rerio.* The portions of an ortholog of human paracrine FGF1 include portions corresponding to the above-identified amino acid sequences of human FGF1. Corresponding portions may be determined by, for example, sequence analysis and structural analysis.

In one embodiment, the portion of the FGF1 of the chimeric protein of the present invention is derived from an ortholog of human FGF1 having the amino acid sequence shown in Table 1.

TABLE 1

```
Amino acid sequence of human FGF1 (SEQ ID NO: 1)(GenBank accession no.
AAH32697, which is hereby incorporated by reference in its entirety):
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD Amino acid sequence of Papio anubis (olive baboon) FGF1(SEQ ID NO: 2)
(GenBank accession no. NP_001162557, which is hereby incorporated by
reference in its entirety):
  1 MAEGEITTFT ALTEKFNLPP ANYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD Amino acid sequence of Pongo abelii (Sumatran orangutan) FGF1 (SEQ ID
NO: 3) (GenBank accession no. NP_001127073, which is hereby
incorporated by reference in its entirety)
 60                                                                   M
 61 AEGEITTFTA LTEKFNLPPG NYKKPKLLYC SNGGHFLRIL PDGTVDGTRD RSDQHIQLQL
121 SAESVGEVYI KSTETGQYLA MDTDGLLYGS QTPNEECLFL ERLEENHYNT YISKKHAEKN
181 WFVGLKKNGS CKRGPRTHYG QKAILFLPLP VSSD Amino acid sequence of Callithrix jacchus (white-tufted-ear marmoset)
FGF1(SEQ ID NO: 4) (GenBank accession no. XP_002744341, which is
hereby incorporated by reference in its entirety):
  1 MAEGEITTFT ALTEKFDLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD Amino acid sequence of Equus caballus (horse) FGF1(SEQ ID NO: 5)
(GenBank accession no. NP_001157358, which is hereby incorporated by
reference in its entirety):
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

TABLE 1 -continued

Amino acid sequence of *Pan troglodytes* (chimpanzee) FGF1(SEQ ID NO: 6)
(GenBank accession no. JAA29511, which is hereby incorporated by
reference in its entirety):
```
  1 MAEGEITTFT ALTEKFNLPS GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of *Loxodonta africana* (elephant) FGF1(SEQ ID NO: 7)
(GenBank accession no. XP_003404621, which is hereby incorporated by
reference in its entirety):
```
  1 MAEGEITTFT ALTEKFNLPP GNYKKPKLLY CSNGGHFLRI LPDGTVDGTR DRSDQHIQLQ
 61 LSAESVGEVY IKGTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Canis lupus familiaris* (dog) FGF1(SEQ ID NO: 8)
(GenBank accession no. XP_849274, which is hereby incorporated by
reference in its entirety):
```
  1 MAEGEITTFT ALTEKFNLPP GNYMKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Ailuropoda melanoleuca* (giant panda) FGF1(SEQ
ID NO: 9) (GenBank accession no. XP_002912581, which is hereby
incorporated by reference in its entirety):
```
  1 MAEGEITTFT ALTEKFNLPA GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Saimiri boliviensis boliviensis* (Bolivian
squirrel monkey) FGF1(SEQ ID NO: 10) (GenBank accession no.
XP_003920596, which is hereby incorporated by reference in its
entirety):
```
  1 MAEGEITTFT ALTEKFDLPP GNYKKPKLLY CSNGGHFLRI LPDGTVDGTR DRSDLHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of *Sus scrofa* (pig) FGF1(SEQ ID NO: 11) (GenBank
accession no. XP_003124058, which is hereby incorporated by reference
in its entirety):
```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTSGLLYG SQTPSEECLF LERLEENHYN TYTSKKHAEK
121 NWFVGLKKNG SCKRGPRTHY GQKAILFLPL PVSSD
```

Amino acid sequence of *Otolemur garnettii* (small-eared galago)
FGF1(SEQ ID NO: 12) (GenBank accession no. XP_003782135, which is
hereby incorporated by reference in its entirety):
```
  1 MAEGEITTFT ALTEKFNLPL GNYKKPKLLY CSNGGHFLRI LPDGTVDGTQ DRSDQHIQLQ
 61 LSAESVGEVY IKSTQTGQYL AMDSDGLLYG SQTPNEECLF LERLEENHYN TYVSKKHAEK
121 NWFVGLKKNG SCKRGPRTHY GQKAILFLPL PVSSD
```

Amino acid sequence of *Rhinolophus ferrumequinum* (greater horseshoe
bat) FGF1(SEQ ID NO: 13) (GenBank accession no. ACC62496, which is
hereby incorporated by reference in its entirety):
```
  1 MAEGEVTTFT ALTEKFNLPT GNYKKPKLLY CSNGGHFLRI LPDGTVDGTR DKSDQHIQLQ
 61 LSAESVGEVY IKSTESGQYL AMDSDGLLYG SQTPNEECLF LERLEENHYN TYTSKKHAEK
121 NWFVGLKKNG SCKRGPRTHY GQKAILFLPL PVSSD
```

Amino acid sequence of *Sorex araneus* (European shrew) FGF1(SEQ ID
NO: 14) (GenBank accession no. ACE75805, which is hereby incorporated
by reference in its entirety):
```
  1 MAEGEITTFG ALMEKFNLPP GNYKKPKLLY CSNGGHFLRI LPDGTVDGTR DRSDQHIQLQ
 61 LSAESVGEVY IKSTETGHYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Oryctolagus cuniculus* (rabbit) FGF1(SEQ ID
NO: 15) (GenBank accession no. NP_001164959, which is hereby
incorporated by reference in its entirety):
```
  1 MAEGEVTTFT ALTEKFNLPA GNYKLPKLLY CSNGGHFLRI LPDGTVDGTR DRSDQHIQLQ
 61 LSAESVGEVY IKSTETGQYL AMDTDGLLYG SQTPSEECLF LERLEENHYN TYTSKKHAEK
121 NWFVGLKKNG SCKRGPRTHY GQKAILFLPL PVSSD
```

Amino acid sequence of *Cricetulus griseus* (Chinese hamster) FGF1(SEQ
ID NO: 16) (GenBank accession no. XP_003502469, which is hereby
incorporated by reference in its entirety):
```
  1 MAEGEITTFS ALTERFNLPP GNYKKPKLLY CSNGGHFLRI LPDGTVDGTR DRSDQHIQLQ
 61 LSAESAGEVY IKGTETGQYR NMDTDGLLYG SQTPNEECLF LERLEENHYN TYTSKKHAEK
121 NWFVGLKKNG SCKRGPRTHY GQKAILFLPL PVSSD
```

TABLE 1 -continued

Amino acid sequence of *Sarcophilus harrisii* (Tasmanian devil) FGF1(SEQ ID NO: 17) (GenBank accession no. XP_003756738, which is hereby incorporated by reference in its entirety):
```
  1 MAEGEITTFT ALTERFNLPL GNYKKPKLLY CSNGGHFLRI LPDGKVDGTR DRNDQHIQLQ
 61 LSAESVGEVY IKSTESGQYL AMDTDGLLYG SQTPTEECLF LERLEENHYN TYISKKHAEK
121 NWFVGLKKNG SCKRGPRTHY GQKAILFLPL PVSSE
```

Amino acid sequence of *Mus musculus* (house mouse) FGF1(SEQ ID NO: 18) (GenBank accession no. NP_034327, which is hereby incorporated by reference in its entirety):
```
  1 MAEGEITTFA ALTERFNLPL GNYKKPKLLY CSNGGHFLRI LPDGTVDGTR DRSDQHIQLQ
 61 LSAESAGEVY IKGTETGQYL AMDTEGLLYG SQTPNEECLF LERLEENHYN TYTSKKHAEK
121 NWFVGLKKNG SCKRGPRTHY GQKAILFLPL PVSSD
```

Amino acid sequence of *Cavia porcellus* (domestic guinea pig) FGF1(SEQ ID NO: 19) (GenBank accession no. XP_003477242, which is hereby incorporated by reference in its entirety):
```
  1 MAEGEITTFA ALTEKFNLPP GNYKKPKLLY CSNGGHFLRI LPDGTVDGTR DRSDQHIQLQ
 61 LSAEGVGEVY IQSTETGQYL AMDTDGLLYG SQTPSEECLF LERLEENHYN TYTSKKHVEK
121 NWFVGLKKNG SCKRGPRTHY GQKAILFLPL PVSD
```

Amino acid sequence of *Monodelphis domestica* (gray short-tailed opossum) FGF1(SEQ ID NO: 20) (GenBank accession no. XP_001368921, which is hereby incorporated by reference in its entirety):
```
  1 MAEGEITTFT ALTERFNLPL GNYKKPKLLY CSNGGHFLRI LPDGKVDGTR DRNDQHIQLQ
 61 LSTESVGEVY IKSTESGQYL AMDTDGLLYG SQTPSEECLF LERLEENHYN TYTSKKHAEK
121 NWFVGLKKNG SCKKGPRTHY GQKAILFLPL PVSSE
```

Amino acid sequence of *Desmodus rotundus* (common vampire bat) FGF1(SEQ ID NO: 21) (GenBank accession no. JAA45191, which is hereby incorporated by reference in its entirety):
```
  1 MAEGEVTTFT ALTEKFNLPL ESYKKPKLLY CSNGGHFLRI LPDGTVDGTR DKSDQHIQLQ
 61 LSAESVGEVY IKSTGSGQYL AMDSAGLLYG SQTPNEECLF LERLEENHYN TYTSKKHAEK
121 NWFVGLKKNG SCKRGPRTHY GQKAILFLPL PVNSD
```

Amino acid sequence of *Bos taurus* (cattle) FGF1(SEQ ID NO: 22) (GenBank accession no. NP_776480, which is hereby incorporated by reference in its entirety):
```
  1 MAEGETTTFT ALTEKFNLPL GNYKKPKLLY CSNGGYFLRI LPDGTVDGTK DRSDQHIQLQ
 61 LCAESIGEVY IKSTETGQFL AMDTDGLLYG SQTPNEECLF LERLEENHYN TYISKKHAEK
121 HWFVGLKKNG RSKLGPRTHF GQKAILFLPL PVSSD
```

Amino acid sequence of *Ornithorhynchus anatinus* (platypus) FGF1(SEQ ID NO: 23) (GenBank accession no. XP_001514861, which is hereby incorporated by reference in its entirety):
```
  1 MAEGEITTFT ALMEKFDLPL GNYKKPRLLY CSNGGYFLRI QPDGKVDGTR DRSDQHIQLQ
 61 LSAESVGEVY IKSTESGHYL AMDTEGLLYG SQAPSEDCLF LERLEENHYN TYVSKKHAEK
121 NWFVGLKKNG SCKRGPRTHY GQKAILFLPL PVASD
```

Amino acid sequence of *Taeniopygia guttata* (zebra finch) FGF1(SEQ ID NO: 24) (GenBank accession no. XP_002193287, which is hereby incorporated by reference in its entirety):
```
  1 MAEGEITTFS ALTEKFNLPP GNYKKPKLLY CSNGGHFLRI LPDGTVDGTR DRSDQHIQLQ
 61 LSAESVGVVH IQSTQSGQYL AMDTNGLLYG SQLPPGECLF LERLEENHYN TYVSKMHADK
121 NWFVGLKKNG TSKLGPRTHY GQKAILFLPL PVAAD
```

Amino acid sequence of *Dasypus novemcinctus* (nine-banded armadillo) FGF1(SEQ ID NO: 25) (GenBank accession no. AC006224, which is hereby incorporated by reference in its entirety):
```
  1 MAEGEITTFM ALMEKFNLPL ENYKHPRLLY CRNGGHFLRI LPDGTVDGTR DRSDQHIQLQ
 61 LSAESVGEVY IKSAETGQYL AMDTDGLLYG SETPSEECLF MEKLEENNYN TYISKKHAEK
121 KWFVGLKKDG SSKRGPQTHY GQKAILFLPL PVSSD
```

Amino acid sequence of *Xenopus Silurana tropicalis* (western clawed frog) FGF1(SEQ ID NO: 26) (GenBank accession no. ACJ50585, which is hereby incorporated by reference in its entirety):
```
  1 MAEGDITTFN PIAESFSLPI GNYKKPKLLY CNNGGYFLRI LPDGVVDGTR DRDDLYITLK
 61 LSAQSQGEVH IKSTETGSYL AMDSSGQLYG TLTPNEESLF LETLEENHYN TYKSKKYAEN
121 NWFVGIKKNG ASKKGSRTHY GQKAILFLPL PASPD
```

Amino acid sequence of *Heterocephalus glaber* (naked mole-rat) FGF1(SEQ ID NO: 27) (GenBank accession no. EHA99379, which is hereby incorporated by reference in its entirety):
```
  1 MAEGEITTFT ALTEKFNLPP GNYKKPKLLY CSNGGHFLRI LPDGKVDGTR DRSDQHIQLQ
 61 LSAEGVGEVY IKSTETGQYL AMDTDGLLYG SQTASEECLF LERLEENHYN TYISKKHAEK
121 NWFVGLKKNG SCKRGPRTHY GQKAILFLPL PVSSD
```

TABLE 1 -continued

Amino acid sequence of *Pteropus alecto* (black flying fox) FGF1(SEQ ID
NO: 28) (GenBank accession no. ELK02961, which is hereby incorporated
by reference in its entirety):
```
  1 MAEGEVTTFT ALTERFNLPP GNYKKPKLLY CSNGGHFLRI LPDGTVDGTR DKSDQHIQLQ
 61 LSAESVGEVY IKSTESGQYL AMDSDGLLYG SQTPDEDCLF LERLEENHYN TYTSKKHAEK
121 NWFVGLKKNG SCKRGPRTHY GQKAILFLPL PVSSD
```

Amino acid sequence of *Tupaia chinensis* (Chinese tree shrew) FGF1(SEQ
ID NO: 29) (GenBank accession no. ELW69091, which is hereby
incorporated by reference in its entirety):
```
  1 MAEGEITTFA ALTEKFDLPP GNYKKPKLLY CSNGGHFLRI LPDGTVDGTR DRSDQHIQLQ
 61 LTAENVGEVY IKSTETGQYL AMDADGLLYG SQTPNEECLF LERLEENHYN TYISKKHAEK
121 NWFVALKKNG SCKLGPRTHY GQKAILFLPL PVSSD
```

Amino acid sequence of *Columba livia* (rock pigeon) FGF1(SEQ ID NO: 30)
(GenBank accession no. EMC79997, which is hereby incorporated by
reference in its entirety):
```
  1 MAEGEITTFT ALTEKFNLPP GNYKKPKLLY CSNGGHFLRI LPDGKVDGTR DRSDQHIQLQ
 61 LSAESVGEVY IKSTQSGQYL AMDPTGLLYG SQLLGEECLF LERIEENHYN TYVSKKHADK
121 NWFVGLKKNG NSKLGPRTHY GQKAILFLPL PVSAD
```

Amino acid sequence of *Ovis aries* (sheep) FGF1(SEQ ID NO: 31) (GenBank
accession no. XP_004008958, which is hereby incorporated by reference
in its entirety):
```
  1 MAEGETTTFR ALTEKFNLPL GNYKKPKLLY CSNGGYFLRI LPDGRVDGTK DRSDQHIQLQ
 61 LYAESIGEVY IKSTETGQFL AMDTNGLLYG SQTPSEECLF LERLEENHYN TYISKKHAEK
121 NWFIGLKKNG SSKLGPRTHF GQKAILFLPL PVSSD
```

Amino acid sequence of *Gallus gallus* (chicken) FGF1(SEQ ID NO: 32)
(GenBank accession no. NP_990511, which is hereby incorporated by
reference in its entirety):
```
  1 MAEGEITTFT ALTERFGLPL GNYKKPKLLY CSNGGHFLRI LPDGKVDGTR DRSDQHIQLQ
 61 LSAEDVGEVY IKSTASGQYL AMDTNGLLYG SQLPGEECLF LERLEENHYN TYISKKHADK
121 NWFVGLKKNG NSKLGPRTHY GQKAILFLPL PVSAD
```

Amino acid sequence of *Vicugna pacos* (alpaca) FGF1(SEQ ID NO: 33)
(Ensembl accession no. ENSVPAP00000007810; partial sequence
corresponding to human FGF1 residues 58 to 155, which is hereby
incorporated by reference in its entirety):
```
  1 QLQLSAESVG EVYIKSTETG QYLAMDTDGL LHGSQTPNEE CLFLERLEEN HYNTYTSKKH
 61 AEKNWFVGLK KNGSCKRGPR THYGQKAILF LPLPVSSD
```

Amino acid sequence of *Anolis carolinensis* (anole lizard) FGF1(SEQ ID
NO: 34) (Ensembl accession no. ENSACAP00000013203, which is hereby
incorporated by reference in its entirety):
```
  1 MAEGEITTFT ALTERFALPM ENYKKPKLLY CSNGGHFLRI LPDGKVDGTM DRNDSYIQLL
 61 LTAEDVGVVY IKGTETGQYL AMDANGHLYG SQLPTEECLF VETLEENHYN TYTSKMHGDK
121 KWYVGLKKNG KGKLGPRTHR GQKAILFLPL PVSPD
```

Amino acid sequence of *Otolemur garnettii* (bushbaby) FGF1(SEQ ID
NO: 35) (Ensembl accession no. ENSOGAP00000004540, which is hereby
incorporated by reference in its entirety):
```
  1 MAEGEITTFT ALTEKFNLPL GNYKKPKLLY CSNGGHFLRI LPDGTVDGTQ DRSDQHIQLQ
 61 LSAESVGEVY IKSTQTGQYL AMDSDGLLYG SQTPNEECLF LERLEENHYN TYVSKKHAEK
121 NWFVGLKKNG SCKRGPRTHY GQKAILFLPL PVSSD
```

Amino acid sequence of *Felis catus* (cat) FGF1(SEQ ID NO: 36) (Ensembl
accession no. ENSFCAP00000008457, which is hereby incorporated by
reference in its entirety):
```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Pelodiscus sinensis* (Chinese softshell turtle)
FGF1(SEQ ID NO: 37) (Ensembl accession no. ENSPSIP00000016356, which
is hereby incorporated by reference in its entirety):
```
  1 MAEGEITTFT ALTEKFNLPL GNYKNPKLLY CSNGGYFLRI HPDGKVDGTR DRSDQHIQLQ
 61 LSAESVGEVY IKSTESGQFL AMDANGLLYG SLSPSEECLF LERMEENHYN TYISKKHADK
121 NWFVGLKKNG SCKLGPRTHY GQKAVLFLPL PVSAD
```

Amino acid sequence of *Latimeria chalumnae* (coelacanth) FGF1(SEQ ID
NO: 38) (Ensembl accession no. ENSLACP00000015106, which is hereby
incorporated by reference in its entirety):
```
  1 MAEDKITTLK ALAEKFNLPM GNYKKAKLLY CSNGGYFLRI PPDGKVEGIR ERSDKYIQLQ
 61 MNAESLGMVS IKGVEAGQYL AMNTNGLLYG SQSLTEECLF MEKMEENHYN TYRSKTHADK
121 NWYVGIRKNG SIKPGPRTHI GQKAVLFLPL PASSD
```

TABLE 1 -continued

Amino acid sequence of *Tursiops truncatus* (dolphin) FGF1(SEQ ID NO: 39) (Ensembl accession no. ENSTTRP00000004470, which is hereby incorporated by reference in its entirety):
```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYASKKHAEK
121 NWFVGLKKNG SCKRGPRTHY GQKAILFLPL PVSSD
```

Amino acid sequence of *Mustela putorius furo* (ferret) FGF1(SEQ ID NO: 40) (Ensembl accession no. ENSMPUP00000007888, which is hereby incorporated by reference in its entirety):
```
  1 MAEGEITTFT ALMEKFNLPA GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Nomascus leucogenys* (gibbon) FGF1(SEQ ID NO: 41) (Ensembl accession no. ENSNLEP00000011873, which is hereby incorporated by reference in its entirety):
```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of *Gorilla gorilla* (gorilla) FGF1(SEQ ID NO: 42) (Ensembl accession no. ENSGGOP00000017663, which is hereby incorporated by reference in its entirety):
```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of *Erinaceus europaeus* (hedgehog) FGF1(SEQ ID NO: 43) (Ensembl accession no. ENSEEUP00000005318, which is hereby incorporated by reference in its entirety):
```
  1 MAEGEITTFT ALTEKFNLPL GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Procavia capensis* (hyrax) FGF1(SEQ ID NO: 44) (Ensembl accession no. ENSPCAP00000010969, which is hereby incorporated by reference in its entirety)(partial sequence corresponding to human FGF1 residues 1 to 91):
```
  1 MAEGEITTFT ALTEKFNLPL ENYKKPKLLY CSNGGHFLRI LPDGTVDGTR DRSDQHIQLQ
 61 LSAESVGEVY IKGTETGQYL AMDTDGLLYG S
```

Amino acid sequence of *Dipodomys ordii* (kangaroo rat) FGF1(SEQ ID NO: 45) (Ensembl accession no. ENSDORP00000006889, which is hereby incorporated by reference in its entirety) (partial sequence corresponding to human FGF1 residues 1 to 16 and 58 to 155):
```
  1 MAEGEITTFT ALTERF---- ---------- ---------- ---------- -------QLQ
 61 LSAESVGEVY IKSTETGQYL AMDADGLLYG SQTPDEECLF LERLEENHYN TYIAKKHAEK
121 NWFVGLKKNG SCKRGPRTHY GQKAILFLPL PVSSD
```

Amino acid sequence of *Petromyzon marinus* (lamprey) FGF1(SEQ ID NO: 46) (Ensembl accession no. ENSPMAP00000010683, which is hereby incorporated by reference in its entirety)(partial sequence corresponding to human FGF1 residues 1 to 93):
```
  1 MEVGHIGTLP VVPAGPVFPG SFKEPRRLYC RSAGHHLQIL GDGTVSGTQD ENEPHAVLQL
 61 QAVRRGVVTI RGLCAERFLA MSTEGHLYGA VR
```

Amino acid sequence of *Echinops telfairi* (lesser hedgehog tenrec) FGF1(SEQ ID NO: 47) (Ensembl accession no. ENSETEP00000014504, which is hereby incorporated by reference in its entirety)(partial sequence corresponding to human FGF1 residues 58 to 155)
```
  1 QLKLVAESVG VVYIKSIKTG QYLAMNPDGL LYGSETPEEE CLFLETLEEN HYTTFKSKKH
 61 VEKNWFVGLR KNGRVKIGPR THQGQKAILF LPLPVSSD
```

Amino acid sequence of *Macaca mulatta* (rhesus monkey) FGF1(SEQ ID NO: 48) (Ensembl accession no. ENSMMUP00000030943, which is hereby incorporated by reference in its entirety):
```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Pteropus vampyrus* (megabat) FGF1(SEQ ID NO: 49) (Ensembl accession no. ENSPVAP00000004349, which is hereby incorporated by reference in its entirety):
```
  1 MAEGEVTTFT ALTERFNLPP GNYKKPKLLY CSNGGHFLRI LPDGTVDGTR DKSDQHIQLQ
 61 LSAESVGEVY IKSTESGQYL AMDSDGLLYG SQTPDEDCLF LERLEENHYN TYTSKKHAEK
121 NWFVGLKKNG SCKRGPRTHY GQKAILFLPL PVSSD
```

TABLE 1 -continued

Amino acid sequence of *Myotis lucifugus* (microbat) FGF1(SEQ ID NO: 50) (Ensembl accession no. ENSMLUP00000006481, which is hereby incorporated by reference in its entirety):
```
  1 MAEGEVTTFT ALTERFNLPL ENYKKPKLLY CSNGGHFLRI LPDGTVDGTR DRSDQHIQLQ
 61 LSAESVGEVY IKSTESGQYL AMDSDGLLYG SQTPNEECLF LERLEENHYN TYTSKKHAEK
121 NWFVGLKKNG SCKRGPRTHY GQKAILFLPL PVSSD
```

Amino acid sequence of *Microcebus murinus* (mouse lemur) FGF1(SEQ ID NO: 51) (Ensembl accession no. ENSMICP00000008602, which is hereby incorporated by reference in its entirety):
```
  1 MAEGEITTFT ALTEKFNLPP GNYKKPKLLY CSNGGHFLRI LPDGTVDGTR DRSDQHIQLQ
 61 LSAESAGEVY IKSTQTGRYL AMDADGLLYG SQTPNEECLF LERLEENHYN TYVSKKHAEK
121 NWFVGLKKNG SCKRGPRTHY GQKAILFLPL PVSSD
```

Amino acid sequence of *Ochotona princeps* (pika) FGF1(SEQ ID NO: 52) (Ensembl accession no. ENSOPRP00000011739, which is hereby incorporated by reference in its entirety):
```
  1 MAEGEVTTFS ALTEKFNLPG GNYKLPKLLY CSNGGHFLRI LPDGTVDGTR DRSDLH----
 61 -------EVF IKSTETGQYL AMDTDGLLYG SQTPSEECLF LERLEENHYN TYTSKKHAEK
121 NWFVGIKKNG SCKRGPRTHY GQKAILFLPL PVSSD
```

Amino acid sequence of *Rattus norvegicus* (rat) FGF1(SEQ ID NO: 53) (Ensembl accession no. ENSRNOP00000018577, which is hereby incorporated by reference in its entirety):
```
  1 MAEGEITTFA ALTERFNLPL GNYKKPKLLY CSNGGHFLRI LPDGTVDGTR DRSDQHIQLQ
 61 LSAESAGEVY IKGTETGQYL AMDTEGLLYG SQTPNEECLF LERLEENHYN TYTSKKHAEK
121 NWFVGLKKNG SCKRGPRTHY GQKAILFLPL PVSSD
```

Amino acid sequence of *Choloepus hoffmanni* (sloth) FGF1(SEQ ID NO: 54) (Ensembl accession no. ENSCHOP00000010964, which is hereby incorporated by reference in its entirety):
```
  1 MAEGEITTFT ALMEKFNLPP GNYMKPKLLY CSNGGHFLRI LPDGTVDGTR DRSDLHIQLQ
 61 LSAESVGEVY IKSAETGQYL AMDTGGLLYG SQTPSEECLF LERLEENHYN TYVSKKHAEK
121 NWFVGLKKNG SSKRGPRTHY GQKAILFLPL PVSSD
```

Amino acid sequence of *Ictidomys tridecemlineatus* (squirrel) FGF1(SEQ ID NO: 55) (Ensembl accession no. ENSSTOP00000021782, which is hereby incorporated by reference in its entirety):
```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Tarsius syrichta* (tarsier) FGF1(SEQ ID NO: 56) (Ensembl accession no. ENSTSYP00000006804, which is hereby incorporated by reference in its entirety):
```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYVSKKHAEK
121 NWFVGLKKNG SCKRGPRTHY GQKAILFLPL PVSSD
```

Amino acid sequence of *Tupaia belangeri* (tree shrew) FGF1(SEQ ID NO: 57) (Ensembl accession no. ENSTBEP00000010264, which is hereby incorporated by reference in its entirety):
```
  1 MAEGEITTFA ALTEKFDLPP GNYKKPKLLY CSNGGHFLRI LPDGTVDGTR DRSDQHIQLQ
 61 LTAENVGEVY IKSTETGQYL AMDADGLLYG SQTPNEECLF LERLEENHYN TYISKKHAEK
121 NWFVALKKNG SCKLGPRTHY GQKAILFLPL PVSSD
```

Amino acid sequence of *Meleagris gallopavo* (turkey) FGF1(SEQ ID NO: 58) (Ensembl accession no. ENSMGAP00000016398; partial sequence corresponding to human FGF1 residues 1 to 56, which is hereby incorporated by reference in its entirety):
```
  1 MAEGEITTFT ALTERFGLPL GNYKKPKLLY CSNGGHFLRI LPDGKVDGTR DRSDQH
```

Amino acid sequence of *Macropus eugenii* (wallaby) FGF1(SEQ ID NO: 59) (Ensembl accession no. ENSMEUP00000015084, which is hereby incorporated by reference in its entirety):
```
  1 MAEGEITTFT ALTERFNLPL GNYKKPKLLY CSNGGHFLRI LPDGKVDGTR DRNDQHIQLQ
 61 LSAESVGEVY IKSTESGQYL AMDTNGLLYG SQTPSEECLF LERLEENHYN TYISKKHAEK
121 NWFVGLKKNG SCKRGPRTHY GQKAILFLPL PVSSE
```

Amino acid sequence of *Danio rerio* (zebrafish) FGF1(SEQ ID NO: 60) (Ensembl accession no. ENSDARP00000008825, which is hereby incorporated by reference in its entirety):
```
  1 MTEADIAVKS SPRDYKKLTR LYCMNGGFHL QILADGTVAG AADENTYSIL RIKATSPGVV
 61 VIEGSETGLY LSMNEHGKLY ASSLVTDESY FLEKMEENHY NTYQSQKHGE NWYVGIKKNG
121 KMKRGPRTHI GQKAIFFLPR QVEQEED
```

As noted above, the portion of the paracrine FGF may be modified to decrease binding affinity for heparin and/or heparan sulfate compared to the portion without the modification. In one embodiment, the modified portion of the paracrine FGF includes one or more substitutions, additions, or deletions.

In one embodiment, the one or more substitutions are located at one or more amino acid residues of SEQ ID NO: 1 selected from N33, K127, K128, N129, K133, R134, R137, Q142, K143, and combinations thereof. In one embodiment, the one or more substitutions are selected from N33T, K127D, K128Q, N129T, K133V, R134L, R137H, Q142M, K143T/L/I, and combinations thereof. In one embodiment, the modification is one or more substitutions which are located at one or more amino acid residues corresponding to residues of SEQ ID NO: 1 selected from N33, K127, K128, N129, K133, R134, R137, Q142, K143, and combinations thereof. In one embodiment, the modification is one or more substitutions which are located at one or more amino acid residues corresponding to residues of SEQ ID NO: 1 selected from N33, K127, K128, N129, K133, R134, R137, Q142, K143, and combinations thereof. Amino acid residues corresponding to those of SEQ ID NO: 1 may be determined by, for example, sequence analysis and structural analysis.

Also encompassed within the present invention are portions of paracrine FGFs other than FGF1 (e.g., FGF2, FGF4, FGF5, FGF6, FGF9, FGF16, and FGF20). The portions derived from paracrine FGFs other than FGF1 include portions corresponding to the above-identified amino acid sequences of FGF1. Corresponding portions may be determined by, for example, sequence analysis and structural analysis.

It will be understood that the portion of the paracrine FGF according to the present invention may be derived from a nucleotide sequence that encodes a paracrine FGF protein. For example, in one embodiment, the nucleotide sequence is the nucleotide sequence that encodes human FGF1 (GenBank Accession No. BC032697, which is hereby incorporated by reference in its entirety) (SEQ ID NO: 61), as follows:

```
 91                     ATGGCTGAAG GGGAAATCAC CACCTTCACA
121 GCCCTGACCG AGAAGTTTAA TCTGCCTCCA GGGAATTACA AGAAGCCCAA ACTCCTCTAC
181 TGTAGCAACG GGGGCCACTT CCTGAGGATC CTTCCGGATG GCACAGTGGA TGGGACAAGG
241 GACAGGAGCG ACCAGCACAT TCAGCTGCAG CTCAGTGCGG AAAGCGTGGG GGAGGTGTAT
301 ATAAAGAGTA CCGAGACTGG CCAGTACTTG GCCATGGACA CCGACGGGCT TTTATACGGC
361 TCACAGACAC CAAATGAGGA ATGTTTGTTC CTGGAAAGGC TGGAGGAGAA CCATTACAAC
421 ACCTATATAT CCAAGAAGCA TGCAGAGAAG AATTGGTTTG TTGGCCTCAA GAAGAATGGG
481 AGCTGCAAAC GCGGTCCTCG GACTCACTAT GGCCAGAAAG CAATCTTGTT TCTCCCCCTG
541 CCAGTCTCTT CTGATTAA
```

In another embodiment of the present invention, the portion of the paracrine FGF of the chimeric protein may be derived from a nucleotide sequence that encodes an ortholog of human FGF1. Nucleotide sequences that encode FGF1 orthologs are shown in Table 2.

TABLE 2

Olive Baboon FGF1 gene coding sequence (1-155) (SEQ ID NO: 62) (GenBank accession no. NM_001169086, which is hereby incorporated by reference in its entirety):
```
  1 ATGGCTGAAG GGGAAATCAC CACGTTCACA GCCCTGACCG AGAAGTTTAA TCTGCCTCCA
 61 GCGAATTACA AGAAGCCCAA ACTGCTCTAC TGTAGCAACG GGGACACTT CTTGAGGATC
121 CTTCCGGATG GCACAGTGGA TGGGACAAGG GACAGGAGCG ACCAGCACAT TCAGCTGCAG
181 CTCAGTGCGG AAAGCGTGGG GGAGGTGTAT ATAAAGAGTA CCGAGACTGG CCAGTACTTG
241 GCCATGGACA CCGACGGGCT TTTATACGGC TCACAGACAC CAAATGAGGA ATGTTTGTTC
301 CTGGAAAGGC TGGAGGAGAA CCATTACAAC ACCTATATAT CCAAGAAGCA CGCAGAGAAG
361 AATTGGTTTG TTGGCCTCAA GAAGAATGGA AGCTGCAAAC GTGGTCCTCG GACTCACTAT
421 GGCCAGAAAG CAATCTTGTT TCTTCCCCTG CCAGTCTCTT CTGATTAA
```

Sumatran orangutan FGF1 gene coding sequence (60-214) (SEQ ID NO: 63) (GenBank accession no. NM_001133601, which is hereby incorporated by reference in its entirety):
```
211 ATGGCTGAAG GGGAAATCAC CACCTTCACA
241 GCCCTGACCG AGAAGTTTAA TCTGCCTCCA GGGAATTACA AGAAGCCCAA ACTCCTCTAC
301 TGTAGCAACG GGGGCCACTT CTTGAGGATC CTTCCGGATG GCACAGTGGA TGGGACAAGG
361 GACAGGAGCG ACCAGCACAT TCAGCTGCAG CTCAGTGCGG AAAGCGTGGG GGAGGTGTAT
421 ATAAAGAGTA CCGAGACTGG CCAGTACTTG GCCATGGACA CCGACGGGCT TTTATACGGC
481 TCACAGACAC CAAATGAGGA ATGTTTGTTC CTGGAAAGGC TGGAGGAGAA CCATTACAAC
541 ACCTATATAT CCAAGAAGCA TGCAGAGAAG AATTGGTTTG TTGGCCTCAA GAAGAATGGA
601 AGCTGCAAAC GCGGTCCTCG GACTCACTAT GGCCAGAAAG CAATCTTGTT TCTCCCCCTG
661 CCAGTCTCTT CTGATTAA
```

TABLE 2 -continued

White-tufted-ear marmoset FGF1 gene coding sequence (1-155) (SEQ ID
NO: 64) (GenBank accession no. XM_002744295, which is hereby incorporated
by reference in its entirety):
```
130           A TGGCTGAAGG GGAAATCACC ACCTTCACAG CCCTGACCGA GAAGTTTGAT
181 CTGCCTCCAG GGAATTACAA GAAGCCCAAA CTCCTCTACT GTAGCAATGG GGGCCACTTC
241 TTGAGGATCC TTCCGGATGG CACAGTGGAT GGGACAAGGG ACAGGAGCGA CCAGCACATT
301 CAGCTGCAGC TCAGTGCGGA AAGCGTGGGG GAGGTGTATA TAAAGAGTAC CGAGACTGGC
361 CAGTACTTGG CCATGGACAC CGACGGGCTT TTATACGGCT CACAGACACC AAATGAGGAA
421 TGTTTGTTCC TGGAGAGGCT GGAGGAGAAC CATTACAACA CCTATATATC CAAGAAACAT
481 GCAGAGAAGA ATTGGTTTGT CGGCCTCAAG AAGAATGGAA GCTGTAAACG TGGTCCTCGG
541 ACTCACTATG GTCAGAAAGC GATCTTGTTT CTCCCCCTGC CAGTTTCTTC TGATTAA
```

Horse FGF1 gene coding sequence (1-155) (SEQ ID NO: 65) (GenBank accession
no. NM_001163886, which is hereby incorporated by reference in its
entirety):
```
 34                          ATGGCTG AAGGAGAAAT CACAACCTTC
 61 ACGGCCCTGA CCGAGAAGTT TAATCTGCCT CCAGGGAATT ACAAGAAGCC CAAACTCCTC
121 TACTGTAGCA ATGGGGGCCA CTTCCTGAGG ATCCTTCCAG ATGGCACAGT GGATGGGACA
181 AGGGACAGGA GCGACCAGCA CATTCAGCTG CAGCTCAGTG CGGAAAGCGT GGGGGAGGTG
241 TATATAAAGA GTACCGAGAC TGGCCAGTAC TTGGCCATGG ACACCGACGG GCTGTTGTAC
301 GGCTCACAGA CACCAAACGA GGAATGTTTG TTCCTGGAAA GGCTGGAGGA AAACCATTAC
361 AACACCTACA CATCCAAGAA GCATGCAGAG AAGAACTGGT TCGTTGGTCT CAAGAAGAAT
421 GGGAGCTGCA AACGCGGTCC TCGGACTCAC TATGGGCAGA AGCAATCTT GTTTCTTCCC
481 CTGCCCGTCT CCTCTGACTA A
```

Chimpanzee FGF1 gene coding sequence (1-155) (SEQ ID NO: 66) (GenBank
accession no. GABD01003589, which is hereby incorporated by reference in
its entirety):
```
 80           A TGGCTGAAGG GGAAATCACC ACCTTCACAG CCCTGACCGA
121 GAAGTTTAAT CTGCCTTCAG GGAATTACAA GAAGCCCAAA CTCCTCTACT GTAGCAACGG
181 GGGCCACTTC CTGAGGATCC TTCCGGATGG CACAGTGGAT GGGACAAGGG ACAGGAGCGA
241 CCAGCACATT CAGCTGCAGC TCAGTGCGGA AAGCGTGGGG GAGGTGTATA TAAAGAGTAC
301 CGAGACTGGC CAGTACTTGG CCATGGACAC CGACGGGCTT TTATACGGCT CACAGACACC
361 AAATGAGGAA TGTTTGTTCC TGGAACGGCT GGAGGAGAAC CATTACAACA CCTATATATC
421 CAAGAAGCAT GCAGAGAAGA ATTGGTTTGT TGGCCTCAAG AAGAATGGAA GCTGCAAACG
481 CGGTCCTCGG ACTCACTATG GCCAGAAAGC AATCTTGTTT CTCCCCCTGC CAGTCTCTTC
541 CGATTAA
```

Elephant FGF1 gene coding sequence (1-155) (SEQ ID NO: 67) (GenBank
accession no. XM_003404573, which is hereby incorporated by reference in
its entirety):
```
  1 ATGGCCGAAG GGGAAATCAC AACTTTCACA GCCCTGACAG AGAAGTTCAA CCTGCCTCCA
 61 GGGAATTACA AGAAGCCCAA ACTCCTCTAC TGTAGCAATG GAGGTCACTT CTTAAGGATC
121 CTTCCAGATG GCACAGTGGA TGGCACCAGG GACAGGAGTG ACCAGCACAT TCAGCTGCAG
181 CTCAGTGCGG AAAGCGTGGG GGAGGTGTAT ATAAAGGGCA CCGAGACTGG CCAGTACTTG
241 GCCATGGACA CCGACGGGCT TTTATACGGC TCACAGACAC CAAATGAGGA ATGTTTGTTC
301 CTGGAAAGGC TGGAGGAAAA CCATTACAAC ACCTACACAT CCAAGAAGCA CGCAGAGAAG
361 AATTGGTTCG TTGGTCTCAA GAAGAATGGA AGCTGCAAAC GCGGTCCTCG GACTCACTAT
421 GGCCAGAAAG CAATCTTGTT TCTCCCCCTG CCAGTCTCCT CTGATTAA
```

Dog FGF1 genecoding sequence (1-155) (SEQ ID NO: 68) (GenBank accession
no. XM_844181, which is hereby incorporated by reference in its
entirety):
```
164                            ATGGCTG AAGGGGAAAT
181 CACAACCTTC ACTGCCCTGA CGGAGAAGTT TAATCTGCCT CCGGGGAATT ACATGAAGCC
241 CAAACTCCTC TACTGTAGCA ACGGGGGCCA CTTCCTGAGG ATCCTTCCAG ATGGCACAGT
301 GGATGGGACA AGGGACAGGA GCGACCAGCA CATTCAGCTG CAGCTCAGCG CGGAAAGCGT
361 GGGGGAGGTG TATATAAAGA GCACCGAGAC TGGCCAGTAC TTGGCCATGG ACACCGATGG
421 GCTTCTGTAC GGCTCACAGA CACCGAATGA GGAATGTTTG TTCCTGGAAA GGCTGGAGGA
481 AAACCATTAC AACACCTACA CATCCAAGAA GCATGCAGAA AAAATTGGT TTGTTGGTCT
541 CAAGAAGAAT GGAAGCTGCA AACGCGGTCC TCGGACTCAC TATGGTCAAA AGCAATTTT
601 GTTTCTCCCC CTGCCAGTGT CCTCTGATTA A
```

Giant panda FGF1 gene coding sequence (1-155) (SEQ ID NO: 69) (GenBank
accession no. XM_002912535, which is hereby incorporated by reference in
its entirety):
```
146                        ATGGC TGAAGGGGAG ATCACAACCT TCACCGCCCT
181 GACGGAGAAG TTTAATCTGC CTGCGGGGAA TTACAAGAAG CCCAAACTCC TCTACTGTAG
241 CAACGGGGGC CACTTCCTGA GGATCCTTCC AGATGGCACA GTGGACGGGA CGAGGGACAG
301 GAGCGACCAG CACATTCAAC TGCAGCTCAG CGCGGAAAGC GTAGGGGAGG TGTACATAAA
361 GAGCACCGAG ACCGGCCAGT ACTTGGCCAT GGACACCGAT GGGCTTCTGT ACGGCTCACA
421 GACACCAAAT GAGGAATGTT TGTTCCTGGA AAGGCTGGAG AAAACCATT ACAACACCTA
481 CACATCCAAG AAGCACGCGG AGAAGAATTG GTTTGTTGGT CTCAAGAAGA ATGGAAGCTG
541 CAAACGTGGT CCTCGGACTC ACTATGGCCA GAAAGCAATT CTGTTTCTCC CCTGCCAGT
601 CTCCTCTGAT TAA
```

TABLE 2 -continued

Bolivian squirrel monkey FGF1 gene coding sequence (1-155) (SEQ ID NO: 70) (GenBank accession no. XM_003920547, which is hereby incorporated by reference in its entirety):
```
130         A TGGCTGAAGG GGAAATCACC ACCTTTACAG CCCTGACCGA GAAGTTTGAT
181 CTGCCTCCAG GGAATTACAA GAAGCCCAAA CTCCTCTACT GTAGCAACGG GGGCCACTTC
241 TTGAGGATCC TTCCGGATGG CACAGTGGAT GGGACCAGGG ACAGGAGCGA TCTTCACATT
301 CAGCTGCAGC TCAGTGCGGA AAGCGTGGGG GAGGTGTATA TAAAGAGTAC CGAGACTGGC
361 CAGTACTTGG CCATGGACAC CGACGGGCTT TTATACGGCT CACAGACACC AAATGAGGAA
421 TGTTTGTTCC TGGAAAGGCT GGAGGAGAAC CATTACAACA CCTATATATC CAAGAAACAC
481 GCAGAGAAGA ATTGGTTTGT TGGCCTCAAG AAGAATGGAA GCTGCAAGCG CGGTCCTCGG
541 ACTCACTATG GCCAGAAAGC AATCTTGTTT CTCCCCCTGC CAGTCTCTTC TGATTAA
```

Pig FGF1 gene coding sequence (1-155) (SEQ ID NO: 71) (GenBank accession no. XM_003124010, which is hereby incorporated by reference in its entirety):
```
 35                                   ATGGCT GAAGGCGAAA TCACAACCTT
 61 CACGGCCCTG ACCGAGAAGT TAATCTGCCT TCCAGGAAAT TACAAGAAGC CCAAGCTCCT
121 CTACTGCAGC AACGGGGCC ATTTCCTCAG GATCCTTCCA GATGGCACAG TGGATGGGAC
181 CAGGGACAGG AGCGACCAGC ACATTCAGCT GCAGCTCAGT GCGGAAAGCG TGGGGGAGGT
241 GTATATAAAG AGTACGGAGA CTGGCCAGTA CTTGGCCATG GACACCGACG GCTTTTGTA
301 CGGCTCACAG ACACCCAGTG AGGAGTGTTT GTTCCTGGAG AGGCTGGAGG AAACCATTA
361 CAATACCTAC ACATCCAAGA AGCACGCAGA GAAGAACTGG TTCGTTGGCC TCAAGAAGAA
421 TGGAAGCTGC AAACGCGGTC CTCGGACTCA CTATGGCCAG AAAGCCATCC TGTTTCTCCC
481 CCTGCCAGTA TCCTCGGATT AA
```

Small-eared galago FGF1 gene coding sequence (1-155) (SEQ ID NO: 72) (GenBank accession no. XM_003782087, which is hereby incorporated by reference in its entirety):
```
 28                       ATG GCTGAAGGGG AAATCACAAC CTTCACAGCC
 61 CTCAGAGA AGTTTAATCT GCCTCTAGGA AATTACAAGA AGCCCAAGCT CCTCTACTGT
121 AGCAACGGGG GTCACTTTCT GAGGATCCTG CCGGATGGCA CCGTGGATGG GACACAAGAC
181 AGGAGCGACC AGCACATTCA GCTGCAGCTC AGTGCGGAAA GCGTGGGGGA GGTGTATATA
241 AAGAGTACCC AGACTGGCCA GTACTTGGCC ATGGACTCCG ACGGGCTTTT ATACGGCTCA
301 CAAACACCAA ATGAGGAATG CCTGTTCCTG GAACGGCTGG AGGAAAACCA TTACAACACC
361 TATGTGTCCA AGAAGCACGC CGAGAAGAAT TGGTTTGTCG GTCTCAAGAA GACGGAAGT
421 TGCAAACGTG GTCCTCGGAC TCACTACGGC CAGAAAGCAA TCTTGTTTCT CCCCCTGCCA
481 GTCTCCTCTG ATTAA
```

Greater horseshoe bat FGF1 gene coding sequence (1-155) (SEQ ID NO: 73) (GenBank accession no. DP000705, which is hereby incorporated by reference in its entirety):
```
190120                              T TAATCAGAGG AGACTGGCAG
190141 GGGGAGAAAC AGGATTGCTT TCTGGCCATA GTGAGTCCGA GGACCGCGCT TGCAGCTTCC
190201 ATTCTTCTTG AGCCCAACGA ACCAATTCTT TTCTGCGTGC TTCTTGGACG TGTAGGTGTT
190261 GTAATGGTTT TCCTCCAGCC TTTCCAGGAA CAGACATTCC TCATTTGGTG TCTG
194466      TGAGC CGTACAAAAG CCCGTCGGAG TCCATGGCCA AGTACTGGCC ACTCTCGGTG
194521 CTCTTTATAT ACACCTCCCC CACGCTTTCC GCACTGAGCT GCAGCTGAA
208114                              TGTGCTG GTCACTCTTG TCCCTTGTCC
208141 CATCCACTGT GCCATCTGGA AGGATCCTCA GGAAGTGGCC CCCGTTGCTG CAGTAGAGAA
208201 GTTTGGGTTT CTTGTAATTC CCTGTAGGCA GATTAAACTT CTCAGTAAGG GCTGTGAACG
208261 TGGTGACTTC CCCTTCGGCC AT
```

European shrew FGF1 gene coding sequence (1-155) (SEQ ID NO: 74) (GenBank accession no. DP000767, which is hereby incorporated by reference in its entirety):
```
138344                                      CTAGTCG GAGGAGACGG
138361 GCAGGGGGAG AAACAAGATC GCTTTCTGGC CGTAGTGAGT CCGGGGACCA CGCTTGCAGC
138421 TTCCGTTCTT CTTCAGACCA ACAAACCAAT TCTTCTCGGC ATGCTTCTTG GAGGTATAGG
138481 TGTTGTAATG GTTTTCCTCC AGCCTTTCCA GAACAGACA TTCCTCATTC GGTGTTTG
143512                                             TGAGCCGTA
143521 TAAAAGCCCG TCGGTGTCCA TGGCCAAGTA ATGGCCAGTC TCCGTGCTCT TTATATACAC
143581 CTCCCCCACG CTTTCCGCAC TGAGCTGCAG CTGAA
157009                                             TG TGCTGGTCGC
157021 TGCGGTCCCT GGTCCCATCC ACTGTGCCGT CCGGGAGGAT GCGCAGGAAG TGGCCCCCGT
157081 TGCTGCAGTA CAGGAGTTTG GCTTCTTGT AGTTCCCTGG TGGCAGGTTA AACTTCTCCA
157141 TGAGGGCCCC AAAGGTGGTG ATCTCCCCCT CGGCCAT
```

Rabbit FGF1 gene coding sequence (1-155) (SEQ ID NO: 75) (GenBank accession no. NM_001171488, which is hereby incorporated by reference in its entirety):
```
  1 ATGGCTGAGG GGAGGTCAC CACCTTCACA GCCCTGACCG AGAAGTTCAA CCTGCCTGCA
 61 GGGAACTACA AGTTGCCCAA ACTCCTCTAC TGCAGCAACG GGGCCACTT CCTGAGGATC
121 CTGCCGGACG GCACTGTGGA CGGCACAAGG GACAGGAGCG ACCAGCACAT TCAGCTGCAG
181 CTGAGTGCGG AAAGCGTGGG GAGGTGTAT ATAAAGAGTA CGGAGACCGG CCAGTACTTG
241 GCCATGGACA CCGACGGCCT TTTATACGGC TCGCAAACGC CAGTGAGGA GTGTTTGTTC
301 CTGGAACGGC TGGAGGAGAA CCACTACAAC ACCTACACGT CCAAGAAGCA CGCCGAGAAG
361 AACTGGTTCG TGGGGCTGAA GAAAAACGGG AGCTGCAAGC GCGGTCCTCG GACTCACTAC
421 GGCCAGAAAG CCATCTTGTT CCTCCCCCTG CCGGTCTCCT CCGACTAA
```

TABLE 2 -continued

Chinese hamster FGF1 gene coding sequence (1-155) (SEQ ID NO: 76) (GenBank
accession no. XM_003502421, which is hereby incorporated by reference in
its entirety):
```
  1 ATGGCTGAAG GAGAAATCAC CACCTTCTCA GCCCTGACAG AGAGATTTAA TCTGCCTCCA
 61 GGAAACTACA AGAAGCCCAA ACTGCTCTAC TGCAGCAACG GGGGCCACTT CTTGAGGATC
121 CTTCCAGATG GCACAGTGGA TGGGACAAGG GACAGGAGTG ACCAGCACAT TCAGCTGCAG
181 CTGAGTGCGG AAAGCGCGGG CGAAGTGTAT ATAAAGGGTA CAGAGACAGG CCAGTACAGG
241 AACATGGACA CGGATGGCCT TTTATACGGC TCACAGACAC AAATGAAGA ATGCCTGTTC
301 CTGGAAAGGC TGGAAGAAAA CCATTACAAC ACTTATACAT CCAAGAAGCA CGCAGAGAAG
361 AACTGGTTTG TGGGCCTCAA GAAAAACGGG AGCTGCAAGC GTGGTCCTCG GACTCACTAT
421 GGCCAGAAAG CAATCTTGTT TCTCCCCCTG CCTGTATCTT CTGACTAG
```

Tasmanian devil FGF1 gene coding sequence (1-155) (SEQ ID NO: 77) (GenBank
accession no. XM_003756690, which is hereby incorporated by reference in
its entirety):
```
 24                     ATGGCCG AAGGGGAGAT CACAACCTTC ACAGCCCTGA
 61 CCGAAAGATT TAATCTGCCA CTGGGGAATT ACAAGAAGCC CAAGCTTCTC TACTGTAGCA
121 ATGGGGGCCA CTTTTTGAGG ATTCTTCCTG ATGGTAAAGT GGATGGGACA AGGGACAGAA
181 ATGATCAACA CATTCAACTG CAACTAAGCG CGGAAAGCGT GGGTGAGGTG TATATAAAGA
241 GCACTGAGTC TGGCCAGTAT TTGGCTATGG ACACCGATGG ACTTTTATAC GGCTCACAGA
301 CACCCACTGA AGAATGCTTG TTCCTGGAGA GATTGGAAGA GAATCATTAC AACACCTACA
361 TATCAAAGAA GCATGCGGAG AAAAATTGGT TTGTGGGCCT CAAGAAAAAT GGAAGCTGCA
421 AAAGAGGTCC CAGGACTCAC TATGGCCAGA AAGCCATCCT CTTCCTTCCC CTCCCTGTGT
481 CCTCTGAGTA A
```

House mouse FGF1 gene coding sequence (1-155) (SEQ ID NO: 78) (GenBank
accession no. NM_010197, which is hereby incorporated by reference in its
entirety):
```
188         ATG GCTGAAGGGG AGATCACAAC CTTCGCAGCC CTGACCGAGA GGTTCAACCT
241 GCCTCTAGGA AACTACAAAA AGCCCAAACT GCTCTACTGC AGCAACGGGG GCCACTTCTT
301 GAGGATCCTT CCTGATGGCA CCGTGGATGG GACAAGGGAC AGGAGCGACC AGCACATTCA
361 GCTGCAGCTC AGTGCGAAA GTGCGGGCGA AGTGTATATA AAGGGTACGG AGACCGGCCA
421 GTACTTGGCC ATGGACACCG AAGGGCTTTT ATACGGCTCC CAGACACCAA ATGAGGAATG
481 TCTGTTCCTG GAAAGGCTGG AAGAAAACCA TTATAACACT TACACCTCCA AGAAGCATGC
541 GGAGAAGAAC TGGTTTGTGG GCCTCAAGAA GAACGGGAGC TGTAAGCGCG GTCCTCGGAC
601 TCACTATGGC CAGAAAGCCA TCTTGTTTCT GCCCCTCCCG GTGTCTTCTG ACTAG
```

Domestic guinea pig FGF1 gene coding sequence (1-154) (SEQ ID NO: 79)
(GenBank accession no. XM_003477194, which is hereby incorporated by
reference in its entirety):
```
  1 ATGGCTGAAG GAGAAATCAC AACTTTTGCA GCCCTGACTG AGAAGTTTAA TCTGCCTCCA
 61 GGGAATTATA AGAAGCCCAA ACTGCTCTAC TGCAGCAATG GGGGCCACTT CCTGAGGATC
121 CTTCCAGACG GCACAGTGGA CGGCACAAGA GACAGGAGCG ACCAGCACAT TCAGCTGCAG
181 CTCAGTGCGG AAGGCGTGGG GGAGGTGTAT ATACAGAGCA CCGAGACCGG CCAGTACTTG
241 GCCATGGACA CCGACGGGCT TTTATACGGC TCACAGACAC CAAGTGAGGA ATGCTTGTTC
301 CTGGAAAGGC TGGAGGAAAA CCATTACAAC ACCTACACAT CCAAGAAGCA TGTGGAGAAG
361 AATTGGTTTG TTGGCCTCAA GAAGAACGGA AGCTGCAAGC GTGGTCCTCG GACTCACTAT
421 GGCCAGAAAG CAATCTTGTT CCTCCCCTTG CCAGTCTCTG ATTAG
```

Gray short-tailed opossum FGF1 gene coding sequence (1-155) (SEQ ID
NO: 80) (GenBank accession no. XM_001368884, which is hereby incorporated
by reference in its entirety):
```
  1 ATGGCCGAAG GGGAGATCAC AACCTTCACA GCCCTGACTG AAAGATTTAA CCTGCCACTG
 61 GGGAATTACA AGAAACCCAA GCTTCTCTAC TGTAGCAATG GGGGCCATTT CTTGAGGATC
121 CTTCCTGATG GCAAAGTGGA TGGGACACGG GACAGAAATG ATCAACACAT TCAACTGCAG
181 CTGAGCACGG AAAGTGTGGG TGAGGTGTAT ATAAAGAGCA CTGAGTCTGG CCAGTATTTG
241 GCTATGGACA CCGATGGACT TTTATATGGC TCACAGACAC CAGTGAAGA ATGCTTGTTT
301 CTGGAGAGGT TGGAGGAGAA TCATTACAAC ACCTACACAT CGAAGAAGCA TGCAGAGAAA
361 AATTGGTTTG TTGGTCTCAA GAAGAATGGA AGCTGCAAAA AGGGTCCCAG GACTCACTAC
421 GGCCAGAAAG CCATCCTGTT CCTTCCCCTC CCTGTGTCCT CTGAGTAA
```

Common vampire bat FGF1 gene coding sequence (1-155) (SEQ ID NO: 81)
(GenBank accession no. GABZ01008334, which is hereby incorporated by
reference in its entirety):
```
  1 ATGGCTGAAG GGAAGTCAC CACGTTCACA GCTCTGACTG AGAAGTTTAA TCTGCCTCTG
 61 GAGAGTTACA AGAAGCCCAA ACTTCTCTAC TGCAGCAACG GTGGCCACTT CCTGAGGATC
121 CTTCCAGATG GTACAGTGGA TGGGACAAGG GACAAGAGCG ACCAGCACAT TCAGCTGCAG
181 CTCAGTGCGG AAAGCGTGGG GGAGGTGTAC ATAAAGAGCA CCGGGAGTGG CCAGTACTTG
241 GCCATGGACT CCGCCGGGCT TTTGTATGGC TCACAGACAC CAAATGAGGA ATGTTTGTTC
301 CTGGAAAGGC TGGAGGAAAA CCATTACAAC ACCTACACAT CCAAGAAGCA TGCAGAAAAG
361 AATTGGTTCG TGGGGCTCAA GAAGAATGGA AGCTGCAAGC GTGGCCCCCG GACTCATTAT
421 GGCCAGAAAG CAATCTTGTT TCTCCCCCTG CCAGTCAACT CTGATTAA
```

Cattle FGF1 gene coding sequence (1-155) (SEQ ID NO: 82) (GenBank
accession no. NM_174055, which is hereby incorporated by reference in its
entirety):
```
 918                     ATG GCTGAAGGAG AAACCACGAC CTTCACGGCC CTGACTGAGA
 961 AGTTTAACCT GCCTCTAGGC AATTACAAGA AGCCCAAGCT CCTCTACTGC AGCAACGGGG
1021 GCTACTTCCT GAGAATCCTC CCAGATGCA CAGTGGATGG GACGAAGGAC AGGAGCGACC
1081 AGCACATTCA GCTGCAGCTC TGTGCGGAAA GCATAGGGGA GGTGTATATT AAGAGTACGG
```

TABLE 2 -continued

```
1141 AGACTGGCCA GTTCTTGGCC ATGGACACCG ACGGGCTTTT GTACGGCTCA CAGACACCCA
1201 ATGAGGAATG TTTGTTCCTG GAAAGGTTGG AGGAAAACCA TTACAACACC TACATATCCA
1261 AGAAGCATGC AGAGAAGCAT TGGTTCGTTG GTCTCAAGAA GAACGGAAGG TCTAAACTCG
1321 GTCCTCGGAC TCACTTCGGC CAGAAAGCCA TCTTGTTTCT CCCCCTGCCA GTCTCCTCTG
1381 ATTAA
```

Platypus FGF1 gene coding sequence (1-155) (SEQ ID NO: 83) (GenBank by reference in accession no. XM_001514811, which is hereby incorporated its entirety):
```
    1 ATGGCGGAGG GTGAAATCAC CACGTTCACA GCCCTGATGG AGAAGTTCGA CCTACCCCTG
   61 GGCAACTACA AAAAGCCTAG GCTGCTCTAC TGCAGCAATG GCGGCTACTT CCTGCGCATC
  121 CAGCCAGACG GTAAAGTGGA CGGGACCAGG GATCGGAGCG ATCAGCACAT TCAACTGCAG
  181 CTAAGCGCGG AAAGCGTGGG CGAGGTGTAT ATAAAGAGCA CCGAGTCTGG CCACTATTTG
  241 GCTATGGACA CCGAAGGACT TTTATATGGC TCACAGGCAC CCAGTGAAGA CTGCTTGTTC
  301 CTGGAGCGGC TGGAGGAGAA CCACTATAAC ACGTACGTGT CCAAGAAGCA CGCTGAGAAG
  361 AATTGGTTTG TCGGTCTCAA GAAGAACGGG AGCTGCAAAC GAGGTCCCCG GACTCACTAC
  421 GGCCAGAAAG CCATCCTCTT CCTCCCCGCTC CCCGTGGCAT CCGACTAG
```

Zebra finch FGF1 gene coding sequence (1-155) (SEQ ID NO: 84) (GenBank accession no. XM_002193251, which is hereby incorporated by reference in its entirety):
```
    1 ATGGCCGAGG GGGAGATCAC CACCTTCAGC GCCCTGACGG AGAAGTTCAA CCTGCCCCCG
   61 GGGAACTACA AGAGCCCAA ACTGCTGTAC TGCAGCAACG GGGGGCATTT CCTGCGCATC
  121 CTCCCGGACG GCACCGTGGA TGGCACCAGG GACCGCAGCG ACCAGCACAT TCAGCTCCAG
  181 CTGAGTGCAG AGAGCGTGGG GGTGGTGCAC ATCCAGAGCA CCCAGTCGGG GCAGTACCTG
  241 GCCATGGACA CCAACGGGCT GCTCTACGGC TCGCAGCTGC CACCCGGTGA GTGTCTGTTC
  301 CTGGAAAGGC TGGAGGAGAA CCATTACAAC ACCTACGTCT CCAAAATGCA CGCGGACAAG
  361 AACTGGTTTG TGGGGCTGAA GAAGAACGGG ACAAGCAAGC TGGGCCCGCG GACTCACTAC
  421 GGCCAGAAGG CGATCCTGTT CCTGCCGCTG CCCGTGGCGG CCGACTGA
```

Nine-banded armadillo FGF1 gene coding sequence (1-155) (SEQ ID NO: 85) (GenBank accession no. DP001080, which is hereby incorporated by reference in its entirety):
```
178389          TT AATCAGAGGA GACTGGCAGG GGAAGAAACA AGATAGCTTT CTGGCCATAG
178441 TGAGTCTGAG GACCACGTTT GCTGCTTCCG TCCTTCTTGA GACCAACAAA CCATTCTTC
178501 TCTGCATGCT TCTTGGATAT GTAGGTGTTG TAATTGTTTT CTTCCAGCTT TTCCATGAAC
178561 AAGCATTCCT CACTGGTGT CTC
182873                                                        TGAGCCAT
182881 ATAAAAGCCC GTCGGTGTCC ATGGCTAAGT ACTGGCCGGT CTCTGCACTC TTTATATACA
182941 CCTCCCCCAC GCTTTCCGCA CTGAGCTGCA GCTGAA
197786                             TGTGT TGGTCGCTCC TGTCCCTTGT CCCATCCACC
197821 GTGCCATCTG GAAGGATCCT CAAGAAGTGG CCCCCGTTTC TGCAGTAGAG GAGTCTGGGG
197881 TGCTTGTAAT TTTCTAGGGG CAGGTTGAAC TTCTCCATCA GGGCCATGAA GGTTGTGATC
197941 TCCCCTTCAG CCAT
```

Xenopus Silurana tropicalis FGF1 gene coding sequence (1-155) (SEQ ID NO: 86) (GenBank accession no. FJ428265, which is hereby incorporated by reference in its entirety):
```
    1 ATGGCAGAGG GAGACATCAC AACATTCAAC CCCATTGCAG AGTCCTTCAG TCTTCCAATT
   61 GGCAACTACA AGAAACCAAA ACTTCTGTAC TGTAATAATG GAGGGTATTT TTTGCGCATC
  121 CTCCCAGATG GGGTTGTGGA TGGAACAAGA GACAGAGATG ACCTTTACAT TACACTGAAG
  181 TTAAGCGCAC AAAGCCAAGG GGAGGTGCAT ATCAAAAGCA CAGAGACAGG GAGTTACTTA
  241 GCCATGGACT CCAGTGGACA GTTGTATGGA ACTCTCACAC CAAATGAAGA AAGCCTGTTT
  301 CTGGAGACAT TAGAAGAGAA TCACTATAAC ACATACAAGT CAAAGAAGTA TGCAGAAAAT
  361 AACTGGTTTG TGGGGATAAA GAAGAACGGG GCAAGCAAAA AGGGATCAAG GACTCACTAT
  421 GGACAAAAAG CCATCCTTTTT TCTGCCGCTG CCAGCATCAC CTGACTAG
```

Heterocephalus glaber FGF1 gene coding sequence (1-155) (SEQ ID NO: 87) (generated using SMS Reverse Translate tool on the ExPASy Bioinformatics Resource website (www.expasy.org):
```
    1 ATGGCGGAAG GCGAAATTAC CACCTTTACC GCGCTGACCG AAAAATTTAA CCTGCCGCCG
   61 GGCAACTATA AAAACCGAA ACTGCTGTAT TGCAGCAACG GCGGCCATTT TCTGCGCATT
  121 CTGCCGGATG GCAAAGTGGA TGGCACCCGC GATCGCAGCG ATCAGCATAT TCAGCTGCAG
  181 CTGAGCGCGG AAGCGTGGG CGAAGTGTAT ATTAAAAGCA CCGAAACCGG CCAGTATCTG
  241 GCGATGGATA CCGATGGCCT GCTGTATGGC AGCCAGACCG CGAGCGAAGA TGCCTGTTT
  301 CTGGAACGCC TGGAAGAAAA CCATTATAAC ACCTATATTA GCAAAAAACA TGCGGAAAAA
  361 AACTGGTTTG TGGGCCTGAA AAAAAACGGC AGCTGCAAAC GCGGCCCGCG CACCCATTAT
  421 GGCCAGAAAG CGATTCTGTT TCTGCCGCTG CCGGTGAGCA GCGAT
```

Black flying fox FGF1 gene coding sequence (1-155) (SEQ ID NO: 88) (generated using SMS Reverse Translate tool on the ExPASy Bioinformatics Resource website (www.expasy.org):
```
    1 ATGGCGGAAG GCGAAGTGAC CACCTTTACC GCGCTGACCG AACGCTTTAA CCTGCCGCCG
   61 GGCAACTATA AAAACCGAA ACTGCTGTAT TGCAGCAACG GCGGCCATTT TCTGCGCATT
  121 CTGCCGGATG GCACCGTGGA TGGCACCCGC GATAAAAGCG ATCAGCATAT TCAGCTGCAG
  181 CTGAGCGCGG AAAGCGTGGG CGAAGTGTAT ATTAAAAGCA CCGAAAGCGG CCAGTATCTG
  241 GCGATGGATA CCGATGGCCT GCTGTATGGC AGCCAGACCC GGATGAAGA TTGCCTGTTT
  301 CTGGAACGCC TGGAAGAAAA CCATTATAAC ACCTATACCA GCAAAAAACA TGCGGAAAAA
  361 AACTGGTTTG TGGGCCTGAA AAAAAACGGC AGCTGCAAAC GCGGCCCGCG CACCCATTAT
  421 GGCCAGAAAG CGATTCTGTT TCTGCCGCTG CCGGTGAGCA GCGAT
```

TABLE 2 -continued

Chinese tree shrew FGF1 gene coding sequence (1-155) (SEQ ID NO: 89) (generated using SMS Reverse Translate tool on the ExPASy Bioinformatics Resource website (www.expasy.org)):
```
  1 ATGGCGGAAG GCGAAATTAC CACCTTTGCG GCGCTGACCG AAAAATTTGA TCTGCCGCCG
 61 GGCAACTATA AAAAACCGAA ACTGCTGTAT TGCAGCAACG GCGGCCATTT TCTGCGCATT
121 CTGCCGGATG GCACCGTGGA TGGCACCCGC GATCGCAGCG ATCAGCATAT TCAGCTGCAG
181 CTGACCGCGG AAAACGTGGG CGAAGTGTAT ATTAAAAGCA CCGAAACCGG CCAGTATCTG
241 GCGATGGATG CGGATGGCCT GCTGTATGGC AGCCAGACCC CGAACGAAGA ATGCCTGTTT
301 CTGGAACGCC TGGAAGAAAA CCATTATAAC ACCTATATTA GCAAAAAACA TGCGGAAAAA
361 AACTGGTTTG TGGCGCTGAA AAAAAACGGC AGCTGCAAAC TGGGCCCGCG CACCCATTAT
421 GGCCAGAAAG CGATTCTGTT TCTGCCGCTG CCGGTGAGCA GCGAT
```

Rock pigeon FGF1 gene coding sequence (1-155) (SEQ ID NO: 90) (generated using SMS Reverse Translate tool on the ExPASy Bioinformatics Resource website (www.expasy.org)):
```
  1 ATGGCGGAAG GCGAAATTAC CACCTTTACC GCGCTGACCG AAAAATTTAA CCTGCCGCCG
 61 GGCAACTATA AAAAACCGAA ACTGCTGTAT TGCAGCAACG GCGGCCATTT TCTGCGCATT
121 CTGCCGGATG GCAAAGTGGA TGGCACCCGC GATCGCAGCG ATCAGCATAT TCAGCTGCAG
181 CTGAGCGCGG AAAGCGTGGG CGAAGTGTAT ATTAAAAGCA CCCAGAGCGG CCAGTATCTG
241 GCGATGGATC CGACCGGCCT GCTGTATGGC AGCCAGCTGC TGGGCGAAGA ATGCCTGTTT
301 CTGGAACGCA TTGAAGAAAA CCATTATAAC ACCTATGTGA GCAAAAAACA TGCGGATAAA
361 AACTGGTTTG TGGGCCTGAA AAAAAACGGC AACAGCAAAC TGGGCCCGCG CACCCATTAT
421 GGCCAGAAAG CGATTCTGTT TCTGCCGCTG CCGGTGAGCG CGGAT
```

Sheep FGF1 gene coding sequence (1-155) (SEQ ID NO: 91) (GenBank accession no. XM_004008909, which is hereby incorporated by reference in its entirety):
```
361 ATGGCTGAAG GAGAAACCAC AACCTTCAGG GCCCTGACTG AGAAGTTTAA CCTGCCTCTA
421 GGCAATTACA AGAAGCCCAA GCTCCTCTAT TGCAGCAACG GGGGCTACTT CCTGAGAATC
481 CTCCCAGATG GCAGAGTGGA TGGGACGAAG GACAGGAGCG ACCAGCACAT TCAGCTGCAG
541 CTCTATGCGG AAAGCATAGG GGAGGTGTAT ATTAAGAGTA CGGAGACTGG CCAGTTCTTG
601 GCCATGGACA CCAACGGGCT TTTGTACGGC TCACAAACAC CCAGTGAGGA ATGTTTGTTC
661 CTGGAAAGGC TGGAGGAAAA CCATTATAAC ACCTACATAT CCAAGAAGCA TGCAGAGAAG
721 AATTGGTTCA TTGGTCTCAA GAAGAACGGA AGCTCCAAAC TCGGTCCTCG GACTCACTTC
781 GGCCAGAAAG CCATCTTGTT TCTCCCCCTG CCAGTTTCCT CTGATTAA
```

Chicken FGF1 gene coding sequence (1-155) (SEQ ID NO: 92) (GenBank accession no. NM_205180, which is hereby incorporated by reference in its entirety):
```
 52                                                            ATGGCCGAG
 61 GGGGAGATAA CCACCTTCAC CGCCCTGACC GAGCGCTTCG GCCTGCCGCT GGGCAACTAC
121 AAGAAGCCCA AACTCCTGTA CTGCAGCAAC GGGGGCCACT TCCTACGGAT CCTGCCGGAC
181 GGCAAGGTGG ACGGGACGCG GGACCGGAGT GACCAGCACA TTCAGCTGCA GCTCAGCGCG
241 GAAGATGTGG GCGAGGTCTA TATAAAGAGC ACAGCGTCGG GGCAGTACCT GGCAATGGAC
301 ACCAACGGGC TCCTGTATGG CTCGCAGCTA CCAGGCGAGG AGTGCTTGTT CCTTGAGAGG
361 CTCGAGGAGA ACCATTACAA CACATACATC TCCAAAAAGC ACGCAGACAA GAACTGGTTC
421 GTCGGGCTGA AGAAAAACGG GAACAGCAAG CTGGGGCCGC GGACTCACTA TGGGCAAAAG
481 GCGATCCTCT TCCTCCCATT GCCGGTGTCG GCTGACTGA
```

Alpaca FGF1 gene coding sequence (1-155, excluding 1-57) (SEQ ID NO: 93) (Ensembl accession no. ENSVPAT00000008395, which is hereby incorporated by reference in its entirety):
```
  1 CAGCTGCAGC TCAGTGCGGA AAGCGTGGGG GAGGTGTATA TAAAGAGTAC CGAGACTGGC
 61 CAGTACTTGG CCATGGACAC CGACGGGCTT TTGCACGGCT CACAGACACC AAATGAGGAA
121 TGTTTGTTCC TGGAAAGGCT GGAGGAGAAC CATTACAACA CCTACGTC CAAGAAGCAC
181 GCCGAAAAGA ATTGGTTTGT TGGTCTCAAG AAGAATGGAA GCTGCAAACG CGGTCCTCGG
241 ACTCACTACG GCCAGAAGGC GATCTTGTTT CTCCCCTTGC CAGTCTCCTC TGATTAA
```

Anole lizard FGF1 gene coding sequence (1-155) (SEQ ID NO: 94) (Ensembl accession no. ENSACAT00000013467, which is hereby incorporated by reference in its entirety):
```
  1 ATGGCTGAAG GTGAAATAAC AACATTCACA GCCTTGACCG AGAGGTTTGC TCTCCCAATG
 61 GAGAATTACA AGAAGCCCAA ACTCCTGTAT TGCAGCAATG GAGGCCACTT CCTGAGGATC
121 CTTCCAGATG GAAAAGTGGA TGGCACCATG GACCGGAATG ACAGCTATAT TCAGTTGCTG
181 TTAACAGCAG AAGATGTGGG TGTGGTATAT ATAAAAGGCA CTGAGACCGG GCAGTACTTG
241 GCCATGGATG CCAATGGACA TTTATATGGC TCGCAGTTGC CAACAGAAGA GTGTTTATTT
301 GTGGAAACGC TGGAAGAAAA CCATTACAAT ACATATACCT CAAAGATGCA TGGCGATAAG
361 AAGTGGTATG TTGCTTGAA AAAGAATGGG AAAGGCAAAC TGGGGCCACG GACTCATCGC
421 GGCCAAAAGG CAATACTTTT CCTTCCACTG CCAGTATCAC CTGATTAG
```

Bushbaby FGF1 gene coding sequence (1-155) (SEQ ID NO: 95) (Ensembl accession no. ENSOGAT00000005081, which is hereby incorporated by reference in its entirety):
```
  1 ATGGCTGAAG GGGAAATCAC AACCTTCACA GCCCTCACAG AGAAGTTTAA TCTGCCTCTA
 61 GGAAATTACA AGAAGCCCAA GCTCCTCTAC TGTAGCAACG GGGTCACTTT TCTGAGGATC
121 CTGCCGGATG GCACCGTGGA TGGGACACAA GACAGGAGCG ACCAGCACAT TCAGCTGCAG
181 CTCAGTGCGG AAAGCGTGGG GGAGGTGTAT ATAAAGAGTA CCCAGACTGG CCAGTACTTG
241 GCCATGGACT CCGACGGGCT TTTATACGGC TCACAAACAC CAAATGAGGA ATGCCTGTTC
301 CTGGAACGGC TGGAGGAAAA CCATTACAAC ACCTATGTGT CCAAGAAGCA CGCCGAGAAG
```

TABLE 2 -continued

```
361 AATTGGTTTG TCGGTCTCAA GAAGAACGGA AGTTGCAAAC GTGGTCCTCG GACTCACTAC
421 GGCCAGAAAG CAATCTTGTT TCTCCCCCTG CCAGTCTCCT CTGATTAA
```

Cat FGF1 gene coding sequence (1-155) (SEQ ID NO: 96) (Ensembl accession no. ENSFCAT00000009123, which is hereby incorporated by reference in its entirety):

```
  1 ATGGCTGAAG GGGAAATCAC AACCTTCACG GCCCTGACGG AGAAGTTCAA TCTGCCTCCA
 61 GGGAATTACA AGAAACCCAA ACTCCTCTAC TGTAGCAACG GGGGCCACTT CCTGAGGATC
121 CTTCCAGATG GCACAGTGGA TGGGACGAGG GACAGGAGCG ACCAGCACAT TCAGCTGCAG
181 CTCAGTGCGG AAAGCGTGGG GGAGGTGTAT ATAAAGAGTA CCGAGACTGG CCAGTACTTG
241 GCCATGGACA CCGACGGGCT TTTGTACGGC TCACAGACAC CAAATGAGGA TGCTTGTTC
301 CTGGAAAGGC TGGAAGAAAA CCATTACAAC ACCTACACAT CCAAGAAGCA CGCAGAAAAG
361 AATTGGTTTG TGGGTCTCAA GAAGAATGGA AGCTGCAAAC GCGGTCCCCG GACTCACTAT
421 GGCCAGAAGG CAATTTTGTT TCTCCCCCTG CCAGTCTCCT CTGATTAA
```

Chinese softshell turtle FGF1 gene coding sequence (1-155) (SEQ ID NO: 97) (Ensemb accession no. EN5P5IT00000016432, which is hereby incorporated by reference in its entirety):

```
131            ATGGCTGAAG GGGAAATAAC AACGTTCACC GCCCTGACCG AAAAATTCAA
181 CCTTCCCCTG GGGAATTACA AGAATCCCAA ACTCTTATAT TGCAGCAATG GAGGCTACTT
241 CTTGAGGATA CATCCAGATG GCAAAGTAGA TGGGACAAGG GACCGAAGTG ACCAACACAT
301 TCAGCTGCAG CTAAGTGCGG AAAGCGTGGG TGAGGTATAT ATAAAGAGCA CTGAGTCTGG
361 ACAGTTTTTG GCTATGGACG CCAATGGACT TTTATATGGA TCACTGTCAC CGAGTGAGGA
291 ATGCTTATTC TTGGAAAGAA TGGAAGAAAA TCATTATAAC ACCTACATCT CCAAGAAGCA
351 TGCAGACAAG AACTGGTTCG TTGGCTTAAA GAAGAATGGA AGCTGCAAAC TGGGACCGCG
411 GACGCACTAC GGCCAAAAGG CCGTCCTTTT CCTTCCACTG CCAGTGTCAG CTGATTAA
```

Coelacanth FGF1 gene coding sequence (1-155) (SEQ ID NO: 98) (Ensembl accession no. ENSLACT00000015212, which is hereby incorporated by reference in its entirety):

```
  1 ATGGCTGAAG ACAAAATAAC AACACTGAAG GCCTTGGCTG AAAAATTTAA CCTTCCTATG
 61 GGAAATTACA AGAAAGCAAA ACTCCTCTAC TGCAGCAACG GAGGGTATTT CCTGCGAATA
121 CCCCCAGACG GGAAAGTGGA AGGAATTAGA GAACGAAGCG ACAAGTACAT TCAGCTGCAA
181 ATGAATGCAG AAAGTTTAGG CATGGTGTCT ATAAAGGGTG TGGAGGCAGG GCAATACCTA
241 GCTATGAATA CAAATGGACT CCTGTATGGA TCTCAGTCTC TAACTGAAGA ATGCCTTTTC
301 ATGGAAAAGA TGGAAGAAAA CCACTACAAC ACATACAGGT CTAAGACACA TGCAGATAAA
361 AACTGGTATG TTGGCATTAG AAAGAACGGT AGCATCAAAC CAGGACCAAG GACTCACATT
421 GGCCAAAAGG CTGTTCTTTT TCTCCCTCTG CCTGCCTCGA GTGATTAG
```

Dolphin FGF1 gene coding sequence (1-155) (SEQ ID NO: 99) (Ensembl accession no. ENSTTRT00000004742, which is hereby incorporated by reference in its entirety):

```
  1 ATGGCTGAAG GGGAAATCAC AACCTTCACA GCCCTGACCG AGAAGTTTAA TCTGCCTCCA
 61 GGGAATTACA AGAAGCCCAA ACTCCTCTAC TGTAGCAACG GGGGCCACTT CCTGAGGATC
121 CTTCCAGATG GCACAGTGGA TGGGACAAGG GACAGGAGTG ACCAGCACAT TCAGCTGCAG
181 CTCAGTGCGG AAAGCGTGGG GGAGGTGTAT ATAAAGAGTA CGGAGACTGG CCAGTACTTG
241 GCCATGGACA CCGACGGGCT TTTGTACGGC TCACAGACAC CAATGAGGA TGTTTGTTC
301 CTGGAAAGGT TGGAGGAAAA CCATTACAAC ACCTACGCAT CCAAGAAGCA TGCAGAAAAG
361 AATTGGTTCG TTGGTCTCAA GAAGAACGGA AGCTGCAAAC GCGGTCCTCG GACTCACTAC
421 GGCCAGAAAG CAATCTTGTT TCTCCCCCTG CCAGTCTCCT CCGATTAA
```

Ferret FGF1 gene coding sequence (1-155) (SEQ ID NO: 100) (Ensembl accession no. ENSMPUT00000008013 which is hereby incorporated by reference in its entirety):

```
  1                               ATGGCT GAAGGGGAAA TCACAACCTT
 61 CACAGCCCTG ATGGAGAAGT TTAATCTGCC TGCGGGGAAT TACAAGAAGC CCAAACTCCT
121 CTACTGTAGC AATGGGGGCC ACTTCCTGAG GATCCTTCCA GATGGCACAG TGGACGGCAC
181 AAGGGACAGG AGCGACCAGC ACATTCAGCT GCAGCTCAGT GCGGAAAGCG TGGGGGAGGT
241 GTACATAAAG AGTACCGAGA CTGGCCAGTA CTTGGCCATG GACACCGATG GCTTTTGTA
301 CGGCTCACAA ACACCAAATG AGGAATGTCT GTTCCTGGAA AGGCTGGAGG AAAACCATTA
361 CAACACCTAC ACATCCAAGA AGCACGCTGA AGAGAATTGG TTTGTAGGTC TCAAGAAGAA
421 CGGAAGCTGC AAACGCGGTC CTCGGACTCA CTATGGCCAG AAAGCAATTC TGTTTCTCCC
481 CCTGCCAGTC TCCTCTGATT AA
```

Gibbon FGF1 gene coding sequence (1-155) (SEQ ID NO: 101) (Ensembl accession no. ENSNLET00000012455, which is hereby incorporated by reference in its entirety):

```
241                                           ATGG CCGAAGGGGA
301 AATCACCACC TTCACAGCCC TGACCGAGAA GTTTAATCTG CCTCCAGGGA ATTACAAGAA
361 GCCCAAACTC CTCTACTGTA GCAACGGGGG CCACTTCCTG AGGATCCTTC CGGATGGCAC
421 AGTGGATGGG ACAAGGGACA GGAGCGACCA GCACATTCAG CTGCAGCTCA GTGCGGAAAG
481 CGTGGGGGAG GTGTATATAA AGAGTACCGA GACTGGCCAG TACTTGGCCA TGGACACCGA
541 CGGGCTTTTA TACGGCTCAC AGACACCAAA TGAGGAATGT TTGTTCCTGG AAAGGCTGGA
601 GGAGAACCAT TACAACACCT ATATCCAA GAAGCATGCA GAGAAGAATT GGTTTGTTGG
661 CCTCAAGAAG AATGGAAGCT GCAAACGCGG TCCTCGGACT CACTATGGCC AGAAAGCAAT
721 CTTGTTTCTC CCCCTGCCAG TCTCTTCTGA TTAA
```

TABLE 2 -continued

Gorilla FGF1 gene coding sequence (1-155) (SEQ ID NO: 102) (Ensembl
accession no. ENSGGOT00000025344, which is hereby incorporated by
reference in its entirety):
```
 121                                             ATGG CTGAAGGGGA
 181 AATCACCACC TTCACAGCCC TGACCGAGAA GTTTAATCTG CCTCCAGGGA ATTACAAGAA
 241 GCCCAAACTC CTCTACTGTA GCAATGGGGG CCACTTCTTG AGGATCCTTC CGGATGGCAC
 301 AGTGGATGGG ACAAGGGACA GGAGCGACCA GCACATTCAG CTGCAGCTCA GTGCGGAAAG
 361 CGTGGGGGAG GTGTATATAA AGAGTACCGA GACTGGCCAG TACTTGGCCA TGGACACCGA
 421 CGGGCTTTTA TACGGCTCAC AGACACCCAA TGAGGAATGT TTGTTCCTGG AAAGGCTGGA
 481 GGAGAACCAT TACAACACCT ATATATCCAA GAAGCATGCA GAGAAGAATT GGTTTGTTGG
 541 CCTCAAGAAG AATGGAAGCT GCAAACGCGG TCCTCGGACT CACTATGGCC AGAAAGCAAT
 601 CTTGTTTCTC CCCCTGCCAG TCTCTTCCGA TTAA
```

Hedgehog FGF1 gene coding sequence (1-155) (SEQ ID NO: 103) (Ensembl
accession no. ENSEEUT00000005832, which is hereby incorporated by
reference in its entirety):
```
   1 ATGGCTGAAG GAGAAATCAC CACCTTCACG GCCCTGACTG AGAAGTTTAA TCTGCCACTA
  61 GGGAATTACA AGAAGCCCAA GCTCCTCTAC TGTAGCAACG GGGGCCACTT CCTGAGGATC
 121 CTTCCAGATG GCACCGTGGA TGGGACAAGG GACAGGAGCG ACCAGCATAT TCAGCTGCAG
 181 CTCAGTGCGG AAAGCGTGGG GGAGGTGTAT ATAAAGAGTA CGGAGACTGG CCAGTACTTG
 241 GCCATGGACA CCGACGGGCT TTTATACGGC TCACAAACAC CAAATGAGGA ATGTCTGTTC
 301 CTTGAAAGGC TGGAAGAGAA CCATTACAAT ACCTACACAT CCAAGAAGCA TGCCGAGAAG
 361 AACTGGTTTG TTGGCCTCAA GAAGAATGGA AGCTGCAAGC GTGGTCCTCG GACTCATTAT
 421 GGCCAGAAAG CTATTTTGTT TCTCCCCCTG CCAGTTTCCT CTGATTAA
```

Hyrax FGF1 gene coding sequence (1-155, excluding 1-90) (SEQ ID NO: 104)
(Ensembl accession no. ENSPCAT00000011746, which is hereby incorporated
by reference in its entirety):
```
   1 ATGGCTGAAG GCGAAATCAC AACCTTCACA GCCCTGACTG AGAAGTTTAA CCTGCCACTA
  61 GAGAATTACA AGAAGCCCAA ACTCCTCTAC TGTAGCAACG GAGGCCACTT CCTGAGGATC
 121 CTTCCGGACG GCACAGTGGA TGGCACCAGG GACAGGAGTG ACCAGCACAT TCAGCTGCAG
 181 CTCAGTGCGG AAAGCGTGGG GGAGGTGTAT ATAAGGGGCA CCGAGACTGG CCAGTACTTG
 241 GCCATGGACA CCGACGGGCT TTTATATGGC TCA
```

Kangaroo rat FGF1 gene coding sequence (1-155, excluding 1-16 and 58-155)
(SEQ ID NO: 105) (Ensembl accession no. ENSDORT00000007345, which is
hereby incorporated by reference in its entirety):
```
   1 ATGGCTGAAG GGGAAATCAC AACCTTCACA GCCCTGACGG AAAGGTTTAA ----------
  51 ---------- ---------- ---------- ---------- ---------T TCAGCTGCAA
  62 CTGAGTGCGG AAAGCGTGGG GGAGGTCTAT ATAAAGAGCA CCGAGACTGG CCAATACTTG
 122 GCCATGGATG CCGACGGGCT TTTATACGGC TCACAGACAC CTGATGAAGA ATGCTTGTTC
 182 CTGGAGAGGC TGGAAGAAAA TCATTATAAC ACCTACATAG CCAAGAAACA TGCTGAAAAG
 242 AATTGGTTTG TCGGCCTCAA AAAGAATGGA AGCTGCAAGC GTGGTCCTCG GACTCACTAT
 302 GGCCAGAAAG CAATCCTGTT CCTCCCCTTG CCTGTCTCCT CTGATTAG
```

Lamprey FGF1 gene coding sequence (1-155, excluding 94-155) (SEQ ID
NO: 106) (Ensembl accession no. ENSPMAT00000010729, which is hereby
incorporated by reference in its entirety):
```
   1 ATGGAGGTGG GCCACATCGG CACGCTGCCC GTGGTCCCCG CGGGGCCCGT GTTCCCCGGC
  61 AGTTTCAAGG AGCCACGGCG CCTCTACTGC CGCAGCGCGG GCCACCACCT CCAGATCCTG
 121 GGGGACGGCA CCGTGAGTGG CACCCAGGAC GAGAACGAGC CCCACGCCGT TCTGCAGCTG
 181 CAGGCGGTGC GCCGCGGGGT GGTGACGATC CGTGGGCTCT GCGCCGAGAG GTTCCTCGCC
 241 ATGAGCACGG AGGGACACCT GTACGGGCG GTGAGG
```

Lesser hedgehog tenrec FGF1 gene coding sequence (1-155, excluding 1-57)
(SEQ ID NO: 107) (Ensembl accession no. ENSETET00000017851, which is
hereby incorporated by reference in its entirety):
```
   1 CAGCTGAAGC TCGTTGCCGA AAGCGTGGGG GTGGTGTATA TAAAGAGCAT CAAGACCGGC
  61 CAGTACTTGG CCATGAACCC CGACGGGCTT TTATACGGCT CCGAGACCCC AGAGGAAGAA
 121 TGCTTGTTCC TGGAAACGCT GGAGGAAAAC CACTACACCA CCTTCAAATC TAAGAAGCAC
 181 GTAGAGAAGA ATTGGTTCGT TGGTCTCCGG AAGAATGGAA GGGTCAAGAT CGGGCCTCGG
 241 ACTCACCAAG GCCAGAAAGC AATCTTGTTC CTGCCCCTCC CGGTGTCCTC TGATTAA
```

Rhesus monkey FGF1 gene coding sequence (1-155) (SEQ ID NO: 108) (Ensembl
accession no. ENSMMUT00000033070, which is hereby incorporated by
reference in its entirety):
```
  36 ATGGC TGAAGGGGAA ATCACCACGT
  61 TCACAGCCCT GACCGAGAAG TTTAATCTGC CTCCAGGGAA TTACAAGAAG CCCAAACTGC
 121 TCTACTGTAG CAATGGGGGC CACTTCTTGA GGATCCTTCC GGATGGCACA GTGGATGGGA
 181 CAAGGGACAG GAGCGACCAG CACATTCAGC TGCAGCTCAG TGCGGAAAGC GTGGGGGAGG
 241 TGTATATAAA GAGTACCGAG ACTGGCCAGT ACTTGGCCAT GGACACCGAC GGGCTTTTAT
 301 ACGGCTCACA GACACCCAAT GAGGAATGTT TGTTCCTGGA AAGGCTGGAG GAGAACCATT
 361 ACAACACCTA TATCCAAG AAGCACGCAG AGAAGAATTG GTTTGTTGGC CTCAAGAAGA
 421 ATGGAAGCTG CAAACGTGGT CCTCGGACTC ACTATGGCCA GAAAGCAATC TTGTTTCTTC
 481 CCCTGCCAGT CTCTTCTGAT TAA
```

TABLE 2 -continued

Megabat FGF1 gene coding sequence (1-155) (SEQ ID NO: 109) (Ensembl
accession no. ENSPVAT00000004596, which is hereby incorporated by
reference in its entirety):
```
  1 ATGGCCGAGG GGGAAGTCAC GACGTTCACG GCCCTGACCG AGAGGTTTAA CCTGCCTCCA
 61 GGGAATTACA AGAAGCCCAA ACTTCTCTAC TGCAGCAACG GGGCCACTT CCTGAGGATC
121 CTCCCAGATG GCACAGTGGA TGGGACAAGG GACAAGAGCC ACCAGCACAT TCAGCTGCAG
181 CTCAGTGCGG AAAGTGTGGG GGAGGTGTAT ATAAAGAGCA CCGAGAGTGG CCAGTACTTG
241 GCCATGGACT CCGACGGGCT TTTGTACGGC TCACAGACAC CAGATGAGGA CTGTTTGTTC
301 CTGGAAAGGC TGGAGGAAAA CCATTACAAC ACCTACACAT CCAAGAAGCA CGCAGAGAAG
361 AATTGGTTTG TTGGGCTCAA GAAGAATGGA AGCTGCAAGC GCGGTCCCCG GACTCACTAC
421 GGCCAGAAAG CGATCCTGTT TCTCCCCCTG CCAGTCTCCT CTGATTAG
```

Microbat FGF1 gene coding sequence (1-155) (SEQ ID NO: 110) (Ensembl
accession no. ENSMLUT00000007098, which is hereby incorporated by
reference in its entirety):
```
 66         ATGGC TGAGGGGGAA GTCACCACAT TCACGGCCCT GACCGAGAGG TTCAATCTGC
121 CTCTGGAGAA CTACAAGAAG CCCAAGCTTC TCTACTGCAG CAACGGGGGC CACTTCCTGC
181 GGATCCTCCC AGACGGCACC GTGGACGGGA CGAGGGACAG GAGCGACCAG CACATTCAGC
241 TGCAGCTCAG TGCGGAAAGC GTGGGGGAGG TGTATATAAA GAGCACCGAG AGTGGCCAGT
301 ACTTGGCCAT GGACTCCGAC GGGCTTTTGT ACGGCTCACA AACACCCAAT GGGAATGTT
361 TGTTCCTGGA AAGGCTGGAG GAGAACCACT ACAACCCTA CACGTCCAAG AAGCACGCAG
421 AAAAGAATTG GTTCGTTGGG CTCAAGAAGA ACGGAAGCTG CAAGCGTGGT CCTCGGACGC
481 ATTATGGCCA GAAAGCAATT TTGTTTCTCC CCCTGCCAGT CTCCTCCGAT TAA
```

Mouse lemur FGF1 gene coding sequence (1-155) (SEQ ID NO: 111) (Ensembl
accession no. ENSMICT00000009454, which is hereby incorporated by
reference in its entirety):
```
  1 ATGGCCGAAG GGGAGATCAC AACCTTCACG GCCCTCACCG AGAAGTTTAA CCTGCCTCCG
 61 GGGAACTACA AGAAGCCCAA GCTCCTCTAC TGCAGCAACG GCGGCCACTT CCTGCGCATC
121 CTTCCCGACG GCACCGTGGA TGGCACGAGA GACAGGAGCC ACCAGCACAT TCAGCTGCAG
181 CTCAGTGCGG AAAGCGCGGG GGAGGTGTAT ATAAAGAGCA CCCAGACTGG CCGGTACTTG
241 GCCATGGACG CCGACGGGCT TTTATACGGC TCACAAACAC CAAATGAGGA ATGTTTGTTC
301 CTGGAAAGGC TGGAGGAAAA CCATTACAAC ACCTACGTAT CCAAGAAGCA CGCAGAGAAG
361 AATTGGTTTG TTGGCCTCAA GAAGAATGGA AGTTGCAAAC GCGGCCCCCG GACTCACTAT
421 GGCCAGAAAG CAATCTTGTT TCTGCCCCTG CCAGTCTCCT CTGATTAA
```

Pika FGF1 gene coding sequence (1-155, excluding 57-67) (SEQ ID NO: 112)
(Ensembl accession no. ENSOPRT00000012854, which is hereby incorporated
by reference in its entirety):
```
  1 ATGGCCGAGG GAGAAGTCAC CACCTTCTCA GCCCTGACGG AGAAGTTCAA TCTGCCTGGA
 61 GGAAACTACA AGTTGCCCAA GCTCCTTTAC TGTAGCAACG GAGGCCACTT CCTGAGGATC
121 CTTCCAGATG GCACAGTGGA TGGGACCAGG GACAGGAGCC ACCTGCACA- ----------
170 ---------- ---------- -GAGGTGTTT ATAAAGAGTA CGGAGACTGG CCAGTACTTG
209 GCTATGGACA CCGATGGCCT TTTATATGGC TCGCAGACAC CCAGTGAGGA GTGTTTGTTC
269 CTGGAGCGGC TGGAGGAGAA CCACTACAAC ACCTACACAT CCAAGAAGCA TGCCGAGAAG
329 AACTGGTTTG TGGGCATCAA GAAGAATGGA AGCTGCAAGC GTGGTCCTCG GACTCACTAC
389 GGCCAGAAAG CCATCTTGTT TCTCCCTCTG CCAGTCTCTT CTGACTAA
```

Rat FGF1 gene coding sequence (1-155) (SEQ ID NO: 113) (Ensembl accession
no. ENSRNOT00000018577, which is hereby incorporated by reference in its
entirety):
```
268                          ATG GCCGAAGGGG AGATCACAAC CTTTGCAGCC
301 CTGACCGAGA GGTTCAATCT GCCTCTAGGG AACTACAAAA AACCCAAACT GCTCTACTGC
361 AGCAACGGGG GCCACTTCTT GAGGATTCTT CCCGATGGCA CCGTGGATGG GACCAGGGAC
421 AGGAGCGACC AGCACATTCA GCTGCAGCTC AGTGCGGAAA GCGCGGGCGA AGTGTATATA
481 AAGGGTACAG AGACTGGCCA GTACTTGGCC ATGGACACCG AAGGGCTTTT ATACGGCTCG
541 CAGACACCAA ATGAAGAATG CCTATTCCTG GAAAGGCTAG AGAAAACCA TTATAACACT
601 TACACATCCA AGAAGCACGC GGAGAAGAAC TGGTTTGTGG GCCTCAAGAA GAACGGGAGT
661 TGTAAGCGCG GTCCTCGGAC TCACTACGGC CAGAAAGCCA TCTTGTTTCT CCCCCTCCCG
721 GTATCTTCTG ACTAA
```

Sloth FGF1 gene coding sequence (1-155) (SEQ ID NO: 114) (Ensembl
accession no. ENSCHOT00000012416, which is hereby incorporated by
reference in its entirety):
```
  1 ATGGCTGAAG GGAAATCAC AACCTTCACA GCTCTGATGG AGAAGTTTAA CCTGCCACCA
 61 GGGAATTACA TGAAGCCCAA ACTCCTCTAC TGTAGCAACG GGGGCCACTT CTTGAGGATC
121 CTTCCAGACG GCACAGTGGA TGGGACAAGG GACAGGAGCC ACCTGCACAT TCAGCTGCAG
181 CTCAGTGCGG AAAGCGTGGG GGAGGTGTAT ATAAAGAGTG CGGAGACCGG CCAGTACTTA
241 GCCATGGACA CCGGCGGGCT TTTATACGGC TCACAGACAC CAAGTGAGGA ATGCCTGTTC
301 CTAGAAAGGC TGGAGGAAAA CCATTACAAC ACCTACGTCA TCCAAGAAGCA TGCGGAGAAG
361 AACTGGTTCG TTGGCCTAAA GAAGAATGGA AGCAGCAAAC GCGGCCCCCG GACTCACTAT
421 GGCCAGAAAG CCATCTTGTT TCTTCCCCTG CCAGTCTCCT CTGATTAA
```

Squirrel FGF1 gene coding sequence (1-155) (SEQ ID NO: 115) (Ensembl
accession no. ENSSTOT00000029249, which is hereby incorporated by
reference in its entirety):
```
  1                                                                 ATGG
  5 CTGAAGGGGA AATCACAACC TTCACAGCCC TGACCGAGAA GTTCAATCTG CCTCCAGGGA
 65 ACTACAAGAA GCCCAAACTG CTCTACTGTA GCAACGGAGG CCACTTCTTG AGGATCCTTC
```

TABLE 2 -continued

```
125 CTGATGGCAC AGTGGATGGG ACAAGAGACA GGAGCGACCA ACACATTCAG CTGCAGCTCA
185 GTGCGGAAAG CGTGGGGGAG GTGTATATAA AGAGTACCGA GACCGGCCAG TACTTGGCCA
245 TGGACACCGA CGGGCTTTTA TATGGCTCAC AGACCCCAAA TGAGGAATGC TTATTCCTGG
305 AAAGGCTGGA GGAAAACCAT TACAACACGT ACACATCCAA GAAGCATGCA GAGAAGAATT
365 GGTTTGTTGG CCTCAAGAAG AACGGAAGCT GCAAGCGCGG TCCCCGGACT CACTATGGCC
425 AGAAAGCGAT CTTGTTTCTC CCACTGCCTG TCTCCTCTGA TTAG
```

Tarsier FGF1 gene coding sequence (1-155) (SEQ ID NO: 116) (Ensembl accession no. ENSTSYT00000007425, which is hereby incorporated by reference in its entirety):
```
  1 ATGGCCGAAG GGGAAATCAC AACCTTCACA GCCCTGACCG AGAAGTTCAA CCTGCCCCCG
 61 GGGAATTACA AGAAGCCCAA ACTCCTCTAC TGCAGCAACG GGGCCACTT CTTGAGGATC
121 CTTCCGGATG GCACTGTGGA TGGAACGAGG GACAGGAGCG ACCAGCACAT TCAGCTGCAG
181 CTCAGCGCGG AAAGCGTGGG GGAGGTGTAT ATAAAGAGTA CCGAGACCGG CCAGTACTTG
241 GCCATGGACA CCGACGGGCT TTTGTACGGC TCACAGACAC CAAATGAGGA GTGTCTGTTC
301 CTGGAAAGGC TGGAAGAGAA TCATTACAAT ACCTACGTGT CCAAGAAGCA TGCGGAGAAG
361 AATTGGTTTG TCGGCCTCAA GAAGAATGGA AGCTGCAAAC GCGGTCCTCG GACTCACTAT
421 GGCCAGAAAG CAATCTTGTT TCTCCCCCTG CCAGTTTCCT CTGATTAA
```

Tree shrew FGF1 gene coding sequence (1-155) (SEQ ID NO: 117) (Ensembl accession no. ENSTBET00000011861, which is hereby incorporated by reference in its entirety):
```
  1 ATGGCTGAAG GGGAAATCAC GACCTTCGCA GCCCTGACCG AGAAGTTTGA TCTGCCTCCA
 61 GGGAATTACA AGAAGCCCAA ACTTCTCTAC TGTAGCAACG GGGCCATTT CTTGAGGATT
121 CTTCCAGATG GCACCGTGGA TGGGACAAGA GACAGGAGCG ACCAGCACAT TCAGCTGCAG
181 CTCACTGCGG AAAACGTGGG GGAGGTGTAC ATAAAGAGTA CGGAGACTGG CCAGTACTTG
241 GCCATGGACG CCGACGGGCT TTTATATGGC TCACAGACAC CAAACGAGGA ATGTTTGTTC
301 CTGGAAAGGC TGGAGGAGAA CCATTACAAC ACCTACATAT CCAAGAAGCA CGCAGAGAAG
361 AATTGGTTTG TTGCCCTCAA GAAGAACGGA AGCTGCAAAC TCGGTCCTCG GACTCACTAT
421 GGCCAGAAAG CAATCTTGTT TCTCCCCCTG CCAGTCTCCT CTGATTAA
```

Turkey FGF1 gene coding sequence (1-155, excluding 57-155) (SEQ ID NO: 118) (Ensembl accession no. ENSMGAT00000017372, which is hereby incorporated by reference in its entirety):
```
  1 ATGGCCGAGG GGGAGATAAC CACCTTCACA GCCCTGACCG AGCGCTTCGG CCTGCCGCTG
 61 GGCAACTACA AGAAGCCCAA ACTCCTGTAC TGCAGCAACG GGGCCACTT CCTACGGATC
121 CTGCCGGACG GCAAGGTGGA CGGGACGCGG GACCGGAGCG ACCAGCAC
```

Wallaby FGF1 gene coding sequence (1-155) (SEQ ID NO: 119) (Ensembl accession no. ENSMEUT00000016544, which is hereby incorporated by reference in its entirety):
```
  1 ATGGCCGAAG GGGAGATCAC AACCTTCACA GCCCTGACCG AAAGATTTAA CCTGCCACTG
 61 GGGAATTACA AGAAGCCCAA GCTTCTCTAC TGTAGCAATG GGGCCACTT TTTGAGGATC
121 CTTCCTGATG GCAAAGTGGA TGGGACAAGG GACAGAAATG ATCAACACAT TCAACTGCAA
181 CTAAGCGCGG AAAGCGTGGG TGAGGTGTAT ATAAAGACTA CTGAGTCTGG GCAGTATTTG
241 GCCATGGACA CCAATGGACT TTTATATGGC TCACAGACCC CCAGCGAAGA ATGCTTATTC
301 CTGGAGAGGT TGGAGGAGAA TCATTACAAC ACCTACATAT CAAAGAAGCA TGCGGAGAAA
361 AATTGGTTTG TTGGCCTCAA GAAGAACGGA AGTTGCAAAA GAGGTCCCAG GACTCACTAT
421 GGCCAGAAAG CCATCCTATT CCTTCCCCTC CCTGTGTCCT CTGAGTAA
```

Zebrafish FGF1 gene coding sequence (1-147) (SEQ ID NO: 120) (Ensembl accession no. ENSDART00000005842, which is hereby incorporated by reference in its entirety):
```
178                                                              ATG
181 ACCGAGGCCG ATATTGCGGT AAAGTCCAGC CCGCGCGACT ATAAAAAACT GACGCGGCTG
241 TACTGTATGA ATGGAGGATT TCACCTTCAG ATCCTGGCGG ACGGGACAGT GGCTGGAGCA
124 GCAGACGAAA ACACATACAG CATACTGCGC ATAAAAGCAA CAAGTCCAGG AGTGGTGGTG
184 ATCGAAGGAT CAGAAACAGG TCTTTACCTC TCGATGAATG AACATGGCAA GCTGTACGCT
244 TCATCATTAG TGACGGATGA AAGTTATTTC CTGGAGAAGA TGGAGGAAAA CCACTACAAC
304 ACATATCAGT CTCAAAAGCA CGGTGAAAAC TGGTACGTCG GAATAAAAAA GAACGGGAAA
364 ATGAAACGGG GCCCAAGAAC TCACATCGGA CAAAAGGCCA TTTTCTTTCT TCCACGACAG
424 GTGGAGCAGG AAGAGGACTG A
```

As noted above, also encompassed within the present invention are portions of paracrine FGFs other than FGF1 (e.g., FGF2, FGF4, FGF5, FGF6, FGF9, FGF16, and FGF20). The portions derived from paracrine FGF2 include portions corresponding to the above-identified amino acid sequences of FGF1. Corresponding portions may be determined by, for example, sequence analysis and structural analysis.

In one embodiment, the paracrine FGF is FGF2. In one embodiment, the portion of the FGF2 is derived from human FGF2 having the amino acid sequence of SEQ ID NO: 121 (GenBank Accession No. EAX05222, which is hereby incorporated by reference in its entirety), as follows:

```
  1 MAAGSITTLP ALPEDGGSGA FPPGHFKDPK RLYCKNGGFF LRIHPDGRVD GVREKSDPHI

61 KLQLQAEERG VVSIKGVCAN RYLAMKEDGR LLASKCVTDE CFFFERLESN NYNTYRSRKY

121 TSWYVALKRT GQYKLGSKTG PGQKAILFLP MSAKS
```

In one embodiment, the portion of the paracrine FGF includes an amino acid sequence beginning at any one of residues 1 to 25 and ending at any one of residues 151 to 155 of SEQ ID NO: 121. In one embodiment, the portion of the paracrine FGF includes amino acid residues 1-151, 1-152, 1-153, 1-154, 1-155, 2-151, 2-152, 2-153, 2-154, 2-155, 3-151, 3-152, 3-153, 3-154, 3-155, 4-151, 4-152, 4-153, 4-154, 4-155, 5-151, 5-152, 5-153, 5-154, 5-155, 6-151, 6-152, 6-153, 6-154, 6-155, 7-151, 7-152, 7-153, 7-154, 7-155, 8-151, 8-152, 8-153, 8-154, 8-155, 9-151, 9-152, 9-153, 9-154, 9-155, 10-151, 10-152, 10-153, 10-154, 10-155, 11-151, 11-152, 11-153, 11-154, 11-155, 12-151, 12-152, 12-153, 12-154, 12-155, 13-151, 13-152, 13-153, 13-154, 13-155, 14-151, 14-152, 14-153, 14-154, 14-155, 15-151, 15-152, 15-153, 15-154, 15-155, 16-151, 16-152, 16-153, 16-154, 16-155, 17-151, 17-152, 17-153, 17-154, 17-155, 18-151, 18-152, 18-153, 18-154, 18-155, 19-151, 19-152, 19-153, 19-154, 19-155, 20-151, 20-152, 20-153, 20-154, 21-155, 21-151, 21-152, 21-153, 21-154, 21-155, 22-151, 22-152, 22-153, 22-154, 22-155, 23-151, 23-152, 23-153, 23-154, 23-155, 24-151, 24-152, 24-153, 24-154, 24-155, 25-151, 25-152, 25-153, 25-154, or 25-155 of FGF2 (SEQ ID NO: 121). In one embodiment, the portion of the paracrine FGF includes amino acid residues 1-151 or 1-152 of SEQ ID NO: 121.

In one embodiment, the portion of the paracrine FGF of the chimeric protein includes an amino acid sequence that has at least 80%, at least 85%, at least 90%, at least 95%, at least 97% or at least 99% amino acid sequence identity to the corresponding amino acid sequence of native paracrine FGF (e.g., SEQ ID NO: 121). In one embodiment, the portion of the paracrine FGF includes an amino acid sequence that has at least 80%, at least 85%, at least 90%, at least 95%, at least 97% or at least 99% amino acid sequence identity to an amino acid sequence beginning at any one of residues 1 to 25 and ending at any one of residues 151 to 155 of SEQ ID NO: 121. In one embodiment, the portion of the paracrine FGF includes an amino acid sequence that has at least 80%, at least 85%, at least 90%, at least 95%, at least 97% or at least 99% amino acid sequence homology to the corresponding amino acid sequence of native paracrine FGF (e.g., SEQ ID NO: 121). In one embodiment, the portion of the paracrine FGF includes an amino acid sequence that has at least 80%, at least 85%, at least 90%, at least 95%, at least 97% or at least 99% amino acid sequence homology to an amino acid sequence beginning at any one of residues 1 to 25 and ending at any one of residues 151 to 155 of SEQ ID NO: 121.

Also encompassed within the present invention are portions of paracrine FGFs other than FGF2 (e.g., FGF1, FGF4, FGF5, FGF6, FGF9, FGF16, and FGF20). The portions derived from paracrine FGFs other than FGF2 include portions corresponding to the above-identified amino acid sequences of FGF2. Corresponding portions may be determined by, for example, sequence analysis and structural analysis.

In one embodiment of the present invention, the portion of the paracrine FGF is derived from an ortholog of a human paracrine FGF. In one embodiment of the present invention, the portion of the paracrine FGF of the chimeric protein is derived from an ortholog of human FGF2. In one embodiment, the portion of the FGF2 is derived from *Gorilla gorilla, Pongo abelii, Macaca mulatta, Pan troglodytes, Pan paniscus, Saimiri boliviensis boliviensis, Nomascus leucogenys, Equus caballus, Bos taurus, Papio Anubis, Vicugna pacos, Ovis aries, Capreolus capreolus, Loxodonta Africana, Sus scrofa, Ailuropoda melanoleuca, Choloepus hoffmanni, Bubalus bubalis, Canis lupus familiaris, Rattus norvegicus, Heterocephalus glaber, Otolemur garnettii, Mus musculus, Ictidomys tridecemlineatus, Felis catus, Cavia porcellus, Sarcophilus harrisii, Monodelphis domestica, Oryctolagus cuniculus, Meleagris gallopavo, Gallus gallus, Taeniopygia guttata, Cynops pyrrhogaster, Xenopus laevis, Didelphis albiventris, Myotis lucifugus, Anolis carolinensis, Dasypus novemcinctus, Tupaia belangeri, Xenopus silurana tropicalis, Latimeria chalumnae, Tetraodon nigroviridis, Gasterosteus aculeatus, Takifugu rubripes, Oncorhynchus mykiss, Salmo salar, Danio rerio, Oreochromis niloticus,* or *Oryzias latipes*. The portions of an ortholog of human paracrine FGF include portions corresponding to the above-identified amino acid sequences of FGF2. Corresponding portions may be determined by, for example, sequence analysis and structural analysis.

In one embodiment, the portion of the FGF2 of the chimeric protein of the present invention is derived from an ortholog of human FGF2 having the amino acid sequence shown in Table 3.

TABLE 3

```
Amino acid sequence of Gorilla gorilla (gorilla) FGF2 (SEQ ID NO: 122)
(Ensembl accession no. ENSGGOP00000004720, which is hereby
incorporated by reference in its entirety):
104                                                 MAAGSI TTLPALPEDG
120 GSGAFPPGHF KDPKRLYCKN GGFFLRIHPD GRVDGVREKS DPHIKLQLQA EERGVVSIKG
180 VCANRYLAMK EDGRLLASKC VTDECFFFER LESNNYNTYR SRKYTSWYVA LKRTGQYKLG
240 SKTGPGQKAI LFLPMSAKS Amino acid sequence of Pongo abelii (sumatran orangutan) FGF2 (SEQ ID
NO: 123) (GenBank accession no. XP_002815172, which is hereby
incorporated by reference in its entirety):
168                                                 MAA GSITTLPALP
181 EDGGSGAFPP GHFKDPKRLY CKNGGFFLRI HPDGRVDGVR EKSDPHIKLQ LQAEERGVVS
241 IKGVCANRYL AMKEDGRLLA SKCVTDECFF FERLESNNYN TYRSRKYTSW YVALKRTGQY
301 KLGSKTGPGQ KAILFLPMSA KS
```

TABLE 3 -continued

Amino acid sequence of *Macaca mulatta* (rhesus monkey) FGF2 (SEQ ID
NO: 124) (GenBank accession no. XP_001099284, which is hereby
incorporated by reference in its entirety):
```
 83                 MAAGSITT LPALPEDGGS GAFPPGHFKD PKRLYCKNGG
121 FFLRIHPDGR VDGVREKSDP HIKLQLQAEE RGVVSIKGVC ANRYLAMKED GRLLASKCVT
181 DECFFFERLE SNNYNTYRSR KYTSWYVALK RTGQYKLGSK TGPGQKAILF LPMSAKS
```

Amino acid sequence of *Pan troglodytes* (chimpanzee) FGF2 (SEQ ID
NO: 125) (GenBank accession no. NP_001103711, which is hereby
incorporated by reference in its entirety):
```
134             MAAGSIT TLPALPEDGG SGAFPPGHFK DPKRLYCKNG GFFLRIHPDG
181 RVDGVREKSD PHIKLQLQAE ERGVVSIKGV CANRYLAMKE DGRLLASKCV TDECFFFERL
241 ESNNYNTYRS RKYTSWYVAL KRTGQYKLGS KTGPGQKAIL FLPMSAKS
```

Amino acid sequence of *Pan paniscus* (Pygmy chimpanzee) FGF2 (SEQ ID
NO: 126) (GenBank accession no. XP_003816481, which is hereby
incorporated by reference in its entirety):
```
112                                                     MAAGSITTL
121 PALPEDGGSG AFPPGHFKDP KRLYCKNGGF FLRIHPDGRV DGVREKSDPH IKLQLQAEER
181 GVVSIKGVCA NRYLAMKEDG RLLASKCVTD ECFFFERLES NNYNTYRSRK YTSWYVALKR
241 TGQYKLGSKT GPGQKAILFL PMSAKS
```

Amino acid sequence of *Saimiri boliviensis boliviensis* (Bolivian
squirrel monkey) FGF2 (SEQ ID NO: 127) (GenBank accession no.
XP_003936290, which is hereby incorporated by reference in its
entirety):
```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 TSWYVALKRT GQYKLGSKTG PGQKAILFLP MSAKS
```

Amino acid sequence of *Nomascus leucogenys* (Northern white-cheeked
gibbon) FGF2 (SEQ ID NO: 128) (GenBank accession no. XP_003271404,
which is hereby incorporated by reference in its entirety):
```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 TSWYVALKRT GQYKLGSKTG PGQKAILFLP MSAKS
```

Amino acid sequence of *Equus caballus* (horse) FGF2 (SEQ ID NO: 129)
(GenBank accession no. NP_001182150, which is hereby incorporated by
reference in its entirety):
```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 SSWYVALKRT GQYKLGPKTG PGQKAILFLP MSAKS
```

Amino acid sequence of *Bos taurus* (cattle) FGF2 (SEQ ID NO: 130)
(GenBank accession no. NP_776481, which is hereby incorporated by
reference in its entirety):
```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 SSWYVALKRT GQYKLGPKTG PGQKAILFLP MASKS
```

Amino acid sequence of *Papio anubis* (Olive baboon) FGF2 (SEQ ID
NO: 131) (GenBank accession no. XP_003899210, which is hereby
incorporated by reference in its entirety):
```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 TSWYVALKRT GQYKLGSKTG PGQKAILFLP MSAKS
```

Amino acid sequence of *Vicugna pacos* (alpaca) FGF2 (SEQ ID NO: 132)
(Ensembl accession no. ENSVPAP00000009804, which is hereby
incorporated by reference in its entirety):
```
111 MAAGSITTLP
121 ALPEDGGSGA FPPGHFKDPK RLYCKNGGFF LRIHPDGRVD GVREKSDPHI KLQLQAEERG
181 VVSIKGVCAN RYLAMKEDGR LLASKCVTDE CFFFERLESN NYNTYRSRKY SSWYVALKRT
241 GQYKLGPKTG PGQKAILFLP MSAKS
```

Amino acid sequence of *Ovis aries* (sheep) FGF2 (SEQ ID NO: 133)
(GenBank accession no. NP_001009769, which is hereby incorporated by
reference in its entirety):
```
  1 MAAGSITTLP ALPEDGGSSA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 SSWYVALKRT GQYKLGPKTG PGQKAILFLP MSAKS
```

Amino acid sequence of *Capreolus capreolus* (Western roe deer) FGF2
(partial amino acid sequence corresponding to human FGF2 residues 42
to 149)(SEQ ID NO: 134) (GenBank accession no. AAF73226, which is
hereby incorporated by reference in its entirety):
```
  1 RIHPDGRVDG VREKSDPHIK LQLQAEERGV VSIKGVCANR YLAMKEDGRL LASKCVTDEC
 61 FFFERLESNN YNTYRSRKYS SWYVALKRTG QYKLGPKTGP GQKAILFL
```

TABLE 3 -continued

Amino acid sequence of *Loxodonta africana* (elephant) FGF2 (partial amino acid sequence corresponding to human FGF2 residues 60 to 155) (SEQ ID NO: 135) (Ensembl accession no. ENSLAFP00000008249, which is hereby incorporated by reference in its entirety):
```
  1 VKLQLQAEER GVVSIKGVCA NRYLAMKEDG RLLASRCVTD ECFFFERLES NNYNTYRSRK
 61 YTSWYVALKR TGQYKLGSKT GPGQKAILFL PMSAKS
```

Amino acid sequence of *Sus scrofa* (pig) FGF2 (partial amino acid sequence corresponding to human FGF residues 36 to 155) (SEQ ID NO: 136) (GenBank accession no. CAE11791 and Ensembl accession no. ENSSSCP00000009695, which is hereby incorporated by reference in its entirety):
```
  1 NGGFFLRIHP DGRVDGVREK SDPHIKLQLQ AEERGVVSIK GVCANRYLAM KEDGRLLASK
 61 CVTDECFFFE RLESNNYNTY RSRKYSSWYV ALKRTGQYKL GPKTGPGQKA ILFLPMSAKS
```

Amino acid sequence of *Ailuropoda melanoleuca* (panda) FGF2 (partial amino acid sequence corresponding to human FGF2 residues 60 to 155)(SEQ ID NO: 137) (Ensembl accession no. ENSAMEP00000018489, which is hereby incorporated by reference in its entirety):
```
  1 VKLQLQAEER GVVSIKGVCA NRYLAMKEDG RLLASKCVTD ECFFFERLES NNYNTYRSRK
 61 YSSWYVALKR TGQYKLGPKT GPGQKAILFL PMSAKS
```

Amino acid sequence of *Choloepus hoffmanni* (sloth) FGF2 (SEQ ID NO: 138) (Ensembl accession no. ENSCHOP00000010051, which is hereby incorporated by reference in its entirety):
```
 14                                                        MAAGSIT
 21 TLPALPEDGG SGALPPGHFK DPKRLYCKNG GFFLRIHPDG RVDGVREKSD PHIKLQLQAE
 81 ERGVVSIKGV CANRYLAMKE DGRLQASKCV TDECFFFERL ESNNYNTYRS RKYSSWYVAL
141 KRTGQYKLGP KTGPGQKAIL FLPMSAKS
```

Amino acid sequence of *Bubalus bubalis* (water buffalo) FGF2 (SEQ ID NO: 139) (GenBank accession no. AFH66795, which is hereby incorporated by reference in its entirety):
```
  1 MAAGSITTLP PLPEDGGSGA PPPGHFKDPK RLYCKNGGFF LRIHPDGRVD GVREKSDPHI
 61 KLQLQAEERG VVSIKGVCAN RYLAMKEDGR LLASKCVTDE CFFFERLESS NYNTYRSRKY
121 SSWYVALKRT GQYKLGPKTG PGQKAILFLP MSAKS
```

Amino acid sequence of *Canis lupus familiaris* (dog) FGF2 (SEQ ID NO: 140) (GenBank accession no. XP_003432529, which is hereby incorporated by reference in its entirety):
```
 40                                        M AAGSITTLPA LPEDGGSGAF
 61 PPGHFKDPKR LYCKKGGFFL RIHPDGRVDG VREKSDPHVK LQLQAEERGV VSIKGVCANR
121 YLAMKEDGRL LASKCVTDEC FFFERLESNN YNTYRSRKYS SWYVALKRTG QYKLGPKTGP
181 GQKAILFLPM SAKS
```

Amino acid sequence of *Rattus norvegicus* (Norway rat) FGF2 (SEQ ID NO: 141) (GenBank accession no. NP_062178, which is hereby incorporated by reference in its entirety):
```
  1 MAAGSITSLP ALPEDGGGAF PPGHFKDPKR LYCKNGGFFL RIHPDGRVDG VREKSDPHVK
 61 LQLQAEERGV VSIKGVCANR YLAMKEDGRL LASKCVTEEC FFFERLESNN YNTYRSRKYS
121 SWYVALKRTG QYKLGSKTGP GQKAILFLPM SAKS
```

Amino acid sequence of *Heterocephalus glaber* (naked mole-rat) FGF2 (partial amino acid sequence corresponding to human FGF2 residues 22 to 155) (SEQ ID NO: 142) (GenBank accession no. EHB17407, which is hereby incorporated by reference in its entirety):
```
  1 ppghfkdpkr lycknggffl rihpdgrvdg vreksdphvk lqlqaeergv vsikgvcanr
 61 ylamkedgrl laskcvtdec ffferlesnn yntyrsrkys swyvalkrtg qyklgsktgp
121 gqkailflpm saks
```

Amino acid sequence of *Otolemur garnettii* (bushbaby) FGF (SEQ ID NO: 143) (Ensembl accession no. ENSOGAP00000021960, which is hereby incorporated by reference in its entirety):
```
 52                                                      MAAGSITTL
 61 PSLPEDGGSD AFPPGHFKDP KRLYCKNGGF FLRIHPDGRV DGVREKSDPY IKLQLQAEER
121 GVVSIKGVCA NRYLAMKEDG RLLASKLITD ECFFFERLES NNYNTYRSRK YSSWYVALKR
181 TGQYKLGSKT GPGQKAILFL PMSAKS
```

Amino acid sequence of *Mus musculus* (house mouse) FGF2 (SEQ ID NO: 144) (GenBank accession no. NP_032032, which is hereby incorporated by reference in its entirety):
```
  1 MAAGITSLP ALPEDGGAAF PPGHFKDPKR LYCKNGGFFL RIHPDGRVDG VREKSDPHVK
 61 LQLQAEERGV VSIKGVCANR YLAMKEDGRL LASKCVTEEC FFFERLESNN YNTYRSRKYS
121 SWYVALKRTG QYKLGSKTGP GQKAILFLPM SAKS
```

TABLE 3 -continued

Amino acid sequence of *Ictidomys tridecemlineatus* (squirrel) FGF2
(partial amino acid sequence corresponding to human FGF2 residues 12
to 155) (SEQ ID NO: 145) (Ensembl accession no. EN55T0P00000015653,
which is hereby incorporated by reference in its entirety):
  1 LPEDGGGGAF PPGHFKDPKR LYCKNGGFFL RIHPDGRVDG VREKSDPHIK LQLQAEDRGV
 61 VSIKGVCANR YLAMKEDGRL LASKCVTDEC FFFERLESNN YNTYRSRKYS SWYVALKRTG
121 QYKLGSKTGP GQKAILFLPM SAKS Amino acid sequence of *Felis catus* (domestic cat) FGF2 (partial amino
acid sequence corresponding to human FGF2 residues 25 to 130) (SEQ ID
NO: 146) (GenBank accession no. ABY47638, which is hereby incorporated
by reference in its entirety):
  1 HFKDPKRLYC KNGGFFLRIH PDGRVDGVRE KSDPHIKLQL QAEERGVVSI KGVCANRYLA
 61 MKEDGRLLAS KCVTDECFFF ERLESNNYNT YRSRKYSSWY VALKRT Amino acid sequence of *Cavia porcellus* (guinea pig) FGF2 (partial
amino acid sequence corresponding to human FGF2 residues 60 to 155)
(SEQ ID NO: 147) (Ensembl accession no. ENSCPOP00000004847, which is
hereby incorporated by reference in its entirety):
  1 VKLQLQAEDR GVVSIKGVCA NRYLAMKEDG RLLASKCVTD ECFFFERLES NNYNTYRSRK
 61 YSSWYVALKR TGQYKLGSKT GPGQKAILFL PMSAKS Amino acid sequence of *Sarcophilus harrisii* (Tasmanian devil) FGF2
(SEQ ID NO: 148) (Ensembl accession no. EN55HAP00000012215, which is
hereby incorporated by reference in its entirety):
 48                                            MAA GSITTLPALA
 61 GDGASGGAFP PGHFQDPKRL YCKNGGFFLR IHPDGHVDGI REKSDPHIKL QLQAEERGVV
121 SIKGVCANRY LAMKEDGRLL ALKCVTEECF FFERLESNNY NTYRSRKYSN WYVALKRTGQ
181 YKLGSKTGPG QKAILFLPMS AKS Amino acid sequence of *Monodelphis domestica* (gray short-tailed
opossum) FGF2 (SEQ ID NO: 149) (GenBank accession no. NP_001029148,
which is hereby incorporated by reference in its entirety):
  1 MAAGSITTLP ALSGDGGGGG AFPPGHFKDP KRLYCKNGGF FLRIHPDGRV DGIREKSDPN
 61 IKLQLQAEER GVVSIKGVCA NRYLAMKEDG RLLALKYVTE ECFFFERLES NNYNTYRSRK
121 YSNWYVALKR TGQYKLGSKT GPGQKAILFL PMSAKS Amino acid sequence of *Oryctolagus cuniculus* (rabbit) FGF2 (SEQ ID
NO: 150) (GenBank accession no. XP_002717284, which is hereby
incorporated by reference in its entirety):
  1 MAAESITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 SSWYVALKRT GQYKLGSKTG PGQKAILFLP MSAKS Amino acid sequence of *Meleagris gallopavo* (turkey) FGF2 (partial
amino acid sequence corresponding to human FGF2 residues 31 to 155)
(SEQ ID NO: 151) (Ensembl accession no. ENSMGAP00000010977, which is
hereby incorporated by reference in its entirety):
  1 RLYCKNGGFF LRINPDGRVD GVREKSDPHI KLQLQAEERG VVSIKGVSAN RFLAMKEDGR
 61 LLALKCATEE CFFFERLESN NYNTYRSRKY SDWYVALKRT GQYKPGPKTG PGQKAILFLP
121 MSAKS Amino acid sequence of *Gallus gallus* (chicken) FGF2 (SEQ ID NO: 152)
(GenBank accession no. NP_990764
  1 maagaagsit tlpalpddgg ggafppghfk dpkrlyckng gfflrinpdg rvdgvreksd
 61 PHIKLQLQAE ERGVVSIKGV SANRFLAMKE DGRLLALKCA TEECFFFERL ESNNYNTYRS
121 RKYSDWYVAL KRTGQYKPGP KTGPGQKAIL FLPMSAKS Amino acid sequence of *Taeniopygia guttata* (zebra finch) FGF2 (SEQ ID
NO: 153) (GenBank accession no. XP_002188397, which is hereby
incorporated by reference in its entirety):
  1 MAAAGGIATL PDDGGSGAFP PGHFKDPKRL YCKNGGFFLR INPDGKVDGV REKSDPHIKL
 61 QLQAEERGVV SIKGVSANRF LAMKEDGRLL ALKYATEECF FFERLESNNY NTYRSRKYSD
121 WYVALKRTGQ YKPGPKTGPG QKAILFLPMS AKS Amino acid sequence of *Cynops pyrrhogaster* (Japanese firebelly newt)
FGF2 (SEQ ID NO: 154) (GenBank accession no. BAB63249, which is hereby
incorporated by reference in its entirety):
  1 MAAGSITSLP ALPEDGNGGT FTPGGFKEPK RLYCKNGGFF LRINSDGKVD GAREKSDSYI
 61 KLQLQAEERG VVSIKGVCAN RYLAMKDDGR LMALKWITDE CFFFERLESN NYNTYRSRKY
121 SDWYVALKRT GQYKNGSKTG AGQKAILFLP MSAKS Amino acid sequence of *Xenopus laevis* (African clawed frog) FGF2 (SEQ
ID NO: 155) (GenBank accession no. NP_001093341, which is hereby
incorporated by reference in its entirety):
  1 MAAGSITTLP TESEDGGNTP FSPGSFKDPK RLYCKNGGFF LRINSDGRVD GSRDKSDSHI
 61 KLQLQAVERG VVSIKGITAN RYLAMKEDGR LTSLRCITDE CFFFERLEAN NYNTYRSRKY
121 SSWYVALKRT GQYKNGSSTG PGQKAILFLP MSAKS TABLE 3 -continued Amino acid sequence of *Didelphis albiventris* (white-eared opossum) FGF2 (SEQ ID NO: 156) (GenBank accession no. ABL77404, which is hereby incorporated by reference in its entirety):
```
  1 MAAGSITTLP ALSGDGGGGG AFPPGHFKDP KRLYCKNGGF FLRIHPDGRV DGIREKSDPN
 61 IKLQLQAEER GVVSIKGVCA NRYLAMKEDG RLLALKYVTE ECFFFERLES NNYNTYRSRK
121 YSNWYVALKR TGQYKLGSKT GPGQKAILFS PCLLRC
```

Amino acid sequence of *Myotis lucifugus* (microbat) FGF2 (partial amino acid sequence corresponding to human FGF2 residues 60 to 155) (SEQ ID NO: 157) (Ensembl accession no. ENSMLUP00000017859, which is hereby incorporated by reference in its entirety):
```
  1 VKLQLQAEER GVVSIKGVCA NRYLAMKEDG RLQASKCVTD ECFFFERLES NNYNTYRSRK
 61 YSSWYVALKR NGQYKLGPKT GPGQKAILFL PMSAKS
```

Amino acid sequence of *Anolis carolinensis* (anole lizard) FGF2 (partial amino acid sequence corresponding to human FGF2 residues 16 to 155) (SEQ ID NO: 158) (Ensembl accession no. ENSACAP00000011657, which is hereby incorporated by reference in its entirety):
```
  1 AAAASFPPGP FKDPKRLYCK NGGFFLRINP DGGVDGVREK SDPNIKLLLQ AEERGVVSIK
 61 GVCANRFLAM NEDGRLLALK YVTDECFFFE RLESNNYNTY RSRKYRDWYI ALKRTGQYKL
121 GPKTGRGQKA ILFLPMSAKS
```

Amino acid sequence of *Dasypus novemcinctus* (armadillo) FGF2 (partial amino acid sequence corresponding to human FGF2 residues 1 to 94) (SEQ ID NO: 159) (Ensembl accession no. ENSDNOP00000011351, which is hereby incorporated by reference in its entirety):
```
124    MAAGSIT TLPALPEDGG SGAFPPGHFK DPKRLYCKNG GFFLRIHPDG RVDGVREKSD
181 PNIKLQLQAE ERGVVSIKGV CANRYLAMRE DGRLQAS
```

Amino acid sequence of *Tupaia belangeri* (tree shrew) FGF2 (SEQ ID NO: 160) (Ensembl accession no. ENSTBEP00000000985, which is hereby incorporated by reference in its entirety):
```
  1 AGVRAEREEA PGSGDSRGTD PAARSLIRRP DAAAREALLG ARSRVQGSST SWPASSRTGI
 61 KLPDDSGQGM GGYPLDRPSR STGRGLGGAP DPAVKLQLQA EERGVVSIKG VCANRYLAMK
121 EDGRLLASKC VTDECFFFER LESNNYNTYR SRKYSSWYVA LKRTGQYKLG SKTGPGQKAI
181 LFLPMSAKS
```

Amino acid sequence of *Xenopus silurana tropicalis* (western clawed frog) FGF2 (SEQ ID NO: 161) (GenBank accession no. NP_001017333, which is hereby incorporated by reference in its entirety):
```
  1 MAAGSITTLP TESEDGNTPF PPGNFKDPKR LYCKNGGYFL RINSDGRVDG SRDKSDLHIK
 61 LQLQAVERGV VSIKGITANR YLAMKEDGRL TSLKCITDEC FFYERLEANN YNTYRSRKNN
121 SWYVALKRTG QYKNGSTTGP GQKAILFLPM SAKS
```

Amino acid sequence of *Latimeria chalumnae* (coelacanth) FGF2 (SEQ ID NO: 162) (Ensembl accession no. ENSLACP00000019200, which is hereby incorporated by reference in its entirety):
```
  1 MAAGGITTLP AVPEDGGSST FPPGNFKEPK RLYCKNGGYF LRINPDGRVD GTREKNDPYI
 61 KLQLQAESIG VVSIKGVCSN RYLAMNEDCR LFGLKYPTDE CFFHERLESN NYNTYRSKKY
121 SDWYVALKRT GQYKPGPKTG LGQKAILFLP MSAKS
```

Amino acid sequence of *Tetraodon nigroviridis* (spotted green pufferfish) FGF2 (SEQ ID NO: 163) (GenBank accession no. CAG04681, which is hereby incorporated by reference in its entirety):
```
 34 MATGGIT TLPSTPEDGG SSGFPPGSFK
 61 DPKRLYCKNG GFFLRIKSDG VVDGIREKSD PHIKLQLQAT SVGEVVIKGV CANRYLAMNR
121 DGRLFGTKRA TDECHFLERL ESNNYNTYRS RKYPTMFVGL TRTGQYKSGS KTGPGQKAIL
181 FLPMSAKC
```

Amino acid sequence of *Gasterosteus aculeatus* (stickleback) FGF2 (SEQ ID NO: 164) (Ensembl accession no. ENSGACP00000022078, which is hereby incorporated by reference in its entirety):
```
  1 MATAGFATLP STPEDGGSGG FTPGGFKDPK RLYCKNGGFF LRIRSDGGVD GIREKSDAHI
 61 KLQIQATSVG EVVIKGVCAN RYLAMNRDGR LFGVRRATDE CYFLERLESN NYNTYRSRKY
121 PGMYVALKRT GQYKSGSKTG PGQKAILFLP MSAKC
```

Amino acid sequence of *Takifugu rubripes* (fugu rubripes) FGF2 (SEQ ID NO: 165) (GenBank accession no. CAD19830, which is hereby incorporated by reference in its entirety):
```
  1 MATGGITTLP STPEDGGSGG FPPGSFKDPK RLYCKNGGFF LRIRSDGAVD GTREKTDPHI
 61 KLQLQATSVG EVVIKGVCAN RYLAMNRDGR LFGMKRATDE CHFLERLESN NYNTYRSRKY
121 PNMFVGLTRT GNYKSGTKTG PCQKAILFLP MSAKY
```

Amino acid sequence of *Oncorhynchus mykiss* (rainbow trout) FGF2 (SEQ ID NO: 166) (GenBank accession no. NP_001118008, which is hereby incorporated by reference in its entirety):
```
  1 MATGEITTLP ATPEDGGSGG FLPGNFKEPK RLYCKNGGYF LRINSNGSVD GIRDKNDPHN
 61 KLQLQATSVG EVVIKGVSAN RYLAMNADGR LFGPRRTTDE CYFMERLESN NYNTYRSRKY
121 PEMYVALKRT GQYKSGSKTG PGQKAILFLP MSARR
```

TABLE 3 -continued

Amino acid sequence of *Salmo salar* (salmon) FGF2 (SEQ ID NO: 167)
(GenBank accession no. ACJ02099, which is hereby incorporated by
reference in its entirety):
  1 MATGEITTLP ATPEDGGSGG FPPGNFKDPK RLYCKNGGYF LRINSNGSVD GIREKNDPHK
 61 QPQFVRAWTL QGVKRSTGML AHVDSNASHN CVKVAGCSLG EFGSMSNRPH NRRPRVATPA
121 QDLHIRLLHL RDRLKPATRT ADKTEEYFCL Amino acid sequence of *Danio rerio* (zebrafish) FGF2 (SEQ ID NO: 168)
(GenBank accession no. AAP32155, which is hereby incorporated by
reference in its entirety):
  1 MATGGITTLP AAPDAENSSF PAGSFRDPKR LYCKNGGFFL RINADGRVDG ARDKSDPHIR
 61 LQLQATAVGE VLIKGICTNR FLAMNADGRL FGTKRTTDEC YFLERLESNN YNTYRSRKYP
121 DWYVALKRTG QYKSGSKTSP GQKAILFLPM SAKC Amino acid sequence of *Oreochromis niloticus* (Nile tilapia) FGF2 (SEQ
ID NO: 169) (GenBank accession no. XP_003443412, which is hereby
incorporated by reference in its entirety):
  1 MATGGITTLP ATPEDGGSSG FPPGNFKDPK RLYCKNGGFF LRIKSDGGVD GIREKNDPHI
 61 KLQLQATSVG EVVIKGICAN RYLAMNRDGR LFGARRATDE CYFLERLESN NYNTYRSRKY
121 PNMYVALKRT GQYKSGSKTG PGQKAILFLP MSAKC Amino acid sequence of *Oryzias latipes* (medaka) FGF2 (SEQ ID NO: 170)
(Ensembl accession no. ENSORLP00000025834, which is hereby
incorporated by reference in its entirety):
  1 MATGEITTLP SPAENSRSDG FPPGNYKDPK RLYCKNGGLF LRIKPDGGVD GIREKKDPHV
 61 KLRLQATSAG EVVIKGVCSN RYLAMHGDGR LFGVRQATEE CYFLERLESN NYNTYRSKKY
121 PNMYVALKRT GQYKPGNKTG PGQKAILFLP MSAKY As noted above, the portion of the paracrine FGF may be modified to decrease binding affinity for heparin and/or heparan sulfate compared to the portion without the modification. In one embodiment, the modification of the paracrine FGF includes one or more substitutions, additions, or deletions.

In one embodiment, the modification is one or more substitutions located at one or more amino acid residues of SEQ ID NO: 121 selected from N36, K128, R129, K134, K138, Q143, K144, C78, C96, and combinations thereof. In one embodiment, the one or more substitutions are selected from N36T, K128D, R129Q, K134V, K138H, Q143M, K144T/L/I, C78S, C96S, and combinations thereof. In one embodiment, the modification is one or more substitutions which are located at one or more amino acid residues corresponding to residues of SEQ ID NO: 121 selected from N36, K128, R129, K134, K138, Q143, K144, C78, C96, and combinations thereof. In one embodiment, the modification is one or more substitutions which are located at one or more amino acid residues corresponding to residues of SEQ ID NO: 121 selected from N36, K128, R129, K134, K138, Q143, K144, C78, C96, and combinations thereof. Amino acid residues corresponding to those of SEQ ID NO: 121 may be determined by, for example, sequence analysis and structural analysis.

It will be understood that the portion of the paracrine FGF according to the present invention may be derived from a nucleotide sequence that encodes a paracrine FGF protein. For example, in one embodiment, nucleotide sequence is the nucleotide sequence that encodes human FGF2 (GenBank Accession No. NM_002006, which is hereby incorporated by reference in its entirety)(SEQ ID NO: 171), as follows:

```
468                             ATG GCAGCCGGGA
481 GCATCACCAC GCTGCCCGCC TTGCCCGAGG ATGGCGGCAG CGGCGCCTTC CCGCCCGGCC
541 ACTTCAAGGA CCCCAAGCGG CTGTACTGCA AAAACGGGGG CTTCTTCCTG CGCATCCACC
601 CCGACGGCCG AGTTGACGGG GTCCGGGAGA AGAGCGACCC TCACATCAAG CTACAACTTC
661 AAGCAGAAGA GAGAGGAGTT GTGTCTATCA AAGGAGTGTG TGCTAACCGT TACCTGGCTA
721 TGAAGGAAGA TGGAAGATTA CTGGCTTCTA AATGTGTTAC GGATGAGTGT TTCTTTTTTG
781 AACGATTGGA ATCTAATAAC TACAATACTT ACCGGTCAAG GAAATACACC AGTTGGTATG
841 TGGCACTGAA ACGAACTGGG CAGTATAAAC TTGGATCCAA AACAGGACCT GGGCAGAAAG
901 CTATACTTTT TCTTCCAATG TCTGCTAAGA GCTGA
```

In another embodiment of the present invention, the portion of the paracrine FGF of the chimeric protein may be derived from a nucleotide sequence that encodes an ortholog of human FGF2. Nucleotide sequences that encode FGF2 orthologs are shown in Table 4.

TABLE 4

Gorilla FGF2 gene coding sequence (amino acids ("aa") 104-258) (SEQ ID
NO: 172) (Ensembl accession no. ENSGGOT00000004842, which is hereby
incorporated by reference in its entirety):
```
310          ATGGCAGCC GGGAGCATCA CCACGCTGCC CGCCTTGCCC GAGGATGGCG
359 GCAGCGGCGC CTTCCCGCCC GGCCACTTCA AGGACCCCAA GCGGCTGTAC TGCAAAAACG
419 GGGGCTTCTT CCTGCGCATC CACCCCGACG GCCGAGTTGA CGGGGTCCGG GAGAGAGACG
479 ACCCTCACAT CAAGCTACAA CTTCAAGCAG AAGAGAGAGG AGTTGTGTCT ATCAAAGGAG
539 TGTGTGCTAA CCGTTACCTT GCTATGAAGG AAGATGGAAG ATTACTGGCT TCTAAATGTG
599 TTACGGATGA GTGTTTCTTT TTTGAACGAT GGAATCTAA TAACTACAAT ACTTACCGGT
659 CAAGGAAATA CACCAGTTGG TATGTGGCAC TGAAACGAAC TGGGCAGTAT AAACTTGGAT
719 CCAAAACAGG ACCTGGGCAG AAAGCTATAC TTTTTCTTCC AATGTCTGCT AAGAGCTGA
```

Sumatran orangutan FGF2 gene coding sequence (aa 168-322) (SEQ ID NO: 173)
(GenBank accession no. XM_002815126, which is hereby incorporated by
reference in its entirety):
```
504                ATGGCAG CCGGGAGCAT CACCACGCTG CCCGCCTTGC
541 CCGAGGATGG CGGCAGCGGC GCCTTCCCGC CGGGCCACTT CAAGGACCCC AAGCGGCTGT
601 ACTGCAAAAA CGGGGGCTTC TTCCTGCGCA TCCACCCCGA CGGCCGAGTT GACGGGGTCC
661 GAGAGAAGAG CGACCCTCAC ATCAAACTAC AACTTCAAGC AGAAGAAAGA GGAGTTGTGT
721 CTATCAAAGG AGTGTGTGCT AACCGCTACC TTGCTATGAA GGAAGATGGA AGATTACTGG
781 CTTCTAAATG TGTTACGGAT GAGTGTTTCT TTTTTGAACG ATTGGAATCT AATAACTACA
841 ATACTTACCG GTCAAGGAAA TACACCAGTT GGTATGTGGC ACTGAAACGA ACTGGGCAGT
901 ATAAACTTGG ATCCAAAACA GGACCTGGGC AGAAAGCTAT ACTTTTTCTT CCAATGTCTG
961 CTAAGAGCTG A
```

Rhesus monkey FGF2 gene coding sequence (aa 83-237) (SEQ ID NO: 174)
(GenBank accession no. XM_001099284, which is hereby incorporated by
reference in its entirety):
```
247      ATGG CAGCCGGGAG CATCACCACG CTGCCCGCCT TGCCCGAGGA TGGCGGCAGC
301 GGCGCCTTCC CGCCTGGCCA CTTCAAGGAC CCCAAGCGGC TGTACTGCAA AAACGGGGGC
361 TTCTTCCTGC GCATTCACCC CGACGGCCGA GTTGACGGGG TCCGGGAGAA GAGCGACCCT
421 CACATCAAAT TACAACTTCA AGCAGAAGAG AGAGGAGTTG TGTCTATCAA AGGAGTGTGT
481 GCTAACCGTT ACCTTGCTAT GAAGGAAGAT GGAAGATTAC TGGCTTCTAA ATGTGTTACA
541 GATGAGTGTT TCTTTTTTGA ACGATTGGAA TCTAATAACT ACAATACTTA CCGGTCAAGG
601 AAATACACCA GTTGGTATGT GGCACTGAAA CGAACTGGGC AATATAAACT TGGATCCAAA
661 ACAGGACCTG GGCAGAAAGC TATACTTTTT CTTCCAATGT CTGCTAAGAG CTGA
```

Chimpanzee FGF2 gene coding sequence (aa 134-288) (SEQ ID NO: 175)
(GenBank accession no. NM_001110241, which is hereby incorporated by
reference in its entirety):
```
400                                       A TGGCAGCCGG GAGCATCACC
421 ACGCTGCCCG CCTTGCCCGA GGATGGCGGC AGCGGCGCCT TCCCGCCCGG CCACTTCAAG
481 GACCCCAAGC GGCTGTACTG CAAAAACGGG GGCTTCTTCC TGCGCATCCA CCCCGACGGC
541 CGAGTTGACG GGGTCCGGGA GAAGAGCGAC CCTCACATCA AGCTACAACT TCAAGCAGAA
601 GAGAGAGGAG TTGTGTCTAT CAAAGGAGTG TGTGCTAACC GTTACCTTGC TATGAAGGAA
661 GATGGAAGAT TACTGGCTTC TAAATGTGTT ACGGATGAGT GTTTCTTTTT TGAACGATTG
721 GAATCTAATA ACTACAATAC TTACCGGTCA AGGAAATACA CCAGTTGGTA TGTGGCACTG
781 AAACGAACTG GGCAGTATAA ACTTGGATCC AAAACAGGAC TGGGCAGAA AGCTATACTT
841 TTTCTTCCAA TGTCTGCTAA GAGCTGA
```

Pygmy chimpanzee FGF2 gene coding sequence (112-266) (SEQ ID NO: 176)
(GenBank accession no. XM_003816433, which is hereby incorporated by
reference in its entirety):
```
334                           ATGGCAG CCGGGAGCAT CACCACGCTG
361 CCCGCCTTGC CCGAGGATGG CGGCAGCGGC GCCTTCCCGC CGGCCACTT CAAGGACCCC
421 AAGCGGCTGT ACTGCAAAAA CGGGGGCTTC TTCCTGCGCA TCCACCCCGA CGGCCGAGTT
481 GACGGGGTCC GGGAGAAGAG CGACCCTCAC ATCAAGCTAC AACTTCAAGC AGAAGAGAGG
541 GGAGTTGTGT CTATCAAAGG AGTGTGTGCT AACCGTTACC TTGCTATGAA GGAAGATGGA
601 AGATTACTGG CTTCTAAATG TGTTACGGAT GAGTGTTTCT TTTTTGAACG ATTGGAATCT
661 AATAACTACA ATACTTACCG GTCAAGGAAA TACACCAGTT GGTATGTGGC ACTGAAACGA
721 ACTGGGCAGT ATAAACTTGG ATCCAAAACA GGACCTGGGC AGAAAGCTAT ACTTTTTCTT
781 CCAATGTCTG CTAAGAGCTG A
```

Bolivian squirrel monkey FGF2 gene coding sequence (1-155) (SEQ ID
NO: 177) (GenBank accession no. XM_003936241, which is hereby incorporated
by reference in its entirety):
```
23             ATGGCAGC CGGGAGCATC ACCACGCTGC CGCCCTGCC
61  CGAAGACGGC GGCAGCGGCG CCTTCCCGCC CGGCCACTTC AAGACCCCA AGCGGCTGTA
121 CTGCAAAAAC GGGGGCTTCT TCCTGCGCAAT CCACCCCGAC GGCCGAGTGG ACGGGGTCCG
181 GGAGAAGAGC GACCCTCACA TCAAACTACA ACTTCAAGCA AGAGAGAGG GAGTTGTATC
241 TATCAAAGGA GTGTGTGCTA ACCGTTACCT TGCTATGAAG GAAGATGGAA GATTACTGGC
301 TTCTAAATGT GTTACGGACG AGTGTTTCTT TTTTGAACGA TTGGAATCTA ATAACTACAA
361 TACTTACCGA TCAAGGAAAT ACACCAGTTG GTATGTGGCA CTGAAACGAA CTGGGCAGTA
421 TAAACTTGGA TCCAAAACAG GACCTGGGCA GAAAGCTATA CTTTTTCTTC CAATGTCTGC
481 TAAGAGCT GA
```

TABLE 4 -continued

Northern white-cheeked gibbon FGF2 gene coding sequence (aa 1-155) (SEQ
ID NO: 178) (GenBank accession no. XM_003271356, which is hereby
incorporated by reference in its entirety):
```
    435                                                  ATG GCAGCCGGGA
    481 GCATCACCAC GCTGCCCGCC TTGCCGGAGG ATGGCGGCAG CGGCGCCTTC CCGCCCGGCC
    541 ACTTCAAGGA CCCCAAGCGG CTGTACTGCA AAACGGGGG TTTCTTCCTG CGCATCCACC
    601 CCGACGGTCG AGTTGACGGG GTCCGGGAGA AGAGCGACTG TCACATCAAA CTACAACTTC
    661 AAGCAGAAGA GAGAGGAGTT GTGTCTATCA AAGGAGTGTG TGCTAACCGT TACCTTGCTA
    721 TGAAGGAAGA TGGAAGATTA CTGGCTTCTA AATGTGTTAC GGATGAGTGT TTCTTTTTTG
    781 AACGATTGGA ATCTAATAAC TACAATACTT ACCGGTCAAG GAAATACACC AGTTGGTATG
    841 TGGCACTGAA ACGAACTGGG CAGTATAAAC TTGGATCCAA AACAGGACCT GGGCAGAAAG
    901 CTATACTTTT TCTTCCAATG TCTGCTAAGA GCTGA
```

Horse FGF2 gene coding sequence (aa 1-155) (SEQ ID NO: 179) (GenBank
accession no. NM_001195221, which is hereby incorporated by reference in
its entirety):
```
     54                                                        ATGGCAG
     61 CCGGGAGCAT CACCACGCTG CCCGCCCTGC CCGAGGACGG CGGCAGCGGC GCCTTCCCGC
    121 CCGGCCACTT CAAGGACCCC AAGCGGCTCT ACTGCAAAAA CGGGGGCTTC TTCCTGCGCA
    181 TCCACCCCGA CGGCCGAGTG GACGGGGTCC GGGAGAAGAG CGACCCTCAC ATCAAACTAC
    241 AACTTCAAGC AGAAGAGAGA GGGGTTGTGT CTATCAAAGG AGTGTGTGCG AACCGTTATC
    301 TTGCTATGAA GGAAGATGGA AGGTTACTGG CTTCTAAATG TGTTACGGAC GAGTGTTTCT
    361 TTTTTGAACG ATTGGAATCT AATAACTACA ATACTTACCG GTCAAGGAAA TACTCCAGTT
    421 GGTATGTGGC CCTGAAACGA ACGGGGCAGT ATAAACTTGG ACCCAAAACA GGACCTGGAC
    481 AGAAAGCTAT ACTTTTTCTT CCAATGTCTG CTAAGAGCTG A
```

Cattle FGF2 gene coding sequence (aa 1-155) (SEQ ID NO: 180) (GenBank
accession no. NM_174056, which is hereby incorporated by reference in its
entirety):
```
    104                                                  ATGGCCG CCGGGAGCAT
    121 CACCACGCTG CCAGCCCTGC CGGAGGACGG CGGCAGCGGC GCTTTCCCGC GGGCCACTT
    181 CAAGGACCCC AAGCGGCTGT ACTGCAAGAA CGGGGGCTTC TTCCTGCGCA TCCACCCCGA
    241 CGGCCGAGTG GACGGGGTCC GCGAGAAGAG CGACCCACAC ATCAAACTAC AACTTCAAGC
    301 AGAAGAGAGA GGGGTTGTGT CTATCAAAGG AGTGTGACA AACCGTTACC TTGCTATGAA
    361 AGAAGATGGA AGATTACTAG CTTCTAAATG TGTTACAGAC GAGTGTTTCT TTTTTGAACG
    421 ATTGGAGTCT AATAACTACA ATACTTACCG GTCAAGGAAA TACTCCAGTT GGTATGTGGC
    481 ACTGAAACGA ACTGGGCAGT ATAAACTTGG ACCCAAAACA GGACCTGGGC AGAAAGCTAT
    541 ACTTTTTCTT CCAATGTCTG CTAAGAGCTG A
```

Olive baboon FGF2 gene coding sequence (1-155) (SEQ ID NO: 181) (GenBank
accession no. XM_003899161, which is hereby incorporated by reference in
its entirety):
```
    467                                                ATGG CAGCCGGGAG
    481 CATCACCACG CTGCCCGCCT TGCCCGAGGA TGGCGGCAGC GGCGCCTTCC CGCCCGGCCA
    541 CTTCAAGGAC CCCAAGCGGC TGTACTGCAA AAACGGGGGC TTCTTCCTGC GCATTCACCC
    601 CGACGGCCGA GTTGACGGGG TCCGGAGAA GAGCGACCCT CACATCAAAT TACAACTTCA
    661 AGCAGAAGAG AGAGGAGTTG TGTCTATCAA AGGAGTGTGT GCTAACCGTT ACCTTGCTAT
    721 GAAGGAAGAT GGAAGATTAC TGGCTTCTAA ATGTGTTACG GATGAGTGTT TCTTTTTTGA
    781 ACGATTGGAA TCTAATAACT ACAATACTTA CCGGTCAAGG AAATACACCA GTTGGTATGT
    841 GGCACTGAAA CGAACTGGGC AGTATAAACT TGGATCCAAA ACAGGACCTG GGCAGAAAGC
    901 TATACTTTTT CTTCCAATGT CTGCTAAGAG CTGA
```

Alpaca FGF2 gene coding sequence (aa 111-265) (SEQ ID NO: 182) (Ensembl
accession no. ENSVPAT00000010536, which is hereby incorporated by
reference in its entirety):
```
    341                                   ATGGCAGCTG GGAGCATCAC CACGCTGCCC
    361 GCCCTGCCGG AGGACGGCGG CAGCGGCGCC TTCCCGCCCG GCCACTTCAA GGACCCCAAG
    421 CGGTTGTACT GCAAAAACGG GGGCTTCTTC CTGCGCATCC ACCCCGACGG CCGAGTGGAC
    481 GGGGTCCGGG AGAAGAGCGA CCCTCACATC AAACTACAAC TTCAAGCAGA AGAGAGAGGG
    541 GTCGTGTCTA TCAAAGGAGT GTGTGCAAAC CGTTACCTTG CTATGAAGGA AGATGGAAGA
    601 TTACTGGCTT CTAAATGTGT CACAGACGAG TGTTTCTTTT TTGAACGATT GGAATCTAAT
    661 AACTACAATA CTTACCGGTC AAGGAAATAC TCCAGTTGGT ATGTGGCACT GAAACGAACT
    721 GGGCAGTACA AACTTGGACC CAAAACAGGA CCTGGGCAGA AGCTATACT TTTCCTTCCA
    781 ATGTCTGCTA AGAGCTGA
```

Sheep FGF2 gene coding sequence (aa 1-155) (SEQ ID NO: 183) (GenBank
accession no. NM_001009769, which is hereby incorporated by reference in
its entirety):
```
      1 ATGGCCGCCG GGAGCATCAC CACGCTGCCA GCCCTGCCGG AGGACGGCGG CAGCAGCGCT
     61 TTCCCGCCCG GCCACTTTAA GGACCCCAAG CGGCTGTACT GCAAGAACGG GGGCTTCTTC
    121 CTGCGCATCC ACCCCGACGG CCGAGTGGAC GGGGTCCGGG AGAAGAGCGA CCCTCACATC
    181 AAACTACAAC TTCAAGCAGA AGAGAGAGGG GTTGTGTCTA TCAAAGGAGT GTGTGCAAAC
    241 CGTTACCTTG CTATGAAAGA AGATGGAAGA TTACTAGCTT CTAAATGTGT TACAGACGAG
    301 TGTTTCTTTT TTGAACGATT GGAGTCTAAT AACTACAATA CTTACCGGTC AAGGAAATAC
    361 TCCAGTTGGT ATGTGGCACT GAAACGAACT GGGCAGTATA AACTTGGACC CAAAACAGGA
    421 CCTGGGCAGA AAGCTATACT TTTTCTTCCA ATGTCTGCTA AGAGCTGA
```

TABLE 4 -continued

Western roe deer FGF2 gene coding sequence (1-108; partial amino acid
sequence corresponding to human FGF2 residues 42 to 149) (SEQ ID NO: 184)
(GenBank accession no. AF152587, which is hereby incorporated by
reference in its entirety):
```
     1 GCGCATCCAC CCCGACGGCC GAGTGGACGG GGTCCGCGAG AAGAGTGACC CTCACATCAA
    61 ACTACAACTT CAAGCAGAAG AGAGAGGGGT TGTGTCTATC AAAGGAGTGT GTGCGAACCG
   121 TTATCTTGCT ATGAAAGAAG ACGGAAGATT ATTGGCTTCA AAATGTGTTA CAGACGAATG
   181 TTTCTTTTTT GAACGATTGG AGTCTAATAA CTACAATACT TACCGGTCAA GGAAATACTC
   241 CAGTTGGTAT GTGGCACTGA AACGAACTGG GCAGTATAAA CTTGGACCCA AAACAGGACC
   301 TGGGCAGAAA GCTATACTTT TTCTT
```

Elephant FGF2 gene coding sequence (1-96; partial amino acid sequence
corresponding to human FGF2 residues 60 to 155) (SEQ ID NO: 185) (Ensembl
accession no. ENSLAFT00000008249, which is hereby incorporated by
reference in its entirety):
```
     1 GTTAAACTAC AGCTTCAAGC AGAAGAGAGA GGTGTTGTGT CTATCAAAGG AGTGTGTGCC
    61 AACCGTTATC TGGCTATGAA GGAAGATGGA AGATTGCTGG CTTCTAGATG TGTGACAGAT
   121 GAATGTTTCT TCTTTGAACG ACTGGAATCT AATAACTACA ATACTTACCG GTCAAGGAAA
   181 TACACCAGTT GGTATGTGGC ACTGAAACGA ACGGGGCAGT ATAAACTTGG ATCCAAAACA
   241 GGACCTGGAC AGAAAGCTAT ACTTTTTCTT CCCATGTCTG CTAAGAGC
```

Pig FGF2 gene coding sequence (1-120; partial amino acid sequence
corresponding to human FGF2 residues 36 to 155) (SEQ ID NO: 186) (GenBank
accession no. AJ577089 and Ensembl accession no. EN555CT00000009952,
which is hereby incorporated by reference in its entirety):
```
     1 GAACGGGGGC TTCTTCCTGC GCATCCACCC CGACGGCCGA GTGGATGGGG TCCGGGAGAA
    61 GAGCGACCCT CACATCAAAC TACAACTTCA AGCAGAAGAG AGAGGGGTTG TGTCTATCAA
   121 AGGAGTGTGT GCAAACCGTT ATCTTGCTAT GAAGGAAGAT GGAAGATTAC TGGCTTCTAA
   181 ATGTGTTACA GACGAGTGTT TCTTTTTTGA ACGACTGGAA TCTAATAACT ACAATACTTA
   241 CCGGTCGAGG AAATACTCCA GTTGGTATGT GGCACTGAAA CGAACTGGGC AGTATAAACT
   301 TGGACCCAAA ACAGGACCTG GGCAGAAAGC TATACTTTTT CTTCCAATGT CTGCTAAGAG
   361 C
```

Panda FGF2 gene coding sequence (1-96; partial amino acid sequence
corresponding to human FGF2 residues 60 to 155) (SEQ ID NO: 187) (Ensembl
accession no. ENSAMET00000019232, which is hereby incorporated by
reference in its entirety):
```
     1 GTCAAACTGC AACTTCAAGC GGAAGAGAGA GGGGTTGTAT CCATCAAAGG AGTATGTGCA
    61 AATCGCTATC TTGCCATGAA GGAAGATGGA AGATTACTGG CTTCTAAATG TGTTACCGAT
   121 GAGTGTTTCT TTTTTGAGCG ACTGGAATCT AATAACTACA ATACTTACCG GTCAAGGAAA
   181 TACTCCAGTT GGTATGTGGC ACTGAAACGA ACTGGGCAGT ATAAACTTGG ACCCAAAACA
   241 GGACCTGGGC AGAAAGCTAT ACTTTTTCTT CCAATGTCTG CTAAGAGC
```

Sloth FGF2 gene coding sequence (aa 14-168) (SEQ ID NO: 188) (Ensembl
accession no. EN5CH0T00000011394, which is hereby incorporated by
reference in its entirety):
```
    40                                  A TGGCAGCCGG GAGCATCACC
    61 ACGCTGCCCG CCCTGCCCGA GGACGGAGGC AGCGGCGCCT TACCGCCCGG CCACTTCAAA
   121 GATCCCAAGC GGCTCTACTG CAAAAACGGG GGCTTCTTCC TGCGTATCCA TCCCGACGGC
   181 AGAGTGGACG GGGTCCGGGA GAAGAGCGAC CCCCACATCA AACTACAACT TCAAGCAGAA
   241 GAGAGAGGGG TTGTGTCTAT CAAAGGTGTG TGTGCAAACC GATATCTTGC TATGAAGGAA
   301 GATGGAAGAT TACAGGCTTC TAAATGTGTA ACGGACGAGT GTTTCTTTTT TGAACGATTG
   361 GAATCTAATA ACTACAATAC GTACCGATCA AGGAAATACT CCAGTTGGTA TGTGGCACTG
   421 AAACGAACTG GGCAATATAA ACTTGGACCC AAAACAGGAC CTGGGCAGAA AGCCATACTT
   481 TTTCTTCCAA TGTCTGCTAA GAGCTGA
```

Water buffalo FGF2 gene coding sequence (aa 1-155) (SEQ ID NO: 189)
(GenBank accession no. JQ326277, which is hereby incorporated by
reference in its entirety):
```
     1 ATGGCCGCCG GGAGCATCAC CACGCTGCCA CCCCTGCCGG AGGACGGCGG CAGCGGCGCT
    61 TTCCCGCCCG GCCACTTCAA GGACCCCAAG CGGCTGTACT GCAAGAACGG GGGCTTCTTC
   121 CTGCGCATCC ACCCCGACGG CCGAGTGGAC GGGGTCCGCG AGAAGAGCGA CCCACACATC
   181 AAACTACAAC TTCAAGCAGA AGAGAGAGGG GTTGTGTCTA TCAAAGGAGT GTGTGCAAAC
   241 CGTTACCTTG CTATGAAAGA AGATGGAAGA TTACTAGCTT CCAAATGTGT TACAGACGAG
   301 TGTTTCTTTT TTGAACGATT GGAGTCTAGT AACTACAATA CTTACCGGTC AAGGAAATAC
   361 TCCAGTTGGT ATGTGGCACT GAAACGAACT GGGCAGTATA AACTTGGACC CAAAACAGGA
   421 CCTGGGCAGA AAGCTATACT TTTTCTTCCA ATGTCTGCTA AGAGCTGA
```

Dog FGF2 gene coding sequence (aa 40-194) (SEQ ID NO: 190) (GenBank
accession no. XM_003432481, which is hereby incorporated by reference in
its entirety):
```
   118                                                              ATG
   121 GCAGCCGGGA GCATCACCAC GCTGCCCGCC CTGCCGGAGG ACGGCGGCAG CGGCGCCTTC
   181 CCGCCCGGCC ACTTCAAGGA CCCCAAGAGG CTGTACTGCA AAAAGGGGG CTTCTTCCTG
   241 CGGATCCACC CCGACGGCCG GGTGGACGGG GTCCGGGAGA GAGCGATCC CCACGTCAAA
   301 TTGCAACTTC AAGCAGAAGA GAGAGGCGTT GTGTCCATCA AGGAGTATG TGCAAATCGC
   361 TATCTTGCTA TGAAGGAAGA TGGAAGATTA CTGGCTTCTA AATGTGTTAC TGACGAGTGC
```

TABLE 4 -continued

```
421 TTCTTTTTG AACGATTGGA ATCTAATAAC TACAATACTT ACCGGTCAAG GAAATACTCC
481 AGTTGGTATG TGGCACTGAA ACGAACTGGG CAGTATAAAC TTGGACCAAA AACAGGACCT
541 GGGCAGAAAG CTATACTTTT TCTTCCAATG TCTGCTAAGA GCTGA
```

Norway rat FGF2 gene coding sequence (aa 1-154) (SEQ ID NO: 191) (GenBank accession no. NM_019305, which is hereby incorporated by reference in its entirety):

```
533                                                     ATGGCTGC
541 CGGCAGCATC ACTTCGCTTC CCGCACTGCC GGAGGACGGC GGCGGCGCCT TCCCACCCGG
601 CCACTTCAAG GATCCCAAGC GGCTCTACTG CAAGAACGGC GGCTTCTTCC TGCGCATCCA
661 TCCAGACGGC CGCGTGGACG GCGTCCGGGA GAAGAGCGAC CCACACGTCA AACTACAGCT
721 CCAAGCAGAA GAGAGAGGAG TTGTGTCCAT CAAGGGAGTG TGTGCGAACC GGTACCTGGC
781 TATGAAGGAA GATGGACGGC TGCTGGCTTC TAAGTGTGTT ACAGAAGAGT GTTTCTTCTT
841 TGAACGCCTG GAGTCCAATA ACTACAACAC TTACCGGTCA CGGAAATACT CCAGTTGGTA
901 TGTGGCACTG AAACGAACTG GGCAGTATAA ACTCGGATCC AAAACGGGGC CTGGACAGAA
961 GGCCATACTG TTTCTTCCAA TGTCTGCTAA GAGCTGA
```

Naked mole-rat FGF2 gene coding sequence (1-134; partial amino acid sequence corresponding to human FGF2 residues 22 to 155) (SEQ ID NO: 192) (GenBank accession no. JH173674, which is hereby incorporated by reference in its entirety):

```
378500              C CACCCGGCCA CTTCAAGGAC CCAAAGCGGC
378531 TGTACTGCAA AAACGGGGGC TTCTTCCTGC GCATCCACCC CGACGGCCGC
378581 GTGGACGGGG TCCGGGAGAA GAGCGACCCT CACG
418784      TCAAACT ACAACTTCAA GCAGAAGAGA GAGGAGTTGT GTCTATTAAG
418831 GGAGTGTGTG CGAACCGTTA CCTTGCTATG AAGGAAGATG GAAGATTACT
418881 GGCTTCT
433983      AAATGTGT TACAGATGAG TGTTTCTTTT TTGAACGATT GGAATCTAAT
434031 AACTACAATA CTTATCGGTC AAGGAAATAC TCCAGTTGGT ATGTGGCACT
434081 GAAACGAACT GGACAATATA AACTTGGATC CAAAACAGGA CCGGGGCAGA
434131 AAGCTATACT TTTTCTTCCA ATGTCTGCTA AGAGCTGA
```

Bushbaby FGF2 gene coding sequence (aa 52-206) (SEQ ID NO: 193) (Ensembl accession no. EN50GAT00000025228, which is hereby incorporated by reference in its entirety):

```
154                      ATGGCAG CCGGGAGCAT CACCACGCTG
181 CCCTCCCTGC CCGAGGACGG CGGCAGCGAC GCCTTTCCGC CCGGCCACTT CAAGGACCCC
241 AAGCGACTGT ACTGCAAAAA CGGGGGCTTC TTCCTGCGCA TCCACCCCGA CGGCCGAGTG
301 GACGGGGTCC GGGAGAAGAG CGACCCTTAC ATCAAACTAC AACTTCAAGC AGAAGAGAGA
361 GGAGTTGTGT CTATCAAAGG AGTGTGTGCG AACCGTTACC TTGCTATGAA GGAAGACGGA
421 AGATTGCTGG CTTCTAAATT GATTACAGAC GAGTGCTTCT TTTTTGAACG ACTGGAATCT
481 AATAACTACA ATACTTACCG GTCAAGAAAA TACTCCAGTT GGTATGTGGC ACTGAAACGA
541 ACTGGACAGT ATAAACTTGG ATCCAAAACA GGACCTGGGC AGAAAGCTAT ACTTTTTCTT
601 CCAATGTCTG CTAAGAGCTG A
```

House mouse FGF2 gene coding sequence (aa 1-154) (SEQ ID NO: 194) (GenBank accession no. NM 008006, which is hereby incorporated by reference in its entirety):

```
198                ATG GCTGCCAGCG GCATCACCTC GCTTCCCGCA CTGCCGGAGG
241 ACGGCGGCGC CGCCTTCCCA CCAGGCCACT TCAAGGACCC CAAGCGGCTC TACTGCAAGA
301 ACGGCGGCTT CTTCCTGCGC ATCCATCCCG ACGGCCGCGT GGATGGCGTC CGCGAGAAGA
361 GCGACCCACA CGTCAAACTA CAACTCCAAG CAGAAGAGAG AGGAGTTGTG TCTATCAAGG
421 GAGTGTGTGC CAACCGGTAC CTTGCTATGA AGGAAGATGG ACGGCTGCTG GCTTCTAAGT
481 GTGTTACAGA AGAGTGTTTC TTCTTTGAAC GACTGGAATC TAATAACTAC AATACTTACC
541 GGTCACGGAA ATACTCCAGT TGGTATGTGG CACTGAAACG AACTGGGCAG TATAAACTCG
601 GATCCAAAAC GGGACCTGGA CAGAAGGCCA TACTGTTTCT TCCAATGTCT GCTAAGAGCT
661 GA
```

Squirrel FGF2 gene coding sequence (1-144; partial amino acid sequence corresponding to human FGF2 residues 12 to 155) (SEQ ID NO: 195) (Ensembl accession no. ENSSTOT00000022105, which is hereby incorporated by reference in its entirety):

```
  1 CTGCCCGAGG ACGGCGGCGG CGGCGCCTTC CCGCCCGGCC ACTTTAAGGA CCCCAAGCGG
 61 CTCTACTGCA AAAACGGAGG CTTCTTCCTG CGCATCCACC CCGACGGCCG AGTGGACGGG
121 GTCCGGGAGA GAGCGACCCC CCACATCAAG CTCCAGCTTC AAGCCGAAGA CCGAGGGGTT
181 GTGTCCATCA AGGGAGTGTG TGCAAACCGA TACCTGGCCA TGAAGGAGGA CGGGAGGCTC
241 CTGGCTTCTA AATGTGTTAA GGACGAGTGT TTCTTTTTTG AACGACTGGA ATCAAATAAC
301 TACAATACTT ACCGGTCAAG GAAATACTCC AGTTGGTATG TGGCCCTGAA ACGAACAGGG
361 CAGTATAAAC TTGGATCCAA AACAGGACCT GGGCAGAAAG CTATACTTTT TCTTCCAATG
421 TCTGCTAAGA GC
```

Domestic cat FGF2 gene coding sequence (1-106; partial amino acid sequence corresponding to human FGF2 residues 25 to 130) (SEQ ID NO: 196) (GenBank accession no. EU314952, which is hereby incorporated by reference in its entirety):

```
  1 CCACTTCAAG GACCCCAAGC GTCTGTACTG CAAAAACGGG GGCTTCTTCC TGCGCATCCA
 61 CCCCGACGGC CGAGTGGATG GGGTCCGGGA GAAGAGCGAC CCTCACATCA AACTGCAACT
121 TCAGGCAGAA GAGAGAGGGG TTGTGTCCAT CAAGGAGTC TGTGCAAACC GCTATCTTGC
```

TABLE 4 -continued

```
181 CATGAAGGAA GATGGAAGAT TACTGGCTTC TAAATGTGTT ACGGACGAGT GTTTCTTTTT
241 TGAACGATTG GAATCTAATA ACTACAATAC TTATCGGTCA AGGAAATACT CCAGCTGGTA
301 TGTGGCACTG AAACGAAC
```

Guinea pig FGF2 gene coding sequence (1-96; partial amino acid sequence corresponding to human FGF2 residues 60 to 155) (SEQ ID NO: 197) (Ensembl accession no. ENSCPOT00000005443, which is hereby incorporated by reference in its entirety):
```
  1 GTTAAACTAC AACTTCAAGC CGAAGACAGA GGAGTTGTGT CTATCAAGGG AGTCTGTGCG
 61 AACCGTTACC TTGCTATGAA GGAAGACGGA AGATTATTGG CTTCCAAATG TGTTACAGAT
121 GAATGTTTCT TTTTTGAACG ACTGGAATCT AATAACTACA ACACTTACCG GTCAAGGAAA
181 TACTCCAGTT GGTATGTGGC ACTGAAACGA ACTGGACAAT ATAAACTTGG GTCCAAAACA
241 GGACCAGGGC AGAAAGCCAT ACTTTTTCTT CCAATGTCTG CGAAGAGC
```

Tasmanian devil FGF2 gene coding sequence (aa 48-203) (SEQ ID NO: 198) (Ensembl accession no. EN55HAP00000012215, which is hereby incorporated by reference in its entirety):
```
142                      ATGGCCGCG GGCAGCATCA CCACGTTGCC GGCCCTGGCC
181 GGGGATGGAG CCAGCGGGGG CGCCTTTCCC CCGGGCCACT TCCAGGACCC CAAGCGGCTG
241 TACTGCAAGA ACGGAGGCTT CTTCTTGCGC ATCCATCCCG ACGGTCACGT GGACGGCATC
301 CGCGAGAAGA GCGATCCGCA CATTAAACTT CAGCTTCAGG CAGAAGAGAG AGGAGTAGTG
361 TCTATTAAAG GAGTTTGTGC CAACCGCTAT CTTGCCATGA AGAGGATGG CAGATTACTG
421 GCTCTGAAAT GTGTGACTGA AGAGTGTTTC TTCTTTGAAC GTCTAGAGTC CAACAATTAC
481 AACACTTATC GCTCAAGGAA ATACTCCAAT TGGTATGTGG CATTGAAACG CACAGGCCAG
541 TATAAGCTTG GATCCAAGAC TGGACCAGGG CAGAAAGCCA TCCTTTTCCT TCCCATGTCT
601 GCTAAGAGCT GA
```

Gray short-tailed opossum FGF2 gene coding sequence (aa 1-155) (SEQ ID NO: 199) (GenBank accession no. NM_001033976, which is hereby incorporated by reference in its entirety):
```
 29 AT GGCCGCAGGC AGCATCACCA CGCTGCCAGC
 61 CCTGTCCGGG GACGGAGGCG GCGGGGGCGC CTTTCCCCCG GGCCACTTCA AGGACCCCAA
121 GCGGCTGTAC TGCAAGAACG GAGGCTTCTT CCTGCGCATC CACCCCGACG GCCGTGTGGA
181 CGGCATCCGC GAGAAGAGCC ACCCGAACAT TAAACTACAA CTTCAGGCAG AAGAGAGAGG
241 AGTGGTGTCT ATTAAAGGAG TATGTGCCAA TCGCTATCTT GCCATGAAGG AAGATGGAAG
301 ATTATTGGCT TTGAAATATG TGACCGAAGA GTGTTTCTTT TTCGAACGCT TGGAGTCCAA
361 CAACTACAAC ACTTATCGCT CGAGGAAATA TTCCAATTGA TACGTGGCAC TGAAACGAAC
421 GGGGCAGTAC AAGCTTGGAT CCAAGACTGG CCCGGGGCAG AAAGCCATCC TTTTCCTCCC
481 CATGTCTGCT AAGAGCTGA
```

Rabbit FGF2 gene coding sequence (aa 1-155) (SEQ ID NO: 200) (GenBank accession no. XM_002717238, which is hereby incorporated by reference in its entirety):
```
  1 ATGGCAGCCG AGAGCATCAC CACGCTGCCC GCCCTGCCGG AGGATGGAGG CAGCGGCGCC
 61 TTCCCGCCCG GCCACTTCAA GGACCCCAAG CGGCTGTACT GCAAAAACGG GGGTTTCTTC
121 CTGCGTATCC ACCCCGACGG CCGCGTGGAC GGGGTCCGGG AGAAGAGCGA CCCACACATC
181 AAATTACAAC TTCAAGCAGA AGAGAGAGGA GTTGTATCCA TCAAAGGTGT GTGTGCAAAC
241 CGTTACCTTG CTATGAAGGA AGATGGAAGA CTGCTGGCTT CTAAATGTGT TACAGACGAG
301 TGCTTCTTTT TTGAACGACT GGAGTCTAAT AACTACAATA CTTACCGGTC AAGGAAATAT
361 TCCAGCTGGT ATGTGGCACT GAAACGAACT GGGCAGTATA ACTTGGATC CAAAACAGGA
421 CCTGGGCAGA AGGCTATACT TTTTCTTCCA ATGTCTGCTA AGAGCTGA
```

Turkey FGF2 gene coding sequence (1-125; partial amino acid sequence corresponding to human FGF2 residues 31 to 155) (SEQ ID NO: 201) (Ensembl accession no. ENSMGAT00000011845, which is hereby incorporated by reference in its entirety):
```
  1 CGGCTCTACT GTAAGAACGG CGGCTTCTTC CTGCGCATCA ATCCCGACGG CAGAGTGGAC
 61 GGCGTCCGCG AGAAGAGCGA TCCGCACATC AAACTGCAGC TTCAGGCAGA AGAAAGAGGA
121 GTGGTATCAA TCAAGGGTGT AAGTGCAAAC CGCTTTCTGG CTATGAAGGA GGATGGCAGA
181 TTGCTGGCAC TGAAATGTGC AACAGAAGAA TGTTTCTTTT TTGAGCGTTT GGAATCTAAT
241 AATTATAACA CTTACCGGTC ACGGAAGTAC TCTGATTGGT ATGTGGCACT GAAAAGAACT
301 GGACAGTACA AGCCCGGACC AAAAACTGGA CCTGGACAGA AAGCTATCCT TTTTCTTCCA
361 ATGTCTGCTA AAAGC
```

Gallus gallus FGF2 gene coding sequence (aa 1-158) (SEQ ID NO: 202) (GenBank accession no. NM_205433, which is hereby incorporated by reference in its entirety):
```
 98 ATG GCGGCGGGGG CGGCGGGGAG
121 CATCACCACG CTGCCGGCGC TGCCCGACGA CGGGGGCGGC GGCGCTTTTC CCCCCGGGCA
181 CTTCAAGGAC CCCAAGCGGC TCTACTGCAA GAACGGCGGC TTCTTCCTGC GCATCAACCC
241 CGACGGCAGG GTGGACGGCG TCCGCGAGAA GAGCGATCCG CACATCAAAC TGCAGCTTCA
301 AGCAGAAGAA AGAGGAGTAG TATCAATCAA GGCGTAAGT GCAAACCGCT TTCTGGCTAT
361 GAAGGAGGAT GGCAGATTGC TGGCACTGAA ATGTGCAACA GAGGAATGTT TCTTTTTCGA
421 GCGCTTGGAA TCTAATAACT ATAACACTTA CCGGTCACGG AAGTACTCTG ATTGGTATGT
481 GGCACTGAAA AGGACTGGAC AGTACAAGCC CGGACCAAAA ACTGGACCTG ACAGAAAGC
541 TATCCTTTTT CTTCCAATGT CTGCTAAAAG CTGA
```

TABLE 4 -continued

Zebra finch FGF2 gene coding sequence (aa 1-153) (SEQ ID NO: 203) (GenBank
accession no. XM_002188361, which is hereby incorporated by reference in
its entirety):
```
  1 ATGGCGGCGG CGGGGGGCAT CGCTACGCTG CCCGACGACG GCGGCAGCGG CGCCTTTCCC
 61 CCGGGGCACT TCAAGGACCC CAAGCGCCTG TACTGCAAGA ACGGCGGCTT CTTCCTGCGC
121 ATCAACCCCG ACGGGAAGGT GGACGGCGTC CGCGAGAAGA GCGACCCGCA CATCAAGCTG
181 CAGCTTCAGG CGGAGGAACG AGGAGTGGTG TCCATCAAGA GTGTCAGTGC CAATCGCTTC
241 CTGGCCATGA AAGAGGATGG CAGATTGCTG GCCTTGAAAT ATGCAACAGA AGAATGTTTC
301 TTTTTTGAAC GTTTGGAATC CAATAACTAT AACACTTACC GGTCACGGAA ATACTCGGAT
361 TGGTATGTGG CACTGAAAAG AACTGGACAG TACAAACCTG ACCAAAAAC TGGACCTGGA
421 CAGAAAGCTA TCCTTTTCCT TCCTATGTCT GCTAAAAGCT GA
```

Japanese firebelly newt FGF2 gene coding sequence (aa 1-155) (SEQ ID
NO: 204) (GenBank accession no. AB064664, which is hereby incorporated by
reference in its entirety):
```
384 ATGGCTG CTGGGAGCAT CACCAGTCTC CCTGCCCTAC
421 CCGAGGACGG GAATGGCGGC ACCTTCACAC CCGGCGGATT CAAAGAGCCG AAGAGGCTGT
481 ACTGCAAGAA CGGGGGCTTC TTTCTCCGGA TCAACTCCGA CGGCAAGGTG GACGGAGCCC
541 GGGAGAAGAG CGACTCCTAC ATTAAACTGC AGCTTCAAGC AGAAGAGCGC GGTGTGGTGT
601 CCATCAAGGG AGTATGTGCA AACCGCTATC TCGCTATGAA GGATGATGGC AGGCTGATGG
661 CGCTGAAATG GATAACCGAT GAATGCTTCT TTTTCGAGCG ACTGGAGTCC AACAACTATA
721 ACACGTATCG ATCACGGAAA TATTCCGATT GGTATGTGGC GCTGAAAAGA ACTGGGCAAT
781 ACAAAAATGG ATCAAAAACC GGAGCAGGAC AGAAAGCAAT CCTTTTTCTA CCCATGTCGG
841 CCAAGAGTTG A
```

African clawed frog FGF2 gene coding sequence (aa 1-155) (SEQ ID NO: 205)
(GenBank accession no. NM_001099871, which is hereby incorporated by
reference in its entirety):
```
335 ATGGCG GCAGGGAGCA TCACAACTCT
361 GCCAACTGAA TCCGAGGATG GGGGAAACAC TCCTTTTTCA CCAGGGAGTT TTAAAGACCC
421 CAAGAGGCTC TACTGCAAGA ACGGGGGCTT CTTCCTCAGG ATAAACTCAG ACGGGAGAGT
481 GGACGGGTCA AGGGACAAAA GTGACTCGCA CATAAAATTA CAGCTACAAG CTGTAGAGCG
541 GGGAGTGGTA TCAATAAAGG GAATCACTGC AAATCGCTAC CTTGCCATGA AGGAAGATGG
601 GAGATTAACA TCGCTGAGGT GTATAACAGA TGAATGCTTC TTTTTTGAAC GACTGGAAGC
661 TAATAACTAC AACACTTACC GGTCTCGGAA ATACAGCAGC TGGTATGTGG CACTAAAGCG
721 AACCGGGCAG TACAAAAATG GATCGAGCAC TGGACCGGGA CAAAAAGCTA TTTTATTTCT
781 CCCAATGTCC GCAAAGAGCT GA
```

White-eared opossum FGF2 gene coding sequence (aa 1-156) (SEQ ID NO: 206)
(GenBank accession no. EF057322, which is hereby incorporated by
reference in its entirety):
```
  1 ATGGCAGCAG GCAGCATCAC CACATTGCCG GCCCTGTCCG GGGACGGAGG CGGCGGGGGA
 61 GCCTTTCCTC CAGGCCACTT CAAGGACCCC AAGCGGCTGT ACTGCAAGAA CGGAGGCTTC
121 TTCCTGCGCA TCCACCCCGA CGGCCGCGTG GACGGCATCC GCGAGAAGAG CGACCCGAAC
181 ATTAAACTAC AACTTCAGGC AGAAGAGAGA GGAGTAGTGT CTATTAAAGG AGTATGTGCC
241 AACCGATATC TTGCCATGAA GGAGGATGGC AGATTATTGG CTTTGAAATA TGTGACCGAA
301 GAGTGTTTCT TTTTTGAACG TTTGGAGTCC AACAACTACA ACACTTATCG CTCAAGAAAA
361 TATTCCAATT GGTATGTGGC ACTGAAACGA ACGGGGCAGT ATAAGCTTGG ATCCAAGACT
421 GGCCCGGGGC AGAAAGCCAT CCTTTTCTCC CCATGTCTGC TAAGATGCTG A
```

Microbat FGF2 gene coding sequence (1-96; partial amino acid sequence
corresponding to human FGF2 residues 60 to 155) (SEQ ID NO: 207) (Ensembl
accession no. ENSMLUT00000027717 , which is hereby incorporated by
reference in its entirety):
```
  1 GTCAAACTCC AACTTCAAGC AGAAGAGAGA GGGGTCGTGT CTATCAAAGG AGTGTGTGCC
 61 AACCGCTATC TCGCTATGAA GGAGGACGGC CGGTTACAGG CTTCTAAATG TGTTACGGAT
121 GAGTGTTTCT TTTTTGAACG GTTGGAATCC AATAACTACA ACACTTACCG GTCAAGAAAG
181 TACTCCAGTT GGTATGTGGC ATTGAAGCGG AATGGGCAGT ATAAACTTGG ACCCAAAACA
241 GGACCTGGCC AGAAAGCCAT ACTTTTTCTT CCCATGTCTG CTAAGAGC
```

Anole lizard FGF2 gene coding sequence (1-140; partial amino acid
sequence corresponding to human FGF2 residues 16 to 155) (SEQ ID NO: 208)
(Ensembl accession no. ENSACAT00000011897, which is hereby incorporated
by reference in its entirety):
```
  1 GCGGCGGCGG CCTCTTTCCC CCCGGGCCCC TTCAAGGACC CCAAGCGCCT CTACTGCAAG
 61 AACGGGGGCT TCTTCCTGCG GATCAACCCC GGACGGCCGG TGGACGGCGT CCGAGAGAAG
121 AGCGACCCCA ACATCAAATT GCTGCTCCAG GCAGAGGAGA GAGGTGTAGT GTCCATCAAA
181 GGTGTATGCG CAAACCGTTT CCTGGCTATG AATGAAGACG GTCGATTGTT AGCACTGAAA
241 TACGTAACAG ATGAATGCTT CTTTTTTGAA CGCTTGGAAT CTAATAATTA CAATACTTAT
301 CGGTCTCGTA AATACCGTGA TTGGTACATT GCACTGAAAC GAACTGGTCA GTACAAACTT
361 GGACCAAAAA CTGGACGAGG CCAGAAAGCT ATCCTTTTCC TTCCAATGTC TGCCAAAAGT
```

Armadillo FGF2 gene coding sequence (124-217; partial amino acid sequence
corresponding to human FGF2 residues 1 to 94) (SEQ ID NO: 209) (Ensembl
accession no. EN5DN0T00000014647, which is hereby incorporated by
reference in its entirety):
```
361           A TGGCAGCCGG GAGCATCACC ACGCTGCCCG CTCTGCCCGA GGACGGCGGC
421 AGCGGCGCCT TCCCGCCGGG CCACTTCAAG GACCCCAAGC GGCTGTACTG CAAAAACGGG
481 GGCTTCTTCC TGCGCATCCA TCCCGACGGC CGAGTGGACG GGTCCGGGA GAAGAGCGAC
```

TABLE 4 -continued

```
541 CCTAACATCA AACTACAACT TCAAGCAGAA GAGAGAGGGG TCGTGTCTAT CAAAGGCGTG
601 TGTGCGAACC GTTACCTTGC TATGCGGGAA GACGGAAGAC TCCAGGCGTC T
```

Tree shrew FGF2 gene coding sequence (1-189) (SEQ ID NO: 210) (Ensembl
accession no. ENSTBET00000001143, which is hereby incorporated by
reference in its entirety):
```
  1 GCGGGGGTTA GAGCTGAGAG GGAGGAGGCA CCGGGGAGCG GTGACAGCCG GGGGACCGAT
 61 CCCGCCGCGC GTTCGCTCAT CAGGAGGCCG GATGCTGCAG CGCGAGAGGC GCTTCTTGGA
121 GCCAGGAGCC GGGTTCAGGG CAGCTCCACC TCCTGGCCAG CCTCGTCACG AACCGGGATC
181 AAGTTGCCGG ACGACTCAGG TCAAGGAATG GGCGGCTATC CTCTGGACCG CCCGAGCCGG
241 AGCACAGGGC GAGGGCTGGG CGGTGCCCCG GACCCTGCCG TAAAACTACA GCTTCAAGCG
301 GAAGAGAGAG GGGTCGTGTC TATCAAAGGA GTGTGTGCAA ACCGTTACCT GGCCATGAAG
361 GAGGATGGGC GACTGCTGGC TTCTAAATGT GTTACAGATG AGTGTTTCTT TTTTGAACGA
421 CTGGAATCTA ATAACTACAA TACTTACCGG TCCCGAAAGT ACTCCAGCTG GTATGTGGCA
481 CTGAAACGAA CTGGGCAGTA TAAACTTGGA TCCAAAACAG GACCTGGGCA GAAAGCTATA
541 CTTTTTCTTC CAATGTCTGC TAAAAGC
```

Western clawed frog FGF2 gene coding sequence (aa 1-154) (SEQ ID NO: 211)
(GenBank accession no. NM_001017333, which is hereby incorporated by
reference in its entirety):
```
171 ATGGCAGCAG
181 GAAGCATCAC AACCCTACCA ACCGAATCTG AGGATGGAAA CACTCCTTTC CCACCGGGGA
241 ACTTTAAGGA CCCCAAGAGG CTCTACTGCA AGAATGGGGG CTACTTCCTC AGGATTAACT
301 CAGACGGGAG AGTGGACGGA TCAAGGGATA AAAGTGACTT ACACATAAAA TTACAGCTAC
361 AAGCAGTAGA GCGGGGAGTG GTATCAATAA AGGGAATCAC TGCAAATCGC TACCTTGCCA
421 TGAAGGAAGA TGGGAGATTA ACATCGCTGA AGTGTATAAC AGATGAATGC TTCTTTTATG
481 AACGATTGGA AGCTAATAAC TACAACACTT ACCGGTCTCG GAAAAACAAC AGCTGGTATG
541 TGGCACTAAA GCGAACTGGG CAGTATAAAA ATGGATCGAC CACTGGACCA GGACAAAAAG
601 CTATTTTGTT TCTCCCAATG TCAGCAAAAA GCTGA
```

Coelacanth FGF2 gene coding sequence (aa 1-155) (SEQ ID NO: 212) (Ensembl
accession no. ENSLACT00000019333, which is hereby incorporated by
reference in its entirety):
```
  1 ATGGCTGCGG GAGGAATCAC TACCCTGCCG GCGGTACCTG
 41 AGGATGGAGG CAGCAGCACC TTCCCTCCAG GAAACTTCAA GGAGCCCAAG AGACTTTACT
101 GTAAGAATGG AGGCTATTTC TTAAGGATAA ACCCCGATGG AAGAGTGGAT GGAACAAGGG
161 AGAAAAATGA TCCTTATATA AAATTACAAC TGCAAGCTGA ATCTATAGGA GTGGTGTCGA
221 TAAAGGGAGT TTGTTCAAAC CGTTACCTAG CGATGAATGA AGACTGTAGA CTTTTTGGAT
281 TGAAATATCC AACGGATGAA TGTTTCTTCC ATGAGAGGCT GGAGTCCAAC AACTACAATA
341 CTTATCGTTC AAAGAAGTAT TCGGATTGGT ATGTGGCGCT GAAACGGACT GGTCAGTACA
401 AACCTGGGCC AAAAACTGGA CTGGGACAAA AAGCAATCCT TTTCCTTCCG ATGTCTGCCA
461 AGAGTTGA
```

Spotted green pufferfish FGF2 gene coding sequence (aa 34-188) (SEQ ID
NO: 213) (Ensembl accession no. EN5TNIT00000016254, which is hereby
incorporated by reference in its entirety):
```
  1 ATGGCCACGG GAGGGATCAC GACGCTTCCA TCCACACCTG AAGACGGCGG CAGCAGCGGC
 61 TTTCCTCCCG GCAGCTTCAA GGATCCCAAA AGGCTCTACT GTAAAAACGG AGGTTTCTTC
121 CTGAGGATCA AGTCCGACGG GGTCGTGGAC GGAATCCGGG AGAAGAGTGA CCCCCACATA
181 AAGCTTCAGC TCCAGGCGAC CTCTGTGGGG GAGGTGGTCA TCAAGGGGGT GTGCGCTAAC
241 CGCTATCTGG CCATGAACAG AGATGGACGG CTGTTCGGAA CGAAACGAGC CACGGACGAA
301 TGCCATTTCT TAGAGCGGCT TGAGAGCAAC AACTACAACA CTTACCGCTC CAGGAAGTAC
361 CCAACCATGT TTGTGGGACT GACGCGGACG GGCCAGTACA AGTCTGGGAG CAAAACTGGA
421 CCGGGCCAAA AGGCCATCCT TTTTCTTCCG ATGTCCGCCA ATGCTAA
```

Stickleback FGF2 gene coding sequence (aa 1-155) (SEQ ID NO: 214) (Ensembl
accession no. ENSGACT00000022120, which is hereby incorporated by
reference in its entirety):
```
  1 AT GGCCACGGCA GGCTTCGCGA CGCTTCCCTC CACGCCCGAA
 43 GACGGCGGCA GCGGCGGCTT CACCCCCGGG GGATTCAAGG ATCCCAAGAG GCTGTACTGC
103 AAAAACGGGG GCTTCTTCTT GAGGATCAGG TCCGACGGAG GTGTAGATGG AATCAGGGAG
163 AAGAGCGACG CCCACATAAA GCTCCAAATC CAGGCGACGT CGGTGGGGGA GGTGGTCATC
223 AAAGGAGTCT GTGCCAACCG CTATCTGGCC ATGAACAGAG ACGGCCGGCT GTTCGGAACG
283 AGACGGGCGA CGGACGAATG CTACTTCCTG GAGCGGCTGG AGAGTAACAA CTACAACACC
343 TACCGCTCCA GGAAGTACCC CGGCATGTAC GTGGCTCTGA GCGGACCGG CCAGTACAAG
403 TCCGGAGCA AAACCGGACC CGGTCAAAAG GCCATTCTGT TCCTCCCCAT GTCGGCTAAG
463 TGCTAA
```

Fugu rubripes FGF2 gene coding sequence (aa 1-155) (SEQ ID NO: 215)
(Ensembl accession no. ENSTRUT00000022363, which is hereby incorporated
by reference in its entirety):
```
127 ATGG CCACGGGAGG GATCACAACA CTTCCATCCA CACCTGAAGA CGGCGGCAGC
181 GGCGGTTTTC CTCCCGGGAG CTTCAAGGAT CCCAAAAGGC TGTACTGTAA AAACGGCGGC
241 TTCTTCCTGA GGATCAGGTC CGACGGGGCC GTGGACGGAA CCCGGGAGAA GACTGACCCC
301 CACATAAAGC TTCAGCTCCA GGCGACCTCT GTGGGGGAGG TGGTCATCAA GGGGGTTTGT
361 GCTAATCGTT ATCTGGCCAT GAACAGAGAT GGACGCTGT TTGGAATGAA ACGGGCGACG
421 GATGAATGCC ACTTCTTAGA GCGGCTCGAG AGCAACAACT ACAACACCTA CCGCTCCAGG
481 AAGTACCCCA ACATGTTTGT GGGACTGACG CGAACTGGCA ACTACAAGTC TGGGACTAAA
541 ACTGGACCGG GCCAAAAGGC CATCCTCTTT CTTCCGATGT CGGCCAAATA CTAA
```

TABLE 4 -continued

Rainbow trout FGF2 gene coding sequence (aa 1-155) (SEQ ID NO: 216)
(GenBank accession no. NM_001124536, which is hereby incorporated by
reference in its entirety):
```
390 A TGGCCACAGG AGAAATCACC ACTCTACCCG
421 CCACACCTGA AGATGGAGGC AGTGGCGGCT TCCTTCCAGG AAACTTTAAG GAGCCCAAGA
481 GGTTGTACTG TAAAAATGGA GGCTACTTCT TGAGGATAAA CTCTAACGGA AGCGTGGACG
541 GGATCAGAGA TAAGAACGAC CCCCACAATA AGCTTCAACT CCAGGCGACC TCAGTGGGGG
601 AAGTAGTAAT CAAAGGGGTC TCAGCCAACC GCTATCTGGC CATGAATGCA GATGGAAGAC
661 TGTTTGGACC GAGACGGACA ACAGATGAAT GCTACTTCAT GGAGAGGCTG GAGAGTAACA
721 ACTACAACAC CTACCGCTCT CGAAAGTACC CTGAAATGTA TGTGGCACTG AAAAGGACTG
781 GCCAGTACAA GTCAGGATCC AAAACTGGAC CCGGCCAAAA AGCCATCCTC TTCCTCCCCA
841 TGTCAGCCAG ACGCTGA
```

Salmon FGF2 gene coding sequence (1-150) (SEQ ID NO: 217) (GenBank
accession no. EU816603, which is hereby incorporated by reference in its
entirety):
```
99402  AT GGCCACA GGAGAAAT CA
99421  CCACTCTACC CGCCACACCT GAAGATGGAG GCAGTGGCGG CTTCCCTCCA GGAAACTTTA
99481  AGGATCCCAA GAGGCTGTAC TGTAAAAACG GGGGCTACTT CTTGAGAATA AACTCTAATG
99541  GAAGCGTGGA CGGGATCCGA GAGAAGAACG ACCCCCACA
100968 AAC AGCCTCAATT
100981 TGTCAGGGCA TGGACTCTTC AAGGTGTCAA ACGTTCCACA GGGATGCTGG CCCATGTTGA
101041 CTCCAACGCT TCCCACAATT GTGTCAAGGT GGCTGGATGT TCTTTGGGAG
101845 AATTTG GCAGTATGTC CAACCGGCCT CATAACCGCA
101881 GACCACGTGT AGCTACACCA GCCCAGGACC TCCACATTGA GCTTCTTCAT CTACGGGATC
101941 GTCTGAAACC AGCCACCCGA ACAGCTGATA AAACTGAGGA GTATTTCTGT CTGTAA
```

Zebrafish FGF2 gene coding sequence (aa 1-154) (SEQ ID NO: 218) (GenBank
accession no. AY269790, which is hereby incorporated by reference in its
entirety):
```
 43 ATGGCCAC CGGAGGGATC
 61 ACCACACTCC CGGCCGCTCC GGACGCCGAA AACAGCAGCT TTCCCGCGGG CAGCTTCAGG
121 GATCCCAAGC GCCTGTACTG CAAAAACGGA GGATTCTTCC TGCGGATCAA CGCGGACGGC
181 CGAGTGGACG GAGCCCGAGA CAAGAGCGAC CCGCACATTC GTCTGCAGCT GCAGGCGACG
241 GCAGTGGGTG AAGTACTCAT TAAAGGCATC TGTACCAACC GTTTCCTTGC CATGAACGCA
301 GACGGACGAC TGTTCGGGAC GAAAAGGACC ACAGATGAAT GTTATTTCCT GGAGCGCCTG
361 GAGTCCAACA ACTACAACAC ATACAGATCC CGCAAGTATC CGGACTGGTA CGTGGCTCTG
421 AAGAGAACCG GCCAGTATAA AAGCGGCTCT AAAACCAGCC GGGACAGAA GGCCATCCTG
481 TTTCTGCCCA TGTCGGCCAA ATGCTGA
```

Nile tilapia FGF2 gene coding sequence (aa 1-155) (SEQ ID NO: 219)
(GenBank accession no. XM_003443364, which is hereby incorporated by
reference in its entirety):
```
  1 ATGGCCACGG GAGGAATCAC AACACTTCCC GCTACACCTG AAGACGGCGG CAGCAGCGGC
 61 TTTCCTCCTG GGAACTTCAA GGACCCTAAA AGGCTGTACT GTAAAAATGG TGGCTTCTTC
121 TTGAGGATAA AATCTGATGG AGGAGTGGAT GGAATACGGA AGAAAAACGA CCCCCACATA
181 AAGCTTCAAC TCCAGGCGAC CTCAGTGGGA GAAGTGGTCA TCAAAGGGAT TTGTGCAAAC
241 CGATATCTGG CAATGAACAG AGATGGACGA CTGTTTGGAG CGAGAAGAGC AACAGATGAG
301 TGCTACTTCT TAGAGCGGCT CGAGAGCAAC AACTACAACA CCTACCGCTC CAGGAAGTAC
361 CCAAACATGT ACGTGGCGCT GAAGCGGACT GGCCAGTACA AGTCTGGAAG CAAAACTGGA
421 CCGGGTCAAA AGGCAATTCT CTTTCTCCCA ATGTCTGCTA ATGCTAA
```

Medaka FGF2 gene coding sequence (aa 1-155) (SEQ ID NO: 220) (Ensembl
accession no. EN5ORLT00000025835, which is hereby incorporated by
reference in its entirety):
```
  1 ATGGCTACGG GAGAAATCAC AACACTTCCC TCCCCAGCTG AAAACAGCAG AAGCGATGGC
 61 TTTCCTCCAG GGAACTACAA GGATCCTAAG AGGCTCTACT GTAAAAATGG AGGTTTGTTT
121 TTGAGGATTA AACCTGATGG AGGAGTGGAT GGAATCCGGA AAAAAAAGA TCCCCACGTT
181 AAGCTTCGCC TTCAGGCTAC CTCAGCGGGA GAGGTGGTGA TCAAAGGAGT TTGTTCAAAC
241 AGATATCTGG CGATGCATGG AGATGGACGT CTATTTGGAG TGAGACAAGC AACAGAGGAA
301 TGCTACTTCT TGGAGCGACT AGAGAGCAAC AACTATAACA CCTATCGCTC TAAAAAGTAC
361 CCAAACATGT ACGTGGCACT GAAGCGGACA GGCCAGTACA AACCTGGAAA CAAAACTGGA
421 CCAGGTCAAA AGGCCATTCT CTTTCTGCCT ATGTCTGCCA AGTACTAA
```

As noted above, also encompassed within the present invention are portions of paracrine FGFs other than FGF1 and/or FGF2 (e.g., FGF4, FGF5, FGF6, FGF9, FGF16, and FGF20). The portion of the paracrine FGF may be from human FGF4, FGF5, FGF6, FGF9, FGF16, and/or FGF20 having the amino acid sequences shown in Table 5, or orthologs thereof.

TABLE 5

Amino acid sequence of human FGF4 (SEQ ID NO: 221) (GenBank accession
no. NP_001998, which is hereby incorporated by reference in its
entirety):
```
  1 MSGPGTAAVA LLPAVLLALL APWAGRGGAA APTAPNGTLE AELERRWESL VALSLARLPV
 61 AAQPKEAAVQ SGAGDYLLGI KRLRRLYCNV GIGFHLQALP DGRIGGAHAD TRDSLLELSP
```

TABLE 5 -continued

```
121 VERGVVSIFG VASRFFVAMS SKGKLYGSPF FTDECTFKEI LLPNNYNAYE SYKYPGMFIA
181 LSKNGKTKKG NRVSPTMKVT HFLPRL
```

Amino acid sequence of human FGF5(SEQ ID NO: 222) (GenBank Accession No. NP_004455, which is hereby incorporated by reference in its entirety):
```
  1 MSLSFLLLLF FSHLILSAWA HGEKRLAPKG QPGPAATDRN PRGSSSRQSS SSAMSSSSAS
 61 SSPAASLGSQ GSGLEQSSFQ WSPSGRRTGS LYCRVGIGPH LQIYPDGKVN GSHEANMLSV
121 LEIFAVSQGI VGIRGVFSNK FLAMSKKGKL HASAKFTDDC KFRERFQENS YNTYASAIHR
181 TEKTGREWYV ALNKRGKAKR GCSPRVKPQH ISTHFLPRFK QSEQPELSFT VTVPEKKKPP
241 SPIKPKIPLS APRKNTNSVK YRLKFRFG
```

Amino acid sequence of human FGF6(SEQ ID NO: 223) (NP_066276, which is hereby incorporated by reference in its entirety):
```
  1 MALGQKLFIT MSRGAGRLQG TLWALVFLGI LVGMVVPSPA GTRANNTLLD SRGWGTLLSR
 61 SRAGLAGEIA GVNWESGYLV GIKRQRRLYC NVGIGFHLQV LPDGRISGTH EENPYSLLEI
121 STVERGVVSL FGVRSALFVA MNSKGRLYAT PSFQEECKFR ETLLPNNYNA YESDLYQGTY
181 IALSKYGRVK RGSKVSPIMT VTHFLPRI
```

Amino acid sequence of human FGF9(SEQ ID NO: 224) (GenBank accession no. NP_002001, which is hereby incorporated by reference in its entirety):
```
  1 MAPLGEVGNY FGVQDAVPFG NVPVLPVDSP VLLSDHLGQS EAGGLPRGPA VTDLDHLKGI
 61 LRRRQLYCRT GFHLEIFPNG TIQGTRKDHS RFGILEFISI AVGLVSIRGV DSGLYLGMNE
121 KGELYGSEKL TQECVFREQF EENWYNTYSS NLYKHVDTGR RYYVALNKDG TPREGTRTKR
181 HQKFTHFLPR PVDPDKVPEL YKDILSQS
```

Amino acid sequence of human FGF16(SEQ ID NO: 225) (GenBank accession no. NP_003859, which is hereby incorporated by reference in its entirety):
```
  1 MAEVGGVFAS LDWDLHGFSS SLGNVPLADS PGFLNERLGQ IEGKLQRGSP TDFAHLKGIL
 61 RRRQLYCRTG FHLEIFPNGT VHGTRHDHSR FGILEFISLA VGLISIRGVD SGLYLGMNER
121 GELYGSKKLT RECVFREQFE ENWYNTYAST LYKHSDSERQ YYVALNKDGS PREGYRTKRH
181 QKFTHFLPRP VDPSKLPSMS RDLFHYR
```

Amino acid sequence of human FGF20(SEQ ID NO: 226) (GenBank accession no. NP_062825, which is hereby incorporated by reference in its entirety):
```
  1 MAPLAEVGGF LGGLEGLGQQ VGSHFLLPPA GERPPLLGER RSAAERSARG GPGAAQLAHL
 61 HGILRRRQLY CRTGFHLQIL PDGSVQGTRQ DHSLFGILEF ISVAVGLVSI RGVDSGLYLG
121 MNDKGELYGS EKLTSECIFR EQFEENWYNT YSSNIYKHGD TGRRYFVALN KDGTPRDGAR
181 SKRHQKFTHF LPRPVDPERV PELYKDLLMY T
```

It will be understood that the portion of the paracrine FGF according to the present invention may be derived from a nucleotide sequence that encodes human FGF4, FGF5, FGF6, FGF9, FGF16, and/or FGF20 having the nucleotide sequences shown in Table 6, or orthologs thereof.

TABLE 6

Human FGF4 gene coding sequence (1-206) (SEQ ID NO: 227) (GenBank accession no. NM_002007, which is hereby incorporated by reference in its entirety):
```
320                 A TGTCGGGGCC CGGGACGGCC GCGGTAGCGC TGCTCCCGGC
361 GGTCCTGCTG GCCTTGCTGG CGCCCTGGGC GGGCCGAGGG GGCGCCGCCG CACCCACTGC
421 ACCCAACGGC ACGCTGGAGG CCGAGCTGGA GCGCCGCTGG GAGAGCCTGG TGGCGCTCTC
481 GTTGGCGCGC CTGCCGGTGG CAGCGCAGCC CAAGGAGGCG GCCGTCCAGA GCGGCGCCGG
541 CGACTACCTG CTGGGCATCA AGCGGCTGCG GCGGCTCTAC TGCAACGTGG GCATCGGCTT
601 CCACCTCCAG GCGCTCCCCG ACGGCCGCAT CGGCGGCGCG CACGCGGACA CCCGCGACAG
661 CCTGCTGGAG CTCTCGCCCG TGGAGCGGGG CGTGGTGAGC ATCTTCGGCG TGGCCAGCCG
721 GTTCTTCGTG GCCATGAGCA GCAAGGGCAA GCTCTATGGC TCGCCCTTCT TCACCGATGA
781 GTGCACGTTC AAGGAGATTC TCCTTCCCAA CAACTACAAC GCCTACGAGT CCTACAAGTA
841 CCCCGGCATG TTCATCGCCC TGAGCAAGAA TGGGAAGACC AAGAAGGGGA ACCGAGTGTC
901 GCCCACCATG AAGGTCACCC ACTTCCTCCC CAGGCTGTGA
```

Human FGF5 gene coding sequence (1-268) (SEQ ID NO: 228) (GenBank Accession No. NM_004464, which is hereby incorporated by reference in its entirety):
```
238                                                                 ATG
241 AGCTTGTCCT TCCTCCTCCT CCTCTTCTTC AGCCACCTGA TCCTCAGCGC CTGGGCTCAC
301 GGGGAGAAGC GTCTCGCCCC CAAAGGGCAA CCCGGACCCG CTGCCACTGA TAGGAACCCT
361 AGAGGCTCCA GCAGCAGACA GAGCAGCAGT AGCGCTATGT CTTCCTCTTC TGCCTCCTCC
421 TCCCCCGCAG CTTCTCTGGG CAGCCAAGGA AGTGGCTTGG AGCAGAGCAG TTTCCAGTGG
481 AGCCCCTCGG GGCGCCGGAC CGGCAGCCTC TACTGCAGAG TGGGCATCGG TTTCCATCTG
541 CAGATCTACC CGGATGGCAA AGTCAATGGA TCCCACGAAG CCAATATGTT AAGTGTTTTG
601 GAAATATTTG CTGTGTCTCA GGGGATTGTA GGAATACGAG GAGTTTTCAG CAACAAATTT
```

TABLE 6 -continued

```
 661 TTAGCGATGT CAAAAAAAGG AAAACTCCAT GCAAGTGCCA AGTTCACAGA TGACTGCAAG
 721 TTCAGGGAGC GTTTTCAAGA AAATAGCTAT AATACCTATG CCTCAGCAAT ACATAGAACT
 781 GAAAAAACAG GGCGGGAGTG GTATGTGGCC CTGAATAAAA GAGGAAAAGC CAAACGAGGG
 841 TGCAGCCCCC GGGTTAAACC CCAGCATATC TCTACCCATT TTCTGCCAAG ATTCAAGCAG
 901 TCGGAGCAGC CAGAACTTTC TTTCACGGTT ACTGTTCCTG AAAAGAAAAA GCCACCTAGC
 961 CCTATCAAGC CAAAGATTCC CCTTTCTGCA CCTCGGAAAA ATACCAACTC AGTGAAATAC
1021 AGACTCAAGT TTCGCTTTGG ATAA
```

Human FGF6 gene coding sequence (1-208) (SEQ ID NO: 229) (NM_020996, which is hereby incorporated by reference in its entirety):
```
  45                                                    ATGGCC CTGGGACAGA
  61 AACTGTTCAT CACTATGTCC CGGGGAGCAG GACGTCTGCA GGGCACGCTG TGGGCTCTCG
 121 TCTTCCTAGG CATCCTAGTG GGCATGGTGG TGCCCTCGCC TGCAGGCACC CGTGCCAACA
 181 ACACGCTGCT GGACTCGAGG GGCTGGGGCA CCCTGCTGTC CAGGTCTCGC GCGGGGCTAG
 241 CTGGAGAGAT TGCCGGGGTG AACTGGGAAA GTGGCTATTT GGTGGGGATC AAGCGGCAGC
 301 GGAGGCTCTA CTGCAACGTG GGCATCGGCT TCCACCTTCA GGTGCTCCCC GACGGCCGGA
 361 TCAGCGGGAC CCACGAGGAG AACCCCTACA GCCTGCTGGA AATTTCCACT GTGGAGCGAG
 421 GCGTGGTGAG TCTCTTTGGA GTGAGAAGTG CCCTCTTCGT TGCCATGAAC AGTAAAGGAA
 481 GATTGTACGC AACGCCCAGC TTCCAAGAAG AATGCAAGTT CAGAGAAACC CTCCTGCCCA
 541 ACAATTACAA TGCCTACGAG TCAGACTTGT ACCAAGGGAC CTACATTGCC CTGAGCAAAT
 601 ACGGACGGGT AAAGCGGGGC AGCAAGGTGT CCCCGATCAT GACTGTCACT CATTTCCTTC
 661 CCAGGATCTA A
```

Human FGF9 gene coding sequence (1-208)(SEQ ID NO: 230) (GenBank accession no. NM_002010, which is hereby incorporated by reference in its entirety):
```
 838                                                                ATG
 841 GCTCCCTTAG GTGAAGTTGG GAACTATTTC GGTGTGCAGG ATGCGGTACC GTTTGGGAAT
 901 GTGCCCGTGT TGCCGGTGGA CAGCCCGGTT TTGTTAAGTG ACCACCTGGG TCAGTCCGAA
 961 GCAGGGGGGC TCCCCAGGGG ACCCGCAGTC ACGGACTTGG ATCATTTAAA GGGGATTCTC
1021 AGGCGGAGGC AGCTATACTG CAGGACTGGA TTTCACTTAG AAATCTTCCC CAATGGTACT
1081 ATCCAGGGAA CCAGGAAAGA CCACAGCCGA TTTGGCATTC TGGAATTTAT CAGTATAGCA
1141 GTGGGCCTGG TCAGCATTCG AGGCGTGGAC AGTGGACTCT ACCTCGGGAT GAATGAGAAG
1201 GGGGAGCTGT ATGGATCAGA AAAACTAACC CAAGAGTGTG TATTCAGAGA ACAGTTCGAA
1261 GAAAACTGGT ATAATACGTA CTCATCAAAC CTATATAAGC ACGTGGACAC TGGAAGGCGA
1321 TACTATGTTG CATTAAATAA AGATGGGACC CCGAGAGAAG GGACTAGGAC TAAACGGCAC
1381 CAGAAATTCA CACATTTTTT ACCTAGACCA GTGGACCCCG ACAAAGTACC TGAACTGTAT
1441 AAGGATATTC TAAGCCAAAG TTGA
```

Human FGF16 gene coding sequence (1-207) (SEQ ID NO: 231) (GenBank accession no. NM_003868, which is hereby incorporated by reference in its entirety):
```
   1 ATGGCAGAGG TGGGGGGCGT CTTCGCCTCC TTGGACTGGG ATCTACACGG CTTCTCCTCG
  61 TCTCTGGGGA ACGTGCCCTT AGCTGACTCC CCAGGTTTCC TGAACGAGCG CCTGGGCCAA
 121 ATCGAGGGGA AGCTGCAGCG TGGCTCACCC ACAGACTTCG CCCACCTGAA GGGGATCCTG
 181 CGGCGCCGCC AGCTCTACTG CCGCACCGGC TTCCACCTGG AGATCTTCCC CAACGGCACG
 241 GTGCACGGGA CCCGCCACGA CCACAGCCGC TTCGGAATCC TGGAGTTTAT CAGCCTGGCT
 301 GTGGGGCTGA TCAGCATCCG GGGAGTGGAC TCTGGCCTGT ACCTAGGAAT GAATGAGCGA
 361 GGAGAACTCT ATGGGTCGAA GAAACTCACA CGTGAATGTG TTTTCCGGGA ACAGTTTGAA
 421 GAAAACTGGT ACAACACCTA TGCCTCAACC TTGTACAAAC ATTCGGACTC AGAGAGACAG
 481 TATTACGTGG CCCTGAACAA AGATGGCTCA CCCCGGGAGG GATACAGGAC TAAACGACAC
 541 CAGAAATTCA CTCACTTTTT ACCCAGGCCT GTAGATCCTT CTAAGTTGCC CTCCATGTCC
 601 AGAGACCTCT TCACTATAG GTAA
```

Human FGF20 gene coding sequence (1-211) (SEQ ID NO: 232) (GenBank accession no. NM_019851, which is hereby incorporated by reference in its entirety):
```
 134            ATGGCTC CCTTAGCCGA AGTCGGGGGC TTTCTGGGCG GCCTGGAGGG
 181 CTTGGGCCAG CAGGTGGGTT CGCATTTCCT GTTGCCTCCT GCCGGGGAGC GGCCGCCGCT
 241 GCTGGGCGAG CGCAGGAGCG CGGCGGAGCG GAGCGCGCGC GGCGGGCCGG GGCTGCGCA
 301 GCTGGCGCAC CTGCACGGCA TCCTGCGCCG CCGGCAGCTC TATTGCCGCA CCGGCTTCCA
 361 CCTGCAGATC CTGCCCGACG GCAGCGTGCA GGGCACCCGG CAGGACCACA GCCTCTTCGG
 421 TATCTTGGAA TTCATCAGTG TGGCAGTGGG ACTGGTCAGT ATTAGAGGTG TGGACAGTGG
 481 TCTCTATCTT GGAATGAATG ACAAAGGAGA ACTCTATGGA TCAGAAAAC TTACTTCCGA
 541 ATGCATCTTT AGGGAGCAGT TTGAAGAGAA CTGGTATAAC ACCTATTCAT CTAACATATA
 601 TAAACATGGA GACACTGGCC GCAGGTATTT TGTGGCACTT AACAAAGACG GAACTCCAAG
 661 AGATGGCGCC AGGTCCAAGA GGCATCAGAA ATTTACACAT TTCTTACCTA GACCAGTGGA
 721 TCCAGAAAGA GTTCCAGAAT TGTACAAGGA CCTACTGATG TACACTTGA
```

As noted above, the chimeric protein includes a portion of a paracrine FGF coupled to a C-terminal region derived from an FGF21 molecule. FGF21 is an endocrine FGF expressed primarily by the pancreas (Fon Tacer et al., "Research Resource: Comprehensive Expression Atlas of the Fibroblast Growth Factor System in Adult Mouse," *Mol Endocrinol* 24(10):2050-2063 (2010), which is hereby incorporated by reference in its entirety) and has metabolic effects similar to that of FGF19, such as increased energy metabolism, weight loss, lowered blood glucose levels, and resistance to obesity and diabetes (Kharitonenkov et al., "FGF-21 as a Novel Metabolic Regulator," *J Clin Invest* 115(6), 1627-1635 (2005); Coskun et al., "Fibroblast growth factor 21 corrects obesity in mice," *Endocrinology* 149(12): 6018-6027 (2008), which are hereby incorporated by reference in their entirety). Transgenic mice overexpressing FGF21 are also resistant to diet-induced obesity (Kharitonenkov et al., "FGF-21 as a Novel Metabolic Regulator," *J Clin Invest* 115(6), 1627-1635 (2005), which is hereby incorporated by reference in its entirety). Moreover, in diabetic rodent models, FGF21 administration lowers blood glucose and triglyceride levels (Kharitonenkov et al., "FGF-21 as a Novel Metabolic Regulator," *J Clin Invest* 115(6), 1627-1635 (2005), which is hereby incorporated by reference in its entirety).

In one embodiment, the C-terminal portion of FGF21 of the chimeric protein of the present invention is from human FGF21 having the amino acid sequence of SEQ ID NO: 233 (GenBank Accession No. NP_061986, which is hereby incorporated by reference in its entirety), as follows:

```
  1 MDSDETGFEH SGLWVSVLAG LLLGACQAHP IPDSSPLLQF GGQVRQRYLY TDDAQQTEAH

61 LEIREDGTVG GAADQSPESL LQLKALKPGV IQILGVKTSR FLCQRPDGAL YGSLHFDPEA

121 CSFRELLLED GYNVYQSEAH GLPLHLPGNK SPHRDPAPRG PARFLPLPGL PPALPEPPGI

181 LAPQPPDVGS SDPLSMVGPS QGRSPSYAS.
```

In one embodiment, the C-terminal portion of FGF21 of the chimeric protein of the present invention includes a β-Klotho co-receptor binding domain.

In one embodiment, the C-terminal portion of FGF21 of the chimeric protein of the present invention includes amino acid residues 168-209 of SEQ ID NO: 233.

In one embodiment, the C-terminal portion of FGF21 of the chimeric protein further includes one or more substitutions, deletions, or additions. In one embodiment, the C-terminal portion of FGF21 of the chimeric protein further includes one or more substitutions, deletions, or additions while retaining the ability to bind β-Klotho. In one embodiment, the C-terminal portion of FGF21 of the chimeric protein further includes one or more substitutions, deletions, or additions while retaining the ability to selectively bind β-Klotho. In one embodiment, the C-terminal portion of FGF21 of the chimeric protein further includes one or more substitutions, additions, or deletions to enhance binding affinity for β-Klotho.

In one embodiment of the present invention, the C-terminal portion of the chimeric protein according to the present invention is or is derived from a mammalian FGF21. In one embodiment of the present invention, the C-terminal portion of the chimeric protein according to the present invention is or is derived from a vertebrate FGF21. In one embodiment, the C-terminal portion of the chimeric protein according to the present invention is derived from a non-human vertebrate FGF21. It will be understood that this includes orthologs of human FGF21, or a polypeptide or protein obtained from one species that is the functional counterpart of a polypeptide or protein from a different species. In one embodiment of the present invention, the C-terminal portion of FGF21 of the chimeric protein according to the present invention is derived from human, *pongo abelii, pan troglodytes, canis lupus familiaris, bos taurus, equus caballus, ailuropoda melanoleuca, oryctolagus cuniculus, gorilla gorilla, nomascus leucogenys, procavia capensis, cavia porcellus, tupaia belangeri, sorex araneus, ictidomys tridecemlineatus, loxodonta africana, sus scrofa, felis catus, otolemur garnettii, rattus norvegicus, mus musculus, vicugna pacos, anolis carolinensis, gadus morhua, latimeria chalumnae, tursiops truncatus, mustela putorius furo, takifugu rubripes, dipodomys ordii, echinops telfairi, macaca mulatta, microcebus murinus, ochotona princeps, xiphophorus maculatus, gasterosteus aculeatus, sarcophilus harrisii, macropus eugenii, xenopus tropicalis, danio rerio, bos grunniens mutus, saimiri boliviensis boliviensis, callithrix jacchus, tupaia chinensis, papio anubis, pteropus alecto, heterocephalus glaber, cricetulus griseus, ovies aries, pan paniscus, macaca fascicularis, mesocricetus auratus,* or *oreochromis niloticus.*

In one embodiment of the present invention, the portion of FGF21 of the chimeric protein of the present invention is from an ortholog of human FGF21 having an amino acid sequence as shown in Table 7. The portions of an ortholog of human FGF21 of a chimeric protein according to the present invention include portions corresponding to the above-identified amino acid sequences of human FGF21. Corresponding portions may be determined by, for example, sequence analysis and structural analysis.

TABLE 7

*Pongo abelii* (Sumatran orangutan) FGF21 (GenBank Accession No.
XP_002829565, which is hereby incorporated by reference in its
entirety) (SEQ ID NO: 234)
```
  1 MDSDETGFEH SGLWVPVLAG LLLGACQAHP IPDSSPLLQF GGVRQRYLY  TDDAQQTEAH
 61 LEIREDGTVG GAADQSPESL LQLKALKPGV IQILGVKTSR FLCQRPDGAL YGSLHFDPEA
121 CSFRELLLED GYNVYQSEAH GLPLHLPGNK SPHRDPAPRG aARFLPLPGL PPAPPEPPGI
181 LAPQPPDVGS SDPLSMVGPS QGRSPSYAS
```

*Pan troglodytes* (chimpanzee) FGF21 (GenBank Accession No. XP_524333,
which is hereby incorporated by reference in its entirety)
(SEQ ID NO: 235)
```
  1 MDSDETGFEH SGLWVSVLAG LLLGACQAHP IPDSSPLLQF GGVRQRYLY  TDDAQQTEAH
 61 LEIREDGTVG GAADQSPESL LQLKALKPGV IQILGVKTSR FLCQRPDGAL YGSLHFDPEA
121 CSFRELLLED GYNVYQSEAH GLPLHLPGNK SPHRDPAPRG aARFLPLPGL PPAPPEPPGI
181 LAPQPPDVGS SDPLSMVGPS QGRSPSYTS
```

*Canis lupus familiaris* (dog) FGF21 (GenBank Accession No. XP_541510,
which is hereby incorporated by reference in its entirety)
(SEQ ID NO: 236)
```
  1 MGWAEAGFEH LGLWVPVLAV LLLEACRAHP IPDSSPLLQF GGVRQRYLY  TDDAQETEAH
 61 LEIRADGTVV GAARQSPESL LELKALKPGV IQILGVKTSR FLCQGPDGTL YGSLHFDPVA
121 CSFRELLLED GYNIYHSETL GLPLRLRPHN SAYRDLAPRG aARFLPLPGL LPAPPEPPGI
181 LAPEPPDVGS SDPLSMVGPS QGRSPSYAS
```

*Bos taurus* (bovine) FGF21 (GenBank Accession No. XP_001789639, which
is hereby incorporated by reference in its entirety)
(SEQ ID NO: 237)
```
  1 MGWDEAKFKH LGLWVPVLAV LLLGTCRAHP IPDSSPLLQF GGVRQRYLY  TDDAQETEAH
 61 LEIRADGTVV GAARQSPESL LELKALKPGV IQILGVKTSR FLCQGPDGKL YGSLHFDPKA
121 CSFRELLLED GYNVYQSETL GLPLRLPPQR SSNRDPAPRG PARFLPLPGL PAAPPDPPGI
181 LAPEPPDVGS SDPLSMVGPS YGRSPSYTS
```

*Equus caballus* (horse) FGF21 (GenBank Accession No. XP_001489202,
which is hereby incorporated by reference in its entirety)
(SEQ ID NO: 238)
```
  1 MDWDKTGFKY QGLWVPVLAV LLLGACQSHP IPDSSPLLQF GGVRQRHLY  TDDAQETEAH
 61 LEIRADGTVA GAVHRSPESL LELKALKPGV IQILGVKTSR FLCQGPDGTL YGSLHFDPVA
121 CSFRELLLED GYNVYQSETL GLPLRLPHHS SPYQDPAPRA PARFLPLPGF PPAPPEPPGI
181 PAPEPPDVGS SDPLSMVGPS RSRSPSYTS
```

*Ailuropoda melanoleuca* (giant panda) FGF21 (GenBank Accession No.
XP_002917910, which is hereby incorporated by reference in its
entirety) (SEQ ID NO: 239)
```
  1 MGWDEARSEQ LGLWVPVLAV LLLEACQAHP IPDSSPLLQF GGVRQRYLY  TDDAQETEAH
 61 LAIRADGTVV GAASRSPESL LELKALKPGV IQILGVKTSR FLCQGPDGTL YGSVRFDPVA
121 CSFRELLLED GYNIYHSETL GLPLRLPAHN SPYRDSAPRG PARFLPLPGL LPVPPDPPGI
181 LGPEPPDVGS SDPLSMVGPS QGRSPSYAS
```

*Oryctolagus cuniculus* (rabbit) FGF21 (GenBank Accession No.
XP_002723745, which is hereby incorporated by reference in its
entirety) (SEQ ID NO: 240)
```
  1 MDWGKAKCRP PGLWVPALAA LLLGACQAHP IPDSSPLLQF GDQVRQQHLY  TDDAQETEAH
 61 LEIRADGTVV GAARRSPESL LQMKALQPGI IQILGVQTSR FLCQRPDGTL YGSLHFDREA
121 CSFRELLRED GYNVYLSEAL GLPLRLSPGS SPRRAPAPRG PARFLPLPGL PPDLPEPPGL
181 LAAAPPDVDS PDPLSMVQPA LDQSPSYTS
```

*Gorilla gorilla* (gorilla) FGF21 (Ensembl Accession No.
ENSGGOP00000001229, which is hereby incorporated by reference in its
entirety) (SEQ ID NO: 241)
```
  1 MDSDETGFEH SGLWVSVLAG LLLGACQAHP IPDSSPLLQF GGVRQRYLY  TDDAQQTEAH
 61 LEIREDGTVG GAADQSPESL LQLKALKPGV IQILGVKTSR FLCQRPDGAL YGSLHFDPEA
121 CSFRELLLED GYNVYQSEAH GLPLHLPGNK SPHRDPAPRG PARFLPLPGL PPAPPEPPGI
181 LAPQPPDVGS SDPLSMVGPS QGRSPSYAS
```

*Nomascus leucogenys* (Northern white-cheeked gibbon) FGF21 (Ensembl
Accession No. ENSNLEP00000005639, which is hereby incorporated by
reference in its entirety) (SEQ ID NO: 242)
```
  1 MDSDETGFEH SGLWVPVLAG LLLGACQAHP IPDSSPLLQF GGVRQRYLY  TDDAQQTEAH
 61 LEIREDGTVG GAADQSPESL LQLKALKPGV IQILGVKTSR FLCQRPDGAL YGSLHFDPEA
121 CSFRELLLED GYNVYQSEAH GLPLHLPGNK SPHRDPAPRG PARFLPLPGL PPAPPEPPGI
181 LAPQPPDVGS SDPLSMVGPS QGRSPSYAS
```

*Procavia capensis* (hyrax) FGF21 (Ensembl Accession No.
ENSOGAG00000001210, which is hereby incorporated by reference in its
entirety) (SEQ ID NO: 243)
```
  1 MDWAKFGIEH PGLWVPVMAV LLLGACQGYP IPDSSPLLQF GGVRQRYLY  TDDAQETEAH
 61 LEIRADGTVV GAAHRSPESL LELKALKPGI IQILGVKTSR FLCQGPDGVL YGSLRFDPVA
121 CSFRELLLED GYNVYQSEAH GLPLRLPSHN SPQRDLASRV PARFLPLPGR LTVLPEPSGV
181 LGPEPPDVDS SDPLSMVGPS QGRSPSYAS
```

TABLE 7 -continued

*Cavia porcellus* (guinea pig) FGF21 (Ensembl Accession No. ENSCPOP00000000237, which is hereby incorporated by reference in its entirety) (SEQ ID NO: 244)

```
  1 MDWARTECER PRLWVSMLAI LLVGACQAHP IPDSSPLLQF GGQVRQRYLY TDDAQDTEVH
 61 LEIRADGSVR GIAHRSPESL LELKALKPGV IQILGIRTSR FLCQRPDGSL YGSLHFDPEA
121 CSFRELLLAD GYNVYKSEAH GLPLHLLRGD SLSQEPAPPG PARFLPLPGL PATPPEPPRM
181 LPPGPPDVGS SDPLSMVGPL WDRSPSYTS
```

*Tupaia belangeri* (tree shrew) FGF21 (Ensembl Accession No. ENSTBEP00000013946, which is hereby incorporated by reference in its entirety) (SEQ ID NO: 245)

```
  1 MGWDKARFEH LGAWAPVLAV LLLGACQAYP IPDSSPLLQF GGQVRQRYLY TDDTQDTEAH
 61 LEIRADGTVV GAAHQSPESL LELKALKPGV IQILGVKTSR FLCQRPDGAL YGSLHFDPEA
121 CSFRELLLED GYNIYQSEAR GLPLRLPPHD SPHRDRTPRG PARFLPLPGL PLVPPELPGV
181 LALEPPDVGS SDPLSMMGPS QGQSPSYAS
```

*Sorex araneus* (shrew) FGF21 (Ensembl Accession No. ENSSARP00000002784, which is hereby incorporated by reference in its entirety) (SEQ ID NO: 246)

```
  1 MVWDKARGQQ LGLWAPMLLG LLLGACQAHP LPDSSPLLQF GGQVRLRFLY TDDAQRTGAH
 61 LEIRADGTVQ GAAHRTPECL LELKALKPGV IQILGVSTSR FLCQRPDGVL YGSLRFDPEA
121 CSFRELLLQD GYNVYQSEAL GLPLYLHPPS APVSQEPASR GAVRFLPLPG LPPASLEPPR
181 PPAPVPPDVG SSDPLSMVGP PERHSPSYTS
```

*Ictidomys tridecemlineatus* (squirrel) FGF21 (SEQ ID NO: 247)

```
  1 MDWVKAKLEP LGLWVLVLAA LVLGACQAYP IPDSSPLLQF GGQVRQRYLY TDDAQETEAH
 61 LEIRADGTVV GAAHQSPESL LELKALKPGV IQILGVKTSR FLCQRPDGVL YGSLHFDPEA
121 CSFREQLLED GYNVYQSESH GLPVRLPPNS PYRDPAPPGP ARFLPLPGLP PAALEPPGIL
181 GPEPPDVGSS DPLSMVGPLQ GRSPSYAS
```

*Loxodonta africana* (elephant) FGF21 (Ensembl Accession No. ENSLAFP00000016854, which is hereby incorporated by reference in its entirety) (SEQ ID NO: 248)

```
  1 MDWAKFGLE HPGLWVPVMA VLLLGACQGH PIPDSSPLLQ FGGQVRQRYL YTDDQETEAH
 60 LEIRADGTVA GAAHRSSESL LELKALKPGI IQILGVKTSR FLCQGPDGVL YGSLHFDPAA
120 CSFRELLLED GYNVYWSEAH GLPIRLPSHN SPYRDPASRV PARFLPLPGL LPMLQEPPGV
180 LAPEPPDVDS SDPLSMVGPS QGRSPSYAS
```

*Sus scrofa* (pig) FGF21 (GenBank Accession No. NP_001156882, which is hereby incorporated by reference in its entirety) (SEQ ID NO: 249)

```
  1 MGWAEAKFER LGLWVPVLAV LLGACQARPI PDSSPLLQFG GQVRQRYLYT DDAQETEAHL
 61 EIRADGTVAG VARQSPESLL ELKALKPGVI QILGVQTSRF LCQGPDGRLY GSLHFDPEAC
121 SFRELLLEDG YNVYQSEALG LPLRLPPHRS SNRDLAPRGP ARFLPLPGLP PAPPEPPGIL
181 APEPPDVGSS DPLSMVGPSH GRSPSYTS
```

*Felis catus* (cat) FGF21 (Ensembl Accession No. ENSFCAP00000006832, which is hereby incorporated by reference in its entirety) (SEQ ID NO: 250)

```
  1 MDWDEAGSQ RLGLWVVLGV LLPEACQAHP IPDSSPLLQF GGQVRQRFLY TDDAQETEVH
 60 LEIKADGTVV GTARRSPESL LELKALKPGV IQILGVKTSR FLCQGPDGTL YGSLRFDPAA
120 CSFRELLLED GYNIYHSETL GLPLRLPPHN SPYRDLAPRA PARFLPLPGL LPAPPEPPGI
180 LAPEPPDVGS SDPLSMVGPS QGRSPSYAS
```

*Otolemur garnettii* (bushbaby) FGF21 (Ensembl Accession No. ENSOGAG00000003581, which is hereby incorporated by reference in its entirety) (SEQ ID NO: 251)

```
  1 DKARTGFKH PGPWFPLLAV LLLGACQAHP IPDSSPLLQF GGQVRQRYLY TDDAQETEAH
 60 LEIREDGTVV GAAQQSPESL LELKALKPGV IQILGVKTSR FLCQRPDGGL YGSLYFDPKA
120 CSFRELLLED GYNVWSETY GLPLHLPPAN SPYWGPSLRS PARFLPLPGP PAASPELPGI
180 LALEPPDVGS SDPLSMVGPS QGRSPSYAS
```

*Rattus norvegicus* (Norway rat) FGF21 (GenBank Accession No. NP_570108, which is hereby incorporated by reference in its entirety) (SEQ ID NO: 252)

```
  1 MDWMKSRVGA PGLWVCLLLP VFLLGVCEAY PISDSSPLLQ FGGQVRQRYL YTDDDQDTEA
 61 HLEIREDGTV VGTAHRSPES LLELKALKPG VIQILGVKAS RFLCQQPDGT LYGSPHFDPE
121 ACSFRELLLK DGYNVYQSEA HGLPLRLPQK DSQDPATRGP VRFLPMPGLP HEPQEQPGVL
181 PPEPPDVGSS DPLSMVEPLQ GRSPSYAS
```

*Mus musculus* (house mouse) FGF21 (GenBank Accession No. NP_064397, which is hereby incorporated by reference in its entirety) (SEQ ID NO: 253)

```
  1 MEWMRSRVGT LGLWVRLLLA VFLLGVYQAY PIPDSSPLLQ FGGQVRQRYL YTDDDQDTEA
 61 HLEIREDGTV VGAAHRSPES LLELKALKPG VIQILGVKAS RFLCQQPDGA LYGSPHFDPE
121 ACSFRELLLE DGYNVYQSEA HGLPLRLPQK DSPNQDATSW GPVRFLPMPG LLHEPQDQAG
181 FLPPEPPDVG SSDPLSMVEP LQGRSPSYAS
```

TABLE 7 -continued

*Vicugna pacos* (alpaca) FGF21 (Ensembl Accession No.
ENSVPAP00000005562, which is hereby incorporated by reference in its
entirety) (SEQ ID NO: 254); partial sequence corresponding to human
FGF21 residues 1 to 78, 169 to 171, and 183 to 209
```
  1 MDWDEAKFEH RGLWVPVLTV LLLGACQARP IPDSSPLLQF GGQVRQRYLY TDDAQETEAH
 61 LEIRADGTVV GVARQPE--- ---------- ---------- ---------- ----------
121 ---------- ---------- ---------- ---------- --------GI P---------
181 --PEPPDVGS SDPLSMVGPS YSRSPSYTS
```

*Anolis carolinensis* (anole lizard) FGF21 (Ensembl Accession No.
ENSACAP00000016895, which is hereby incorporated by reference in its
entirety) (SEQ ID NO: 255)
```
  1 CKSKGGGKGG ERMWVDLVFW AALLRTAPAL PLRNSNPIYQ FDGQVRLRHL YTADEQTHLH
 61 LEILPDGTVG GSRFQNPFSL MEIKAVKPGV IRMQAKKTSR FLCMKPNGRL YGSLFYSEEA
121 CNFHEKVLSD GYNLYYSENY NIPVSLSSAG NLGQSRQLPP FSQFLPLVNK IPLEPVLEDF
181 DFYGHQLDVE SADPLSILGQ NPGFMSPSYV F
```

*Gadus morhua* (cod) FGF21 (Ensembl Accession No. ENSGMOP00000013789,
which is hereby incorporated by reference in its entirety) (SEQ ID
NO: 256)
```
  1 LLLATLLHIG LSFYVPDSGP LLWLGDQVRE RHLYTAESHR RGLFLEMSPD GQVTGSAAQT
 61 PLSVLELRSV RAGDTVIRAR LSSLYLCVDR AGHLTGQRQY TESDCTFREV ILEDGYTHFL
121 SVHHGLPISL APRHSPGRQG LRFSRFLPLR SSLSEDRVAE PPDSPLNLDS EDPLGMGLGS
181 LLSPAFSM
```

*Latimeria chalumnae* (coelacanth) FGF21 (Ensembl Accession No.
ENSLACP00000003781, which is hereby incorporated by reference in its
entirety) (SEQ ID NO: 257)
```
  1 MLCQSFVILS QKFIFGLFLT GLGLTGLAWT RPFQDSNPIL QYSDSIRLRH LYTASESRHL
 61 HLQINSDGQV GGTTKQSPYS LLEMKAVKTG FVVIRGKKSA RYLCMERSGR LYGSLQYTEK
121 DCTFKEVVLA DGYNLYVSEE HQATVTLSPM RARIAQGKKI PPFSHFLPMV NKVPVEDVAA
181 EMEFVQVLRE MTADVDSPDP FGMTWEESVH SPSFFA
```

*Tursiops truncatus* (dolphin) FGF21 (Ensembl Accession No.
ENSTTRP00000013808, which is hereby incorporated by reference in its
entirety) (SEQ ID NO: 258)
```
  1 MGWDKTKLEH LGLWVPVLAV LLGPCQAHPI PDSSPLLQFG GQVRQRYLYT DDAQETEAHL
 61 EIRADGTVVG TARRSPEGVK TSRFLCQGPE GRLYGSLHFN PQACSFRELL LEDGYNVYQS
121 EALGIPLRLP PHRSSNWDLA PRGPARFLPL PGFLPPPLEP PGILAPEPPN VGSSDPLSMV
181 GPSHGRSPSY TS
```

*Mustela putorius furo* (ferret) FGF21 (Ensembl Accession No.
ENSMPUP00000003687, which is hereby incorporated by reference in its
entirety) (SEQ ID NO: 259)
```
  1 MGWEEARSEH LGLWVPVLAV LLLGACQAYP IPDSSPLLQF GGQVRQRYLY TDDAQETEAH
 61 LEIRADGTVV GAARRSPESL LELKALKPGV IQILGVKTSR FLCQGPNGTL YGSFHFDPVA
121 CSFREVLLED GYNIYHSETL GLPLRLPPHN SPHRDLAPRG PARFLPLPGL LPATPESRGI
181 PAPEPPNVGS SDPLSMVGPL QGQSPSYTS
```

*Takifugu rubripes* (fugu) FGF21 (Ensembl Accession No.
ENSTRUP00000033950, which is hereby incorporated by reference in its
entirety) (SEQ ID NO: 260)
```
  1 FIYLFIQTAL FSPSKWFNFY LPDSNPLLSF DSHGRGIHLY TDNQRRGMYL QMSTDGSVSG
 61 SDVQTANSVL ELKSVRNGHV VIRGKSSSLF LCMDSRGRLW GQRHPTEADC TFREVLLADG
121 YTRFLSLHNG TPVSLAPKQS PDQHTVPFTR FLPLRNTLAE ESMSEPPSNQ QRYFNIDSDD
181 LLGMDLNAMV SPQFSGDK
```

*Dipodomys ordii* (kangaroo rat) FGF21 (Ensembl Accession No.
ENSDORP00000001155, which is hereby incorporated by reference in its
entirety) (SEQ ID NO: 261)
```
  1 MDQAKTRVGA RGLGGLVLAV IILGACKARP IPDSSPLLQF GGQVRLRHLY TDDTQETEAH
 61 LEIRADGTVV GTAHRSPESL LELKALKPGV IQILGIKTSR FLCQRPDGTL YGSLHFDPEV
121 CSFQELLLED GYNIYRSEAL GLPLRLSPDP APWGPARFLP LPGVPPAPPE PPGILAPEPP
181 DVGSSDPLSM VGLLQGRSPS YAS
```

*Echinops telfairi* (lesser hedgehog tenrec) FGF21 (Ensembl Accession
No. ENSETEP00000008707, which is hereby incorporated by reference in
its entirety) (SEQ ID NO: 262)
```
  1 MGCTKSGWKS PGLWVPVLAS LLLGGCGAHP IPDSSPLLQF GGQVRQRYLY TDDAQTTEAH
 61 LEIRADGTVG GVAHQSPEKF LSQWREKPLR SLHFDPAACS FREKLLEDGY NLYHSETHGL
121 PLRLPPRGGD PSSQPGARFP PLPGQLPQLQ ETPGVLAPEP PDVGSSDPLS MVGPWRGQSP
181 SYAS
```

*Macaca mulatta* (rhesus monkey) FGF21 (Ensembl Accession No.
ENSMMUP00000031540, which is hereby incorporated by reference in its
entirety) (SEQ ID NO: 263)
```
  1 MDSDETGFEH SGLWVPVLAG LLLGACQAHP IPDSSPLLQF GGQVRQRYLY TDDAQQTEAH
 61 LEIREDGTVG GAAHQSPESE CGPEPGSEGG GAVGGAEGPG LLGLREAGLG PGSWLHFDPE
```

TABLE 7 -continued

```
121 ACSFRELLLE NGYNVYQSEA HGLPLHLPGN KSPHRDPASQ GPARFLPLPG LPPAPPEPPG
181 ILAPQPPDVG SSDPLSMVGP SQARSPSYAS
```

*Microcebus murinus* (mouse lemur) FGF21 (Ensembl Accession No. ENSMICP00000012089, which is hereby incorporated by reference in its entirety) (SEQ ID NO: 264)

```
  1 MGWDEAGAGF EHPGLWFPML GVLLLGACQA YPIPDSSPLL QFGGQVRQRH LYTDDIQETE
 61 AHLEIRADGT VVGAARQSPE LELKALKPGV IQILGVKTSR FLCQRPDGAL YGSLHFDPEC
121 SFRELLLEDG YNVYCPYLPL HLSPRIELAG SRSALPLPPA PERRILAPEP PDGSSDPLSM
181 VGPSQGRSPS YAS
```

*Ochotona princeps* (pika) FGF21 (Ensembl Accession No. ENSOPRP00000006754, which is hereby incorporated by reference in its entirety) (SEQ ID NO: 265)

```
  1 KDMDGLQPPG LRVPVLAALL LGVGQARPIP DSSPLLQFGG QVRQRHLYTD DAQESEVHLE
 61 IRADGTVAGT ARRSPESLLE MKALKPGVIQ ILGVHTSRFL CQRPDGTLYG SLHFDHKACS
121 FREQLLEDGY NVYHSETHGL PLRLSPDRAP RGPARFLPLP GPPPDLLVPP LPPDVLAPEP
181 PDVDSPDPLS MVGPLQGQSP SYTS
```

*Xiphophorus maculatus* (platyfish) FGF21 (Ensembl Accession No. ENSXMAP00000001576, which is hereby incorporated by reference in its entirety) (SEQ ID NO: 266)

```
  1 CPFPFLFLIL SLPFFSSSFY IPESNPIFAF RNQLREVHLY TENHRRGLYV EIHLDGRVTG
 61 SDAQSPYSVL QIKSVKPGHV VIKGQTSSLF LCMDDSGNLR GQTTYDEADC SFRELLLADG
121 YTRFLNSQHG VPLSLASRNS PDRHSVPFTR FLPLRNTLTV SEESTKTQRD FNLDSDDLLG
181 MG
```

*Gasterosteus aculeatus* (stickleback) FGF21 (Ensembl Accession No. ENSGACP00000010703, which is hereby incorporated by reference in its entirety) (SEQ ID NO: 267)

```
  1 SLLLMVPLPF CSSFYLTDSS PLLPFNNQVK EVHLYTAENH RRAMYLQIAL DGSVSGSDAR
 61 STYSVLQLKS IQPGHVVIRG KASSMFLCVD SGGRLRGQGP YSEADCSFRE LLLGDGYTRF
121 LSSQHGSPLS LASRPSPDPN SVPFTRFLPI RTAPEAESVI EEPPSNQRYV NVDSEDLLGM
181 GLNTVVSPQF SA
```

*Sarcophilus harrisii* (tasmanian devil) FGF21 (Ensembl Accession No. ENSSHAP00000005963, which is hereby incorporated by reference in its entirety) (SEQ ID NO: 268); partial sequence corresponding to human FGF21 residues 3 to 172

```
  1 VSAMGLRERA PRYLAPLLSL LLACRASGHP LPDSSPMLLF GGQVRLRHLY TDVGQEAEAH
 61 VELASDGTVR AAARRSPNSL LELKAVKPGI VRILAVHSSR FLCMRPNGEL YGAIHYDPSA
121 CNFRERLLGD GYNVYESEAH GRTLRLPPKA APGPAGPSRF LPLPG
```

*Macropus eugenii* (wallaby) FGF21 (Ensembl Accession No. ENSMEUP00000013936, which is hereby incorporated by reference in its entirety) (SEQ ID NO: 269)

```
  1 TEEPSTGSRH LGQWAPGLPG PLLSLLLAYR GWGSPIPDSS PMLLFGGQVR LRHLYTDDGQ
 61 DTEAHVELGP DGVVRAVAER SPNSLLELKA VKPGVIRILA VQSSRFLCMR PNGELYGAVH
121 YDPSACNFRE HLLGDGYNVY ESETHRRTLR LSPSLGQAGP SRFLPLPGDW LPGPDPPWAQ
181 GPEPPDVGSA DPLSMVGAVQ GLSPSYSS
```

*Xenopus tropicalis* (Western clawed frog) FGF21 (Ensembl Accession No. ENSXETP00000009917, which is hereby incorporated by reference in its entirety) (SEQ ID NO: 270); partial sequence corresponding to human FGF21 residues 1 to 169

```
  1 RGGRTKKKTL LRKWLCLLAI MLSRSRFSLA NPIQNSNPIL SNDNQVRTQY LYTDNNNMHL
 61 YLQITHNGVV TGTEEKNDYG VLEIKAVKAG VVVIKGIRSN LYLCMDSRHQ LYASAYDKDD
121 CHFHEKITPD NYNMYSSEKH SEYVSLAPLK GSQMARFLPI
```

*Danio rerio* (zebrafish) FGF21 (Ensembl Accession No. ENSDARP00000094287, which is hereby incorporated by reference in its entirety) (SEQ ID NO: 271)

```
  1 MLLACFFIFF ALFPHLRWCM YVPAQNVLLQ FGTQVRERLL YTDGLFLEMN PDGSVKGSPE
 61 KNLNCVLELR SVKAGETVIQ SAATSLYLCV DDQDKLKGQH HYSALDCTFQ ELLLDGYSFF
121 LSPHTNLPVS LLSKRQKHGN PLSRFLPVSR AEDSRTQEVK QYIQDINLDS DDPLGMGHRS
181 HLQTVFSPSL HTKK
```

*Bos grunniens mutus* (yak) FGF21 (GenBank Accession No. ELR56628, which is hereby incorporated by reference in its entirety) (SEQ ID NO: 272)

```
  1 MGWDEAKFKH LGLWVPVLAV LLLGTCRAHP IPDSSPLLQF GGQVRQRYLY TDDAQETEAH
 61 LEIRADGTVV GAARQSPESL LELKALKPGV IQILGVKTSR FLCQGPDGKL YGSLHFDPKA
121 CSFRELLLED GYNVYQSETL GLPLRLPPQR SSNRDPAPRG PARFLPLPGL PAEPPDPPGI
181 LAPEPPDVGS SDPLSMVGPS YGRSPSYTS
```

*Saimiri boliviensis boliviensis* (Bolivian squirrel monkey) FGF21 (GenBank Accession No. XP_003940375, which is hereby incorporated by reference in its entirety) (SEQ ID NO: 273)

```
  1 MGSEEVALER PALWVSVLAG LLLGTCQAYP IPDSSPLLQF GGQVRQRYLY TDDAQQTEAH
 61 LEIREDGTVA GAAHQSPESL LQLKALKPGV IQILGVKTSR FLCQRPDGAL YGSLYFDPEA
```

TABLE 7 -continued

```
121 CSFRELLLED GYNVYQSVAH SLPLHLPGGR SPPWDPAPRG PARFLPLPGL PPEPPEAPGI
181 LAPEPPDVGS SDPLSMVGPS QGQSPSYTS
```

*Callithrix jacchus* (white-tufted-ear marmoset) FGF21 (GenBank Accession No. XP_003735669, which is hereby incorporated by reference in its entirety) (SEQ ID NO: 274)

```
  1 MGSEEVGLEH PALWVSVLAG LLLGTCQAHP IPDSSPLLQF GGQVRQRYLY TDDAQQKEAH
 61 LEIXEDGTVA GAATKVPKVS LLQLKALKPG VIQILGVKTS RFLCQRPDGA LYGSLHFDPE
121 ACSFRELLLE DGYNVYQSVA HGLPLHLPES RSPPRDPAPR GPARFLPLPG LPPEPPEPPG
181 ILAPEPPDVG SSDPLSMVGP SQGQSPSYAS
```

*Tupaia chinensis* (Chinese tree shrew) FGF21 (GenBank Accession No. ELW47159, which is hereby incorporated by reference in its entirety) (SEQ ID NO: 275)

```
  1 MGWDKARFEH LGAWAPVLAV LLLGACQAYP IPDSSPLLQF GGQVRQRYLY TDDTQDTEAH
 61 LEIRADGTVV GAAHQSPESL LELKALKPGV IQILGVKTSR FLCQRPDGAL YGSLHFDPEA
121 CSFRELLLED GYNIYQSEAR GLPLRLPPHD SPHRDRTPQG PARFLPLPGL PLVPPELPGV
181 LALEPPDVGS SDPLSMMGPS QGQSPSYAS
```

*Papio anubis* (olive baboon) FGF21 (GenBank Accession No. XP_003915900, which is hereby incorporated by reference in its entirety) (SEQ ID NO: 276)

```
  1 MDSDETGFEH SGLWVPVLAG LLLGACQAHP IPDSSPLLQF GGQVRQRYLY TDDAQQTEAH
 61 LEIREDGTVG GAAHQSPESK CGPEPGSEGG GALHFDPEAC SFRELLLENG YNVYQSEAHG
121 LPLHLPGNKS PHRDPASRGP ARFLPLPGLP PAPPEPPGIL APQPPDVGSS DPLSMVGPSQ
181 ARSPSYAS
```

*Pteropus alecto* (black flying fox) FGF21 (GenBank Accession No. ELK18566, which is hereby incorporated by reference in its entirety) (SEQ ID NO: 277)

```
  1 MGWGKARLQH PGLWGPVLAV LLGACQAHPI LDSSPLFQFG SQVRRRYLYT DDAQDTEAHL
 61 EIRADGTVAG AARRSPESLL ELKALKPGVI QVLGVKTSRF LCQRPDGTLY GSLHFDPAAC
121 SFRELLLKDG YNVYQSEALA RPLRLPPYSS PSSDPARRGP ARFLPLPGPP PEPPQPPGRL
181 APEPPDVGSS DPLSMVWPSR GRSPSYTS
```

*Heterocephalus glaber* (naked mole-rat) FGF21 (GenBank Accession No. EHB06286, which is hereby incorporated by reference in its entirety) (SEQ ID NO: 278)

```
  1 MDWARAESER PGLWVPAVLA VLLLGACQAH PIPDSSPLLQ FGGQVRQRHL YTDDAQDTEV
 61 HLEIRADGSV GGAAHRSPES LLELKALKPG VIQILGVRTS RFLCQRPDGT LYGSLHFDPE
121 ACSFRELLLA DGYNIYQSEA YGLPLRMLPS DSASRDPVPP GPARFLPLPG LHPPPLEPPG
181 MLPPEPPDVG SSDPLSMVGP LQGRSPSYAF
```

*Cricetulus griseus* (Chinese hamster) FGF21 (GenBank Accession No. XP_003508726, which is hereby incorporated by reference in its entirety) (SEQ ID NO: 279)

```
  1 MDWMKSGVGV PGLWVPLLPI FLLGVSQAHP IPDSSPLLQF GGQVRHRHLY TDDNQETEVH
 61 LEIRQDGTVI GTTHRSPESL LELKALKPEV IPVLGVKASR FLCQQPDGTL YGSPHFDPEA
121 CSFRELLLED GYNVYQSEVH GLPLRLPQRD SPNQAPASWG PVPPLPVPGL LHQPQELPGF
181 LAPEPPDVGS SDPLSMVGPL QGRSPSYAS
```

*Ovis aries* (sheep) FGF21 (GenBank Accession No. XP_004015845, which is hereby incorporated by reference in its entirety) (SEQ ID NO: 280)

```
  1 MGWDEAKFKH LGLWVPVLAV LLLGTCRAHP IPDSSPLLQF GGQVRQRYLY TDDAQETEAH
 61 LEIRADGTVV GAARQSPESL LELKALKPGV IQIFGVKTSR FLCQGPDGKL YGSLHFDPKA
121 CSFRELLLED GYNVYQSETL GLPLRLPPQR SSNRDPAPRG PPKPQLHFLK TSAVQYWPRY
181 EKVPAFLHPF PG
```

*Pan paniscus* (pygmy chimpanzee) FGF21 (GenBank Accession No. XP_003814163, which is hereby incorporated by reference in its entirety) (SEQ ID NO: 281); partial sequence corresponding to human FGF21 residues 1 to 116 and 195 to 201

```
  1 MDSDETGFEH SGLWVSVLAG LLLGACQAHP IPDSSPLLQF GGQVRQRYLY TDDAQQTEAH
 61 LEIREDGTVG GAADQSPESL LQLKALKPGV IQILGVKTSR FLCQRPDGAL YGSVSF----
121 ---------- ---------- ---------- ----Q----- ---------- -----DPP--
181 --HHPP---C S---SYMSPS Q---PG---
```

*Macaca fascicularis* (crab-eating macaque) FGF21 (GenBank Accession No. EHH59757, which is hereby incorporated by reference in its entirety) (SEQ ID NO: 282); partial sequence corresponding to human FGF21 residues 1 to 116

```
  1 MDSDETGFEH SGLWVPVLAG LLLGACQAHP IPDSSPLLQF GGQVRQRYLY TDDAQQTEAH
 61 LEIREDGTVG GAAHQSPESL LQLKALKPGV IQILGVKTSR FLCQKPDGAL YGSVSF
```

*Mesocricetus auratus* (golden hamster) FGF21 (GenBank Accession No. ACB30542, which is hereby incorporated by reference in its entirety) (SEQ ID NO: 283); partial sequence corresponding to human FGF21 residues 90 to 193

```
  1 VIQILGVKAA RFPCQQPDGS LYGSPHFDPE ACSFRELLLE DGYNVYQSEA HGLPLRLPQR
 61 DAPSQPPASW GPVRFLPVPG LFQPPHDLPG RPAPEPPDVG SSDP
```

TABLE 7 -continued

*Oreochromis niloticus* (Nile tilapia) FGF21 (GenBank Accession No. XP_003438516, which is hereby incorporated by reference in its entirety) (SEQ ID NO: 284); partial sequence corresponding to human FGF21 residues 59 to 209

```
  1 MYLQMNMDGR VTGSDAQTPY SLMQLKSVKP GHVIIKGPSS SLFLCVDSEG NLRGQSHYSE
 61 TSCTFREMLL ADGYTRFISS QYGFPMSLAS RHSPDRHALP FTRFLPLRNN LKTDSVSEQL
121 PNNQRLFNVD SDDLLGMGLN SMGSPQFSMD K
```

In certain embodiments according to the present invention, the C-terminal portion of FGF21 of the chimeric protein of the present invention includes a polypeptide sequence that has at least 80%, at least 85%, at least 90%, at least 95%, at least 97%, or at least 99% amino acid sequence identity to amino acid residues 168-209 of SEQ ID NO: 233. In certain embodiments according to the present invention, the C-terminal portion of FGF21 of the chimeric protein of the present invention includes a polypeptide sequence that has at least 80%, at least 85%, at least 90%, at least 95%, at least 97%, or at least 99% amino acid sequence homology to amino acid residues 168-209 of SEQ ID NO: 233.

It will be understood that the portion of FGF21 of the chimeric protein of the present invention may be derived from a nucleotide sequence that encodes a vertebrate or a non-vertebrate FGF21 protein. In one embodiment, the portion of FGF21 of the chimeric protein of the present invention may be derived from a nucleotide sequence that encodes a mammalian FGF21 protein. Nucleotide sequences encoding a vertebrate FGF21 protein according to the present invention may include, but are not limited to, those shown in Table 8. The portion of FGF21 of the chimeric protein of the present invention derived from an ortholog of human FGF21 include portions corresponding to the above-identified amino acid sequences of FGF21. Corresponding portions may be determined by, for example, sequence analysis and structural analysis.

TABLE 8

Human FGF21 gene coding sequence (SEQ ID NO: 285) (GenBank Accession No. NM_019113, which is hereby incorporated by reference in its entirety)
```
151 ATGGACTCGG ACGAGACCGG GTTCGAGCAC TCAGGACTGT GGGTTTCTGT GCTGGCTGGT
211 CTTCTGCTGG GAGCCTGCCA GGCACACCCC ATCCCTGACT CCAGTCCTCT CCTGCAATTC
271 GGGGGCCAAG TCCGGCAGCG GTACCTCTAC ACAGATGATG CCCAGCAGAC AGAAGCCCAC
331 CTGGAGATCA GGGAGGATGG GACGGTGGGG GGCGCTGCTG ACCAGAGCCC CGAAAGTCTC
391 CTGCAGCTGA AAGCCTTGAA GCCGGGAGTT ATTCAAATCT TGGGAGTCAA GACATCCAGG
451 TTCCTGTGCC AGCGGCCAGA TGGGGCCCTG TATGGATCGC TCCACTTTGA CCCTGAGGCC
511 TGCAGCTTCC GGGAGCTGCT TCTTGAGGAC GGATACAATG TTTACCAGTC CGAAGCCCAC
571 GGCCTCCCGC TGCACCTGCC AGGGAACAAG TCCCCACACC GGGACCCTGC ACCCCGAGGA
631 CCAGCTCGCT TCCTGCCACT ACCAGGCCTG CCCCCCGCAC TCCCGGAGCC ACCCGGAATC
691 CTGGCCCCCC AGCCCCCCGA TGTGGGCTCC TCGGACCCTC TGAGCATGGT GGGACCTTCC
751 CAGGGCCGAA GCCCCAGCTA CGCTTCCTGA
```

*Pongo abelii* (Sumatran orangutan) FGF21 gene coding sequence (SEQ ID NO: 286) (GenBank Accession No. XM_002829519, which is hereby incorporated by reference in its entirety)
```
165    ATGGAC TCGGACGAGA CCGGGTTCGA GCACTCAGGA CTGTGGGTTC CTGTGCTGGC
221 TGGTCTTCTG CTGGGAGCCT GCCAGGCACA CCCCATCCCT GACTCCAGTC CTCTCCTGCA
281 ATTCGGGGGC CAAGTCCGGC AGCGGTACCT CTACACAGAT GATGCCCAGC AGACAGAAGC
341 CCACCTGGAG ATCAGGGAGG ATGGGACGGT GGGGGGCGCT GCTGACCAGA GCCCCGAAAG
401 TCTCCTGCAG CTGAAAGCCT TGAAGCCGGG AGTTATTCAA ATCTTGGGAG TCAAGACATC
461 CAGGTTCCTG TGCCAGAGGC CAGATGGGGC CCTGTATGGA TCGCTCCACT TTGACCCTGA
521 GGCCTGCAGC TTCCGGGAGC TGCTTCTTGA GGACGGATAC AATGTTTATC AGTCCGAGGC
581 CCATGGCCTC CCGCTGCACC TGCCGGGAAA CAAGTCCCCA CACCGGGACC CTGCACCCCG
641 AGGACCAGCT CGCTTCCTGC CACTACCAGG CCTGCCCCCC GCACCCCCAG AGCCGCCCGG
701 AATCCTGGCC CCCCAGCCCC CCGATGTGGG CTCCTCGGAC CCTCTGAGCA TGGTGGGACC
761 TTCCCAGGGC CGAAGCCCCA GCTATGCTTC CTGA
```

*Pan troglodytes* (chimpanzee) FGF21 gene coding sequence (SEQ ID NO: 287) (GenBank Accession No. XM_524333, which is hereby incorporated by reference in its entirety)
```
 573    ATGGACTC GGACGAGACC GGGTTCGAGC ACTCAGGACT GTGGGTTTCT GTGCTGGCTG
 631 GTCTTCTGCT AGGAGCCTGC CAGGCACACC CCATCCCTGA CTCCAGTCCT CTCCTGCAAT
 691 TCGGGGGCCA AGTCCGGCAG CGGTACCTCT ACACAGATGA TGCCCAGCAG ACAGAAGCCC
 751 ACCTGGAGAT CAGGGAGGAT GGGACGGTGG GGGGCGCTGC TGACCAGAGC CCCGAAAGTC
 811 TCCTGCAGCT GAAAGCCTTG AAGCCGGGAG TTATTCAAAT CTTGGGAGTC AAGACATCCA
 871 GGTTCCTGTG CCAGAGGCCA GATGGGGCCC TGTATGGATC GCTCCACTTT GACCCTGAGG
 931 CCTGCAGCTT CCGGGAGCTG CTTCTTGAGG ACGGATACAA TGTTTACCAG TCCGAGGCCC
 991 ACGGCCTCCC GCTGCACCTG CCGGGGAACA AGTCCCCACA CCGGGACCCT GCACCCCGAG
1051 GACCAGCTCG CTTCCTGCCA CTACCAGGCC TGCCCCCCGC ACCCCGGAG CCACCCGGAA
1111 TCCTGGCCCC CCAGCCCCCC GATGTGGGCT CCTCAGACCC TCTGAGCATG GTGGGACCTT
1171 CCCAGGGCCG AAGCCCCAGC TACACTTCCT GA
```

TABLE 8 -continued

*Canis lupus familiaris* (dog) FGF21 gene coding sequence (SEQ ID
NO: 288) (GenBank Accession No. XM_541510, which is hereby
incorporated by reference in its entirety)
```
  1 ATGGGCTGGG CCGAGGCCGG GTTCGAGCAC CTGGGACTGT GGGTCCCTGT GCTGGCTGTG
 61 CTTTTGCTGG AAGCCTGCCG GGCACATCCG ATCCCTGACT CCAGCCCCCT CCTACAATTT
121 GGAGGTCAAG TTCGACAGCG GTACCTCTAC ACCGACGATG CCCAGGAGAC AGAGGCCCAC
181 CTAGAGATCA GGGCCGATGG CACAGTGGTG GGGGCTGCCC GCCAGAGCCC TGAAAGTCTC
241 CTGGAGCTGA AAGCCCTAAA GCCAGGGGTC ATTCAAATCT GGGAGTCAA AACATCCAGG
301 TTCCTGTGCC AGGGCCCAGA TGGGACACTA TATGGCTCGC TCCATTTCGA CCCTGTGGCC
361 TGCAGTTTCC GAGAACTGCT TCTTGAGGAT GGGTACAACA TCTACCACTC CGAGACCCTT
421 GGTCTCCCGC TTCGCCTGCG CCCCCACAAC TCCGCATACC GGGACTTGGC ACCCCGCGGG
481 CCTGCCCGCT TCCTGCCACT GCCAGGCCTG CTTCCAGCAC CCCCAGAGCC TCCAGGGATC
541 CTGGCCCCGG AGCCTCCTGA CGTGGGCTCC TCGGACCCTC TGAGCATGGT GGGGCCTTCA
601 CAGGGCCGGA GTCCCAGCTA TGCTTCCTAA
```

*Bos taurus* (bovine) FGF21 gene coding sequence (SEQ ID NO: 289)
(GenBank Accession No. XP_001789587, which is hereby incorporated by
reference in its entirety)
```
  1 ATGGGCTGGG ACGAGGCCAA GTTCAAGCAC TTGGGACTGT GGGTCCCTGT GCTGGCTGTC
 61 CTCCTGCTAG GAACCTGCCG GCGCATCCC ATTCCAGACT CCAGCCCCCT CCTCCAGTTT
121 GGGGGCCAAG TCCGCCAGCG GTACCTCTAC ACGGATGATG CCCAGGAGAC AGAGGCCCAC
181 CTGGAGATCA GGGCCGATGG CACAGTGGTG GGGGCAGCCC GCCAGAGCCC CGAAAGTCTC
241 TTGGAGCTGA AAGCCCTGAA GCCAGGCGTC ATTCAGATCT GGGAGTTAA AACATCCAGG
301 TTTCTCTGCC AGGGGCCAGA TGGGAAGCTG TACGGATCGC TGCACTTTGA CCCCAAAGCC
361 TGCAGCTTTC GGGAGCTGCT TCTTGAAGAT GGATACAACA TCTACCAGTC GGAGACCCTG
421 GGCCTTCCAC TCCGCCTGCC CCCCCAGCGC TCGTCCAACC GGGACCCGGC CCCGCGGGGA
481 CCTGCTCGCT TCCTTCCACT GCCGGGCCTG CCCGCGGCGC CCCCGGATCC TCCAGGGATC
541 TTGGCCCCCG AGCCTCCCGA CGTGGGCTCC TCGGATCCCC TGAGTATGGT GGGACCCTCG
601 TATGGCCGAA GCCCCAGCTA CACTTCTTGA
```

*Equus caballus* (horse) FGF21 gene coding sequence (SEQ ID NO: 290)
(GenBank Accession No. XM_001489152, which is hereby incorporated by
reference in its entirety)
```
  1 ATGGACTGGG ACAAGACGGG GTTCAAGTAC CAGGGACTGT GGGTCCCTGT GCTGGCTGTC
 61 CTTCTGCTGG GAGCCTGCCA GTCACACCCC ATCCCTGACT CCAGTCCCCT CCTCCAATTC
121 GGGGGCCAAG TCAGGCAGCG CCACCTCTAC ACAGATGATG CCCAGGAGAC AGAGGCGCAC
181 CTGGAGATCA GGGCTGACGG CACTGTGGCA GGGGCTGTCC ACCGGAGCCC AGAAAGTCTC
241 TTGGAGCTGA AAGCCCTGAA GCCAGGGGTA ATTCAAATCT GGGAGTCAA GACATCCAGG
301 TTTCTGTGCC AGGGGCCAGA CGGGACGCTG TACGGATCGC TCCACTTCGA CCCCGTGGCC
361 TGCAGCTTCC GGGAGCTGCT TCTCGAAGAC GGCTACAACG TTTACCAGTC TGAGACCCTT
421 GGCCTCCCAC TCCGCCTGCC CCACCACAGC TCCCCATACC AGGATCCGGC CCCTCGGGCA
481 CCCGCCCGCT TCCTGCCGCT GCCAGGCTTT CCCCCAGCAC CCCCGGAGCC TCCAGGGATC
541 CCGGCCCCCG AGCCCCCGGA CGTGGGCTCC TCGGACCCCC TGAGCATGGT GGGGCCTTCA
601 CGCAGCCGGA GCCCCAGCTA CACTTCCTGA
```

*Ailuropoda melanoleuca* (giant panda) FGF21 gene coding sequence (SEQ
ID NO: 291) (GenBank Accession No. XM_002917864, which is hereby
incorporated by reference in its entirety)
```
  1 ATGGGCTGGG ACGAGGCCAG GTCCGAGCAG CTGGGGCTGT GGGTCCCTGT GCTGGCTGTC
 61 CTTTTGCTGG AAGCTTGCCA GGCACACCCT ATCCCTGACT CCAGCCCCCT CCTCCAATTC
121 GGAGGCCAAG TTCGACAGCG GTACCTCTAC ACGGACGATG CCCAGGAGAC AGAGGCCCAC
181 CTAGCGATCA GGGCTGATGG CACAGTGGTG GGGGCTGCCA GCCGGAGCCC AGAAAGTCTC
241 TTGGAGCTGA AAGCCCTGAA ACCGGGGGTC ATTCAAATCC TGGGAGTGAA AACATCTAGG
301 TTCCTGTGCC AGGGCCCAGA TGGGACACTG TACGGATCGG TCCGCTTCGA CCCCGTAGCC
361 TGCAGCTTCC GGGAACTGCT CCTGGAGGAT GGGTACAACA TCTACCACTC TGAGACCCTC
421 GGCCTCCCAC TTCGCCTGCC CGCCCACAAC TCTCCATACC GGGACTCGGC GCCCCGGGGG
481 CCTGCCCGCT TCCTGCCCCT GCCAGGCCTG CTTCCGGTCC CCCCGGACCC CCCAGGGATC
541 CTGGGCCCCG AGCCTCCCGA CGTGGGCTCC TCGGACCCCC TGAGCATGGT GGGGCCTTCA
601 CAGGGCCGAA GTCCCAGCTA CGCTTCCTGA
```

*Oryctolagus cuniculus* (rabbit) FGF21 gene coding sequence (SEQ ID NO:
292) (GenBank Accession No. XM_002723699, which is hereby incorporated
by reference in its entirety)
```
  1 ATGGACTGGG GCAAGGCCAA GTGCCGGCCC CCGGGGCTGT GGGTCCCCGC GCTCGCTGCC
 61 CTGCTGCTGG GGGCCTGCCA GGCACACCCC ATCCCCGACT CCAGCCCCCT CCTCCAGTTT
121 GGGGACCAAG TGCGGCAGCA GCACCTGTAC ACGGACGATG CGCAGGAAAC AGAAGCCCAC
181 CTGGAGATCA GGGCGGATGG CACGGTGGTG GGGGCTGCCC GGAGGAGCCC AGAAAGTCTC
241 TTGCAGATGA AAGCCTTACA ACCGGGGATC ATTCAGATCT GGGGGTCCA GACGTCCAGG
301 TTCCTCTGCC AGAGGCCGGA TGGCACGCTC TACGGCTCGC TCCACTTCGA CCGCGAGGCC
361 TGCAGCTTCC GGGAGCTGCT GCGTGAGGAT GGGTACAACG TTTACCTCTC GGAGGCCCTG
421 GGCCTGCCCC TGCGCCTGTC CCCCGGCAGC TCCCCACGCA GGGCGCCGGC CCCCGGGGA
481 CCAGCCCGCT TCCTGCCGCT GCCCGGCCTG CCGCCAGACC TTCCGGAACC GCCAGGCCTC
541 CTGGCCGCCG CGCCCCCCGA TGTCGACTCC CCGGACCCCC TGAGCATGGT GCAGCCTGCG
601 CTGGACCAGA GCCCCAGCTA CACCTCCTGA
```

TABLE 8 -continued

*Gorilla gorilla* (gorilla) FGF21 gene coding sequence (SEQ ID NO: 293)
(Ensembl Accession No. ENSGGOT00000001253, which is hereby
incorporated by reference in its entirety)

```
151 ATGGACTCGG ACGAGACCGG GTTCGAGCAC TCAGGACTGT GGGTTTCTGT GCTGGCTGGT
211 CTTCTGCTGG GAGCCTGCCA GGCACACCCC ATCCCTGACT CCAGTCCTCT CCTGCAATTC
271 GGGGGCCAAG TCCGGCAGCG GTACCTCTAC ACAGATGATG CCCAGCAGAC AGAAGCCCAC
331 CTGGAGATCA GGGAGGATGG GACGGTGGGG GGTGCTGCTG ACCAGAGCCC TGAAAGTCTC
391 CTGCAGCTGA AAGCCTTGAA GCCGGGAGTT ATTCAAATCT TGGGAGTCAA GACATCCAGG
451 TTCCTGTGCC AGAGGCCAGA TGGGGCCCTG TATGGATCGC TCCACTTTGA CCCTGAGGCC
511 TGCAGCTTCC GGGAGCTGCT TCTTGAGGAC GGATACAATG TTTACCAGTC CGAGGCCCAC
571 GGCCTCCCGC TGCACCTGCC GGGGAACAAG TCCCCACACC GGGACCCTGC ACCCCGAGGA
631 CCAGCTCGCT TCCTGCCACT ACCAGGCCTG CCCCCCGCAC CCCCGGAGCC ACCCGGAATC
691 CTGGCCCCCC AGCCCCCCGA TGTGGGCTCC TCGGACCCTC TGAGCATGGT GGGACCTTCC
751 CAGGGCCGAA GCCCCAGCTA CGCTTCCTGA
```

*Nomascus leucogenys* (Northern white-cheeked gibbon) FGF21 gene coding
sequence (SEQ ID NO: 294) (Ensembl Accession No. ENSNLET00000005931,
which is hereby incorporated by reference in its entirety)

```
 587      ATGG ACTCGGACGA GACCGGGTTC GAGCACTCAG GACTGTGGGT TCCTGTGCTG
 647 GCTGGTCTTC TGCTGGGAGC CTGCCAGGCA CACCCCATCC CTGACTCCAG TCCTCTCCTG
 707 CAATTCGGGG GCCAAGTCCG GCAGCGGTAC CTCTACACAG ATGATGCCCA GCAGACAGAA
 767 GCCCACCTGG AGATCAGGGA GGATGGGACG GTGGGGGGCG CTGCTGACCA GAGCCCTGAA
 831 AGTCCTGCA GCTGAAAGC CTTGAAGCCG GGAGTTATTC AAATCTTGGG AGTCAAGACA
 891 TCCAGGTTCC TATGCCAGAG GCCAGATGGG GCCCTGTATG GATCGCTCCA CTTTGACCCT
 951 GAGGCCTGCA GCTTCCGGGA GCTGCTTCTT GAGGACGGAT ACAATGTTTA CCAGTCCGAG
1011 GCCCATGGCC TCCCGCTGCA CCTGCCGGGG AACAAGTCCC CACACCGGGA CCCTGCACCC
1071 CGAGGACCAG CTCGCTTCCT GCCACTACCA GGCCTGCCCC CTGCACCCCC AGAGCCGCCC
1131 GGAATCCTGG CCCCCCAGCC CCCGATGTG GCTCCTCGG ACCCTCTGAG CATGGTGGGA
1191 CCTTCCCAGG GCCGAAGCCC CAGCTACGCT TCCTGA
```

*Procavia capensis* (hyrax) FGF21 gene coding sequence (SEQ ID NO: 295)
(Ensembl Accession No. ENSPCAT00000001288, which is hereby
incorporated by reference in its entirety)

```
   1 ATGGACTGGG CCAAGTTTGG GATCGAGCAC CCGGGACTGT GGGTCCCGGT GATGGCAGTA
  61 CTTCTGCTGG GAGCCTGCCA AGGATACCCT ATTCCTGACT CCAGCCCCCT TCTCCAATTC
 121 GGAGGCCAGG TCCGGCAACG TTACCTCTAC ACAGATGACG CGCAGGAGAC CGAGGCCCAC
 181 CTGGAGATCC GAGCAGACGG CACGGTGGTG GGGGCTGCCC ACCGGAGCCC GGAGAGTCTC
 241 TTGGAGCTGA AAGCTTTGAA GCCCGGCATA ATTCAGATCT TGGGAGTCAA GACATCCAGA
 301 TTCCTCTGCC AGGGTCCTGA TGGGGTGCTG TATGGATCGC TCCGTTTTGA CCCAGTGGCC
 361 TGCAGCTTCC GGGAGCTGCT TCTTGAAGAT GGATACAATG TTTACCAGTC TGAGGCCCAC
 421 GGCCTCCCGC TTCGCCTACC ATCCCACAAT TCCCCACAGA GGGACCTGGC GTCCCGGGTG
 481 CCAGCCCGCT TCCTGCCACT GCCAGGCCGG CTCACGGTGC TCCCAGAACC TTCGGGGGTC
 541 CTGGGCCCTG AGCCCCCCGA TGTGGACTCC TCAGACCCCC TGAGCATGGT GGGGCCTTCG
 601 CAGGGCCGAA GCCCCAGTTA CGCCTCCTGA
```

*Cavia porcellus* (guinea pig) FGF21 gene coding sequence (SEQ ID
NO: 296) (Ensembl Accession No. ENSCPOT00000000273, which is hereby
incorporated by reference in its entirety)

```
   1 ATGGACTGGG CCCGGACTGA GTGTGAGCGC CCAAGGCTGT GGGTCTCCAT GCTGGCCATC
  61 CTTCTGGTGG GAGCCTGCCA GGCACACCCT ATCCCTGACT CCAGCCCCCT CCTCCAGTTT
 121 GGGGGCCAGG TCCGGCAGCG GTACCTCTAC ACAGATGATG CTCAGGACAC TGAAGTGCAC
 181 CTGGAGATCA GGGCCGATGG CTCAGTACGG GGCATTGCCC ACAGGAGCCC TGAAAGTCTC
 241 CTGGAGCTGA AAGCCTTGAA GCCAGGAGTC ATTCAGATCT TGGGAATCGA GACTTCCAGG
 301 TTCCTGTGCC AGAGGCCCGA TGGGAGTCTG TATGGATCAC TCCACTTTGA TCCTGAGGCC
 361 TGCAGCTTCC GGGAGCTGCT GCTTGCTGAT GGCTACAATG TCTACAAGTC TGAAGCCCAC
 421 GGCCTCCCTC TGCACCTGCT GCGCGGTGAC TCTCTATCGC AGGAACCAGC ACCCCCAGGA
 481 CCAGCCCGAT TTCTGCCACT ACCAGGCCTG CCCGCAACAC CCCCGGAGCC ACCCAGGATG
 541 CTGCCCCCAG GGCCCCAGA TGTGGGCTCC TCGGACCCTT TGAGCATGGT GGGGCCTTTA
 601 TGGGACCGAA GCCCCAGCTA TACTTCCTGA
```

*Tupaia belangeri* (tree shrew) FGF21 gene coding sequence (SEQ ID
NO: 297) (Ensembl Accession No. ENSTBET00000016056, which is hereby
incorporated by reference in its entirety)

```
   1 ATGGGCTGGG ACAAGGCCCG GTTCGAGCAC CTGGGAGCGT GGGCTCCTGT GCTGGCTGTC
  61 CTCCTCCTGG GAGCCTGCCA GGCATACCCC ATCCCTGACT CCAGCCCCCT CCTACAATTC
 121 GGGGGCCAGG TCCGGCAGCG GTACCTCTAC ACGGACGACA CGCAGGACAC AGAAGCCCAC
 181 CTTGAGATCA GGGCCGACGG CACCGTGGTG GGGGCCGCCC ACCAAAGCCC GGAAAGTCTC
 241 CTGGAGCTGA AAGCCTTGAA GCCGGGGGTC ATTCAAATCC TGGGAGTCAA GACCTCCAGG
 301 TTCCTGTGCC AGAGGCCAGA CGGGGCCCTG TACGGGTCGC TTCACTTCGA CCCCGAGGCC
 361 TGCAGCTTCC GGGAGCTGCT TCTCGAGGAT GGATACAACA TTTACCAGTC TGAGGCTCGT
 421 GGCCTCCCCC TGCGCCTGCC GCCCCACGAC TCCCCACATC GGGACCGGAC CCCTCGGGGA
 481 CCAGCTCGTT TCCTGCCGCT GCCTGGCCTG CCCCTGGTTC CTCCAGAGCT GCCAGGGGTC
 541 CTGGCCCTTG AGCCCCCCGA CGTGGGCTCC TCAGACCCGC TGA
```

*Sorex araneus* (shrew) FGF21 gene coding sequence (SEQ ID NO: 298)
(Ensembl Accession No. ENSSART00000003074, which is hereby
incorporated by reference in its entirety)

```
   1 ATGGTCTGGG ACAAGGCCAG GGGGCAGCAG TTGGGACTGT GGGCCCCCAT GCTGCTGGGC
  61 TTGCTGCTGG GTGCCTGCCA GGCACACCCC CTCCCTGACT CCAGCCCCCT CCTCCAATTT
```

TABLE 8 -continued

```
121 GGGGGCCAAG TCCGACTGAG GTTCCTGTAC ACCGACGATG CCCAGAGGAC AGGGGCGCAC
181 CTGGAGATCA GGGCCGACGG CACAGTGCAG GGTGCGGCCC ACAGGACCCC AGAATGTCTC
241 CTGGAGCTGA AAGCCTTGAA GCCAGGCGTA ATTCAAATCC TTGGGGTCAG CACATCCAGA
301 TTCCTGTGCC AGCGGCCCGA TGGGGTCCTG TATGGATCGC TTCGCTTTGA CCCAGAGGCC
361 TGCAGTTTCC GGGAACTTCT TCTCCAGGAT GGATATAACG TTTACCAGTC TGAGGCCCTG
421 GGTCTCCCGC TCTACCTACA CCCGCCCAGT GCCCCAGTGT CCCAGGAACC AGCCTCACGG
481 GGCGCCGTCC GCTTCCTGCC ACTGCCAGGA CTGCCACCTG CCTCCCTGGA GCCCCCCAGG
541 CCCCCCGCCC CGGTGCCTCC AGACGTGGGT TCCTCAGACC CCTGA
```

*Ictidomys tridecemlineatus* (squirrel) FGF21 gene coding sequence (SEQ ID NO: 299)

```
  1 ATGTACCCCA TCCCTGACTC AAGCCCCCTC CTCCAATTTG GGGGCCAAGT CCGGCAGCGG
 61 TACCTGTACA CAGATGATGC CCAGGAGACT GAGGCCCACC TGGAGATCAG GGCTGATGGC
121 ACCGTGGTGG GGGCTGCCCA TCAAAGCCCG GAAAGTCTCT TGGAACTGAA AGCCTTGAAG
181 CCTGGGGTCA TTCAAATCTT GGGGGTCAAA ACATCCAGGT TCCTGTGCCA GAGGCCAGAT
241 GGAGTGCTGT ATGGATCGCT CCACTTTGAC CCTGAGGCCT GCAGCTTCCG GGAGCAGCTT
301 CTGGAGGACG GGTACAACGT TTACCAGTCA GAATCCCACG GCCTCCCCGT GCGCCTGCCC
361 CCTAACTCAC CATACCGGGA CCCAGCGCCG CCAGGACCAG CCCGCTTCCT TCCACTGCCA
421 GGCCTGCCCC CAGCAGCCCT GGAGCCGCCA GGGATCCTGG GCCCTGAGCC CCCTGATGTG
481 GGCTCCTCCG ACCCACTCAG CATGGTGGGG CCTTTGCAGG GCCGAAGCCC CAGTTACGCT
541 TCCTGA
```

*Loxodonta africana* (elephant) FGF21 gene coding sequence (SEQ ID NO: 300) (Ensembl Accession No. ENSLAFT00000022429, which is hereby incorporated by reference in its entirety)

```
  1 ATGGACTGGG CCAAGTTTGG GTTGGAGCAC CCAGGACTGT GGGTCCCTGT GATGGCTGTC
 61 CTTCTGCTGG GAGCCTGCCA GGGACACCCC ATCCCTGACT CCAGCCCCCT CCTCCAATTC
121 GGGGGCCAGG TCCGGCAACG TTACCTCTAC ACAGATGATC AGGAGACCGA GGCCCACCTG
181 GAGATCAGAG CAGATGGCAC AGTGGCGGGA GCCGCTCAGA GAGTCTCTTG
241 GAGCTGAAAG CTTTGAAGCC TGGAATAATT CAGATCTTGG GGGTCAAGAC ATCCCGGTTC
301 CTGTGCCAGG GGCCTGATGG GGTGCTGTAC GGATCGCTCC ATTTCGACCC AGCCGCCTGC
361 AGCTTCCGGG AGCTGCTTCT TGAAGATGGA TACAATGTTT ACTGGTCCGA GGCCCATGGA
421 CTCCCAATCC GCCTGCCCTC CCACAACTCC CCATATAGGG ACCCAGCATC CCGGGTACCA
481 GCCCGCTTCC TGCCACTGCC AGGCCTGCTC CCAATGCTCC AAGAACCTCC AGGGGTCCTG
541 GCCCCTGAGC CCCCTGATGT GGACTCCTCA GACCCCCTGA GCATGGTGGG GCCTTCACAG
601 GGCCGAAGCC CCAGCTATGC CTCCTGA
```

*Sus scrofa* (pig) FGF21 gene coding sequence (SEQ ID NO: 301) (GenBank Accession No. NM_001163410, which is hereby incorporated by reference in its entirety

```
131 ATGGGCTGGG CCGAGGCCAA GTTCGAGCGC TTGGGACTGT GGGTCCCTGT GCTGGCTGTC
191 CTGCTGGGAG CCTGCCAGGC ACGTCCCATT CCTGACTCCA GCCCCCTCCT CCAATTTGGG
251 GGCCAAGTGC GCCAACGATA CCTCTACACG GATGATGCCC AGGAAACTGA AGCCCACCTG
311 GAGATCAGAG CTGATGGCAC CGTGGCAGGG GTAGCCCGCC AGAGCCCTGA AAGTCTCTTG
371 GAGCTGAAAG CCCTGAAGCC AGGGGTCATT CAAATTTTGG GAGTCCAGAC ATCCCGGTTC
431 CTGTGCCAGG GGCCAGACGG GAGACTGTAC GGATCGCTCC ACTTCGACCC TGAGGCCTGC
491 AGCTTCCGGG AGCTGCTTCT TGAGGATGGA TACAACGTTT ACCAGTCTGA GGCCCTTGGC
551 CTCCCACTCG GGCTGCCTCC GCACCGCTCC TCCAACCGGG ACCTGGCCCC CGGGGACCT
611 GCTCGCTTCC TGCCACTGCC AGGCCTGCCC CCGGCACCCC CGGAGCCGCC AGGGATCTTG
671 GCCCCTGAAC CTCCCGACGT GGGCTCCTCG GACCCCCTGA GCATGGTGGG GCCTTCACAC
731 GGCCGGAGCC CCAGCTACAC TTCTTGA
```

*Felis catus* (cat) FGF21 gene coding sequence (SEQ ID NO: 302) (Ensembl Accession No. ENSFCAT00000007367, which is hereby incorporated by reference in its entirety)

```
  1 ATGGGCTGGG ACGAGGCCGG GTCCCAGCGC CTGGGACTGT GGGTCGTGCT GGGGGTCCTT
 61 TTGCCGGAAG CCTGCCAGGC ACACCCTATC CCTGACTCCA GCCCCCTCCT CCAATTCGGG
121 GGCCAAGTTC GACAGCGGTT CCTCTACACG GACGACGCCC AGGAGACAGA GGTCCACCTC
181 GAGATCAAGG CTGATGGCAC AGTGGTGGGG ACCGCTCGCC GGAGCCCTGA GAGTCTCTTG
241 GAGCTAAAAG CCCTGAAGCC GGGGGTAATT CAAATCTTGG GGGTCAAAAC GTCCAGGTTC
301 CTGTGCCAGG GCCCAGATGG GACACTGTAT GGATCGCTCC GCTTTGACCC CGCAGCCTGC
361 AGCTTCCGGG AACTGCTCCT GGAGGACGGA TACAACATCT ACCACTCGGA AGCCCTTGGC
421 CTCCCACTCC GCCTGCCCCC CCACAACTCC CCATACCGGG ACTTGGCCCC CGGGCACCCT
481 GCCCGCTTCC TGCCGCTGCC AGGCCTGCTT CCGGCACCCC CGGAGCCTCC AGGGATCCTG
541 GCCCCCGAGC CCCCGGACGT GGGCTCCTCG ACCCTCTGA GCATGGTGGG GCCTTCCCAG
601 GGCCGAAGTC CCAGCTACGC TTCCTGA
```

*Otolemur garnettii* (bushbaby) FGF21 gene coding sequence (SEQ ID NO: 303) (Ensembl Accession No. ENSOGAT00000003585, which is hereby incorporated by reference in its entirety)

```
  1 GACAAGGCCA GGACTGGGTT CAAGCACCCA GGACCATGGT TTCCCCTGCT GGCTGTACTT
 61 TTGTTGGGAG CCTGCCAGGC ACACCCTATC CCTGACTCCA GCCCCCTACT CCAGTTTGGT
121 GGCCAAGTCC GGCAGCGGTA CCTCTACACA GATGATGCCC AGGAGACAGA AGCCCACCTG
181 GAGATCAGGG AAGATGGCAC GGTGGTGGGG GCTGCACACC AGTCGTGA AAGTCTCTTG
241 GAGCTGAAAG CTTTAAAGCC AGGGGTCATT CAAATCTTGG GAGTCAAGAC ATCCAGGTTC
301 CTGTGCCAGA GGCCAGATGG GGGCTATATG GATCGCTCT ACTTTGACCC CAAGGCCTGC
361 AGTTTCCGGG AGCTGCTTCT TGAGGATGGA TACAACGTTT ACTGGTCTGA GACCTATGGC
421 CTCCCACTGC ACCTGCCTCC TGCCAATTCC CCATACTGGG GCCCATCCCT TCGGAGCCCA
481 GCCCGCTTCC TGCCACTGCC AGGCCCTCCT GCAGCATCCC CAGAGCTGCC GGGGATCTTG
```

TABLE 8 -continued

```
541 GCCCTGGAAC CCCCCGATGT GGGCTCCTCG GACCCTCTGA GCATGGTGGG GCCTTCGCAG
601 GGCCGAAGCC CCAGCTATGC TTCCTGA
```

*Rattus norvegicus* (Norway rat) FGF21 gene coding sequence (SEQ ID NO: 304) (GenBank Accession No. NM_130752, which is hereby incorporated by reference in its entirety)

```
  1 ATGGACTGGA TGAAATCTAG AGTTGGGGCC CCGGGACTGT GGGTCTGTCT CCTGCTGCCT
 61 GTCTTCCTGC TGGGGGTGTG CGAGGCATAC CCCATCTCTG ACTCCAGCCC CCTCCTCCAG
121 TTTGGGGGTC AAGTCCGACA GAGGTATCTC TACACAGATG ACGACCAGGA CACCGAAGCC
181 CACCTGGAGA TCAGGGAGGA CGGAACAGTG GTGGGCACAG CACACCGCAG TCCAGAAAGT
241 CTCCTGGAGC TCAAAGCCTT GAAGCCAGGG GTCATTCAAA TCCTGGGTGT CAAAGCCTCT
301 AGGTTTCTTT GCCAACAACC AGATGGAACT CTCTATGGAT CGCCTCACTT TGATCCTGAG
361 GCCTGCAGTT TCAGAGAGCT GCTGCTTAAG GACGGATACA ATGTGTACCA GTCTGAGGCC
421 CATGGCCTGC CCCTGCGTCT GCCCCAGAAG GACTCCCAGG ATCCAGCAAC CCGGGGACCT
481 GTGCGCTTCC TGCCCATGCC AGGCCTGCCC CACGAGCCCC AAGAGCAACC AGGAGTCCTT
541 CCCCCAGAGC CCCCAGATGT GGGTTCCTCC GACCCCCTGA GCATGGTAGA GCCTTTGCAA
601 GGCCGAAGCC CCAGCTATGC ATCTTGA
```

*Mus musculus* (house mouse) FGF21 gene coding sequence (SEQ ID NO: 305) (GenBank Accession No. NM_020013, which is hereby incorporated by reference in its entirety)

```
185 ATGGAA TGGATGAGAT CTAGAGTTGG GACCCTGGGA CTGTGGGTCC GACTGCTGCT
241 GGCTGTCTTC CTGCTGGGGG TCTACCAAGC ATACCCCATC CCTGACTCCA GCCCCCTCCT
301 CCAGTTTGGG GGTCAAGTCC GGCAGAGGTA CCTCTACACA GATGACGACC AAGACACTGA
361 AGCCCACCTG GAGATCAGGG AGGATGGAAC AGTGGTAGGC GCAGCACACC GCAGTCCAGA
421 AAGTCTCCTG GAGCTCAAAG CCTTGAAGCC AGGGGTCATT CAAATCCTGG GTGTCAAAGC
481 CTCTAGGTTT CTTTGCCAAC AGCCAGATGG AGCTCTCTAT GGATCGCTC ACTTTGATCC
541 TGAGGCCTGC AGCTTCAGAG AACTGCTGCT GGAGGACGGT TACAATGTGT ACCAGTCTGA
601 AGCCCATGGC CTGCCCCTGC GTCTGCCTCA GAAGGACTCC CCAAACCAGG ATGCAACATC
661 CTGGGGACCT GTGCGCTTCC TGCCCATGCC AGGCCTGCTC CACGAGCCCC AAGACCAAGC
721 AGGATTCCTG CCCCCAGAGC CCCCAGATGT GGGCTCCTCT GACCCCCTGA GCATGGTAGA
781 GCCTTTACAG GGCCGAAGCC CCAGCTATGC GTCCTGA
```

*Vicugna pacos* (alpaca) FGF21 gene coding sequence (SEQ ID NO: 306) (Ensembl accession no. ENSVPAT00000005993, which is hereby incorporated by reference in its entirety) (1-209, excluding 79-168 and 172-182)

```
  1 ATGGACTGGG ACGAGGCCAA GTTCGAGCAT CGGGGACTGT GGGTCCCAGT GCTCACTGTC
 61 CTTCTGCTGG GAGCCTGCCA GGCACGCCCC ATTCCTGACT CCAGCCCCCT CCTCCAATTC
121 GGGGGCCAAG TCCGGCAGCG GTACCTCTAC ACGGATGACG CCCAGGAGAC AGAAGCCCAC
181 CTGGAGATCA GGGCTGATGG CACAGTGGTG GGGGTGGCCC GCCAG---CC CGAA------
241 ---------- ---------- ---------- ---------- ---------- ----------
301 ---------- ---------- ---------- ---------- ---------- ----------
361 ---------- ---------- ---------- ---------- ---------- ----------
421 ---------- ---------- ---------- ---------- ---------- ----------
481 ---------- ---------- ----GGAATT CCT------- ---------- ----------
541 ------CCCG AGCCTCCTGA CGTGGGCTCC TCAGACCCCC TGAGCATGGT GGGGCCTTCA
601 TACAGCAGAA GCCCCAGCTA CACTTCCTGA
```

*Anolis carolinensis* (anole lizard) FGF21 gene coding sequence (SEQ ID NO: 307) (Ensembl accession no. ENSACAT00000017230, which is hereby incorporated by reference in its entirety)

```
  1 TGTAAAAGCA AGGGAGGAGG GAAGGGGGGA GAGAGGATGT GGGTAGACCT AGTTTTCTGG
 61 GCTGCCTTGC TCCGCACAGC TCCTGCTCTT CCCTTGCGGA ATTCCAACCC CATCTACCAA
121 TTTGATGGGC AGGTCCGGCT TCGGCACCTC TACACAGCAG ATGAACAGAC GCACCTCCAC
181 TTGGAGATCT TGCCAGACGG TACCGTGGGT GGATCCAGGT TTCAGAATCC CTTCAGTTTG
241 ATGGAGATCA AAGCTGTGAA GCCAGGAGTC ATTCGCATGC AGGCCAAGAA GACCTCTAGA
301 TTTCTCTGTA TGAAACCCAA TGGACGACTG TATGGCTCGC TGTTCTACTC TGAGGAGGCA
361 TGCAACTTCC ATGAGAAGGT TCTCAGCGAT GGCTACAACC TCTACTATTC TGAAAACTAC
421 AACATACCTG TCAGCCTCAG CTCGGCAGGG AACCTGGGTC AGAGCCGTCA GTTGCCTCCC
481 TTCTCCCAAT TCCTGCCGTT AGTCAACAAA ATTCCTCTTG AGCCTGTGCT TGAAGACTTT
541 GACTTCTATG GACATCAATT GGATGTTGAA TCAGCTGATC CTTTGAGCAT TTTAGGACAA
601 AACCCTGGTT TCATGAGTCC GAGCTATGTC TTC
```

*Gadus morhua* (cod) FGF21 gene coding sequence (SEQ ID NO: 308) (Ensembl accession no. ENSGMOT00000014151, which is hereby incorporated by reference in its entirety)

```
  1 CTCCTCCTCG CCACCCTCCT CCACATCGGC CTCTCCTTCT ACGTCCCCGA CTCCGGCCCC
 61 CTGCTGTGGC TGGGCGACCA GGTCAGGGAG AGACACCTCT ACACAGCAGA GAGCCACCGG
121 AGGGGGCTGT TCCTGGAGAT GAGCCCGGAC GGTCAGGTGA CAGGAAGTGC TGCTCAGACG
181 CCGCTCAGTG TTCTGGAGCT GAGGTCGGTC AGAGCAGGAG ATACGGTCAT CAGAGCGCGC
241 CTCTCCTCTC TCTACCTGTG TGTGGACAGG GCAGGTCACC TGACAGGACA GAGACAGTAC
301 ACAGAGTCCG ACTGCACCTT CAGAGAGGTC ATCCTTGAGG ACGGCTACAC CCACTTCCTG
361 TCCGTGCACC ACGGACTTCC TATTTCGCTG GCGCCGAGAC ACTCCCCAGG GAGACAGGGG
421 CTGCGCTTCA GCAGGTTCCT CCCGCTGAGG AGCAGTCTGT CAGAGGATAG GGTCGCCGAG
481 CCCCCAGACA GCCCACTGAA CCTGGACTCT GAAGACCCCC TGGGGATGGG TCTGGGTTCG
541 CTCCTCAGCC CGGCCTTCTC CATG
```

TABLE 8 -continued

*Latimeria chalumnae* (coelacanth) FGF21 gene coding sequence (SEQ ID
NO: 309) (Ensembl accession no. ENSLACT00000003815, which is hereby
incorporated by reference in its entirety)
```
  1 ATGTTATGCC AGAGTTTTGT GATATTAAGT CAGAAATTCA TTTTTGGGCT CTTTTTGACT
 61 GGATTGGGGC TAACAGGATT GGCTTGGACA AGGCCCTTCC AGGATTCCAA TCCCATCCTG
121 CAGTATTCCG ATTCCATCCG GCTCCGACAT CTGTACACTG CCAGTGAGAG TCGGCACCTT
181 CACCTACAAA TCAACTCGGA TGGACAGGTG GGAGGGACAA CCAAGCAAAG CCCTTACAGT
241 CTGTTGGAGA TGAAGGCGGT GAAGACAGGT TTTGTGGTCA TCAGGGGCAA GAAAAGCGCC
301 CGTTACCTCT GTATGGAACG TAGTGGACGG CTCTATGGAT CGCTGCAGTA TACAGAAAAA
361 GACTGCACCT TCAAAGAGGT TGTGTTGGCA GATGGATACA ACCTGTATGT CTCAGAGGAA
421 CACCAGGCCA CAGTGACGCT GAGCCCCATG AGGGCGAGGA TAGCGCAAGG GAAAAAGATC
481 CCACCCTTTT CCCATTTCCT TCCAATGGTG AACAAGGTGC CTGTGGAGGA TGTTGCCGCT
541 GAGATGGAGT TTGTCCAGGT GCTGCGGGAA ATGACGGCCG ACGTGGACTC TCCGGATCCC
601 TTTGGAATGA CCTGGGAAGA ATCGGTTCAC AGTCCGAGCT TTTTTGCC
```

*Tursiops truncatus* (dolphin) FGF21 gene coding sequence (SEQ ID
NO: 310) (Ensembl accession no. ENSTTRT00000014561, which is hereby
incorporated by reference in its entirety)
```
  1 ATGGGCTGGG ACAAGACCAA ACTGAGCAC CTGGGACTGT GGGTCCCTGT GCTAGCTGTC
 61 CTGCTGGGAC CCTGCCAGGC ACATCCCATT CCTGACTCCA GCCCCCTCCT CCAATTTGGG
121 GGCCAAGTCC GCCAGCGATA CCTCTACACG GATGACGCCC AGGAGACGGA GGCCCACCTG
181 GAGATCAGGG CTGATGGCAC AGTGGTGGGG ACGCCCGCC GGAGCCCCGA AGGAGTTAAA
241 ACATCCAGGT TCCTGTGCCA GGGGCAGAG GGGAGGCTGT ATGGATCGCT CCACTTCAAC
301 CCCCAGGCCT GCAGCTTCCG GGAGCTGCTT TTGAGGATG GATACAACGT TTACCAGTCT
361 GAGGCTCTTG GCATTCCCCT CCGCCTGCCC CCGCACCGCT CCTCCAACTG GGACCTGGCC
421 CCCCGGGGAC CTGCTCGCTT CCTGCCGCTG CCAGGCTTCC TCCCGCCACC CCTGGAGCCT
481 CCAGGGATCT TGGCCCCCGA GCCTCCCAAC GTAGGTTCCT CGGACCCCTT GAGCATGGTG
541 GGACCTTCAC ATGGCCGAAG CCCCAGCTAC ACTTCCTGA
```

*Mustela putorius furo* (ferret) FGF21 gene coding sequence (SEQ ID
NO: 311) (Ensembl accession no. ENSMPUT00000003755, which is hereby
incorporated by reference in its entirety)
```
188 ATG GGCTGGGAAG AGGCCAGGTC CGAGCACCTG GGGCTGTGGG TCCCTGTGCT
241 GGCGGTCCTT TTGCTGGGAG CCTGCCAGGC ATACCCTATT CCTGACTCCA GCCCCCTCCT
301 CCAATTTGGA GGCCAAGTTC GACAGCGGTA CCTCTACACA GACGACGCTC AGGAGACGGA
361 GGCCCACCTA GAGATCAGGG CTGATGGCAC GGTGGTGGGG GCTGCCCGCC GGAGCCCCGA
421 AAGTCTCTTG GAGCTGAAAG CCCTGAAGCC AGGGGTCATT CAGATCTTGG GAGTGAAAAC
481 ATCCAGGTTC CTGTGCCAGG GCCCGAATGG GACACTGTAC GGATCGTTCC ACTTCGACCC
541 CGTAGCCTGC AGCTTCCGGG AAGTGCTTCT GGAAGATGGA TACAACATCT ACCACTCTGA
601 GACCCTGGGC CTCCCACTGC GCCTGCCCCC CACAACTCC CCACACAGGG ACCTGGCGCC
661 CCGGGGCCT GCCCGCTTCC TGCCCCTGCC AGGCCTGCTT CCGGCCACCC CGGAGTCCCG
721 GGGGATCCCA GCCCCCGAGC CTCCCAACGT GGGCTCCTCA GACCCCCTGA GCATGGTGGG
781 GCCTTTGCAG GGTCAAAGTC CCAGCTACAC TTCCTGA
```

*Takifugu rubripes* (fugu) FGF21 gene coding sequence (SEQ ID NO: 312)
(Ensembl accession no. ENSTRUT00000034076, which is hereby
incorporated by reference in its entirety)
```
  1 TTTATTTATT TATTTATTCA AACTGCACTT TTTTCCCCTT CCAAATGGTT CAACTTTTAT
 61 CTCCCTGACT CCAACCCGCT CTTATCCTTT GACAGTCATG GCAGAGGCAT CCACCTCTAC
121 ACAGATAATC AAAGGCGAGG GATGTATCTG CAGATGAGCA CAGATGGAAG CGTTTCCGGG
181 AGTGATGTCC AGACGGCGAA CAGTGTGCTG GAACTGAAGT CAGTCAGAAA CGGCCACGTC
241 GTCATCCGAG GAAAATCGTC TTCTCTGTTT CTCTGTATGG ACAGCAGAGG CCGTTTATGG
301 GGGCAGAGGC ACCCCACTGA GGCCGACTGC ACTTTCAGGG AAGTGTTGCT GGCAGATGGA
361 TACACTCGCT TCCTGTCCCT GCACAACGGA ACTCCTGTGT CTCTGGCACC TAAACAATCT
421 CCAGACCAGC ACACAGTCCC CTTCACTCGT TTCCTGCCGC TCAGGAATAC ACTGGCAGAG
481 GAGAGCATGT CTGAACCACC ATCAAACCAA CAGAGATATT TTAACATTGA CTCTGATGAT
541 CTTCTTGGAA TGGATTTAAA TGCGATGGTC AGTCCTCAGT TTTCAGGGGA CAAGTGA
```

*Dipodomys ordii* (kangaroo rat) FGF21 gene coding sequence (SEQ ID NO:
313) (Ensembl accession no. ENSDORT00000001234, which is hereby
incorporated by reference in its entirety)
```
  1 ATGGACCAGG CAAAGACCAG GGTTGGGGCC CGGGGGCTGG GGGGCCTTGT GCTGGCTGTC
 61 ATAATTCTGG GAGCATGCAA GGCACGGCCT ATCCCTGACT CCAGCCCCCT CCTCCAATTT
121 GGGGGTCAAG TTCGGCTTCG GCACCTCTAC ACAGATGACA CTCAGGAGAC GGAAGCCCAT
181 CTGGAGATCA GGGCAGATGG CACGGTAGTG GGGACTGCCC ACCGGAGCCC TGAAAGTCTC
241 TTGGAGCTGA AAGCCTTGAA GCCAGGAGTC ATTCAAATCT TAGGGATCAA GACATCCAGA
301 TTCTTATGCC AGAGACCAGA CGGGACACTG TATGGATCAC TCCACTTTGA CCCTGAGGTT
361 TGCAGCTTCC AGGAGCTGCT TCTGAAGAT GGATACAACA TTTACCGTTC TGAAGCCCTG
421 GGTCTCCCCC TGCGCCTGTC CCCAGATCCA GCACCCTGGG GGCCAGCCCG CTTCCTGCCC
481 CTGCCTGGTG TGCCCCCCGC ACCGCCGGAG CCCCCCGGGA TCCTGGCTCC CGAACCCCCT
541 GATGTCGGCT CCTCCGACCC TCTGAGTATG GTGGGACTGT GCAGGGCCG AAGCCCCAGC
601 TATGCATCCT GA
```

*Echinops telfairi* (lesser hedgehog tenrec) FGF21 gene coding sequence
(SEQ ID NO: 314) (Ensembl accession no. ENSETET00000010721, which is
hereby incorporated by reference in its entirety)
```
  1 ATGGGTTGCA CCAAATCTGG GTGGAAGTCC CCGGGACTGT GGGTCCCTGT GCTGGCCAGC
 61 CTTCTGCTGG GAGGCTGCGG AGCACACCCC ATCCCTGACT CCAGCCCCCT CCTCCAATTC
121 GGGGGCCAAG TCCGGCAGCG ATACCTCTAT ACGGATGACG CCCAGACCAC CGAGGCCCAC
```

TABLE 8 -continued

```
181 CTGGAGATCA GAGCGGATGG CACAGTGGGG GGCGTCGCCC ACCAGAGCCC AGAGAAGTTC
241 CTGAGTCAAT GGCGTGAAAA GCCCCTGAGA TCACTCCATT TCGACCCAGC CGCCTGCAGC
301 TTCCGGGAGA AGCTTCTAGA AGACGGATAC AACTTGTACC ACTCTGAGAC CCACGGCCTC
361 CCCCTCCGCC TCCCACCCCG TGGGGGCGAC CCCTCTTCTC AGCCTGGGGC CCGCTTCCCA
421 CCGCTGCCGG GCCAGCTCCC ACAACTCCAA GAGACGCCAG GGGTCCTCGC CCCCGAACCC
481 CCCGACGTGG GCTCTTCAGA CCCCCTGAGC ATGGTGGGGC CTTGGCGAGG GCAAAGTCCC
541 AGTTATGCCT CCTGA
```

*Macaca mulatta* (rhesus monkey) FGF21 gene coding sequence (SEQ ID NO: 315) (Ensembl accession no. ENSMMUT00000038440, which is hereby incorporated by reference in its entirety)

```
  1 ATGGACTCGG ACGAGACCGG GTTCGAGCAC TCAGGACTGT GGGTTCCTGT GCTGGCTGGT
 61 CTTCTGCTGG GAGCCTGCCA GGCACACCCC ATCCCTGACT CCAGTCCTCT CCTGCAATTC
121 GGGGGCCAAG TCCGGCAACG GTACCTCTAC ACAGATGATG CCCAGCAGAC AGAAGCCCAC
181 CTGGAGATCA GGGAGGATGG GACAGTGGGG GGCGCTGCTC ACCAGAGCCC CGAAAGTGAG
241 TGTGGGCCAG AGCCTGGGTC TGAGGGAGGA GGGGCTGTGG GAGGTGCTGA GGGACCTGGA
301 CTCCTGGGTC TGAGGGAGGC AGGGCTGGGG CCTGGATCGT GGCTCCACTT TGACCCTGAG
361 GCCTGCAGCT TCCGGGAGCT GCTTCTTGAG AACGGATACA ATGTTTACCA GTCCGAGGCC
421 CACGGCCTCC CACTGCACCT GCCGGGAAAC AAGTCCCCAC ACCGGGACCC TGCATCCCAA
481 GGACCAGCTC GCTTCCTGCC ACTACCAGGC CTGCCCCCCG CACCCCCGGA GCCGCCAGGA
541 ATCCTCGCCC CCCAGCCCCC CGATGTGGGC TCCTCGGACC CTCTGAGCAT GGTGGGACCT
601 TCCCAGGCCC GAAGCCCCAG CTATGCTTCC TGA
```

*Microcebus murinus* (mouse lemur) FGF21 gene coding sequence (SEQ ID NO: 316) (Ensembl accession no. EN5MICT00000013258, which is hereby incorporated by reference in its entirety)

```
  1 ATGGGCTGGG ACGAGGCCGG CGCCGGGTTC GAGCACCCAG GACTGTGGTT TCCCATGCTG
 61 GGTGTCCTGC TGCTGGGAGC CTGCCAGGCG TACCCCATCC CTGACTCCAG CCCCCTCCTC
121 CAATTTGGCG GCCAAGTCCG GCAGCGGCAC CTCTACACAG ACGATATCCA GGAGACAGAA
181 GCCCACCTGG AGATCAGGGC GGACGGCACA GTGGTGGGGG CCGCCCGACA GAGCCCTGAG
241 TTGGAGCTGA AAGCCTTAAA GCCAGGGGTC ATTCAAATCT TGGGAGTCAA GACCTCCAGG
301 TTCCTGTGCC AGAGGCCAGA CGGGGCCCTG TACGGATCGC TCCACTTTGA CCCCGAGTGC
361 AGCTTCCGGG AGCTGCTTCT TGAGGATGGA TACAACGTCT ACTGTCCCTA CCTCCCGCTG
421 CACCTGTCCC CACGCATCGA ACTGCCGGA TCACGCTCTG CGCTGCCACT GCCCCCAGCA
481 CCTGAACGCA GGATTTTGGC CCCGGAGCCC CCGATGGCC CCTCGGACCC TCTGAGCATG
541 GTGGGGCCTT CGCAGGGCCG AAGTCCCAGC TATGCTTCCT GA
```

*Ochotona princeps* (pika) FGF21 gene coding sequence (SEQ ID NO: 317) (Ensembl accession no. ENSOPRT00000007373, which is hereby incorporated by reference in its entirety)

```
  1 AAAGACATGG ACGGGCTCCA GCCTCCGGGG CTGCGGGTTC CTGTGCTGGC TGCCCTGCTT
 61 TTGGGAGTTG GCCAGGCACG CCCCATCCCT GATTCTAGCC CTCTCCTCCA ATTCGGGGGC
121 CAGGTCCGGC AGAGGCACCT CTACACGGAT GACGCCAGG AATCGAAGT ACACCTGGAG
181 ATCCGGGCAG ACGGCACCGT GGCAGGGACT GCCCGCCGGA GCCCTGAAAG TCTCTTAGAA
241 ATGAAAGCGT TGAAGCCAGG CGTCATTCAG ATCCTGGGGG TCCACACATC CAGGTTCCTG
301 TGCCAGAGAC CAGACGGGAC GCTGTACGGC TCGCTCCACT TCGACCACAA GGCCTGCAGC
361 TTCCGGGAGC AGCTGCTGGA GGATGGGTAC AACGTGTACC ACTCAGAGAC ACACGGCCTC
421 CCGCTGCGCC TGTCTCCAGA CCGAGCCCCC CGGGGCCCAG CCCGCTTCCT GCCACTGCCA
481 GGCCCTCCTC CTGACCTCCT GGTGCCACCC CTGCCACCGG ACGTCCTAGC CCCTGAGCCC
541 CCCGACGTGG ACTCCCCAGA CCCCCTGAGC ATGGTGGGGC CCTTGCAGGG CCAAAGCCCC
601 AGCTACACTT CCTGA
```

*Xiphophorus maculatus* (platyfish) FGF21 gene coding sequence (SEQ ID NO: 318) (Ensembl accession no. ENSXMAT00000001579, which is hereby incorporated by reference in its entirety)

```
  1 TGCCCGTTCC CCTTCCTTTT CTTAATCCTC TCTCTTCCCT TTTTCTCTTC CTCGTTTTAC
 61 ATCCCAGAAT CCAACCCAAT CTTTGCCTTC AGGAATCAGC TCAGAGAGGT GCATCTCTAC
121 ACAGAAAATC ACAGACGGGG TTTGTATGTG GAGATACATC TGGATGGGAG AGTGACTGGA
181 AGTGATGCTC AGAGTCCTTA TAGTGTGTTG CAGATAAAGT CTGTTAAACC GGGTCATGTG
241 GTCATAAAGG GACAGACATC GTCCCTGTTC CTCTGCATGG ACGACTCCGG GAATCTAAGA
301 GGACAGACAA CCTATGACGA GGCTGACTGC TCCTTCAGGG AACTGCTGCT GGCCGATGGC
361 TACACCCGTT TCCTGAACTC ACAACATGGC GTTCCTTTAT CACTGGCATC CAGAAACTCT
421 CCAGATCGAC ACTCCGTTCC TTTCACAAGA TTTTTACCTC TCAGGAATAC TTTAACGGTT
481 TCGAAGAAT CAACAAAAAC TCAGAGGGAC TTCAACCTGG ACTCGGACGA CCTTCTCGGG
541 ATGGGA
```

*Gasterosteus aculeatus* (stickleback) FGF21 gene coding sequence (SEQ ID NO: 319) (Ensembl accession no. ENSGACT00000010725, which is hereby incorporated by reference in its entirety)

```
  1 TCTCTCCTCC TCATGGTCCC ACTTCCTTTC TGTTCATCCT TTTATCTCAC TGACTCCAGC
 61 CCACTTCTAC CCTTCAATAA TCAAGTCAAA GAGGTGCACC TCTACACAGC AGAGAATCAC
121 AGAAGAGCGA TGTACCTGCA GATCGCTCTG GACGGGAGCG TGTCGGGAAG CGACGCTCGG
181 TCCACTTACA GTGTGCTGCA GCTGAAATCT ATCCAGCCGG GCCACGTGGT CATCAGAGGG
241 AAGGCCTCCT CCATGTTCCT CTGCGTGGAC AGCGGGGCC GTTTGAGAGG ACAGGGGCCG
301 TACTCAGAGG CCGACTGCAG CTTCAGGGAG CTGCTGCTGG GGATGGCTA CACCCGGTTC
361 CTGTCCTCGC AGCACGGGTC CCCGCTGTCT CTGGCGTCGA GGCCTTCCCC GGATCCCAAC
421 TCGGTGCCCT TCACTCGATT CCTACCCATC CGGACCGCCC CGAGGCTGA GAGCGTGATC
481 GAAGAGCCAC CGAGCAATCA GAGATACGTC AACGTGGACT CCGAGGATCT TCTTGGAATG
541 GGCCTGAACA CTGTGGTCAG TCCTCAGTTC TCGGCG
```

TABLE 8 -continued

*Sarcophilus harrisii* (Tasmanian devil) FGF21 gene coding sequence (SEQ
ID NO: 320) (Ensembl accession no. ENSSHAT00000006017, which is hereby
incorporated by reference in its entirety) (1-209, excluding 1-2 and
173-209)
```
132 GTGTCTGCC ATGGGCCTGA GGGAGCGAGC TCCCAGGTAC CTGGCCCCGC
181 TGCTGTCCTT GCTCTTGGCC TGCAGGGCCT CGGGTCACCC CCTCCCGGAT TCCAGCCCCA
241 TGCTCCTGTT TGGGGGGCAG GTCCGCCTCC GGCACCTCTA CACGGATGTG GGCCAGGAGG
301 CCGAGGCCCA CGTGGAACTG GCGTCCGACG GCACAGTCCG GGCGGCAGCG CGGAGGAGTC
361 CCAACAGTCT CCTGGAGCTG AAGGCTGTGA AGCCGGGCAT CGTCCGAATC CTGGCCGTCC
421 ACAGCTCTCG GTTTCTGTGT ATGAGGCCCA ACGGGGAGCT GTACGGAGCG ATACACTACG
481 ACCCTTCCGC CTGCAACTTT CGGGAGCGCC TGCTGGGGGA CGGCTACAAC GTGTACGAGT
541 CCGAGGCTCA CGGGAGGACC CTCCGCCTGC CCCCCAAGGC CGCACCGGGA CCCGCCGGAC
601 CTTCTCGCTT CCTGCCGCTC CCCGGC
```

*Macropus eugenii* (wallaby) FGF21 gene coding sequence (SEQ ID NO: 321)
(Ensembl accession no. ENSMEUT00000015309, which is hereby
incorporated by reference in its entirety)
```
  1 ACAGAGGAGC CTTCTACTGG GTCCAGGCAC CTGGGACAAT GGGCTCCCGG GCTGCCTGGT
 61 CCTCTGCTGT CCTTGCTCCT GGCCTACAGG GGCTGGGGCT CCCCCATCCC TGATTCCAGC
121 CCCATGCTCC TGTTTGGTGG CCAGGTCCGC CTCCGACACC TGTACACAGA TGATGGCCAG
181 GACACGGAGG CCCATGTGGA GCTGGGGCCA GATGGAGTGG TTCGAGCTGT GGCTGAGAGG
241 AGCCCCAACA GTCTTCTGGA ACTGAAGGCG GTGAAGCCTG GAGTCATCCG AATCCTCGCT
301 GTCCAGAGCT CTCGGTTTCT GTGTATGAGG CCCAACGGGG AACTGTATGG AGCGGTACAC
361 TATGACCCTT CTGCCTGCAA CTTTCGGGAA CATCTGCTGG GGGATGGTTA TAATGTGTAT
421 GAATCAGAGA CTCACAGAAG GACCCTCCGT CTGTCCCCAT CCCTGGGTCA GGCTGGCCCC
481 TCTCGCTTCC TGCCACTTCC AGGCGACTGG CTGCCCGGCC CTGATCCACC TTGGGCACAG
541 GGCCCTGAGC CCCAGACGT GGGCTCTGCA GACCCCCTGA GCATGGTGGG GGCCGTGCAG
601 GGCCTCAGCC CCAGCTACTC CTCCTGA
```

*Xenopus tropicalis* (Western clawed frog) FGF21 gene coding sequence
(SEQ ID NO: 322) (Ensembl accession no. ENSXETT00000009917, which is
hereby incorporated by reference in its entirety) (1-209, excluding
170-209)
```
  1 AGAGGGGGTA GGACCAAAAA AAAGACGTTA CTCAGGAAAT GGCTTTGCCT TTTAGCCATT
 61 ATGTTGAGTA GGTCAAGGTT TTCTTTAGCA AATCCTATCC AGAATTCGAA CCCAATCTTA
121 TCCAACGACA ACCAAGTACG GACTCAGTAT TTATACACAG ATAACAATAA CATGCACCTG
181 TATCTTCAGA TCACCCACAA TGGAGTAGTA ACTGGTACCG AAGAAAAGAA TGACTATGGT
241 GTGCTGGAAA TAAAGGCAGT AAAAGCTGGG GTTGTAGTTA TAAAAGGAAT TCGAAGCAAT
301 CTCTACCTAT GCATGGATTC TAGACACCAA TTGTATGCGT CGGCATATGA TAAAGATGAC
361 TGCCATTTCC ATGAAAAGAT CACACCAGAT AATTACAACA TGTATAGCTC AGAGAAGCAT
421 TCAGAATACG TGTCCTTAGC TCCATTAAAA GGAAGCCAGA TGGCTCGTTT TCTACCTATA
```

*Danio rerio* (zebrafish) FGF21 gene coding sequence (SEQ ID NO: 323)
(Ensembl accession no. ENSDART00000103511, which is hereby
incorporated by reference in its entirety)
```
 30 A TGCTTCTTGC CTGCTTTTTT ATATTTTTTG
 61 CTCTTTTTCC TCATCTTCGG TGGTGTATGT ATGTTCCTGC ACAGAACGTG CTTCTGCAGT
121 TTGGCACACA AGTCAGGGAA CGCCTGCTTT ACACAGATGG GTTGTTTCTT GAAATGAATC
181 CAGATGGCTC CGTCAAAGGC TCTCCTGAAA AGAATCTAAA TTGTGTGCTG GAGCTGCGTT
241 CAGTCAAAGC GGGTGAAACC GTCATCCAGA GTGCAGCTAC ATCTCTCTAC CTCTGCGTCG
301 ATGATCAAGA CAAGCTGAAA GGACAGCATC ATTACTCTGC ACTAGACTGC ACCTTTCAGG
361 AATTGCTACT GGATGGATAT TCGTTTTTCC TTTCTCCACA CACTAATCTT CCCGTATCGC
421 TCCTCTCGAA ACGTCAGAAA CACGGCAATC CTCTTTCTCG CTTCCTCCCT GTTAGCAGAG
481 CAGAGGACAG CCGGACACAG GAGGTGAAAC AGTATATTCA GGATATAAAC CTGGACTCTG
541 ACGACCCACT AGGAATGGGA CATCGGTCAC ACTTACGAGC CGTCTTCAGT CCCAGTCTGC
572 ATACTAAAAA ATGA
```
*Tupaia chinensis* (Chinese tree shrew) FGF21 gene coding sequence (SEQ
ID NO: 327)(generated using SMS Reverse Translate tool on the ExPASy
Bioinformatics Resource website (www.expasy.org))
```
  1 ATGGGCTGGG ATAAAGCGCG CTTTGAACAT CTGGGCGCGT GGGCGCCGGT GCTGGCGGTG
 61 CTGCTGCTGG GCGCGTGCCA GGCGTATCCG ATTCCGGATA GCAGCCCGCT GCTGCAGTTT
121 GGCGGCCAGG TGCGCCAGCG CTATCTGTAT ACCGATGATA CCCAGGATAC CGAAGCGCAT
181 CTGGAAATTC GCGCGGATGG CACCGTGGTG GGCGCGGCGC ATCAGAGCCC GGAAAGCCTG
241 CTGGAACTGA AAGCGCTGAA ACCGGGCGTG ATTCAGATTC TGGGCGTGAA AACCAGCCGC
301 TTTCTGTGCC AGCGCCCGGA TGGCGCGCTG TATGGCAGCC TGCATTTTGA TCCGGAAGCG
361 TGCAGCTTTC GCGAACTGCT GCTGGAAGAT GGCTATAACA TTTATCAGAG CGAAGCGCGC
421 GGCCTGCCGC TGCGCCTGCC GCCGCATGAT AGCCCGCATC GCGATCGCAC CCCGCAGGGC
481 CCGGCGCGCT TTCTGCCGCT CCGGGCCTG CCGCTGGTGC CGCCGGAACT GCCGGGCGTG
541 CTGGCGCTGG AACCGCCGGA TGTGGGCAGC AGCGATCCGC TGAGCATGAT GGGCCCGAGC
601 CAGGGCCAGA GCCCGAGCTA TGCGAGCTAA
```

*Papio anubis* (olive baboon) FGF21 gene coding sequence (SEQ ID NO:
328) (GenBank accession no. XM_003915851, which is hereby incorporated
by reference in its entirety)
```
  1 ATGGACTCGG ACGAGACCGG GTTCGAGCAC TCAGGACTGT GGGTTCCTGT GCTGGCTGGT
 61 CTTCTGCTGG GAGCCTGCCA GGCACACCCC ATCCCTGACT CCAGTCCTCT CCTGCAATTC
121 GGGGGCCAAG TCCGGCAACG GTACCTCTAC ACAGATGATG CCCAGCAGAC AGAAGCCCAC
181 CTGGAGATCA GGGAGGATGG GACAGTGGGG GGCGCTGCTC ACCAGAGCCC CGAAAGTAAG
241 TGTGGGCCAG AGCCTGGGTC TGAGGGAGGA GGGGCTCTCC ACTTTGACCC TGAGGCCTGC
301 AGCTTCCGCG AGCTGCTTCT TGAGAACGGA TACAATGTTT ACCAGTCCGA GGCCCACGGC
```

TABLE 8 -continued

```
361 CTCCCACTGC ACCTGCCGGG AAACAAGTCC CCACACCGGG ACCCTGCATC CCGAGGACCA
421 GCTCGCTTCC TGCCACTACC AGGCCTGCCC CCCGCACCCC CAGAGCCACC AGGAATCCTC
481 GCCCCCCAGC CCCCCGATGT GGGCTCCTCG GACCCTCTGA GCATGGTGGG ACCTTCCCAG
541 GCCCGAAGCC CTAGCTACGC TTCCTGA
```

*Pteropus alecto* (black flying fox) FGF21 gene coding sequence (SEQ ID NO: 329) (generated using SMS Reverse Translate tool on the ExPASy Bioinformatics Resource website (www.expasy.org))

```
  1 ATGGGCTGGG GCAAAGCGCG CCTGCAGCAT CCGGGCCTGT GGGGCCCGGT GCTGGCGGTG
 61 CTGCTGGGCG CGTGCCAGGC GCATCCGATT CTGGATAGCA GCCCGCTGTT TCAGTTTGGC
121 AGCCAGGTGC GCCGCCGCTA TCTGTATACC GATGATGCGC AGGATACCGA AGCGCATCTG
181 GAAATTCGCG CGGATGGCAC CGTGGCGGGC GCGGCGCGCC GCAGCCCGGA AAGCCTGCTG
241 GAACTGAAAG CGCTGAAACC GGGCGTGATT CAGGTGCTGG GCGTGAAAAC CAGCCGCTTT
301 CTGTGCCAGC GCCCGGATGG CACCCTGTAT GGCAGCCTGC ATTTTGATCC GGCGGCGTGC
361 AGCTTTCGCG AACTGCTGCT GAAAGATGGC TATAACGTGT ATCAGAGCGA AGCGCTGGCG
421 CGCCCGCTGC GCCTGCCGCC GTATAGCAGC CCGAGCAGCG ATCCGGCGCG CCGCGGCCCG
481 GCGCGCTTTC TGCCGCTGCC GGGCCCGCCG CCGGAACCGC CGCAGCCGCC GGGCCGCCTG
541 GCGCCGGAAC CGCCGGATGT GGGCAGCAGC GATCCGCTGA GCATGGTGTG GCCGAGCCGC
601 GGCCGCAGCC CGAGCTATAC CAGCTAA
```

*Heterocephalus glaber* (naked mole-rat) FGF21 gene coding sequence (SEQ ID NO: 330) (generated using SMS Reverse Translate tool on the ExPASy Bioinformatics Resource website (www.expasy.org))

```
  1 ATGGATTGGG CGCGCGCGGA AAGCAACGC CCGGGCCTGT GGGTGCCGGC GGTGCTGGCG
 61 GTGCTGCTGC TGGGCGCGTG CCAGGCGCAT CCGATTCCGG ATAGCAGCC GCTGCTGCAG
121 TTTGGCGGCC AGGTGCGCCA GCGCCATCTG TATACCGATG ATGCGCAGGA TACCGAAGTG
181 CATCTGGAAA TTCGCGCGGA TGGCAGCGTG GGCGGCGCGG CGCATCGCAG CCCGGAAAGC
241 CTGCTGGAAC TGAAAGCGCT GAAACCGGGC GTGATTCAGA TTCTGGGCGT GCGCACCAGC
301 CGCTTTCTGT GCCAGCGCCC GGATGGCACC CTGTATGGCA GCCTGCATTT TGATCCGGAA
361 GCGTGCAGCT TTCGCGAACT GCTGCTGGCG GATGGCTATA ACATTTATCA GAGCGAAGCG
421 TATGGCCTGC CGCTGCGCAT GCTGCCGAGC GATAGCGCGA GCCGCGATCC GGTGCCGCCG
481 GGCCCGGCGC GCTTTCTGCC GCTGCCGGGC CTGCATCCGC CGCCGCTGGA ACCGCCGGGC
541 ATGCTGCCGC CGGAACCGCC GGATGTGGGC AGCAGCGATC CGCTGAGCAT GGTGGGCCCG
601 CTGCAGGGCC GCAGCCCGAG CTATGCGTTT TAA
```

*Cricetulus griseus* (Chinese hamster) FGF21 gene coding sequence (SEQ ID NO: 331) (GenBank accession no. XM_003508678, which is hereby incorporated by reference in its entirety)

```
  1 ATGGACTGGA TGAAATCTGG AGTTGGGGTC CCGGGACTGT GGGTCCCTCT GCTGCCTATC
 61 TTCCTGCTGG GGGTCTCCCA GGCACACCCC ATCCCTGACT CCAGCCCCCT CCTCCAGTTT
121 GGGGGTCAAG TCCGGCACAG GCACCTCTAC ACAGATGACA ACCAGGAAAC TGAAGTCCAC
181 CTGGAGATTA GGCAGGATGG CACGGTGATA GGACCACAC GCCAGCCC AGAAAGTCTC
241 CTGGAGCTCA AAGCCTTGAA GCCAGAGGTC ATCCCAGTGC TGGGTGTCAA GGCCTCCAGG
301 TTTCTTTGCC AACAACCAGA CGGAACCCTG TATGGATCGC CTCACTTTGA TCCTGAGGCC
361 TGCAGTTTCA GGGAGCTCTT GCTTGAGGAT GGATACAATG TGTACCAATC TGAAGTCCAT
421 GGCCTGCCCC TGCGCCTGCC CCAGAGGGAC TCTCCAAACC AGGCCCCAGC ATCCTGGGGA
481 CCTGTGCCCC CCCTGCCAGT GCCAGGACTG CTCCACCAGC CCCAGGAGCT ACCAGGGTTC
541 CTGGCCCCAG AACCTCCAGA TGTGGGCTCC TCTGACCCAC TGAGCATGGT GGGACCTTTG
601 CAGGGCCGAA GCCCCAGCTA TGCTTCCTGA
```

*Ovis aries* (sheep) FGF21 gene coding sequence (SEQ ID NO: 332) (GenBank accession no. XM_004015796, which is hereby incorporated by reference in its entirety)

```
  1 ATGGGCTGGG ACGAGGCCAA GTTCAAGCAC TTGGGACTGT GGGTCCCTGT GCTGGCTGTC
 61 CTCCTGCTAG GAACCTGCCG GGCGCATCCA ATTCCAGACT CCAGCCCCCT CCTCCAGTTT
121 GGGGGCCAAG TCCGCCAGCG GTACCTCTAC ACGGATGATG CCCAGGAGAC AGAGGCCCAC
181 CTGGAGATCA GGGCCGATGG CACAGTGGTG GGGGCGGCCC GCCAGAGTCC CGAAAGTCTC
241 TTGGAGCTGA AAGCCCTGAA GCCAGGAGTC ATTCAGATCT TTGGAGTTAA AACATCCAGG
301 TTCCTGTGCC AGGGGCCAGA TGGGAAGCTG TATGGATCGC TGCACTTTGA CCCCAAAGCC
361 TGCAGCTTCC GGGAGCTGCT TCTTGAAGAT GGGTACAATG TCTACCAGTC GGAGACCCTG
421 GGCCTTCCAC TCCGCCTGCC GCCGCAGCGC TCATCCAACC GGGACCCGGC CCGCGGGGA
481 CCTCCGAAGC CCCAGCTACA CTTCTTGAAG ACGTCCGCTG TGCAGTACTG GCCACGTTAT
541 GAGAAGGTCC AGCTTTTCT GCACCCCTTC CCCGGCTGA
```

*Pan paniscus* (pygmy chimpanzee) FGF21 gene coding sequence (SEQ ID NO: 333) (GenBank accession no. XM_003814115, which is hereby incorporated by reference in its entirety) (1-209, excluding 117-194 and 202-209)

```
573                                 ATGGACTC GGACGAGACC GGGTTCGAGC
601 ACTCAGGACT GTGGGTTTCT GTGCTGGCTG GTCTTCTGCT GGGAGCCTGC CAGGCACACC
661 CCATCCCTGA CTCCAGTCCT CTCCTGCAAT TCGGGGCCA AGTCCGGCAG CGGTACCTCT
721 ACACAGATGA TGCCCAGCAG ACAGAAGCCC ACCTGGAGAT CAGGGAGGAT GGGACGGTGG
781 GGGGCGCTGC TGACCAGAGC CCCGAAAGTC TCCTGCAGCT GAAAGCCTTG AAGCCGGGAG
841 TTATTCAAAT CTTGGGAGTC AAGACATCCA GGTTCCTGTG CCAGAGGCCA GATGGGGCCC
901 TGTATGGATC GGTGAGTTTC ---------- ---------- ---------- ----------
    ---------- ---------- ---------- ---------- ---------- ----------
921 ---------- ----CAG--- ---------- ---------- ---------- ----------
924 ---------- -------GAC CCTCCT---- --------CA CCACCCACCA ---------T
946 GCTCC----- ----TCCTAT ATGTCGCCCTCACAG------ ---CCTGGG
```

TABLE 8 -continued

*Macaca fascicularis* (crab-eating macaque) FGF21 gene coding sequence
(SEQ ID NO: 334) (generated using SMS Reverse Translate tool on the
ExPASy Bioinformatics Resource website (www.expasy.org)) (1-209,
excluding 117-209)
```
  1 ATGGATAGCG ATGAAACCGG CTTTGAACAT AGCGGCCTGT GGGTGCCGGT GCTGGCGGGC
 61 CTGCTGCTGG GCGCGTGCCA GGCGCATCCG ATTCCGGATA GCAGCCCGCT GCTGCAGTTT
121 GGCGGCCAGG TGCGCCAGCG CTATCTGTAT ACCGATGATG CGCAGCAGAC CGAAGCGCAT
181 CTGGAAATTC GCGAAGATGG CACCGTGGGC GGCGCGGCGC ATCAGAGCCC GGAAAGCCTG
241 CTGCAGCTGA AAGCGCTGAA ACCGGGCGTG ATTCAGATTC TGGGCGTGAA AACCAGCCGC
301 TTTCTGTGCC AGAAACCGGA TGGCGCGCTG TATGGCAGCG TGAGCTTTTA A
```

*Mesocricetus auratus* (golden hamster) FGF21 gene coding sequence (SEQ
ID NO: 335) (GenBank accession no. EU497769, which is hereby
incorporated by reference in its entirety) (1-209, excluding 1-89 and
194-209)
```
  1 GGTCATCCAA ATCCTGGGTG TCAAGGCTGC TAGGTTTCCT TGCCAGCAAC CAGACGGAAG
 61 CCTGTACGGA TCGCCTCACT TCGATCCCGA GGCCTGCAGT TTCCGGGAGC TCCTGCTTGA
121 GGATGGATAC AATGTGTACC AGTCGGAAGC CCACGGCCTG CCCCTGCGCC TGCCCCAGAG
181 GGACGCTCCG AGCCAGCCCC CAGCATCCTG GGGACCGGTG CGCTTCCTGC CAGTGCCCGG
241 ACTGTTCCAG CCGCCCCACG ACCTCCCAGG GCGCCCGGCC CCAGAGCCTC CGGACGTGGG
301 CTCCTCCGAC CCAC
```

*Nile tilapia* FGF21 gene coding sequence (SEQ ID NO: 336) (GenBank
accession no. XM_003438468, which is hereby incorporated by reference
in its entirety) (1-209, excluding 1-58)
```
  1 ATGTATTTGC AGATGAACAT GGATGGGAGA GTCACAGGAA GTGATGCTCA GACACCTTAC
 61 AGTTTGATGC AGCTGAAATC AGTTAAACCA GGCCATGTAA TCATTAAAGG ACCATCATCA
121 TCTCTTTTTC TCTGTGTGGA CAGCGAAGGC AATCTGGAAG GGCAGAGTCA CTACTCAGAA
181 ACCAGCTGCA CCTTCAGAGA AATGCTGCTG GCTGACGGAT ACACCCGTTT CATTTCCTCA
241 CAATATGGAT TTCCCATGTC ACTGGCATCA AGACATTCCC CAGATCGACA CGCGCTTCCC
301 TTTACGCGGT TCCTACCACT GAGGAATAAC TTGAAAACGG ATAGCGTATC AGAGCAGCTG
361 CCAAACAATC AGAGACTCTT CAACGTGGAC TCTGATGACC TTCTTGGAAT GGGTCTAAAT
421 TCTATGGGCA GTCCTCAGTT TTCTATGGAC AAATAA
```

In one embodiment of the present invention, the chimeric protein may include one or more substitutions for or additions of amino acids from another FGF. In one embodiment, the C-terminal portion from FGF21 includes a modification that includes a substitution for or addition of amino acid residues from an FGF19 (including a human FGF19 and orthologs of human FGF19). In one embodiment the FGF19 is a human FGF19 protein having an amino acid sequence of SEQ ID NO: 337 (GenBank Accession No. NP_005108, which is hereby incorporated by reference in its entirety) or a portion or ortholog thereof, as follows:

```
  1 MRSGCVVVHV WILAGLWLAV AGRPLAFSDA GPHVHYGWGD PIRLRHLYTS GPHGLSSCFL

61 RIRADGVVDC ARGQSAHSLL EIKAVALRTV AIKGVHSVRY LCMGADGKMQ GLLQYSEEDC

121 AFEEEIRPDG YNVYRSEKHR LPVSLSSAKQ RQLYKNRGFL PLSHFLPMLP MVPEEPEDLR

181 GHLESDMFSS PLETDSMDPF GLVTGLEAVR SPSFEK
```

Figure 12:
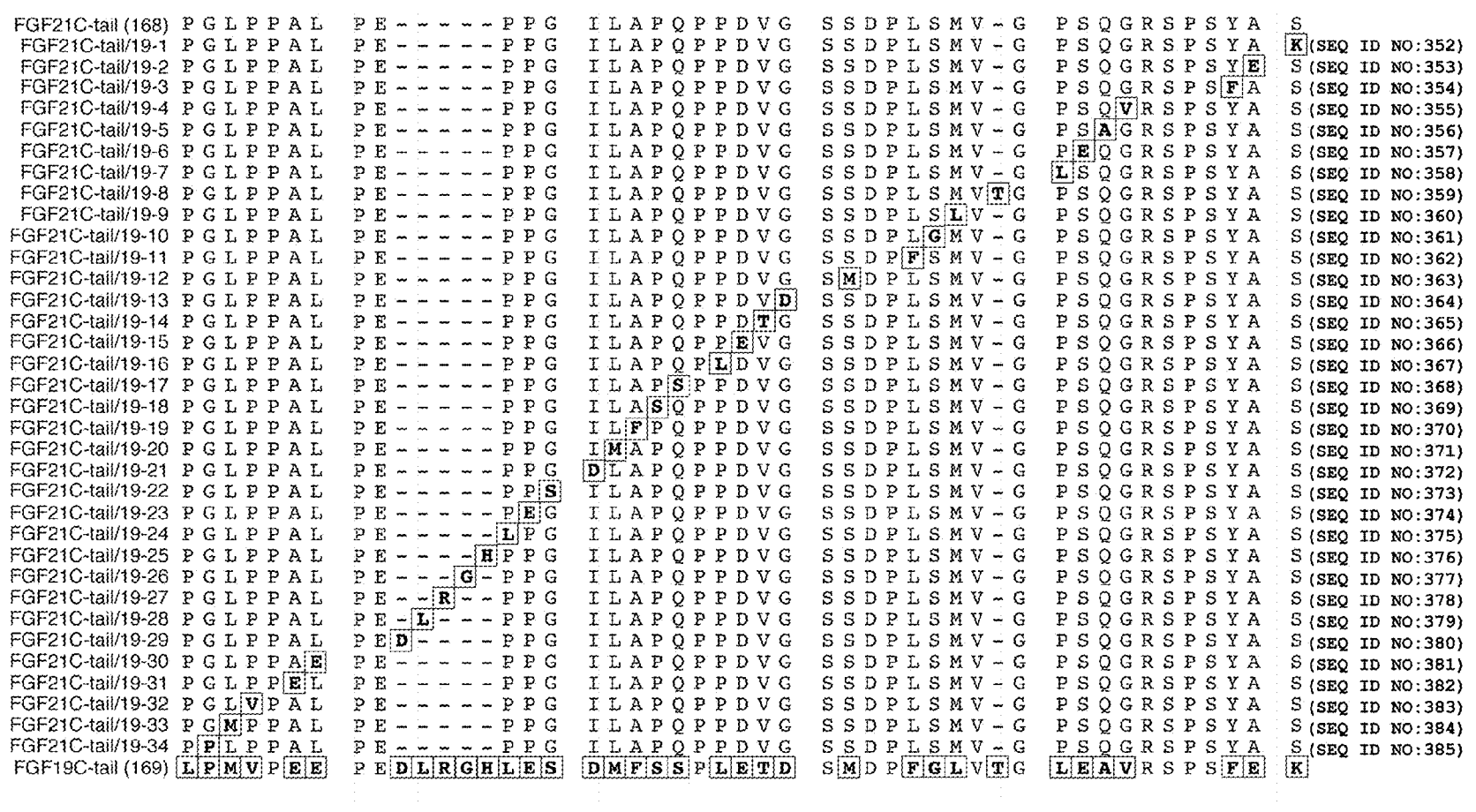
Figure 13:
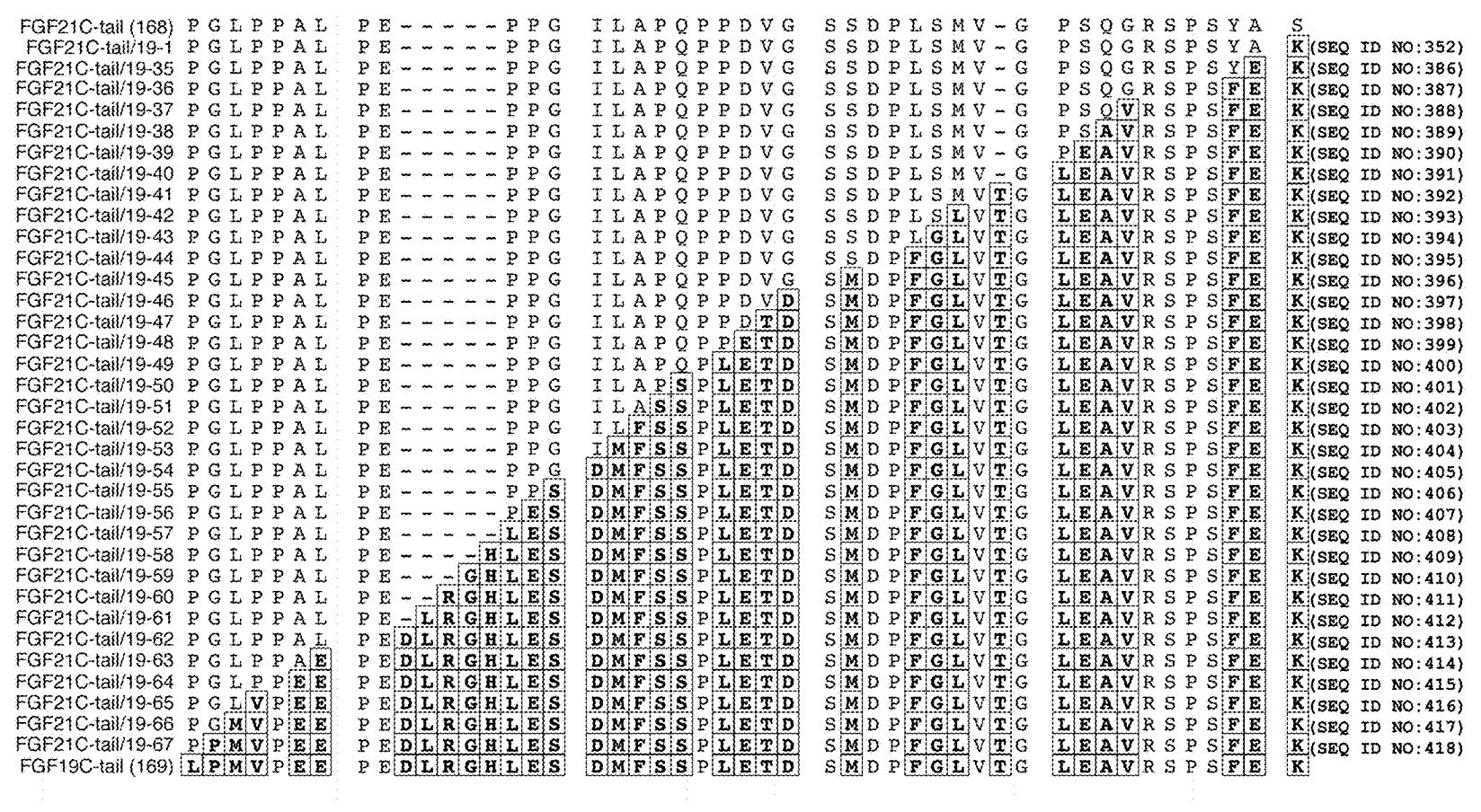

Exemplary substitutions and additions of such residues are shown in FIGS. 12 and 13.

In one embodiment, the C-terminal portion from FGF21 includes a modification that includes a substitution of amino acid residues from an FGF19 molecule. In one embodiment, the modification includes a substitution for or addition of amino acid residues 169 to 216 of SEQ ID NO: 337 (FGF19). In one embodiment, the modification is a substitution of amino acid residues from SEQ ID NO: 337 (FGF19) for corresponding amino acid residues of SEQ ID NO: 233 (FGF21). The corresponding residues of FGFs may be identified by sequence analysis and/or structural analysis. See FIGS. 2, 11, 12, and 13. In one embodiment, the modification includes a substitution of a contiguous stretch of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 amino acid residues 169 to 216 of SEQ ID NO: 337 (FGF19) for the corresponding contiguous stretch of amino acid residues of SEQ ID NO: 233 (FGF21). In one embodiment, amino acid residues 168 to 209, 191 to 209, or 198 to 209 of SEQ ID NO: 233 (FGF21) are substituted with the corresponding amino acid residues selected from the sequence including amino acid residues 169 to 216 of SEQ ID NO: 337 (FGF19).

In one embodiment, the modification includes a substitution of one or more individual amino acid residues from residues 169 to 216 of SEQ ID NO: 337 (FGF19) for the corresponding amino acid residues of SEQ ID NO: 233 (FGF21). In one embodiment, the C-terminal portion includes substitutions of one or more of amino acid residues 168, 169, 170, 171, 173, 174, 177, 178, 179, 180, 181, 182, 183, 184, 186, 187, 188, 189, 191, 194, 195, 196, 199, 200, 201, 202, 207, 208, or 209 of SEQ ID NO: 233 (FGF21) for the corresponding amino acid residues of SEQ ID NO:337 (FGF19).

In one embodiment of the present invention, the C-terminal portion from FGF21 includes a modification that includes an addition of amino acid residues that are present in the corresponding C-terminal portion from FGF19. As shown in FIGS. 11, 12, and 13, FGF19 residues that are absent in the corresponding C-terminal portion of FGF21 may be identified by sequence analysis and/or structural analysis. In one embodiment, the modification includes an addition of amino acid residues selected from residues 204 to 216, 197 to 216, 174 to 216, or 169 to 216 of SEQ ID NO: 337 (FGF19). In one embodiment, the modification includes an addition of amino acid residue 204 of SEQ ID NO: 337 (FGF19). In one embodiment, the modification includes an addition of amino acid residues 178, 179, 180, 181, and/or 182 of SEQ ID NO: 337 (FGF19) individually or in combination.

It will be understood that the C-terminal portion from FGF21 that includes a substitution of amino acid residues from an FGF19 molecule may be derived using a nucleotide sequence that encodes a human FGF19 protein having a nucleotide sequence of SEQ ID NO: 338 (Human FGF19 gene coding sequence (1-216); GenBank Accession No. NM_005117, which is hereby incorporated by reference in its entirety) or a portion or ortholog thereof, as follows:

```
 464    ATGCGGA GCGGGTGTGT GGTGGTCCAC GTATGGATCC TGGCCGGCCT CTGGCTGGCC

521 GTGGCCGGGC GCCCCCTCGC CTTCTCGGAC GCGGGGCCCC ACGTGCACTA CGGCTGGGGC

581 GACCCCATCC GCCTGCGGCA CCTGTACACC TCCGGCCCCC ACGGGCTCTC CAGCTGCTTC

641 CTGCGCATCC GTGCCGACGG CGTCGTGGAC TGCGCGCGGG GCCAGAGCGC GCACAGTTTG

701 CTGGAGATCA AGGCAGTCGC TCTGCGGACC GTGGCCATCA AGGGCGTGCA CAGCGTGCGG

761 TACCTCTGCA TGGGCGCCGA CGGCAAGATG CAGGGGCTGC TTCAGTACTC GGAGGAAGAC

821 TGTGCTTTCG AGGAGGAGAT CCGCCCAGAT GGCTACAATG TGTACCGATC CGAGAAGCAC

881 CGCCTCCCCG TCTCCCTGAG CAGTGCCAAA CAGCGGCAGC TGTACAAGAA CAGAGGCTTT

941 CTTCCACTCT CTCATTTCCT GCCCATGCTG CCCATGGTCC CAGAGGAGCC TGAGGACCTC

1001 AGGGGCCACT TGGAATCTGA CATGTTCTCT TCGCCCCTGG AGACCGACAG CATGGACCCA

1061 TTTGGGCTTG TCACCGGACT GGAGGCCGTG AGGAGTCCCA GCTTTGAGAA GTAA
```

In one embodiment, the chimeric protein of the present invention includes the amino acid sequence of SEQ ID NO: 339, SEQ ID NO: 340, SEQ ID NO: 341, or SEQ ID NO: 342, as shown in Table 9.

TABLE 9

| Description of Chimeric Protein | Sequence |
|---|---|
| Amino acid sequence of a FGF1/FGF21 chimera composed of residues M1 to L150 of human FGF1 harboring K127D/K128Q/K133V triple mutation (bold) and residues P168 to S209 of human FGF21 (bold) | SEQ ID NO: 339<br>MAEGEITTFT ALTEKFNLPP GNYKKPKLLY<br>CSNGGHFLRI LPDGTVDGTR DRSDQHIQLQ<br>LSAESVGEVY IKSTETGQYL AMDTDGLLYG<br>SQTPNEECLF LERLEENHYN TYISKKHAEK<br>NWFVGLDQNG SCVRGPRTHY GQKAILFLPL<br>PGLPPALPEP PGILAPQPPD VGSSDPLSMV<br>GPSQGRSPSY AS |
| Amino acid sequence of a FGF1/FGF21 chimera composed of residues K25 to L150 of human FGF1 harboring K127D/K128Q/K133V triple mutation (bold) and residues P168 to S209 of human FGF21 (bold) | SEQ ID NO: 340<br>                                           KPKLLY<br>CSNGGHFLRI LPDGTVDGTR DRSDQHIQLQ<br>LSAESVGEVY IKSTETGQYL AMDTDGLLYG<br>SQTPNEECLF LERLEENHYN TYISKKHAEK<br>NWFVGLDQNG SCVRGPRTHY GQKAILFLPL<br>PGLPPALPEP PGILAPQPPD VGSSDPLSMV<br>GPSQGRSPSY AS |
| Amino acid sequence of a FGF2/FGF21 chimera composed of residues M1 to M151 of human FGF2 harboring K128D/R129Q/K134V triple mutation (bold) and residues P168 to S209 of human FGF21 (bold) | SEQ ID NO: 341<br>MAAGSITTLP ALPEDGGSGA FPPGHFKDPK<br>RLYCKNGGFF LRIHPDGRVD GVREKSDPHI<br>KLQLQAEERG VVSIKGVCAN RYLAMKEDGR<br>LLASKCVTDE CFFFERLESN NYNTYRSRKY<br>TSWYVALDQT GQYVLGSKTG PGQKAILFLP<br>MPGLPPALPE PPGILAPQPP DVGSSDPLSM<br>VGPSQGRSPS YAS |
| Amino acid sequence of a FGF2/FGF21 chimera composed of residues H25 to M151 of human FGF2 harboring K128D/R129Q/K134V triple mutation (bold) and residues P168 to S209 of human FGF21 (bold) | SEQ ID NO: 342<br>                                   HFKDPK<br>RLYCKNGGFF LRIHPDGRVD GVREKSDPHI<br>KLQLQAEERG VVSIKGVCAN RYLAMKEDGR<br>LLASKCVTDE CFFFERLESN NYNTYRSRKY<br>TSWYVALDQT GQYVLGSKTG PGQKAILFLP<br>MPGLPPALPE PPGILAPQPP DVGSSDPLSM<br>VGPSQGRSPS YAS |

Chimeric proteins according to the present invention may be isolated proteins or polypeptides. The isolated chimeric proteins of the present invention may be prepared for use in accordance with the present invention using standard methods of synthesis known in the art, including solid phase peptide synthesis (Fmoc or Boc strategies) or solution phase peptide synthesis. Alternatively, peptides of the present invention may be prepared using recombinant expression systems.

Accordingly, another aspect of the present invention relates to an isolated nucleic acid molecule encoding a chimeric protein according to the present invention. In one embodiment, the nucleic acid molecule includes the nucleotide sequence of SEQ ID NO: 343, SEQ ID NO: 344, SEQ ID NO: 345, or SEQ ID NO: 346 (as shown in Table 10).

TABLE 10

| Description of Chimeric Protein | Sequence |
|---|---|
| Nucleotide sequence of a FGF1/FGF21 chimera composed of residues M1 to L150 of human FGF1 harboring K127D/K128Q/K133V triple mutation (bold) and residues P168 to S209 of human FGF21 (bold) | SEQ ID NO: 343<br>ATGGCTGAAG GGGAAATCAC CACCTTCACA<br>GCCCTGACCG AGAAGTTTAA TCTGCCTCCA<br>GGGAATTACA AGAAGCCCAA ACTCCTCTAC<br>TGTAGCAACG GGGGCCACTT CCTGAGGATC<br>CTTCCGGATG GCACAGTGGA TGGGACAAGG<br>GACAGGAGCG ACCAGCACAT TCAGCTGCAG<br>CTCAGTGCGG AAAGCGTGGG GGAGGTGTAT<br>ATAAAGAGTA CCGAGACTGG CCAGTACTTG<br>GCCATGGACA CCGACGGGCT TTTATACGGC<br>TCACAGACAC CAAATGAGGA ATGTTTGTTC<br>CTGGAAAGGC TGGAGGAGAA CCATTACAAC<br>ACCTATATAT CCAAGAAGCA TGCAGAGAAG<br>AATTGGTTTG TTGGCCTCGA TCAGAATGGG<br>AGCTGCGTTC GCGGTCCTCG GACTCACTAT<br>GGCCAGAAAG CAATCTTGTT TCTCCCCCTG<br>CCAGGCCTGC CCCCCGCACT CCCGGAGCCA<br>CCCGGAATCC TGGCCCCCCA GCCCCCCGAT<br>GTGGGCTCCT CGGACCCTCT GAGCATGGTG<br>GGACCTTCCC AGGGCCGAAG CCCCAGCTAC<br>GCTTCC |
| Nucleotide sequence of a FGF1/FGF21 chimera composed of residues 1 (25 to L150 of human FGF1 harboring K127D/K128Q/K133V triple mutation (bold) and residues P168 to S209 of human FGF21 (bold) | SEQ ID NO: 344<br>AAGCCCAA ACTCCTCTAC<br>TGTAGCAACG GGGGCCACTT CCTGAGGATC<br>CTTCCGGATG GCACAGTGGA TGGGACAAGG<br>GACAGGAGCG ACCAGCACAT TCAGCTGCAG<br>CTCAGTGCGG AAAGCGTGGG GGAGGTGTAT<br>ATAAAGAGTA CCGAGACTGG CCAGTACTTG<br>GCCATGGACA CCGACGGGCT TTTATACGGC<br>TCACAGACAC CAAATGAGGA ATGTTTGTTC<br>CTGGAAAGGC TGGAGGAGAA CCATTACAAC<br>ACCTATATAT CCAAGAAGCA TGCAGAGAAG<br>AATTGGTTTG TTGGCCTCGA TCAGAATGGG<br>AGCTGCGTTC GCGGTCCTCG GACTCACTAT<br>GGCCAGAAAG CAATCTTGTT TCTCCCCCTG<br>CCAGGCCTGC CCCCCGCACT CCCGGAGCCA<br>CCCGGAATCC TGGCCCCCCA GCCCCCCGAT<br>GTGGGCTCCT CGGACCCTCT GAGCATGGTG<br>GGACCTTCCC AGGGCCGAAG CCCCAGCTAC<br>GCTTCC |
| Nucleotide sequence of a FGF2/FGF21 chimera composed of residues M1 to M151 of human FGF2 harboring K128D/R129Q/K134V triple mutation (bold) and residues P168 to S209 of human FGF21 (bold) | SEQ ID NO: 345<br>ATG GCAGCCGGGA<br>GCATCACCAC GCTGCCCGCC TTGCCCGAGG<br>ATGGCGGCAG CGGCGCCTTC CCGCCCGGCC<br>ACTTCAAGGA CCCCAAGCGG CTGTACTGCA<br>AAAACGGGGG CTTCTTCCTG CGCATCCACC<br>CCGACGGCCG AGTTGACGGG GTCCGGGAGA<br>AGAGCGACCC TCACATCAAG CTACAACTTC<br>AAGCAGAAGA GAGAGGAGTT GTGTCTATCA<br>AAGGAGTGTG TGCTAACCGT TACCTGGCTA<br>TGAAGGAAGA TGGAAGATTA CTGGCTTCTA<br>AATGTGTTAC GGATGAGTGT TTCTTTTTTG<br>AACGATTGGA ATCTAATAAC TACAATACTT<br>ACCGGTCAAG GAAATACACC AGTTGGTATG<br>TGGCACTGGA TCAGACTGGG CAGTATGTTC |
| Nucleotide sequence of a FGF2/FGF21 chimera composed of residues M1 to M151 of human FGF2 harboring K128D/R129Q/K134V triple mutation (bold) and residues P168 to S209 of human FGF21 (bold) | SEQ ID NO: 346<br>c<br>ACTTCAAGGA CCCCAAGCGG CTGTACTGCA<br>AAAACGGGGG CTTCTTCCTG CGCATCCACC<br>CCGACGGCCG AGTTGACGGG GTCCGGGAGA<br>AGAGCGACCC TCACATCAAG CTACAACTTC<br>AAGCAGAAGA GAGAGGAGTT GTGTCTATCA<br>AAGGAGTGTG TGCTAACCGT TACCTGGCTA<br>TGAAGGAAGA TGGAAGATTA CTGGCTTCTA<br>AATGTGTTAC GGATGAGTGT TTCTTTTTTG<br>AACGATTGGA ATCTAATAAC TACAATACTT<br>ACCGGTCAAG GAAATACACC AGTTGGTATG<br>TGGCACTGGA TCAGACTGGG CAGTATGTTC<br>TTGGATCCAA AACAGGACCT GGGCAGAAAG<br>CTATACTTTT TCTTCCAATG CCAGGCCTGC<br>CCCCCGCACT CCCGGAGCCA CCCGGAATCC<br>TGGCCCCCCA GCCCCCCGAT GTGGGCTCCT<br>CGGACCCTCT GAGCATGGTG GGACCTTCCC<br>AGGGCCGAAG CCCCAGCTAC GCTTCC |

Another aspect of the present invention relates to a nucleic acid construct including a nucleic acid molecule encoding a chimeric protein according to the present invention, a 5' DNA promoter sequence, and a 3' terminator sequence. The nucleic acid molecule, the promoter, and the terminator are operatively coupled to permit transcription of the nucleic acid molecule.

Also encompassed are vectors or expression vectors including such nucleic acid molecules and host cells including such nucleic acid molecules. Nucleic acid molecules according to the present invention can be expressed in a host cell, and the encoded polynucleotides isolated, according to techniques that are known in the art.

Generally, the use of recombinant expression systems involves inserting the nucleic acid molecule encoding the amino acid sequence of the desired peptide into an expression system to which the molecule is heterologous (i.e., not normally present). One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize protein production. For the purposes of expressing a cloned nucleic acid sequence encoding a desired protein, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize protein production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding an isolated protein of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999); and U.S. Pat. No. 4,237,224 to Cohen and Boyer, which are hereby incorporated by reference in their entirety.

Once the nucleic acid molecule encoding the protein has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK et al., MOLECULAR CLONING: A LABORATORY MANUAL (Cold Springs Harbor 1989), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purified proteins may be obtained by several methods readily known in the art, including ion exchange chromatography, hydrophobic interaction chromatography, affinity chromatography, gel filtration, and reverse phase chromatography. The protein is preferably produced in purified form (preferably at least about 80% or 85% pure, more preferably at least about 90% or 95% pure) by conventional techniques. Depending on whether the recombinant host cell is made to secrete the protein into growth medium (see U.S. Pat. No. 6,596,509 to Bauer et al., which is hereby incorporated by reference in its entirety), the protein can be isolated and purified by centrifugation (to separate cellular components from supernatant containing the secreted protein) followed by sequential ammonium sulfate precipitation of the supernatant. The fraction containing the protein is subjected to gel filtration in an appropriately sized dextran or polyacrylamide column to separate the protein of interest from other proteins. If necessary, the protein fraction may be further purified by HPLC.

Another aspect of the present invention relates to a pharmaceutical composition that includes a chimeric protein according to the present invention and a pharmaceutically acceptable carrier.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONIC S™.

The term "pharmaceutically acceptable" means it is, within the scope of sound medical judgment, suitable for use in contact with the cells of humans and lower animals without undue toxicity, irritation, allergic response, and the like, and is commensurate with a reasonable benefit/risk ratio.

In one embodiment, the pharmaceutical composition includes an organotropic targeting agent. In one embodiment, the targeting agent is covalently linked to the chimeric protein via a linker that is cleaved under physiological conditions.

Chimeric and/or modified proteins according to the present invention may also be modified using one or more additional or alternative strategies for prolonging the in vivo half-life of the protein. One such strategy involves the generation of D-peptide chimeric proteins, which consist of unnatural amino acids that are not cleaved by endogenous proteases. Alternatively, the chimeric and/or modified proteins may be fused to a protein partner that confers a longer half-life to the protein upon in vivo administration. Suitable fusion partners include, without limitation, immunoglobulins (e.g., the Fc portion of an IgG), human serum albumin (HAS) (linked directly or by addition of the albumin binding domain of streptococcal protein G), fetuin, or a fragment of any of these. The chimeric and/or modified proteins may also be fused to a macromolecule other than protein that confers a longer half-life to the protein upon in vivo administration. Suitable macromolecules include, without limitation, polyethylene glycols (PEGs). Methods of conjugating proteins or peptides to polymers to enhance stability for therapeutic administration are described in U.S. Pat. No. 5,681,811 to Ekwuribe, which is hereby incorporated by reference in its entirety. Nucleic acid conjugates are described in U.S. Pat. No. 6,528,631 to Cook et al., U.S. Pat. No. 6,335,434 to Guzaev et al., U.S. Pat. No. 6,235,886 to Manoharan et al., U.S. Pat. No. 6,153,737 to Manoharan et al., U.S. Pat. No. 5,214,136 to Lin et al., or U.S. Pat. No. 5,138,045 to Cook et al., which are hereby incorporated by reference in their entirety.

The pharmaceutical composition according to the present invention can be formulated for administration orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The formulations may conveniently be presented in unit dosage form and may be prepared by any of the methods well known in the art of pharmacy.

Another aspect of the present invention relates to a method for treating a subject suffering from a disorder. This method involves selecting a subject suffering from the disorder and administering the pharmaceutical composition according to the present invention to the selected subject under conditions effective to treat the disorder. In one embodiment the disorder is diabetes, obesity, or metabolic syndrome.

Another aspect of the present invention relates to a method for treating a subject suffering from a disorder. This method involves selecting a subject suffering from the disorder and providing a chimeric FGF protein, where the chimeric FGF protein includes an N-terminus coupled to a C-terminus. The N-terminus includes a portion of a paracrine FGF and the C-terminus includes a C-terminal portion of FGF21. The portion of the paracrine FGF is modified to decrease binding affinity for heparin and/or heparan sulfate compared to the portion without the modification. This method also involves administering a therapeutically effective amount of the chimeric FGF protein to the selected subject under conditions effective to treat the disorder.

Suitable chimeric proteins for use in accordance with this aspect of the present invention are described above and throughout the present application.

In one embodiment, the selected subject is a mammal. In one embodiment, the selected subject is a human. In another embodiment, the selected subject is a rodent.

In one embodiment, the selected subject is in need of increased FGF21-βKlotho-FGF receptor ("FGFR") complex formation.

In one embodiment, the disorder is a selected from diabetes, obesity, and metabolic syndrome. As used herein, diabetes includes type I diabetes, type II diabetes, gestational diabetes, and drug-induced diabetes. In yet another embodiment, the subject has obesity. In yet another embodiment, the subject has metabolic syndrome.

The chimeric protein of the present invention or pharmaceutical composition thereof can be used to treat a number of conditions. In one embodiment, the condition is one which the therapeutic outcome includes a decrease in blood glucose, a decrease in blood fructosamine, an increase in energy expenditure, an increase in fat utilization, a decrease in body weight, a decrease in body fat, a decrease in triglycerides, a decrease in free fatty acids, an increase in fat excretion, an improvement, or even a preservation, of pancreatic β-cell function and mass, a decrease in total blood cholesterol, a decrease in blood low-density lipoprotein cholesterol, an increase in blood high-density lipoprotein cholesterol, an increase in blood adiponectin, an increase in insulin sensitivity, an increase in leptin sensitivity, a decrease in blood insulin, a decrease in blood leptin, a decrease in blood glucagon, an increase in glucose uptake by adipocytes, a decrease in fat accumulation in hepatocytes, and/or an increase in fat oxidation in hepatocytes. Each of these parameters can be measured by standard methods, for example, by measuring oxygen consumption to determine metabolic rate, using scales to determine weight, and measuring lean body mass composition or mass to determine fat. Moreover, the presence and amount of triglycerides, free fatty acids, glucose and leptin can be determined by standard methods (e.g., blood test).

Additional conditions that are treatable in accordance with the present invention include one or more of type 1 diabetes, type 2 diabetes, gestational diabetes, drug-induced diabetes, high blood glucose, metabolic syndrome, lipodystrophy syndrome, dyslipidemia, insulin resistance, leptin resistance, atherosclerosis, vascular disease, inflammatory disease, fibrotic disease, hypercholesterolemia, hypertriglyceridemia, non-alcoholic fatty liver disease, overweight, and obesity.

In one embodiment, the chimeric protein of the present invention or pharmaceutical composition thereof is administered with a pharmaceutically-acceptable carrier.

The chimeric protein according to the present invention or pharmaceutical composition thereof can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The most suitable route may depend on the condition and disorder of the recipient. Formulations including chimeric proteins according to the present invention may conveniently be presented in unit dosage form and may be prepared by any of the methods well known in the art of pharmacy.

Dosages and desired drug concentrations of pharmaceutical compositions of the present invention may vary depending on the particular use envisioned. The determination of the appropriate dosage or route of administration is well within the skill of an ordinary physician. Those skilled in the art can readily optimize pharmaceutically effective dosages and administration regimens for therapeutic compositions including the chimeric protein according to the present invention, as determined by good medical practice and the clinical condition of the individual patient.

When in vivo administration of a chimeric protein of the present invention or is employed, normal dosage amounts may vary from, for example, about 10 ng/kg to up to 100 mg/kg of mammal body weight or more per day. In one embodiment, the dosage may be from about 1 g/kg/day to 10 mg/kg/day, depending upon the route of administration. In one embodiment, the chimeric protein according to the present invention is administered at a dose of about 0.1 to 10 mg/kg once or twice daily. In one embodiment, the chimeric protein according to the present invention is administered at a dose of about 1 to 9, 1 to 8, 1 to 7, 1 to 6, 1 to 5, 1 to 4, 1 to 3, or 1 to 2 mg/kg. In one embodiment, the dosage is the same as that of a native FGF21 therapeutic. In one embodiment, the dosage is less than that of a native FGF21 therapeutic, but has the same effect as a higher dosage of a native FGF21 therapeutic. Guidance as to particular dosages and methods of delivery of proteins is provided in the literature; see, for example, U.S. Pat. No. 4,657,760; 5,206,344; or 5,225,212, which are hereby incorporated by reference in their entirety. It is anticipated that different formulations will be effective for different treatment compounds and different disorders, that administration targeting one organ or tissue, for example, may necessitate delivery in a manner different from that to another organ or tissue.

Where sustained-release administration of a chimeric protein of the present invention is desired in a formulation with release characteristics suitable for the treatment of any disease or disorder requiring administration of the chimeric protein of the present invention, microencapsulation is contemplated. Microencapsulation of recombinant proteins for sustained release has been successfully performed with human growth hormone (rhGH), interferon-(rhIFN-), interleukin-2, and MN rgp120. Johnson et al., "Preparation and Characterization of Poly(D,L-lactide-co-glycolide) Microspheres for Controlled Release of Human Growth Hormone," Nat. Med. 2:795-799 (1996); Yasuda, "Sustained Release Formulation of Interferon," Biomed. Ther. 27:1221-1223 (1993); Hora et al., "Controlled Release of Interleukin-2 from Biodegradable Microspheres," Nat. Biotechnol. 8:755-758 (1990); Cleland, "Design and Production of Single Immunization Vaccines Using Polylactide Polyglycolide Microsphere Systems," in VACCINE DESIGN: THE SUBUNIT AND ADJUVANT APPROACH 439-462 (Powell and Newman, eds. 1995); WO 97/03692; WO 96/40072; WO 96/07399; and U.S. Pat. No. 5,654,010, which are hereby incorporated by reference in their entirety. The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: BIODEGRADABLE POLYMERS AS DRUG DELIVERY SYSTEMS 1-41 (M. Chasin and R. Langer eds. 1990), which is hereby incorporated by reference in its entirety.

The chimeric protein of the present invention or pharmaceutical composition thereof may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. For other patients, it will be necessary to prescribe not more than one or two doses per day.

In some embodiments, the chimeric protein of the present invention or a pharmaceutical composition thereof is administered in a therapeutically effective amount in combination with a therapeutically effective amount of a second agent. In one embodiment, the chimeric protein of the present invention or pharmaceutical composition thereof is administered in conjunction with the second agent, i.e., the respective periods of administration are part of a single administrative regimen. In one embodiment, the chimeric protein of the present invention or pharmaceutical composition thereof and the second agent are administered concurrently, i.e., the respective periods of administration overlap each other. In one embodiment, the chimeric protein of the present invention or pharmaceutical composition thereof and the second agent are administered non-concurrently, i.e., the respective periods of administration do not overlap each other. In one embodiment, the chimeric protein of the present invention or pharmaceutical composition thereof and the second agent are administered sequentially, i.e., the chimeric protein of the present invention or pharmaceutical composition thereof is administered prior to and/or after the administration of the second agent. In one embodiment, the chimeric protein of the present invention or pharmaceutical composition thereof and the second agent are administered simultaneously as separate compositions. In one embodiment, the chimeric protein of the present invention or pharmaceutical composition thereof and the second agent are administered simultaneously as part of the same compositions.

In one embodiment, the second agent is an anti-inflammatory agent, an anti-fibrotic agent, an antihypertensive agent, an anti-diabetic agent, a triglyceride-lowering agent, and/or cholesterol-lowering drug such as a drug of the "statin" class. In one embodiment, the second agent is insulin. In one embodiment, the insulin is rapid acting, short acting, regular acting, intermediate acting, or long acting insulin. In one embodiment, the insulin is and/or comprises Humalog®, Lispro, Novolog®, Apidra®, Humulin®, Aspart, regular insulin, NPH, Lente, Ultralente, Lantus®, Glargine, Levemir®, or Detemir. In one embodiment, the second agent is a statin. In one embodiment, the statin is and/or comprises Atorvastatin (e.g., Lipitor® or Torvast®), Cerivastatin (e.g., Lipobay® or Baycol®), Fluvastatin (e.g., Lescol® or LescolXL®), Lovastatin (e.g., Mevacor®, Altocor®, or Altoprev®) Mevastatin, Pitavastatin (e.g., Livalo® or Pitava®), Pravastatin (e.g., Pravachol®, Selektine, or Lipostat®) Rosuvastatin (e.g., Crestor®), Simvastatin (e.g., Zocor® or Lipex®), Vytorin®, Advicor®, Besylate Caduet® or Simcor®.

In one embodiment of the present invention, the chimeric protein according to the present invention or the pharmaceutical composition thereof is administered with an anti-inflammatory agent, an antifibrotic agent, an antihypertensive agent, an antidiabetic agent, a triglyceride-lowering agent, and/or a cholesterol-lowering agent.

Another aspect of the present invention relates to a method of making a chimeric FGF protein possessing enhanced endocrine activity. This method involves introducing one or more modifications to an FGF protein, where the modification decreases the affinity of the FGF protein for heparin and/or heparan sulfate and coupling a Klotho co-receptor binding domain to the modified FGF protein's C-terminus, whereby a chimeric FGF protein possessing enhanced endocrine activity is made.

In one embodiment, the method includes selecting a Klotho co-receptor binding domain, where the Klotho co-receptor binding domain is selected to target an endocrine FGF target tissue. In one embodiment, the Klotho co-receptor binding domain is selected to home the chimeric FGF protein into a target tissue of endocrine FGF. In one embodiment, the Klotho co-receptor binding domain is selected to target white adipose tissue, brown adipose tissue, skeletal muscle, pancreas, and/or liver.

In one embodiment, the Klotho co-receptor binding domain includes a β-Klotho co-receptor binding domain. In one embodiment, the β-Klotho co-receptor binding domain includes a C-terminal portion from FGF21. In one embodiment, the C-terminal portion from the FGF21 includes amino acid residues 168-209 of SEQ ID NO: 233. In one embodiment, the C-terminal portion derived from FGF21 further includes one or more substitutions while retaining the ability to bind β-Klotho. In one embodiment, the C-terminal portion derived from FGF21 further includes one or more substitutions to enhance its binding affinity for β-Klotho. In one embodiment, the C-terminal portion from FGF21 is derived from a mammalian FGF21. In one embodiment, the C-terminal portion derived from FGF21 is from a vertebrate FGF21. Suitable FGF21 molecules, C-terminal portions thereof, and modifications thereto, are described above.

In one embodiment, the chimeric FGF protein has greater binding affinity for FGFR than native endocrine FGF ligand having the Klotho co-receptor binding domain. In one embodiment, the chimeric FGF protein possesses enhanced endocrine activity compared to the chimeric FGF protein in the absence of the modification or the Klotho co-receptor binding domain. In one embodiment, the native endocrine FGF ligand having the Klotho co-receptor binding domain is native FGF21. In one embodiment, the FGFR is FGFR1c, FGFR2c, or FGFR4.

In one embodiment, the chimeric FGF protein has greater stability than a native endocrine FGF ligand possessing the Klotho co-receptor binding domain. In one embodiment, increasing the stability includes an increase in thermal stability of the protein as compared to either wild type protein or native endocrine FGF ligand. In one embodiment, increasing the stability includes increasing the half-life of the protein in the blood circulation as compared to wild type protein or native endocrine FGF ligand.

In one embodiment, the method involves introducing one or more modifications to the FGF protein, where the modification alters the receptor-binding specificity of the FGF protein. In one embodiment, the method involves introducing one or more modifications to the FGF protein, where the modification alters the receptor-binding affinity of the FGF protein.

In one embodiment, the FGF is derived from a mammalian FGF. In one embodiment, the FGF is derived from a vertebrate FGF. In one embodiment, the FGF protein is a paracrine FGF molecule. In one embodiment the FGF molecule is FGF1 or FGF2. In one embodiment, the FGF protein is an FGF protein that possesses intrinsically greater binding affinity for FGF receptor than a native endocrine FGF ligand. In one embodiment, the FGF protein is an FGF protein that possesses intrinsically greater thermal stability than a native endocrine FGF ligand. In one embodiment, the method involves introducing one or more modifications to the FGF protein, where the modification alters receptor-binding specificity and/or receptor-binding affinity of the FGF protein. In one embodiment, the method involves introducing one or more modifications to the FGF protein, where the modification alters the stability of the FGF protein. For example, receptor-binding specificity of FGF1, which by nature binds to all the seven principal FGFRs, may be altered to, for example, reduce any risk for adverse effects (e.g., mitogenicity). Paracrine FGFs, portions of paracrine FGFs, and modifications thereto are described above.

In one embodiment, the chimeric FGF protein is effective to treat diabetes, obesity, and/or metabolic syndrome.

Suitable methods of generating chimeric proteins according to the present invention include standard methods of synthesis known in the art, as described above.

Yet another aspect of the present invention relates to a method of facilitating fibroblast growth factor receptor ("FGFR")-βKlotho co-receptor complex formation. This method involves providing a cell that includes a βKlotho co-receptor and an FGFR and providing a chimeric FGF protein. The chimeric FGF protein includes a C-terminal portion of FGF21 and a portion of a paracrine FGF, where the portion of the paracrine FGF is modified to decrease binding affinity for heparin and/or heparan sulfate compared to the portion without the modification. This method also involves contacting the cell and the chimeric FGF protein under conditions effective to cause FGFR-βKlotho co-receptor complex formation.

The portion of the paracrine FGF may also be modified to alter receptor-binding specificity and/or receptor-binding affinity of the FGF, as noted above. Suitable portions of the paracrine FGFs for use in accordance with the present invention, as well as modifications to alter receptor-binding specificity and/or receptor-binding affinity of the FGF, are described above. Suitable modifications to the paracrine FGFs for use in accordance with the present invention are also described above. Suitable C-terminal portions from FGF21 are described above and throughout the present application.

In one embodiment according to the present invention, βKlotho is mammalian βKlotho. In one embodiment, βKlotho is human or mouse βKlotho. In one particular embodiment of the present invention, βKlotho is human or mouse βKlotho having the amino acid sequence of SEQ ID NO: 347 (i.e., GenBank Accession No. NP_783864, which is hereby incorporated by reference in its entirety) or SEQ ID NO: 348 (i.e., GenBank Accession No. NP_112457, which is hereby incorporated by reference in its entirety), respectively, as follows:

```
SEQ ID NO: 348:
  1 MKPGCAAGSP GNEWIFFSTD EITTRYRNTM SNGGLQRSVI LSALILLRAV TGFSGDGRAI

61 WSKNPNFTPV NESQLFLYDT FPKNFFWGIG TGALQVEGSW KKDGKGPSIW DHFIHTHLKN

121 VSSTNGSSDS YIFLEKDLSA LDFIGVSFYQ FSISWPRLFP DGIVTVANAK GLQYYSTLLD

181 ALVLRNIEPI VTLYHWDLPL ALQEKYGGWK NDTIIDIFND YATYCFQMFG DRVKYWITIH

241 NPYLVAWHGY GTGMHAPGEK GNLAAVYTVG HNLIKAHSKV WHNYNTHFRP HQKGWLSITL

301 GSHWIEPNRS ENTMDIFKCQ QSMVSVLGWF ANPIHGDGDY PEGMRKKLFS VLPIFSEAEK

361 HEMRGTADFF AFSFGPNNFK PLNTMAKMGQ NVSLNLREAL NWIKLEYNNP RLIAENGWF

421 TDSRVKTEDT TAIYMMKNFL SQVLQAIRLD EIRVFGYTAW SLLDGFEWQD AYTIRRGLFY

481 VDFNSKQKER KPKSSAHYYK QIIRENGFSL KESTPDVQGQ FPCDFSWGVT ESVLKPESVA

541 SSPQFSDPHL YVWNATGNRL LHRVEGVRLK TRPAQCTDFV NIKKQLEMLA RMKVTHYRFA

601 LDWASVLPTG NLSAVNRQAL RYYRCVVSEG LKLGISAMVT LYYPTHAHLG LPEPLLHADG
```

```
661 WLNPSTAEAF QAYAGLCFQE LGDLVKLWIT INEPNRLSDI YNRSGNDTYG AAHNLLVAHA

721 LAWRLYDRQF RPSQRGAVSL SLHADWAEPA NPYADSHWRA AERFLQFEIA WFAEPLFKTG

781 DYPAAMREYI ASKHRRGLSS SALPRLTEAE RRLLKGTVDF CALNHFTTRF VMHEQLAGSR

841 YDSDRDIQFL QDITRLSSPT RLAVIPWGVR KLLRWVRRNY GDMDIYITAS GIDDQALEDD

901 RLRKYYLGKY LQEVLKAYLI DKVRIKGYYA FKLAEEKSKP RFGFFTSDFK AKSSIQFYNK

961 VISSRGFPFE NSSSRCSQTQ ENTECTVCLF LVQKKPLIFL GCCFFSTLVL LLSIAIFQRQ

1021 KRRKFWKAKN LQHIPLKKGK RVVS

SEQ ID NO: 348:
   1 MKTGCAAGSP GNEWIFFSSD ERNTRSRKTM SNRALQRSAV LSAFVLLRAV TGFSGDGKAI

61 WDKKQYVSPV NPSQLFLYDT FPKNFSWGVG TGAFQVEGSW KTDGRGPSIW DRYVYSHLRG

121 VNGTDRSTDS YIFLEKDLLA LDFLGVSFYQ FSISWPRLFP NGTVAAVNAQ GLRYYRALLD

181 SLVLRNIEPI VTLYHWDLPL TLQEEYGGWK NATMIDLFND YATYCFQTFG DRVKYWITIH

241 NPYLVAWHGF GTGMHAPGEK GNLTAVYTVG HNLIKAHSKV WHNYDKNFRP HQKGWLSITL

301 GSHWIEPNRT DNMEDVINCQ HSMSSVLGWF ANPIHGDGDY PEFMKTGAMI PEFSEAEKEE

361 VRGTADFFAF SFGPNNFRPS NTVVKMGQNV SLNLRQVLNW IKLEYDDPQI LISENGWFTD

421 SYIKTEDTTA IYMMKNFLNQ VLQAIKFDEI RVFGYTAWTL LDGFEWQDAY TTRRGLFYVD

481 FNSEQKERKP KSSAHYYKQI IQDNGFPLKE STPDMKGRFP CDFSWGVTES VLKPEFTVSS

541 PQFTDPHLYV WNVTGNRLLY RVEGVRLKTR PSQCTDYVSI KKRVEMLAKM KVTHYQFALD

601 WTSILPTGNL SKVNRQVLRY YRCVVSEGLK LGVFPMVTLY HPTHSHLGLP LPLLSSGGWL

661 NMNTAKAFQD YAELCFRELG DLVKLWITIN EPNRLSDMYN RTSNDTYRAA HNLMIAHAQV

721 WHLYDRQYRP VQHGAVSLSL HCDWAEPANP FVDSHWKAAE RFLQFEIAWF ADPLFKTGDY

781 PSVMKEYIAS KNQRGLSSSV LPRFTAKESR LVKGTVDFYA LNHFTTRFVI HKQLNTNRSV

841 ADRDVQFLQD ITRLSSPSRL AVTPWGVRKL LAWIRRNYRD RDIYITANGI DDLALEDDQI

901 RKYYLEKYVQ EALKAYLIDK VKIKGYYAFK LTEEKSKPRF GFFTSDFRAK SSVQFYSKLI

961 SSSGLPAENR SPACGQPAED TDCTICSFLV EKKPLIFFGC CFISTLAVLL SITVFHHQKR

1021 RKFQKARNLQ NIPLKKGHSR VFS
```

In one particular embodiment of the present invention, βKlotho is human or mouse βKlotho encoded by a nucleotide sequence having the nucleotide sequences of SEQ ID NO: 349 (GenBank Accession No. NM_175737, which is hereby incorporated by reference in its entirety) and SEQ ID NO: 350 (GenBank Accession No. NM_031180, which is hereby incorporated by reference in its entirety), as follows:

```
(Human βKlotho gene coding sequence):
                                                        SEQ ID NO: 349
  98      ATG AAGCCAGGCT GTGCGGCAGG ATCTCCAGGG AATGAATGGA TTTTCTTCAG

151 CACTGATGAA ATAACCACAC GCTATAGGAA TACAATGTCC AACGGGGGAT TGCAAAGATC

211 TGTCATCCTG TCAGCACTTA TTCTGCTACG AGCTGTTACT GGATTCTCTG GAGATGGAAG

271 AGCTATATGG TCTAAAAATC CTAATTTTAC TCCGGTAAAT GAAAGTCAGC TGTTTCTCTA

331 TGACACTTTC CCTAAAAACT TTTTCTGGGG TATTGGGACT GGAGCATTGC AAGTGGAAGG

391 GAGTTGGAAG AAGGATGGAA AAGGACCTTC TATATGGGAT CATTTCATCC ACACACACCT

451 TAAAAATGTC AGCAGCACGA ATGGTTCCAG TGACAGTTAT ATTTTTCTGG AAAAAGACTT

511 ATCAGCCCTG GATTTTATAG GAGTTTCTTT TTATCAATTT CAATTTCCT GGCCAAGGCT

571 TTTTCCCGAT GGAATAGTAA CAGTTGCCAA CGCAAAAGGT CTGCAGTACT ACAGTACTCT

631 TCTGGACGCT CTAGTGCTTA GAAACATTGA ACCTATAGTT ACTTTATACC ACTGGGATTT
```

-continued

```
 691 GCCTTTGGCA CTACAAGAAA AATATGGGGG GTGGAAAAAT GATACCATAA TAGATATCTT

751 CAATGACTAT GCCACATACT GTTTCCAGAT GTTTGGGGAC CGTGTCAAAT ATTGGATTAC

811 AATTCACAAC CCATATCTAG TGGCTTGGCA TGGGTATGGG ACAGGTATGC ATGCCCCTGG

871 AGAGAAGGGA AATTTAGCAG CTGTCTACAC TGTGGGACAC AACTTGATCA AGGCTCACTC

931 GAAAGTTTGG CATAACTACA ACACACATTT CCGCCCACAT CAGAAGGGTT GGTTATCGAT

991 CACGTTGGGA TCTCATTGGA TCGAGCCAAA CCGGTCGGAA ACACGATGG ATATATTCAA

1051 ATGTCAACAA TCCATGGTTT CTGTGCTTGG ATGGTTTGCC AACCCTATCC ATGGGGATGG

1111 CGACTATCCA GAGGGGATGA GAAAGAAGTT GTTCTCCGTT CTACCCATTT TCTCTGAAGC

1171 AGAGAAGCAT GAGATGAGAG GCACAGCTGA TTTCTTTGCC TTTTCTTTTG GACCCAACAA

1231 CTTCAAGCCC CTAAACACCA TGGCTAAAAT GGGACAAAAT GTTTCACTTA ATTTAAGAGA

1291 AGCGCTGAAC TGGATTAAAC TGGAATACAA CAACCCTCGA ATCTTGATTG CTGAGAATGG

1351 CTGGTTCACA GACAGTCGTG TGAAAACAGA AGACACCACG GCCATCTACA TGATGAAGAA

1411 TTTCCTCAGC CAGGTGCTTC AAGCAATAAG GTTAGATGAA ATACGAGTGT TTGGTTATAC

1471 TGCCTGGTCT CTCCTGGATG GCTTTGAATG GCAGGATGCT TACACCATCC GCCGAGGATT

1531 ATTTTATGTG GATTTTAACA GTAAACAGAA AGAGCGGAAA CCTAAGTCTT CAGCACACTA

1591 CTACAAACAG ATCATACGAG AAAATGGTTT TCTTTAAAA GAGTCCACGC AGATGTGCA

1651 GGGCCAGTTT CCCTGTGACT TCTCCTGGGG TGTCACTGAA TCTGTTCTTA AGCCCGAGTC

1711 TGTGGCTTCG TCCCCACAGT TCAGCGATCC TCATCTGTAC GTGTGGAACG CCACTGGCAA

1771 CAGACTGTTG CACCGAGTGG AAGGGGTGAG GCTGAAAACA CGACCCGCTC AATGCACAGA

1831 TTTTGTAAAC ATCAAAAAAC AACTTGAGAT GTTGGCAAGA ATGAAAGTCA CCCACTACCG

1891 GTTTGCTCTG GATTGGGCCT CGGTCCTTCC CACTGGCAAC CTGTCCGCGG TGAACCGACA

1951 GGCCCTGAGG TACTACAGGT GCGTGGTCAG TGAGGGGCTG AAGCTTGGCA TCTCCGCGAT

2011 GGTCACCCTG TATTATCCGA CCCACGCCCA CCTAGGCCTC CCCGAGCCTC TGTTGCATGC

2071 CGACGGGTGG CTGAACCCAT CGACGGCCGA GGCCTTCCAG GCCTACGCTG GCTGTGCTT

2131 CCAGGAGCTG GGGGACCTGG TGAAGCTCTG GATCACCATC AACGAGCCTA ACCGGCTAAG

2191 TGACATCTAC AACCGCTCTG GCAACGACAC CTACGGGCG GCGCACAACC TGCTGGTGGC

2251 CCACGCCCTG GCCTGGCGCC TCTACGACCG GCAGTTCAGG CCCTCACAGC GCGGGGCCGT

2311 GTCGCTGTCG CTGCACGCGG ACTGGGCGGA ACCCGCCAAC CCCTATGCTG ACTCGCACTG

2371 GAGGGCGGCC GAGCGCTTCC TGCAGTTCGA GATCGCCTGG TTCGCCGAGC CGCTCTTCAA

2431 GACCGGGGAC TACCCCGCGG CCATGAGGGA ATACATTGCC TCCAAGCACC GACGGGGCT

2491 TTCCAGCTCG GCCCTGCCGC GCCTCACCGA GGCCGAAAGG AGGCTGCTCA GGGCACGGT

2551 CGACTTCTGC GCGCTCAACC ACTTCACCAC TAGGTTCGTG ATGCACGAGC AGCTGGCCGG

2611 CAGCCGCTAC GACTCGGACA GGGACATCCA GTTTCTGCAG GACATCACCC GCCTGAGCTC

2671 CCCCACGCGC CTGGCTGTGA TTCCCTGGGG GGTGCGCAAG CTGCTGCGGT GGGTCCGGAG

2731 GAACTACGGC GACATGGACA TTTACATCAC CGCCAGTGGC ATCGACGACC AGGCTCTGGA

2791 GGATGACCGG CTCCGGAAGT ACTACCTAGG GAAGTACCTT CAGGAGGTGC TGAAAGCATA

2851 CCTGATTGAT AAAGTCAGAA TCAAAGGCTA TTATGCATTC AAACTGGCTG AAGAGAAATC

2911 TAAACCCAGA TTTGGATTCT TCACATCTGA TTTTAAAGCT AAATCCTCAA TACAATTTTA

2971 CAACAAAGTG ATCAGCAGCA GGGGCTTCCC TTTTGAGAAC AGTAGTTCTA GATGCAGTCA

3031 GACCCAAGAA AATACAGAGT GCACTGTCTG CTTATTCCTT GTGCAGAAGA AACCACTGAT

3091 ATTCCTGGGT TGTTGCTTCT TCTCCACCCT GGTTCTACTC TTATCAATTG CCATTTTTCA
```

-continued

```
3151 AAGGCAGAAG AGAAGAAAGT TTTGGAAAGC AAAAAACTTA CAACACATAC CATTAAAGAA

3211 AGGCAAGAGA GTTGTTAGCT AA
```

(House mouse βKlotho gene coding sequence):

SEQ ID NO: 350

```
   2 ATGAAGACA GGCTGTGCAG CAGGGTCTCC GGGGAATGAA TGGATTTTCT TCAGCTCTGA

61 TGAAAGAAAC ACACGCTCTA GGAAAACAAT GTCCAACAGG GCACTGCAAA GATCTGCCGT

121 GCTGTCTGCG TTTGTTCTGC TGCGAGCTGT TACCGGCTTC TCCGGAGACG GGAAAGCAAT

181 ATGGGATAAA AAACAGTACG TGAGTCCGGT AAACCCAAGT CAGCTGTTCC TCTATGACAC

241 TTTCCCTAAA AACTTTTCCT GGGGCGTTGG GACCGGAGCA TTTCAAGTGG AAGGGAGTTG

301 GAAGACAGAT GGAAGAGGAC CCTCGATCTG GGATCGGTAC GTCTACTCAC ACCTGAGAGG

361 TGTCAACGGC ACAGACAGAT CCACTGACAG TTACATCTTT CTGGAAAAAG ACTTGTTGGC

421 TCTGGATTTT TTAGGAGTTT CTTTTTATCA GTTCTCAATC TCCTGGCCAC GGTTGTTTCC

481 CAATGGAACA GTAGCAGCAG TGAATGCGCA AGGTCTCCGG TACTACCGTG CACTTCTGGA

541 CTCGCTGGTA CTTAGGAATA TCGAGCCCAT TGTTACCTTG TACCATTGGG ATTTGCCTCT

601 GACGCTCCAG GAAGAATATG GGGCTGGAA AAATGCAACT ATGATAGATC TCTTCAACGA

661 CTATGCCACA TACTGCTTCC AGACCTTTGG AGACCGTGTC AAATATTGGA TTACAATTCA

721 CAACCCTTAC CTTGTTGCTT GGCATGGGTT TGGCACAGGT ATGCATGCAC CAGGAGAGAA

781 GGGAAATTTA ACAGCTGTCT ACACTGTGGG ACACAACCTG ATCAAGGCAC ATTCGAAAGT

841 GTGGCATAAC TACGACAAAA ACTTCCGCCC TCATCAGAAG GGTTGGCTCT CCATCACCTT

901 GGGGTCCCAT TGGATAGAGC CAAACAGAAC AGACAACATG GAGGACGTGA TCAACTGCCA

961 GCACTCCATG TCCTCTGTGC TTGGATGGTT CGCCAACCCC ATCCACGGGG ACGGCGACTA

1021 CCCTGAGTTC ATGAAGACGG GCGCCATGAT CCCCGAGTTC TCTGAGGCAG AGAAGGAGGA

1081 GGTGAGGGGC ACGGCTGATT TCTTTGCCTT TTCCTTCGGG CCCAACAACT TCAGGCCCTC

1141 AAACACCGTG GTGAAAATGG ACAAAATGT ATCACTCAAC TTAAGGCAGG TGCTGAACTG

1201 GATTAAACTG GAATACGATG ACCCTCAAAT CTTGATTTCG GAGAACGGCT GGTTCACAGA

1261 TAGCTATATA AAGACAGAGG ACACCACGGC CATCTACATG ATGAAGAATT TCCTAAACCA

1321 GGTTCTTCAA GCAATAAAAT TTGATGAAAT CCGCGTGTTT GGTTATACGG CCTGGACTCT

1381 CCTGGATGGC TTTGAGTGGC AGGATGCCTA TACGACCCGA CGAGGGCTGT TTTATGTGGA

1441 CTTTAACAGT GAGCAGAAAG AGAGGAAACC CAAGTCCTCG GCTCATTACT ACAAGCAGAT

1501 CATACAAGAC AACGGCTTCC CTTTGAAAGA GTCCACGCCA GACATGAAGG GTCGGTTCCC

1561 CTGTGATTTC TCTTGGGGAG TCACTGAGTC TGTTCTTAAG CCCGAGTTTA CGGTCTCCTC

1621 CCCGCAGTTT ACCGATCCTC ACCTGTATGT GTGGAATGTC ACTGGCAACA GATTGCTCTA

1681 CCGAGTGGAA GGGGTAAGGC TGAAAACAAG ACCATCCCAG TGCACAGATT ATGTGAGCAT

1741 CAAAAAACGA GTTGAAATGT TGGCAAAAAT GAAAGTCACC CACTACCAGT TTGCTCTGGA

1801 CTGGACCTCT ATCCTTCCCA CTGGCAATCT GTCCAAAGTT AACAGACAAG TGTTAAGGTA

1861 CTATAGGTGT GTGGTGAGCG AAGGACTGAA GCTGGGCGTC TTCCCCATGG TGACGTTGTA

1921 CCACCCAACC CACTCCCATC TCGGCCTCCC CCTGCCACTT CTGAGCAGTG GGGGTGGCT

1981 AAACATGAAC ACAGCCAAGG CCTTCCAGGA CTACGCTGAG CTGTGCTTCC GGGAGTTGGG

2041 GGACTTGGTG AAGCTCTGGA TCACCATCAA TGAGCCTAAC AGGCTGAGTG ACATGTACAA

2101 CCGCACGAGT AATGACACCT ACCGTGCAGC CCACAACCTG ATGATCGCCC ATGCCCAGGT

2161 CTGGCACCTC TATGATAGGC AGTATAGGCC GGTCCAGCAT GGGGCTGTGT CGCTGTCCTT
```

```
-continued
2221 ACATTGCGAC TGGGCAGAAC CTGCCAACCC CTTTGTGGAT TCACACTGGA AGGCAGCCGA

2281 GCGCTTCCTC CAGTTTGAGA TCGCCTGGTT TGCAGATCCG CTCTTCAAGA CTGGCGACTA

2341 TCCATCGGTT ATGAAGGAAT ACATCGCCTC CAAGAACCAG CGAGGGCTGT CTAGCTCAGT

2401 CCTGCCGCGC TTCACCGCGA AGGAGAGCAG GCTGGTGAAG GGTACCGTCG ACTTCTACGC

2461 ACTGAACCAC TTCACTACGA GGTTCGTGAT ACACAAGCAG CTGAACACCA ACCGCTCAGT

2521 TGCAGACAGG GACGTCCAGT TCCTGCAGGA CATCACCCGC CTAAGCTCGC CCAGCCGCCT

2581 GGCTGTAACA CCCTGGGGAG TGCGCAAGCT CCTTGCGTGG ATCCGGAGGA ACTACAGAGA

2641 CAGGGATATC TACATCACAG CCAATGGCAT CGATGACCTG GCTCTAGAGG ATGATCAGAT

2701 CCGAAAGTAC TACTTGGAGA AGTATGTCCA GGAGGCTCTG AAAGCATATC TCATTGACAA

2761 GGTCAAAATC AAAGGCTACT ATGCATTCAA ACTGACTGAA GAGAAATCTA AGCCTAGATT

2821 TGGATTTTTC ACCTCTGACT TCAGAGCTAA GTCCTCTGTC CAGTTTTACA GCAAGCTGAT

2881 CAGCAGCAGT GGCCTCCCCG CTGAGAACAG AAGTCCTGCG TGTGGTCAGC CTGCGGAAGA

2941 CACAGACTGC ACCATTTGCT CATTTCTCGT GGAGAAGAAA CCACTCATCT TCTTCGGTTG

3001 CTGCTTCATC TCCACTCTGG CTGTACTGCT ATCCATCACC GTTTTTCATC ATCAAAAGAG

3061 AAGAAAATTC CAGAAAGCAA GGAACTTACA AAATATACCA TTGAAGAAAG GCCACAGCAG

3121 AGTTTTCAGC TAA
```

In one embodiment, the FGFR is FGFR1c, FGFR2c, or FGFR4. In one embodiment of the present invention, the FGF receptor is FGFR1c receptor. In one particular embodiment, the FGFR1c receptor is the human FGFR1c receptor (GenBank Accession No. NP_075598, which is hereby incorporated by reference in its entirety). In another embodiment, the FGF receptor is FGFR2c receptor. In one particular embodiment, the FGFR2c receptor is the human FGFR2c receptor (GenBank Accession No. NP_000132, which is hereby incorporated by reference in its entirety). In another embodiment, the FGF receptor is FGFR4 receptor. In one particular embodiment, the FGFR4 receptor is the human FGFR4 receptor (GenBank Accession No. NP_002002, which is hereby incorporated by reference in its entirety).

In one embodiment, the method of facilitating FGFR-βKlotho co-receptor complex formation is carried out in vitro. In one embodiment, the method is carried out in an adipocyte. In another embodiment, the method is carried out in a skeletal muscle cell, a pancreatic β cell, or a hepatocyte.

In one embodiment, the method of facilitating FGFR-Klotho co-receptor complex formation is carried out in vivo. In one embodiment, the method is carried out in a mammal. In one particular embodiment, the mammal is a mouse.

Yet a further aspect of the present invention relates to a method of screening for agents capable of facilitating FGFR-βKlotho complex formation in the treatment of a disorder. This method involves providing a chimeric FGF that includes an N-terminus coupled to a C-terminus, where the N-terminus includes a portion of a paracrine FGF and the C-terminus includes a C-terminal portion of FGF21. The portion of the paracrine FGF is modified to decrease binding affinity for heparin and/or heparan sulfate compared to the portion without the modification. This method also involves providing binary βKlotho-FGFR complex and providing one or more candidate agents. This method further involves combining the chimeric FGF, the binary βKlotho-FGFR complex, and the one or more candidate agents under conditions permitting the formation of a ternary complex between the chimeric FGF and the binary βKlotho-FGFR complex in the absence of the one or more candidate agents. This method also involves identifying the one or more candidate agents that decrease ternary complex formation between the chimeric FGF and the binary βKlotho-FGFR complex compared to the ternary complex formation in the absence of the one or more candidate agents as suitable for treating the disorder.

The portion of the paracrine FGF may also be modified to alter receptor-binding specificity and/or reduce receptor-binding affinity compared to the portion without the modification.

Suitable chimeric proteins for use in accordance with this aspect of the present invention are described above and throughout the present application. Suitable paracrine FGFs, as well as suitable modifications to decrease binding affinity for heparin and/or heparan sulfate, to alter receptor-binding specificity and/or to reduce receptor-binding affinity compared to the portion without the modification, are also described above.

In one embodiment, the modulation is a competitive interaction between the chimeric FGF molecule and the one or more candidate agents for binding to the binary βKlotho-FGFR complex.

In one embodiment, the FGFR is FGFR1c, FGFR2c, or FGFR4.

In one embodiment, the disorder is a selected from diabetes, obesity, and metabolic syndrome. In one embodiment, the disorder is diabetes selected from type II diabetes, gestational diabetes, or drug-induced diabetes. In one embodiment, the disorder is type I diabetes. In one embodiment, the disorder is obesity. In one embodiment, the disorder is metabolic syndrome.

In one embodiment of the screening aspects of the present invention, a plurality of compounds or agents is tested. Candidate agents may include small molecule compounds or larger molecules (e.g., proteins or fragments thereof). In one embodiment, the candidate compounds are biomolecules. In one embodiment, the biomolecules are proteins. In one embodiment, the biomolecules are peptides. In one embodiment, the candidates are peptides or peptide mimetics having similar structural features to native FGF ligand. In one embodiment, the candidate agent is a second chimeric FGF molecule. In one particular embodiment, the peptides are synthetic peptides. In one embodiment, the compounds are small organic molecules.

In one embodiment of the screening aspects of the present invention, the method is carried out using a cell-based assay. In one embodiment, the identifying is carried out using a cell-based assay.

In one embodiment of the screening aspects of the present invention, the method is carried out using a binding assay. In one embodiment, the binding assay is a direct binding assay. In one embodiment, the binding assay is a competition-binding assay. In one embodiment, the modulation stabilizes the ternary complex between the chimeric FGF molecule and the binary βKlotho-FGFR complex. In one embodiment, the stabilization is compared to the native ternary complex.

In one embodiment, the modulation is an allosteric or kinetic modulation. In one embodiment, the allosteric or kinetic modulation is compared to the native ternary complex. Such stabilization or allosteric or kinetic modulation can be measured using methods known in the art (e.g., by use of surface plasmon resonance (SPR) spectroscopy experiments as described in the Examples infra).

In one embodiment, the binding assay is carried out using surface plasmon resonance spectroscopy. In one embodiment, the identifying is carried out using a binding assay. In one embodiment, the identifying is carried out using surface plasmon resonance spectroscopy.

In one embodiment of the screening aspects of the present invention, the cell-based assay is carried out with adipocytes. In one embodiment, the cell-based assay is carried out with skeletal muscle cells. In one embodiment, the cell-based assay is carried out with pancreatic β cells. In one embodiment, the cell-based assay is carried out with hepatocytes. In one embodiment, stimulation of glucose uptake is the assay readout. In one embodiment, induction of glucose transporter 1 gene expression is the assay readout. In one embodiment, a dose-response curve is generated for the stimulation of glucose uptake by a candidate compound to determine potency and efficacy of the candidate compound. In one embodiment, a dose-response curve is generated for the induction of glucose transporter 1 gene expression by a candidate compound to determine potency and efficacy of the candidate compound. For example, if the dose-response curve is shifted to the left compared to that obtained for the chimeric FGF protein, the candidate compound has greater potency than the chimeric FGF protein and/or native FGF21. In one embodiment, an $IC_{50}$ value is derived from the dose-response curve of a candidate compound to determine potency of the candidate compound. An $IC_{50}$ value smaller than that obtained for the chimeric FGF protein identifies a candidate compound as more potent than the chimeric FGF protein and/or native FGF21.

In one embodiment of the screening aspects of the present invention, the cell-based assay is carried out with mammalian cells ectopically expressing βKlotho. In one particular embodiment, the cells are HEK293 cells. In one embodiment, activation of FGF receptor is the assay readout. In one embodiment, tyrosine phosphorylation of an FGF receptor substrate is used as readout for FGF receptor activation. In one particular embodiment, the FGF receptor substrate is FGF receptor substrate 2α. In one embodiment, activation of downstream mediators of FGF signaling is used as readout for (or an indicator of) FGF receptor activation. In one particular embodiment, the downstream mediator of FGF signaling is 44/42 mitogen-activated protein kinase. In one embodiment, the downstream mediator of FGF signaling is a transcription factor. In one particular embodiment, the transcription factor is early growth response 1. In one embodiment, a dose-response curve is generated for βKlotho-dependent activation of FGF receptor by a candidate compound to determine potency and efficacy of the candidate compound. For example, if the dose-response curve is shifted to the left compared to that obtained for the chimeric FGF protein, the candidate compound is more potent than the chimeric FGF protein and/or native FGF21. In one embodiment, an $IC_{50}$ value is derived from the dose-response curve of a candidate compound to determine potency of the candidate compound. An $IC_{50}$ value smaller than that obtained for the chimeric FGF protein identifies a candidate compound as more potent than the chimeric FGF protein and/or native FGF21.

In one embodiment of the screening aspects of the present invention, the surface plasmon resonance spectroscopy-based assay is carried out using the chimeric FGF protein as ligand coupled to a biosensor chip. In one embodiment, mixtures of βKlotho ectodomain with increasing concentrations of a candidate compound are passed over a biosensor chip containing chimeric FGF protein. In one embodiment, mixtures of the binary complex of FGFR ligand-binding domain and βKlotho ectodomain with increasing concentrations of a candidate compound are passed over a biosensor chip containing chimeric FGF protein. In one particular embodiment, the FGFR ligand-binding domain is the FGFR1c ligand-binding domain. In one embodiment, an inhibition-binding curve is plotted for a candidate compound to determine potency of the candidate compound. For example, if the inhibition-binding curve is shifted to the left compared to that obtained for the chimeric FGF protein, the candidate compound has greater potency than the chimeric FGF protein and/or native FGF21. In one embodiment, an $IC_{50}$ value is derived from the inhibition-binding curve of a candidate compound to determine potency of the candidate compound. An $IC_{50}$ value smaller than that obtained for containing chimeric FGF protein identifies a candidate compound as more potent than the chimeric FGF protein and/or native FGF21. In one embodiment, the inhibition constant $K_i$ is determined for a candidate compound to determine potency of the candidate compound. A $K_i$ value smaller than that obtained for native FGF21 identifies a candidate compound as more potent than the chimeric FGF protein and/or native FGF21.

In one embodiment of the screening aspects of the present invention, the method is carried out in vivo. In one embodiment, the method is carried out in a mammal. In one particular embodiment, the mammal is a mouse. In one embodiment, the mammal has obesity, diabetes, or a related metabolic disorder. In one embodiment, the ability of a candidate compound to potentiate the hypoglycemic effect of insulin is used as readout for FGF21-like metabolic activity. This involves fasting the mammal for a period of time prior to insulin injection and measuring fasting blood glucose levels. The mammal is then injected with insulin alone or co-injected with insulin plus a candidate compound. Blood glucose levels are measured at several time points after the injection. If a candidate compound potentiates the hypoglycemic effect of insulin to a greater degree than the chimeric FGF protein and/or native FGF21 does, the candidate compound exhibits enhanced efficacy. Likewise, if a candidate compound potentiates the hypoglycemic effect of insulin to a similar degree than the chimeric FGF protein and/or native FGF21 does but at a lower dose compared to that of the chimeric FGF protein and/or native FGF21 and/or for a longer period of time compared to the chimeric FGF protein and/or native FGF21, the candidate compound has enhanced agonistic properties. In one embodiment, the ability of a candidate compound to elicit a hypoglycemic effect in a mammal with diabetes, obesity, or a related metabolic disorder is used as readout for FGF21-like metabolic activity. This involves injecting a mammal suffering from diabetes, obesity, or a related metabolic disorder with the candidate compound. Blood glucose levels are measured before the injection and at several time points thereafter. If a candidate compound has a greater hypoglycemic effect than the chimeric FGF protein and/or native FGF21 does, the candidate compound exhibits enhanced efficacy. Likewise, if a candidate compound shows a similar hypoglycemic effect than the chimeric FGF protein and/or native FGF21 does but at a lower dose compared to that of the chimeric FGF protein and/or native FGF21 and/or for a longer period of time compared to the chimeric FGF protein and/or native FGF21, the candidate compound has enhanced agonistic properties.

EXAMPLES

Example 1—Purification of FGF, FGFR, and Klotho Proteins

Figures 5A, 5B, 5C, 5D, 5E, 5F, 5G:
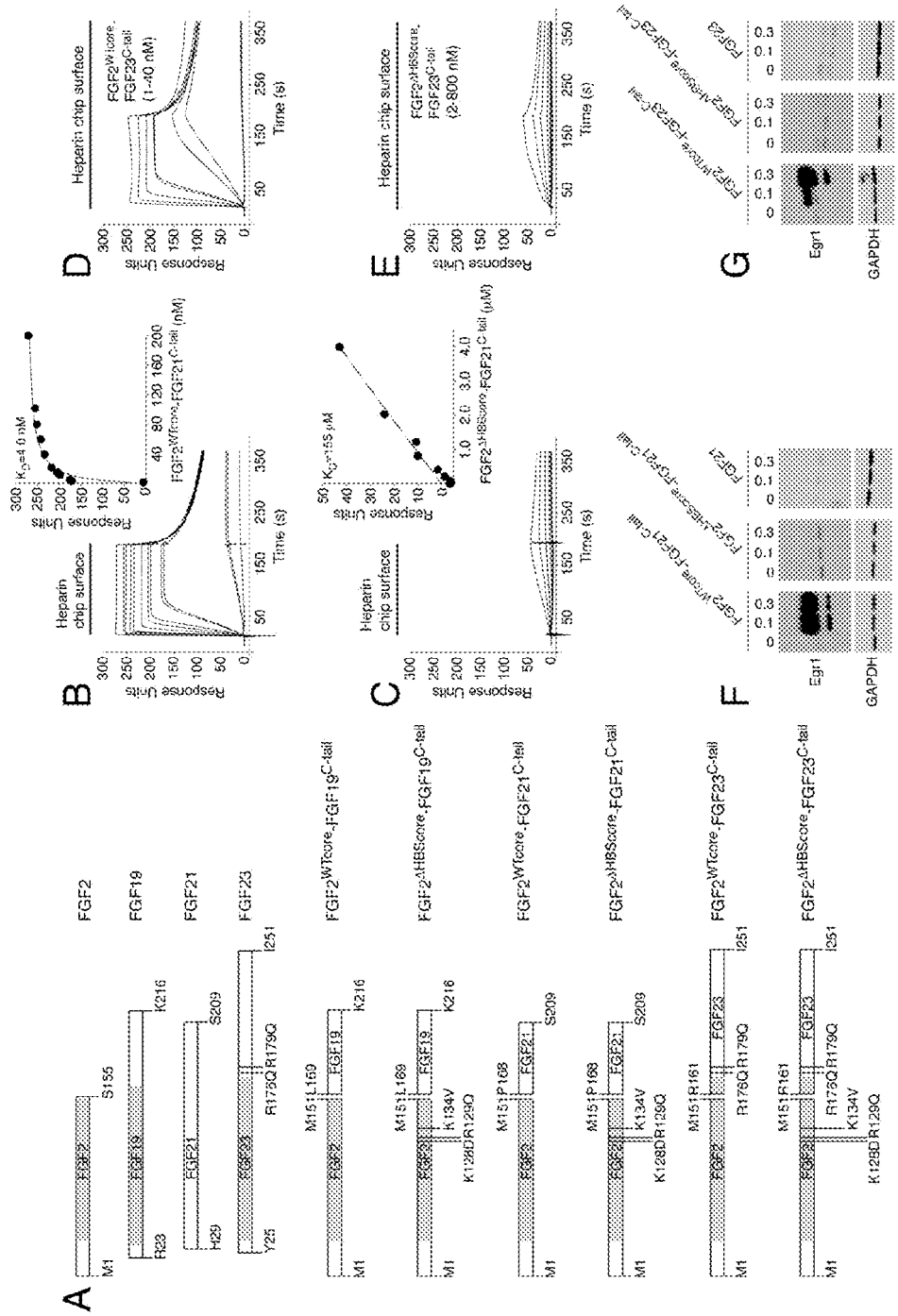
FIGS. 5A-5G show design and results relating to the conversion of FGF2 into an endocrine ligand.

The N-terminally hexahistidine-tagged, mature form of human FGF19 (SEQ ID NO: 337) (R23 to K216), human FGF21 (SEQ ID NO:233) (H29 to S209; FIG. 5A), and human FGF23 (SEQ ID NO: 351) (Y25 to I251; FIG. 5A) was refolded in vitro from bacterial inclusion bodies, and purified by published protocols (Ibrahimi et al., *Hum. Mol. Genet.* 13:2313-2324 (2004); Plotnikov et al., *Cell* 101:413-424 (2000), which is hereby incorporated by reference in its entirety). The amino acid sequence of human FGF23 (SEQ ID NO:351) (GenBank accession no. AAG09917, which is hereby incorporated by reference in its entirety) is as follows:

```
  1 MLGARLRLWV CALCSVCSMS VLRAYPNASP LLGSSWGGLI HLYTATARNS YHLQIHKNGH

61 VDGAPHQTIY SALMIRSEDA GFVVITGVMS RRYLCMDFRG NIFGSHYFDP ENCRFQHQTL

121 ENGYDVYHSP QYHFLVSLGR AKRAFLPGMN PPPYSQFLSR RNEIPLIHFN TPIPRRHTRS

181 AEDDSERDPL NVLKPRARMT PAPASCSQEL PSAEDNSPMA SDPLGVVRGG RVNTHAGGTG

241 PEGCRPFAKF I
```

Figure 6:
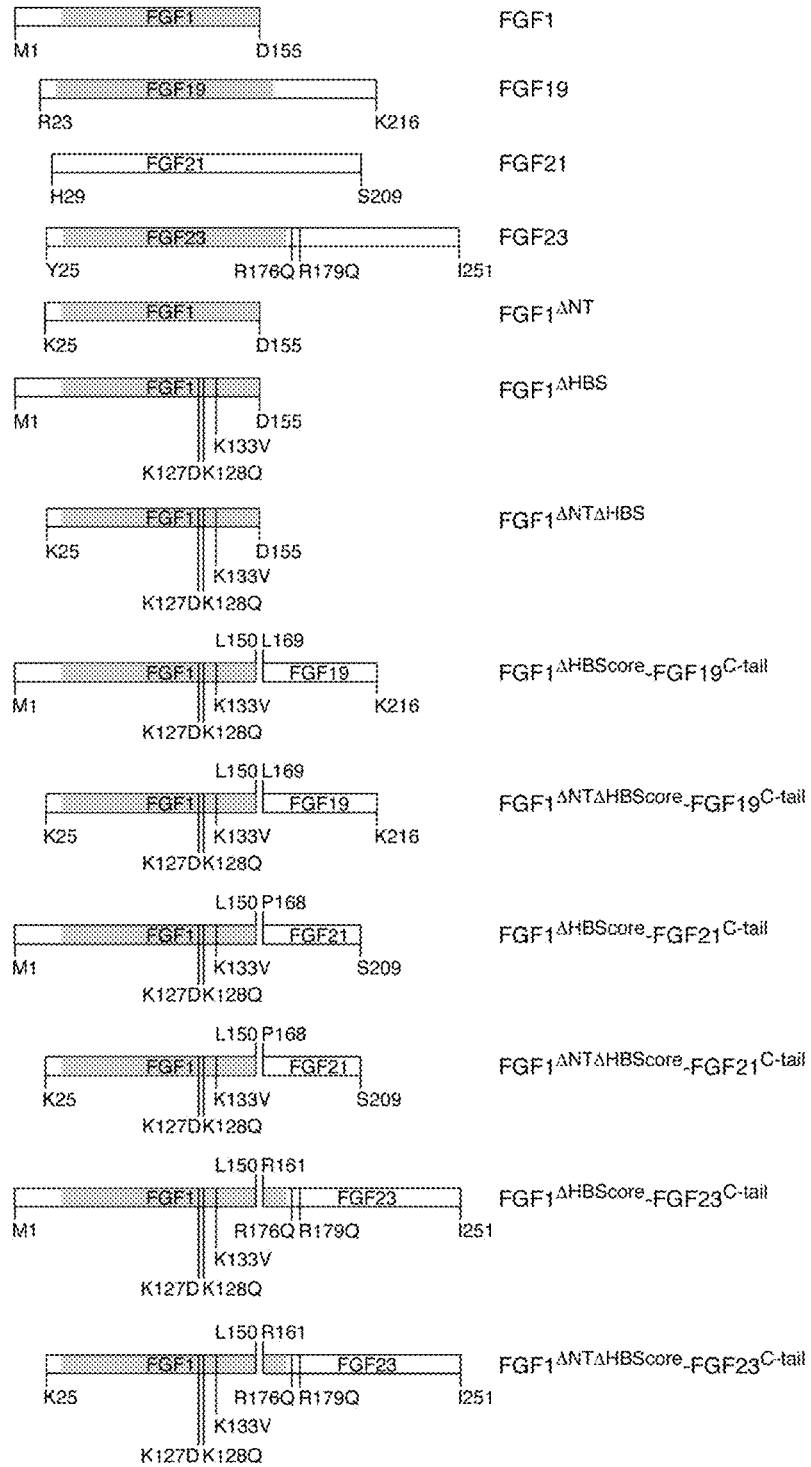
FIG. 6 is a schematic illustrating the conversion of FGF1 into an endocrine ligand. Shown are schematic drawings of human FGF1, FGF19, FGF21, FGF23, and exemplary FGF1-FGF19, FGF1-FGF21, and FGF1-FGF23 chimeras according to the present invention. Amino acid boundaries of each ligand and of each component of the chimeras are labeled with residue letter and number. The β-trefoil core domain for the known ligand crystal structures is shaded gray. HS-binding residues mutated in the FGF1 portion of chimeras are labeled with residue letter and number. Also labeled are the arginine residues of the proteolytic cleavage site in the C-terminal region of FGF23 that were mutated to glutamine in both FGF23 and the FGF1-FGF23 chimeras.

HS-binding site mutants of FGF19 (K149A) and FGF23 (R140A/R143A) were purified from bacterial inclusion bodies by similar protocols as the wild-type proteins. In order to minimize proteolysis of FGF23 wild-type and mutant proteins, arginine residues 176 and 179 of the proteolytic cleavage site $^{176}$RXXR$^{179}$ were replaced with glutamine as it occurs in the phosphate wasting disorder "autosomal dominant hypophosphatemic rickets" (ADHR) (White et al., *Nat. Genet.* 26:345-348 (2000); White et al., *Kidney Int.* 60:2079-2086 (2001), which are hereby incorporated by reference in their entirety). Human FGF1 (SEQ ID NO:1) (M1 to D155; FIG. 6), N-terminally truncated human FGF1 (K25 to D155, termed FGF1$^{\Delta NT}$; FIG. 6), human FGF2 (SEQ ID NO: 121) (M1 to S155; FIG. 5A), and human FGF homologous factor 1B (FHF1B; M1 to T181) were purified by published protocols (Plotnikov et al., *Cell* 101:413-424 (2000); Olsen et al., *J. Biol. Chem.* 278:34226-34236 (2003), which are hereby incorporated by reference in their entirety).

Chimeras composed of the core domain of FGF2 (M1 to M151) and the C-terminal region of either FGF21 (P168 to S209) or FGF23 (R161 to I251) (termed FGF2$^{WTcore}$-FGF21$^{C-tail}$ and FGF2$^{WTcore}$-FGF23$^{C-tail}$, respectively; FIG. 5A) were purified by the same protocol as that for native FGF2 (Plotnikov et al., *Cell* 101:413-424 (2000), which is hereby incorporated by reference in its entirety). Analogous chimeras containing three mutations in the HS-binding site of the FGF2 core (K128D/R129Q/K134V) (termed FGF2$^{\Delta HBScore}$-FGF21$^{C-tail}$ and FGF2$^{\Delta HBScore}$-FGF23$^{C-tail}$, respectively, FIG. 5A) were purified from the soluble bacterial cell lysate fraction by ion-exchange and size-exclusion chromatographies. In order to minimize proteolysis of the chimeras containing the C-terminal sequence from R161 to I251 of FGF23, arginine residues 176 and 179 of the proteolytic cleavage site $^{176}$RXXR$^{179}$ located within this sequence were replaced with glutamine as it occurs in ADHR (White et al., *Nat. Genet.* 26:345-348 (2000); White et al., *Kidney Int.* 60:2079-2086 (2001), which are hereby incorporated by reference in their entirety). In addition, in order to prevent disulfide-mediated dimerization of FGF2 and chimeric FGF2 proteins, cysteine residues 78 and 96 were mutated to serine. An HS-binding site mutant of FGF1 (K127D/K128Q/K133V) (termed FGF1$^{\Delta HBScore}$; FIG. 6) and chimeras composed of the core domain of the HS-binding site mutant of FGF1 (M1 to L150, K127D/K128Q/K133V) and the C-terminal region of either FGF19 (L169 to K216) or FGF21 (P168 to S209) (termed FGF1$^{\Delta HBScore}$-FGF19$^{C-tail}$ and FGF1$^{\Delta HBScore}$-FGF21$^{C-tail}$ respectively; FIG. 6) were purified from the soluble bacterial cell lysate fraction by ion-exchange and size-exclusion chromatographies. The N-terminally hexahistidine-tagged C-terminal tail peptide of FGF23 (S180 to I251, termed FGF23$^{C-tail}$) was purified by a published protocol (Goetz et al., *Proc. Nat'l. Acad. Sci. U.S.A.* 107:407-412 (2010), which is hereby incorporated by reference in its entirety). The ligand-binding domain of human FGFR1c (D142 to R365) was refolded in vitro from bacterial inclusion bodies, and purified by published protocols (Ibrahimi et al., *Hum. Mol. Genet.* 13:2313-2324 (2004); Plotnikov et al., *Cell* 101:413-424 (2000), which are hereby incorporated by reference in their entirety). The ectodomain of murine αKlotho (A35 to K982) and the ectodomain of murine βKlotho (F53 to L995) were expressed in HEK293 cells as fusion proteins with a C-terminal FLAG tag (Kurosu et al., *J. Biol. Chem.* 281:6120-6123 (2006); Kurosu et al., *Science* 309:1829-1833 (2005), which are hereby incorporated by reference in their entirety). The binary complex of FGFR1c ligand-binding domain with αKlotho ectodomain (referred to as αKlotho-FGFR1c complex) was prepared by a published protocol (Goetz et al., *Proc. Nat'l. Acad. Sci. U.S.A.* 107:407-412 (2010), which is hereby incorporated by reference in its entirety). The binary complex of FGFR1c ligand-binding domain with βKlotho ectodomain (referred to as βKlotho-FGFR1c complex) was prepared in the same fashion as the αKlotho-FGFR1c complex.

Example 2—Analysis of FGF-Heparin and FGF-FGFR-α/Klotho Interactions by Surface Plasmon Resonance Spectroscopy Surface plasmon resonance (SPR) experiments were performed on a Biacore 2000 instrument (Biacore AB), and the interactions were studied at 25° C. in HBS-EP buffer (10 mM HEPES-NaOH, pH 7.4, 150 mM NaCl, 3 mM EDTA, 0.005% (v/v) polysorbate 20). To study endocrine FGF-heparin interactions, a heparin chip was prepared by immobilizing biotinylated heparin (Sigma-Aldrich) on flow channels of a research-grade streptavidin chip (Biacore AB). The coupling density was ~5 fmol mm$^{-2}$ of flow channel. To measure binding of chimeric FGF2 proteins to heparin, biotinylated heparin was coupled to a streptavidin chip at an approximately 4-fold lower density as judged based on the binding responses obtained for FGF1. To study FGF-FGFR-α/βKlotho interactions, FGF chips were prepared by covalent coupling of FGF proteins through their free amino groups on flow channels of research grade CM5 chips (Biacore AB). Proteins were injected over a chip at a flow rate of 50 µl min$^{-1}$, and at the end of each protein injection (180 and 300 s, respectively), HBS-EP buffer (50 µl min$^{-1}$) was flowed over the chip to monitor dissociation for 180 or 240 s. The heparin chip surface was regenerated by injecting 50 µl of 2.0 M NaCl in 10 mM sodium acetate, pH 4.5. For FGF chips, regeneration was achieved by injecting 2.0 M NaCl in 10 mM sodium/potassium phosphate, pH 6.5. To control for nonspecific binding in experiments where an FGF ligand was immobilized on the chip, FHF1B, which shares structural similarity with FGFs but does not exhibit any FGFR binding (Olsen et al., *J. Biol. Chem.* 278:34226-34236 (2003), which is hereby incorporated by reference in its entirety), was coupled to the control flow channel of the chip (~15-30 fmol mm$^{-2}$). In experiments where heparin was immobilized on the chip, the control flow channel was left blank. The data were processed with BiaEvaluation software (Biacore AB). For each protein injection over the heparin chip, the nonspecific responses from the control flow channel were subtracted from the responses recorded for the heparin flow channel. Similarly, for each protein injection over a FGF chip, the nonspecific responses from the FHF1B control flow channel were subtracted from the responses recorded for the FGF flow channel. Where possible, equilibrium dissociation constants ($K_D$s) were calculated from fitted saturation binding curves. Fitted binding curves were judged to be accurate based on the distribution of the residuals (even and near zero) and $\chi^2$ (<10% of $R_{max}$).

To examine whether the K149A mutation abrogates residual heparin binding of FGF19, increasing concentrations of wild-type FGF19 were passed over a heparin chip. Thereafter, the FGF19$^{K149A}$ mutant was injected over the heparin chip at the highest concentration tested for the wild-type ligand. The effect of the R140A/R143A double mutation in the HS-binding site of FGF23 on residual heparin binding of FGF23 was examined in the same fashion as was the effect of the HS-binding site mutation in FGF19. To verify that the K128D/R129Q/K134V triple mutation in the HS-binding site of the FGF2 core domain diminishes heparin-binding affinity of the FGF2 core, increasing concentrations of FGF2$^{\Delta HBScore}$-FGF21$^{C\text{-}tail}$ and FGF2$^{\Delta HBScore}$-FGF23$^{C\text{-}tail}$ were passed over a heparin chip. As a control, binding of FGF2$^{WTcore}$-FGF21$^{C\text{-}tail}$ and FGF2$^{WTcore}$-FGF23$^{C\text{-}tail}$ to heparin was studied.

To examine whether the FGF2$^{\Delta HBScore}$-FGF23$^{C\text{-}tail}$ chimera can compete with FGF23 for binding to the αKlotho-FGFR1c complex, FGF23 was immobilized on a chip (~16 fmol mm$^{-2}$ of flow channel). Increasing concentrations of FGF2$^{\Delta HBScore}$-FGF23$^{C\text{-}tail}$ were mixed with a fixed concentration of αKlotho-FGFR1c complex in HBS-EP buffer, and the mixtures were injected over the FGF23 chip. As controls, the binding competition was carried out with FGF23 or FGF2 as the competitor in solution. As an additional specificity control, competition of the FGF2$^{\Delta HBScore}$-FGF23$^{C\text{-}tail}$ chimera with FGF21 for binding to the αKlotho-FGFR1c complex was studied. αKlotho-FGFR1c complex was mixed with FGF2$^{\Delta HBScore}$-FGF23$^{C\text{-}tail}$ or FGF23 at a molar ratio of 1:10, and the mixture was injected over a chip containing immobilized FGF21 (~12 fmol mm$^{-2}$ of flow channel).

To test whether the FGF2$^{\Delta HBScore}$-FGF21$^{C\text{-}tail}$ chimera can compete with FGF21 for binding to the βKlotho-FGFR1c complex, increasing concentrations of FGF2$^{\Delta HBScore}$-FGF21$^{C\text{-}tail}$ were mixed with a fixed concentration of βKlotho-FGFR1c complex in HBS-EP buffer, and the mixtures were passed over a chip containing immobilized FGF21 (~19 fmol mm$^{-2}$ of flow channel). As controls, the binding competition was carried out with FGF21 or FGF2 as the competitor in solution. As an additional specificity control, competition of the FGF2$^{\Delta HBScore}$-FGF21$^{C\text{-}tail}$ chimera with FGF23 for binding to the αKlotho-FGFR1c complex was studied. αKlotho-FGFR1c complex was mixed with FGF2$^{\Delta HBScore}$-FGF21$^{C\text{-}tail}$ or FGF21 at a molar ratio of 1:10, and the mixture was injected over a chip containing immobilized FGF23 (~12 fmol mm$^{-2}$ of flow channel).

To measure binding of FGFR1c to each of the three endocrine FGFs, increasing concentrations of FGFR1c ligand-binding domain were injected over a chip containing immobilized FGF19, FGF21, and FGF23 (~30 fmol mm$^{-2}$ of flow channel). As a control, binding of FGFR1c to FGF2 immobilized on a chip was studied. As additional controls, binding of the αKlotho-FGFR1c complex to FGF23 and binding of FGFR1c to the C-terminal tail peptide of FGF23 was measured.

Example 3—Analysis of Phosphorylation of FRS2α and 44/42 MAP Kinase in Hepatoma and Epithelial Cell Lines To examine whether the FGF19$^{K149A}$ and FGF23$^{R140A/R143A}$ mutants can activate FGFR in a α/βKlotho-dependent fashion, induction of tyrosine phosphorylation of FGFR substrate 2α (FRS2α) and downstream activation of MAP kinase cascade was used as readout for FGFR activation. Subconfluent cells of the H4IIE rat hepatoma cell line, which endogenously expresses βKlotho (Kurosu et al., *J. Biol. Chem.* 282:26687-26695 (2007), which is hereby incorporated by reference in its entirety), were serum starved for 16 h and then stimulated for 10 min with the FGF19$^{K149A}$ mutant or wild-type FGF19 (0.2 ng ml$^{-1}$ to 2.0 µg ml$^{-1}$). Similarly, subconfluent cells of a HEK293 cell line ectopically expressing the transmembrane isoform of murine αKlotho (Kurosu et al., *J. Biol. Chem.* 281:6120-6123 (2006), which is hereby incorporated by reference in its entirety) were treated with the FGF23$^{R140A/R143A}$ mutant or wild-type FGF23 (0.1 to 100 ng ml$^{-1}$). After stimulation, the cells were lysed (Kurosu et al., *Science* 309:1829-1833 (2005), which is hereby incorporated by reference in its entirety), and cellular proteins were resolved on SDS-polyacrylamide gels and transferred to nitrocellulose membranes. The protein blots were probed with antibodies to phosphorylated FRS2α, phosphorylated 44/42 MAP kinase, total (phosphorylated and nonphosphorylated) 44/42 MAP kinase, and αKlotho. Except for the anti-αKlotho antibody (KM2119) (Kato et al., *Biochem. Biophys. Res. Commun.* 267:597-602 (2000), which is hereby incorporated by reference in its entirety), all antibodies were from Cell Signaling Technology.

Example 4—Analysis of Egr1 Protein Expression in an Epithelial Cell Line

To examine whether the FGF2$^{\Delta HBScore}$-FGF21$^{C\text{-}tail}$ and FGF2$^{\Delta HBScore}$-FGF23$^{C\text{-}tail}$ chimeras can activate FGFR in a HS-dependent fashion, induction of protein expression of the transcription factor early growth response 1 (Egr1), a known downstream mediator of FGF signaling, was used as readout for FGFR activation. HEK293 cells were serum starved overnight and then stimulated for 90 min with FGF2$^{\Delta HBScore}$-FGF21$^{C\text{-}tail}$ or FGF2$^{\Delta HBScore}$-FGF23$^{C\text{-}tail}$ (0.1 and 0.3 nM). Cell stimulation with FGF2$^{WTcore}$-FGF21$^{C\text{-}tail}$, FGF2$^{WTcore}$-FGF23$^{C\text{-}tail}$, FGF21, and FGF23 served as controls. To test whether the FGF2$^{\Delta HBScore}$-FGF21$^{C\text{-}tail}$ chimera can activate FGFR in a βKlotho-dependent fashion, HEK293 cells transfected with murine βKlotho were serum starved overnight and then stimulated for 90 min with FGF2$^{\Delta HBScore}$-FGF21$^{C\text{-}tail}$ or FGF21 (3 to 300 ng ml$^{-1}$). After stimulation, the cells were lysed (Kurosu et al., *Science* 309:1829-1833 (2005), which is hereby incorporated by reference in its entirety), and cellular proteins were resolved on SDS-polyacrylamide gels and transferred to nitrocellulose membranes. The protein blots were probed with antibodies to Egr1 and glyceraldehyde 3-phosphate dehydrogenase (GAPDH). The anti-Egr1 antibody was from Cell Signaling Technology and the anti-GAPDH antibody was from Abcam.

Example 5—Analysis of CYP7A1 and CYP8B1 mRNA Expression in Murine Liver Tissue

To examine the metabolic activity of the FGF19$^{K149A}$ mutant in vivo, 6- to 8-week old C57BL/6 mice were fasted overnight and then given intraperitoneally a single dose (1 mg kg body weight$^{-1}$) of FGF19$^{K149A}$ or FGF19 as a control. 6 h after the injection, the mice were sacrificed, and liver tissue was excised and frozen. Total RNA was isolated from liver tissue, and mRNA levels of cholesterol 7α-hydroxylase (CYP7A1) and sterol 12α-hydroxylase (CYP8B1) were measured using quantitative real time RT-PCR as described previously (Inagaki et al., *Cell Metab.* 2:217-225 (2005); Kim et al., *J. Lipid Res.* 48:2664-2672 (2007), which are hereby incorporated by reference in their entirety). The Institutional Animal Care and Use Committee at the University of Texas Southwestern Medical Center at Dallas had approved the experiments.

Example 6—Measurement of Serum Phosphate in Mice

The metabolic activity of the FGF23$^{R140A/R143A}$ mutant was examined both in normal mice and in Fgf23 knockout mice. 4- to 5-week old C57BL/6 mice were given intraperitoneally a single dose (0.29 mg kg body weight$^{-1}$) of FGF23$^{R140A/R143A}$ or FGF23 as a control. Before the injection and 8 h after the injection, blood was drawn from the cheek pouch and spun at 3,000×g for 10 min to obtain serum. Phosphate concentration in serum was measured using the Phosphorus Liqui-UV Test (Stanbio Laboratory). 6- to 8-week old Fgf23 knockout mice (Sitara et al., *Matrix Biol.* 23:421-432 (2004), which is hereby incorporated by reference in its entirety) (56) were given two injections of FGF23$^{R140A/R143A}$ or FGF23 at 8 h intervals (0.71 mg kg body weight$^{-1}$ each), and blood samples were collected for phosphate analysis before the first injection and 8 h after the second injection.

To test whether the FGF2$^{\Delta HBScore}$-FGF23$^{C\text{-}tail}$ chimera exhibits FGF23-like metabolic activity, 5- to 6-week old C57BL/6 mice were given a single injection of FGF2$^{\Delta HBScore}$-FGF23$^{C\text{-}tail}$ (0.21 mg kg body weight$^{-1}$). As controls, mice were injected with FGF2$^{WTcore}$-FGF23$^{C\text{-}tail}$ or FGF23. Before the injection and 8 h after the injection, blood samples were collected for measurement of serum phosphate. To confirm that αKlotho is required for the metabolic activity of the FGF2$^{\Delta HBScore}$-FGF23$^{C\text{-}tail}$ chimera, 7- to 8-week old αKlotho knockout mice (Lexicon Genetics) were injected once with FGF2$^{\Delta HBScore}$-FGF23$^{C\text{-}tail}$ or FGF23 as a control (0.51 mg kg body weight$^{-1}$). Before the injection and 8 h after the injection, blood samples were collected for phosphate analysis. The Harvard University Animal Care and Research committee board had approved all the experiments.

Example 7—Analysis of CYP27B1 mRNA Expression in Murine Renal Tissue

The ability of the FGF2$^{\Delta HBScore}$-FGF23$^{C\text{-}tail}$ chimera to reduce renal expression of 25-hydroxyvitamin D$_3$ 1α-hydroxylase (CYP27B1) was used as another readout for FGF23-like metabolic activity. C57BL/6 mice injected with FGF2$^{\Delta HBScore}$-FGF23$^{C\text{-}tail}$, FGF2$^{WTcore}$-FGF23$^{C\text{-}tail}$, or FGF23 were sacrificed 8 h after the protein injection, and renal tissue was excised and frozen. CYP27B1 mRNA levels in total renal tissue RNA were measured using real time quantitative PCR as described previously (Nakatani et al., *FASEB J.* 23:3702-3711 (2009); Ohnishi et al., *Kidney Int.* 75:1166-1172 (2009), which are hereby incorporated by reference in their entirety). The Harvard University Animal Care and Research committee board had approved the experiments.

Example 8—Insulin Tolerance Test in Mice

Figures 7A, 7B, 7C, 7D, 7E, 7F, 7G:
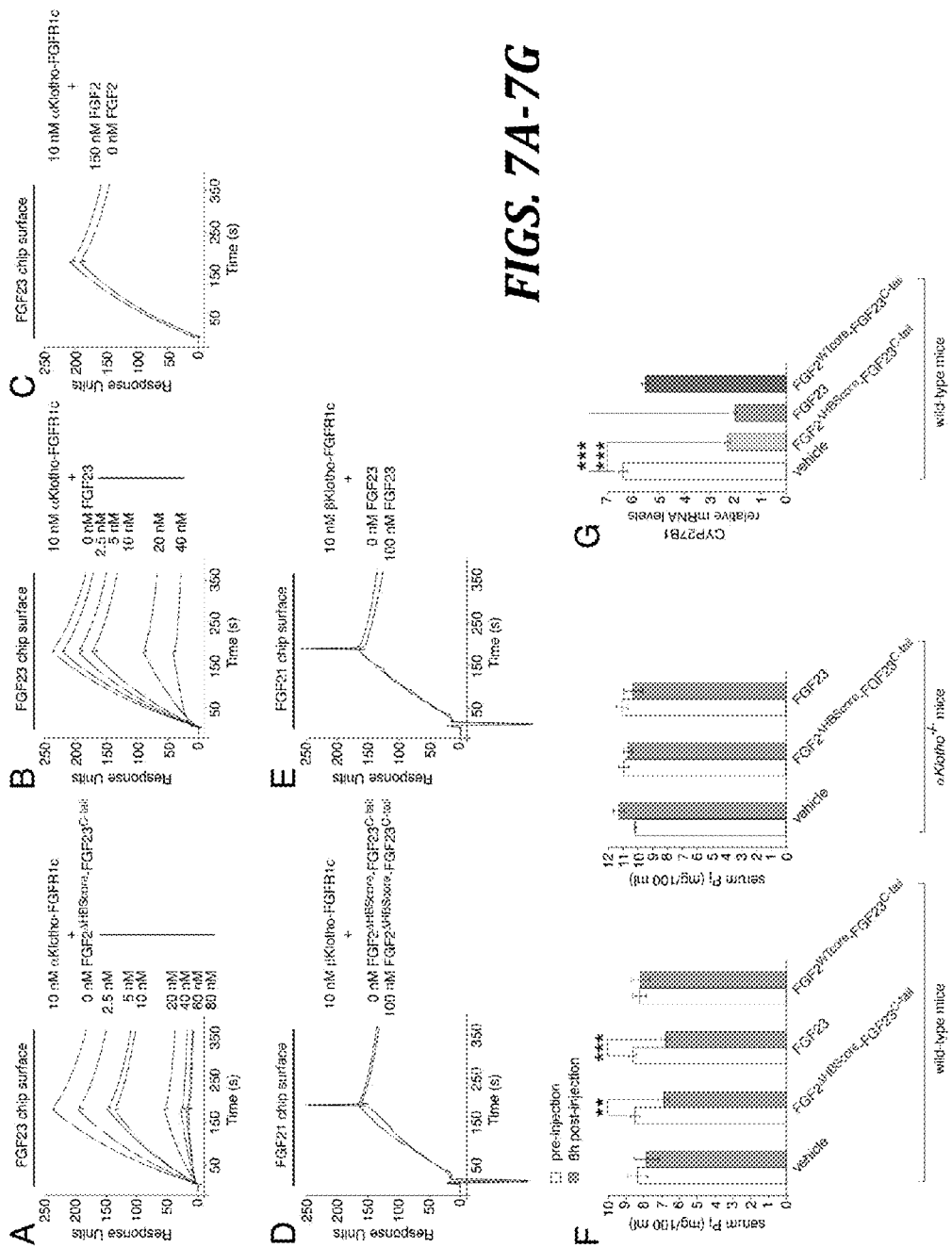
FIGS. 7A-7G show results demonstrating that the $FGF2^{\Delta HBScore}$-$FGF23^{C-tail}$ chimera exhibits FGF23-like activity.
Figures 8A, 8B, 8C, 8D, 8E, 8F, 8G:
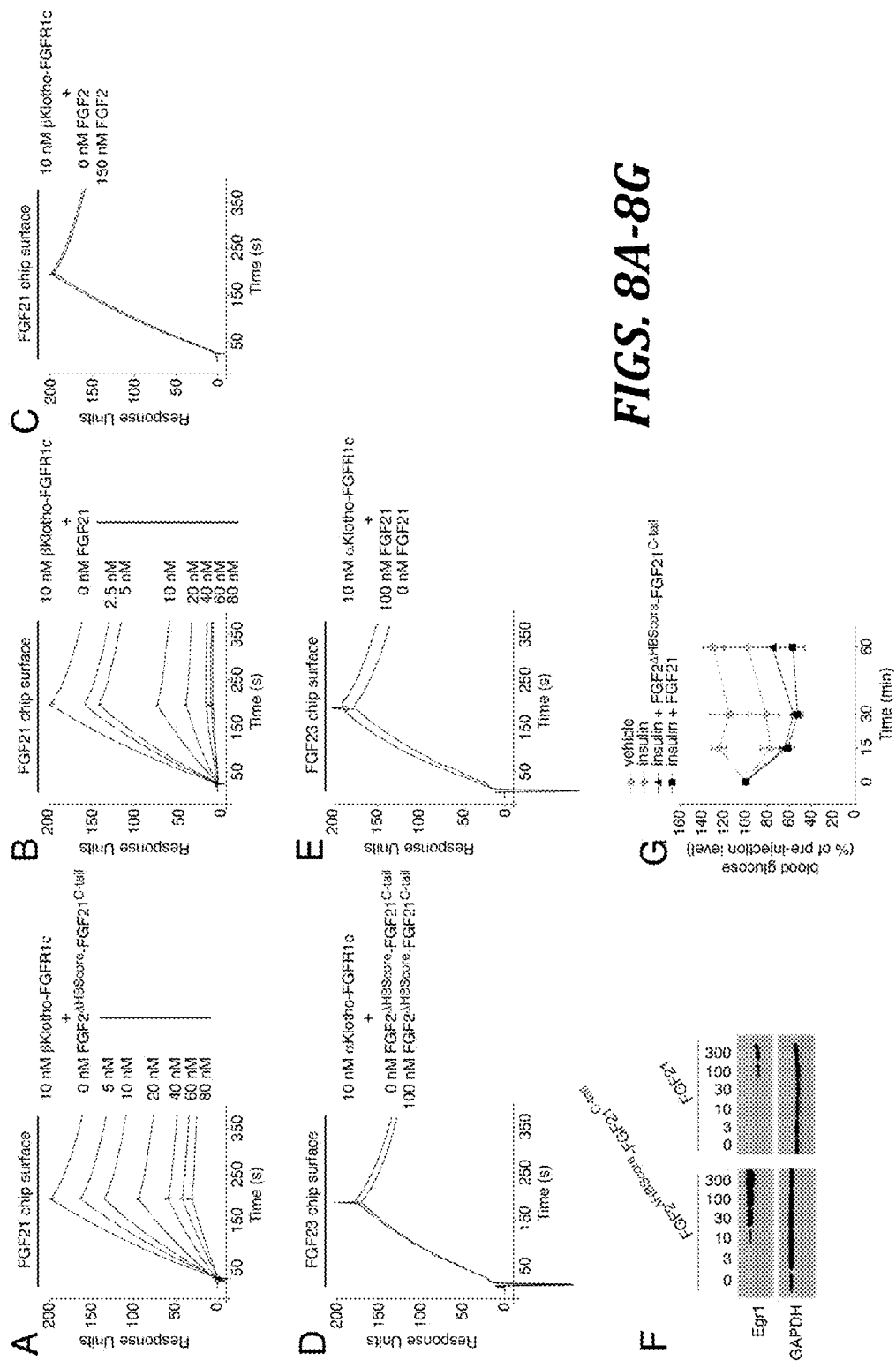
FIGS. 8A-8G show results demonstrating that the $FGF2^{\Delta HBScore}$-$FGF21^{C-tail}$ chimera exhibits FGF21-like activity.

The ability of the FGF2$^{\Delta HBScore}$-FGF21$^{C\text{-}tail}$ chimera to potentiate the hypoglycemic effect of insulin was used as readout for FGF21-like metabolic activity (Ohnishi et al., *FASEB J.* 25:2031-2039 (2011), which is hereby incorporated by reference in its entirety). 8- to 12-week old C57BL/6 mice were kept on normal chow. On the day of the insulin tolerance test, mice were fasted for 4 h and then bled from the cheek pouch for measuring fasting blood glucose levels. Thereafter, mice were administered intraperitoneally insulin (0.5 units kg body weight$^{-1}$) alone or insulin (0.5 units-kg body weight$^{-1}$) plus FGF2$^{\Delta HBScore}$-FGF21$^{C\text{-}tail}$ chimera (0.3 mg kg body weight$^{-1}$). As a control, mice were co-injected with insulin plus FGF21. At the indicated time points after the injection (FIG. 7G), blood was drawn from the tail vein. Glucose concentrations in the blood samples were determined using Bayer Contour® blood glucose test strips (Bayer Corp.). The Harvard University Animal Care and Research committee board had approved the experiments.

Example 9—Analysis of Blood Glucose in ob/ob Mice ob/ob mice were injected subcutaneously with FGF1$^{\Delta NT}$, FGF1$^{\Delta HBS}$, or FGF1$^{\Delta HBScore}$-FGF21$^{C-tail}$ chimera. Injection of native FGF1 or native FGF21 served as controls. A single bolus of 0.5 mg of protein per kg of body weight was injected. This dose was chosen on the basis that maximal efficacy of the hypoglycemic effect of native FGF1 is seen at this dose. Before the protein injection and at the indicated time points after the injection (FIGS. 9A-9C), blood glucose concentrations were measured using an OneTouch Ultra glucometer (Lifescan). The Institutional Animal Care and Use Committee at the Salk Institute for Biological Sciences at La Jolla had approved the experiments.

Example 10—Statistical Analysis

Data are expressed as mean±SEM. A Student's t test or analysis of variance (ANOVA) was used as appropriate to make statistical comparisons. A value of P<0.05 was considered significant.

Example 11—HS is Dispensable for the Metabolic Activity of FGF19 and FGF23

Figure 2:
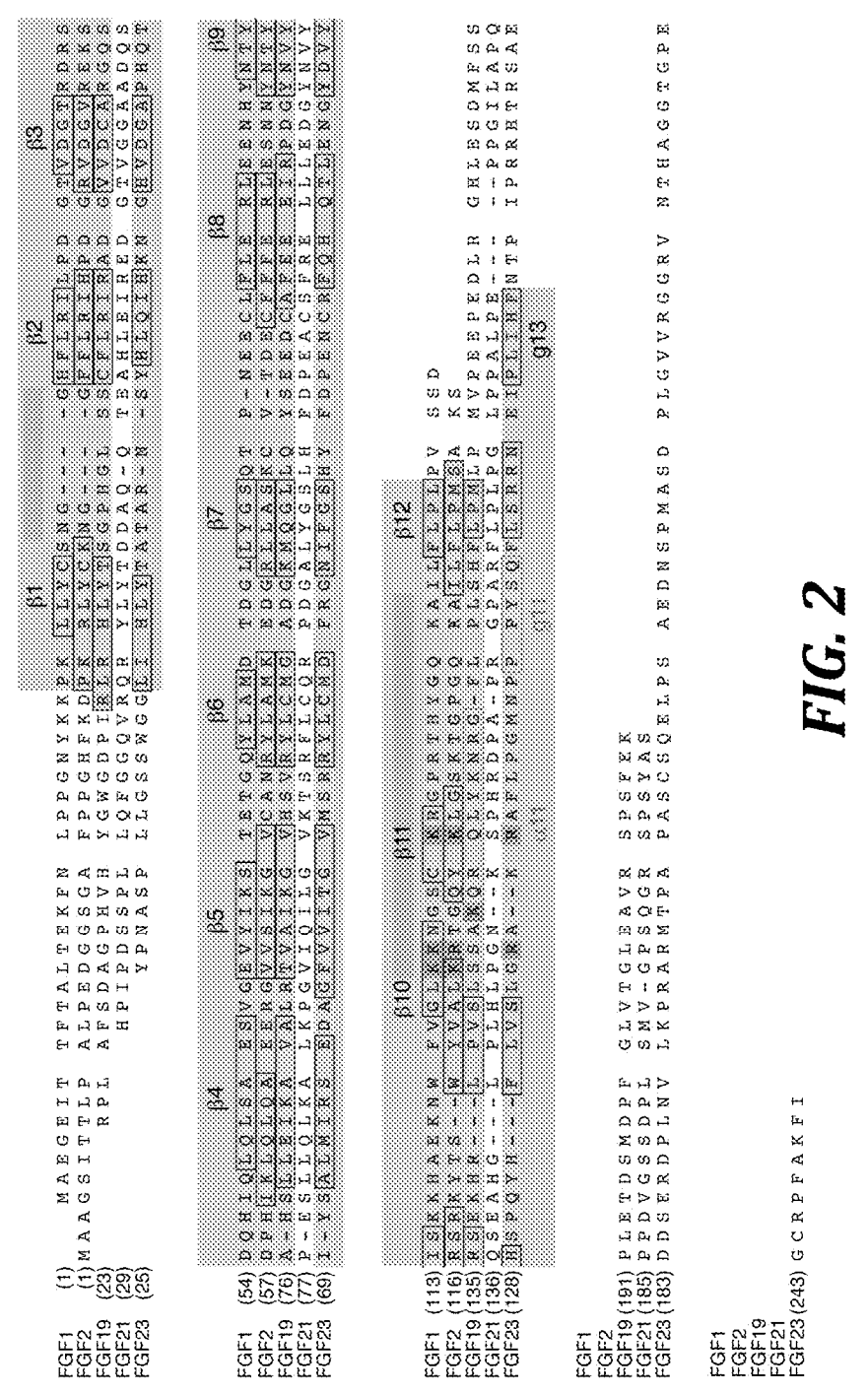

In order to engineer endocrine FGFs devoid of HS binding, the FGF19 crystal structure (PDB ID: 2P23; (Goetz et al., *Mol. Cell Biol.* 27:3417-3428 (2007), which is hereby incorporated by reference in its entirety) was compared with that of FGF2 bound to a heparin hexasaccharide (PDB ID: 1FQ9; (Schlessinger et al., *Mol. Cell* 6:743-750 (2000), which is hereby incorporated by reference in its entirety)). This analysis shows that solvent-exposed residues K149, Q150, Q152, and R157 of FGF19 lie at the corresponding HS-binding site of this ligand, and hence could account for the residual HS binding of FGF19 (FIGS. 1A, 1B, and 2). Likewise, comparative analysis of the FGF23 crystal structure (PDB ID: 2P39; (Goetz et al., *Mol. Cell Biol.* 27:3417-3428 (2007), which is hereby incorporated by reference in its entirety) (29)) with that of heparin-bound FGF2 (PDB ID: 1FQ9; (Schlessinger et al., *Mol. Cell* 6:743-750 (2000), which is hereby incorporated by reference in its entirety)) points to R48, N49, R140, and R143 as candidates mediating the residual HS binding of this ligand (FIGS. 1A, 1C, and 2). In agreement with the structural predictions, replacement of K149 alone in FGF19 with alanine and combined substitution of R140 and R143 in FGF23 for alanine were sufficient to abolish residual HS binding of these ligands (FIGS. 3B-3G).

Figures 4A, 4B, 4C, 4D:
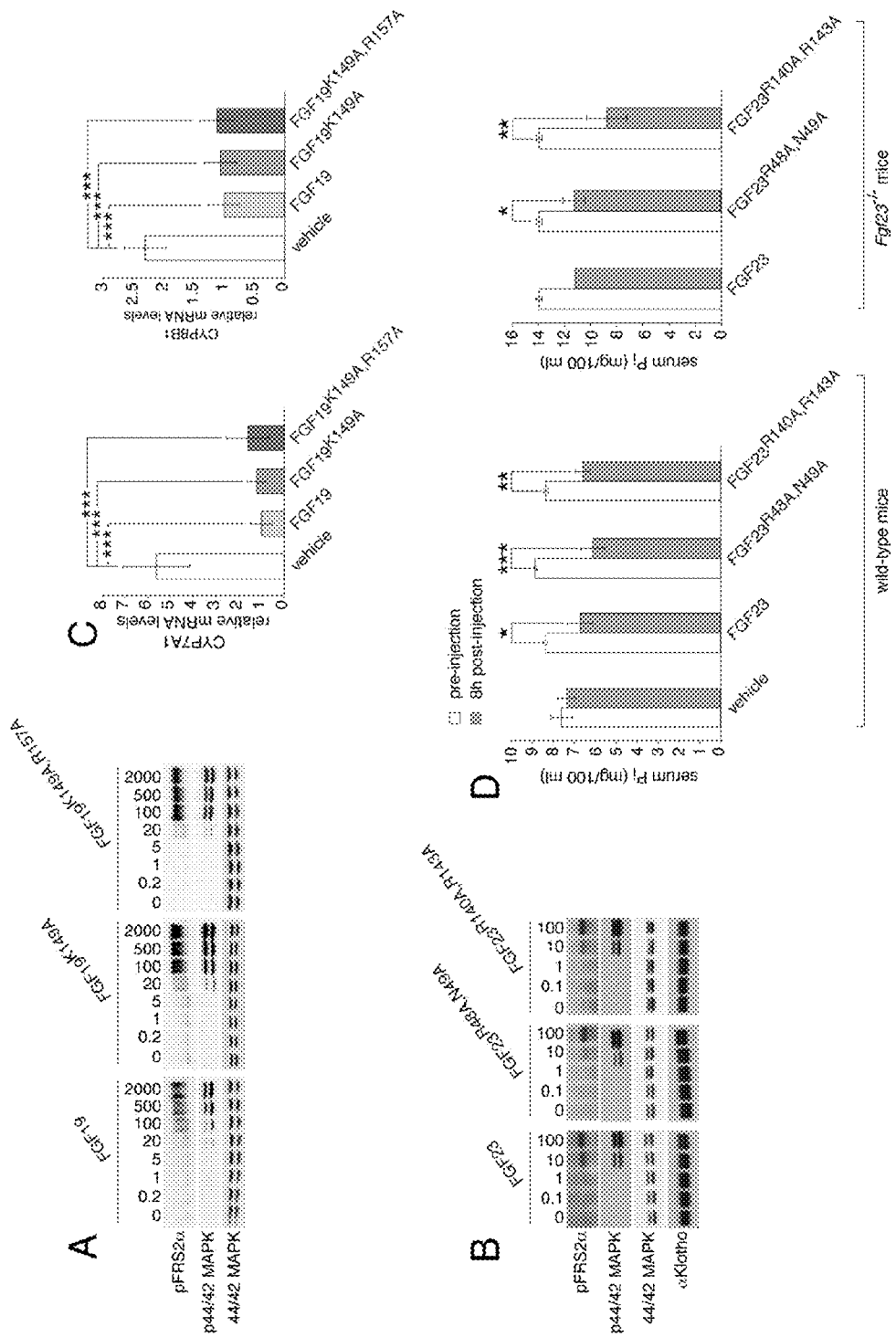
FIGS. 4A-4D show results demonstrating that HS is dispensable for the metabolic activity of FGF19 and FGF23.

To test the impact of knocking out residual HS binding of FGF19 on the signaling by this ligand, H4IIE hepatoma cells were stimulated with the FGF19$^{K149A}$ mutant or wild-type FGF19. H4IIE cells endogenously express FGFR4 and βKlotho (Kurosu et al., *J. Biol. Chem.* 282:26687-26695 (2007), which is hereby incorporated by reference in its entirety), the cognate receptor and co-receptor, respectively, for FGF19. The FGF19$^{K149A}$ mutant was as effective as wild-type FGF19 in inducing tyrosine phosphorylation of FRS2α and downstream activation of MAP kinase cascade (FIG. 4A). These data show that elimination of residual HS binding has no impact on the ability of FGF19 to signal in cultured cells. To test whether the same holds true for FGF23 signaling, HEK293 cells, which naturally express two of the three cognate receptors of FGF23, namely FGFR1c and FGFR3c (Kurosu et al., *J. Biol. Chem.* 281:6120-6123 (2006), which is hereby incorporated by reference in its entirety) were transfected with the transmembrane isoform of αKlotho, the co-receptor of FGF23. These cells were treated with the FGF23$^{R140A/R143A}$ double mutant or wild-type FGF23. The FGF23$^{R140A/R143A}$ mutant had the same capacity as wild-type FGF23 in inducing phosphorylation of FRS2α and downstream activation of MAP kinase cascade (FIG. 4B). These data show that similar to FGF19, FGF23 does not need to bind HS in order to activate FGFR in cultured cells.

To substantiate the findings in cells, the metabolic activity of wild-type and mutated ligands in vivo were compared. Mice were injected with the FGF19$^{K149A}$ mutant or wild-type FGF19 and liver gene expression of CYP7A1 and CYP8B1, which are key enzymes in the major bile acid biosynthetic pathway (Russell, D. W., *Annu. Rev. Biochem.* 72:137-174 (2003), which is hereby incorporated by reference in its entirety), was analyzed. Like wild-type FGF19, the FGF19$^{K149A}$ mutant markedly decreased CYP7A1 and CYP8B1 mRNA levels (FIG. 4C), demonstrating that knockout of residual HS binding does not affect the metabolic activity of FGF19. To examine whether residual HS binding is also dispensable for the metabolic activity of FGF23, mice were injected with the FGF23$^{R140A/R143A}$ mutant or wild-type FGF23 and serum phosphate concentrations were measured. The FGF23$^{R140A/R143A}$ mutant reduced serum phosphate as effectively as wild-type FGF23 (FIG. 4D). Moreover, when injected into Fgf23 knockout mice, the FGF23$^{R140A/R143A}$ mutant exhibited as much of phosphate-lowering activity as wild-type FGF23 (FIG. 4D). These data show that, as in the case of FGF19, abolishment of residual HS binding does not impact the metabolic activity of FGF23 leading to the conclusion that HS is not a component of the endocrine FGF signal transduction unit (FIG. 1D).

Figures 9A, 9B, 9C:
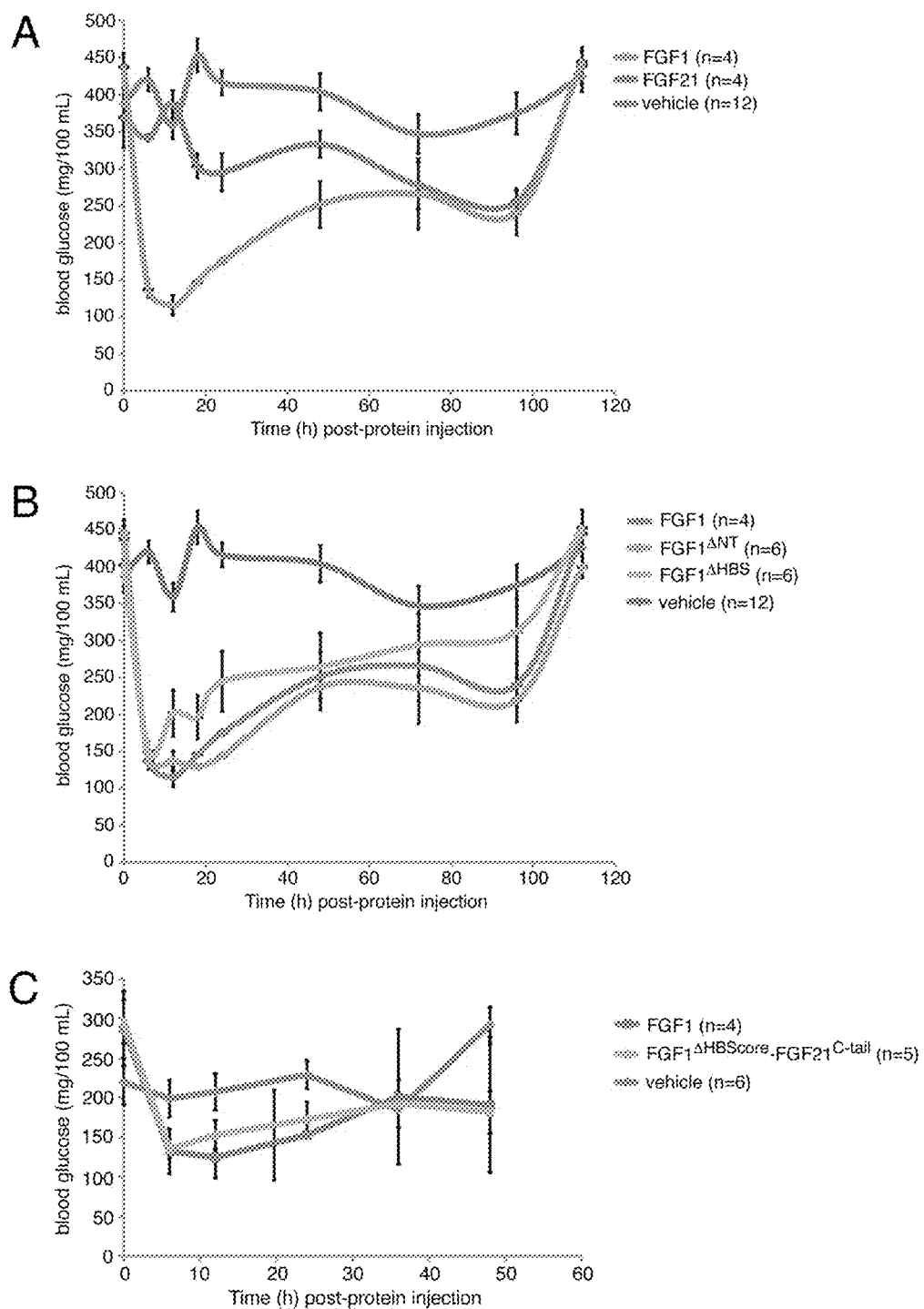
FIGS. 9A-9C show the glucose-lowering effects in ob/ob mice of FGF1 variants according to the present invention.

Example 12—Conversion of a Paracrine FGF into an Endocrine Ligand Confirms that HS is Dispensable for the Metabolic Activity of Endocrine FGFs If HS is dispensable for the metabolic activity of endocrine FGFs, then it should be feasible to convert a paracrine FGF into an endocrine FGF by eliminating HS-binding affinity of the paracrine FGF and substituting its C-terminal tail for that of an endocrine FGF containing the Klotho co-receptor binding site. Reducing HS-binding affinity will allow the ligand to freely diffuse and enter the blood circulation while attaching the C-terminal tail of an endocrine FGF will home the ligand into its target tissues. FGF2, a prototypical paracrine FGF, was chosen for conversion into FGF23-like and FGF21-like ligands, respectively. FGF2 was selected as paracrine ligand for this protein engineering exercise because it preferentially binds to the "c" isoform of FGFR1, the principal receptor mediating the metabolic activity of FGF23 (Gattineni et al., *Am. J. Physiol. Renal Physiol.* 297:F282-291 (2009); Liu et al., *J. Am. Soc. Nephrol.* 19:2342-2350 (2008), which are hereby incorporated by reference in their entirety) and FGF21 (Kurosu et al., *J. Biol. Chem.* 282:26687-26695 (2007), which is hereby incorporated by reference in its entirety), respectively. In the crystal structure of heparin-bound FGF2 (PDB ID: 1FQ9; (Schlessinger et al., *Mol. Cell* 6:743-750 (2000), which is hereby incorporated by reference in its entirety)), K128, R129, and K134 mediate the majority of hydrogen bonds with heparin and hence mutation of these residues was predicted to cause a major reduction in HS-binding affinity of FGF2 (FIGS. 1A, 2, and 5A). Accordingly, these three residues were mutated and then the short C-terminal tail of the mutated FGF2 was replaced with the C-terminal tail of FGF23 (R161 to I251) or the C-terminal tail of FGF21 (P168 to S209) (FIG. 5A). The resulting chimeras were termed FGF2$^{\Delta HBScore}$-FGF23$^{C\text{-}tail}$ and FGF2$^{\Delta HBScore}$-FGF21$^{C\text{-}tail}$ (FIG. 5A). To demonstrate that reduction in HS-binding affinity is required for converting FGF2 into an endocrine ligand, two control chimeras were made in which the 394 (2012), which is hereby incorporated by reference in its entirety). Notably, similar to FGF21, FGF1 is induced postprandially in gonadal white adipose tissue by the nuclear hormone receptor PPARγ (peroxisome proliferator activated receptor-γ) (Jonker et al., "A PPARγ-FGF1 Axis is Required for Adaptive Adipose Remodelling and Metabolic Homeostasis," *Nature* 485:391-394 (2012); Dutchak et al., "Fibroblast Growth Factor-21 Regulates PPARγ Activity and the Antidiabetic Actions of Thiazolidinediones," *Cell* 148:556-567 (2012), which are hereby incorporated by reference in their entirety). FGF1 is required for the remodeling of adipose tissue to adjust to fluctuations in nutrient availability (Jonker et al., "A PPARγ-FGF1 Axis is Required for Adaptive Adipose Remodelling and Metabolic Homeostasis," *Nature* 485:391-394 (2012), which is hereby incorporated by reference in its entirety), and this process is influenced by FGF21 (Hotta et al., "Fibroblast Growth Factor 21 Regulates Lipolysis in White Adipose Tissue But is Not Required for Ketogenesis and Triglyceride Clearance in Liver," *Endocrinology* 150:4625-4633 (2009); Dutchak et al., "Fibroblast Growth Factor-21 Regulates PPARγ Activity and the Antidiabetic Actions of Thiazolidinediones," *Cell* 148:556-567 (2012), which are hereby incorporated by reference in their entirety). As part of a positive feedback loop, FGF21 stimulates PPARγ activity in adipocytes (Dutchak et al., "Fibroblast Growth Factor-21 Regulates PPARγ Activity and the Antidiabetic Actions of Thiazolidinediones," *Cell* 148:556-567 (2012), which is hereby incorporated by reference in its entirety), raising the intriguing possibility that FGF21 regulates FGF1 signaling in adipose tissue through PPARγ. An FGF1$^{\Delta HBScore}$-FGF21$^{C\text{-}tail}$ chimera was generated in the same manner as the FGF2$^{\Delta HBScore}$-FGF21$^{C\text{-}tail}$ chimera (FIGS. 5 and 6). Specifically, K127, K128, and K133 of FGF1, which correspond to the key HS-binding residues identified in the crystal structure of heparin-bound FGF2 (PDB ID: 1FQ9; (Schlessinger et al., *Mol. Cell* 6:743-750 (2000), which is hereby incorporated by reference in its entirety)), were mutated and then the short C-terminal tail of the mutated FGF1 was replaced with the C-terminal tail of FGF21 (P168 to S209) (FIG. 6). A full-length FGF1 protein harboring the HS-binding site mutations was used as a control (FIG. 6). Consistent with the structural prediction, this protein exhibited poor binding affinity for HS compared to wild-type FGF1 as evidenced by the fact that, unlike the wild-type ligand, the mutant protein did not bind to a Heparin sepharose column. A subcutaneous bolus injection of the FGF1$^{\Delta HBScore}$-FGF21$^{C\text{-}tail}$ chimera elicited a hypoglycemic effect in ob/ob mice (FIG. 9C), demonstrating that the chimera has metabolic activity. The effect was of similar magnitude as that observed for native FGF1 (FIG. 9C), which itself has a much greater hypoglycemic effect in ob/ob mice than native FGF21 (FIG. 9A). The HS-binding site mutant of FGF1, which was included as a control in these experiments, showed a similar hypoglycemic effect as the wild-type ligand (FIG. 9B), indicating that the loss in HS-binding affinity had no impact on the metabolic activity of FGF1. To alter the receptor-binding specificity of FGF1 such that FGF1 selectively binds to the "c" splice isoform of FGFR1, the principal receptor mediating the metabolic activity of FGF21, an N-terminally truncated FGF1 protein was made (FIG. 6). The truncated FGF1 ligand lacked twenty four residues from the N-terminus including the nine residues that are critical for the promiscuous binding of FGF1 to both splice isoforms of FGFR1-3 (Beenken et al., "Plasticity in Interactions of Fibroblast Growth Factor 1 (FGF1) N Terminus with FGF Receptors Underlies Promiscuity of FGF1," *J Biol Chem* 287(5):3067-3078 (2012), which is hereby incorporated by reference in its entirety). Based on the crystal structures of FGF1-FGFR complexes, the truncation was also predicted to reduce the receptor-binding affinity of FGF1, and hence the ligand's mitogenicity. The truncated FGF1 protein induced a similar hypoglycemic effect in ob/ob mice as native FGF1 did, indicating that the metabolic activity of FGF1 is mediated through the "c" splice isoform of FGFR. Together, these findings provide a starting point for engineering FGF1 ligands that have no mitogenicity but the same or enhanced metabolic activity compared to native FGF1.

The demonstrated ability to convert a paracrine FGF into an endocrine ligand by means of reducing HS-binding affinity of the paracrine FGF and adding the Klotho co-receptor binding site substantiates that HS does not participate in the formation of the endocrine FGF signal transduction unit. The dispensability of HS for the metabolic activity of endocrine FGFs has an intriguing implication as to how these FGFs have evolved to become hormones. It appears that these ligands have lost the requirement to bind HS in order to signal, while acquiring the ability to bind Klotho co-receptors, which is necessary to direct these ligands to their target organs.

Figures 10A, 10B, 10C, 10D, 10E, 10F:
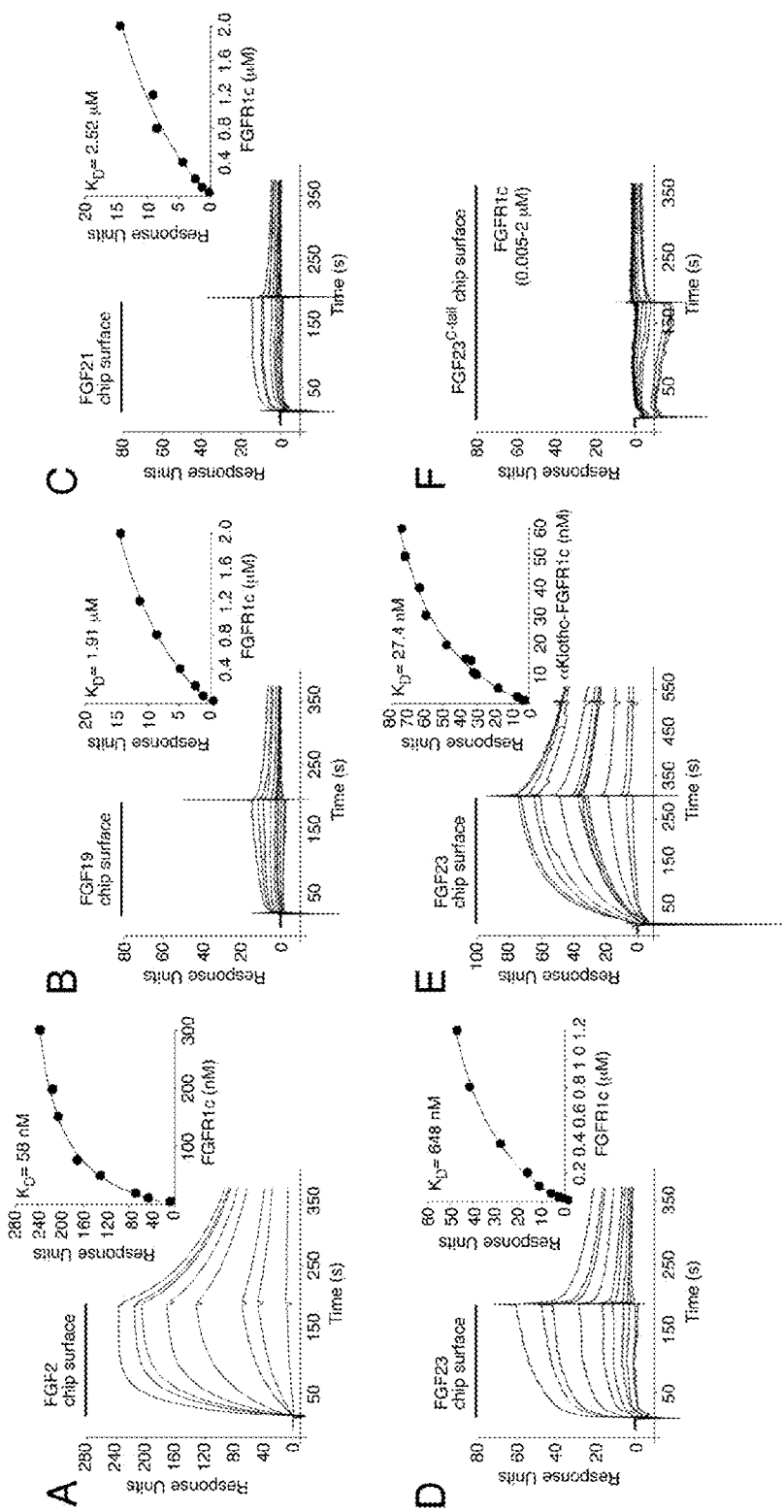
FIGS. 10A-10F show results demonstrating that endocrine FGFs have low binding affinity for FGFR1c compared to FGF2.

In the target tissue, Klotho co-receptors constitutively associate with cognate receptors of endocrine FGFs to offset the inherently low receptor-binding affinity of endocrine FGFs (FIGS. 10B-10D; Kurosu et al., *J. Biol. Chem.* 282:26687-26695 (2007); Kurosu et al., *J. Biol. Chem.* 281:6120-6123 (2006); Ogawa et al., *Proc. Nat'l. Acad. Sci. U.S.A.* 104:7432-7437 (2007); Urakawa et al., *Nature* 444:770-774 (2006), which are hereby incorporated by reference in their entirety). This low binding affinity is due to the fact that key receptor-binding residues in the β-trefoil core of endocrine FGFs are replaced by residues that are suboptimal for receptor binding (Goetz et al., *Mol. Cell Biol.* 27:3417-3428 (2007), which is hereby incorporated by reference in its entirety). To measure the degree to which Klotho co-receptors enhance the receptor-binding affinity of endocrine FGFs, SPR experiments were conducted using FGF23 and FGFR1c and αKlotho co-receptor as an example (see FIGS. 10A-10F). The SPR data show that αKlotho enhances the affinity of FGF23 for FGFR1c by over 20-fold (FIGS. 10D and 10E). The affinity of FGF23 for FGFR1c in the presence of αKlotho is comparable to that of FGF2 for FGFR1c in the absence of its HS cofactor (FIGS. 10A and 10E). It should be noted, however, that HS further increases the binding affinity of FGF2 for FGFR1c by at least an order of magnitude (Pantoliano et al., *Biochemistry* 33:10229-10248 (1994); Roghani et al., *J. Biol. Chem.* 269:3976-3984 (1994), which are hereby incorporated by reference in their entirety). Hence, the receptor-binding affinity of FGF23 in the presence of αKlotho co-receptor still is lower than that of FGF2 in the presence of HS cofactor. These observations imply that the signaling capacity of the endocrine FGF signal transduction unit should be weaker than that of the paracrine FGF signaling unit. Indeed, cell-based studies show that even in the presence of their Klotho co-receptor, endocrine FGFs are inferior to paracrine FGFs at activating FGFR-induced intracellular signaling pathways (Kurosu et al., *J. Biol. Chem.* 282:26687-26695 (2007); Urakawa et al., *Nature* 444:770-774 (2006), which are hereby incorporated by reference in their entirety).

The finding that endocrine FGFs do not need to rely on HS for signaling has another important implication in regard to the role of Klotho co-receptors. Since FGFR dimerization is a prerequisite for FGF signaling in general, it is proposed that Klotho co-receptors not only enhance the binding affinity of endocrine ligand for receptor but also promote receptor dimerization upon ligand binding. In other words, Klotho co-receptors must fulfill the same dual role that HS plays in signaling by paracrine FGFs (FIG. 1D). The ligand conversion also provides the framework for the rational design of endocrine FGF-like molecules for the treatment of metabolic disorders. An FGF23-like molecule, for example, will be useful for the treatment of inherited or acquired hyperphosphatemia, and an FGF21-like molecule, for example, for the treatment of type 2 diabetes, obesity, and related metabolic disorders.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A chimeric protein comprising:
   an N-terminus coupled to a C-terminus,
   wherein the N-terminus comprises an FGF1 portion beginning at any one of residues 1 to 25 and ending at any one of residues 150 to 155 of SEQ ID NO: 1,
   wherein the FGF1 amino acid positions corresponding to those selected from the group consisting of N33, K127, K128, N129, K133, R134, R137, Q142, K143, and combinations thereof are substituted to decrease binding affinity for heparin and/or heparan sulfate compared to FGF1 without the substitution, and
   wherein the C-terminus comprises a C-terminal portion of an FGF21 comprising amino acid residues 168 to 209 of SEQ ID NO: 233.

2. The chimeric protein according to claim 1, wherein the FGF1 portion is amino acid residues 1-150 of SEQ ID NO: 1.

3. The chimeric protein according to claim 1, wherein the FGF1 portion is amino acid residues 1-151, 1-152, 1-153, 1-154, 1-155, 2-150, 2-151, 2-152, 2-153, 2-154, 2-155, 3-150, 3-151, 3-152, 3-153, 3-154, 3-155, 4-150, 4-151, 4-152, 4-153, 4-154, 4-155, 5-150, 5-151, 5-152, 5-153, 5-154, 5-155, 6-150, 6-151, 6-152, 6-153, 6-154, 6-155, 7-150, 7-151, 7-152, 7-153, 7-154, 7-155, 8-150, 8-151, 8-152, 8-153, 8-154, 8-155, 9-150, 9-151, 9-152, 9-153, 9-154, 9-155, 10-150, 10-151, 10-152, 10-153, 10-154, 10-155, 11-150, 11-151, 11-152, 11-153, 11-154, 11-155, 12-150, 12-151, 12-152, 12-153, 12-154, 12-155, 13-150, 13-151, 13-152, 13-153, 13-154, 13-155, 14-150, 14-151, 14-152, 14-153, 14-154, 14-155, 15-150, 15-151, 15-152, 15-153, 15-154, 15-155, 16-150, 16-151, 16-152, 16-153, 16-154, 16-155, 17-150, 17-151, 17-152, 17-153, 17-154, 17-155, 18-150, 18-151, 18-152, 18-153, 18-154, 18-155, 19-150, 19-151, 19-152, 19-153, 19-154, 19-155, 20-150, 20-151, 20-152, 20-153, 20-154, 20-155, 21-150, 21-151, 21-152, 21-153, 21-154, 21-155, 22-150, 22-151, 22-152, 22-153, 22-154, 22-155, 23-150, 23-151, 23-152, 23-153, 23-154, 23-155, 24-150, 24-151, 24-152, 24-153, 24-154, 24-155, 25-151, 25-152, 25-153, 25-154, or 25-155 of SEQ ID NO: 1.

4. The chimeric protein according to claim 1, wherein the one or more substitutions are selected from the group consisting of N33T; K127D; K128Q; N129T; K133V; R134L; R137H; Q142M; K143T, K143L, or K143I; and combinations thereof.

5. The chimeric protein according to claim 1, wherein the FGF1 portion is amino acid residues 25-150 of SEQ ID NO: 1.

6. The chimeric protein according to claim 1, wherein the chimeric protein comprises the amino acid sequence of SEQ ID NO: 339 or SEQ ID NO: 340.

7. A pharmaceutical composition comprising the chimeric protein of claim 1 and a pharmaceutically-acceptable carrier.

8. The pharmaceutical composition according to claim 7 further comprising:
   one or more agents selected from the group consisting of an anti-inflammatory agent, an antifibrotic agent, an antihypertensive agent, an antidiabetic agent, a triglyceride-lowering agent, and a cholesterol-lowering agent.

9. The chimeric protein according to claim 1, wherein the one or more amino acid substitutions comprises a substitution at amino acid residue N33.

10. The chimeric protein according to claim 9, wherein the substitution is N33T.

11. The chimeric protein according to claim 1, wherein the one or more amino acid substitutions comprises a substitution at amino acid residue K127.

12. The chimeric protein according to claim 11, wherein the substitution is K127D.

13. The chimeric protein according to claim 1, wherein the one or more amino acid substitutions comprises a substitution at amino acid residue K128.

14. The chimeric protein according to claim 13, wherein the substitution is K128Q.

15. The chimeric protein according to claim 1, wherein the one or more amino acid substitutions comprises a substitution at amino acid residue N129.

16. The chimeric protein according to claim 15, wherein the substitution is N129T.

17. The chimeric protein according to claim 1, wherein the one or more amino acid substitutions comprises a substitution at amino acid residue K133.

18. The chimeric protein according to claim 17, wherein the substitution is K133V.

19. The chimeric protein according to claim 1, wherein the one or more amino acid substitutions comprises a substitution at amino acid residue R134.

20. The chimeric protein according to claim 19, wherein the substitution is R134L.

21. The chimeric protein according to claim 1, wherein the one or more amino acid substitutions comprises a substitution at amino acid residue R137.

22. The chimeric protein according to claim 21, wherein the substitution is R137H.

23. The chimeric protein according to claim 1, wherein the one or more amino acid substitutions comprises a substitution at amino acid residue Q142.

24. The chimeric protein according to claim 23, wherein the substitution is Q142M.

25. The chimeric protein according to claim 1, wherein the one or more amino acid substitutions comprises a substitution at amino acid residue K143.

26. The chimeric protein according to claim 25, wherein the substitution is K143T.

27. The chimeric protein according to claim 25, wherein the substitution is K143L.

28. The chimeric protein according to claim 25, wherein the substitution is K143I.

29. The chimeric protein according to claim 1, wherein the one or more amino acid substitutions comprises substitutions at amino acid residues K127, K128, and K133.

30. The chimeric protein according to claim 29, wherein the substitutions are K127D, K128Q, and K133V.

31. An isolated FGF1 peptide comprising at least 90% sequence identity to amino acid residues 25-155 of SEQ ID NO:1 with K127D, K128Q, and K133V substitutions (FGF1$^{\Delta NT\Delta HBS}$), wherein the isolated FGF1 peptide comprises K127D, K128Q, and K133V substitutions.

32. The isolated FGF1 peptide according to claim 31, wherein the isolated FGF1 peptide comprises at least 95% sequence identity to amino acid residues 25-155 of SEQ ID NO:1 with K127D, K128Q, and K133V substitutions (FGF1$^{\Delta NT\Delta HBS}$).

33. The isolated FGF1 peptide according to claim 31, wherein the isolated FGF1 peptide comprises at least 99% sequence identity to amino acid residues 25-155 of SEQ ID NO:1 with K127D, K128Q, and K133V substitutions (FGF1$^{\Delta NT\Delta HBS}$).

34. The isolated FGF1 peptide according to claim 31, wherein the isolated FGF1 peptide comprises amino acid residues 25-155 of SEQ ID NO:1 with K127D, K128Q, and K133V substitutions (FGF1$^{\Delta NT\Delta HBS}$).

35. The isolated FGF1 peptide according to claim 31, wherein the isolated FGF1 peptide consists of amino acid residues 25-155 of SEQ ID NO:1 with K127D, K128Q, and K133V substitutions (FGF1$^{\Delta NT\Delta HBS}$).

36. An isolated FGF1 peptide comprising at least 90% sequence identity to amino acid residues 1-155 of SEQ ID NO:1 with K127D, K128Q, and K133V substitutions (FGF1$^{\Delta HBS}$), wherein the isolated FGF1 peptide comprises K127D, K128Q, and K133V substitutions.

37. The isolated FGF1 peptide according to claim 36, wherein the isolated FGF1 peptide comprises at least 95% sequence identity to amino acid residues 1-155 of SEQ ID NO:1 with K127D, K128Q, and K133V substitutions (FGF1$^{\Delta HBS}$).

38. The isolated FGF1 peptide according to claim 36, wherein the isolated FGF1 peptide comprises at least 99% sequence identity to amino acid residues 1-155 of SEQ ID NO:1 with K127D, K128Q, and K133V substitutions (FGF1$^{\Delta HBS}$).

39. The isolated FGF1 peptide according to claim 36, wherein the isolated FGF1 peptide comprises amino acid residues 1-155 of SEQ ID NO:1 with K127D, K128Q, and K133V substitutions (FGF1$^{\Delta HBS}$).

40. The isolated FGF1 peptide according to claim 36, wherein the isolated FGF1 peptide consists of amino acid residues 1-155 of SEQ ID NO:1 with K127D, K128Q, and K133V substitutions (FGF1$^{\Delta HBS}$).

41. An isolated FGF1 peptide fragment consisting of amino acid residues 25-155 of SEQ ID NO:1 (FGF1$^{\Delta NT}$).

* * * * *

SEQUENCE LISTING

```
<160> NUMBER OF SEQ ID NOS: 418

<210> SEQ ID NO 1
<211> LENGTH: 155
<212> TYPE: PRT
<213> ORGANISM: Homo sapiens

<400> SEQUENCE: 1

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 2
<211> LENGTH: 155
<212> TYPE: PRT
<213> ORGANISM: Papio anubis

<400> SEQUENCE: 2

Met Ala Glu Gly Glu Ile Thr Thr Phe Thr Ala Leu Thr Glu Lys Phe
1               5                   10                  15

Asn Leu Pro Pro Ala Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95
```

```
Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 3
<211> LENGTH: 155
<212> TYPE: PRT
<213> ORGANISM: Pongo abelii

<400> SEQUENCE: 3

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 4
<211> LENGTH: 155
<212> TYPE: PRT
<213> ORGANISM: Callithrix jacchus

<400> SEQUENCE: 4

Met Ala Glu Gly Glu Ile Thr Thr Phe Thr Ala Leu Thr Glu Lys Phe
1               5                   10                  15

Asp Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110
```

```
Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 5
<211> LENGTH: 155
<212> TYPE: PRT
<213> ORGANISM: Equus caballus

<400> SEQUENCE: 5

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 6
<211> LENGTH: 155
<212> TYPE: PRT
<213> ORGANISM: Pan troglodytes

<400> SEQUENCE: 6

Met Ala Glu Gly Glu Ile Thr Thr Phe Thr Ala Leu Thr Glu Lys Phe
1               5                   10                  15

Asn Leu Pro Ser Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125
```

```
Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 7
<211> LENGTH: 155
<212> TYPE: PRT
<213> ORGANISM: Loxodonta Africana

<400> SEQUENCE: 7

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Gly Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 8
<211> LENGTH: 155
<212> TYPE: PRT
<213> ORGANISM: Canis lupus familiaris

<400> SEQUENCE: 8

Met Ala Glu Gly Glu Ile Thr Thr Phe Thr Ala Leu Thr Glu Lys Phe
1               5                   10                  15

Asn Leu Pro Pro Gly Asn Tyr Met Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140
```

```
Ile Leu Phe Leu Pro Leu Pro Val Ser Ser Asp
145                 150                 155

<210> SEQ ID NO 9
<211> LENGTH: 155
<212> TYPE: PRT
<213> ORGANISM: Ailuropoda melanoleuca

<400> SEQUENCE: 9

Met Ala Glu Gly Glu Ile Thr Thr Phe Thr Ala Leu Thr Glu Lys Phe
1               5                   10                  15

Asn Leu Pro Ala Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 10
<211> LENGTH: 155
<212> TYPE: PRT
<213> ORGANISM: Saimiri boliviensis boliviensis

<400> SEQUENCE: 10

Met Ala Glu Gly Glu Ile Thr Thr Phe Thr Ala Leu Thr Glu Lys Phe
1               5                   10                  15

Asp Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Leu His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 11
<211> LENGTH: 155
<212> TYPE: PRT
<213> ORGANISM: Sus scrofa

<400> SEQUENCE: 11

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Ser Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 12
<211> LENGTH: 155
<212> TYPE: PRT
<213> ORGANISM: Otolemur garnettii

<400> SEQUENCE: 12

Met Ala Glu Gly Glu Ile Thr Thr Phe Thr Ala Leu Thr Glu Lys Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Gln Asp Arg Ser Asp Gln His Ile Gln Leu Gln Leu Ser Ala Glu
    50                  55                  60

Ser Val Gly Glu Val Tyr Ile Lys Ser Thr Gln Thr Gly Gln Tyr Leu
65                  70                  75                  80

Ala Met Asp Ser Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 13

```
<211> LENGTH: 155
<212> TYPE: PRT
<213> ORGANISM: Rhinolophus ferrumequinum

<400> SEQUENCE: 13

Met Ala Glu Gly Glu Val Thr Thr Phe Thr Ala Leu Thr Glu Lys Phe
1               5                   10                  15

Asn Leu Pro Thr Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Lys Ser Asp Gln His Ile Gln Leu Gln Leu Ser Ala Glu
        50                  55                  60

Ser Val Gly Glu Val Tyr Ile Lys Ser Thr Glu Ser Gly Gln Tyr Leu
65                  70                  75                  80

Ala Met Asp Ser Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 14
<211> LENGTH: 155
<212> TYPE: PRT
<213> ORGANISM: Sorex araneus

<400> SEQUENCE: 14

Met Ala Glu Gly Glu Ile Thr Thr Phe Gly Ala Leu Met Glu Lys Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Glu Val Tyr Ile Lys Ser Thr Glu Thr Gly His Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 15
<211> LENGTH: 155
<212> TYPE: PRT
<213> ORGANISM: Oryctolagus cuniculus
```

<400> SEQUENCE: 15

Met Ala Glu Gly Glu Val Thr Thr Phe Thr Ala Leu Thr Glu Lys Phe
1               5                   10                  15

Asn Leu Pro Ala Gly Asn Tyr Lys Leu Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 16
<211> LENGTH: 155
<212> TYPE: PRT
<213> ORGANISM: Cricetulus griseus

<400> SEQUENCE: 16

Met Ala Glu Gly Glu Ile Thr Thr Phe Ser Ala Leu Thr Glu Arg Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Ala Gly Glu Val Tyr Ile Lys Gly Thr Glu Thr Gly Gln Tyr Arg
65                  70                  75                  80

Asn Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 17
<211> LENGTH: 155
<212> TYPE: PRT
<213> ORGANISM: Sarcophilus harrisii

<400> SEQUENCE: 17

Met Ala Glu Gly Glu Ile Thr Thr Phe Thr Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Asn Asp Gln His Ile Gln Leu Gln Leu Ser Ala Glu
50                  55                  60

Ser Val Gly Glu Val Tyr Ile Lys Ser Thr Glu Ser Gly Gln Tyr Leu
65                  70                  75                  80

Ala Met Asp Thr Asp Gly Leu Leu Tyr Gly Ser Gln Thr Pro Thr Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Glu
145                 150                 155

<210> SEQ ID NO 18
<211> LENGTH: 155
<212> TYPE: PRT
<213> ORGANISM: Mus musculus

<400> SEQUENCE: 18

Met Ala Glu Gly Glu Ile Thr Thr Phe Ala Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
50                  55                  60

Ser Ala Gly Glu Val Tyr Ile Lys Gly Thr Glu Thr Gly Gln Tyr Leu
65                  70                  75                  80

Ala Met Asp Thr Glu Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 19
<211> LENGTH: 154
<212> TYPE: PRT
<213> ORGANISM: Cavia porcellus

<400> SEQUENCE: 19

Met Ala Glu Gly Glu Ile Thr Thr Phe Ala Ala Leu Thr Glu Lys Phe
1               5                   10                  15

```
Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
50                  55                  60

Gly Val Gly Glu Val Tyr Ile Gln Ser Thr Glu Thr Gly Gln Tyr Leu
65                  70                  75                  80

Ala Met Asp Thr Asp Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
                100                 105                 110

Thr Ser Lys Lys His Val Glu Lys Asn Trp Phe Val Gly Leu Lys Lys
            115                 120                 125

Asn Gly Ser Cys Lys Arg Gly Pro Arg Thr His Tyr Gly Gln Lys Ala
130                 135                 140

Ile Leu Phe Leu Pro Leu Pro Val Ser Asp
145                 150

<210> SEQ ID NO 20
<211> LENGTH: 155
<212> TYPE: PRT
<213> ORGANISM: Monodelphis domestica

<400> SEQUENCE: 20

Met Ala Glu Gly Glu Ile Thr Thr Phe Thr Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Asn Asp Gln His Ile Gln Leu Gln Leu Ser Thr Glu
50                  55                  60

Ser Val Gly Glu Val Tyr Ile Lys Ser Thr Glu Ser Gly Gln Tyr Leu
65                  70                  75                  80

Ala Met Asp Thr Asp Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
            115                 120                 125

Asn Gly Ser Cys Lys Lys Gly Pro Arg Thr His Tyr Gly Gln Lys Ala
130                 135                 140

Ile Leu Phe Leu Pro Leu Pro Val Ser Ser Glu
145                 150                 155

<210> SEQ ID NO 21
<211> LENGTH: 155
<212> TYPE: PRT
<213> ORGANISM: Desmodus rotundus

<400> SEQUENCE: 21

Met Ala Glu Gly Glu Val Thr Thr Phe Thr Ala Leu Thr Glu Lys Phe
1               5                   10                  15

Asn Leu Pro Leu Glu Ser Tyr Lys Lys Pro Lys Leu Leu Tyr Cys Ser
            20                  25                  30
```

```
Asn Gly Gly His Phe Leu Arg Ile Leu Pro Asp Gly Thr Val Asp Gly
            35                  40                  45

Thr Arg Asp Lys Ser Asp Gln His Ile Gln Leu Gln Leu Ser Ala Glu
 50                  55                  60

Ser Val Gly Glu Val Tyr Ile Lys Ser Thr Gly Ser Gly Gln Tyr Leu
 65                  70                  75                  80

Ala Met Asp Ser Ala Gly Leu Leu Tyr Gly Ser Gln Thr Pro Asn Glu
                 85                  90                  95

Glu Cys Leu Phe Leu Glu Arg Leu Glu Asn His Tyr Asn Thr Tyr
             100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
            130                 135                 140

Ile Leu Phe Leu Pro Leu Pro Val Asn Ser Asp
145                 150                 155
```

```
<210> SEQ ID NO 22
<211> LENGTH: 155
<212> TYPE: PRT
<213> ORGANISM: Bos taurus

<400> SEQUENCE: 22

Met Ala Glu Gly Glu Thr Thr Phe Thr Ala Leu Thr Glu Lys Phe
  1               5                  10                  15

Asn Leu Pro Leu Gly Asn Tyr Lys Lys Pro Lys Leu Leu Tyr Cys Ser
             20                  25                  30

Asn Gly Gly Tyr Phe Leu Arg Ile Leu Pro Asp Gly Thr Val Asp Gly
            35                  40                  45

Thr Lys Asp Arg Ser Asp Gln His Ile Gln Leu Gln Leu Cys Ala Glu
 50                  55                  60

Ser Ile Gly Glu Val Tyr Ile Lys Ser Thr Glu Thr Gly Gln Phe Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
             100                 105                 110

Ile Ser Lys Lys His Ala Glu Lys His Trp Phe Val Gly Leu Lys Lys
            115                 120                 125

Asn Gly Arg Ser Lys Leu Gly Pro Arg Thr His Phe Gly Gln Lys Ala
            130                 135                 140

Ile Leu Phe Leu Pro Leu Pro Val Ser Ser Asp
145                 150                 155
```

```
<210> SEQ ID NO 23
<211> LENGTH: 155
<212> TYPE: PRT
<213> ORGANISM: Ornithorhynchus anatinus

<400> SEQUENCE: 23

Met Ala Glu Gly Glu Ile Thr Thr Phe Thr Ala Leu Met Glu Lys Phe
  1               5                  10                  15

Asp Leu Pro Leu Gly Asn Tyr Lys Lys Pro Arg Leu Leu Tyr Cys Ser
             20                  25                  30

Asn Gly Gly Tyr Phe Leu Arg Ile Gln Pro Asp Gly Lys Val Asp Gly
            35                  40                  45
```

```
Thr Arg Asp Arg Ser Asp Gln His Ile Gln Leu Gln Leu Ser Ala Glu
 50                  55                  60

Ser Val Gly Glu Val Tyr Ile Lys Ser Thr Glu Ser Gly His Tyr Leu
 65                  70                  75                  80

Ala Met Asp Thr Glu Gly Leu Leu Tyr Gly Ser Gln Ala Pro Ser Glu
                 85                  90                  95

Asp Cys Leu Phe Leu Glu Arg Leu Glu Glu Asn His Tyr Asn Thr Tyr
                100                 105                 110

Val Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
130                 135                 140

Ile Leu Phe Leu Pro Leu Pro Val Ala Ser Asp
145                 150                 155

<210> SEQ ID NO 24
<211> LENGTH: 155
<212> TYPE: PRT
<213> ORGANISM: Taeniopygia guttata

<400> SEQUENCE: 24

Met Ala Glu Gly Glu Ile Thr Thr Phe Ser Ala Leu Thr Glu Lys Phe
 1               5                  10                  15

Asn Leu Pro Pro Gly Asn Tyr Lys Lys Pro Lys Leu Leu Tyr Cys Ser
                 20                  25                  30

Asn Gly Gly His Phe Leu Arg Ile Leu Pro Asp Gly Thr Val Asp Gly
             35                  40                  45

Thr Arg Asp Arg Ser Asp Gln His Ile Gln Leu Gln Leu Ser Ala Glu
 50                  55                  60

Ser Val Gly Val Val His Ile Gln Ser Thr Gln Ser Gly Gln Tyr Leu
 65                  70                  75                  80

Ala Met Asp Thr Asn Gly Leu Leu Tyr Gly Ser Gln Leu Pro Pro Gly
                 85                  90                  95

Glu Cys Leu Phe Leu Glu Arg Leu Glu Glu Asn His Tyr Asn Thr Tyr
                100                 105                 110

Val Ser Lys Met His Ala Asp Lys Asn Trp Phe Val Gly Leu Lys Lys
            115                 120                 125

Asn Gly Thr Ser Lys Leu Gly Pro Arg Thr His Tyr Gly Gln Lys Ala
130                 135                 140

Ile Leu Phe Leu Pro Leu Pro Val Ala Ala Asp
145                 150                 155

<210> SEQ ID NO 25
<211> LENGTH: 155
<212> TYPE: PRT
<213> ORGANISM: Dasypus novemcinctus

<400> SEQUENCE: 25

Met Ala Glu Gly Glu Ile Thr Thr Phe Met Ala Leu Met Glu Lys Phe
 1               5                  10                  15

Asn Leu Pro Leu Glu Asn Tyr Lys His Pro Arg Leu Leu Tyr Cys Arg
                 20                  25                  30

Asn Gly Gly His Phe Leu Arg Ile Leu Pro Asp Gly Thr Val Asp Gly
             35                  40                  45

Thr Arg Asp Arg Ser Asp Gln His Ile Gln Leu Gln Leu Ser Ala Glu
 50                  55                  60
```

```
Ser Val Gly Glu Val Tyr Ile Lys Ser Ala Glu Thr Gly Gln Tyr Leu
 65                  70                  75                  80

Ala Met Asp Thr Asp Gly Leu Leu Tyr Gly Ser Glu Thr Pro Ser Glu
                 85                  90                  95

Glu Cys Leu Phe Met Glu Lys Leu Glu Glu Asn Asn Tyr Asn Thr Tyr
            100                 105                 110

Ile Ser Lys Lys His Ala Glu Lys Lys Trp Phe Val Gly Leu Lys Lys
        115                 120                 125

Asp Gly Ser Lys Arg Gly Pro Gln Thr His Tyr Gly Gln Lys Ala
130                 135                 140

Ile Leu Phe Leu Pro Leu Pro Val Ser Ser Asp
145                 150                 155

<210> SEQ ID NO 26
<211> LENGTH: 155
<212> TYPE: PRT
<213> ORGANISM: Xenopus Silurana tropicalis

<400> SEQUENCE: 26

Met Ala Glu Gly Asp Ile Thr Thr Phe Asn Pro Ile Ala Glu Ser Phe
 1               5                  10                  15

Ser Leu Pro Ile Gly Asn Tyr Lys Lys Pro Lys Leu Leu Tyr Cys Asn
                 20                  25                  30

Asn Gly Gly Tyr Phe Leu Arg Ile Leu Pro Asp Gly Val Val Asp Gly
             35                  40                  45

Thr Arg Asp Arg Asp Asp Leu Tyr Ile Thr Leu Lys Leu Ser Ala Gln
         50                  55                  60

Ser Gln Gly Glu Val His Ile Lys Ser Thr Glu Thr Gly Ser Tyr Leu
 65                  70                  75                  80

Ala Met Asp Ser Ser Gly Gln Leu Tyr Gly Thr Leu Thr Pro Asn Glu
                 85                  90                  95

Glu Ser Leu Phe Leu Glu Thr Leu Glu Glu Asn His Tyr Asn Thr Tyr
            100                 105                 110

Lys Ser Lys Lys Tyr Ala Glu Asn Asn Trp Phe Val Gly Ile Lys Lys
        115                 120                 125

Asn Gly Ala Ser Lys Lys Gly Ser Arg Thr His Tyr Gly Gln Lys Ala
130                 135                 140

Ile Leu Phe Leu Pro Leu Pro Ala Ser Pro Asp
145                 150                 155

<210> SEQ ID NO 27
<211> LENGTH: 155
<212> TYPE: PRT
<213> ORGANISM: Heterocephalus glaber

<400> SEQUENCE: 27

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
                 20                  25                  30

Asn Gly Gly His Phe Leu Arg Ile Leu Pro Asp Gly Lys Val Asp Gly
             35                  40                  45

Thr Arg Asp Arg Ser Asp Gln His Ile Gln Leu Gln Leu Ser Ala Glu
         50                  55                  60

Gly Val Gly Glu Val Tyr Ile Lys Ser Thr Glu Thr Gly Gln Tyr Leu
 65                  70                  75                  80
```

```
Ala Met Asp Thr Asp Gly Leu Leu Tyr Gly Ser Gln Thr Ala Ser Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 28
<211> LENGTH: 155
<212> TYPE: PRT
<213> ORGANISM: Pteropus alecto

<400> SEQUENCE: 28

Met Ala Glu Gly Glu Val Thr Thr Phe Thr Ala Leu Thr Glu Arg Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Lys Ser Asp Gln His Ile Gln Leu Gln Leu Ser Ala Glu
50                  55                  60

Ser Val Gly Glu Val Tyr Ile Lys Ser Thr Glu Ser Gly Gln Tyr Leu
65                  70                  75                  80

Ala Met Asp Ser Asp Gly Leu Leu Tyr Gly Ser Gln Thr Pro Asp Glu
                85                  90                  95

Asp Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 29
<211> LENGTH: 155
<212> TYPE: PRT
<213> ORGANISM: Tupaia chinensis

<400> SEQUENCE: 29

Met Ala Glu Gly Glu Ile Thr Thr Phe Ala Ala Leu Thr Glu Lys Phe
1               5                   10                  15

Asp Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Thr Ala Glu
50                  55                  60

Asn Val Gly Glu Val Tyr Ile Lys Ser Thr Glu Thr Gly Gln Tyr Leu
65                  70                  75                  80

Ala Met Asp Ala Asp Gly Leu Leu Tyr Gly Ser Gln Thr Pro Asn Glu
                85                  90                  95
```

```
Glu Cys Leu Phe Leu Glu Arg Leu Glu Asn His Tyr Asn Thr Tyr
                100                 105                 110

Ile Ser Lys Lys His Ala Glu Lys Asn Trp Phe Val Ala Leu Lys Lys
        115                 120                 125

Asn Gly Ser Cys Lys Leu Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 30
<211> LENGTH: 155
<212> TYPE: PRT
<213> ORGANISM: Columba livia

<400> SEQUENCE: 30

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Gln Ser Gly Gln Tyr Leu
65                  70                  75                  80

Ala Met Asp Pro Thr Gly Leu Leu Tyr Gly Ser Gln Leu Leu Gly Glu
                85                  90                  95

Glu Cys Leu Phe Leu Glu Arg Ile Glu Glu Asn His Tyr Asn Thr Tyr
                100                 105                 110

Val Ser Lys Lys His Ala Asp Lys Asn Trp Phe Val Gly Leu Lys Lys
        115                 120                 125

Asn Gly Asn Ser Lys Leu Gly Pro Arg Thr His Tyr Gly Gln Lys Ala
    130                 135                 140

Ile Leu Phe Leu Pro Leu Pro Val Ser Ala Asp
145                 150                 155
```

<210> SEQ ID NO 31
<211> LENGTH: 155
<212> TYPE: PRT
<213> ORGANISM: Ovis aries

<400> SEQUENCE: 31

```
Met Ala Glu Gly Glu Thr Thr Thr Phe Arg Ala Leu Thr Glu Lys Phe
1               5                   10                  15

Asn Leu Pro Leu Gly Asn Tyr Lys Lys Pro Lys Leu Leu Tyr Cys Ser
            20                  25                  30

Asn Gly Gly Tyr Phe Leu Arg Ile Leu Pro Asp Gly Arg Val Asp Gly
        35                  40                  45

Thr Lys Asp Arg Ser Asp Gln His Ile Gln Leu Gln Leu Tyr Ala Glu
    50                  55                  60

Ser Ile Gly Glu Val Tyr Ile Lys Ser Thr Glu Thr Gly Gln Phe Leu
65                  70                  75                  80

Ala Met Asp Thr Asn Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
                100                 105                 110
```

```
Ile Ser Lys Lys His Ala Glu Lys Asn Trp Phe Ile Gly Leu Lys Lys
            115                 120                 125

Asn Gly Ser Ser Lys Leu Gly Pro Arg Thr His Phe Gly Gln Lys Ala
        130                 135                 140

Ile Leu Phe Leu Pro Leu Pro Val Ser Ser Asp
145                 150                 155

<210> SEQ ID NO 32
<211> LENGTH: 155
<212> TYPE: PRT
<213> ORGANISM: Gallus gallus

<400> SEQUENCE: 32

Met Ala Glu Gly Glu Ile Thr Thr Phe Thr Ala Leu Thr Glu Arg Phe
1               5                   10                  15

Gly Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Ser Asp Gln His Ile Gln Leu Gln Leu Ser Ala Glu
50                  55                  60

Asp Val Gly Glu Val Tyr Ile Lys Ser Thr Ala Ser Gly Gln Tyr Leu
65                  70                  75                  80

Ala Met Asp Thr Asn Gly Leu Leu Tyr Gly Ser Gln Leu Pro Gly Glu
                85                  90                  95

Glu Cys Leu Phe Leu Glu Arg Leu Glu Glu Asn His Tyr Asn Thr Tyr
            100                 105                 110

Ile Ser Lys Lys His Ala Asp Lys Asn Trp Phe Val Gly Leu Lys Lys
            115                 120                 125

Asn Gly Asn Ser Lys Leu Gly Pro Arg Thr His Tyr Gly Gln Lys Ala
        130                 135                 140

Ile Leu Phe Leu Pro Leu Pro Val Ser Ala Asp
145                 150                 155

<210> SEQ ID NO 33
<211> LENGTH: 98
<212> TYPE: PRT
<213> ORGANISM: Vicugna pacos

<400> SEQUENCE: 33

Gln Leu Gln Leu Ser Ala Glu Ser Val Gly Glu Val Tyr Ile Lys Ser
1               5                   10                  15

Thr Glu Thr Gly Gln Tyr Leu Ala Met Asp Thr Asp Gly Leu Leu His
            20                  25                  30

Gly Ser Gln Thr Pro Asn Glu Glu Cys Leu Phe Leu Glu Arg Leu Glu
        35                  40                  45

Glu Asn His Tyr Asn Thr Tyr Thr Ser Lys Lys His Ala Glu Lys Asn
50                  55                  60

Trp Phe Val Gly Leu Lys Lys Asn Gly Ser Cys Lys Arg Gly Pro Arg
65                  70                  75                  80

Thr His Tyr Gly Gln Lys Ala Ile Leu Phe Leu Pro Leu Pro Val Ser
                85                  90                  95

Ser Asp

<210> SEQ ID NO 34
<211> LENGTH: 155
<212> TYPE: PRT
```

-continued

<213> ORGANISM: Anolis carolinensis

<400> SEQUENCE: 34

Met Ala Glu Gly Glu Ile Thr Thr Phe Thr Ala Leu Thr Glu Arg Phe
1               5                   10                  15

Ala Leu Pro Met Glu Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Met Asp Arg Asn Asp Ser Tyr Ile Gln Leu Leu Leu Thr Ala Glu
    50                  55                  60

Asp Val Gly Val Val Tyr Ile Lys Gly Thr Glu Thr Gly Gln Tyr Leu
65                  70                  75                  80

Ala Met Asp Ala Asn Gly His Leu Tyr Gly Ser Gln Leu Pro Thr Glu
                85                  90                  95

Glu Cys Leu Phe Val Glu Thr Leu Glu Glu Asn His Tyr Asn Thr Tyr
            100                 105                 110

Thr Ser Lys Met His Gly Asp Lys Lys Trp Tyr Val Gly Leu Lys Lys
        115                 120                 125

Asn Gly Lys Gly Lys Leu Gly Pro Arg Thr His Arg Gly Gln Lys Ala
    130                 135                 140

Ile Leu Phe Leu Pro Leu Pro Val Ser Pro Asp
145                 150                 155

<210> SEQ ID NO 35
<211> LENGTH: 155
<212> TYPE: PRT
<213> ORGANISM: Otolemur garnettii

<400> SEQUENCE: 35

Met Ala Glu Gly Glu Ile Thr Thr Phe Thr Ala Leu Thr Glu Lys Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Gln Asp Arg Ser Asp Gln His Ile Gln Leu Gln Leu Ser Ala Glu
    50                  55                  60

Ser Val Gly Glu Val Tyr Ile Lys Ser Thr Gln Thr Gly Gln Tyr Leu
65                  70                  75                  80

Ala Met Asp Ser Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 36
<211> LENGTH: 155
<212> TYPE: PRT
<213> ORGANISM: Felis catus

<400> SEQUENCE: 36

```
Met Ala Glu Gly Glu Ile Thr Thr Phe Thr Ala Leu Thr Glu Lys Phe
1               5                   10                  15

Asn Leu Pro Pro Gly Asn Tyr Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 37
<211> LENGTH: 155
<212> TYPE: PRT
<213> ORGANISM: Pelodiscus sinensis

<400> SEQUENCE: 37

Met Ala Glu Gly Glu Ile Thr Thr Phe Thr Ala Leu Thr Glu Lys Phe
1               5                   10                  15

Asn Leu Pro Leu Gly Asn Tyr Lys Asn Pro Lys Leu Leu Tyr Cys Ser
            20                  25                  30

Asn Gly Gly Tyr Phe Leu Arg Ile His Pro Asp Gly Lys Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Ser Gly Gln Phe Leu
65                  70                  75                  80

Ala Met Asp Ala Asn Gly Leu Leu Tyr Gly Ser Leu Ser Pro Ser Glu
                85                  90                  95

Glu Cys Leu Phe Leu Glu Arg Met Glu Glu Asn His Tyr Asn Thr Tyr
                100                 105                 110

Ile Ser Lys Lys His Ala Asp Lys Asn Trp Phe Val Gly Leu Lys Lys
                115                 120                 125

Asn Gly Ser Cys Lys Leu Gly Pro Arg Thr His Tyr Gly Gln Lys Ala
            130                 135                 140

Val Leu Phe Leu Pro Leu Pro Val Ser Ala Asp
145                 150                 155

<210> SEQ ID NO 38
<211> LENGTH: 155
<212> TYPE: PRT
<213> ORGANISM: Latimeria chalumnae

<400> SEQUENCE: 38

Met Ala Glu Asp Lys Ile Thr Thr Leu Lys Ala Leu Ala Glu Lys Phe
1               5                   10                  15
```

```
Asn Leu Pro Met Gly Asn Tyr Lys Lys Ala Lys Leu Leu Tyr Cys Ser
            20                  25                  30

Asn Gly Gly Tyr Phe Leu Arg Ile Pro Pro Asp Gly Lys Val Glu Gly
        35                  40                  45

Ile Arg Glu Arg Ser Asp Lys Tyr Ile Gln Leu Gln Met Asn Ala Glu
 50                  55                  60

Ser Leu Gly Met Val Ser Ile Lys Gly Val Glu Ala Gly Gln Tyr Leu
 65                  70                  75                  80

Ala Met Asn Thr Asn Gly Leu Leu Tyr Gly Ser Gln Ser Leu Thr Glu
                85                  90                  95

Glu Cys Leu Phe Met Glu Lys Met Glu Glu Asn His Tyr Asn Thr Tyr
                100                 105                 110

Arg Ser Lys Thr His Ala Asp Lys Asn Trp Tyr Val Gly Ile Arg Lys
                115                 120                 125

Asn Gly Ser Ile Lys Pro Gly Pro Arg Thr His Ile Gly Gln Lys Ala
            130                 135                 140

Val Leu Phe Leu Pro Leu Pro Ala Ser Ser Asp
145                 150                 155

<210> SEQ ID NO 39
<211> LENGTH: 155
<212> TYPE: PRT
<213> ORGANISM: Tursiops truncatus

<400> SEQUENCE: 39

Met Ala Glu Gly Glu Ile Thr Thr Phe Thr Ala Leu Thr Glu Lys Phe
  1               5                  10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
 50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Ala Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 40
<211> LENGTH: 155
<212> TYPE: PRT
<213> ORGANISM: Mustela putorius furo

<400> SEQUENCE: 40

Met Ala Glu Gly Glu Ile Thr Thr Phe Thr Ala Leu Met Glu Lys Phe
  1               5                  10                  15

Asn Leu Pro Ala Gly Asn Tyr Lys Lys Pro Lys Leu Leu Tyr Cys Ser
            20                  25                  30
```

```
Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
 50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
               100                 105                 110

Thr Ser Lys Lys His Ala Glu Lys Asn Trp Phe Val Gly Leu Lys Lys
               115                 120                 125

Asn Gly Ser Cys Lys Arg Gly Pro Arg Thr His Tyr Gly Gln Lys Ala
           130                 135                 140

Ile Leu Phe Leu Pro Leu Pro Val Ser Ser Asp
145                 150                 155

<210> SEQ ID NO 41
<211> LENGTH: 155
<212> TYPE: PRT
<213> ORGANISM: Nomascus leucogenys

<400> SEQUENCE: 41

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
 50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
               100                 105                 110

Ile Ser Lys Lys His Ala Glu Lys Asn Trp Phe Val Gly Leu Lys Lys
               115                 120                 125

Asn Gly Ser Cys Lys Arg Gly Pro Arg Thr His Tyr Gly Gln Lys Ala
           130                 135                 140

Ile Leu Phe Leu Pro Leu Pro Val Ser Ser Asp
145                 150                 155

<210> SEQ ID NO 42
<211> LENGTH: 155
<212> TYPE: PRT
<213> ORGANISM: Gorilla gorilla

<400> SEQUENCE: 42

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45
```

-continued

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 43
<211> LENGTH: 155
<212> TYPE: PRT
<213> ORGANISM: Erinaceus europaeus

<400> SEQUENCE: 43

Met Ala Glu Gly Glu Ile Thr Thr Phe Thr Ala Leu Thr Glu Lys Phe
1               5                   10                  15

Asn Leu Pro Leu Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 44
<211> LENGTH: 91
<212> TYPE: PRT
<213> ORGANISM: Procavia capensis

<400> SEQUENCE: 44

Met Ala Glu Gly Glu Ile Thr Thr Phe Thr Ala Leu Thr Glu Lys Phe
1               5                   10                  15

Asn Leu Pro Leu Glu Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
    50                  55                  60

```
Ser Val Gly Glu Val Tyr Ile Lys Gly Thr Glu Thr Gly Gln Tyr Leu
 65                  70                  75                  80

Ala Met Asp Thr Asp Gly Leu Leu Tyr Gly Ser
                 85                  90
```

<210> SEQ ID NO 45
<211> LENGTH: 114
<212> TYPE: PRT
<213> ORGANISM: Dipodomys ordii

<400> SEQUENCE: 45

```
Met Ala Glu Gly Glu Ile Thr Thr Phe Thr Ala Leu Thr Glu Arg Phe
 1               5                  10                  15

Gln Leu Gln Leu Ser Ala Glu Ser Val Gly Glu Val Tyr Ile Lys Ser
                20                  25                  30

Thr Glu Thr Gly Gln Tyr Leu Ala Met Asp Ala Asp Gly Leu Leu Tyr
             35                  40                  45

Gly Ser Gln Thr Pro Asp Glu Glu Cys Leu Phe Leu Glu Arg Leu Glu
 50                  55                  60

Glu Asn His Tyr Asn Thr Tyr Ile Ala Lys Lys His Ala Glu Lys Asn
 65                  70                  75                  80

Trp Phe Val Gly Leu Lys Lys Asn Gly Ser Cys Lys Arg Gly Pro Arg
                 85                  90                  95

Thr His Tyr Gly Gln Lys Ala Ile Leu Phe Leu Pro Leu Pro Val Ser
            100                 105                 110

Ser Asp
```

<210> SEQ ID NO 46
<211> LENGTH: 92
<212> TYPE: PRT
<213> ORGANISM: Petromyzon marinus

<400> SEQUENCE: 46

```
Met Glu Val Gly His Ile Gly Thr Leu Pro Val Pro Ala Gly Pro
 1               5                  10                  15

Val Phe Pro Gly Ser Phe Lys Glu Pro Arg Arg Leu Tyr Cys Arg Ser
                20                  25                  30

Ala Gly His His Leu Gln Ile Leu Gly Asp Gly Thr Val Ser Gly Thr
             35                  40                  45

Gln Asp Glu Asn Glu Pro His Ala Val Leu Gln Leu Gln Ala Val Arg
 50                  55                  60

Arg Gly Val Val Thr Ile Arg Gly Leu Cys Ala Glu Arg Phe Leu Ala
 65                  70                  75                  80

Met Ser Thr Glu Gly His Leu Tyr Gly Ala Val Arg
                 85                  90
```

<210> SEQ ID NO 47
<211> LENGTH: 98
<212> TYPE: PRT
<213> ORGANISM: Echinops telfairi

<400> SEQUENCE: 47

```
Gln Leu Lys Leu Val Ala Glu Ser Val Gly Val Val Tyr Ile Lys Ser
 1               5                  10                  15

Ile Lys Thr Gly Gln Tyr Leu Ala Met Asn Pro Asp Gly Leu Leu Tyr
                20                  25                  30

Gly Ser Glu Thr Pro Glu Glu Glu Cys Leu Phe Leu Glu Thr Leu Glu
```

```
                35                  40                  45
Glu Asn His Tyr Thr Thr Phe Lys Ser Lys His Val Glu Lys Asn
 50                  55                  60

Trp Phe Val Gly Leu Arg Lys Asn Gly Arg Val Lys Ile Gly Pro Arg
 65                  70                  75                  80

Thr His Gln Gly Gln Lys Ala Ile Leu Phe Leu Pro Leu Pro Val Ser
                 85                  90                  95

Ser Asp

<210> SEQ ID NO 48
<211> LENGTH: 155
<212> TYPE: PRT
<213> ORGANISM: Macaca mulatta

<400> SEQUENCE: 48

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
             35                  40                  45

Thr Arg Asp Arg Ser Asp Gln His Ile Gln Leu Gln Leu Ser Ala Glu
 50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 49
<211> LENGTH: 155
<212> TYPE: PRT
<213> ORGANISM: Pteropus vampyrus

<400> SEQUENCE: 49

Met Ala Glu Gly Glu Val Thr Thr Phe Thr Ala Leu Thr Glu Arg Phe
 1               5                  10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
             35                  40                  45

Thr Arg Asp Lys Ser Asp Gln His Ile Gln Leu Gln Leu Ser Ala Glu
 50                  55                  60

Ser Val Gly Glu Val Tyr Ile Lys Ser Thr Glu Ser Gly Gln Tyr Leu
 65                  70                  75                  80

Ala Met Asp Ser Asp Gly Leu Leu Tyr Gly Ser Gln Thr Pro Asp Glu
                 85                  90                  95

Asp Cys Leu Phe Leu Glu Arg Leu Glu Glu Asn His Tyr Asn Thr Tyr
            100                 105                 110
```

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 50
<211> LENGTH: 155
<212> TYPE: PRT
<213> ORGANISM: Myotis lucifugus

<400> SEQUENCE: 50

Met Ala Glu Gly Glu Val Thr Thr Phe Thr Ala Leu Thr Glu Arg Phe
1               5                   10                  15

Asn Leu Pro Leu Glu Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
50                  55                  60

Ser Val Gly Glu Val Tyr Ile Lys Ser Thr Glu Ser Gly Gln Tyr Leu
65                  70                  75                  80

Ala Met Asp Ser Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 51
<211> LENGTH: 155
<212> TYPE: PRT
<213> ORGANISM: Microcebus murinus

<400> SEQUENCE: 51

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
50                  55                  60

Ser Ala Gly Glu Val Tyr Ile Lys Ser Thr Gln Thr Gly Arg Tyr Leu
65                  70                  75                  80

Ala Met Asp Ala Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
                130                 135                 140

Ile Leu Phe Leu Pro Leu Pro Val Ser Ser Asp
145                 150                 155

<210> SEQ ID NO 52
<211> LENGTH: 144
<212> TYPE: PRT
<213> ORGANISM: Ochotona princeps

<400> SEQUENCE: 52

Met Ala Glu Gly Glu Val Thr Thr Phe Ser Ala Leu Thr Glu Lys Phe
1               5                   10                  15

Asn Leu Pro Gly Gly Asn Tyr Lys Leu Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Leu His Glu Val Phe Ile Lys Ser Thr Glu
50                  55                  60

Thr Gly Gln Tyr Leu Ala Met Asp Thr Asp Gly Leu Leu Tyr Gly Ser
65                  70                  75                  80

Gln Thr Pro Ser Glu Glu Cys Leu Phe Leu Glu Arg Leu Glu Glu Asn
                85                  90                  95

His Tyr Asn Thr Tyr Thr Ser Lys Lys His Ala Glu Lys Asn Trp Phe
            100                 105                 110

Val Gly Ile Lys Lys Asn Gly Ser Cys Lys Arg Gly Pro Arg Thr His
        115                 120                 125

Tyr Gly Gln Lys Ala Ile Leu Phe Leu Pro Leu Pro Val Ser Ser Asp
    130                 135                 140

<210> SEQ ID NO 53
<211> LENGTH: 155
<212> TYPE: PRT
<213> ORGANISM: Rattus norvegicus

<400> SEQUENCE: 53

Met Ala Glu Gly Glu Ile Thr Thr Phe Ala Ala Leu Thr Glu Arg Phe
1               5                   10                  15

Asn Leu Pro Leu Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
50                  55                  60

Ser Ala Gly Glu Val Tyr Ile Lys Gly Thr Glu Thr Gly Gln Tyr Leu
65                  70                  75                  80

Ala Met Asp Thr Glu Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 54
<211> LENGTH: 155
<212> TYPE: PRT
<213> ORGANISM: Choloepus hoffmanni

<400> SEQUENCE: 54

Met Ala Glu Gly Glu Ile Thr Thr Phe Thr Ala Leu Met Glu Lys Phe
1               5                   10                  15

Asn Leu Pro Pro Gly Asn Tyr Met Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Leu His Ile Gln Leu Gln Leu Ser Ala Glu
50                  55                  60

Ser Val Gly Glu Val Tyr Ile Lys Ser Ala Glu Thr Gly Gln Tyr Leu
65                  70                  75                  80

Ala Met Asp Thr Gly Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
                100                 105                 110

Val Ser Lys Lys His Ala Glu Lys Asn Trp Phe Val Gly Leu Lys Lys
            115                 120                 125

Asn Gly Ser Ser Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 55
<211> LENGTH: 155
<212> TYPE: PRT
<213> ORGANISM: Ictidomys tridecemlineatus

<400> SEQUENCE: 55

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 56

<211> LENGTH: 155
<212> TYPE: PRT
<213> ORGANISM: Tarsius syrichta

<400> SEQUENCE: 56

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 57
<211> LENGTH: 155
<212> TYPE: PRT
<213> ORGANISM: Tupaia belangeri

<400> SEQUENCE: 57

Met Ala Glu Gly Glu Ile Thr Thr Phe Ala Ala Leu Thr Glu Lys Phe
1               5                   10                  15

Asp Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Thr Ala Glu
    50                  55                  60

Asn Val Gly Glu Val Tyr Ile Lys Ser Thr Glu Thr Gly Gln Tyr Leu
65                  70                  75                  80

Ala Met Asp Ala Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Ala Leu Lys Lys
        115                 120                 125

Asn Gly Ser Cys Lys Leu Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 58
<211> LENGTH: 56
<212> TYPE: PRT
<213> ORGANISM: Meleagris gallopavo

<400> SEQUENCE: 58

Met Ala Glu Gly Glu Ile Thr Thr Phe Thr Ala Leu Thr Glu Arg Phe
1               5                   10                  15

Gly Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Ser Asp Gln His
    50                  55

<210> SEQ ID NO 59
<211> LENGTH: 155
<212> TYPE: PRT
<213> ORGANISM: Macropus eugenii

<400> SEQUENCE: 59

Met Ala Glu Gly Glu Ile Thr Thr Phe Thr Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Asn Asp Gln His Ile Gln Leu Gln Leu Ser Ala Glu
    50                  55                  60

Ser Val Gly Glu Val Tyr Ile Lys Ser Thr Glu Ser Gly Gln Tyr Leu
65                  70                  75                  80

Ala Met Asp Thr Asn Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Glu
145                 150                 155

<210> SEQ ID NO 60
<211> LENGTH: 147
<212> TYPE: PRT
<213> ORGANISM: Danio rerio

<400> SEQUENCE: 60

Met Thr Glu Ala Asp Ile Ala Val Lys Ser Ser Pro Arg Asp Tyr Lys
1               5                   10                  15

Lys Leu Thr Arg Leu Tyr Cys Met Asn Gly Gly Phe His Leu Gln Ile
            20                  25                  30

Leu Ala Asp Gly Thr Val Ala Gly Ala Ala Asp Glu Asn Thr Tyr Ser
        35                  40                  45

Ile Leu Arg Ile Lys Ala Thr Ser Pro Gly Val Val Val Ile Glu Gly
    50                  55                  60

Ser Glu Thr Gly Leu Tyr Leu Ser Met Asn Glu His Gly Lys Leu Tyr
65                  70                  75                  80

Ala Ser Ser Leu Val Thr Asp Glu Ser Tyr Phe Leu Glu Lys Met Glu
                85                  90                  95

```
Glu Asn His Tyr Asn Thr Tyr Gln Ser Gln Lys His Gly Glu Asn Trp
            100                 105                 110

Tyr Val Gly Ile Lys Lys Asn Gly Lys Met Lys Arg Gly Pro Arg Thr
        115                 120                 125

His Ile Gly Gln Lys Ala Ile Phe Phe Leu Pro Arg Gln Val Glu Gln
    130                 135                 140

Glu Glu Asp
145

<210> SEQ ID NO 61
<211> LENGTH: 468
<212> TYPE: DNA
<213> ORGANISM: Homo sapiens

<400> SEQUENCE: 61
atggctgaag ggaaatcac caccttcaca gccctgaccg agaagtttaa tctgcctcca      60
gggaattaca agaagcccaa actcctctac tgtagcaacg ggggccactt cctgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
aattggtttg ttggcctcaa gaagaatggg agctgcaaac gcggtcctcg gactcactat    420
ggccagaaag caatcttgtt tctccccctg ccagtctctt ctgattaa                 468

<210> SEQ ID NO 62
<211> LENGTH: 468
<212> TYPE: DNA
<213> ORGANISM: Olive Baboon

<400> SEQUENCE: 62
atggctgaag ggaaatcac cacgttcaca gccctgaccg agaagtttaa tctgcctcca      60
gcgaattaca agaagcccaa actgctctac tgtagcaacg ggggacactt cttgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctacatat ccaagaagca cgcagagaag    360
aattggtttg ttggcctcaa gaagaatgga agctgcaaac gtggtcctcg gactcactat    420
ggccagaaag caatcttgtt tcttccctg ccagtctctt ctgattaa                  468

<210> SEQ ID NO 63
<211> LENGTH: 468
<212> TYPE: DNA
<213> ORGANISM: Sumatran orangutan

<400> SEQUENCE: 63
atggctgaag ggaaatcac caccttcaca gccctgaccg agaagtttaa tctgcctcca      60
gggaattaca agaagcccaa actcctctac tgtagcaacg ggggccactt cttgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
```
aattggtttg ttggcctcaa gaagaatgga agctgcaaac gcggtcctcg gactcactat    420
ggccagaaag caatcttgtt tctccccctg ccagtctctt ccgattaa                 468

<210> SEQ ID NO 64
<211> LENGTH: 468
<212> TYPE: DNA
<213> ORGANISM: White-tufted-ear marmoset

<400> SEQUENCE: 64
atggctgaag gggaaatcac caccttcaca gccctgaccg agaagtttga tctgcctcca    60
gggaattaca agaagcccaa actcctctac tgtagcaatg ggggccactt cttgaggatc   120
cttccggatg gcacagtgga tgggacaagg acaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggagaggc tggaggagaa ccattacaac acctatatat ccaagaaaca tgcagagaag    360
aattggtttg tcggcctcaa gaagaatgga agctgtaaac gtggtcctcg gactcactat    420
ggtcagaaag cgatcttgtt tctccccctg ccagtttctt ctgattaa                 468

<210> SEQ ID NO 65
<211> LENGTH: 468
<212> TYPE: DNA
<213> ORGANISM: Horse

<400> SEQUENCE: 65
atggctgaag gagaaatcac aaccttcacg gccctgaccg agaagtttaa tctgcctcca    60
gggaattaca agaagcccaa actcctctac tgtagcaatg ggggccactt cctgaggatc   120
cttccagatg gcacagtgga tgggacaagg acaggagcg accagcacat tcagctgcag    180
ctcagtgcgg aaagcgtggg ggaggtgtat ataaagagta ccgagactgg ccagtacttg    240
gccatggaca ccgacgggct gttgtacggc tcacagacac caaacgagga atgtttgttc    300
ctggaaaggc tggaggaaaa ccattacaac acctacacat ccaagaagca tgcagagaag    360
aactggttcg ttggtctcaa gaagaatggg agctgcaaac gcggtcctcg gactcactat    420
gggcagaaag caatcttgtt tcttcccctg cccgtctcct ctgactaa                 468

<210> SEQ ID NO 66
<211> LENGTH: 468
<212> TYPE: DNA
<213> ORGANISM: Chimpanzee

<400> SEQUENCE: 66
atggctgaag gggaaatcac caccttcaca gccctgaccg agaagtttaa tctgccttca    60
gggaattaca agaagcccaa actcctctac tgtagcaacg ggggccactt cctgaggatc   120
cttccggatg gcacagtgga tgggacaagg acaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaacggc tggaggagaa ccattacaac acctatatat ccaagaagca tgcagagaag    360
aattggtttg ttggcctcaa gaagaatgga agctgcaaac gcggtcctcg gactcactat    420
ggccagaaag caatcttgtt tctccccctg ccagtctctt ccgattaa                 468

<210> SEQ ID NO 67

<211> LENGTH: 468
<212> TYPE: DNA
<213> ORGANISM: Elephant

<400> SEQUENCE: 67

| | | | | | |
|---|---|---|---|---|---|
| atggccgaag | gggaaatcac | aactttcaca | gccctgacag | agaagttcaa | cctgcctcca | 60 |
| gggaattaca | agaagcccaa | actcctctac | tgtagcaatg | gaggtcactt | cttaaggatc | 120 |
| cttccagatg | gcacagtgga | tggcaccagg | acaggagtg | accagcacat | tcagctgcag | 180 |
| ctcagtgcgg | aaagcgtggg | ggaggtgtat | ataaagggca | ccgagactgg | ccagtacttg | 240 |
| gccatggaca | ccgacgggct | tttatacggc | tcacagacac | caaatgagga | atgtttgttc | 300 |
| ctggaaaggc | tggaggaaaa | ccattacaac | acctacacat | ccaagaagca | cgcagagaag | 360 |
| aattggttcg | ttggtctcaa | gaagaatgga | agctgcaaac | gcggtcctcg | gactcactat | 420 |
| ggccagaaag | caatcttgtt | tctcccctg | ccagtctcct | ctgattaa | | 468 |

<210> SEQ ID NO 68
<211> LENGTH: 468
<212> TYPE: DNA
<213> ORGANISM: Dog

<400> SEQUENCE: 68

| | | | | | |
|---|---|---|---|---|---|
| atggctgaag | gggaaatcac | aaccttcact | gccctgacgg | agaagtttaa | tctgcctccg | 60 |
| gggaattaca | tgaagcccaa | actcctctac | tgtagcaacg | gggccactt | cctgaggatc | 120 |
| cttccagatg | gcacagtgga | tgggacaagg | acaggagcg | accagcacat | tcagctgcag | 180 |
| ctcagcgcgg | aaagcgtggg | ggaggtgtat | ataagagca | ccgagactgg | ccagtacttg | 240 |
| gccatggaca | ccgatgggct | tctgtacggc | tcacagacac | cgaatgagga | atgtttgttc | 300 |
| ctggaaaggc | tggaggaaaa | ccattacaac | acctacacat | ccaagaagca | tgcagaaaaa | 360 |
| aattggtttg | ttggtctcaa | gaagaatgga | agctgcaaac | gcggtcctcg | gactcactat | 420 |
| ggtcaaaaag | caattttgtt | tctcccctg | ccagtgtcct | ctgattaa | | 468 |

<210> SEQ ID NO 69
<211> LENGTH: 468
<212> TYPE: DNA
<213> ORGANISM: Giant panda

<400> SEQUENCE: 69

| | | | | | |
|---|---|---|---|---|---|
| atggctgaag | gggagatcac | aaccttcacc | gccctgacgg | agaagtttaa | tctgcctgcg | 60 |
| gggaattaca | agaagcccaa | actcctctac | tgtagcaacg | gggccactt | cctgaggatc | 120 |
| cttccagatg | gcacagtgga | cgggacgagg | acaggagcg | accagcacat | tcaactgcag | 180 |
| ctcagcgcgg | aaagcgtagg | ggaggtgtac | ataagagca | ccgagaccgg | ccagtacttg | 240 |
| gccatggaca | ccgatgggct | tctgtacggc | tcacagacac | caaatgagga | atgtttgttc | 300 |
| ctggaaaggc | tggaggaaaa | ccattacaac | acctacacat | ccaagaagca | cgcggagaag | 360 |
| aattggtttg | ttggtctcaa | gaagaatgga | agctgcaaac | gtggtcctcg | gactcactat | 420 |
| ggccagaaag | caattctgtt | tctcccctg | ccagtctcct | ctgattaa | | 468 |

<210> SEQ ID NO 70
<211> LENGTH: 468
<212> TYPE: DNA
<213> ORGANISM: Bolivian squirrel monkey

<400> SEQUENCE: 70

| | | | | | |
|---|---|---|---|---|---|
| atggctgaag | gggaaatcac | cacctttaca | gccctgaccg | agaagtttga | tctgcctcca | 60 |

| gggaattaca agaagcccaa actcctctac tgtagcaacg ggggccactt cttgaggatc | 120 |
| cttccggatg gcacagtgga tgggaccagg gacaggagcg atcttcacat tcagctgcag | 180 |
| ctcagtgcgg aaagcgtggg ggaggtgtat ataaagagta ccgagactgg ccagtacttg | 240 |
| gccatggaca ccgacgggct tttatacggc tcacagacac caaatgagga atgtttgttc | 300 |
| ctggaaaggc tggaggagaa ccattacaac acctatatat ccaagaaaca cgcagagaag | 360 |
| aattggtttg ttggcctcaa gaagaatgga agctgcaagc gcggtcctcg gactcactat | 420 |
| ggccagaaag caatcttgtt tctccccctg ccagtctctt ctgattaa | 468 |

<210> SEQ ID NO 71
<211> LENGTH: 468
<212> TYPE: DNA
<213> ORGANISM: Pig

<400> SEQUENCE: 71

| atggctgaag gcgaaatcac aaccttcacg gccctgaccg agaagtttaa tctgcctcca | 60 |
| ggaaattaca agaagcccaa gctcctctac tgcagcaacg ggggccattt cctcaggatc | 120 |
| cttccagatg gcacagtgga tgggaccagg gacaggagcg accagcacat tcagctgcag | 180 |
| ctcagtgcgg aaagcgtggg ggaggtgtat ataaagagta cggagactgg ccagtacttg | 240 |
| gccatggaca ccagcgggct tttgtacggc tcacagacac ccgtgaggga gtgtttgttc | 300 |
| ctggagaggc tggaggaaaa ccattacaat acctacacat ccaagaagca cgcagagaag | 360 |
| aactggtttcg ttggcctcaa gaagaatgga agctgcaaac gcggtcctcg gactcactat | 420 |
| ggccagaaag ccatcctgtt tctccccctg ccagtatcct cggattaa | 468 |

<210> SEQ ID NO 72
<211> LENGTH: 468
<212> TYPE: DNA
<213> ORGANISM: Small-eared galago

<400> SEQUENCE: 72

| atggctgaag gggaaatcac aaccttcaca gccctcacag agaagtttaa tctgcctcta | 60 |
| ggaaattaca agaagcccaa gctcctctac tgtagcaacg gggtcacttt tctgaggatc | 120 |
| ctgccggatg gcaccgtgga tgggacacaa gacaggagcg accagcacat tcagctgcag | 180 |
| ctcagtgcgg aaagcgtggg ggaggtgtat ataaagagta cccagactgg ccagtacttg | 240 |
| gccatggact ccgacgggct tttatacggc tcacaaacac caaatgagga atgcctgttc | 300 |
| ctggaacggc tggaggaaaa ccattacaac acctatgtgt ccaagaagca cgccgagaag | 360 |
| aattggtttg tcggtctcaa gaagaacgga agttgcaaac gtggtcctcg gactcactac | 420 |
| ggccagaaag caatcttgtt tctccccctg ccagtctcct ctgattaa | 468 |

<210> SEQ ID NO 73
<211> LENGTH: 468
<212> TYPE: DNA
<213> ORGANISM: Greater horseshoe bat

<400> SEQUENCE: 73

| ttaatcagag gagactggca ggggagaaa caggattgct ttctggccat agtgagtccg | 60 |
| aggaccgcgc ttgcagcttc cattcttctt gagcccaacg aaccaattct tttctgcgtg | 120 |
| cttcttggac gtgtaggtgt tgtaatggtt ttcctccagc ctttccagga acagacattc | 180 |
| ctcatttggt gtctgtgagc cgtacaaaag cccgtcggag tccatggcca agtactggcc | 240 |

```
actctcggtg ctctttatat acacctcccc cacgctttcc gcactgagct gcagctgaat    300
gtgctggtca ctcttgtccc ttgtcccatc cactgtgcca tctggaagga tcctcaggaa    360
gtggcccccg ttgctgcagt agagaagttt gggtttcttg taattccctg taggcagatt    420
aaacttctca gtaagggctg tgaacgtggt gacttcccct tcggccat                 468
```

<210> SEQ ID NO 74
<211> LENGTH: 468
<212> TYPE: DNA
<213> ORGANISM: European shrew

<400> SEQUENCE: 74

```
ctagtcggag gagacgggca gggggagaaa caagatcgct ttctggccgt agtgagtccg     60
gggaccacgc ttgcagcttc cgttcttctt cagaccaaca aaccaattct tctcggcatg    120
cttcttggag gtataggtgt tgtaatggtt ttcctccagc ctttcagaa acagacattc     180
ctcattcggt gtttgtgagc cgtataaaag cccgtcggtg tccatggcca agtaatggcc    240
agtctccgtg ctctttatat acacctcccc cacgctttcc gcactgagct gcagctgaat    300
gtgctggtcg ctgcggtccc tggtcccatc cactgtgccg tccgggagga tgcgcaggaa    360
gtggcccccg ttgctgcagt acaggagttt gggcttcttg tagttccctg gtggcaggtt    420
aaacttctcc atgagggccc caaggtggt gatctccccc tcggccat                  468
```

<210> SEQ ID NO 75
<211> LENGTH: 468
<212> TYPE: DNA
<213> ORGANISM: Rabbit

<400> SEQUENCE: 75

```
atggctgagg gggaggtcac caccttcaca gccctgaccg agaagttcaa cctgcctgca     60
gggaactaca agttgcccaa actcctctac tgcagcaacg ggggccactt cctgaggatc    120
ctgccggacg gcactgtgga cggcacaagg gacaggagcg accagcacat tcagctgcag    180
ctgagtgcgg aaagcgtggg ggaggtgtat ataaagagta cggagaccgg ccagtacttg    240
gccatggaca ccgacggcct tttatacggc tcgcaaacgc ccagtgagga gtgtttgttc    300
ctggaacggc tggaggagaa ccactacaac acctacacgt ccaagaagca cgccgagaag    360
aactggtttg tggggctgaa gaaaaacggg agctgcaagc gcggtcctcg gactcactac    420
ggccagaaag ccatcttgtt cctccccctg ccggtctcct ccgactaa                 468
```

<210> SEQ ID NO 76
<211> LENGTH: 468
<212> TYPE: DNA
<213> ORGANISM: Chinese hamster

<400> SEQUENCE: 76

```
atggctgaag gagaaatcac caccttctca gccctgacag agagatttaa tctgcctcca     60
ggaaactaca gaagcccaa actgctctac tgcagcaacg ggggccactt cttgaggatc    120
cttccagatg gcacagtgga tgggacaagg acaggagtg accagcacat tcagctgcag    180
ctgagtgcgg aaagcgcggg cgaagtgtat ataagggta cagagacagg ccagtacagg    240
aacatggaca cggatggcct tttatacggc tcacagacac caaatgaaga tgcctgttc    300
ctggaaggc tggaagaaaa ccattacaac acttatacat ccaagaagca cgcagagaag    360
aactggtttg tgggcctcaa gaaaacggg agctgcaagc gtggtcctcg gactcactat    420
ggccagaaag caatcttgtt tctcccctg cctgtatctt ctgactag                  468
```

<210> SEQ ID NO 77
<211> LENGTH: 468
<212> TYPE: DNA
<213> ORGANISM: Tasmanian devil

<400> SEQUENCE: 77

| | | | | | |
|---|---|---|---|---|---|
| atggccgaag | gggagatcac | aaccttcaca | gccctgaccg | aaagatttaa | tctgccactg | 60 |
| gggaattaca | agaagcccaa | gcttctctac | tgtagcaatg | ggggccactt | tttgaggatt | 120 |
| cttcctgatg | gtaaagtgga | tgggacaagg | acagaaatg | atcaacacat | tcaactgcaa | 180 |
| ctaagcgcgg | aaagcgtggg | tgaggtgtat | ataaagagca | ctgagtctgg | ccagtatttg | 240 |
| gctatggaca | ccgatggact | tttatacggc | tcacagacac | ccactgaaga | atgcttgttc | 300 |
| ctggagagat | tggaggagaa | tcattacaac | acctacatat | caagaagca | tgcggagaaa | 360 |
| aattggtttg | tgggcctcaa | gaaaaatgga | agctgcaaaa | gaggtcccag | gactcactat | 420 |
| ggccagaaag | ccatcctctt | ccttcccctc | cctgtgtcct | ctgagtaa | | 468 |

<210> SEQ ID NO 78
<211> LENGTH: 468
<212> TYPE: DNA
<213> ORGANISM: House mouse

<400> SEQUENCE: 78

| | | | | | |
|---|---|---|---|---|---|
| atggctgaag | gggagatcac | aaccttcgca | gccctgaccg | agaggttcaa | cctgcctcta | 60 |
| ggaaactaca | aaaagcccaa | actgctctac | tgcagcaacg | ggggccactt | cttgaggatc | 120 |
| cttcctgatg | gcaccgtgga | tgggacaagg | acaggagcg | accagcacat | tcagctgcag | 180 |
| ctcagtgcgg | aaagtgcggg | cgaagtgtat | ataaagggta | cggagaccgg | ccagtacttg | 240 |
| gccatggaca | ccgaagggct | tttatacggc | tcgcagacac | caaatgagga | atgtctgttc | 300 |
| ctggaaaggc | tggaagaaaa | ccattataac | acttacacct | caagaagca | tgcggagaag | 360 |
| aactggtttg | tgggcctcaa | gaagaacggg | agctgtaagc | gcggtcctcg | gactcactat | 420 |
| ggccagaaag | ccatcttgtt | tctgcccctc | ccggtgtctt | ctgactag | | 468 |

<210> SEQ ID NO 79
<211> LENGTH: 465
<212> TYPE: DNA
<213> ORGANISM: Domestic guinea pig

<400> SEQUENCE: 79

| | | | | | |
|---|---|---|---|---|---|
| atggctgaag | gagaaatcac | aacttttgca | gccctgactg | agaagtttaa | tctgcctcca | 60 |
| gggaattata | agaagcccaa | actgctctac | tgcagcaatg | ggggccactt | cctgaggatc | 120 |
| cttccagacg | gcacagtgga | cggcacaaga | gacaggagcg | accagcacat | tcagctgcag | 180 |
| ctcagtgcgg | aaggcgtggg | ggaggtgtat | atacagagca | ccgagaccgg | ccagtacttg | 240 |
| gccatggaca | ccgacgggct | tttatacggc | tcacagacac | caagtgagga | atgcttgttc | 300 |
| ctggaaaggc | tggaggaaaa | ccattacaac | acctacacat | ccaagaagca | tgtggagaag | 360 |
| aattggtttg | ttggcctcaa | gaagaacgga | agctgcaagc | gtggtcctcg | gactcactat | 420 |
| ggccagaaag | caatcttgtt | cctcccctty | ccagtctctg | attag | | 465 |

<210> SEQ ID NO 80
<211> LENGTH: 468
<212> TYPE: DNA
<213> ORGANISM: Gray short-tailed opossum

<400> SEQUENCE: 80

```
atggccgaag gggagatcac aaccttcaca gccctgactg aaagatttaa cctgccactg      60
gggaattaca agaaacccaa gcttctctac tgtagcaatg ggggccattt cttgaggatc     120
cttcctgatg gcaaagtgga tgggacacgg gacagaaatg atcaacacat tcaactgcag     180
ctgagcacgg aaagtgtggg tgaggtgtat ataaagagca ctgagtctgg ccagtatttg     240
gctatggaca ccgatggact tttatatggc tcacagacac ccagtgaaga atgcttgttt     300
ctggagaggt tggaggagaa tcattacaac acctacacat cgaagaagca tgcagagaaa     360
aattggtttg ttggtctcaa gaagaatgga agctgcaaaa aggtcccag  gactcactac     420
ggccagaaag ccatcctgtt ccttccctc  cctgtgtcct ctgagtaa                  468
```

<210> SEQ ID NO 81
<211> LENGTH: 468
<212> TYPE: DNA
<213> ORGANISM: Common vampire bat

<400> SEQUENCE: 81

```
atggctgaag gggaagtcac cacgttcaca gctctgactg agaagtttaa tctgcctctg      60
gagagttaca agaagcccaa acttctctac tgcagcaacg gtggccactt cctgaggatc     120
cttccagatg gtacagtgga tgggacaagg acaagagcg  accagcacat tcagctgcag     180
ctcagtgcgg aaagcgtggg ggaggtgtac ataaagagca ccgggagtgg ccagtacttg     240
gccatggact ccgccgggct tttgtatggc tcacagacac caaatgagga atgtttgttc     300
ctggaaaggc tggaggaaaa ccattacaac acctacacat ccaagaagca tgcagaaaag     360
aattggttcg tggggctcaa gaagaatgga agctgcaagc gtggcccccg gactcattat     420
ggccagaaag caatcttgtt ctcccccctg ccagtcaact ctgattaa                  468
```

<210> SEQ ID NO 82
<211> LENGTH: 468
<212> TYPE: DNA
<213> ORGANISM: Cattle

<400> SEQUENCE: 82

```
atggctgaag gagaaaccac gaccttcacg gccctgactg agaagtttaa cctgcctcta      60
ggcaattaca agaagcccaa gctcctctac tgcagcaacg ggggctactt cctgagaatc     120
ctcccagatg gcacagtgga tgggacgaag gacaggagcg accagcacat tcagctgcag     180
ctctgtgcgg aaagcatagg ggaggtgtat attaagagta cggagactgg ccagttcttg     240
gccatggaca ccgacgggct tttgtacggc tcacagacac ccaatgagga atgtttgttc     300
ctggaaaggt tggaggaaaa ccattacaac acctacatat ccaagaagca tgcagagaag     360
cattggttcg ttggtctcaa gaagaacgga aggtctaaac tcggtcctcg gactcacttc     420
ggccagaaag ccatcttgtt ctccccctg  ccagtctcct ctgattaa                  468
```

<210> SEQ ID NO 83
<211> LENGTH: 468
<212> TYPE: DNA
<213> ORGANISM: Platypus

<400> SEQUENCE: 83

```
atggcggagg gtgaaatcac cacgttcaca gccctgatgg agaagttcga cctaccctg       60
ggcaactaca aaaagcctag gctgctctac tgcagcaatg cggctactt  cctgcgcatc     120
cagccagacg gtaaagtgga cgggaccagg gatcggagcg atcagcacat tcaactgcag     180
```

```
ctaagcgcgg aaagcgtggg cgaggtgtat ataaagagca ccgagtctgg ccactatttg      240
gctatggaca ccgaaggact tttatatggc tcacaggcac ccagtgaaga ctgcttgttc      300
ctggagcggc tggaggagaa ccactataac acgtacgtgt ccaagaagca cgctgagaag      360
aattggtttg tcggtctcaa gaagaacggg agctgcaaac gaggtccccg gactcactac      420
ggccagaaag ccatcctctt cctcccgctc cccgtggcat ccgactag                   468
```

<210> SEQ ID NO 84
<211> LENGTH: 468
<212> TYPE: DNA
<213> ORGANISM: Zebra finch

<400> SEQUENCE: 84

```
atggccgagg gggagatcac caccttcagc gccctgacgg agaagttcaa cctgcccccg      60
gggaactaca agaagcccaa actgctgtac tgcagcaacg gggggcattt cctgcgcatc     120
ctcccggacg gcaccgtgga tgcaccagg accgcagcg accagcacat tcagctccag      180
ctgagtgcag agagcgtggg ggtggtgcac atccagagca cccagtcggg gcagtacctg     240
gccatggaca ccaacgggct gctctacggc tcgcagctgc acccggtga gtgtctgttc     300 ctggaaaggc tggaggagaa ccattacaac acctacgtct ccaaaatgca cgcggacaag    360
aactggtttg tggggctgaa gaagaacggg acaagcaagc tgggcccgcg gactcactac    420
ggccagaagg cgatcctgtt cctgccgctg cccgtggcgg ccgactga                  468
```

<210> SEQ ID NO 85
<211> LENGTH: 468
<212> TYPE: DNA
<213> ORGANISM: Nine-banded armadillo

<400> SEQUENCE: 85

```
ttaatcagag gagactggca ggggaagaaa caagatagct ttctggccat agtgagtctg      60
aggaccacgt ttgctgcttc cgtccttctt gagaccaaca aaccatttct tctctgcatg     120
cttcttggat atgtaggtgt tgtaattgtt ttcttccagc ttttccatga acaagcattc     180
ctcacttggt gtctctgagc catataaaag cccgtcggtg tccatggcta agtactggcc     240
ggtctctgca ctctttatat acacctcccc cacgctttcc gcactgagct gcagctgaat     300
gtgttggtcg ctccctgtccc ttgtcccatc caccgtgcca tctggaagga tcctcaagaa    360
gtggcccccg tttctgcagt agaggagtct ggggtgcttg taatttttcta ggggcaggtt    420 gaacttctcc atcagggcca tgaaggttgt gatctcccct tcagccat                   468
```

<210> SEQ ID NO 86
<211> LENGTH: 468
<212> TYPE: DNA
<213> ORGANISM: Xenopus Silurana tropicalis

<400> SEQUENCE: 86

```
atggcagagg gagacatcac aacattcaac cccattgcag agtccttcag tcttccaatt      60
ggcaactaca agaaaccaaa acttctgtac tgtaataatg gagggtattt tttgcgcatc     120
ctcccagatg gggttgtgga tggaacaaga gacagagatg acctttacat tacactgaag     180
ttaagcgcac aaagccaagg ggaggtgcat atcaaaagca cagagacagg gagttactta     240
gccatggact ccagtggaca gttgtatgga actctcacac caaatgaaga aagcctgttt     300
ctggagacat tagaagagaa tcactataac acatacaagt caaagaagta tgcagaaaat     360
```

```
aactggtttg tggggataaa gaagaacggg gcaagcaaaa agggatcaag gactcactat    420
ggacaaaaag ccatcctttt tctgccgctg ccagcatcac ctgactag                468
```

<210> SEQ ID NO 87
<211> LENGTH: 465
<212> TYPE: DNA
<213> ORGANISM: Heterocephalus glaber

<400> SEQUENCE: 87

```
atggcggaag gcgaaattac cacctttacc gcgctgaccg aaaaatttaa cctgccgccg     60
ggcaactata aaaaaccgaa actgctgtat tgcagcaacg gcggccattt tctgcgcatt    120
ctgccggatg gcaaagtgga tggcacccgc gatcgcagcg atcagcatat tcagctgcag    180
ctgagcgcgg aaggcgtggg cgaagtgtat attaaaagca ccgaaaccgg ccagtatctg    240
gcgatggata ccgatggcct gctgtatggc agccagaccg cgagcgaaga atgcctgttt    300
ctggaacgcc tggaagaaaa ccattataac acctatatta gcaaaaaaca tgcggaaaaa    360
aactggtttg tgggcctgaa aaaaaacggc agctgcaaac gcggcccgcg cacccattat    420
ggccagaaag cgattctgtt tctgccgctg ccggtgagca gcgat                    465
```

<210> SEQ ID NO 88
<211> LENGTH: 465
<212> TYPE: DNA
<213> ORGANISM: Black flying fox

<400> SEQUENCE: 88

```
atggcggaag gcgaagtgac cacctttacc gcgctgaccg aacgctttaa cctgccgccg     60
ggcaactata aaaaaccgaa actgctgtat tgcagcaacg gcggccattt tctgcgcatt    120
ctgccggatg gcaccgtgga tggcacccgc gataaaagcg atcagcatat tcagctgcag    180
ctgagcgcgg aaagcgtggg cgaagtgtat attaaaagca ccgaaagcgg ccagtatctg    240
gcgatggata gcgatggcct gctgtatggc agccagaccc cggatgaaga ttgcctgttt    300
ctggaacgcc tggaagaaaa ccattataac acctatacca gcaaaaaaca tgcggaaaaa    360
aactggtttg tgggcctgaa aaaaaacggc agctgcaaac gcggcccgcg cacccattat    420
ggccagaaag cgattctgtt tctgccgctg ccggtgagca gcgat                    465
```

<210> SEQ ID NO 89
<211> LENGTH: 465
<212> TYPE: DNA
<213> ORGANISM: Chinese tree shrew

<400> SEQUENCE: 89

```
atggcggaag gcgaaattac cacctttgcg gcgctgaccg aaaaatttga tctgccgccg     60
ggcaactata aaaaaccgaa actgctgtat tgcagcaacg gcggccattt tctgcgcatt    120
ctgccggatg gcaccgtgga tggcacccgc gatcgcagcg atcagcatat tcagctgcag    180
ctgaccgcgg aaaacgtggg cgaagtgtat attaaaagca ccgaaaccgg ccagtatctg    240
gcgatggatg cggatggcct gctgtatggc agccagaccc gaacgaaga atgcctgttt    300 ctggaacgcc tggaagaaaa ccattataac acctatatta gcaaaaaaca tgcggaaaaa    360
aactggtttg tggcgctgaa aaaaaacggc agctgcaaac tgggcccgcg cacccattat    420
ggccagaaag cgattctgtt tctgccgctg ccggtgagca gcgat                    465
```

<210> SEQ ID NO 90
<211> LENGTH: 465

<212> TYPE: DNA
<213> ORGANISM: Rock pigeon

<400> SEQUENCE: 90

| | |
|---|---|
| atggcggaag gcgaaattac cacctttacc gcgctgaccg aaaaatttaa cctgccgccg | 60 |
| ggcaactata aaaaaccgaa actgctgtat tgcagcaacg gcggccattt tctgcgcatt | 120 |
| ctgccggatg gcaaagtgga tggcacccgc gatcgcagcg atcagcatat tcagctgcag | 180 |
| ctgagcgcgg aaagcgtggg cgaagtgtat attaaaagca cccagagcgg ccagtatctg | 240 |
| gcgatggatc cgaccggcct gctgtatggc agccagctgc tgggcgaaga tgcctgtttt | 300 |
| ctggaacgca ttgaagaaaa ccattataac acctatgtga gcaaaaaaca tgcggataaa | 360 |
| aactggtttg tgggcctgaa aaaaaacggc aacagcaaac tgggcccgcg cacccattat | 420 |
| ggccagaaag cgattctgtt tctgccgctg ccggtgagcg cggat | 465 |

<210> SEQ ID NO 91
<211> LENGTH: 468
<212> TYPE: DNA
<213> ORGANISM: Sheep

<400> SEQUENCE: 91

| | |
|---|---|
| atggctgaag gagaaaccac aaccttcagg gccctgactg agaagtttaa cctgcctcta | 60 |
| ggcaattaca agaagcccaa gctcctctat tgcagcaacg ggggctactt cctgagaatc | 120 |
| ctcccagatg gcagagtgga tgggacgaag gacaggagcg accagcacat tcagctgcag | 180 |
| ctctatgcgg aaagcatagg ggaggtgtat attaagagta cggagactgg ccagttcttg | 240 |
| gccatggaca ccaacgggct tttgtacggc tcacaaacac ccagtgagga atgtttgttc | 300 |
| ctggaaaggc tggaggaaaa ccattataac acctacatat ccaagaagca tgcagagaag | 360 |
| aattggttca ttggtctcaa gaagaacgga agctccaaac tcggtcctcg gactcacttc | 420 |
| ggccagaaag ccatcttgtt tctcccccctg ccagtttcct ctgattaa | 468 |

<210> SEQ ID NO 92
<211> LENGTH: 468
<212> TYPE: DNA
<213> ORGANISM: Chicken

<400> SEQUENCE: 92

| | |
|---|---|
| atggccgagg gggagataac caccttcacc gccctgaccg agcgcttcgg cctgccgctg | 60 |
| ggcaactaca agaagcccaa actcctgtac tgcagcaacg ggggccactt cctacggatc | 120 |
| ctgccggacg gcaaggtgga cgggacgcgg gaccggagtg accagcacat tcagctgcag | 180 |
| ctcagcgcgg aagatgtggg cgaggtctat ataaagagca cagcgtcggg gcagtacctg | 240 |
| gcaatggaca ccaacgggct cctgtatggc tcgcagctac caggcgagga gtgcttgttc | 300 |
| cttgagaggc tcgaggagaa ccattacaac acatacatct ccaaaaagca cgcagacaag | 360 |
| aactggttcg tcgggctgaa gaaaacgggg aacagcaagc tggggccgcg gactcactat | 420 |
| gggcaaaagg cgatcctctt cctcccattg ccggtgtcgg ctgactga | 468 |

<210> SEQ ID NO 93
<211> LENGTH: 297
<212> TYPE: DNA
<213> ORGANISM: Alpaca

<400> SEQUENCE: 93

| | |
|---|---|
| cagctgcagc tcagtgcgga aagcgtgggg gaggtgtata taaagagtac cgagactggc | 60 |

```
cagtacttgg ccatggacac cgacgggctt ttgcacggct cacagacacc aaatgaggaa    120
tgtttgttcc tggaaaggct ggaggagaac cattacaaca cctacacgtc caagaagcac    180
gccgaaaaga attggtttgt tggtctcaag aagaatggaa gctgcaaacg cggtcctcgg    240
actcactacg gccagaaggc gatcttgttt ctcccctgc cagtctcctc tgattaa       297
```

<210> SEQ ID NO 94
<211> LENGTH: 468
<212> TYPE: DNA
<213> ORGANISM: Anole lizard

<400> SEQUENCE: 94

```
atggctgaag gtgaaataac aacattcaca gccttgaccg agaggtttgc tctcccaatg    60
gagaattaca agaagcccaa actcctgtat tgcagcaatg gaggccactt cctgaggatc    120
cttccagatg gaaaagtgga tggcaccatg gaccggaatg acagctatat tcagttgctg    180
ttaacagcag aagatgtggg tgtggtatat ataaaaggca ctgagaccgg gcagtacttg    240
gccatggatg ccaatggaca tttatatggc tcgcagttgc caacagaaga gtgtttattt    300
gtggaaacgc tggaagaaaa ccattacaat acatatacct caaagatgca tggcgataag    360
aagtggtatg ttggcttgaa aaagaatggg aaaggcaaac tggggccacg gactcatcgc    420
ggccaaaagg caatactttt ccttccactg ccagtatcac ctgattag              468
```

<210> SEQ ID NO 95
<211> LENGTH: 468
<212> TYPE: DNA
<213> ORGANISM: Bushbaby

<400> SEQUENCE: 95

```
atggctgaag gggaaatcac aaccttcaca gccctcacag agaagtttaa tctgcctcta    60
ggaaattaca agaagcccaa gctcctctac tgtagcaacg ggggtcactt tctgaggatc    120
ctgccggatg gcaccgtgga tgggacacaa gacaggagcg accagcacat tcagctgcag    180
ctcagtgcgg aaagcgtggg ggaggtgtat ataaagagta cccagactgg ccagtacttg    240
gccatggact ccgacgggct tttatacggc tcacaaacac caaatgagga atgcctgttc    300
ctggaacggc tggaggaaaa ccattacaac acctatgtgt ccaagaagca cgccgagaag    360
aattggtttg tcggtctcaa gaagaacgga agttgcaaac gtggtcctcg gactcactac    420
ggccagaaag caatcttgtt tctcccctg ccagtctcct ctgattaa              468
```

<210> SEQ ID NO 96
<211> LENGTH: 468
<212> TYPE: DNA
<213> ORGANISM: Cat

<400> SEQUENCE: 96

```
atggctgaag gggaaatcac aaccttcacg gccctgacgg agaagttcaa tctgcctcca    60
gggaattaca agaaacccaa actcctctac tgtagcaacg ggggccactt cctgaggatc    120
cttccagatg gcacagtgga tgggacgagg gacaggagcg accagcacat tcagctgcag    180
ctcagtgcgg aaagcgtggg ggaggtgtat ataaagagta ccgagactgg ccagtacttg    240
gccatggaca ccgacgggct tttgtacggc tcacagacac caaatgagga atgcttgttc    300
ctggaaaggc tggaagaaaa ccattacaac acctacacat ccaagaagca cgcagaaaag    360
aattggtttg tgggtctcaa gaagaatgga agctgcaaac gcggtcccg gactcactat    420 ggccagaagg caattttgtt tctcccctg ccagtctcct ctgattaa              468
```

<210> SEQ ID NO 97
<211> LENGTH: 468
<212> TYPE: DNA
<213> ORGANISM: Chinese softshell turtle

<400> SEQUENCE: 97

```
atggctgaag gggaaataac aacgttcacc gccctgaccg aaaaattcaa ccttcccctg      60
gggaattaca agaatcccaa actcttatat tgcagcaatg gaggctactt cttgaggata     120
catccagatg gcaaagtaga tgggacaagg gaccgaagtg accaacacat tcagctgcag     180
ctaagtgcgg aaagcgtggg tgaggtatat ataaagagca ctgagtctgg acagttttg      240 gctatggacg ccaatggact tttatatgga tcactgtcac cgagtgagga atgcttattc     300
ttggaaagaa tggaagaaaa tcattataac acctacatct ccaagaagca tgcagacaag     360
aactggttcg ttggcttaaa gaagaatgga agctgcaaac tgggaccgcg gacgcactac     420
ggccaaaagg ccgtcctttt ccttccactg ccagtgtcag ctgattaa                  468
```

<210> SEQ ID NO 98
<211> LENGTH: 468
<212> TYPE: DNA
<213> ORGANISM: Coelacanth

<400> SEQUENCE: 98

```
atggctgaag acaaaataac aacactgaag gccttggctg aaaaatttaa ccttcctatg      60
ggaaattaca agaaagcaaa actcctctac tgcagcaacg gagggtattt cctgcgaata     120
cccccagacg ggaaagtgga aggaattaga gaacgaagcg acaagtacat tcagctgcaa     180
atgaatgcag aaagtttagg catggtgtct ataaagggtg tggaggcagg caataccta      240 gctatgaata caaatggact cctgtatgga tctcagtctc taactgaaga atgcctttc      300 atggaaagag tggaagaaaa ccactacaac acatacaggt ctaagacaca tgcagataaa     360
aactggtatg ttggcattag aaagaacggt agcatcaaac caggaccaag gactcacatt     420
ggccaaaagg ctgttctttt tctccctctg cctgcctcga gtgattag                  468
```

<210> SEQ ID NO 99
<211> LENGTH: 468
<212> TYPE: DNA
<213> ORGANISM: Dolphin

<400> SEQUENCE: 99

```
atggctgaag gggaaatcac aaccttcaca gccctgaccg agaagtttaa tctgcctcca      60
gggaattaca agaagcccaa actcctctac tgtagcaacg ggggccactt cctgaggatc     120
cttccagatg gcacagtgga tgggacaagg gacaggagtg accagcacat tcagctgcag     180
ctcagtgcgg aaagcgtggg ggaggtgtat ataaagagta cggagactgg ccagtacttg     240
gccatggaca ccgacgggct tttgtacggc tcacagacac ccaatgagga atgtttgttc     300
ctggaaaggt tggaggaaaa ccattacaac acctacgcat ccaagaagca tgcagaaaag     360
aattggttcg ttggtctcaa gaagaacgga agctgcaaac gcggtcctcg gactcactac     420
ggccagaaag caatccttgtt tctccccctg ccagtctcct ccgattaa                 468
```

<210> SEQ ID NO 100
<211> LENGTH: 468
<212> TYPE: DNA
<213> ORGANISM: Ferret

<400> SEQUENCE: 100

```
atggctgaag gggaaatcac aaccttcaca gccctgatgg agaagtttaa tctgcctgcg      60
gggaattaca agaagcccaa actcctctac tgtagcaatg ggggccactt cctgaggatc     120
cttccagatg gcacagtgga cggcacaagg gacaggagcg accagcacat tcagctgcag     180
ctcagtgcgg aaagcgtggg ggaggtgtac ataaagagta ccgagactgg ccagtacttg     240
gccatggaca ccgatgggct tttgtacggc tcacaaacac caaatgagga atgtctgttc     300
ctggaaaggc tggaggaaaa ccattacaac acctacacat ccaagaagca cgctgagaag     360
aattggtttg taggtctcaa gaagaacgga agctgcaaac gcggtcctcg gactcactat     420
ggccagaaag caattctgtt tctcccctg ccagtctcct ctgattaa                   468
```

<210> SEQ ID NO 101
<211> LENGTH: 468
<212> TYPE: DNA
<213> ORGANISM: Gibbon

<400> SEQUENCE: 101

```
atggccgaag gggaaatcac caccttcaca gccctgaccg agaagtttaa tctgcctcca      60
gggaattaca agaagcccaa actcctctac tgtagcaacg ggggccactt cttgaggatc     120
cttccggatg gcacagtgga tgggacaagg gacaggagcg accagcacat tcagctgcag     180
ctcagtgcgg aaagcgtggg ggaggtgtat ataaagagta ccgagactgg ccagtacttg     240
gccatggaca ccgacgggct tttatacggc tcacagacac caaatgagga atgtttgttc     300
ctggaaaggc tggaggagaa ccattacaac acctatatat ccaagaagca tgcagagaag     360
aattggtttg ttggcctcaa gaagaatgga agctgcaaac gcggtcctcg gactcactat     420
ggccagaaag caatcttgtt tctcccctg ccagtctctt ctgattaa                   468
```

<210> SEQ ID NO 102
<211> LENGTH: 468
<212> TYPE: DNA
<213> ORGANISM: Gorilla

<400> SEQUENCE: 102

```
atggctgaag gggaaatcac caccttcaca gccctgaccg agaagtttaa tctgcctcca      60
gggaattaca agaagcccaa actcctctac tgtagcaatg ggggccactt cttgaggatc     120
cttccggatg gcacagtgga tgggacaagg gacaggagcg accagcacat tcagctgcag     180
ctcagtgcgg aaagcgtggg ggaggtgtat ataaagagta ccgagactgg ccagtacttg     240
gccatggaca ccgacgggct tttatacggc tcacagacac caaatgagga atgtttgttc     300
ctggaaaggc tggaggagaa ccattacaac acctatatat ccaagaagca tgcagagaag     360
aattggtttg ttggcctcaa gaagaatgga agctgcaaac gcggtcctcg gactcactat     420
ggccagaaag caatcttgtt tctcccctg ccagtctctt ccgattaa                   468
```

<210> SEQ ID NO 103
<211> LENGTH: 468
<212> TYPE: DNA
<213> ORGANISM: Hedgehog

<400> SEQUENCE: 103

```
atggctgaag gagaaatcac caccttcacg gccctgactg agaagtttaa tctgccacta      60
gggaattaca agaagcccaa gctcctctac tgtagcaacg ggggccactt cctgaggatc     120
cttccagatg gcaccgtgga tgggacaagg gacaggagcg accagcatat tcagctgcag     180
```

```
ctcagtgcgg aaagcgtggg ggaggtgtat ataaagagta cggagactgg ccagtacttg      240
gccatggaca ccgacgggct tttatacggc tcacaaacac caaatgagga atgtctgttc      300
cttgaaaggc tggaagagaa ccattacaat acctacacat ccaagaagca tgccgagaag      360
aactggtttg ttggcctcaa gaagaatgga agctgcaagc gtggtcctcg gactcattat      420
ggccagaaag ctattttgtt tctcccctg ccagtttcct ctgattaa                   468
```

<210> SEQ ID NO 104
<211> LENGTH: 273
<212> TYPE: DNA
<213> ORGANISM: Hyrax

<400> SEQUENCE: 104

```
atggctgaag gcgaaatcac aaccttcaca gccctgactg agaagtttaa cctgccacta       60
gagaattaca agaagcccaa actcctctac tgtagcaacg gaggccactt cctgaggatc      120
cttccggacg gcacagtgga tgcaccagga acaggagtg accagcacat tcagctgcag      180
ctcagtgcgg aaagcgtggg ggaggtgtat ataaagggca ccgagactgg ccagtacttg      240
gccatggaca ccgacgggct tttatatggc tca                                  273
```

<210> SEQ ID NO 105
<211> LENGTH: 349
<212> TYPE: DNA
<213> ORGANISM: Kangaroo rat

<400> SEQUENCE: 105

```
atggctgaag gggaaatcac aaccttcaca gccctgacgg aaaggtttaa ttcagctgca       60
actgagtgcg gaaagcgtgg gggaggtcta tataaagagc accgagactg gccaatactt      120
ggccatggat gccgacgggc ttttatacgg ctcacagaca cctgatgaag aatgcttgtt      180
cctggagagg ctggaagaaa atcattataa cacctacata gccaagaaac atgctgaaaa      240
gaattggttt gtcggcctca aaaagaatgg aagctgcaag cgtggtcctc ggactcacta      300
tggccagaaa gcaatcctgt tcctcccctt gcctgtctcc tctgattag                  349
```

<210> SEQ ID NO 106
<211> LENGTH: 276
<212> TYPE: DNA
<213> ORGANISM: Lamprey

<400> SEQUENCE: 106

```
atggaggtgg gccacatcgg cacgctgccc gtggtccccg cggggcccgt gttccccggc       60
agtttcaagg agccacggcg cctctactgc cgcagcgcgg ccaccacct ccagatcctg       120 ggggacggca ccgtgagtgg cacccaggac gagaacgagc ccacgccgt tctgcagctg      180 caggcggtgc gccgcggggt ggtgacgatc cgtgggctct cgccgagag gttcctcgcc      240 atgagcacgg agggacacct gtacggggcg gtgagg                               276
```

<210> SEQ ID NO 107
<211> LENGTH: 297
<212> TYPE: DNA
<213> ORGANISM: Lesser hedgehog tenrec

<400> SEQUENCE: 107

```
cagctgaagc tcgttgccga aagcgtgggg gtggtgtata taaagagcat caagaccggc       60
cagtacttgg ccatgaaccc cgacgggctt ttatacggct ccgagacccc agaggaagaa      120
```

```
tgcttgttcc tggaaacgct ggaggaaaac cactacacca ccttcaaatc taagaagcac    180
gtagagaaga attggttcgt tggtctccgg aagaatggaa gggtcaagat cgggcctcgg    240
actcaccaag gccagaaagc aatcttgttc ctgcccctcc cggtgtcctc tgattaa       297

<210> SEQ ID NO 108
<211> LENGTH: 468
<212> TYPE: DNA
<213> ORGANISM: Rhesus monkey

<400> SEQUENCE: 108
atggctgaag gggaaatcac cacgttcaca gccctgaccg agaagtttaa tctgcctcca     60
gggaattaca agaagcccaa actgctctac tgtagcaatg ggggccactt cttgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatacat ccaagaagca cgcagagaag    360
aattggtttg ttggcctcaa gaagaatgga agctgcaaac gtggtcctcg gactcactat    420
ggccagaaag caatcttgtt cttcccctg ccagtctctt ctgattaa                  468

<210> SEQ ID NO 109
<211> LENGTH: 468
<212> TYPE: DNA
<213> ORGANISM: Megabat

<400> SEQUENCE: 109
atggccgagg gggaagtcac gacgttcacg gccctgaccg agaggtttaa cctgcctcca     60
gggaattaca agaagcccaa acttctctac tgcagcaacg ggggccactt cctgaggatc    120
ctcccagatg gcacagtgga tgggacaagg gacaagagcg accagcacat tcagctgcag    180
ctcagtgcgg aaagtgtggg ggaggtgtat ataaagagca ccgagagtgg ccagtacttg    240
gccatggact ccgacgggct tttgtacggc tcacagacac cagatgagga ctgtttgttc    300
ctggaaaggc tggaggaaaa ccattacaac acctacacat ccaagaagca cgcagagaag    360
aattggtttg ttgggctcaa gaagaatgga agctgcaagc gcggtccccg gactcactac    420
ggccagaaag cgatcctgtt ctcccccctg ccagtctcct ctgattag                 468

<210> SEQ ID NO 110
<211> LENGTH: 468
<212> TYPE: DNA
<213> ORGANISM: Microbat

<400> SEQUENCE: 110
atggctgagg gggaagtcac cacattcacg gccctgaccg agaggttcaa tctgcctctg     60
gagaactaca agaagcccaa gcttctctac tgcagcaacg ggggccactt cctgcggatc    120
ctcccagacg gcaccgtgga cgggacgagg gacaggagcg accagcacat tcagctgcag    180
ctcagtgcgg aaagcgtggg ggaggtgtat ataaagagca ccgagagtgg ccagtacttg    240
gccatggact ccgacgggct tttgtacggc tcacaaacac ccaatgagga atgtttgttc    300
ctggaaaggc tggaggagaa ccactacaac acctacacgt ccaagaagca cgcagaaaag    360
aattggttcg ttgggctcaa gaagaacgga agctgcaagc gtggtcctcg gacgcattat    420
ggccagaaag caatcttgtt ctccccctg ccagtctcct ccgattaa                  468
```

-continued

<210> SEQ ID NO 111
<211> LENGTH: 468
<212> TYPE: DNA
<213> ORGANISM: Mouse lemur

<400> SEQUENCE: 111

| | | | | | |
|---|---|---|---|---|---|
| atggccgaag | gggagatcac | aaccttcacg | gccctcaccg | agaagtttaa | cctgcctccg | 60 |
| gggaactaca | agaagcccaa | gctcctctac | tgcagcaacg | gcggccactt | cctgcgcatc | 120 |
| cttcccgacg | gcaccgtgga | tggcacgaga | gacaggagcg | accagcacat | tcagctgcag | 180 |
| ctcagtgcgg | aaagcgcggg | ggaggtgtat | ataaagagca | cccagactgg | ccggtacttg | 240 |
| gccatggacg | ccgacgggct | tttatacggc | tcacaaacac | caaatgagga | atgtttgttc | 300 |
| ctggaaaggc | tggaggaaaa | ccattacaac | acctacgtat | ccaagaagca | cgcagagaag | 360 |
| aattggtttg | ttggcctcaa | gaagaatgga | agttgcaaac | gcggcccccg | gactcactat | 420 |
| ggccagaaag | caatcttgtt | tctgccccctg | ccagtctcct | ctgattaa | | 468 |

<210> SEQ ID NO 112
<211> LENGTH: 436
<212> TYPE: DNA
<213> ORGANISM: Pika

<400> SEQUENCE: 112

| | | | | | |
|---|---|---|---|---|---|
| atggccgagg | gagaagtcac | caccttctca | gccctgacgg | agaagttcaa | tctgcctgga | 60 |
| ggaaactaca | agttgcccaa | gctccttac | tgtagcaacg | gaggccactt | cctgaggatc | 120 |
| cttccagatg | gcacagtgga | tgggaccagg | gacaggagcg | acctgcacag | aggtgtttat | 180 |
| aaagagtacg | gagactggcc | agtacttggc | tatggacacc | gatggccttt | tatatggctc | 240 |
| gcagacaccc | agtgaggagt | gtttgttcct | ggagcggctg | gaggagaacc | actcaacac | 300 |
| ctacacatcc | aagaagcatg | ccgagaagaa | ctggtttgtg | ggcatcaaga | agaatggaag | 360 |
| ctgcaagcgt | ggtcctcgga | ctcactacgg | ccagaaagcc | atcttgtttc | tccctctgcc | 420 |
| agtctcttct | gactaa | | | | | 436 |

<210> SEQ ID NO 113
<211> LENGTH: 468
<212> TYPE: DNA
<213> ORGANISM: Rat

<400> SEQUENCE: 113

| | | | | | |
|---|---|---|---|---|---|
| atggccgaag | gggagatcac | aacctttgca | gccctgaccg | agaggttcaa | tctgcctcta | 60 |
| gggaactaca | aaaaacccaa | actgctctac | tgcagcaacg | ggggccactt | cttgaggatt | 120 |
| cttcccgatg | gcaccgtgga | tgggaccagg | gacaggagcg | accagcacat | tcagctgcag | 180 |
| ctcagtgcgg | aaagcgcggg | cgaagtgtat | ataaagggta | cagagactgg | ccagtacttg | 240 |
| gccatggaca | ccgaagggct | tttatacggc | tcgcagacac | caaatgaaga | atgcctattc | 300 |
| ctggaaaggc | tagaagaaaa | ccattataac | acttacacat | ccaagaagca | cgcggagaag | 360 |
| aactggtttg | tgggcctcaa | gaagaacggg | agttgtaagc | gcggtcctcg | gactcactac | 420 |
| ggccagaaag | ccatcttgtt | tctccccctc | ccggtatctt | ctgactaa | | 468 |

<210> SEQ ID NO 114
<211> LENGTH: 468
<212> TYPE: DNA
<213> ORGANISM: Sloth

<400> SEQUENCE: 114

```
atggctgaag ggaaatcac aaccttcaca gctctgatgg agaagtttaa cctgccacca      60
gggaattaca tgaagcccaa actcctctac tgtagcaacg ggggccactt cttgaggatc     120
cttccagacg gcacagtgga tgggacaagg gacaggagcg acctgcacat tcagctgcag     180
ctcagtgcgg aaagcgtggg ggaggtgtat ataaagagtg cggagaccgg ccagtactta     240
gccatggaca ccggcgggct tttatacggc tcacagacac caagtgagga atgcctgttc     300
ctagaaaggc tggaggaaaa ccattacaac acctacgtat ccaagaagca tgcggagaag     360
aactggttcg ttggcctaaa gaagaatgga agcagcaaac gcggcccccg gactcactat     420
ggccagaaag ccatcttgtt tcttcccctg ccagtctcct ctgattaa                  468
```

<210> SEQ ID NO 115
<211> LENGTH: 468
<212> TYPE: DNA
<213> ORGANISM: Squirrel

<400> SEQUENCE: 115

```
atggctgaag ggaaatcac aaccttcaca gccctgaccg agaagttcaa tctgcctcca      60
gggaactaca agaagcccaa actgctctac tgtagcaacg gaggccactt cttgaggatc     120
cttcctgatg gcacagtgga tgggacaaga gacaggagcg accaacacat tcagctgcag     180
ctcagtgcgg aaagcgtggg ggaggtgtat ataaagagta ccgagaccgg ccagtacttg     240
gccatggaca ccgacgggct tttatatggc tcacagaccc caaatgagga atgcttattc     300
ctggaaaggc tggaggaaaa ccattacaac acgtacacat ccaagaagca tgcagagaag     360
aattggtttg ttggcctcaa gagaacgga agctgcaagc gcggtccccg gactcactat     420
ggccagaaag cgatcttgtt tctcccactg cctgtctcct ctgattag                  468
```

<210> SEQ ID NO 116
<211> LENGTH: 468
<212> TYPE: DNA
<213> ORGANISM: Tarsier

<400> SEQUENCE: 116

```
atggccgaag ggaaatcac aaccttcaca gccctgaccg agaagttcaa cctgccccg      60 gggaattaca agaagcccaa actcctctac tgcagcaacg ggggccactt cttgaggatc     120
cttccggatg gcactgtgga tggaacgagg gacaggagcg accagcacat tcagctgcag     180
ctcagcgcgg aaagcgtggg ggaggtgtat ataaagagta ccgagaccgg ccagtacttg     240
gccatggaca ccgacgggct tttgtacggc tcacagacac caaatgagga gtgtctgttc     300
ctggaaaggc tggaagagaa tcattacaat acctacgtgt ccaagaagca tgcggagaag     360
aattggtttg tcggcctcaa gaagaatgga agctgcaaac gcggtcctcg gactcactat     420
ggccagaaag caatcttgtt tctcccctg ccagtttcct ctgattaa                   468
```

<210> SEQ ID NO 117
<211> LENGTH: 468
<212> TYPE: DNA
<213> ORGANISM: Tree shrew

<400> SEQUENCE: 117

```
atggctgaag ggaaatcac gaccttcgca gccctgaccg agaagtttga tctgcctcca      60
gggaattaca agaagcccaa acttctctac tgtagcaacg ggggccattt cttgaggatt     120
cttccagatg gcaccgtgga tgggacaaga gacaggagcg accagcacat tcagctgcag     180
ctcactgcgg aaaacgtggg ggaggtgtac ataaagagta cggagactgg ccagtacttg     240
```

```
gccatggacg ccgacgggct tttatatggc tcacagacac caaacgagga atgtttgttc        300
ctggaaaggc tggaggagaa ccattacaac acctacatat ccaagaagca cgcagagaag        360
aattggtttg ttgccctcaa gaagaacgga agctgcaaac tcggtcctcg gactcactat        420
ggccagaaag caatcttgtt tctcccctg ccagtctcct ctgattaa                      468
```

<210> SEQ ID NO 118
<211> LENGTH: 168
<212> TYPE: DNA
<213> ORGANISM: Turkey

<400> SEQUENCE: 118

```
atggccgagg gggagataac caccttcaca gccctgaccg agcgcttcgg cctgccgctg         60
ggcaactaca agaagcccaa actcctgtac tgcagcaacg ggggccactt cctacggatc        120
ctgccggacg gcaaggtgga cgggacgcgg gaccggagcg accagcac                     168
```

<210> SEQ ID NO 119
<211> LENGTH: 468
<212> TYPE: DNA
<213> ORGANISM: Wallaby

<400> SEQUENCE: 119

```
atggccgaag gggagatcac aaccttcaca gccctgaccg aaagatttaa cctgccactg         60
gggaattaca agaagcccaa gcttctctac tgtagcaatg ggggccactt tttgaggatc        120
cttcctgatg gcaaagtgga tgggacaagg gacagaaatg atcaacacat tcaactgcaa        180
ctaagcgcgg aaagcgtggg tgaggtgtat ataaagagca ctgagtctgg gcagtatttg        240
gccatggaca ccaatggact tttatatggc tcacagaccc ccagcgaaga atgcttattc        300
ctggagaggt tggaggagaa tcattacaac acctacatat caaagaagca tgcggagaaa        360
aattggtttg ttggcctcaa gaagaacgga agttgcaaaa gaggtcccag gactcactat        420
ggccagaaag ccatcctatt ccttcccctc cctgtgtcct ctgagtaa                     468
```

<210> SEQ ID NO 120
<211> LENGTH: 444
<212> TYPE: DNA
<213> ORGANISM: Zebrafish

<400> SEQUENCE: 120

```
atgaccgagg ccgatattgc ggtaaagtcc agcccgcgcg actataaaaa actgacgcgg         60
ctgtactgta tgaatggagg atttcacctt cagatcctgg cggacgggac agtggctgga        120
gcagcagacg aaaacacata cagcatactg cgcataaaag caacaagtcc aggagtggtg        180
gtgatcgaag gatcagaaac aggtctttac ctctcgatga atgaacatgg caagctgtac        240
gcttcatcat tagtgacgga tgaaagttat ttcctggaga agatggagga aaaccactac        300
aacacatatc agtctcaaaa gcacggtgaa aactggtacg tcgaataaaa aagaacgggg        360
aaaatgaaac ggggcccaag aactcacatc ggacaaaagg ccattttctt tcttccacga        420
caggtggagc aggaagagga ctga                                               444
```

<210> SEQ ID NO 121
<211> LENGTH: 155
<212> TYPE: PRT
<213> ORGANISM: Homo sapiens

<400> SEQUENCE: 121

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
            130                 135                 140

Ala Ile Leu Phe Leu Pro Met Ser Ala Lys Ser
145                 150                 155

<210> SEQ ID NO 122
<211> LENGTH: 155
<212> TYPE: PRT
<213> ORGANISM: Gorilla gorilla

<400> SEQUENCE: 122

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
            130                 135                 140

Ala Ile Leu Phe Leu Pro Met Ser Ala Lys Ser
145                 150                 155

<210> SEQ ID NO 123
<211> LENGTH: 155
<212> TYPE: PRT
<213> ORGANISM: Pongo abelii

<400> SEQUENCE: 123

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
            130                 135                 140

Ala Ile Leu Phe Leu Pro Met Ser Ala Lys Ser
145                 150                 155

<210> SEQ ID NO 124
<211> LENGTH: 155
<212> TYPE: PRT
<213> ORGANISM: Macaca mulatta

<400> SEQUENCE: 124

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
            130                 135                 140

Ala Ile Leu Phe Leu Pro Met Ser Ala Lys Ser
145                 150                 155

<210> SEQ ID NO 125
<211> LENGTH: 155
<212> TYPE: PRT
<213> ORGANISM: Pan troglodytes

<400> SEQUENCE: 125

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

```
Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155

<210> SEQ ID NO 126
<211> LENGTH: 155
<212> TYPE: PRT
<213> ORGANISM: Pan paniscus

<400> SEQUENCE: 126

Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155

<210> SEQ ID NO 127
<211> LENGTH: 155
<212> TYPE: PRT
<213> ORGANISM: Saimiri boliviensis boliviensis

<400> SEQUENCE: 127

Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45
```

```
Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
             115                 120                 125

Arg Thr Gly Gln Tyr Lys Leu Gly Ser Lys Thr Gly Pro Gly Gln Lys
         130                 135                 140

Ala Ile Leu Phe Leu Pro Met Ser Ala Lys Ser
145                 150                 155

<210> SEQ ID NO 128
<211> LENGTH: 155
<212> TYPE: PRT
<213> ORGANISM: Nomascus leucogenys

<400> SEQUENCE: 128

Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
                 20                  25                  30

Tyr Cys Lys Asn Gly Gly Phe Phe Leu Arg Ile His Pro Asp Gly Arg
             35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
             115                 120                 125

Arg Thr Gly Gln Tyr Lys Leu Gly Ser Lys Thr Gly Pro Gly Gln Lys
         130                 135                 140

Ala Ile Leu Phe Leu Pro Met Ser Ala Lys Ser
145                 150                 155

<210> SEQ ID NO 129
<211> LENGTH: 155
<212> TYPE: PRT
<213> ORGANISM: Equus caballus

<400> SEQUENCE: 129

Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
                 20                  25                  30

Tyr Cys Lys Asn Gly Gly Phe Phe Leu Arg Ile His Pro Asp Gly Arg
             35                  40                  45

Val Asp Gly Val Arg Glu Lys Ser Asp Pro His Ile Lys Leu Gln Leu
 50                  55                  60
```

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 130
<211> LENGTH: 155
<212> TYPE: PRT
<213> ORGANISM: Bos Taurus

<400> SEQUENCE: 130

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 131
<211> LENGTH: 155
<212> TYPE: PRT
<213> ORGANISM: Papio Anubis

<400> SEQUENCE: 131

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155

<210> SEQ ID NO 132
<211> LENGTH: 155
<212> TYPE: PRT
<213> ORGANISM: Vicugna pacos

<400> SEQUENCE: 132

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
            115                 120                 125

Arg Thr Gly Gln Tyr Lys Leu Gly Pro Lys Thr Gly Pro Gly Gln Lys
        130                 135                 140

Ala Ile Leu Phe Leu Pro Met Ser Ala Lys Ser
145                 150                 155

<210> SEQ ID NO 133
<211> LENGTH: 155
<212> TYPE: PRT
<213> ORGANISM: Ovis aries

<400> SEQUENCE: 133

Met Ala Ala Gly Ser Ile Thr Thr Leu Pro Ala Leu Pro Glu Asp Gly
1               5                   10                  15

Gly Ser Ser Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 134
<211> LENGTH: 108
<212> TYPE: PRT
<213> ORGANISM: Capreolus capreolus

<400> SEQUENCE: 134

Arg Ile His Pro Asp Gly Arg Val Asp Gly Val Arg Glu Lys Ser Asp
1               5                   10                  15

Pro His Ile Lys Leu Gln Leu Gln Ala Glu Glu Arg Gly Val Val Ser
            20                  25                  30

Ile Lys Gly Val Cys Ala Asn Arg Tyr Leu Ala Met Lys Glu Asp Gly
        35                  40                  45

Arg Leu Leu Ala Ser Lys Cys Val Thr Asp Glu Cys Phe Phe Phe Glu
    50                  55                  60

Arg Leu Glu Ser Asn Asn Tyr Asn Thr Tyr Arg Ser Arg Lys Tyr Ser
65                  70                  75                  80

Ser Trp Tyr Val Ala Leu Lys Arg Thr Gly Gln Tyr Lys Leu Gly Pro
                85                  90                  95

Lys Thr Gly Pro Gly Gln Lys Ala Ile Leu Phe Leu
            100                 105

<210> SEQ ID NO 135
<211> LENGTH: 96
<212> TYPE: PRT
<213> ORGANISM: Loxodonta Africana

<400> SEQUENCE: 135

Val Lys Leu Gln Leu Gln Ala Glu Glu Arg Gly Val Val Ser Ile Lys
1               5                   10                  15

Gly Val Cys Ala Asn Arg Tyr Leu Ala Met Lys Glu Asp Gly Arg Leu
            20                  25                  30

Leu Ala Ser Arg Cys Val Thr Asp Glu Cys Phe Phe Phe Glu Arg Leu
        35                  40                  45

Glu Ser Asn Asn Tyr Asn Thr Tyr Arg Ser Arg Lys Tyr Thr Ser Trp
    50                  55                  60

Tyr Val Ala Leu Lys Arg Thr Gly Gln Tyr Lys Leu Gly Ser Lys Thr
65                  70                  75                  80

Gly Pro Gly Gln Lys Ala Ile Leu Phe Leu Pro Met Ser Ala Lys Ser
                85                  90                  95

<210> SEQ ID NO 136
<211> LENGTH: 120
<212> TYPE: PRT
<213> ORGANISM: Sus scrofa

<400> SEQUENCE: 136

Asn Gly Gly Phe Phe Leu Arg Ile His Pro Asp Gly Arg Val Asp Gly
1               5                   10                  15

Val Arg Glu Lys Ser Asp Pro His Ile Lys Leu Gln Leu Gln Ala Glu

```
                    20                  25                  30

Glu Arg Gly Val Val Ser Ile Lys Gly Val Cys Ala Asn Arg Tyr Leu
            35                  40                  45

Ala Met Lys Glu Asp Gly Arg Leu Leu Ala Ser Lys Cys Val Thr Asp
 50                  55                  60

Glu Cys Phe Phe Phe Glu Arg Leu Glu Ser Asn Asn Tyr Asn Thr Tyr
 65                  70                  75                  80

Arg Ser Arg Lys Tyr Ser Ser Trp Tyr Val Ala Leu Lys Arg Thr Gly
                85                  90                  95

Gln Tyr Lys Leu Gly Pro Lys Thr Gly Pro Gly Gln Lys Ala Ile Leu
            100                 105                 110

Phe Leu Pro Met Ser Ala Lys Ser
            115                 120

<210> SEQ ID NO 137
<211> LENGTH: 96
<212> TYPE: PRT
<213> ORGANISM: Ailuropoda melanoleuca

<400> SEQUENCE: 137

Val Lys Leu Gln Leu Gln Ala Glu Glu Arg Gly Val Val Ser Ile Lys
 1               5                  10                  15

Gly Val Cys Ala Asn Arg Tyr Leu Ala Met Lys Glu Asp Gly Arg Leu
                20                  25                  30

Leu Ala Ser Lys Cys Val Thr Asp Glu Cys Phe Phe Phe Glu Arg Leu
            35                  40                  45

Glu Ser Asn Asn Tyr Asn Thr Tyr Arg Ser Arg Lys Tyr Ser Ser Trp
 50                  55                  60

Tyr Val Ala Leu Lys Arg Thr Gly Gln Tyr Lys Leu Gly Pro Lys Thr
 65                  70                  75                  80

Gly Pro Gly Gln Lys Ala Ile Leu Phe Leu Pro Met Ser Ala Lys Ser
                85                  90                  95

<210> SEQ ID NO 138
<211> LENGTH: 155
<212> TYPE: PRT
<213> ORGANISM: Choloepus hoffmanni

<400> SEQUENCE: 138

Met Ala Ala Gly Ser Ile Thr Thr Leu Pro Ala Leu Pro Glu Asp Gly
 1               5                  10                  15

Gly Ser Gly Ala Leu Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Gln Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
            115                 120                 125

Arg Thr Gly Gln Tyr Lys Leu Gly Pro Lys Thr Gly Pro Gly Gln Lys
```

```
            130                 135                 140

Ala Ile Leu Phe Leu Pro Met Ser Ala Lys Ser
145                 150                 155

<210> SEQ ID NO 139
<211> LENGTH: 155
<212> TYPE: PRT
<213> ORGANISM: Bubalus bubalis

<400> SEQUENCE: 139

Met Ala Ala Gly Ser Ile Thr Thr Leu Pro Pro Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Ser Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 140
<211> LENGTH: 155
<212> TYPE: PRT
<213> ORGANISM: Canis lupus familiaris

<400> SEQUENCE: 140

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Lys Gly Gly Phe Phe Leu Arg Ile His Pro Asp Gly Arg
        35                  40                  45

Val Asp Gly Val Arg Glu Lys Ser Asp Pro His Val Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
```

<210> SEQ ID NO 141
<211> LENGTH: 154
<212> TYPE: PRT
<213> ORGANISM: Rattus norvegicus

<400> SEQUENCE: 141

Met Ala Ala Gly Ser Ile Thr Ser Leu Pro Ala Leu Pro Glu Asp Gly
1               5                   10                  15
Gly Gly Ala Phe Pro Pro Gly His Phe Lys Asp Pro Lys Arg Leu Tyr
            20                  25                  30
Cys Lys Asn Gly Gly Phe Phe Leu Arg Ile His Pro Asp Gly Arg Val
        35                  40                  45
Asp Gly Val Arg Glu Lys Ser Asp Pro His Val Lys Leu Gln Leu Gln
    50                  55                  60
Ala Glu Glu Arg Gly Val Val Ser Ile Lys Gly Val Cys Ala Asn Arg
65                  70                  75                  80
Tyr Leu Ala Met Lys Glu Asp Gly Arg Leu Leu Ala Ser Lys Cys Val
                85                  90                  95
Thr Glu Glu Cys Phe Phe Phe Glu Arg Leu Glu Ser Asn Asn Tyr Asn
            100                 105                 110
Thr Tyr Arg Ser Arg Lys Tyr Ser Ser Trp Tyr Val Ala Leu Lys Arg
        115                 120                 125
Thr Gly Gln Tyr Lys Leu Gly Ser Lys Thr Gly Pro Gly Gln Lys Ala
    130                 135                 140
Ile Leu Phe Leu Pro Met Ser Ala Lys Ser
145                 150

<210> SEQ ID NO 142
<211> LENGTH: 134
<212> TYPE: PRT
<213> ORGANISM: Heterocephalus glaber

<400> SEQUENCE: 142

Pro Pro Gly His Phe Lys Asp Pro Lys Arg Leu Tyr Cys Lys Asn Gly
1               5                   10                  15
Gly Phe Phe Leu Arg Ile His Pro Asp Gly Arg Val Asp Gly Val Arg
            20                  25                  30
Glu Lys Ser Asp Pro His Val Lys Leu Gln Leu Gln Ala Glu Glu Arg
        35                  40                  45
Gly Val Val Ser Ile Lys Gly Val Cys Ala Asn Arg Tyr Leu Ala Met
    50                  55                  60
Lys Glu Asp Gly Arg Leu Leu Ala Ser Lys Cys Val Thr Asp Glu Cys
65                  70                  75                  80
Phe Phe Phe Glu Arg Leu Glu Ser Asn Asn Tyr Asn Thr Tyr Arg Ser
                85                  90                  95
Arg Lys Tyr Ser Ser Trp Tyr Val Ala Leu Lys Arg Thr Gly Gln Tyr
            100                 105                 110
Lys Leu Gly Ser Lys Thr Gly Pro Gly Gln Lys Ala Ile Leu Phe Leu
        115                 120                 125
Pro Met Ser Ala Lys Ser
    130

<210> SEQ ID NO 143
<211> LENGTH: 155
<212> TYPE: PRT

<213> ORGANISM: Otolemur garnettii

<400> SEQUENCE: 143

Met Ala Ala Gly Ser Ile Thr Thr Leu Pro Ser Leu Pro Glu Asp Gly
1               5                   10                  15

Gly Ser Asp Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro Tyr Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Leu
                85                  90                  95

Ile Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 144
<211> LENGTH: 154
<212> TYPE: PRT
<213> ORGANISM: Mus musculus

<400> SEQUENCE: 144

Met Ala Ala Ser Gly Ile Thr Ser Leu Pro Ala Leu Pro Glu Asp Gly
1               5                   10                  15

Gly Ala Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150

<210> SEQ ID NO 145
<211> LENGTH: 144
<212> TYPE: PRT
<213> ORGANISM: Ictidomys tridecemlineatus

<400> SEQUENCE: 145

Leu Pro Glu Asp Gly Gly Gly Ala Phe Pro Gly His Phe Lys
1               5                   10                  15

Asp Pro Lys Arg Leu Tyr Cys Lys Asn Gly Gly Phe Phe Leu Arg Ile
            20                  25                  30

His Pro Asp Gly Arg Val Asp Gly Val Arg Glu Lys Ser Asp Pro His
        35                  40                  45

Ile Lys Leu Gln Leu Gln Ala Glu Asp Arg Gly Val Val Ser Ile Lys
    50                  55                  60

Gly Val Cys Ala Asn Arg Tyr Leu Ala Met Lys Glu Asp Gly Arg Leu
65                  70                  75                  80

Leu Ala Ser Lys Cys Val Thr Asp Glu Cys Phe Phe Phe Glu Arg Leu
                85                  90                  95

Glu Ser Asn Asn Tyr Asn Thr Tyr Arg Ser Arg Lys Tyr Ser Ser Trp
                100                 105                 110

Tyr Val Ala Leu Lys Arg Thr Gly Gln Tyr Lys Leu Gly Ser Lys Thr
            115                 120                 125

Gly Pro Gly Gln Lys Ala Ile Leu Phe Leu Pro Met Ser Ala Lys Ser
130                 135                 140

<210> SEQ ID NO 146
<211> LENGTH: 106
<212> TYPE: PRT
<213> ORGANISM: Felis catus

<400> SEQUENCE: 146

His Phe Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Ser Ser Trp Tyr Val Ala Leu Lys Arg Thr
            100                 105

<210> SEQ ID NO 147
<211> LENGTH: 96
<212> TYPE: PRT
<213> ORGANISM: Cavia porcellus

<400> SEQUENCE: 147

Val Lys Leu Gln Leu Gln Ala Glu Asp Arg Gly Val Val Ser Ile Lys
1               5                   10                  15

Gly Val Cys Ala Asn Arg Tyr Leu Ala Met Lys Glu Asp Gly Arg Leu
            20                  25                  30

Leu Ala Ser Lys Cys Val Thr Asp Glu Cys Phe Phe Phe Glu Arg Leu
        35                  40                  45

Glu Ser Asn Asn Tyr Asn Thr Tyr Arg Ser Arg Lys Tyr Ser Ser Trp
    50                  55                  60

Tyr Val Ala Leu Lys Arg Thr Gly Gln Tyr Lys Leu Gly Ser Lys Thr
65                  70                  75                  80

Gly Pro Gly Gln Lys Ala Ile Leu Phe Leu Pro Met Ser Ala Lys Ser
            85                  90                  95

<210> SEQ ID NO 148
<211> LENGTH: 156
<212> TYPE: PRT
<213> ORGANISM: Sarcophilus harrisii

<400> SEQUENCE: 148

Met Ala Ala Gly Ser Ile Thr Thr Leu Pro Ala Leu Ala Gly Asp Gly
1               5                   10                  15

Ala Ser Gly Gly Ala Phe Pro Pro Gly His Phe Gln Asp Pro Lys Arg
            20                  25                  30

Leu Tyr Cys Lys Asn Gly Gly Phe Phe Leu Arg Ile His Pro Asp Gly
        35                  40                  45

His Val Asp Gly Ile Arg Glu Lys Ser Asp Pro His Ile Lys Leu Gln
    50                  55                  60

Leu Gln Ala Glu Glu Arg Gly Val Val Ser Ile Lys Gly Val Cys Ala
65                  70                  75                  80

Asn Arg Tyr Leu Ala Met Lys Glu Asp Gly Arg Leu Leu Ala Leu Lys
                85                  90                  95

Cys Val Thr Glu Glu Cys Phe Phe Phe Glu Arg Leu Glu Ser Asn Asn
            100                 105                 110

Tyr Asn Thr Tyr Arg Ser Arg Lys Tyr Ser Asn Trp Tyr Val Ala Leu
        115                 120                 125

Lys Arg Thr Gly Gln Tyr Lys Leu Gly Ser Lys Thr Gly Pro Gly Gln
    130                 135                 140

Lys Ala Ile Leu Phe Leu Pro Met Ser Ala Lys Ser
145                 150                 155

<210> SEQ ID NO 149
<211> LENGTH: 156
<212> TYPE: PRT
<213> ORGANISM: Monodelphis domestica

<400> SEQUENCE: 149

Met Ala Ala Gly Ser Ile Thr Thr Leu Pro Ala Leu Ser Gly Asp Gly
1               5                   10                  15

Gly Gly Gly Gly Ala Phe Pro Pro Gly His Phe Lys Asp Pro Lys Arg
            20                  25                  30

Leu Tyr Cys Lys Asn Gly Gly Phe Phe Leu Arg Ile His Pro Asp Gly
        35                  40                  45

Arg Val Asp Gly Ile Arg Glu Lys Ser Asp Pro Asn Ile Lys Leu Gln
    50                  55                  60

Leu Gln Ala Glu Glu Arg Gly Val Val Ser Ile Lys Gly Val Cys Ala
65                  70                  75                  80

Asn Arg Tyr Leu Ala Met Lys Glu Asp Gly Arg Leu Leu Ala Leu Lys
                85                  90                  95

Tyr Val Thr Glu Glu Cys Phe Phe Phe Glu Arg Leu Glu Ser Asn Asn
            100                 105                 110

Tyr Asn Thr Tyr Arg Ser Arg Lys Tyr Ser Asn Trp Tyr Val Ala Leu
        115                 120                 125

Lys Arg Thr Gly Gln Tyr Lys Leu Gly Ser Lys Thr Gly Pro Gly Gln
    130                 135                 140

Lys Ala Ile Leu Phe Leu Pro Met Ser Ala Lys Ser
145                 150                 155

<210> SEQ ID NO 150
<211> LENGTH: 155
<212> TYPE: PRT
<213> ORGANISM: Oryctolagus cuniculus

<400> SEQUENCE: 150

```
Met Ala Ala Glu Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 151
<211> LENGTH: 125
<212> TYPE: PRT
<213> ORGANISM: Meleagris gallopavo

<400> SEQUENCE: 151

```
Arg Leu Tyr Cys Lys Asn Gly Gly Phe Phe Leu Arg Ile Asn Pro Asp
1               5                   10                  15

Gly Arg Val Asp Gly Val Arg Glu Lys Ser Asp Pro His Ile Lys Leu
            20                  25                  30

Gln Leu Gln Ala Glu Glu Arg Gly Val Val Ser Ile Lys Gly Val Ser
        35                  40                  45

Ala Asn Arg Phe Leu Ala Met Lys Glu Asp Gly Arg Leu Leu Ala Leu
    50                  55                  60

Lys Cys Ala Thr Glu Glu Cys Phe Phe Phe Glu Arg Leu Glu Ser Asn
65                  70                  75                  80

Asn Tyr Asn Thr Tyr Arg Ser Arg Lys Tyr Ser Asp Trp Tyr Val Ala
                85                  90                  95

Leu Lys Arg Thr Gly Gln Tyr Lys Pro Gly Pro Lys Thr Gly Pro Gly
            100                 105                 110

Gln Lys Ala Ile Leu Phe Leu Pro Met Ser Ala Lys Ser
        115                 120                 125
```

<210> SEQ ID NO 152
<211> LENGTH: 158
<212> TYPE: PRT
<213> ORGANISM: Gallus gallus

<400> SEQUENCE: 152

Met Ala Ala Gly Ala Gly Ser Ile Thr Thr Leu Pro Ala Leu Pro
1               5                   10                  15

Asp Asp Gly Gly Gly Ala Phe Pro Pro Gly His Phe Lys Asp Pro
            20                  25                  30

Lys Arg Leu Tyr Cys Lys Asn Gly Gly Phe Phe Leu Arg Ile Asn Pro
            35                  40                  45

Asp Gly Arg Val Asp Gly Val Arg Glu Lys Ser Asp Pro His Ile Lys
50                  55                  60

Leu Gln Leu Gln Ala Glu Arg Gly Val Val Ser Ile Lys Gly Val
65                  70                  75                  80

Ser Ala Asn Arg Phe Leu Ala Met Lys Glu Asp Gly Arg Leu Leu Ala
                85                  90                  95

Leu Lys Cys Ala Thr Glu Glu Cys Phe Phe Phe Glu Arg Leu Glu Ser
            100                 105                 110

Asn Asn Tyr Asn Thr Tyr Arg Ser Arg Lys Tyr Ser Asp Trp Tyr Val
            115                 120                 125

Ala Leu Lys Arg Thr Gly Gln Tyr Lys Pro Gly Pro Lys Thr Gly Pro
            130                 135                 140

Gly Gln Lys Ala Ile Leu Phe Leu Pro Met Ser Ala Lys Ser
145                 150                 155

<210> SEQ ID NO 153
<211> LENGTH: 153
<212> TYPE: PRT
<213> ORGANISM: Taeniopygia guttata

<400> SEQUENCE: 153

Met Ala Ala Gly Gly Ile Ala Thr Leu Pro Asp Asp Gly Gly Ser
1               5                   10                  15

Gly Ala Phe Pro Pro Gly His Phe Lys Asp Pro Lys Arg Leu Tyr Cys
            20                  25                  30

Lys Asn Gly Gly Phe Phe Leu Arg Ile Asn Pro Asp Gly Lys Val Asp
            35                  40                  45

Gly Val Arg Glu Lys Ser Asp Pro His Ile Lys Leu Gln Leu Gln Ala
50                  55                  60

Glu Glu Arg Gly Val Val Ser Ile Lys Gly Val Ser Ala Asn Arg Phe
65                  70                  75                  80

Leu Ala Met Lys Glu Asp Gly Arg Leu Leu Ala Leu Lys Tyr Ala Thr
                85                  90                  95

Glu Glu Cys Phe Phe Phe Glu Arg Leu Glu Ser Asn Asn Tyr Asn Thr
            100                 105                 110

Tyr Arg Ser Arg Lys Tyr Ser Asp Trp Tyr Val Ala Leu Lys Arg Thr
            115                 120                 125

Gly Gln Tyr Lys Pro Gly Pro Lys Thr Gly Pro Gly Gln Lys Ala Ile
            130                 135                 140

Leu Phe Leu Pro Met Ser Ala Lys Ser
145                 150

<210> SEQ ID NO 154
<211> LENGTH: 155
<212> TYPE: PRT
<213> ORGANISM: Cynops pyrrhogaster

<400> SEQUENCE: 154

Met Ala Ala Gly Ser Ile Thr Ser Leu Pro Ala Leu Pro Glu Asp Gly
1               5                   10                  15

Asn Gly Gly Thr Phe Thr Pro Gly Gly Phe Lys Glu Pro Lys Arg Leu
            20                  25                  30

Tyr Cys Lys Asn Gly Gly Phe Phe Leu Arg Ile Asn Ser Asp Gly Lys
            35                  40                  45

Val Asp Gly Ala Arg Glu Lys Ser Asp Ser Tyr Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Asp Asp Gly Arg Leu Met Ala Leu Lys Trp
                85                  90                  95

Ile Thr Asp Glu Cys Phe Phe Phe Glu Arg Leu Glu Ser Asn Asn Tyr
            100                 105                 110

Asn Thr Tyr Arg Ser Arg Lys Tyr Ser Asp Trp Tyr Val Ala Leu Lys
            115                 120                 125

Arg Thr Gly Gln Tyr Lys Asn Gly Ser Lys Thr Gly Ala Gly Gln Lys
    130                 135                 140

Ala Ile Leu Phe Leu Pro Met Ser Ala Lys Ser
145                 150                 155

<210> SEQ ID NO 155
<211> LENGTH: 155
<212> TYPE: PRT
<213> ORGANISM: Xenopus laevis

<400> SEQUENCE: 155

Met Ala Ala Gly Ser Ile Thr Thr Leu Pro Thr Glu Ser Glu Asp Gly
1               5                   10                  15

Gly Asn Thr Pro Phe Ser Pro Gly Ser Phe Lys Asp Pro Lys Arg Leu
            20                  25                  30

Tyr Cys Lys Asn Gly Gly Phe Phe Leu Arg Ile Asn Ser Asp Gly Arg
            35                  40                  45

Val Asp Gly Ser Arg Asp Lys Ser Asp Ser His Ile Lys Leu Gln Leu
    50                  55                  60

Gln Ala Val Glu Arg Gly Val Val Ser Ile Lys Gly Ile Thr Ala Asn
65                  70                  75                  80

Arg Tyr Leu Ala Met Lys Glu Asp Gly Arg Leu Thr Ser Leu Arg Cys
                85                  90                  95

Ile Thr Asp Glu Cys Phe Phe Phe Glu Arg Leu Glu Ala Asn Asn Tyr
            100                 105                 110

Asn Thr Tyr Arg Ser Arg Lys Tyr Ser Ser Trp Tyr Val Ala Leu Lys
            115                 120                 125

Arg Thr Gly Gln Tyr Lys Asn Gly Ser Ser Thr Gly Pro Gly Gln Lys
    130                 135                 140

Ala Ile Leu Phe Leu Pro Met Ser Ala Lys Ser
145                 150                 155

<210> SEQ ID NO 156
<211> LENGTH: 156
<212> TYPE: PRT
<213> ORGANISM: Didelphis albiventris

<400> SEQUENCE: 156

Met Ala Ala Gly Ser Ile Thr Thr Leu Pro Ala Leu Ser Gly Asp Gly
1               5                   10                  15

Gly Gly Gly Gly Ala Phe Pro Pro Gly His Phe Lys Asp Pro Lys Arg
            20                  25                  30

Leu Tyr Cys Lys Asn Gly Gly Phe Leu Arg Ile His Pro Asp Gly
                35                  40                  45

Arg Val Asp Gly Ile Arg Glu Lys Ser Asp Pro Asn Ile Lys Leu Gln
 50                  55                  60

Leu Gln Ala Glu Glu Arg Gly Val Val Ser Ile Lys Gly Val Cys Ala
 65                  70                  75                  80

Asn Arg Tyr Leu Ala Met Lys Glu Asp Gly Arg Leu Leu Ala Leu Lys
                 85                  90                  95

Tyr Val Thr Glu Glu Cys Phe Phe Glu Arg Leu Glu Ser Asn Asn
                100                 105                 110

Tyr Asn Thr Tyr Arg Ser Arg Lys Tyr Ser Asn Trp Tyr Val Ala Leu
                115                 120                 125

Lys Arg Thr Gly Gln Tyr Lys Leu Gly Ser Lys Thr Gly Pro Gly Gln
                130                 135                 140

Lys Ala Ile Leu Phe Ser Pro Cys Leu Leu Arg Cys
145                 150                 155

<210> SEQ ID NO 157
<211> LENGTH: 96
<212> TYPE: PRT
<213> ORGANISM: Myotis lucifugus

<400> SEQUENCE: 157

Val Lys Leu Gln Leu Gln Ala Glu Glu Arg Gly Val Val Ser Ile Lys
 1               5                  10                  15

Gly Val Cys Ala Asn Arg Tyr Leu Ala Met Lys Glu Asp Gly Arg Leu
                20                  25                  30

Gln Ala Ser Lys Cys Val Thr Asp Glu Cys Phe Phe Phe Glu Arg Leu
                35                  40                  45

Glu Ser Asn Asn Tyr Asn Thr Tyr Arg Ser Arg Lys Tyr Ser Ser Trp
 50                  55                  60

Tyr Val Ala Leu Lys Arg Asn Gly Gln Tyr Lys Leu Gly Pro Lys Thr
 65                  70                  75                  80

Gly Pro Gly Gln Lys Ala Ile Leu Phe Leu Pro Met Ser Ala Lys Ser
                 85                  90                  95

<210> SEQ ID NO 158
<211> LENGTH: 140
<212> TYPE: PRT
<213> ORGANISM: Anolis carolinensis

<400> SEQUENCE: 158

Ala Ala Ala Ala Ser Phe Pro Pro Gly Pro Phe Lys Asp Pro Lys Arg
 1               5                  10                  15

Leu Tyr Cys Lys Asn Gly Gly Phe Phe Leu Arg Ile Asn Pro Asp Gly
                20                  25                  30

Gly Val Asp Gly Val Arg Glu Lys Ser Asp Pro Asn Ile Lys Leu Leu
                35                  40                  45

Leu Gln Ala Glu Glu Arg Gly Val Val Ser Ile Lys Gly Val Cys Ala
 50                  55                  60

Asn Arg Phe Leu Ala Met Asn Glu Asp Gly Arg Leu Leu Ala Leu Lys
 65                  70                  75                  80

Tyr Val Thr Asp Glu Cys Phe Phe Glu Arg Leu Glu Ser Asn Asn
                 85                  90                  95

Tyr Asn Thr Tyr Arg Ser Arg Lys Tyr Arg Asp Trp Tyr Ile Ala Leu
                100                 105                 110

```
Lys Arg Thr Gly Gln Tyr Lys Leu Gly Pro Lys Thr Gly Arg Gly Gln
            115                 120                 125

Lys Ala Ile Leu Phe Leu Pro Met Ser Ala Lys Ser
    130                 135                 140

<210> SEQ ID NO 159
<211> LENGTH: 94
<212> TYPE: PRT
<213> ORGANISM: Dasypus novemcinctus

<400> SEQUENCE: 159

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro Asn Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Arg Glu Asp Gly Arg Leu Gln Ala Ser
                85                  90

<210> SEQ ID NO 160
<211> LENGTH: 189
<212> TYPE: PRT
<213> ORGANISM: Tupaia belangeri

<400> SEQUENCE: 160

Ala Gly Val Arg Ala Glu Arg Glu Ala Pro Gly Ser Gly Asp Ser
1               5                   10                  15

Arg Gly Thr Asp Pro Ala Ala Arg Ser Leu Ile Arg Arg Pro Asp Ala
            20                  25                  30

Ala Ala Arg Glu Ala Leu Leu Gly Ala Arg Ser Arg Val Gln Gly Ser
        35                  40                  45

Ser Thr Ser Trp Pro Ala Ser Ser Arg Thr Gly Ile Lys Leu Pro Asp
    50                  55                  60

Asp Ser Gly Gln Gly Met Gly Gly Tyr Pro Leu Asp Arg Pro Ser Arg
65                  70                  75                  80

Ser Thr Gly Arg Gly Leu Gly Gly Ala Pro Asp Pro Ala Val Lys Leu
                85                  90                  95

Gln Leu Gln Ala Glu Glu Arg Gly Val Val Ser Ile Lys Gly Val Cys
            100                 105                 110

Ala Asn Arg Tyr Leu Ala Met Lys Glu Asp Gly Arg Leu Leu Ala Ser
        115                 120                 125

Lys Cys Val Thr Asp Glu Cys Phe Phe Phe Glu Arg Leu Glu Ser Asn
    130                 135                 140

Asn Tyr Asn Thr Tyr Arg Ser Arg Lys Tyr Ser Ser Trp Tyr Val Ala
145                 150                 155                 160

Leu Lys Arg Thr Gly Gln Tyr Lys Leu Gly Ser Lys Thr Gly Pro Gly
                165                 170                 175

Gln Lys Ala Ile Leu Phe Leu Pro Met Ser Ala Lys Ser
            180                 185

<210> SEQ ID NO 161
<211> LENGTH: 154
```

<212> TYPE: PRT
<213> ORGANISM: Xenopus silurana tropicalis

<400> SEQUENCE: 161

```
Met Ala Ala Gly Ser Ile Thr Thr Leu Pro Thr Glu Ser Glu Asp Gly
1               5                   10                  15

Asn Thr Pro Phe Pro Pro Gly Asn Phe Lys Asp Pro Lys Arg Leu Tyr
            20                  25                  30

Cys Lys Asn Gly Gly Tyr Phe Leu Arg Ile Asn Ser Asp Gly Arg Val
        35                  40                  45

Asp Gly Ser Arg Asp Lys Ser Asp Leu His Ile Lys Leu Gln Leu Gln
    50                  55                  60

Ala Val Glu Arg Gly Val Val Ser Ile Lys Gly Ile Thr Ala Asn Arg
65                  70                  75                  80

Tyr Leu Ala Met Lys Glu Asp Gly Arg Leu Thr Ser Leu Lys Cys Ile
                85                  90                  95

Thr Asp Glu Cys Phe Phe Tyr Glu Arg Leu Glu Ala Asn Asn Tyr Asn
            100                 105                 110

Thr Tyr Arg Ser Arg Lys Asn Asn Ser Trp Tyr Val Ala Leu Lys Arg
        115                 120                 125

Thr Gly Gln Tyr Lys Asn Gly Ser Thr Thr Gly Pro Gly Gln Lys Ala
    130                 135                 140

Ile Leu Phe Leu Pro Met Ser Ala Lys Ser
145                 150
```

<210> SEQ ID NO 162
<211> LENGTH: 155
<212> TYPE: PRT
<213> ORGANISM: Latimeria chalumnae

<400> SEQUENCE: 162

```
Met Ala Ala Gly Gly Ile Thr Thr Leu Pro Ala Val Pro Glu Asp Gly
1               5                   10                  15

Gly Ser Ser Thr Phe Pro Pro Gly Asn Phe Lys Glu Pro Lys Arg Leu
            20                  25                  30

Tyr Cys Lys Asn Gly Gly Tyr Phe Leu Arg Ile Asn Pro Asp Gly Arg
        35                  40                  45

Val Asp Gly Thr Arg Glu Lys Asn Asp Pro Tyr Ile Lys Leu Gln Leu
    50                  55                  60

Gln Ala Glu Ser Ile Gly Val Val Ser Ile Lys Gly Val Cys Ser Asn
65                  70                  75                  80

Arg Tyr Leu Ala Met Asn Glu Asp Cys Arg Leu Phe Gly Leu Lys Tyr
                85                  90                  95

Pro Thr Asp Glu Cys Phe Phe His Glu Arg Leu Glu Ser Asn Asn Tyr
            100                 105                 110

Asn Thr Tyr Arg Ser Lys Lys Tyr Ser Asp Trp Tyr Val Ala Leu Lys
        115                 120                 125

Arg Thr Gly Gln Tyr Lys Pro Gly Lys Thr Gly Leu Gly Gln Lys
    130                 135                 140

Ala Ile Leu Phe Leu Pro Met Ser Ala Lys Ser
145                 150                 155
```

<210> SEQ ID NO 163
<211> LENGTH: 155
<212> TYPE: PRT
<213> ORGANISM: Tetraodon nigroviridis

<400> SEQUENCE: 163

Met Ala Thr Gly Gly Ile Thr Thr Leu Pro Ser Thr Pro Glu Asp Gly
1               5                   10                  15

Gly Ser Ser Gly Phe Pro Pro Gly Ser Phe Lys Asp Pro Lys Arg Leu
            20                  25                  30

Tyr Cys Lys Asn Gly Gly Phe Phe Leu Arg Ile Lys Ser Asp Gly Val
        35                  40                  45

Val Asp Gly Ile Arg Glu Lys Ser Asp Pro His Ile Lys Leu Gln Leu
    50                  55                  60

Gln Ala Thr Ser Val Gly Glu Val Val Ile Lys Gly Val Cys Ala Asn
65                  70                  75                  80

Arg Tyr Leu Ala Met Asn Arg Asp Gly Arg Leu Phe Gly Thr Lys Arg
                85                  90                  95

Ala Thr Asp Glu Cys His Phe Leu Glu Arg Leu Glu Ser Asn Asn Tyr
            100                 105                 110

Asn Thr Tyr Arg Ser Arg Lys Tyr Pro Thr Met Phe Val Gly Leu Thr
        115                 120                 125

Arg Thr Gly Gln Tyr Lys Ser Gly Ser Lys Thr Gly Pro Gly Gln Lys
    130                 135                 140

Ala Ile Leu Phe Leu Pro Met Ser Ala Lys Cys
145                 150                 155

<210> SEQ ID NO 164
<211> LENGTH: 155
<212> TYPE: PRT
<213> ORGANISM: Gasterosteus aculeatus

<400> SEQUENCE: 164

Met Ala Thr Ala Gly Phe Ala Thr Leu Pro Ser Thr Pro Glu Asp Gly
1               5                   10                  15

Gly Ser Gly Gly Phe Thr Pro Gly Gly Phe Lys Asp Pro Lys Arg Leu
            20                  25                  30

Tyr Cys Lys Asn Gly Gly Phe Phe Leu Arg Ile Arg Ser Asp Gly Gly
        35                  40                  45

Val Asp Gly Ile Arg Glu Lys Ser Asp Ala His Ile Lys Leu Gln Ile
    50                  55                  60

Gln Ala Thr Ser Val Gly Glu Val Val Ile Lys Gly Val Cys Ala Asn
65                  70                  75                  80

Arg Tyr Leu Ala Met Asn Arg Asp Gly Arg Leu Phe Gly Val Arg Arg
                85                  90                  95

Ala Thr Asp Glu Cys Tyr Phe Leu Glu Arg Leu Glu Ser Asn Asn Tyr
            100                 105                 110

Asn Thr Tyr Arg Ser Arg Lys Tyr Pro Gly Met Tyr Val Ala Leu Lys
        115                 120                 125

Arg Thr Gly Gln Tyr Lys Ser Gly Ser Lys Thr Gly Pro Gly Gln Lys
    130                 135                 140

Ala Ile Leu Phe Leu Pro Met Ser Ala Lys Cys
145                 150                 155

<210> SEQ ID NO 165
<211> LENGTH: 155
<212> TYPE: PRT
<213> ORGANISM: Takifugu rubripes

<400> SEQUENCE: 165

Met Ala Thr Gly Gly Ile Thr Thr Leu Pro Ser Thr Pro Glu Asp Gly

```
               1               5                  10                 15
Gly Ser Gly Gly Phe Pro Pro Gly Ser Phe Lys Asp Pro Lys Arg Leu
            20                  25                 30

Tyr Cys Lys Asn Gly Gly Phe Phe Leu Arg Ile Arg Ser Asp Gly Ala
            35                  40                 45

Val Asp Gly Thr Arg Glu Lys Thr Asp Pro His Ile Lys Leu Gln Leu
 50                  55                 60

Gln Ala Thr Ser Val Gly Glu Val Val Ile Lys Gly Val Cys Ala Asn
 65                  70                 75                  80

Arg Tyr Leu Ala Met Asn Arg Asp Gly Arg Leu Phe Gly Met Lys Arg
                85                  90                 95

Ala Thr Asp Glu Cys His Phe Leu Glu Arg Leu Glu Ser Asn Asn Tyr
                100                 105                110

Asn Thr Tyr Arg Ser Arg Lys Tyr Pro Asn Met Phe Val Gly Leu Thr
                115                 120                125

Arg Thr Gly Asn Tyr Lys Ser Gly Thr Lys Thr Gly Pro Cys Gln Lys
                130                 135                140

Ala Ile Leu Phe Leu Pro Met Ser Ala Lys Tyr
145                 150                 155

<210> SEQ ID NO 166
<211> LENGTH: 155
<212> TYPE: PRT
<213> ORGANISM: Oncorhynchus mykiss

<400> SEQUENCE: 166

Met Ala Thr Gly Glu Ile Thr Thr Leu Pro Ala Thr Pro Glu Asp Gly
 1               5                  10                 15

Gly Ser Gly Gly Phe Leu Pro Gly Asn Phe Lys Glu Pro Lys Arg Leu
            20                  25                 30

Tyr Cys Lys Asn Gly Gly Tyr Phe Leu Arg Ile Asn Ser Asn Gly Ser
            35                  40                 45

Val Asp Gly Ile Arg Asp Lys Asn Asp Pro His Asn Lys Leu Gln Leu
 50                  55                 60

Gln Ala Thr Ser Val Gly Glu Val Val Ile Lys Gly Val Ser Ala Asn
 65                  70                 75                  80

Arg Tyr Leu Ala Met Asn Ala Asp Gly Arg Leu Phe Gly Pro Arg Arg
                85                  90                 95

Thr Thr Asp Glu Cys Tyr Phe Met Glu Arg Leu Glu Ser Asn Asn Tyr
                100                 105                110

Asn Thr Tyr Arg Ser Arg Lys Tyr Pro Glu Met Tyr Val Ala Leu Lys
                115                 120                125

Arg Thr Gly Gln Tyr Lys Ser Gly Ser Lys Thr Gly Pro Gly Gln Lys
                130                 135                140

Ala Ile Leu Phe Leu Pro Met Ser Ala Arg Arg
145                 150                 155

<210> SEQ ID NO 167
<211> LENGTH: 150
<212> TYPE: PRT
<213> ORGANISM: Salmo salar

<400> SEQUENCE: 167

Met Ala Thr Gly Glu Ile Thr Thr Leu Pro Ala Thr Pro Glu Asp Gly
 1               5                  10                 15

Gly Ser Gly Gly Phe Pro Pro Gly Asn Phe Lys Asp Pro Lys Arg Leu
```

```
                20                  25                  30

Tyr Cys Lys Asn Gly Gly Tyr Phe Leu Arg Ile Asn Ser Asn Gly Ser
            35                  40                  45

Val Asp Gly Ile Arg Glu Lys Asn Asp Pro His Lys Gln Pro Gln Phe
 50                  55                  60

Val Arg Ala Trp Thr Leu Gln Gly Val Lys Arg Ser Thr Gly Met Leu
 65                  70                  75                  80

Ala His Val Asp Ser Asn Ala Ser His Asn Cys Val Lys Val Ala Gly
                 85                  90                  95

Cys Ser Leu Gly Glu Phe Gly Ser Met Ser Asn Arg Pro His Asn Arg
            100                 105                 110

Arg Pro Arg Val Ala Thr Pro Ala Gln Asp Leu His Ile Arg Leu Leu
            115                 120                 125

His Leu Arg Asp Arg Leu Lys Pro Ala Thr Arg Thr Ala Asp Lys Thr
            130                 135                 140

Glu Glu Tyr Phe Cys Leu
145                 150

<210> SEQ ID NO 168
<211> LENGTH: 154
<212> TYPE: PRT
<213> ORGANISM: Danio rerio

<400> SEQUENCE: 168

Met Ala Thr Gly Gly Ile Thr Thr Leu Pro Ala Ala Pro Asp Ala Glu
  1               5                  10                  15

Asn Ser Ser Phe Pro Ala Gly Ser Phe Arg Asp Pro Lys Arg Leu Tyr
             20                  25                  30

Cys Lys Asn Gly Gly Phe Phe Leu Arg Ile Asn Ala Asp Gly Arg Val
            35                  40                  45

Asp Gly Ala Arg Asp Lys Ser Asp Pro His Ile Arg Leu Gln Leu Gln
 50                  55                  60

Ala Thr Ala Val Gly Glu Val Leu Ile Lys Gly Ile Cys Thr Asn Arg
 65                  70                  75                  80

Phe Leu Ala Met Asn Ala Asp Gly Arg Leu Phe Gly Thr Lys Arg Thr
                 85                  90                  95

Thr Asp Glu Cys Tyr Phe Leu Glu Arg Leu Glu Ser Asn Asn Tyr Asn
            100                 105                 110

Thr Tyr Arg Ser Arg Lys Tyr Pro Asp Trp Tyr Val Ala Leu Lys Arg
            115                 120                 125

Thr Gly Gln Tyr Lys Ser Gly Ser Lys Thr Ser Pro Gly Gln Lys Ala
            130                 135                 140

Ile Leu Phe Leu Pro Met Ser Ala Lys Cys
145                 150

<210> SEQ ID NO 169
<211> LENGTH: 155
<212> TYPE: PRT
<213> ORGANISM: Oreochromis niloticus

<400> SEQUENCE: 169

Met Ala Thr Gly Gly Ile Thr Thr Leu Pro Ala Thr Pro Glu Asp Gly
  1               5                  10                  15

Gly Ser Ser Gly Phe Pro Pro Gly Asn Phe Lys Asp Pro Lys Arg Leu
             20                  25                  30

Tyr Cys Lys Asn Gly Gly Phe Phe Leu Arg Ile Lys Ser Asp Gly Gly
```

```
                35                  40                  45
Val Asp Gly Ile Arg Glu Lys Asn Asp Pro His Ile Lys Leu Gln Leu
 50                  55                  60

Gln Ala Thr Ser Val Gly Glu Val Val Ile Lys Gly Ile Cys Ala Asn
 65                  70                  75                  80

Arg Tyr Leu Ala Met Asn Arg Asp Gly Arg Leu Phe Gly Ala Arg Arg
                 85                  90                  95

Ala Thr Asp Glu Cys Tyr Phe Leu Glu Arg Leu Glu Ser Asn Asn Tyr
                100                 105                 110

Asn Thr Tyr Arg Ser Arg Lys Tyr Pro Asn Met Tyr Val Ala Leu Lys
                115                 120                 125

Arg Thr Gly Gln Tyr Lys Ser Gly Ser Lys Thr Gly Pro Gly Gln Lys
                130                 135                 140

Ala Ile Leu Phe Leu Pro Met Ser Ala Lys Cys
145                 150                 155

<210> SEQ ID NO 170
<211> LENGTH: 155
<212> TYPE: PRT
<213> ORGANISM: Oryzias latipes

<400> SEQUENCE: 170

Met Ala Thr Gly Glu Ile Thr Thr Leu Pro Ser Pro Ala Glu Asn Ser
  1               5                  10                  15

Arg Ser Asp Gly Phe Pro Pro Gly Asn Tyr Lys Asp Pro Lys Arg Leu
                 20                  25                  30

Tyr Cys Lys Asn Gly Gly Leu Phe Leu Arg Ile Lys Pro Asp Gly Gly
                 35                  40                  45

Val Asp Gly Ile Arg Glu Lys Lys Asp Pro His Val Lys Leu Arg Leu
 50                  55                  60

Gln Ala Thr Ser Ala Gly Glu Val Val Ile Lys Gly Val Cys Ser Asn
 65                  70                  75                  80

Arg Tyr Leu Ala Met His Gly Asp Gly Arg Leu Phe Gly Val Arg Gln
                 85                  90                  95

Ala Thr Glu Glu Cys Tyr Phe Leu Glu Arg Leu Glu Ser Asn Asn Tyr
                100                 105                 110

Asn Thr Tyr Arg Ser Lys Lys Tyr Pro Asn Met Tyr Val Ala Leu Lys
                115                 120                 125

Arg Thr Gly Gln Tyr Lys Pro Gly Asn Lys Thr Gly Pro Gly Gln Lys
                130                 135                 140

Ala Ile Leu Phe Leu Pro Met Ser Ala Lys Tyr
145                 150                 155

<210> SEQ ID NO 171
<211> LENGTH: 468
<212> TYPE: DNA
<213> ORGANISM: Homo sapiens

<400> SEQUENCE: 171
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttacctgg ctatgaagga agatggaaga ttactggctt ctaaatgtgt tacggatgag     300
```

```
tgtttctttt ttgaacgatt ggaatctaat aactacaata cttaccggtc aaggaaatac    360
accagttggt atgtggcact gaaacgaact gggcagtata aacttggatc caaaacagga    420
cctgggcaga aagctatact ttttcttcca atgtctgcta agagctga                 468

<210> SEQ ID NO 172
<211> LENGTH: 468
<212> TYPE: DNA
<213> ORGANISM: Gorilla

<400> SEQUENCE: 172
atggcagccg ggagcatcac cacgctgccc gccttgcccg aggatggcgg cagcggcgcc     60
ttcccgcccg gccacttcaa ggaccccaag cggctgtact gcaaaaacgg gggcttcttc    120
ctgcgcatcc accccgacgg ccgagttgac ggggtccggg agaagagcga ccctcacatc    180
aagctacaac ttcaagcaga agagagagga gttgtgtcta tcaaaggagt gtgtgctaac    240
cgttaccttg ctatgaagga agatggaaga ttactggctt ctaaatgtgt tacggatgag    300
tgtttctttt ttgaacgatt ggaatctaat aactacaata cttaccggtc aaggaaatac    360
accagttggt atgtggcact gaaacgaact gggcagtata aacttggatc caaaacagga    420
cctgggcaga aagctatact ttttcttcca atgtctgcta agagctga                 468

<210> SEQ ID NO 173
<211> LENGTH: 468
<212> TYPE: DNA
<213> ORGANISM: Sumatran orangutan

<400> SEQUENCE: 173
atggcagccg ggagcatcac cacgctgccc gccttgcccg aggatggcgg cagcggcgcc     60
ttcccgccgg gccacttcaa ggaccccaag cggctgtact gcaaaaacgg gggcttcttc    120
ctgcgcatcc accccgacgg ccgagttgac ggggtccgag agaagagcga ccctcacatc    180
aaactacaac ttcaagcaga agaaagagga gttgtgtcta tcaaaggagt gtgtgctaac    240
cgctaccttg ctatgaagga agatggaaga ttactggctt ctaaatgtgt tacggatgag    300
tgtttctttt ttgaacgatt ggaatctaat aactacaata cttaccggtc aaggaaatac    360
accagttggt atgtggcact gaaacgaact gggcagtata aacttggatc caaaacagga    420
cctgggcaga aagctatact ttttcttcca atgtctgcta agagctga                 468

<210> SEQ ID NO 174
<211> LENGTH: 468
<212> TYPE: DNA
<213> ORGANISM: Rhesus monkey

<400> SEQUENCE: 174
atggcagccg ggagcatcac cacgctgccc gccttgcccg aggatggcgg cagcggcgcc     60
ttcccgcctg gccacttcaa ggaccccaag cggctgtact gcaaaaacgg gggcttcttc    120
ctgcgcattc accccgacgg ccgagttgac ggggtccggg agaagagcga ccctcacatc    180
aaattacaac ttcaagcaga agagagagga gttgtgtcta tcaaaggagt gtgtgctaac    240
cgttaccttg ctatgaagga agatggaaga ttactggctt ctaaatgtgt tacagatgag    300
tgtttctttt ttgaacgatt ggaatctaat aactacaata cttaccggtc aaggaaatac    360
accagttggt atgtggcact gaaacgaact gggcaatata aacttggatc caaaacagga    420
cctgggcaga aagctatact ttttcttcca atgtctgcta agagctga                 468
```

<210> SEQ ID NO 175
<211> LENGTH: 468
<212> TYPE: DNA
<213> ORGANISM: Chimpanzee

<400> SEQUENCE: 175

| | | | | | |
|---|---|---|---|---|---|
| atggcagccg | ggagcatcac | cacgctgccc | gccttgcccg | aggatggcgg | cagcggcgcc | 60 |
| ttcccgcccg | gccacttcaa | ggaccccaag | cggctgtact | gcaaaaacgg | gggcttcttc | 120 |
| ctgcgcatcc | accccgacgg | ccgagttgac | ggggtccggg | agaagagcga | ccctcacatc | 180 |
| aagctacaac | ttcaagcaga | agagagagga | gttgtgtcta | tcaaaggagt | gtgtgctaac | 240 |
| cgttaccttg | ctatgaagga | agatggaaga | ttactggctt | ctaaatgtgt | tacggatgag | 300 |
| tgtttctttt | ttgaacgatt | ggaatctaat | aactacaata | cttaccggtc | aaggaaatac | 360 |
| accagttggt | atgtggcact | gaaacgaact | gggcagtata | aacttggatc | caaaacagga | 420 |
| cctgggcaga | aagctatact | ttttcttcca | atgtctgcta | agagctga | | 468 |

<210> SEQ ID NO 176
<211> LENGTH: 468
<212> TYPE: DNA
<213> ORGANISM: Pygmy chimpanzee

<400> SEQUENCE: 176

| | | | | | |
|---|---|---|---|---|---|
| atggcagccg | ggagcatcac | cacgctgccc | gccttgcccg | aggatggcgg | cagcggcgcc | 60 |
| ttcccgcccg | gccacttcaa | ggaccccaag | cggctgtact | gcaaaaacgg | gggcttcttc | 120 |
| ctgcgcatcc | accccgacgg | ccgagttgac | ggggtccggg | agaagagcga | ccctcacatc | 180 |
| aagctacaac | ttcaagcaga | agagagagga | gttgtgtcta | tcaaaggagt | gtgtgctaac | 240 |
| cgttaccttg | ctatgaagga | agatggaaga | ttactggctt | ctaaatgtgt | tacggatgag | 300 |
| tgtttctttt | ttgaacgatt | ggaatctaat | aactacaata | cttaccggtc | aaggaaatac | 360 |
| accagttggt | atgtggcact | gaaacgaact | gggcagtata | aacttggatc | caaaacagga | 420 |
| cctgggcaga | aagctatact | ttttcttcca | atgtctgcta | agagctga | | 468 |

<210> SEQ ID NO 177
<211> LENGTH: 468
<212> TYPE: DNA
<213> ORGANISM: Bolivian squirrel monkey

<400> SEQUENCE: 177

| | | | | | |
|---|---|---|---|---|---|
| atggcagccg | ggagcatcac | cacgctgccc | gccctgcccg | aagacggcgg | cagcggcgcc | 60 |
| ttcccgcccg | gccacttcaa | agaccccaag | cggctgtact | gcaaaaacgg | gggcttcttc | 120 |
| ctgcgaatcc | accccgacgg | ccgagtggac | ggggtccggg | agaagagcga | ccctcacatc | 180 |
| aaactacaac | ttcaagcaga | agagagagga | gttgtatcta | tcaaaggagt | gtgtgctaac | 240 |
| cgttaccttg | ctatgaagga | agatggaaga | ttactggctt | ctaaatgtgt | tacggacgag | 300 |
| tgtttctttt | ttgaacgatt | ggaatctaat | aactacaata | cttaccgatc | aaggaaatac | 360 |
| accagttggt | atgtggcact | gaaacgaact | gggcagtata | aacttggatc | caaaacagga | 420 |
| cctgggcaga | aagctatact | ttttcttcca | atgtctgcta | agagctga | | 468 |

<210> SEQ ID NO 178
<211> LENGTH: 468
<212> TYPE: DNA
<213> ORGANISM: Northern white-cheeked gibbon

<400> SEQUENCE: 178

```
atggcagccg ggagcatcac cacgctgccc gccttgccgg aggatggcgg cagcggcgcc      60
ttcccgcccg gccacttcaa ggaccccaag cggctgtact gcaaaaacgg gggtttcttc     120
ctgcgcatcc accccgacgg tcgagttgac ggggtccggg agaagagcga ccctcacatc     180
aaactacaac ttcaagcaga agagagagga gttgtgtcta tcaaaggagt gtgtgctaac     240
cgttaccttg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctga                 468
```

<210> SEQ ID NO 179
<211> LENGTH: 468
<212> TYPE: DNA
<213> ORGANISM: Horse

<400> SEQUENCE: 179

```
atggcagccg ggagcatcac cacgctgccc gccctgcccg aggacggcgg cagcggcgcc      60
ttcccgcccg gccacttcaa ggaccccaag cggctctact gcaaaaacgg gggcttcttc     120
ctgcgcatcc accccgacgg ccgagtggac ggggtccggg agaagagcga ccctcacatc     180
aaactacaac ttcaagcaga agagagaggg gttgtgtcta tcaaaggagt gtgtgcgaac     240
cgttatcttg ctatgaagga agatggaagg ttactggctt ctaaatgtgt tacggacgag     300
tgtttctttt ttgaacgatt ggaatctaat aactacaata cttaccggtc aaggaaatac     360
tccagttggt atgtggccct gaaacgaacg gggcagtata aacttggacc caaaacagga     420
cctggacaga aagctatact ttttcttcca atgtctgcta agagctga                 468
```

<210> SEQ ID NO 180
<211> LENGTH: 468
<212> TYPE: DNA
<213> ORGANISM: Cattle

<400> SEQUENCE: 180

```
atggccgccg ggagcatcac cacgctgcca gccctgccgg aggacggcgg cagcggcgct      60
ttcccgccgg gccacttcaa ggaccccaag cggctgtact gcaagaacgg gggcttcttc     120
ctgcgcatcc accccgacgg ccgagtggac ggggtccgcg agaagagcga cccacacatc     180
aaactacaac ttcaagcaga agagagaggg gttgtgtcta tcaaaggagt gtgtgcaaac     240
cgttaccttg ctatgaaaga agatggaaga ttactagctt ctaaatgtgt tacagacgag     300
tgtttctttt ttgaacgatt ggagtctaat aactacaata cttaccggtc aaggaaatac     360
tccagttggt atgtggcact gaaacgaact gggcagtata aacttggacc caaaacagga     420
cctgggcaga aagctatact ttttcttcca atgtctgcta agagctga                 468
```

<210> SEQ ID NO 181
<211> LENGTH: 468
<212> TYPE: DNA
<213> ORGANISM: Olive baboon

<400> SEQUENCE: 181

```
atggcagccg ggagcatcac cacgctgccc gccttgccgg aggatggcgg cagcggcgcc      60
ttcccgcccg gccacttcaa ggaccccaag cggctgtact gcaaaaacgg gggcttcttc     120
ctgcgcattc accccgacgg ccgagttgac ggggtccggg agaagagcga ccctcacatc     180
aaattacaac ttcaagcaga agagagagga gttgtgtcta tcaaaggagt gtgtgctaac     240
```

```
cgttaccttg ctatgaagga agatggaaga ttactggctt ctaaatgtgt tacggatgag    300
tgtttctttt ttgaacgatt ggaatctaat aactacaata cttaccggtc aaggaaatac    360
accagttggt atgtggcact gaaacgaact gggcagtata aacttggatc caaaacagga    420
cctgggcaga aagctatact ttttcttcca atgtctgcta agagctga                468
```

<210> SEQ ID NO 182
<211> LENGTH: 468
<212> TYPE: DNA
<213> ORGANISM: Alpaca

<400> SEQUENCE: 182

```
atggcagctg ggagcatcac cacgctgccc gccctgccgg aggacggcgg cagcggcgcc    60
ttcccgcccg ccacttcaa ggaccccaag cggttgtact gcaaaaacgg gggcttcttc    120
ctgcgcatcc accccgacgg ccgagtggac ggggtccggg agaagagcga ccctcacatc    180
aaactacaac ttcaagcaga agagagaggg gtcgtgtcta tcaaaggagt gtgtgcaaac    240
cgttaccttg ctatgaagga agatggaaga ttactggctt ctaaatgtgt cacagacgag    300
tgtttctttt ttgaacgatt ggaatctaat aactacaata cttaccggtc aaggaaatac    360
tccagttggt atgtggcact gaaacgaact gggcagtaca aacttggacc caaaacagga    420
cctgggcaga aagctatact ttccttcca atgtctgcta gagagctga                468
```

<210> SEQ ID NO 183
<211> LENGTH: 468
<212> TYPE: DNA
<213> ORGANISM: Sheep

<400> SEQUENCE: 183

```
atggccgccg ggagcatcac cacgctgcca gccctgccgg aggacggcgg cagcagcgct    60
ttcccgcccg ccactttaa ggaccccaag cggctgtact gcaagaacgg gggcttcttc    120
ctgcgcatcc accccgacgg ccgagtggac ggggtccgcg agaagagcga ccctcacatc    180
aaactacaac ttcaagcaga agagagaggg gttgtgtcta tcaaaggagt gtgtgcaaac    240
cgttaccttg ctatgaaaga agatggaaga ttactagctt ctaaatgtgt tacagacgag    300
tgtttctttt ttgaacgatt ggagtctaat aactacaata cttaccggtc aaggaaatac    360
tccagttggt atgtggcact gaaacgaact gggcagtata aacttggacc caaaacagga    420
cctgggcaga aagctatact ttttcttcca atgtctgcta agagctga                468
```

<210> SEQ ID NO 184
<211> LENGTH: 325
<212> TYPE: DNA
<213> ORGANISM: Western roe deer

<400> SEQUENCE: 184

```
gcgcatccac cccgacggcc gagtggacgg ggtccgcgag aagagtgacc ctcacatcaa    60
actacaactt caagcagaag agagaggggt tgtgtctatc aaaggagtgt gtgcgaaccg    120
ttatcttgct atgaaagaag acggaagatt attggcttca aatgtgtta cagacgaatg    180 tttcttttt gaacgattgg agtctaataa ctacaatact taccggtcaa ggaaatactc    240
cagttggtat gtggcactga aacgaactgg gcagtataaa cttggaccca aaacaggacc    300
tgggcagaaa gctatacttt ttctt                                         325
```

<210> SEQ ID NO 185

```
<211> LENGTH: 288
<212> TYPE: DNA
<213> ORGANISM: Elephant

<400> SEQUENCE: 185
gttaaactac agcttcaagc agaagagaga ggtgttgtgt ctatcaaagg agtgtgtgcc    60
aaccgttatc tggctatgaa ggaagatgga agattgctgg cttctagatg tgtgacagat   120
gaatgtttct tctttgaacg actggaatct aataactaca atacttaccg gtcaaggaaa   180
tacaccagtt ggtatgtggc actgaaacga acggggcagt ataaacttgg atccaaaaca   240
ggacctggac agaaagctat acttttctt cccatgtctg ctaagagc                 288

<210> SEQ ID NO 186
<211> LENGTH: 361
<212> TYPE: DNA
<213> ORGANISM: Pig

<400> SEQUENCE: 186
gaacgggggc ttcttcctgc gcatccaccc cgacggccga gtggatgggg tccgggagaa    60
gagcgaccct cacatcaaac tacaacttca agcagaagag agaggggttg tgtctatcaa   120
aggagtgtgt gcaaaccgtt atcttgctat gaaggaagat ggaagattac tggcttctaa   180
atgtgttaca gacgagtgtt ctttttttga acgactggaa tctaataact acaatactta   240
ccggtcgagg aaatactcca gttggtatgt ggcactgaaa cgaactgggc agtataaact   300
tggacccaaa acaggacctg gcagaaaagc tatactttt cttccaatgt ctgctaagag   360
c                                                                  361

<210> SEQ ID NO 187
<211> LENGTH: 288
<212> TYPE: DNA
<213> ORGANISM: Panda

<400> SEQUENCE: 187
gtcaaactgc aacttcaagc ggaagagaga ggggttgtat ccatcaaagg agtatgtgca    60
aatcgctatc ttgccatgaa ggaagatgga agattactgg cttctaaatg tgttaccgat   120
gagtgtttct tttttgagcg actggaatct aataactaca atacttaccg gtcaaggaaa   180
tactccagtt ggtatgtggc actgaaacga actgggcagt ataaacttgg acccaaaaca   240
ggacctgggc agaaagctat acttttctt ccaatgtctg ctaagagc                 288

<210> SEQ ID NO 188
<211> LENGTH: 468
<212> TYPE: DNA
<213> ORGANISM: Sloth

<400> SEQUENCE: 188
atggcagccg ggagcatcac cacgctgccc gccctgcccg aggacggagg cagcggcgcc    60
ttaccgcccg gccacttcaa agatcccaag cggctctact gcaaaaacgg ggcttcttc   120
ctgcgtatcc atcccgacgg cagagtggac ggggtccggg agaagagcga cccccacatc   180
aaactacaac ttcaagcaga gagagaggg gttgtgtcta tcaaaggtgt gtgtgcaaac   240
cgatatcttg ctatgaagga agatggaaga ttacaggctt ctaaatgtgt aacggacgag   300
tgtttctttt ttgaacgatt ggaatctaat aactacaata cgtaccgatc aaggaaatac   360
tccagttggt atgtggcact gaaacgaact gggcaatata aacttggacc caaaacagga   420
cctgggcaga aagccatact ttttcttcca atgtctgcta agagctga               468
```

<210> SEQ ID NO 189
<211> LENGTH: 468
<212> TYPE: DNA
<213> ORGANISM: Water buffalo

<400> SEQUENCE: 189

```
atggccgccg ggagcatcac cacgctgcca cccctgccgg aggacggcgg cagcggcgct    60
ttcccgcccg ccacttcaa ggaccccaag cggctgtact gcaagaacgg gggcttcttc   120
ctgcgcatcc accccgacgg ccgagtggac ggggtccgcg agaagagcga cccacacatc   180
aaactacaac ttcaagcaga agagagaggg gttgtgtcta tcaaaggagt gtgtgcaaac   240
cgttaccttg ctatgaaaga agatggaaga ttactagctt ccaaatgtgt tacagacgag   300
tgtttctttt ttgaacgatt ggagtctagt aactacaata cttaccggtc aaggaaatac   360
tccagttggt atgtggcact gaaacgaact gggcagtata aacttggacc caaaacagga   420
cctgggcaga aagctatact ttttcttcca atgtctgcta agagctga               468
```

<210> SEQ ID NO 190
<211> LENGTH: 468
<212> TYPE: DNA
<213> ORGANISM: Dog

<400> SEQUENCE: 190

```
atggcagccg ggagcatcac cacgctgccc gccctgccgg aggacggcgg cagcggcgcc    60
ttcccgcccg ccacttcaa ggaccccaag aggctgtact gcaaaaaagg gggcttcttc   120
ctgcggatcc accccgacgg ccgggtggac ggggtccggg agaagagcga tccccacgtc   180
aaattgcaac ttcaagcaga agagagaggc gttgtgtcca tcaaaggagt atgtgcaaat   240
cgctatcttg ctatgaagga agatggaaga ttactggctt ctaaatgtgt tactgacgag   300
tgcttctttt ttgaacgatt ggaatctaat aactacaata cttaccggtc aaggaaatac   360
tccagttggt atgtggcact gaaacgaact gggcagtata aacttggacc aaaaacagga   420
cctgggcaga aagctatact ttttcttcca atgtctgcta agagctga               468
```

<210> SEQ ID NO 191
<211> LENGTH: 465
<212> TYPE: DNA
<213> ORGANISM: Norway rat

<400> SEQUENCE: 191

```
atggctgccg gcagcatcac ttcgcttccc gcactgccgg aggacggcgg cggcgccttc    60
ccacccggcc acttcaagga tcccaagcgg ctctactgca gaacggcgg cttcttcctg   120
cgcatccatc cagacggccg cgtggacggc gtccggagga gagcgaccc acacgtcaaa   180
ctacagctcc aagcagaaga gagggagtt gtgtccatca agggagtgtg tgcgaaccgg   240
tacctggcta tgaaggaaga tggacggctg ctggcttcta agtgtgttac agaagagtgt   300
ttcttctttg aacgcctgga gtccaataac tacaacactt accggtcacg gaaatactcc   360
agttggtatg tggcactgaa acgaactggg cagtataaac tcggatccaa acgggggcct   420
ggacagaagg ccatactgtt tcttccaatg tctgctaaga gctga                  465
```

<210> SEQ ID NO 192
<211> LENGTH: 405
<212> TYPE: DNA
<213> ORGANISM: Naked mole-rat

<400> SEQUENCE: 192

```
ccacccggcc acttcaagga cccaaagcgg ctgtactgca aaaacggggg cttcttcctg      60
cgcatccacc ccgacggccg cgtggacggg gtccgggaga agagcgaccc tcacgtcaaa     120
ctacaacttc aagcagaaga gagaggagtt gtgtctatta agggagtgtg tgcgaaccgt     180
taccttgcta tgaaggaaga tggaagatta ctggcttcta aatgtgttac agatgagtgt     240
ttcttttttg aacgattgga atctaataac tacaatactt atcggtcaag gaaatactcc     300
agttggtatg tggcactgaa acgaactgga caatataaac ttggatccaa aacaggaccg     360
gggcagaaag ctatactttt tcttccaatg tctgctaaga gctga                    405
```

<210> SEQ ID NO 193
<211> LENGTH: 468
<212> TYPE: DNA
<213> ORGANISM: Bushbaby

<400> SEQUENCE: 193

```
atggcagccg ggagcatcac cacgctgccc tccctgcccg aggacggcgg cagcgacgcc      60
tttccgcccg gccacttcaa ggaccccaag cgactgtact gcaaaaacgg gggcttcttc     120
ctgcgcatcc accccgacgg ccgagtggac ggggtccggg agaagagcga cccttacatc     180
aaactacaac ttcaagcaga agagagagga gttgtgtcta tcaaaggagt gtgtgcgaac     240
cgttaccttg ctatgaagga agacggaaga ttgctggctt ctaaattgat tacagacgag     300
tgcttctttt ttgaacgact ggaatctaat aactacaata cttaccggtc aagaaaatac     360
tccagttggt atgtggcact gaaacgaact ggacagtata aacttggatc caaaacagga     420
cctgggcaga aagctatact ttttcttcca atgtctgcta agagctga                 468
```

<210> SEQ ID NO 194
<211> LENGTH: 465
<212> TYPE: DNA
<213> ORGANISM: House mouse

<400> SEQUENCE: 194

```
atggctgcca gcggcatcac ctcgcttccc gcactgccgg aggacggcgg cgccgccttc      60
ccaccaggcc acttcaagga ccccaagcgg ctctactgca agaacggcgg cttcttcctg     120
cgcatccatc ccgacggccg cgtggatggc gtccgcgaga agagcgaccc acacgtcaaa     180
ctacaactcc aagcagaaga gagaggagtt gtgtctatca agggagtgtg tgccaaccgg     240
taccttgcta tgaaggaaga tggacggctg ctggcttcta agtgtgttac agaagagtgt     300
ttcttctttg aacgactgga atctaataac tacaatactt accggtcacg gaaatactcc     360
agttggtatg tggcactgaa acgaactggg cagtataaac tcggatccaa aacgggacct     420
ggacagaagg ccatactgtt tcttccaatg tctgctaaga gctga                    465
```

<210> SEQ ID NO 195
<211> LENGTH: 432
<212> TYPE: DNA
<213> ORGANISM: Squirrel

<400> SEQUENCE: 195

```
ctgcccgagg acggcggcgg cggcgccttc ccgcccggcc actttaagga ccccaagcgg      60
ctctactgca aaaacggagg cttcttcctg cgcatccacc ccgacggccg agtggacggg     120
gtccgggaga agagcgaccc ccacatcaag ctccagcttc aagccgaaga ccgagggctt     180
gtgtccatca agggagtgtg tgcaaaccga tacctggcca tgaaggagga cgggaggctc     240
```

```
ctggcttcta aatgtgttac ggacgagtgt ttcttttttg aacgactgga atcaaataac      300
tacaatactt accggtcaag gaaatactcc agttggtatg tggccctgaa acgaacaggg      360
cagtataaac ttggatccaa aacaggacct gggcagaaag ctatacttt tcttccaatg      420 tctgctaaga gc                                                         432
```

<210> SEQ ID NO 196
<211> LENGTH: 318
<212> TYPE: DNA
<213> ORGANISM: Domestic cat

<400> SEQUENCE: 196

```
ccacttcaag gaccccaagc gtctgtactg caaaaacggg ggcttcttcc tgcgcatcca      60
ccccgacggc cgagtggatg gggtccggga aagagcgac cctcacatca aactgcaact      120
tcaggcagaa gagagagggg ttgtgtccat caaaggagtc tgtgcaaacc gctatcttgc     180
catgaaggaa gatggaagat tactggcttc taaatgtgtt acggacgagt gtttcttttt     240
tgaacgattg gaatctaata actacaatac ttatcggtca aggaaatact ccagctggta     300
tgtggcactg aaacgaac                                                  318
```

<210> SEQ ID NO 197
<211> LENGTH: 288
<212> TYPE: DNA
<213> ORGANISM: Guinea pig

<400> SEQUENCE: 197

```
gttaaactac aacttcaagc cgaagacaga ggagttgtgt ctatcaaggg agtctgtgcg      60
aaccgttacc ttgctatgaa ggaagacgga agattattgg cttccaaatg tgttacagat     120
gaatgtttct ttttgaacg actggaatct aataactaca acacttaccg gtcaaggaaa     180
tactccagtt ggtatgtggc actgaaacga actggacaat ataaacttgg gtccaaaaca     240
ggaccagggc agaaagccat actttttctt ccaatgtctg cgaagagc                  288
```

<210> SEQ ID NO 198
<211> LENGTH: 471
<212> TYPE: DNA
<213> ORGANISM: Tasmanian devil

<400> SEQUENCE: 198

```
atggccgcgg gcagcatcac cacgttgccg gccctggccg gggatggagc cagcgggggc      60
gcctttcccc cgggccactt ccaggacccc aagcggctgt actgcaagaa cggaggcttc     120
ttcttgcgca tccatcccga cggtcacgtg gacggcatcc gcgagaagag cgatccgcac     180
attaaacttc agcttcaggc agaagagaga ggagtagtgt ctattaaagg agtttgtgcc     240
aaccgctatc ttgccatgaa agaggatggc agattactgg ctctgaaatg tgtgactgaa     300 gagtgttct tctttgaacg tctagagtcc aacaattaca cacttatcg ctcaaggaaa      360 tactccaatt ggtatgtggc attgaaacgc acaggccagt ataagcttgg atccaagact     420
ggaccagggc agaaagccat ccttttcctt cccatgtctg ctaagagctg a              471
```

<210> SEQ ID NO 199
<211> LENGTH: 471
<212> TYPE: DNA
<213> ORGANISM: Gray short-tailed opossum

<400> SEQUENCE: 199

```
atggccgcag gcagcatcac cacgctgcca gccctgtccg gggacggagg cggcggggc      60 gcctttcccc cgggccactt caaggacccc aagcggctgt actgcaagaa cggaggcttc     120
ttcctgcgca tccaccccga cggccgtgtg gacggcatcc gcgagaagag cgacccgaac     180
attaaactac aacttcaggc agaagagaga ggagtggtgt ctattaaagg agtatgtgcc     240
aatcgctatc ttgccatgaa ggaagatgga agattattgg ctttgaaata tgtgaccgaa     300
gagtgtttct ttttcgaacg cttggagtcc aacaactaca cacttatcg ctcgaggaaa      360 tattccaatt ggtacgtggc actgaaacga acggggcagt acaagcttgg atccaagact     420
ggcccggggc agaaagccat cctttttcctc ccatgtctg ctaagagctg a              471

<210> SEQ ID NO 200
<211> LENGTH: 468
<212> TYPE: DNA
<213> ORGANISM: Rabbit

<400> SEQUENCE: 200
atggcagccg agagcatcac cacgctgccc gccctgccgg aggatggagg cagcggcgcc      60
ttcccgcccg gccacttcaa ggaccccaag cggctgtact gcaaaaacgg gggtttcttc     120
ctgcgtatcc accccgacgg ccgcgtgac ggggtccggg agaagagcga cccacacatc      180
aaattacaac ttcaagcaga agagagagga gttgtatcca tcaaaggtgt gtgtgcaaac     240
cgttaccttg ctatgaagga agatggaaga ctgctggctt ctaaatgtgt tacagacgag     300
tgcttctttt ttgaacgact ggagtctaat aactacaata cttaccggtc aaggaaatat     360
tccagctggt atgtggcact gaaacgaact gggcagtata aacttggatc caaaacagga     420
cctgggcaga aggctatact ttttcttcca atgtctgcta agagctga                  468

<210> SEQ ID NO 201
<211> LENGTH: 375
<212> TYPE: DNA
<213> ORGANISM: Turkey

<400> SEQUENCE: 201
cggctctact gtaagaacgg cggcttcttc ctgcgcatca atcccgacgg cagagtggac      60
ggcgtccgcg agaagagcga tccgcacatc aaactgcagc ttcaggcaga agaaagagga     120
gtggtatcaa tcaaaggtgt aagtgcaaac cgctttctgg ctatgaagga ggatggcaga     180 tgctggcac tgaaatgtgc aacagaagaa tgtttctttt ttgagcgttt ggaatctaat      240
aattataaca cttaccggtc acggaagtac tctgattggt atgtggcact gaaaagaact     300
ggacagtaca agcccggacc aaaaactgga cctggacaga agctatcct tttttcttcca    360 atgtctgcta aaagc                                                      375

<210> SEQ ID NO 202
<211> LENGTH: 477
<212> TYPE: DNA
<213> ORGANISM: Gallus gallus

<400> SEQUENCE: 202
atggcggcgg gggcggcggg gagcatcacc acgctgccgg cgctgcccga cgacgggggc      60
ggcggcgctt ttccccccgg gcacttcaag gaccccaagc ggctctactg caagaacggc     120
ggcttcttcc tgcgcatcaa ccccgacggc agggtggacg gcgtccgcga agagagcgat     180
ccgcacatca aactgcagct tcaagcagaa gaaagaggag tagtatcaat caaaggcgta     240
agtgcaaacc gctttctggc tatgaaggag gatggcagat tgctggcact gaaatgtgca     300
```

```
acagaggaat gtttctttt cgagcgcttg gaatctaata actataacac ttaccggtca    360
cggaagtact ctgattggta tgtggcactg aaaaggactg gacagtacaa gcccggacca    420
aaaactggac ctggacagaa agctatcctt tttcttccaa tgtctgctaa aagctga      477
```

<210> SEQ ID NO 203
<211> LENGTH: 462
<212> TYPE: DNA
<213> ORGANISM: Zebra finch

<400> SEQUENCE: 203

```
atggcggcgg cgggggggcat cgctacgctg cccgacgacg gcggcagcgg cgccttcccc    60
ccggggcact tcaaggaccc caagcgcctg tactgcaaga acggcggctt cttcctgcgc   120
atcaaccccg acgggaaggt ggacggcgtc cgcgagaaga gcgacccgca catcaagctg   180
cagcttcagg cggaggaacg aggagtggtg tccatcaaag tgtcagtgc caatcgcttc    240 ctggccatga agaggatgg cagattgctg gccttgaaat atgcaacaga gaatgtttc    300 ttttttgaac gtttggaatc caataactat aacacttacc ggtcacggaa atactcggat   360
tggtatgtgg cactgaaaag aactggacag tacaaacctg gaccaaaaac tggacctgga   420
cagaaagcta tccttttcct tcctatgtct gctaaaagct ga                      462
```

<210> SEQ ID NO 204
<211> LENGTH: 468
<212> TYPE: DNA
<213> ORGANISM: Japanese firebelly newt

<400> SEQUENCE: 204

```
atggctgctg ggagcatcac cagtctccct gccctacccg aggacgggaa tggcggcacc    60
ttcacacccg gcggattcaa agagccgaag aggctgtact gcaagaacgg gggcttcttt   120
ctccggatca actccgacgg caaggtggac ggagcccggg agaagagcga ctcctacatt   180
aaactgcagc ttcaagcaga agagcgcggt gtggtgtcca tcaagggagt atgtgcaaac   240
cgctatctcg ctatgaagga tgatggcagg ctgatggcgc tgaaatggat aaccgatgaa   300
tgcttctttt tcgagcgact ggagtccaac aactataaca cgtatcgatc acggaaatat   360
tccgattggt atgtggcgct gaaaagaact gggcaataca aaatggatc aaaaaccgga   420 gcaggacaga aagcaatcct ttttctaccc atgtcggcca agagttga                468
```

<210> SEQ ID NO 205
<211> LENGTH: 468
<212> TYPE: DNA
<213> ORGANISM: African clawed frog

<400> SEQUENCE: 205

```
atggcggcag ggagcatcac aactctgcca actgaatccg aggatggggg aaacactcct    60
ttttcaccag ggagttttaa agaccccaag aggctctact gcaagaacgg gggcttcttc   120
ctcaggataa actcagacgg gagagtggac gggtcaaggg acaaaagtga ctcgcacata   180
aaattacagc tacaagctgt agagcgggga gtggtatcaa taaagggaat cactgcaaat   240
cgctaccttg ccatgaagga agatgggaga ttaaatcgc tgaggtgtat aacagatgaa   300
tgcttctttt ttgaacgact ggaagctaat aactacaaca cttaccggtc tcggaaatac   360
agcagctggt atgtggcact aaagcgaacc gggcagtaca aaaatggatc gagcactgga   420
ccgggacaaa aagctatttt atttctccca atgtccgcaa agagctga                468
```

<210> SEQ ID NO 206
<211> LENGTH: 471
<212> TYPE: DNA
<213> ORGANISM: White-eared opossum

<400> SEQUENCE: 206

| | | |
|---|---|---|
| atggcagcag gcagcatcac cacattgccg gccctgtccg gggacggagg cggcggggga | 60 |
| gcctttcctc caggccactt caaggacccc aagcggctgt actgcaagaa cggaggcttc | 120 |
| ttcctgcgca tccaccccga cggccgcgtg acggcatcc gcgagaagag cgacccgaac | 180 |
| attaaactac aacttcaggc agaagagaga ggagtagtgt ctattaaagg agtatgtgcc | 240 |
| aaccgatatc ttgccatgaa ggaggatggc agattattgg ctttgaaata tgtgaccgaa | 300 |
| gagtgtttct tttttgaacg tttggagtcc aacaactaca cacttatcg ctcaagaaaa | 360 |
| tattccaatt ggtatgtggc actgaaacga acggggcagt ataagcttgg atccaagact | 420 |
| ggcccggggc agaaagccat cctttttctcc ccatgtctgc taagatgctg a | 471 |

<210> SEQ ID NO 207
<211> LENGTH: 288
<212> TYPE: DNA
<213> ORGANISM: Microbat

<400> SEQUENCE: 207

| | | |
|---|---|---|
| gtcaaactcc aacttcaagc agaagagaga ggggtcgtgt ctatcaaagg agtgtgtgcc | 60 |
| aaccgctatc tcgctatgaa ggaggacggc cggttacagg cttctaaatg tgttacggat | 120 |
| gagtgtttct tttttgaacg gttggaatcc aataactaca cacttaccg gtcaagaaag | 180 |
| tactccagtt ggtatgtggc attgaagcgg aatgggcagt ataaacttgg acccaaaaca | 240 |
| ggacctggcc agaaagccat acttttttctt cccatgtctg ctaagagc | 288 |

<210> SEQ ID NO 208
<211> LENGTH: 420
<212> TYPE: DNA
<213> ORGANISM: Anole lizard

<400> SEQUENCE: 208

| | | |
|---|---|---|
| gcggcggcgg cctctttccc ccgggcccc ttcaaggacc ccaagcgcct ctactgcaag | 60 |
| aacgggggct tcttcctgcg gatcaacccc gacggcggcg tggacggcgt ccgagagaag | 120 |
| agcgacccca acatcaaatt gctgctccag gcagaggaga gaggtgtagt gtccatcaaa | 180 |
| ggtgtatgcg caaaccgttt cctggctatg aatgaagacg tcgattgtt agcactgaaa | 240 |
| tacgtaacag atgaatgctt cttttttgaa cgcttggaat ctaataatta caatacttat | 300 |
| cggtctcgta ataccgtga ttggtacatt gcactgaaac gaactggtca gtacaaactt | 360 |
| ggaccaaaaa ctggacgagg ccagaaagct atccttttcc ttccaatgtc tgccaaaagt | 420 |

<210> SEQ ID NO 209
<211> LENGTH: 282
<212> TYPE: DNA
<213> ORGANISM: Armadillo

<400> SEQUENCE: 209

| | | |
|---|---|---|
| atggcagccg ggagcatcac cacgctgccc gctctgcccg aggacggcgg cagcggcgcc | 60 |
| ttcccgccgg gccacttcaa ggaccccaag cggctgtact gcaaaaacgg ggcttcttc | 120 |
| ctgcgcatcc atcccgacgg ccgagtggac ggggtccggg agaagagcga ccctaacatc | 180 |
| aaactacaac ttcaagcaga agagagaggg gtcgtgtcta tcaaaggcgt gtgtgcgaac | 240 |

```
cgttaccttg ctatgcggga agacggaaga ctccaggcgt ct                        282

<210> SEQ ID NO 210
<211> LENGTH: 567
<212> TYPE: DNA
<213> ORGANISM: Tree shrew

<400> SEQUENCE: 210 gcggggggtta gagctgagag ggaggaggca ccggggagcg gtgacagccg ggggaccgat     60
cccgccgcgc gttcgctcat caggaggccg gatgctgcag cgcgagaggc gcttcttgga    120
gccaggagcc gggttcaggg cagctccacc tcctggccag cctcgtcacg aaccgggatc    180
aagttgccgg acgactcagg tcaaggaatg ggcggctatc ctctggaccg cccgagccgg    240
agcacagggc gagggctggg cggtgccccg gaccctgccg taaaactaca gcttcaagcg    300
gaagagagag gggtcgtgtc tatcaaagga gtgtgtgcaa accgttaccct ggccatgaag    360 gaggatgggc gactgctggc ttctaaatgt gttacagatg agtgtttctt ttttgaacga    420
ctggaatcta ataactacaa tacttaccgg tcccgaaagt actccagctg gtatgtggca    480
ctgaaacgaa ctgggcagta taaacttgga tccaaaacag gacctgggca gaaagctata    540 cttttcttc caatgtctgc taaaagc                                         567

<210> SEQ ID NO 211
<211> LENGTH: 465
<212> TYPE: DNA
<213> ORGANISM: Western clawed frog

<400> SEQUENCE: 211
atggcagcag gaagcatcac aaccctacca accgaatctg aggatggaaa cactcctttc     60
ccaccgggga actttaagga ccccaagagg ctctactgca gaatgggggg ctacttcctc    120
aggattaact cagacgggag agtggacgga tcaagggata aaagtgactt acacataaaa    180
ttacagctac aagcagtaga gcggggagtg gtatcaataa agggaatcac tgcaaatcgc    240
taccttgcca tgaaggaaga tgggagatta acatcgctga agtgtataac agatgaatgc    300
ttcttttatg aacgattgga agctaataac tacaacactt accggtctcg gaaaaacaac    360
agctggtatg tggcactaaa gcgaactggg cagtataaaa atggatcgac cactggacca    420
ggacaaaaag ctattttgtt tctcccaatg tcagcaaaaa gctga                    465

<210> SEQ ID NO 212
<211> LENGTH: 468
<212> TYPE: DNA
<213> ORGANISM: Coelacanth

<400> SEQUENCE: 212
atggctgcgg gaggaatcac taccctgccg gcggtacctg aggatggagg cagcagcacc     60
ttccctccag gaaacttcaa ggagcccaag agacttact gtaagaatgg aggctatttc    120
ttaaggataa accccgatgg aagagtggat ggaacaaggg agaaaaatga tccttatata    180
aaattacaac tgcaagctga atctatagga gtggtgtcga taagggagt ttgttcaaac    240 cgttacctag cgatgaatga agactgtaga cttttttggat tgaaatatcc aacggatgaa    300
tgtttcttcc atgagaggct ggagtccaac aactacaata cttatcgttc aaagaagtat    360
tcggattggt atgtggcgct gaaacggact ggtcagtaca aacctgggcc aaaaactgga    420
ctgggacaaa aagcaatcct tttccttccg atgtctgcca agagttga                 468
```

<210> SEQ ID NO 213
<211> LENGTH: 468
<212> TYPE: DNA
<213> ORGANISM: Spotted green pufferfish

<400> SEQUENCE: 213

| | | | | | | |
|---|---|---|---|---|---|---|
| atggccacgg | gagggatcac | gacgcttcca | tccacacctg | aagacggcgg | cagcagcggc | 60 |
| tttcctcccg | gcagcttcaa | ggatcccaaa | aggctctact | gtaaaaacgg | aggtttcttc | 120 |
| ctgaggatca | agtccgacgg | ggtcgtggac | ggaatccggg | agaagagtga | cccccacata | 180 |
| aagcttcagc | tccaggcgac | ctctgtgggg | gaggtggtca | tcaaggggt | gtgcgctaac | 240 |
| cgctatctgg | ccatgaacag | agatggacgg | ctgttcggaa | cgaaacgagc | cacggacgaa | 300 |
| tgccatttct | tagagcggct | tgagagcaac | aactacaaca | cttaccgctc | caggaagtac | 360 |
| ccaaccatgt | ttgtgggact | gacgcggacg | ggccagtaca | agtctgggag | caaaactgga | 420 |
| ccgggccaaa | aggccatcct | ttttcttccg | atgtccgcca | aatgctaa | | 468 |

<210> SEQ ID NO 214
<211> LENGTH: 468
<212> TYPE: DNA
<213> ORGANISM: Stickleback

<400> SEQUENCE: 214

| | | | | | | |
|---|---|---|---|---|---|---|
| atggccacgg | caggcttcgc | gacgcttccc | tccacgcccg | aagacggcgg | cagcggcggc | 60 |
| ttcaccccg | ggggattcaa | ggatcccaag | aggctgtact | gcaaaaacgg | gggcttcttc | 120 |
| ttgaggatca | ggtccgacgg | aggtgtagat | ggaatcaggg | agaagagcga | cgcccacata | 180 |
| aagctccaaa | tccaggcgac | gtcggtgggg | gaggtggtca | tcaaggagt | ctgtgccaac | 240 |
| cgctatctgg | ccatgaacag | agacggccgg | ctgttcggag | tgagacgggc | gacggacgaa | 300 |
| tgctacttcc | tggagcggct | ggagagtaac | aactacaaca | cctaccgctc | caggaagtac | 360 |
| cccggcatgt | acgtggctct | gaagcggacc | ggccagtaca | agtccgggag | caaaaccgga | 420 |
| cccggtcaaa | aggccattct | gttcctcccc | atgtcggcta | agtgctaa | | 468 |

<210> SEQ ID NO 215
<211> LENGTH: 468
<212> TYPE: DNA
<213> ORGANISM: Fugu rubripes

<400> SEQUENCE: 215

| | | | | | | |
|---|---|---|---|---|---|---|
| atggccacgg | gagggatcac | aacacttcca | tccacacctg | aagacggcgg | cagcggcggt | 60 |
| tttcctcccg | ggagcttcaa | ggatcccaaa | aggctgtact | gtaaaaacgg | cggcttcttc | 120 |
| ctgaggatca | ggtccgacgg | ggccgtggac | ggaacccggg | agaagactga | cccccacata | 180 |
| aagcttcagc | tccaggcgac | ctctgtgggg | gaggtggtca | tcaaggggt | ttgtgctaat | 240 |
| cgttatctgg | ccatgaacag | agatggacga | ctgtttggaa | tgaaacgagc | gacggatgaa | 300 |
| tgccacttct | tagagcggct | cgagagcaac | aactacaaca | cctaccgctc | caggaagtac | 360 |
| cccaacatgt | ttgtgggact | gacgcgaact | ggcaactaca | agtctgggac | taaaactgga | 420 |
| ccgggccaaa | aggccatcct | cttttcttccg | atgtcggcca | aatactaa | | 468 |

<210> SEQ ID NO 216
<211> LENGTH: 468
<212> TYPE: DNA
<213> ORGANISM: Rainbow trout

<400> SEQUENCE: 216

```
atggccacag agaaaatcac cactctaccc gccacacctg aagatggagg cagtggcggc    60
ttccttccag gaaactttaa ggagcccaag aggttgtact gtaaaaatgg aggctacttc   120
ttgaggataa actctaacgg aagcgtggac gggatcagag ataagaacga cccccacaat   180
aagcttcaac tccaggcgac ctcagtgggg gaagtagtaa tcaaaggggt ctcagccaac   240
cgctatctgg ccatgaatgc agatggaaga ctgtttggac cgagacggac aacagatgaa   300
tgctacttca tggagaggct ggagagtaac aactacaaca cctaccgctc tcgaaagtac   360
cctgaaatgt atgtggcact gaaaaggact ggccagtaca agtcaggatc caaaactgga   420
cccggccaaa aagccatcct cttcctcccc atgtcagcca gacgctga              468
```

```
<210> SEQ ID NO 217
<211> LENGTH: 453
<212> TYPE: DNA
<213> ORGANISM: Salmon

<400> SEQUENCE: 217
atggccacag agaaaatcac cactctaccc gccacacctg aagatggagg cagtggcggc    60
ttccctccag gaaactttaa ggatcccaag aggctgtact gtaaaaacgg gggctacttc   120
ttgagaataa actctaatgg aagcgtggac gggatccgag agaagaacga ccccccacaaa  180 cagcctcaat tgtcagggc atggactctt caaggtgtca acgttccac agggatgctg    240 gcccatgttg actccaacgc ttcccacaat tgtgtcaagg tggctggatg ttctttggga   300
gaatttggca gtatgtccaa ccggcctcat aaccgcagac cacgtgtagc tacaccagcc   360
caggacctcc acatccggct tcttcatcta cgggatcgtc tgaaaccagc cacccgaaca   420
gctgataaaa ctgaggagta tttctgtctg taa                                453
```

```
<210> SEQ ID NO 218
<211> LENGTH: 465
<212> TYPE: DNA
<213> ORGANISM: Zebrafish

<400> SEQUENCE: 218
atggccaccg agggatcac cacactcccg gccgctccgg acgccgaaaa cagcagcttt    60
cccgcgggca gcttcaggga tcccaagcgc ctgtactgca aaaacggagg attcttcctg   120
cggatcaacg cggacggccg agtggacgga gcccgagaca agagcgaccc gcacattcgt   180
ctgcagctgc aggcgacggc agtgggtgaa gtactcatta aaggcatctg taccaaccgt   240
ttccttgcca tgaacgcaga cggacgactg ttcgggacga aaaggaccac agatgaatgt   300
tatttcctgg agcgcctgga gtccaacaac tacaacacat acagatcccg caagtatccc   360
gactggtacg tggctctgaa gagaaccggc cagtataaaa gcggctctaa accagcccg   420 ggacagaagg ccatcctgtt tctgcccatg tcggccaaat gctga                  465
```

```
<210> SEQ ID NO 219
<211> LENGTH: 468
<212> TYPE: DNA
<213> ORGANISM: Nile tilapia

<400> SEQUENCE: 219
atggccacgg gaggaatcac aaacacttcc gctacacctg aagacggcgg cagcagcggc    60
tttcctcctg ggaacttcaa ggaccctaaa aggctgtact gtaaaaatgg tggcttcttc   120
ttgaggataa aatctgatgg aggagtggat ggaatacgag agaaaaacga cccccacata   180
```

| aagcttcaac tccaggcgac ctcagtggga gaagtggtca tcaaagggat ttgtgcaaac | 240 |
| cgatatctgg caatgaacag agatggacga ctgtttggag cgagaagagc aacagatgag | 300 |
| tgctacttct tagagcggct cgagagcaac aactacaaca cctaccgctc caggaagtac | 360 |
| ccaaacatgt acgtggcgct gaagcggact ggccagtaca gtctggaag caaaactgga | 420 |
| ccgggtcaaa aggcaattct ctttctccca atgtctgcta aatgctaa | 468 |

<210> SEQ ID NO 220
<211> LENGTH: 468
<212> TYPE: DNA
<213> ORGANISM: Medaka

<400> SEQUENCE: 220

| atggctacgg gagaaatcac aacacttccc tccccagctg aaaacagcag aagcgatggc | 60 |
| tttcctccag ggaactacaa ggatcctaag aggctctact gtaaaaatgg aggtttgttt | 120 |
| ttgaggatta aacctgatgg aggagtggat ggaatccggg aaaaaaaaga tccccacgtt | 180 |
| aagcttcgcc ttcaggctac ctcagcggga gaggtggtga tcaaaggagt ttgttcaaac | 240 |
| agatatctgg cgatgcatgg agatggacgt ctatttggag tgagacaagc aacagaggaa | 300 |
| tgctacttct tggagcgact agagagcaac aactataaca cctatcgctc taaaaagtac | 360 |
| ccaaacatgt acgtggcact gaagcggaca ggccagtaca aacctggaaa caaaactgga | 420 |
| ccaggtcaaa aggccattct ctttctgcct atgtctgcca agtactaa | 468 |

<210> SEQ ID NO 221
<211> LENGTH: 206
<212> TYPE: PRT
<213> ORGANISM: Homo sapiens

<400> SEQUENCE: 221

Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Gly Ala Ala Ala Pro
                20                  25                  30

Thr Ala Pro Asn Gly Thr Leu Glu Ala Glu Leu Glu Arg Arg Trp Glu
            35                  40                  45

Ser Leu Val Ala Leu Ser Leu Ala Arg Leu Pro Val Ala Ala Gln Pro
        50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
        115                 120                 125

Phe Gly Val Ala Ser Arg Phe Phe Val Ala Met Ser Ser Lys Gly Lys
    130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu

```
            195                 200                 205

<210> SEQ ID NO 222
<211> LENGTH: 268
<212> TYPE: PRT
<213> ORGANISM: Homo sapiens

<400> SEQUENCE: 222

Met Ser Leu Ser Phe Leu Leu Leu Phe Ser His Leu Ile Leu
1               5                   10                  15

Ser Ala Trp Ala His Gly Glu Lys Arg Leu Ala Pro Lys Gly Gln Pro
            20                  25                  30

Gly Pro Ala Ala Thr Asp Arg Asn Pro Arg Gly Ser Ser Arg Gln
            35                  40                  45

Ser Ser Ser Ser Ala Met Ser Ser Ser Ala Ser Ser Ser Pro Ala
50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95

Ile Gly Phe His Leu Gln Ile Tyr Pro Asp Gly Lys Val Asn Gly Ser
                100                 105                 110

His Glu Ala Asn Met Leu Ser Val Leu Glu Ile Phe Ala Val Ser Gln
                115                 120                 125

Gly Ile Val Gly Ile Arg Gly Val Phe Ser Asn Lys Phe Leu Ala Met
            130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
                180                 185                 190

Asn Lys Arg Gly Lys Ala Lys Arg Gly Cys Ser Pro Arg Val Lys Pro
            195                 200                 205

Gln His Ile Ser Thr His Phe Leu Pro Arg Phe Lys Gln Ser Glu Gln
        210                 215                 220

Pro Glu Leu Ser Phe Thr Val Thr Val Pro Glu Lys Lys Pro Pro
225                 230                 235                 240

Ser Pro Ile Lys Pro Lys Ile Pro Leu Ser Ala Pro Arg Lys Asn Thr
                245                 250                 255

Asn Ser Val Lys Tyr Arg Leu Lys Phe Arg Phe Gly
                260                 265

<210> SEQ ID NO 223
<211> LENGTH: 208
<212> TYPE: PRT
<213> ORGANISM: Homo sapiens

<400> SEQUENCE: 223

Met Ala Leu Gly Gln Lys Leu Phe Ile Thr Met Ser Arg Gly Ala Gly
1               5                   10                  15

Arg Leu Gln Gly Thr Leu Trp Ala Leu Val Phe Leu Gly Ile Leu Val
            20                  25                  30

Gly Met Val Val Pro Ser Pro Ala Gly Thr Arg Ala Asn Asn Thr Leu
        35                  40                  45

Leu Asp Ser Arg Gly Trp Gly Thr Leu Leu Ser Arg Ser Arg Ala Gly
```

```
                50                  55                  60
Leu Ala Gly Glu Ile Ala Gly Val Asn Trp Glu Ser Gly Tyr Leu Val
 65                  70                  75                  80

Gly Ile Lys Arg Gln Arg Arg Leu Tyr Cys Asn Val Gly Ile Gly Phe
                 85                  90                  95

His Leu Gln Val Leu Pro Asp Gly Arg Ile Ser Gly Thr His Glu Glu
                100                 105                 110

Asn Pro Tyr Ser Leu Leu Glu Ile Ser Thr Val Glu Arg Gly Val Val
                115                 120                 125

Ser Leu Phe Gly Val Arg Ser Ala Leu Phe Val Ala Met Asn Ser Lys
130                 135                 140

Gly Arg Leu Tyr Ala Thr Pro Ser Phe Gln Glu Glu Cys Lys Phe Arg
145                 150                 155                 160

Glu Thr Leu Leu Pro Asn Asn Tyr Asn Ala Tyr Glu Ser Asp Leu Tyr
                165                 170                 175

Gln Gly Thr Tyr Ile Ala Leu Ser Lys Tyr Gly Arg Val Lys Arg Gly
                180                 185                 190

Ser Lys Val Ser Pro Ile Met Thr Val Thr His Phe Leu Pro Arg Ile
                195                 200                 205

<210> SEQ ID NO 224
<211> LENGTH: 208
<212> TYPE: PRT
<213> ORGANISM: Homo sapiens

<400> SEQUENCE: 224

Met Ala Pro Leu Gly Glu Val Gly Asn Tyr Phe Gly Val Gln Asp Ala
 1               5                  10                  15

Val Pro Phe Gly Asn Val Pro Val Leu Pro Val Asp Ser Pro Val Leu
                 20                  25                  30

Leu Ser Asp His Leu Gly Gln Ser Glu Ala Gly Gly Leu Pro Arg Gly
                 35                  40                  45

Pro Ala Val Thr Asp Leu Asp His Leu Lys Gly Ile Leu Arg Arg Arg
 50                  55                  60

Gln Leu Tyr Cys Arg Thr Gly Phe His Leu Glu Ile Phe Pro Asn Gly
 65                  70                  75                  80

Thr Ile Gln Gly Thr Arg Lys Asp His Ser Arg Phe Gly Ile Leu Glu
                 85                  90                  95

Phe Ile Ser Ile Ala Val Gly Leu Val Ser Ile Arg Gly Val Asp Ser
                100                 105                 110

Gly Leu Tyr Leu Gly Met Asn Glu Lys Gly Glu Leu Tyr Gly Ser Glu
                115                 120                 125

Lys Leu Thr Gln Glu Cys Val Phe Arg Glu Gln Phe Glu Glu Asn Trp
130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
                180                 185                 190

Asp Pro Asp Lys Val Pro Glu Leu Tyr Lys Asp Ile Leu Ser Gln Ser
                195                 200                 205

<210> SEQ ID NO 225
<211> LENGTH: 207
```

<212> TYPE: PRT
<213> ORGANISM: Homo sapiens

<400> SEQUENCE: 225

Met Ala Glu Val Gly Gly Val Phe Ala Ser Leu Asp Trp Asp Leu His
1               5                   10                  15

Gly Phe Ser Ser Leu Gly Asn Val Pro Leu Ala Asp Ser Pro Gly
                20                  25                  30

Phe Leu Asn Glu Arg Leu Gly Gln Ile Glu Gly Lys Leu Gln Arg Gly
                35                  40                  45

Ser Pro Thr Asp Phe Ala His Leu Lys Gly Ile Leu Arg Arg Arg Gln
        50                  55                  60

Leu Tyr Cys Arg Thr Gly Phe His Leu Glu Ile Phe Pro Asn Gly Thr
65              70                  75                  80

Val His Gly Thr Arg His Asp His Ser Arg Phe Gly Ile Leu Glu Phe
                85                  90                  95

Ile Ser Leu Ala Val Gly Leu Ile Ser Ile Arg Gly Val Asp Ser Gly
                100                 105                 110

Leu Tyr Leu Gly Met Asn Glu Arg Gly Glu Leu Tyr Gly Ser Lys Lys
                115                 120                 125

Leu Thr Arg Glu Cys Val Phe Arg Glu Gln Phe Glu Glu Asn Trp Tyr
        130                 135                 140

Asn Thr Tyr Ala Ser Thr Leu Tyr Lys His Ser Asp Ser Glu Arg Gln
145             150                 155                 160

Tyr Tyr Val Ala Leu Asn Lys Asp Gly Ser Pro Arg Glu Gly Tyr Arg
                165                 170                 175

Thr Lys Arg His Gln Lys Phe Thr His Phe Leu Pro Arg Pro Val Asp
                180                 185                 190

Pro Ser Lys Leu Pro Ser Met Ser Arg Asp Leu Phe His Tyr Arg
                195                 200                 205

<210> SEQ ID NO 226
<211> LENGTH: 211
<212> TYPE: PRT
<213> ORGANISM: Homo sapiens

<400> SEQUENCE: 226

Met Ala Pro Leu Ala Glu Val Gly Gly Phe Leu Gly Gly Leu Glu Gly
1               5                   10                  15

Leu Gly Gln Gln Val Gly Ser His Phe Leu Leu Pro Pro Ala Gly Glu
                20                  25                  30

Arg Pro Pro Leu Leu Gly Glu Arg Arg Ser Ala Ala Glu Arg Ser Ala
                35                  40                  45

Arg Gly Gly Pro Gly Ala Ala Gln Leu Ala His Leu His Gly Ile Leu
        50                  55                  60

Arg Arg Arg Gln Leu Tyr Cys Arg Thr Gly Phe His Leu Gln Ile Leu
65              70                  75                  80

Pro Asp Gly Ser Val Gln Gly Thr Arg Gln Asp His Ser Leu Phe Gly
                85                  90                  95

Ile Leu Glu Phe Ile Ser Val Ala Val Gly Leu Val Ser Ile Arg Gly
                100                 105                 110

Val Asp Ser Gly Leu Tyr Leu Gly Met Asn Asp Lys Gly Glu Leu Tyr
                115                 120                 125

Gly Ser Glu Lys Leu Thr Ser Glu Cys Ile Phe Arg Glu Gln Phe Glu
        130                 135                 140

```
Glu Asn Trp Tyr Asn Thr Tyr Ser Ser Asn Ile Tyr Lys His Gly Asp
145                 150                 155                 160

Thr Gly Arg Arg Tyr Phe Val Ala Leu Asn Lys Asp Gly Thr Pro Arg
                165                 170                 175

Asp Gly Ala Arg Ser Lys Arg His Gln Lys Phe Thr His Phe Leu Pro
            180                 185                 190

Arg Pro Val Asp Pro Glu Arg Val Pro Glu Leu Tyr Lys Asp Leu Leu
        195                 200                 205

Met Tyr Thr
    210

<210> SEQ ID NO 227
<211> LENGTH: 621
<212> TYPE: DNA
<213> ORGANISM: Homo sapiens

<400> SEQUENCE: 227 atgtcgggc  ccgggacggc  cgcggtagcg  ctgctcccgg  cggtcctgct  ggccttgctg      60
gcgccctggg  cgggccgagg  gggcgccgcc  gcacccactg  cacccaacgg  cacgctggag     120
gccgagctgg  agcgccgctg  ggagagcctg  gtggcgctct  cgttggcgcg  cctgccggtg     180
gcagcgcagc  ccaaggaggc  ggccgtccag  agcggcgccg  gcgactacct  gctgggcatc     240
aagcggctgc  ggcggctcta  ctgcaacgtg  gcatcggct   tccacctcca  ggcgctcccc     300
gacggccgca  tcggcggcgc  gcacgcggac  acccgcgaca  gcctgctgga  gctctcgccc     360
gtggagcggg  gcgtggtgag  catcttcggc  gtggccagcc  ggttcttcgt  ggccatgagc     420
agcaagggca  agctctatgg  ctcgcccttc  ttcaccgatg  agtgcacgtt  caaggagatt     480
ctccttccca  caactacaa   cgcctacgag  tcctacaagt  accccggcat  gttcatcgcc     540
ctgagcaaga  atgggaagac  caagaagggg  aaccgagtgt  cgcccaccat  gaaggtcacc     600
cacttcctcc  ccaggctgtg  a                                                  621

<210> SEQ ID NO 228
<211> LENGTH: 807
<212> TYPE: DNA
<213> ORGANISM: Homo sapiens

<400> SEQUENCE: 228
atgagcttgt  ccttcctcct  cctcctcttc  ttcagccacc  tgatcctcag  cgcctgggct      60
cacggggaga  agcgtctcgc  ccccaaaggg  caacccggac  cgctgccac   tgataggaac     120
cctagaggct  ccagcagcag  acagagcagc  agtagcgcta  tgtcttcctc  ttctgcctcc     180
tcctccccg   cagcttctct  gggcagccaa  ggaagtggct  tggagcagag  cagtttccag     240
tggagcccct  cggggcgccg  gaccggcagc  ctctactgca  gagtgggcat  cggtttccat     300
ctgcagatct  acccggatgg  caaagtcaat  ggatcccacg  aagccaatat  gttaagtgtt     360
ttggaaatat  ttgctgtgtc  tcaggggatt  gtaggaatac  gaggagtttt  cagcaacaaa     420
tttttagcga  tgtcaaaaaa  aggaaaactc  catgcaagtg  ccaagttcac  agatgactgc     480
aagttcaggg  agcgttttca  agaaaatagc  tataatacct  atgcctcagc  aatacataga     540
actgaaaaaa  cagggcggga  gtggtatgtg  ccctgaata   aaagaggaaa  agccaaacga     600
gggtgcagcc  ccgggttaa   ccccagcat   atctctaccc  attttctgcc  aagattcaag     660
cagtcggagc  agccagaact  ttctttcacg  gttactgttc  ctgaaaagaa  aaagccacct     720
agccctatca  agccaaagat  tcccctttct  gcacctcgga  aaaataccaa  ctcagtgaaa     780
```

```
tacagactca agtttcgctt tggataa                                         807
```

<210> SEQ ID NO 229
<211> LENGTH: 627
<212> TYPE: DNA
<213> ORGANISM: Homo sapiens

<400> SEQUENCE: 229

```
atggccctgg gacagaaact gttcatcact atgtcccggg gagcaggacg tctgcagggc     60
acgctgtggg ctctcgtctt cctaggcatc ctagtgggca tggtggtgcc ctcgcctgca    120
ggcacccgtg ccaacaacac gctgctggac tcgaggggct ggggcaccct gctgtccagg    180
tctcgcgcgg ggctagctgg agagattgcc ggggtgaact gggaaagtgg ctatttggtg    240
gggatcaagc ggcagcggag gctctactgc aacgtgggca tcggcttttca cctccaggtg    300
ctccccgacg gccggatcag cgggacccac gaggagaacc cctacagcct gctggaaatt    360
tccactgtgg agcgaggcgt ggtgagtctc tttggagtga agtgcccct cttcgttgcc    420
atgaacagta aaggaagatt gtacgcaacg cccagcttcc aagaagaatg caagttcaga    480
gaaaccctcc tgcccaacaa ttacaatgcc tacgagtcag acttgtacca agggacctac    540
attgccctga gcaaatacgg acgggtaaag cggggcagca aggtgtcccc gatcatgact    600
gtcactcatt tccttcccag gatctaa                                        627
```

<210> SEQ ID NO 230
<211> LENGTH: 627
<212> TYPE: DNA
<213> ORGANISM: Homo sapiens

<400> SEQUENCE: 230

```
atggctccct taggtgaagt tgggaactat ttcggtgtgc aggatgcggt accgtttggg     60
aatgtgcccg tgttgccggt ggacagcccg gttttgttaa gtgaccacct gggtcagtcc    120
gaagcagggg ggctccccag gggacccgca gtcacggact tggatcattt aaagggggatt    180
ctcaggcgga ggcagctata ctgcaggact ggatttcact tagaaatctt ccccaatggt    240
actatccagg gaaccaggaa agaccacagc cgatttggca ttctggaatt tatcagtata    300
gcagtgggcc tggtcagcat tcgaggcgtg gacagtggac tctacctcgg gatgaatgag    360
aaggggggagc tgtatggatc agaaaaaacta acccaagagt gtgtattcag agaacagttc    420
gaagaaaact ggtataatac gtactcatca aacctatata gcacgtgga cactggaagg    480
cgatactatg ttgcattaaa taagatggg accccgagag aagggactag gactaaacgg    540
caccagaaaat tcacacattt tttacctaga ccagtggacc ccgacaaagt acctgaactg    600
tataaggata ttctaagcca aagttga                                        627
```

<210> SEQ ID NO 231
<211> LENGTH: 624
<212> TYPE: DNA
<213> ORGANISM: Homo sapiens

<400> SEQUENCE: 231

```
atggcagagg tgggggggcgt cttcgcctcc ttggactggg atctacacgg cttctcctcg     60
tctctgggga acgtgcccctt agctgactcc ccaggtttcc tgaacgagcg cctgggccaa    120
atcgagggga agctgcagcg tggctcaccc acagacttcg cccacctgaa ggggatcctg    180
cggcgccgcc agctctactg ccgcaccggc ttccacctgg atcttccc caacggcacg    240
gtgcacggga cccgccacga ccacagccgc ttcggaatcc tggagtttat cagcctggct    300
```

```
gtggggctga tcagcatccg ggagtggac tctggcctgt acctaggaat gaatgagcga    360
ggagaactct atgggtcgaa gaaactcaca cgtgaatgtg ttttccggga acagtttgaa    420
gaaaactggt acaacaccta tgcctcaacc ttgtacaaac attcggactc agagagacag    480
tattacgtgg ccctgaacaa agatggctca ccccggagg gatacaggac taaacgacac    540
cagaaattca ctcactttt acccaggcct gtagatcctt ctaagttgcc ctccatgtcc    600
agagacctct ttcactatag gtaa                                           624
```

<210> SEQ ID NO 232
<211> LENGTH: 636
<212> TYPE: DNA
<213> ORGANISM: Homo sapiens

<400> SEQUENCE: 232

```
atggctccct tagccgaagt cgggggcttt ctgggcggcc tggagggctt gggccagcag     60
gtgggttcgc atttcctgtt gcctcctgcc ggggagcggc cgccgctgct gggcgagcgc    120
aggagcgcgg cggagcggag cgcgcgcggc gggccggggg ctgcgcagct ggcgcacctg    180
cacggcatcc tgcgccgccg gcagctctat tgccgcaccg gcttccacct gcagatcctg    240
cccgacggca gcgtgcaggg cacccggcag gaccacagcc tcttcggtat cttggaattc    300
atcagtgtgg cagtgggact ggtcagtatt agaggtgtgg acagtggtct ctatcttgga    360
atgaatgaca aggagaact ctatggatca gagaaactta cttccgaatg catctttagg    420
gagcagtttg aagagaactg gtataacacc tattcatcta acatatataa acatggagac    480
actggccgca ggtattttgt ggcacttaac aaagacggaa ctccaagaga tggcgccagg    540
tccaagaggc atcagaaatt tacacatttc ttacctagac cagtggatcc agaaagagtt    600
ccagaattgt acaaggacct actgatgtac acttga                              636
```

<210> SEQ ID NO 233
<211> LENGTH: 209
<212> TYPE: PRT
<213> ORGANISM: Homo sapiens

<400> SEQUENCE: 233

```
Met Asp Ser Asp Glu Thr Gly Phe Glu His Ser Gly Leu Trp Val Ser
 1               5                  10                  15

Val Leu Ala Gly Leu Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
        50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
               100                 105                 110

Ser Leu His Phe Asp Pro Glu Ala Cys Ser Phe Arg Glu Leu Leu Leu
           115                 120                 125

Glu Asp Gly Tyr Asn Val Tyr Gln Ser Glu Ala His Gly Leu Pro Leu
       130                 135                 140

His Leu Pro Gly Asn Lys Ser Pro His Arg Asp Pro Ala Pro Arg Gly
```

145             150             155             160
Pro Ala Arg Phe Leu Pro Leu Pro Gly Leu Pro Pro Ala Leu Pro Glu
            165                 170                 175
Pro Pro Gly Ile Leu Ala Pro Gln Pro Pro Asp Val Gly Ser Ser Asp
            180                 185                 190
Pro Leu Ser Met Val Gly Pro Ser Gln Gly Arg Ser Pro Ser Tyr Ala
            195                 200                 205
Ser

<210> SEQ ID NO 234
<211> LENGTH: 209
<212> TYPE: PRT
<213> ORGANISM: Pongo abelii

<400> SEQUENCE: 234

Met Asp Ser Asp Glu Thr Gly Phe Glu His Ser Gly Leu Trp Val Pro
1               5                   10                  15
Val Leu Ala Gly Leu Leu Leu Gly Ala Cys Gln Ala His Pro Ile Pro
            20                  25                  30
Asp Ser Ser Pro Leu Leu Gln Phe Gly Gly Gln Val Arg Gln Arg Tyr
        35                  40                  45
Leu Tyr Thr Asp Asp Ala Gln Gln Thr Glu Ala His Leu Glu Ile Arg
    50                  55                  60
Glu Asp Gly Thr Val Gly Gly Ala Ala Asp Gln Ser Pro Glu Ser Leu
65                  70                  75                  80
Leu Gln Leu Lys Ala Leu Lys Pro Gly Val Ile Gln Ile Leu Gly Val
                85                  90                  95
Lys Thr Ser Arg Phe Leu Cys Gln Arg Pro Asp Gly Ala Leu Tyr Gly
            100                 105                 110
Ser Leu His Phe Asp Pro Glu Ala Cys Ser Phe Arg Glu Leu Leu Leu
        115                 120                 125
Glu Asp Gly Tyr Asn Val Tyr Gln Ser Glu Ala His Gly Leu Pro Leu
    130                 135                 140
His Leu Pro Gly Asn Lys Ser Pro His Arg Asp Pro Ala Pro Arg Gly
145             150                 155                 160
Pro Ala Arg Phe Leu Pro Leu Pro Gly Leu Pro Pro Ala Pro Pro Glu
            165                 170                 175
Pro Pro Gly Ile Leu Ala Pro Gln Pro Pro Asp Val Gly Ser Ser Asp
            180                 185                 190
Pro Leu Ser Met Val Gly Pro Ser Gln Gly Arg Ser Pro Ser Tyr Ala
            195                 200                 205
Ser

<210> SEQ ID NO 235
<211> LENGTH: 209
<212> TYPE: PRT
<213> ORGANISM: Pan troglodytes

<400> SEQUENCE: 235

Met Asp Ser Asp Glu Thr Gly Phe Glu His Ser Gly Leu Trp Val Ser
1               5                   10                  15
Val Leu Ala Gly Leu Leu Leu Gly Ala Cys Gln Ala His Pro Ile Pro
            20                  25                  30
Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
            50                  55                  60

Glu Asp Gly Thr Val Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
                 85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
                115                 120                 125

Glu Asp Gly Tyr Asn Val Tyr Gln Ser Glu Ala His Gly Leu Pro Leu
130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Ala Pro Pro Glu
                165                 170                 175

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Thr
                195                 200                 205

Ser

<210> SEQ ID NO 236
<211> LENGTH: 209
<212> TYPE: PRT
<213> ORGANISM: Canis lupus familiaris

<400> SEQUENCE: 236

Met Gly Trp Ala Glu Ala Gly Phe Glu His Leu Gly Leu Trp Val Pro
 1               5                  10                  15

Val Leu Ala Val Leu Leu Leu Glu Ala Cys Arg Ala His Pro Ile Pro
                 20                  25                  30

Asp Ser Ser Pro Leu Leu Gln Phe Gly Gly Gln Val Arg Gln Arg Tyr
             35                  40                  45

Leu Tyr Thr Asp Asp Ala Gln Glu Thr Glu Ala His Leu Glu Ile Arg
            50                  55                  60

Ala Asp Gly Thr Val Val Gly Ala Ala Arg Gln Ser Pro Glu Ser Leu
 65                  70                  75                  80

Leu Glu Leu Lys Ala Leu Lys Pro Gly Val Ile Gln Ile Leu Gly Val
                 85                  90                  95

Lys Thr Ser Arg Phe Leu Cys Gln Gly Pro Asp Gly Thr Leu Tyr Gly
                100                 105                 110

Ser Leu His Phe Asp Pro Val Ala Cys Ser Phe Arg Glu Leu Leu Leu
                115                 120                 125

Glu Asp Gly Tyr Asn Ile Tyr His Ser Glu Thr Leu Gly Leu Pro Leu
130                 135                 140

Arg Leu Arg Pro His Asn Ser Ala Tyr Arg Asp Leu Ala Pro Arg Gly
145                 150                 155                 160

Pro Ala Arg Phe Leu Pro Leu Pro Gly Leu Leu Pro Ala Pro Pro Glu
                165                 170                 175

Pro Pro Gly Ile Leu Ala Pro Glu Pro Pro Asp Val Gly Ser Ser Asp
                180                 185                 190

Pro Leu Ser Met Val Gly Pro Ser Gln Gly Arg Ser Pro Ser Tyr Ala
                195                 200                 205

Ser

<210> SEQ ID NO 237
<211> LENGTH: 209
<212> TYPE: PRT
<213> ORGANISM: Bos taurus

<400> SEQUENCE: 237

Met Gly Trp Asp Glu Ala Lys Phe Lys His Leu Gly Leu Trp Val Pro
1               5                   10                  15

Val Leu Ala Val Leu Leu Leu Gly Thr Cys Arg Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala Arg Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Lys Leu Tyr Gly
            100                 105                 110

Ser Leu His Phe Asp Pro Lys Ala Cys Ser Phe Arg Glu Leu Leu Leu
        115                 120                 125

Glu Asp Gly Tyr Asn Val Tyr Gln Ser Glu Thr Leu Gly Leu Pro Leu
    130                 135                 140

Arg Leu Pro Pro Gln Arg Ser Ser Asn Arg Asp Pro Ala Pro Arg Gly
145                 150                 155                 160

Pro Ala Arg Phe Leu Pro Leu Pro Gly Leu Pro Ala Ala Pro Pro Asp
                165                 170                 175

Pro Pro Gly Ile Leu Ala Pro Glu Pro Pro Asp Val Gly Ser Ser Asp
            180                 185                 190

Pro Leu Ser Met Val Gly Pro Ser Tyr Gly Arg Ser Pro Ser Tyr Thr
        195                 200                 205

Ser

<210> SEQ ID NO 238
<211> LENGTH: 209
<212> TYPE: PRT
<213> ORGANISM: Equus caballus

<400> SEQUENCE: 238

Met Asp Trp Asp Lys Thr Gly Phe Lys Tyr Gln Gly Leu Trp Val Pro
1               5                   10                  15

Val Leu Ala Val Leu Leu Leu Gly Ala Cys Gln Ser His Pro Ile Pro
            20                  25                  30

Asp Ser Ser Pro Leu Leu Gln Phe Gly Gly Gln Val Arg Gln Arg His
        35                  40                  45

Leu Tyr Thr Asp Asp Ala Gln Glu Thr Glu Ala His Leu Glu Ile Arg
    50                  55                  60

Ala Asp Gly Thr Val Ala Gly Ala Val His Arg Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Thr Leu Tyr Gly
            100                 105                 110

Ser Leu His Phe Asp Pro Val Ala Cys Ser Phe Arg Glu Leu Leu Leu
        115                 120                 125

Glu Asp Gly Tyr Asn Val Tyr Gln Ser Glu Thr Leu Gly Leu Pro Leu
    130                 135                 140

Arg Leu Pro His His Ser Ser Pro Tyr Gln Asp Pro Ala Pro Arg Ala
145                 150                 155                 160

Pro Ala Arg Phe Leu Pro Leu Pro Gly Phe Pro Pro Ala Pro Pro Glu
                165                 170                 175

Pro Pro Gly Ile Pro Ala Pro Glu Pro Pro Asp Val Gly Ser Ser Asp
            180                 185                 190

Pro Leu Ser Met Val Gly Pro Ser Arg Ser Arg Ser Pro Ser Tyr Thr
        195                 200                 205

Ser

<210> SEQ ID NO 239
<211> LENGTH: 209
<212> TYPE: PRT
<213> ORGANISM: Ailuropoda melanoleuca

<400> SEQUENCE: 239

Met Gly Trp Asp Glu Ala Arg Ser Glu Gln Leu Gly Leu Trp Val Pro
1               5                   10                  15

Val Leu Ala Val Leu Leu Leu Glu Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Ala Ile Arg
    50                  55                  60

Ala Asp Gly Thr Val Val Gly Ala Ala Ser Arg Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Thr Leu Tyr Gly
            100                 105                 110

Ser Val Arg Phe Asp Pro Val Ala Cys Ser Phe Arg Glu Leu Leu Leu
        115                 120                 125

Glu Asp Gly Tyr Asn Ile Tyr His Ser Glu Thr Leu Gly Leu Pro Leu
    130                 135                 140

Arg Leu Pro Ala His Asn Ser Pro Tyr Arg Asp Ser Ala Pro Arg Gly
145                 150                 155                 160

Pro Ala Arg Phe Leu Pro Leu Pro Gly Leu Leu Pro Val Pro Pro Asp
                165                 170                 175

Pro Pro Gly Ile Leu Gly Pro Glu Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 240
<211> LENGTH: 209
<212> TYPE: PRT
<213> ORGANISM: Oryctolagus cuniculus

<400> SEQUENCE: 240

Met Asp Trp Gly Lys Ala Lys Cys Arg Pro Pro Gly Leu Trp Val Pro

```
  1               5                  10                 15
Ala Leu Ala Ala Leu Leu Gly Ala Cys Gln Ala His Pro Ile Pro
                20                 25                 30
Asp Ser Ser Pro Leu Leu Gln Phe Gly Asp Gln Val Arg Gln Gln His
            35                  40                 45
Leu Tyr Thr Asp Asp Ala Gln Glu Thr Glu Ala His Leu Glu Ile Arg
        50                  55                 60
Ala Asp Gly Thr Val Val Gly Ala Ala Arg Arg Ser Pro Glu Ser Leu
65                  70                  75                 80
Leu Gln Met Lys Ala Leu Gln Pro Gly Ile Ile Gln Ile Leu Gly Val
                85                  90                 95
Gln Thr Ser Arg Phe Leu Cys Gln Arg Pro Asp Gly Thr Leu Tyr Gly
                100                 105                110
Ser Leu His Phe Asp Arg Glu Ala Cys Ser Phe Arg Glu Leu Leu Arg
                115                 120                125
Glu Asp Gly Tyr Asn Val Tyr Leu Ser Glu Ala Leu Gly Leu Pro Leu
            130                 135                 140
Arg Leu Ser Pro Gly Ser Pro Arg Arg Ala Pro Ala Pro Arg Gly
145                 150                 155                160
Pro Ala Arg Phe Leu Pro Leu Pro Gly Leu Pro Pro Asp Leu Pro Glu
                165                 170                 175
Pro Pro Gly Leu Leu Ala Ala Pro Pro Asp Val Asp Ser Pro Asp
            180                 185                 190
Pro Leu Ser Met Val Gln Pro Ala Leu Asp Gln Ser Pro Ser Tyr Thr
            195                 200                 205
Ser

<210> SEQ ID NO 241
<211> LENGTH: 209
<212> TYPE: PRT
<213> ORGANISM: Gorilla gorilla

<400> SEQUENCE: 241

Met Asp Ser Asp Glu Thr Gly Phe Glu His Ser Gly Leu Trp Val Ser
1               5                   10                  15
Val Leu Ala Gly Leu Leu Gly Ala Cys Gln Ala His Pro Ile Pro
                20                  25                  30
Asp Ser Ser Pro Leu Leu Gln Phe Gly Gly Gln Val Arg Gln Arg Tyr
            35                  40                  45
Leu Tyr Thr Asp Asp Ala Gln Gln Thr Glu Ala His Leu Glu Ile Arg
        50                  55                  60
Glu Asp Gly Thr Val Gly Gly Ala Ala Asp Gln Ser Pro Glu Ser Leu
65                  70                  75                  80
Leu Gln Leu Lys Ala Leu Lys Pro Gly Val Ile Gln Ile Leu Gly Val
                85                  90                  95
Lys Thr Ser Arg Phe Leu Cys Gln Arg Pro Asp Gly Ala Leu Tyr Gly
                100                 105                 110
Ser Leu His Phe Asp Pro Glu Ala Cys Ser Phe Arg Glu Leu Leu Leu
                115                 120                 125
Glu Asp Gly Tyr Asn Val Tyr Gln Ser Glu Ala His Gly Leu Pro Leu
            130                 135                 140
His Leu Pro Gly Asn Lys Ser Pro His Arg Asp Pro Ala Pro Arg Gly
145                 150                 155                 160
Pro Ala Arg Phe Leu Pro Leu Pro Gly Leu Pro Pro Ala Pro Pro Glu
```

165                 170                 175
Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser

<210> SEQ ID NO 242
<211> LENGTH: 209
<212> TYPE: PRT
<213> ORGANISM: Nomascus leucogenys

<400> SEQUENCE: 242

Met Asp Ser Asp Glu Thr Gly Phe Glu His Ser Gly Leu Trp Val Pro
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
        50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
        130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser

<210> SEQ ID NO 243
<211> LENGTH: 209
<212> TYPE: PRT
<213> ORGANISM: Procavia capensis

<400> SEQUENCE: 243

Met Asp Trp Ala Lys Phe Gly Ile Glu His Pro Gly Leu Trp Val Pro
1               5                   10                  15

Val Met Ala Val Leu Leu Leu Gly Ala Cys Gln Gly Tyr Pro Ile Pro
            20                  25                  30

Asp Ser Ser Pro Leu Leu Gln Phe Gly Gly Gln Val Arg Gln Arg Tyr
            35                  40                  45

Leu Tyr Thr Asp Asp Ala Gln Glu Thr Glu Ala His Leu Glu Ile Arg
        50                  55                  60

Ala Asp Gly Thr Val Val Gly Ala Ala His Arg Ser Pro Glu Ser Leu
65                  70                  75                  80

Leu Glu Leu Lys Ala Leu Lys Pro Gly Ile Ile Gln Ile Leu Gly Val
                85                  90                  95

Lys Thr Ser Arg Phe Leu Cys Gln Gly Pro Asp Gly Val Leu Tyr Gly
                100                 105                 110

Ser Leu Arg Phe Asp Pro Val Ala Cys Ser Phe Arg Glu Leu Leu Leu
                115                 120                 125

Glu Asp Gly Tyr Asn Val Tyr Gln Ser Glu Ala His Gly Leu Pro Leu
            130                 135                 140

Arg Leu Pro Ser His Asn Ser Pro Gln Arg Asp Leu Ala Ser Arg Val
145                 150                 155                 160

Pro Ala Arg Phe Leu Pro Leu Pro Gly Arg Leu Thr Val Leu Pro Glu
                165                 170                 175

Pro Ser Gly Val Leu Gly Pro Glu Pro Pro Asp Val Asp Ser Ser Asp
                180                 185                 190

Pro Leu Ser Met Val Gly Pro Ser Gln Gly Arg Ser Pro Ser Tyr Ala
                195                 200                 205

Ser

<210> SEQ ID NO 244
<211> LENGTH: 209
<212> TYPE: PRT
<213> ORGANISM: Cavia porcellus

<400> SEQUENCE: 244

Met Asp Trp Ala Arg Thr Glu Cys Glu Arg Pro Arg Leu Trp Val Ser
1               5                   10                  15

Met Leu Ala Ile Leu Leu Val Gly Ala Cys Gln Ala His Pro Ile Pro
                20                  25                  30

Asp Ser Ser Pro Leu Leu Gln Phe Gly Gly Gln Val Arg Gln Arg Tyr
                35                  40                  45

Leu Tyr Thr Asp Asp Ala Gln Asp Thr Glu Val His Leu Glu Ile Arg
        50                  55                  60

Ala Asp Gly Ser Val Arg Gly Ile Ala His Arg Ser Pro Glu Ser Leu
65                  70                  75                  80

Leu Glu Leu Lys Ala Leu Lys Pro Gly Val Ile Gln Ile Leu Gly Ile
                85                  90                  95

Arg Thr Ser Arg Phe Leu Cys Gln Arg Pro Asp Gly Ser Leu Tyr Gly
                100                 105                 110

Ser Leu His Phe Asp Pro Glu Ala Cys Ser Phe Arg Glu Leu Leu Leu
                115                 120                 125

Ala Asp Gly Tyr Asn Val Tyr Lys Ser Glu Ala His Gly Leu Pro Leu
            130                 135                 140

His Leu Leu Arg Gly Asp Ser Leu Ser Gln Glu Pro Ala Pro Pro Gly
145                 150                 155                 160

Pro Ala Arg Phe Leu Pro Leu Pro Gly Leu Pro Ala Thr Pro Pro Glu
                165                 170                 175

Pro Pro Arg Met Leu Pro Pro Gly Pro Pro Asp Val Gly Ser Ser Asp
                180                 185                 190

Pro Leu Ser Met Val Gly Pro Leu Trp Asp Arg Ser Pro Ser Tyr Thr
                195                 200                 205

Ser

```
<210> SEQ ID NO 245
<211> LENGTH: 209
<212> TYPE: PRT
<213> ORGANISM: Tupaia belangeri

<400> SEQUENCE: 245

Met Gly Trp Asp Lys Ala Arg Phe Glu His Leu Gly Ala Trp Ala Pro
1               5                   10                  15

Val Leu Ala Val Leu Leu Leu Gly Ala Cys Gln Ala Tyr Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Thr Gln Asp Thr Glu Ala His Leu Glu Ile Arg
    50                  55                  60

Ala Asp Gly Thr Val Val Gly Ala Ala His Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Ile Tyr Gln Ser Glu Ala Arg Gly Leu Pro Leu
    130                 135                 140

Arg Leu Pro Pro His Asp Ser Pro His Arg Asp Arg Thr Pro Arg Gly
145                 150                 155                 160

Pro Ala Arg Phe Leu Pro Leu Pro Gly Leu Pro Leu Val Pro Pro Glu
                165                 170                 175

Leu Pro Gly Val Leu Ala Leu Glu Pro Pro Asp Val Gly Ser Ser Asp
            180                 185                 190

Pro Leu Ser Met Met Gly Pro Ser Gln Gly Gln Ser Pro Ser Tyr Ala
        195                 200                 205

Ser

<210> SEQ ID NO 246
<211> LENGTH: 210
<212> TYPE: PRT
<213> ORGANISM: Sorex araneus

<400> SEQUENCE: 246

Met Val Trp Asp Lys Ala Arg Gly Gln Gln Leu Gly Leu Trp Ala Pro
1               5                   10                  15

Met Leu Leu Gly Leu Leu Gly Ala Cys Gln Ala His Pro Leu Pro
                20                  25                  30

Asp Ser Ser Pro Leu Leu Gln Phe Gly Gly Gln Val Arg Leu Arg Phe
            35                  40                  45

Leu Tyr Thr Asp Asp Ala Gln Arg Thr Gly Ala His Leu Glu Ile Arg
    50                  55                  60

Ala Asp Gly Thr Val Gln Gly Ala Ala His Arg Thr Pro Glu Cys Leu
65                  70                  75                  80

Leu Glu Leu Lys Ala Leu Lys Pro Gly Val Ile Gln Ile Leu Gly Val
                85                  90                  95

Ser Thr Ser Arg Phe Leu Cys Gln Arg Pro Asp Gly Val Leu Tyr Gly
            100                 105                 110

Ser Leu Arg Phe Asp Pro Glu Ala Cys Ser Phe Arg Glu Leu Leu Leu
        115                 120                 125
```

Gln Asp Gly Tyr Asn Val Tyr Gln Ser Glu Ala Leu Gly Leu Pro Leu
        130                 135                 140

Tyr Leu His Pro Pro Ser Ala Pro Val Ser Gln Glu Pro Ala Ser Arg
145                 150                 155                 160

Gly Ala Val Arg Phe Leu Pro Leu Pro Gly Leu Pro Pro Ala Ser Leu
                165                 170                 175

Glu Pro Pro Arg Pro Pro Ala Pro Val Pro Pro Asp Val Gly Ser Ser
        180                 185                 190

Asp Pro Leu Ser Met Val Gly Pro Pro Glu Arg His Ser Pro Ser Tyr
        195                 200                 205

Thr Ser
    210

<210> SEQ ID NO 247
<211> LENGTH: 208
<212> TYPE: PRT
<213> ORGANISM: Ictidomys tridecemlineatus

<400> SEQUENCE: 247

Met Asp Trp Val Lys Ala Lys Leu Glu Pro Leu Gly Leu Trp Val Leu
1               5                   10                  15

Val Leu Ala Ala Leu Val Leu Gly Ala Cys Gln Ala Tyr Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Glu Thr Glu Ala His Leu Glu Ile Arg
50                  55                  60

Ala Asp Gly Thr Val Val Gly Ala Ala His Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Arg Pro Asp Gly Val Leu Tyr Gly
            100                 105                 110

Ser Leu His Phe Asp Pro Glu Ala Cys Ser Phe Arg Glu Gln Leu Leu
        115                 120                 125

Glu Asp Gly Tyr Asn Val Tyr Gln Ser Glu Ser His Gly Leu Pro Val
        130                 135                 140

Arg Leu Pro Pro Asn Ser Pro Tyr Arg Asp Pro Ala Pro Pro Gly Pro
145                 150                 155                 160

Ala Arg Phe Leu Pro Leu Pro Gly Leu Pro Pro Ala Ala Leu Glu Pro
                165                 170                 175

Pro Gly Ile Leu Gly Pro Glu Pro Pro Asp Val Gly Ser Ser Asp Pro
        180                 185                 190

Leu Ser Met Val Gly Pro Leu Gln Gly Arg Ser Pro Ser Tyr Ala Ser
        195                 200                 205

<210> SEQ ID NO 248
<211> LENGTH: 208
<212> TYPE: PRT
<213> ORGANISM: Loxodonta africana

<400> SEQUENCE: 248

Met Asp Trp Ala Lys Phe Gly Leu Glu His Pro Gly Leu Trp Val Pro
1               5                   10                  15

Val Met Ala Val Leu Leu Leu Gly Ala Cys Gln Gly His Pro Ile Pro
                20                  25                  30

-continued

Asp Ser Ser Pro Leu Leu Gln Phe Gly Gly Gln Val Arg Gln Arg Tyr
                35                  40                  45

Leu Tyr Thr Asp Asp Gln Glu Thr Glu Ala His Leu Glu Ile Arg Ala
 50                  55                  60

Asp Gly Thr Val Ala Gly Ala His Arg Ser Ser Glu Ser Leu Leu
 65                  70                  75                  80

Glu Leu Lys Ala Leu Lys Pro Gly Ile Ile Gln Ile Leu Gly Val Lys
                 85                  90                  95

Thr Ser Arg Phe Leu Cys Gln Gly Pro Asp Gly Val Leu Tyr Gly Ser
                100                 105                 110

Leu His Phe Asp Pro Ala Ala Cys Ser Phe Arg Glu Leu Leu Leu Glu
                115                 120                 125

Asp Gly Tyr Asn Val Tyr Trp Ser Glu Ala His Gly Leu Pro Ile Arg
130                 135                 140

Leu Pro Ser His Asn Ser Pro Tyr Arg Asp Pro Ala Ser Arg Val Pro
145                 150                 155                 160

Ala Arg Phe Leu Pro Leu Pro Gly Leu Leu Pro Met Leu Gln Glu Pro
                165                 170                 175

Pro Gly Val Leu Ala Pro Glu Pro Pro Asp Val Asp Ser Ser Asp Pro
                180                 185                 190

Leu Ser Met Val Gly Pro Ser Gln Gly Arg Ser Pro Ser Tyr Ala Ser
                195                 200                 205

<210> SEQ ID NO 249
<211> LENGTH: 208
<212> TYPE: PRT
<213> ORGANISM: Sus scrofa

<400> SEQUENCE: 249

Met Gly Trp Ala Glu Ala Lys Phe Glu Arg Leu Gly Leu Trp Val Pro
1               5                   10                  15

Val Leu Ala Val Leu Leu Gly Ala Cys Gln Ala Arg Pro Ile Pro Asp
                20                  25                  30

Ser Ser Pro Leu Leu Gln Phe Gly Gly Gln Val Arg Gln Arg Tyr Leu
                35                  40                  45

Tyr Thr Asp Asp Ala Gln Glu Thr Glu Ala His Leu Glu Ile Arg Ala
 50                  55                  60

Asp Gly Thr Val Ala Gly Val Ala Arg Gln Ser Pro Glu Ser Leu Leu
 65                  70                  75                  80

Glu Leu Lys Ala Leu Lys Pro Gly Val Ile Gln Ile Leu Gly Val Gln
                 85                  90                  95

Thr Ser Arg Phe Leu Cys Gln Gly Pro Asp Gly Arg Leu Tyr Gly Ser
                100                 105                 110

Leu His Phe Asp Pro Glu Ala Cys Ser Phe Arg Glu Leu Leu Leu Glu
                115                 120                 125

Asp Gly Tyr Asn Val Tyr Gln Ser Glu Ala Leu Gly Leu Pro Leu Arg
130                 135                 140

Leu Pro Pro His Arg Ser Ser Asn Arg Asp Leu Ala Pro Arg Gly Pro
145                 150                 155                 160

Ala Arg Phe Leu Pro Leu Pro Gly Leu Pro Ala Pro Pro Glu Pro
                165                 170                 175

Pro Gly Ile Leu Ala Pro Glu Pro Pro Asp Val Gly Ser Ser Asp Pro
                180                 185                 190

Leu Ser Met Val Gly Pro Ser His Gly Arg Ser Pro Ser Tyr Thr Ser

<210> SEQ ID NO 250
<211> LENGTH: 208
<212> TYPE: PRT
<213> ORGANISM: Felis catus

<400> SEQUENCE: 250

Met Asp Trp Asp Glu Ala Gly Ser Gln Arg Leu Gly Leu Trp Val Val
1               5                   10                  15

Leu Gly Val Leu Leu Pro Glu Ala Cys Gln Ala His Pro Ile Pro Asp
            20                  25                  30

Ser Ser Pro Leu Leu Gln Phe Gly Gly Gln Val Arg Gln Arg Phe Leu
        35                  40                  45

Tyr Thr Asp Asp Ala Gln Glu Thr Glu Val His Leu Glu Ile Lys Ala
    50                  55                  60

Asp Gly Thr Val Val Gly Thr Ala Arg Arg Ser Pro Glu Ser Leu Leu
65                  70                  75                  80

Glu Leu Lys Ala Leu Lys Pro Gly Val Ile Gln Ile Leu Gly Val Lys
                85                  90                  95

Thr Ser Arg Phe Leu Cys Gln Gly Pro Asp Gly Thr Leu Tyr Gly Ser
            100                 105                 110

Leu Arg Phe Asp Pro Ala Ala Cys Ser Phe Arg Glu Leu Leu Leu Glu
        115                 120                 125

Asp Gly Tyr Asn Ile Tyr His Ser Glu Thr Leu Gly Leu Pro Leu Arg
    130                 135                 140

Leu Pro Pro His Asn Ser Pro Tyr Arg Asp Leu Ala Pro Arg Ala Pro
145                 150                 155                 160

Ala Arg Phe Leu Pro Leu Pro Gly Leu Leu Pro Ala Pro Pro Glu Pro
                165                 170                 175

Pro Gly Ile Leu Ala Pro Glu Pro Pro Asp Val Gly Ser Ser Asp Pro
            180                 185                 190

Leu Ser Met Val Gly Pro Ser Gln Gly Arg Ser Pro Ser Tyr Ala Ser
        195                 200                 205

<210> SEQ ID NO 251
<211> LENGTH: 208
<212> TYPE: PRT
<213> ORGANISM: Otolemur garnettii

<400> SEQUENCE: 251

Asp Lys Ala Arg Thr Gly Phe Lys His Pro Gly Pro Trp Phe Pro Leu
1               5                   10                  15

Leu Ala Val Leu Leu Leu Gly Ala Cys Gln Ala His Pro Ile Pro Asp
            20                  25                  30

Ser Ser Pro Leu Leu Gln Phe Gly Gly Gln Val Arg Gln Arg Tyr Leu
        35                  40                  45

Tyr Thr Asp Asp Ala Gln Glu Thr Glu Ala His Leu Glu Ile Arg Glu
    50                  55                  60

Asp Gly Thr Val Val Gly Ala Ala Gln Gln Ser Pro Glu Ser Leu Leu
65                  70                  75                  80

Glu Leu Lys Ala Leu Lys Pro Gly Val Ile Gln Ile Leu Gly Val Lys
                85                  90                  95

Thr Ser Arg Phe Leu Cys Gln Arg Pro Asp Gly Gly Leu Tyr Gly Ser
            100                 105                 110

Leu Tyr Phe Asp Pro Lys Ala Cys Ser Phe Arg Glu Leu Leu Leu Glu

```
                   115                 120                 125

Asp Gly Tyr Asn Val Tyr Trp Ser Glu Thr Tyr Gly Leu Pro Leu His
    130                 135                 140

Leu Pro Pro Ala Asn Ser Pro Tyr Trp Gly Pro Ser Leu Arg Ser Pro
145                 150                 155                 160

Ala Arg Phe Leu Pro Leu Pro Gly Pro Ala Ala Ser Pro Glu Leu
                165                 170                 175

Pro Gly Ile Leu Ala Leu Glu Pro Pro Asp Val Gly Ser Ser Asp Pro
                180                 185                 190

Leu Ser Met Val Gly Pro Ser Gln Gly Arg Ser Pro Ser Tyr Ala Ser
                195                 200                 205

<210> SEQ ID NO 252
<211> LENGTH: 208
<212> TYPE: PRT
<213> ORGANISM: Rattus norvegicus

<400> SEQUENCE: 252

Met Asp Trp Met Lys Ser Arg Val Gly Ala Pro Gly Leu Trp Val Cys
1               5                   10                  15

Leu Leu Leu Pro Val Phe Leu Leu Gly Val Cys Glu Ala Tyr Pro Ile
                20                  25                  30

Ser Asp Ser Ser Pro Leu Leu Gln Phe Gly Gly Gln Val Arg Gln Arg
            35                  40                  45

Tyr Leu Tyr Thr Asp Asp Gln Asp Thr Glu Ala His Leu Glu Ile
    50                  55                  60

Arg Glu Asp Gly Thr Val Val Gly Thr Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Lys Ala Ser Arg Phe Leu Cys Gln Gln Pro Asp Gly Thr Leu Tyr
                100                 105                 110

Gly Ser Pro His Phe Asp Pro Glu Ala Cys Ser Phe Arg Glu Leu Leu
                115                 120                 125

Leu Lys Asp Gly Tyr Asn Val Tyr Gln Ser Glu Ala His Gly Leu Pro
                130                 135                 140

Leu Arg Leu Pro Gln Lys Asp Ser Gln Asp Pro Ala Thr Arg Gly Pro
145                 150                 155                 160

Val Arg Phe Leu Pro Met Pro Gly Leu Pro His Glu Pro Gln Glu Gln
                165                 170                 175

Pro Gly Val Leu Pro Pro Glu Pro Pro Asp Val Gly Ser Ser Asp Pro
                180                 185                 190

Leu Ser Met Val Glu Pro Leu Gln Gly Arg Ser Pro Ser Tyr Ala Ser
                195                 200                 205

<210> SEQ ID NO 253
<211> LENGTH: 210
<212> TYPE: PRT
<213> ORGANISM: Mus musculus

<400> SEQUENCE: 253

Met Glu Trp Met Arg Ser Arg Val Gly Thr Leu Gly Leu Trp Val Arg
1               5                   10                  15

Leu Leu Leu Ala Val Phe Leu Leu Gly Val Tyr Gln Ala Tyr Pro Ile
                20                  25                  30

Pro Asp Ser Ser Pro Leu Leu Gln Phe Gly Gly Gln Val Arg Gln Arg
```

```
                35                  40                  45
Tyr Leu Tyr Thr Asp Asp Gln Asp Thr Glu Ala His Leu Glu Ile
 50                  55                  60

Arg Glu Asp Gly Thr Val Val Gly Ala Ala His Arg Ser Pro Glu Ser
 65                  70                  75                  80

Leu Leu Glu Leu Lys Ala Leu Lys Pro Gly Val Ile Gln Ile Leu Gly
                 85                  90                  95

Val Lys Ala Ser Arg Phe Leu Cys Gln Gln Pro Asp Gly Ala Leu Tyr
            100                 105                 110

Gly Ser Pro His Phe Asp Pro Glu Ala Cys Ser Phe Arg Glu Leu Leu
        115                 120                 125

Leu Glu Asp Gly Tyr Asn Val Tyr Gln Ser Glu Ala His Gly Leu Pro
130                 135                 140

Leu Arg Leu Pro Gln Lys Asp Ser Pro Asn Gln Asp Ala Thr Ser Trp
145                 150                 155                 160

Gly Pro Val Arg Phe Leu Pro Met Pro Gly Leu Leu His Glu Pro Gln
                165                 170                 175

Asp Gln Ala Gly Phe Leu Pro Pro Glu Pro Pro Asp Val Gly Ser Ser
            180                 185                 190

Asp Pro Leu Ser Met Val Glu Pro Leu Gln Gly Arg Ser Pro Ser Tyr
        195                 200                 205

Ala Ser
    210

<210> SEQ ID NO 254
<211> LENGTH: 107
<212> TYPE: PRT
<213> ORGANISM: Vicugna pacos

<400> SEQUENCE: 254

Met Asp Trp Asp Glu Ala Lys Phe Glu His Arg Gly Leu Trp Val Pro
 1               5                  10                  15

Val Leu Thr Val Leu Leu Gly Ala Cys Gln Ala Arg Pro Ile Pro
                 20                  25                  30

Asp Ser Ser Pro Leu Leu Gln Phe Gly Gly Val Arg Gln Arg Tyr
             35                  40                  45

Leu Tyr Thr Asp Asp Ala Gln Glu Thr Glu Ala His Leu Glu Ile Arg
 50                  55                  60

Ala Asp Gly Thr Val Val Gly Val Ala Arg Gln Pro Glu Gly Ile Pro
 65                  70                  75                  80

Pro Glu Pro Pro Asp Val Gly Ser Ser Asp Pro Leu Ser Met Val Gly
                 85                  90                  95

Pro Ser Tyr Ser Arg Ser Pro Ser Tyr Thr Ser
            100                 105

<210> SEQ ID NO 255
<211> LENGTH: 211
<212> TYPE: PRT
<213> ORGANISM: Anolis carolinensis

<400> SEQUENCE: 255

Cys Lys Ser Lys Gly Gly Gly Lys Gly Gly Glu Arg Met Trp Val Asp
 1               5                  10                  15

Leu Val Phe Trp Ala Ala Leu Leu Arg Thr Ala Pro Ala Leu Pro Leu
                 20                  25                  30

Arg Asn Ser Asn Pro Ile Tyr Gln Phe Asp Gly Gln Val Arg Leu Arg
```

```
            35                  40                  45
His Leu Tyr Thr Ala Asp Glu Gln Thr His Leu His Leu Glu Ile Leu
 50                  55                  60

Pro Asp Gly Thr Val Gly Gly Ser Arg Phe Gln Asn Pro Phe Ser Leu
 65                  70                  75                  80

Met Glu Ile Lys Ala Val Lys Pro Gly Val Ile Arg Met Gln Ala Lys
                 85                  90                  95

Lys Thr Ser Arg Phe Leu Cys Met Lys Pro Asn Gly Arg Leu Tyr Gly
                100                 105                 110

Ser Leu Phe Tyr Ser Glu Glu Ala Cys Asn Phe His Glu Lys Val Leu
            115                 120                 125

Ser Asp Gly Tyr Asn Leu Tyr Tyr Ser Glu Asn Tyr Asn Ile Pro Val
            130                 135                 140

Ser Leu Ser Ser Ala Gly Asn Leu Gly Gln Ser Arg Gln Leu Pro Pro
145                 150                 155                 160

Phe Ser Gln Phe Leu Pro Leu Val Asn Lys Ile Pro Leu Glu Pro Val
                165                 170                 175

Leu Glu Asp Phe Asp Phe Tyr Gly His Gln Leu Asp Val Glu Ser Ala
                180                 185                 190

Asp Pro Leu Ser Ile Leu Gly Gln Asn Pro Gly Phe Met Ser Pro Ser
                195                 200                 205

Tyr Val Phe
210

<210> SEQ ID NO 256
<211> LENGTH: 188
<212> TYPE: PRT
<213> ORGANISM: Gadus morhua

<400> SEQUENCE: 256

Leu Leu Leu Ala Thr Leu Leu His Ile Gly Leu Ser Phe Tyr Val Pro
  1               5                  10                  15

Asp Ser Gly Pro Leu Leu Trp Leu Gly Asp Gln Val Arg Glu Arg His
                 20                  25                  30

Leu Tyr Thr Ala Glu Ser His Arg Arg Gly Leu Phe Leu Glu Met Ser
             35                  40                  45

Pro Asp Gly Gln Val Thr Gly Ser Ala Ala Gln Thr Pro Leu Ser Val
 50                  55                  60

Leu Glu Leu Arg Ser Val Arg Ala Gly Asp Thr Val Ile Arg Ala Arg
 65                  70                  75                  80

Leu Ser Ser Leu Tyr Leu Cys Val Asp Arg Ala Gly His Leu Thr Gly
                 85                  90                  95

Gln Arg Gln Tyr Thr Glu Ser Asp Cys Thr Phe Arg Glu Val Ile Leu
                100                 105                 110

Glu Asp Gly Tyr Thr His Phe Leu Ser Val His His Gly Leu Pro Ile
            115                 120                 125

Ser Leu Ala Pro Arg His Ser Pro Gly Arg Gln Gly Leu Arg Phe Ser
            130                 135                 140

Arg Phe Leu Pro Leu Arg Ser Ser Leu Ser Glu Asp Arg Val Ala Glu
145                 150                 155                 160

Pro Pro Asp Ser Pro Leu Asn Leu Asp Ser Glu Asp Pro Leu Gly Met
                165                 170                 175

Gly Leu Gly Ser Leu Leu Ser Pro Ala Phe Ser Met
            180                 185
```

<210> SEQ ID NO 257
<211> LENGTH: 216
<212> TYPE: PRT
<213> ORGANISM: Latimeria chalumnae

<400> SEQUENCE: 257

```
Met Leu Cys Gln Ser Phe Val Ile Leu Ser Gln Lys Phe Ile Phe Gly
1               5                   10                  15

Leu Phe Leu Thr Gly Leu Gly Leu Thr Gly Leu Ala Trp Thr Arg Pro
            20                  25                  30

Phe Gln Asp Ser Asn Pro Ile Leu Gln Tyr Ser Asp Ser Ile Arg Leu
        35                  40                  45

Arg His Leu Tyr Thr Ala Ser Glu Ser Arg His Leu His Leu Gln Ile
    50                  55                  60

Asn Ser Asp Gly Gln Val Gly Gly Thr Thr Lys Gln Ser Pro Tyr Ser
65                  70                  75                  80

Leu Leu Glu Met Lys Ala Val Lys Thr Gly Phe Val Val Ile Arg Gly
                85                  90                  95

Lys Lys Ser Ala Arg Tyr Leu Cys Met Glu Arg Ser Gly Arg Leu Tyr
            100                 105                 110

Gly Ser Leu Gln Tyr Thr Glu Lys Asp Cys Thr Phe Lys Glu Val Val
        115                 120                 125

Leu Ala Asp Gly Tyr Asn Leu Tyr Val Ser Glu Glu His Gln Ala Thr
    130                 135                 140

Val Thr Leu Ser Pro Met Arg Ala Arg Ile Ala Gln Gly Lys Lys Ile
145                 150                 155                 160

Pro Pro Phe Ser His Phe Leu Pro Met Val Asn Lys Val Pro Val Glu
                165                 170                 175

Asp Val Ala Ala Glu Met Glu Phe Val Gln Val Leu Arg Glu Met Thr
            180                 185                 190

Ala Asp Val Asp Ser Pro Asp Pro Phe Gly Met Thr Trp Glu Glu Ser
        195                 200                 205

Val His Ser Pro Ser Phe Phe Ala
    210                 215
```

<210> SEQ ID NO 258
<211> LENGTH: 192
<212> TYPE: PRT
<213> ORGANISM: Tursiops truncates

<400> SEQUENCE: 258

```
Met Gly Trp Asp Lys Thr Lys Leu Glu His Leu Gly Leu Trp Val Pro
1               5                   10                  15

Val Leu Ala Val Leu Leu Gly Pro Cys Gln Ala His Pro Ile Pro Asp
            20                  25                  30

Ser Ser Pro Leu Leu Gln Phe Gly Gly Gln Val Arg Gln Arg Tyr Leu
        35                  40                  45

Tyr Thr Asp Asp Ala Gln Glu Thr Glu Ala His Leu Glu Ile Arg Ala
    50                  55                  60

Asp Gly Thr Val Val Gly Thr Ala Arg Arg Ser Pro Glu Gly Val Lys
65                  70                  75                  80

Thr Ser Arg Phe Leu Cys Gln Gly Pro Glu Gly Arg Leu Tyr Gly Ser
                85                  90                  95

Leu His Phe Asn Pro Gln Ala Cys Ser Phe Arg Glu Leu Leu Leu Glu
            100                 105                 110
```

```
Asp Gly Tyr Asn Val Tyr Gln Ser Glu Ala Leu Gly Ile Pro Leu Arg
            115                 120                 125

Leu Pro Pro His Arg Ser Ser Asn Trp Asp Leu Ala Pro Arg Gly Pro
        130                 135                 140

Ala Arg Phe Leu Pro Leu Pro Gly Phe Leu Pro Pro Leu Glu Pro
145                 150                 155                 160

Pro Gly Ile Leu Ala Pro Glu Pro Pro Asn Val Gly Ser Ser Asp Pro
                165                 170                 175

Leu Ser Met Val Gly Pro Ser His Gly Arg Ser Pro Ser Tyr Thr Ser
            180                 185                 190
```

<210> SEQ ID NO 259
<211> LENGTH: 209
<212> TYPE: PRT
<213> ORGANISM: Mustela putorius furo

<400> SEQUENCE: 259

```
Met Gly Trp Glu Glu Ala Arg Ser Glu His Leu Gly Leu Trp Val Pro
1               5                   10                  15

Val Leu Ala Val Leu Leu Gly Ala Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
50                  55                  60

Ala Asp Gly Thr Val Val Gly Ala Ala Arg Arg Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asn Gly Thr Leu Tyr Gly
            100                 105                 110

Ser Phe His Phe Asp Pro Val Ala Cys Ser Phe Arg Glu Val Leu Leu
        115                 120                 125

Glu Asp Gly Tyr Asn Ile Tyr His Ser Glu Thr Leu Gly Leu Pro Leu
130                 135                 140

Arg Leu Pro Pro His Asn Ser Pro His Arg Asp Leu Ala Pro Arg Gly
145                 150                 155                 160

Pro Ala Arg Phe Leu Pro Leu Pro Gly Leu Leu Pro Ala Thr Pro Glu
                165                 170                 175

Ser Arg Gly Ile Pro Ala Pro Glu Pro Pro Asn Val Gly Ser Ser Asp
            180                 185                 190

Pro Leu Ser Met Val Gly Pro Leu Gln Gly Gln Ser Pro Ser Tyr Thr
        195                 200                 205

Ser
```

<210> SEQ ID NO 260
<211> LENGTH: 198
<212> TYPE: PRT
<213> ORGANISM: Takifugu rubripes

<400> SEQUENCE: 260

```
Phe Ile Tyr Leu Phe Ile Gln Thr Ala Leu Phe Ser Pro Ser Lys Trp
1               5                   10                  15

Phe Asn Phe Tyr Leu Pro Asp Ser Asn Pro Leu Leu Ser Phe Asp Ser
            20                  25                  30

His Gly Arg Gly Ile His Leu Tyr Thr Asp Asn Gln Arg Arg Gly Met
```

```
            35                  40                  45
Tyr Leu Gln Met Ser Thr Asp Gly Ser Val Ser Gly Ser Asp Val Gln
 50                  55                  60

Thr Ala Asn Ser Val Leu Glu Leu Lys Ser Val Arg Asn Gly His Val
 65                  70                  75                  80

Val Ile Arg Gly Lys Ser Ser Ser Leu Phe Leu Cys Met Asp Ser Arg
                 85                  90                  95

Gly Arg Leu Trp Gly Gln Arg His Pro Thr Glu Ala Asp Cys Thr Phe
                100                 105                 110

Arg Glu Val Leu Leu Ala Asp Gly Tyr Thr Arg Phe Leu Ser Leu His
                115                 120                 125

Asn Gly Thr Pro Val Ser Leu Ala Pro Lys Gln Ser Pro Asp Gln His
                130                 135                 140

Thr Val Pro Phe Thr Arg Phe Leu Pro Leu Arg Asn Thr Leu Ala Glu
145                 150                 155                 160

Glu Ser Met Ser Glu Pro Pro Ser Asn Gln Gln Arg Tyr Phe Asn Ile
                165                 170                 175

Asp Ser Asp Asp Leu Leu Gly Met Asp Leu Asn Ala Met Val Ser Pro
                180                 185                 190

Gln Phe Ser Gly Asp Lys
                195

<210> SEQ ID NO 261
<211> LENGTH: 203
<212> TYPE: PRT
<213> ORGANISM: Dipodomys ordii

<400> SEQUENCE: 261

Met Asp Gln Ala Lys Thr Arg Val Gly Ala Arg Gly Leu Gly Gly Leu
 1               5                  10                  15

Val Leu Ala Val Ile Ile Leu Gly Ala Cys Lys Ala Arg Pro Ile Pro
                 20                  25                  30

Asp Ser Ser Pro Leu Leu Gln Phe Gly Gly Gln Val Arg Leu Arg His
                 35                  40                  45

Leu Tyr Thr Asp Thr Gln Glu Thr Glu Ala His Leu Glu Ile Arg
 50                  55                  60

Ala Asp Gly Thr Val Val Gly Thr Ala His Arg Ser Pro Glu Ser Leu
 65                  70                  75                  80

Leu Glu Leu Lys Ala Leu Lys Pro Gly Val Ile Gln Ile Leu Gly Ile
                 85                  90                  95

Lys Thr Ser Arg Phe Leu Cys Gln Arg Pro Asp Gly Thr Leu Tyr Gly
                100                 105                 110

Ser Leu His Phe Asp Pro Glu Val Cys Ser Phe Gln Glu Leu Leu
                115                 120                 125

Glu Asp Gly Tyr Asn Ile Tyr Arg Ser Glu Ala Leu Gly Leu Pro Leu
                130                 135                 140

Arg Leu Ser Pro Asp Pro Ala Pro Trp Gly Pro Ala Arg Phe Leu Pro
145                 150                 155                 160

Leu Pro Gly Val Pro Pro Ala Pro Pro Glu Pro Gly Ile Leu Ala
                165                 170                 175

Pro Glu Pro Pro Asp Val Gly Ser Ser Asp Pro Leu Ser Met Val Gly
                180                 185                 190

Leu Leu Gln Gly Arg Ser Pro Ser Tyr Ala Ser
                195                 200
```

<210> SEQ ID NO 262
<211> LENGTH: 184
<212> TYPE: PRT
<213> ORGANISM: Echinops telfairi

<400> SEQUENCE: 262

```
Met Gly Cys Thr Lys Ser Gly Trp Lys Ser Pro Gly Leu Trp Val Pro
1               5                   10                  15

Val Leu Ala Ser Leu Leu Leu Gly Gly Cys Gly Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Thr Thr Glu Ala His Leu Glu Ile Arg
    50                  55                  60

Ala Asp Gly Thr Val Gly Gly Val Ala His Gln Ser Pro Glu Lys Phe
65                  70                  75                  80

Leu Ser Gln Trp Arg Glu Lys Pro Leu Arg Ser Leu His Phe Asp Pro
                85                  90                  95

Ala Ala Cys Ser Phe Arg Glu Lys Leu Leu Glu Asp Gly Tyr Asn Leu
            100                 105                 110

Tyr His Ser Glu Thr His Gly Leu Pro Leu Arg Leu Pro Arg Gly
        115                 120                 125

Gly Asp Pro Ser Ser Gln Pro Gly Ala Arg Phe Pro Pro Leu Pro Gly
    130                 135                 140

Gln Leu Pro Gln Leu Gln Glu Thr Pro Gly Val Leu Ala Pro Glu Pro
145                 150                 155                 160

Pro Asp Val Gly Ser Ser Asp Pro Leu Ser Met Val Gly Pro Trp Arg
                165                 170                 175

Gly Gln Ser Pro Ser Tyr Ala Ser
            180
```

<210> SEQ ID NO 263
<211> LENGTH: 210
<212> TYPE: PRT
<213> ORGANISM: Macaca mulatta

<400> SEQUENCE: 263

```
Met Asp Ser Asp Glu Thr Gly Phe Glu His Ser Gly Leu Trp Val Pro
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala His Gln Ser Pro Glu Ser Glu
65                  70                  75                  80

Cys Gly Pro Glu Pro Gly Ser Glu Gly Gly Ala Val Gly Gly Ala
                85                  90                  95

Glu Gly Pro Gly Leu Leu Gly Leu Arg Glu Ala Gly Leu Gly Pro Gly
            100                 105                 110

Ser Trp Leu His Phe Asp Pro Glu Ala Cys Ser Phe Arg Glu Leu Leu
        115                 120                 125

Leu Glu Asn Gly Tyr Asn Val Tyr Gln Ser Glu Ala His Gly Leu Pro
    130                 135                 140
```

Leu His Leu Pro Gly Asn Lys Ser Pro His Arg Asp Pro Ala Ser Gln
145                 150                 155                 160

Gly Pro Ala Arg Phe Leu Pro Leu Pro Gly Leu Pro Ala Pro Pro
            165                 170                 175

Glu Pro Pro Gly Ile Leu Ala Pro Gln Pro Pro Asp Val Gly Ser Ser
            180                 185                 190

Asp Pro Leu Ser Met Val Gly Pro Ser Gln Ala Arg Ser Pro Ser Tyr
        195                 200                 205

Ala Ser
    210

<210> SEQ ID NO 264
<211> LENGTH: 193
<212> TYPE: PRT
<213> ORGANISM: Microcebus murinus

<400> SEQUENCE: 264

Met Gly Trp Asp Glu Ala Gly Ala Gly Phe Glu His Pro Gly Leu Trp
1               5                   10                  15

Phe Pro Met Leu Gly Val Leu Leu Gly Ala Cys Gln Ala Tyr Pro
            20                  25                  30

Ile Pro Asp Ser Ser Pro Leu Leu Gln Phe Gly Gly Gln Val Arg Gln
        35                  40                  45

Arg His Leu Tyr Thr Asp Asp Ile Gln Glu Thr Glu Ala His Leu Glu
    50                  55                  60

Ile Arg Ala Asp Gly Thr Val Val Gly Ala Ala Arg Gln Ser Pro Glu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Cys Ser Phe Arg Glu Leu Leu Leu Glu
        115                 120                 125

Asp Gly Tyr Asn Val Tyr Cys Pro Tyr Leu Pro Leu His Leu Ser Pro
130                 135                 140

Arg Ile Glu Leu Ala Gly Ser Arg Ser Ala Leu Pro Leu Pro Pro Ala
145                 150                 155                 160

Pro Glu Arg Arg Ile Leu Ala Pro Glu Pro Asp Gly Ser Ser Asp
            165                 170                 175

Pro Leu Ser Met Val Gly Pro Ser Gln Gly Arg Ser Pro Ser Tyr Ala
        180                 185                 190

Ser

<210> SEQ ID NO 265
<211> LENGTH: 204
<212> TYPE: PRT
<213> ORGANISM: Ochotona princeps

<400> SEQUENCE: 265

Lys Asp Met Asp Gly Leu Gln Pro Pro Gly Leu Arg Val Pro Val Leu
1               5                   10                  15

Ala Ala Leu Leu Leu Gly Val Gly Gln Ala Arg Pro Ile Pro Asp Ser
            20                  25                  30

Ser Pro Leu Leu Gln Phe Gly Gly Gln Val Arg Gln Arg His Leu Tyr
        35                  40                  45

Thr Asp Asp Ala Gln Glu Ser Glu Val His Leu Glu Ile Arg Ala Asp

```
Gly Thr Val Ala Gly Thr Ala Arg Arg Ser Pro Glu Ser Leu Leu Glu
 65                  70                  75                  80

Met Lys Ala Leu Lys Pro Gly Val Ile Gln Ile Leu Gly Val His Thr
                 85                  90                  95

Ser Arg Phe Leu Cys Gln Arg Pro Asp Gly Thr Leu Tyr Gly Ser Leu
            100                 105                 110

His Phe Asp His Lys Ala Cys Ser Phe Arg Glu Gln Leu Leu Glu Asp
        115                 120                 125

Gly Tyr Asn Val Tyr His Ser Glu Thr His Gly Leu Pro Leu Arg Leu
    130                 135                 140

Ser Pro Asp Arg Ala Pro Arg Gly Pro Ala Arg Phe Leu Pro Leu Pro
145                 150                 155                 160

Gly Pro Pro Pro Asp Leu Leu Val Pro Pro Leu Pro Pro Asp Val Leu
                165                 170                 175

Ala Pro Glu Pro Pro Asp Val Asp Ser Pro Asp Pro Leu Ser Met Val
            180                 185                 190

Gly Pro Leu Gln Gly Gln Ser Pro Ser Tyr Thr Ser
        195                 200

<210> SEQ ID NO 266
<211> LENGTH: 182
<212> TYPE: PRT
<213> ORGANISM: Xiphophorus maculatus

<400> SEQUENCE: 266

Cys Pro Phe Pro Phe Leu Phe Leu Ile Leu Ser Leu Pro Phe Phe Ser
  1               5                  10                  15

Ser Ser Phe Tyr Ile Pro Glu Ser Asn Pro Ile Phe Ala Phe Arg Asn
                 20                  25                  30

Gln Leu Arg Glu Val His Leu Tyr Thr Glu Asn His Arg Arg Gly Leu
            35                  40                  45

Tyr Val Glu Ile His Leu Asp Gly Arg Val Thr Gly Ser Asp Ala Gln
     50                  55                  60

Ser Pro Tyr Ser Val Leu Gln Ile Lys Ser Val Lys Pro Gly His Val
 65                  70                  75                  80

Val Ile Lys Gly Gln Thr Ser Ser Leu Phe Leu Cys Met Asp Asp Ser
                 85                  90                  95

Gly Asn Leu Arg Gly Gln Thr Thr Tyr Asp Glu Ala Asp Cys Ser Phe
            100                 105                 110

Arg Glu Leu Leu Leu Ala Asp Gly Tyr Thr Arg Phe Leu Asn Ser Gln
        115                 120                 125

His Gly Val Pro Leu Ser Leu Ala Ser Arg Asn Ser Pro Asp Arg His
    130                 135                 140

Ser Val Pro Phe Thr Arg Phe Leu Pro Leu Arg Asn Thr Leu Thr Val
145                 150                 155                 160

Ser Glu Glu Ser Thr Lys Thr Gln Arg Asp Phe Asn Leu Asp Ser Asp
                165                 170                 175

Asp Leu Leu Gly Met Gly
            180

<210> SEQ ID NO 267
<211> LENGTH: 192
<212> TYPE: PRT
<213> ORGANISM: Gasterosteus aculeatus
```

```
<400> SEQUENCE: 267

Ser Leu Leu Leu Met Val Pro Leu Pro Phe Cys Ser Ser Phe Tyr Leu
1               5                   10                  15

Thr Asp Ser Ser Pro Leu Leu Pro Phe Asn Asn Gln Val Lys Glu Val
            20                  25                  30

His Leu Tyr Thr Ala Glu Asn His Arg Arg Ala Met Tyr Leu Gln Ile
        35                  40                  45

Ala Leu Asp Gly Ser Val Ser Gly Ser Asp Ala Arg Ser Thr Tyr Ser
    50                  55                  60

Val Leu Gln Leu Lys Ser Ile Gln Pro Gly His Val Val Ile Arg Gly
65                  70                  75                  80

Lys Ala Ser Ser Met Phe Leu Cys Val Asp Ser Gly Arg Leu Arg
                85                  90                  95

Gly Gln Gly Pro Tyr Ser Glu Ala Asp Cys Ser Phe Arg Glu Leu Leu
            100                 105                 110

Leu Gly Asp Gly Tyr Thr Arg Phe Leu Ser Ser Gln His Gly Ser Pro
        115                 120                 125

Leu Ser Leu Ala Ser Arg Pro Ser Pro Asp Pro Asn Ser Val Pro Phe
    130                 135                 140

Thr Arg Phe Leu Pro Ile Arg Thr Ala Pro Glu Ala Glu Ser Val Ile
145                 150                 155                 160

Glu Glu Pro Pro Ser Asn Gln Arg Tyr Val Asn Val Asp Ser Glu Asp
                165                 170                 175

Leu Leu Gly Met Gly Leu Asn Thr Val Val Ser Pro Gln Phe Ser Ala
            180                 185                 190

<210> SEQ ID NO 268
<211> LENGTH: 165
<212> TYPE: PRT
<213> ORGANISM: Sarcophilus harrisii

<400> SEQUENCE: 268

Val Ser Ala Met Gly Leu Arg Glu Arg Ala Pro Arg Tyr Leu Ala Pro
1               5                   10                  15

Leu Leu Ser Leu Leu Leu Ala Cys Arg Ala Ser Gly His Pro Leu Pro
            20                  25                  30

Asp Ser Ser Pro Met Leu Leu Phe Gly Gly Gln Val Arg Leu Arg His
        35                  40                  45

Leu Tyr Thr Asp Val Gly Gln Glu Ala Glu Ala His Val Glu Leu Ala
    50                  55                  60

Ser Asp Gly Thr Val Arg Ala Ala Arg Arg Ser Pro Asn Ser Leu
65                  70                  75                  80

Leu Glu Leu Lys Ala Val Lys Pro Gly Ile Val Arg Ile Leu Ala Val
                85                  90                  95

His Ser Ser Arg Phe Leu Cys Met Arg Pro Asn Gly Glu Leu Tyr Gly
            100                 105                 110

Ala Ile His Tyr Asp Pro Ser Ala Cys Asn Phe Arg Glu Arg Leu Leu
        115                 120                 125

Gly Asp Gly Tyr Asn Val Tyr Glu Ser Glu Ala His Gly Arg Thr Leu
    130                 135                 140

Arg Leu Pro Pro Lys Ala Ala Pro Gly Pro Ala Gly Pro Ser Arg Phe
145                 150                 155                 160

Leu Pro Leu Pro Gly
                165
```

<210> SEQ ID NO 269
<211> LENGTH: 208
<212> TYPE: PRT
<213> ORGANISM: Macropus eugenii

<400> SEQUENCE: 269

Thr Glu Glu Pro Ser Thr Gly Ser Arg His Leu Gly Gln Trp Ala Pro
1               5                   10                  15

Gly Leu Pro Gly Pro Leu Leu Ser Leu Leu Ala Tyr Arg Gly Trp
            20                  25                  30

Gly Ser Pro Ile Pro Asp Ser Ser Pro Met Leu Leu Phe Gly Gly Gln
            35                  40                  45

Val Arg Leu Arg His Leu Tyr Thr Asp Asp Gly Gln Asp Thr Glu Ala
    50                  55                  60

His Val Glu Leu Gly Pro Asp Gly Val Val Arg Ala Val Ala Glu Arg
65                  70                  75                  80

Ser Pro Asn Ser Leu Leu Glu Leu Lys Ala Val Lys Pro Gly Val Ile
                85                  90                  95

Arg Ile Leu Ala Val Gln Ser Ser Arg Phe Leu Cys Met Arg Pro Asn
            100                 105                 110

Gly Glu Leu Tyr Gly Ala Val His Tyr Asp Pro Ser Ala Cys Asn Phe
        115                 120                 125

Arg Glu His Leu Leu Gly Asp Gly Tyr Asn Val Tyr Glu Ser Glu Thr
    130                 135                 140

His Arg Arg Thr Leu Arg Leu Ser Pro Ser Leu Gly Gln Ala Gly Pro
145                 150                 155                 160

Ser Arg Phe Leu Pro Leu Pro Gly Asp Trp Leu Pro Gly Pro Asp Pro
                165                 170                 175

Pro Trp Ala Gln Gly Pro Glu Pro Pro Asp Val Gly Ser Ala Asp Pro
            180                 185                 190

Leu Ser Met Val Gly Ala Val Gln Gly Leu Ser Pro Ser Tyr Ser Ser
        195                 200                 205

<210> SEQ ID NO 270
<211> LENGTH: 160
<212> TYPE: PRT
<213> ORGANISM: Xenopus tropicalis

<400> SEQUENCE: 270

Arg Gly Gly Arg Thr Lys Lys Thr Leu Leu Arg Lys Trp Leu Cys
1               5                   10                  15

Leu Leu Ala Ile Met Leu Ser Arg Ser Arg Phe Ser Leu Ala Asn Pro
            20                  25                  30

Ile Gln Asn Ser Asn Pro Ile Leu Ser Asn Asp Asn Gln Val Arg Thr
            35                  40                  45

Gln Tyr Leu Tyr Thr Asp Asn Asn Met His Leu Tyr Leu Gln Ile
    50                  55                  60

Thr His Asn Gly Val Val Thr Gly Thr Glu Glu Lys Asn Asp Tyr Gly
65                  70                  75                  80

Val Leu Glu Ile Lys Ala Val Lys Ala Gly Val Val Ile Lys Gly
                85                  90                  95

Ile Arg Ser Asn Leu Tyr Leu Cys Met Asp Ser Arg His Gln Leu Tyr
            100                 105                 110

Ala Ser Ala Tyr Asp Lys Asp Asp Cys His Phe His Glu Lys Ile Thr
        115                 120                 125

Pro Asp Asn Tyr Asn Met Tyr Ser Ser Glu Lys His Ser Glu Tyr Val
            130                 135                 140

Ser Leu Ala Pro Leu Lys Gly Ser Gln Met Ala Arg Phe Leu Pro Ile
145                 150                 155                 160

<210> SEQ ID NO 271
<211> LENGTH: 194
<212> TYPE: PRT
<213> ORGANISM: Danio rerio

<400> SEQUENCE: 271

Met Leu Leu Ala Cys Phe Phe Ile Phe Phe Ala Leu Phe Pro His Leu
1               5                   10                  15

Arg Trp Cys Met Tyr Val Pro Ala Gln Asn Val Leu Leu Gln Phe Gly
            20                  25                  30

Thr Gln Val Arg Glu Arg Leu Leu Tyr Thr Asp Gly Leu Phe Leu Glu
        35                  40                  45

Met Asn Pro Asp Gly Ser Val Lys Gly Ser Pro Glu Lys Asn Leu Asn
    50                  55                  60

Cys Val Leu Glu Leu Arg Ser Val Lys Ala Gly Glu Thr Val Ile Gln
65                  70                  75                  80

Ser Ala Ala Thr Ser Leu Tyr Leu Cys Val Asp Asp Gln Asp Lys Leu
                85                  90                  95

Lys Gly Gln His His Tyr Ser Ala Leu Asp Cys Thr Phe Gln Glu Leu
            100                 105                 110

Leu Leu Asp Gly Tyr Ser Phe Phe Leu Ser Pro His Thr Asn Leu Pro
        115                 120                 125

Val Ser Leu Leu Ser Lys Arg Gln Lys His Gly Asn Pro Leu Ser Arg
    130                 135                 140

Phe Leu Pro Val Ser Arg Ala Glu Asp Ser Arg Thr Gln Glu Val Lys
145                 150                 155                 160

Gln Tyr Ile Gln Asp Ile Asn Leu Asp Ser Asp Pro Leu Gly Met
                165                 170                 175

Gly His Arg Ser His Leu Gln Thr Val Phe Ser Pro Ser Leu His Thr
            180                 185                 190

Lys Lys

<210> SEQ ID NO 272
<211> LENGTH: 209
<212> TYPE: PRT
<213> ORGANISM: Bos grunniens mutus

<400> SEQUENCE: 272

Met Gly Trp Asp Glu Ala Lys Phe Lys His Leu Gly Leu Trp Val Pro
1               5                   10                  15

Val Leu Ala Val Leu Leu Leu Gly Thr Cys Arg Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala Arg Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Lys Leu Tyr Gly

-continued

```
                100                 105                 110
Ser Leu His Phe Asp Pro Lys Ala Cys Ser Phe Arg Glu Leu Leu Leu
            115                 120                 125

Glu Asp Gly Tyr Asn Val Tyr Gln Ser Glu Thr Leu Gly Leu Pro Leu
        130                 135                 140

Arg Leu Pro Pro Gln Arg Ser Ser Asn Arg Asp Pro Ala Pro Arg Gly
145                 150                 155                 160

Pro Ala Arg Phe Leu Pro Leu Pro Gly Leu Pro Ala Glu Pro Pro Asp
                165                 170                 175

Pro Pro Gly Ile Leu Ala Pro Glu Pro Pro Asp Val Gly Ser Ser Asp
            180                 185                 190

Pro Leu Ser Met Val Gly Pro Ser Tyr Gly Arg Ser Pro Ser Tyr Thr
        195                 200                 205

Ser

<210> SEQ ID NO 273
<211> LENGTH: 209
<212> TYPE: PRT
<213> ORGANISM: Saimiri boliviensis boliviensis

<400> SEQUENCE: 273

Met Gly Ser Glu Glu Val Ala Leu Glu Arg Pro Ala Leu Trp Val Ser
1               5                   10                  15

Val Leu Ala Gly Leu Leu Leu Gly Thr Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Ala Gly Ala Ala His Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu Tyr Phe Asp Pro Glu Ala Cys Ser Phe Arg Glu Leu Leu Leu
        115                 120                 125

Glu Asp Gly Tyr Asn Val Tyr Gln Ser Val Ala His Ser Leu Pro Leu
    130                 135                 140

His Leu Pro Gly Gly Arg Ser Pro Pro Trp Asp Pro Ala Pro Arg Gly
145                 150                 155                 160

Pro Ala Arg Phe Leu Pro Leu Pro Gly Leu Pro Pro Glu Pro Pro Glu
                165                 170                 175

Ala Pro Gly Ile Leu Ala Pro Glu Pro Pro Asp Val Gly Ser Ser Asp
            180                 185                 190

Pro Leu Ser Met Val Gly Pro Ser Gln Gly Gln Ser Pro Ser Tyr Thr
        195                 200                 205

Ser

<210> SEQ ID NO 274
<211> LENGTH: 210
<212> TYPE: PRT
<213> ORGANISM: Callithrix jacchus
<220> FEATURE:
<221> NAME/KEY: misc_feature
<222> LOCATION: (64)..(64)
```

<223> OTHER INFORMATION: Xaa can be any naturally occurring amino acid

<400> SEQUENCE: 274

Met Gly Ser Glu Glu Val Gly Leu Glu His Pro Ala Leu Trp Val Ser
1               5                   10                  15

Val Leu Ala Gly Leu Leu Leu Gly Thr Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Lys Glu Ala His Leu Glu Ile Xaa
    50                  55                  60

Glu Asp Gly Thr Val Ala Gly Ala Ala Thr Lys Val Pro Lys Val Ser
65                  70                  75                  80

Leu Leu Gln Leu Lys Ala Leu Lys Pro Gly Val Ile Gln Ile Leu Gly
                85                  90                  95

Val Lys Thr Ser Arg Phe Leu Cys Gln Arg Pro Asp Gly Ala Leu Tyr
            100                 105                 110

Gly Ser Leu His Phe Asp Pro Glu Ala Cys Ser Phe Arg Glu Leu Leu
        115                 120                 125

Leu Glu Asp Gly Tyr Asn Val Tyr Gln Ser Val Ala His Gly Leu Pro
    130                 135                 140

Leu His Leu Pro Glu Ser Arg Ser Pro Pro Arg Asp Pro Ala Pro Arg
145                 150                 155                 160

Gly Pro Ala Arg Phe Leu Pro Leu Pro Gly Leu Pro Pro Glu Pro Pro
                165                 170                 175

Glu Pro Pro Gly Ile Leu Ala Pro Glu Pro Pro Asp Val Gly Ser Ser
            180                 185                 190

Asp Pro Leu Ser Met Val Gly Pro Ser Gln Gly Gln Ser Pro Ser Tyr
        195                 200                 205

Ala Ser
210

<210> SEQ ID NO 275
<211> LENGTH: 209
<212> TYPE: PRT
<213> ORGANISM: Tupaia chinensis

<400> SEQUENCE: 275

Met Gly Trp Asp Lys Ala Arg Phe Glu His Leu Gly Ala Trp Ala Pro
1               5                   10                  15

Val Leu Ala Val Leu Leu Leu Gly Ala Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Thr Gln Asp Thr Glu Ala His Leu Glu Ile Arg
    50                  55                  60

Ala Asp Gly Thr Val Val Gly Ala Ala His Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Ile Tyr Gln Ser Glu Ala Arg Gly Leu Pro Leu

```
                    130                 135                 140

Arg Leu Pro Pro His Asp Ser Pro His Arg Asp Arg Thr Pro Gln Gly
145                 150                 155                 160

Pro Ala Arg Phe Leu Pro Leu Pro Gly Leu Pro Leu Val Pro Pro Glu
                    165                 170                 175

Leu Pro Gly Val Leu Ala Leu Glu Pro Pro Asp Val Gly Ser Ser Asp
                180                 185                 190

Pro Leu Ser Met Met Gly Pro Ser Gln Gly Gln Ser Pro Ser Tyr Ala
            195                 200                 205

Ser

<210> SEQ ID NO 276
<211> LENGTH: 188
<212> TYPE: PRT
<213> ORGANISM: Papio Anubis

<400> SEQUENCE: 276

Met Asp Ser Asp Glu Thr Gly Phe Glu His Ser Gly Leu Trp Val Pro
1               5                   10                  15

Val Leu Ala Gly Leu Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
        50                  55                  60

Glu Asp Gly Thr Val Gly Gly Ala Ala His Gln Ser Pro Glu Ser Lys
65                  70                  75                  80

Cys Gly Pro Glu Pro Gly Ser Glu Gly Gly Ala Leu His Phe Asp
                85                  90                  95

Pro Glu Ala Cys Ser Phe Arg Glu Leu Leu Leu Glu Asn Gly Tyr Asn
                100                 105                 110

Val Tyr Gln Ser Glu Ala His Gly Leu Pro Leu His Leu Pro Gly Asn
            115                 120                 125

Lys Ser Pro His Arg Asp Pro Ala Ser Arg Gly Pro Ala Arg Phe Leu
130                 135                 140

Pro Leu Pro Gly Leu Pro Ala Pro Pro Glu Pro Pro Gly Ile Leu
145                 150                 155                 160

Ala Pro Gln Pro Pro Asp Val Gly Ser Ser Asp Pro Leu Ser Met Val
                165                 170                 175

Gly Pro Ser Gln Ala Arg Ser Pro Ser Tyr Ala Ser
            180                 185

<210> SEQ ID NO 277
<211> LENGTH: 208
<212> TYPE: PRT
<213> ORGANISM: Pteropus alecto

<400> SEQUENCE: 277

Met Gly Trp Gly Lys Ala Arg Leu Gln His Pro Gly Leu Trp Gly Pro
1               5                   10                  15

Val Leu Ala Val Leu Gly Ala Cys Gln Ala His Pro Ile Leu Asp
                20                  25                  30

Ser Ser Pro Leu Phe Gln Phe Gly Ser Gln Val Arg Arg Arg Tyr Leu
            35                  40                  45

Tyr Thr Asp Asp Ala Gln Asp Thr Glu Ala His Leu Glu Ile Arg Ala
        50                  55                  60
```

```
Asp Gly Thr Val Ala Gly Ala Ala Arg Arg Ser Pro Glu Ser Leu Leu
 65                  70                  75                  80

Glu Leu Lys Ala Leu Lys Pro Gly Val Ile Gln Val Leu Gly Val Lys
                 85                  90                  95

Thr Ser Arg Phe Leu Cys Gln Arg Pro Asp Gly Thr Leu Tyr Gly Ser
            100                 105                 110

Leu His Phe Asp Pro Ala Ala Cys Ser Phe Arg Glu Leu Leu Leu Lys
        115                 120                 125

Asp Gly Tyr Asn Val Tyr Gln Ser Glu Ala Leu Ala Arg Pro Leu Arg
    130                 135                 140

Leu Pro Pro Tyr Ser Ser Pro Ser Ser Asp Pro Ala Arg Arg Gly Pro
145                 150                 155                 160

Ala Arg Phe Leu Pro Leu Pro Gly Pro Pro Glu Pro Pro Gln Pro
                165                 170                 175

Pro Gly Arg Leu Ala Pro Glu Pro Pro Asp Val Gly Ser Ser Asp Pro
            180                 185                 190

Leu Ser Met Val Trp Pro Ser Arg Gly Arg Ser Pro Ser Tyr Thr Ser
        195                 200                 205

<210> SEQ ID NO 278
<211> LENGTH: 210
<212> TYPE: PRT
<213> ORGANISM: Heterocephalus glaber

<400> SEQUENCE: 278

Met Asp Trp Ala Arg Ala Glu Ser Glu Arg Pro Gly Leu Trp Val Pro
  1               5                  10                  15

Ala Val Leu Ala Val Leu Leu Gly Ala Cys Gln Ala His Pro Ile
                 20                  25                  30

Pro Asp Ser Ser Pro Leu Leu Gln Phe Gly Gly Gln Val Arg Gln Arg
             35                  40                  45

His Leu Tyr Thr Asp Asp Ala Gln Asp Thr Glu Val His Leu Glu Ile
     50                  55                  60

Arg Ala Asp Gly Ser Val Gly Gly Ala Ala His Arg Ser Pro Glu Ser
 65                  70                  75                  80

Leu Leu Glu Leu Lys Ala Leu Lys Pro Gly Val Ile Gln Ile Leu Gly
                 85                  90                  95

Val Arg Thr Ser Arg Phe Leu Cys Gln Arg Pro Asp Gly Thr Leu Tyr
            100                 105                 110

Gly Ser Leu His Phe Asp Pro Glu Ala Cys Ser Phe Arg Glu Leu Leu
        115                 120                 125

Leu Ala Asp Gly Tyr Asn Ile Tyr Gln Ser Glu Ala Tyr Gly Leu Pro
    130                 135                 140

Leu Arg Met Leu Pro Ser Asp Ser Ala Ser Arg Asp Pro Val Pro Pro
145                 150                 155                 160

Gly Pro Ala Arg Phe Leu Pro Leu Pro Gly Leu His Pro Pro Leu
                165                 170                 175

Glu Pro Pro Gly Met Leu Pro Glu Pro Pro Asp Val Gly Ser Ser
            180                 185                 190

Asp Pro Leu Ser Met Val Gly Pro Leu Gln Gly Arg Ser Pro Ser Tyr
        195                 200                 205

Ala Phe
210
```

-continued

```
<210> SEQ ID NO 279
<211> LENGTH: 209
<212> TYPE: PRT
<213> ORGANISM: Cricetulus griseus

<400> SEQUENCE: 279
```

Met Asp Trp Met Lys Ser Gly Val Gly Val Pro Gly Leu Trp Val Pro
1               5                   10                  15

Leu Leu Pro Ile Phe Leu Leu Gly Val Ser Gln Ala His Pro Ile Pro
            20                  25                  30

Asp Ser Ser Pro Leu Leu Gln Phe Gly Gly Gln Val Arg His Arg His
        35                  40                  45

Leu Tyr Thr Asp Asp Asn Gln Glu Thr Glu Val His Leu Glu Ile Arg
    50                  55                  60

Gln Asp Gly Thr Val Ile Gly Thr Thr His Arg Ser Pro Glu Ser Leu
65                  70                  75                  80

Leu Glu Leu Lys Ala Leu Lys Pro Glu Val Ile Pro Val Leu Gly Val
                85                  90                  95

Lys Ala Ser Arg Phe Leu Cys Gln Gln Pro Asp Gly Thr Leu Tyr Gly
            100                 105                 110

Ser Pro His Phe Asp Pro Glu Ala Cys Ser Phe Arg Glu Leu Leu Leu
        115                 120                 125

Glu Asp Gly Tyr Asn Val Tyr Gln Ser Glu Val His Gly Leu Pro Leu
    130                 135                 140

Arg Leu Pro Gln Arg Asp Ser Pro Asn Gln Ala Pro Ala Ser Trp Gly
145                 150                 155                 160

Pro Val Pro Pro Leu Pro Val Pro Gly Leu His Gln Pro Gln Glu
                165                 170                 175

Leu Pro Gly Phe Leu Ala Pro Glu Pro Pro Asp Val Gly Ser Ser Asp
            180                 185                 190

Pro Leu Ser Met Val Gly Pro Leu Gln Gly Arg Ser Pro Ser Tyr Ala
        195                 200                 205

Ser

```
<210> SEQ ID NO 280
<211> LENGTH: 192
<212> TYPE: PRT
<213> ORGANISM: Ovis aries

<400> SEQUENCE: 280
```

Met Gly Trp Asp Glu Ala Lys Phe Lys His Leu Gly Leu Trp Val Pro
1               5                   10                  15

Val Leu Ala Val Leu Leu Leu Gly Thr Cys Arg Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala Arg Gln Ser Pro Glu Ser Leu
65                  70                  75                  80

Leu Glu Leu Lys Ala Leu Lys Pro Gly Val Ile Gln Ile Phe Gly Val
                85                  90                  95

Lys Thr Ser Arg Phe Leu Cys Gln Gly Pro Asp Gly Lys Leu Tyr Gly
            100                 105                 110

Ser Leu His Phe Asp Pro Lys Ala Cys Ser Phe Arg Glu Leu Leu Leu
        115                 120                 125

```
Glu Asp Gly Tyr Asn Val Tyr Gln Ser Glu Thr Leu Gly Leu Pro Leu
    130                 135                 140

Arg Leu Pro Pro Gln Arg Ser Ser Asn Arg Asp Pro Ala Pro Arg Gly
145                 150                 155                 160

Pro Pro Lys Pro Gln Leu His Phe Leu Lys Thr Ser Ala Val Gln Tyr
                165                 170                 175

Trp Pro Arg Tyr Glu Lys Val Pro Ala Phe Leu His Pro Phe Pro Gly
                180                 185                 190

<210> SEQ ID NO 281
<211> LENGTH: 135
<212> TYPE: PRT
<213> ORGANISM: Pan paniscus

<400> SEQUENCE: 281

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Val Ser Phe Gln Asp Pro Pro His His Pro Pro Cys Ser Ser Tyr
            115                 120                 125

Met Ser Pro Ser Gln Pro Gly
    130                 135

<210> SEQ ID NO 282
<211> LENGTH: 116
<212> TYPE: PRT
<213> ORGANISM: Macaca fascicularis

<400> SEQUENCE: 282

Met Asp Ser Asp Glu Thr Gly Phe Glu His Ser Gly Leu Trp Val Pro
1               5                   10                  15

Val Leu Ala Gly Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala His Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Lys Pro Asp Gly Ala Leu Tyr Gly
                100                 105                 110

Ser Val Ser Phe
            115
```

<210> SEQ ID NO 283
<211> LENGTH: 104
<212> TYPE: PRT
<213> ORGANISM: Mesocricetus auratus

<400> SEQUENCE: 283

Val Ile Gln Ile Leu Gly Val Lys Ala Ala Arg Phe Pro Cys Gln Gln
1               5                   10                  15

Pro Asp Gly Ser Leu Tyr Gly Ser Pro His Phe Asp Pro Glu Ala Cys
            20                  25                  30

Ser Phe Arg Glu Leu Leu Leu Glu Asp Gly Tyr Asn Val Tyr Gln Ser
        35                  40                  45

Glu Ala His Gly Leu Pro Leu Arg Leu Pro Gln Arg Asp Ala Pro Ser
    50                  55                  60

Gln Pro Pro Ala Ser Trp Gly Pro Val Arg Phe Leu Pro Val Pro Gly
65                  70                  75                  80

Leu Phe Gln Pro Pro His Asp Leu Pro Gly Arg Pro Ala Pro Glu Pro
                85                  90                  95

Pro Asp Val Gly Ser Ser Asp Pro
            100

<210> SEQ ID NO 284
<211> LENGTH: 151
<212> TYPE: PRT
<213> ORGANISM: Oreochromis niloticus

<400> SEQUENCE: 284

Met Tyr Leu Gln Met Asn Met Asp Gly Arg Val Thr Gly Ser Asp Ala
1               5                   10                  15

Gln Thr Pro Tyr Ser Leu Met Gln Leu Lys Ser Val Lys Pro Gly His
            20                  25                  30

Val Ile Ile Lys Gly Pro Ser Ser Leu Phe Leu Cys Val Asp Ser
        35                  40                  45

Glu Gly Asn Leu Arg Gly Gln Ser His Tyr Ser Glu Thr Ser Cys Thr
    50                  55                  60

Phe Arg Glu Met Leu Leu Ala Asp Gly Tyr Thr Arg Phe Ile Ser Ser
65                  70                  75                  80

Gln Tyr Gly Phe Pro Met Ser Leu Ala Ser Arg His Ser Pro Asp Arg
                85                  90                  95

His Ala Leu Pro Phe Thr Arg Phe Leu Pro Leu Arg Asn Asn Leu Lys
            100                 105                 110

Thr Asp Ser Val Ser Glu Gln Leu Pro Asn Asn Gln Arg Leu Phe Asn
        115                 120                 125

Val Asp Ser Asp Asp Leu Leu Gly Met Gly Leu Asn Ser Met Gly Ser
    130                 135                 140

Pro Gln Phe Ser Met Asp Lys
145                 150

<210> SEQ ID NO 285
<211> LENGTH: 630
<212> TYPE: DNA
<213> ORGANISM: Homo sapiens

<400> SEQUENCE: 285
atggactcgg acgagaccgg gttcgagcac tcaggactgt gggtttctgt gctggctggt      60
cttctgctgg gagcctgcca ggcacacccc atccctgact ccagtcctct cctgcaattc     120

```
ggggccaag tccggcagcg gtacctctac acagatgatg cccagcagac agaagcccac      180
ctggagatca gggaggatgg gacggtgggg ggcgctgctg accagagccc cgaaagtctc      240
ctgcagctga aagccttgaa gccgggagtt attcaaatct tgggagtcaa gacatccagg      300
ttcctgtgcc agcggccaga tggggccctg tatggatcgc tccactttga ccctgaggcc      360
tgcagcttcc gggagctgct tcttgaggac ggatacaatg tttaccagtc cgaagcccac      420
ggcctcccgc tgcacctgcc agggaacaag tccccacacc gggaccctgc accccgagga      480
ccagctcgct tcctgccact accaggcctg ccccccgcac tcccggagcc acccggaatc      540
ctggcccccc agccccccga tgtgggctcc tcggaccctc tgagcatggt gggaccttcc      600
cagggccgaa gccccagcta cgcttcctga                                      630
```

<210> SEQ ID NO 286
<211> LENGTH: 630
<212> TYPE: DNA
<213> ORGANISM: Pongo abelii

<400> SEQUENCE: 286

```
atggactcgg acgagaccgg gttcgagcac tcaggactgt gggttcctgt gctggctggt      60
cttctgctgg gagcctgcca ggcacacccc atccctgact ccagtcctct cctgcaattc     120 ggggccaag tccggcagcg gtacctctac acagatgatg cccagcagac agaagcccac      180
ctggagatca gggaggatgg gacggtgggg ggcgctgctg accagagccc cgaaagtctc      240
ctgcagctga aagccttgaa gccgggagtt attcaaatct tgggagtcaa gacatccagg      300
ttcctgtgcc agaggccaga tggggccctg tatggatcgc tccactttga ccctgaggcc      360
tgcagcttcc gggagctgct tcttgaggac ggatacaatg tttatcagtc cgaggcccat      420
ggcctcccgc tgcacctgcc gggaaacaag tccccacacc gggaccctgc accccgagga      480
ccagctcgct tcctgccact accaggcctg ccccccgcac cccagagccc gcccggaatc      540
ctggcccccc agccccccga tgtgggctcc tcggaccctc tgagcatggt gggaccttcc      600
cagggccgaa gccccagcta tgcttcctga                                      630
```

<210> SEQ ID NO 287
<211> LENGTH: 630
<212> TYPE: DNA
<213> ORGANISM: Pan troglodytes

<400> SEQUENCE: 287

```
atggactcgg acgagaccgg gttcgagcac tcaggactgt gggtttctgt gctggctggt      60
cttctgctag gagcctgcca ggcacacccc atccctgact ccagtcctct cctgcaattc     120 ggggccaag tccggcagcg gtacctctac acagatgatg cccagcagac agaagcccac      180
ctggagatca gggaggatgg gacggtgggg ggcgctgctg accagagccc cgaaagtctc      240
ctgcagctga aagccttgaa gccgggagtt attcaaatct tgggagtcaa gacatccagg      300
ttcctgtgcc agaggccaga tggggccctg tatggatcgc tccactttga ccctgaggcc      360
tgcagcttcc gggagctgct tcttgaggac ggatacaatg tttaccagtc cgaggcccac      420
ggcctcccgc tgcacctgcc ggggaacaag tccccacacc gggaccctgc accccgagga      480
ccagctcgct tcctgccact accaggcctg ccccccgcac cccggagcc acccggaatc      540 ctggcccccc agccccccga tgtgggctcc tcagaccctc tgagcatggt gggaccttcc      600
cagggccgaa gccccagcta cacttcctga                                      630
```

<210> SEQ ID NO 288
<211> LENGTH: 630
<212> TYPE: DNA
<213> ORGANISM: Canis lupus familiaris

<400> SEQUENCE: 288

| | | | | | |
|---|---|---|---|---|---|
| atgggctggg | ccgaggccgg | gttcgagcac | ctgggactgt | gggtccctgt | gctggctgtg | 60 |
| cttttgctgg | aagcctgccg | ggcacatccg | atccctgact | ccagcccct | cctacaattt | 120 |
| ggaggtcaag | ttcgacagcg | gtacctctac | accgacgatg | cccaggagac | agaggcccac | 180 |
| ctagagatca | gggccgatgg | cacagtggtg | ggggctgccc | gccagagccc | tgaaagtctc | 240 |
| ctggagctga | agccctaaa | gccaggggtc | attcaaatct | gggagtcaa | acatccagg | 300 |
| ttcctgtgcc | agggcccaga | tgggacacta | tatggctcgc | tccatttcga | ccctgtggcc | 360 |
| tgcagtttcc | gagaactgct | tcttgaggat | gggtacaaca | tctaccactc | cgagaccctt | 420 |
| ggtctcccgc | ttcgcctgcg | cccccacaac | tccgcatacc | gggacttggc | acccgcggg | 480 |
| cctgcccgct | tcctgccact | gccaggcctg | cttccagcac | cccagagcc | tccagggatc | 540 |
| ctggccccgg | agcctcctga | cgtgggctcc | tcggaccctc | tgagcatggt | ggggccttca | 600 |
| cagggccgga | gtcccagcta | tgcttcctaa | | | | 630 |

<210> SEQ ID NO 289
<211> LENGTH: 630
<212> TYPE: DNA
<213> ORGANISM: Bos taurus

<400> SEQUENCE: 289

| | | | | | |
|---|---|---|---|---|---|
| atgggctggg | acgaggccaa | gttcaagcac | ttgggactgt | gggtccctgt | gctggctgtc | 60 |
| ctcctgctag | gaacctgccg | ggcgcatccc | attccagact | ccagcccct | cctccagttt | 120 |
| gggggccaag | tccgccagcg | gtacctctac | acggatgatg | cccaggagac | agaggcccac | 180 |
| ctggagatca | gggccgatgg | cacagtggtg | ggggcagccc | gccagagccc | cgaaagtctc | 240 |
| ttggagctga | agccctgaa | gccaggcgtc | attcagatct | gggagttaa | acatccagg | 300 |
| tttctctgcc | aggggccaga | tgggaagctg | tacggatcgc | tgcactttga | ccccaaagcc | 360 |
| tgcagctttc | gggagctgct | tcttgaagat | ggatacaacg | tctaccagtc | ggagaccctg | 420 |
| ggccttccac | tccgcctgcc | ccccagcgc | tcgtccaacc | gggacccggc | cccgcgggga | 480 |
| cctgctcgct | tccttccact | gccgggcctg | cccgcggcgc | cccggatcc | tccagggatc | 540 |
| ttggcccccg | agcctcccga | cgtgggctcc | tcggatcccc | tgagtatggt | gggaccctcg | 600 |
| tatggccgaa | gccccagcta | cacttcttga | | | | 630 |

<210> SEQ ID NO 290
<211> LENGTH: 630
<212> TYPE: DNA
<213> ORGANISM: Equus caballus

<400> SEQUENCE: 290

| | | | | | |
|---|---|---|---|---|---|
| atggactggg | acaagacggg | gttcaagtac | cagggactgt | gggtccctgt | gctggctgtc | 60 |
| cttctgctgg | gagcctgcca | gtcacacccc | atccctgact | ccagtcccct | cctccaattc | 120 |
| gggggccaag | tcaggcagcg | ccacctctac | acagatgatg | cccaggagac | agaggcgcac | 180 |
| ctggagatca | gggctgacgg | cactgtggca | ggggctgtcc | accggagccc | agaaagtctc | 240 |
| ttggagctga | agccctgaa | gccaggggta | attcaaatct | gggagtcaa | gacatccagg | 300 |
| tttctgtgcc | aggggccaga | cgggacgctg | tacggatcgc | tccacttcga | ccccgtggcc | 360 |

```
tgcagcttcc gggagctgct tctcgaagac ggctacaacg tttaccagtc tgagaccctt      420
ggcctcccac tccgcctgcc ccaccacagc tccccatacc aggatccggc ccctcgggca      480
cccgcccgct tcctgccgct gccaggcttt ccccccagcac ccccggagcc tccagggatc     540
ccggcccccg agcccccgga cgtgggctcc tcggaccccc tgagcatggt ggggccttca      600
cgcagccgga gccccagcta cacttcctga                                       630
```

`<210> SEQ ID NO 291`
`<211> LENGTH: 630`
`<212> TYPE: DNA`
`<213> ORGANISM: Ailuropoda melanoleuca`

`<400> SEQUENCE: 291`

```
atgggctggg acgaggccag gtccgagcag ctggggctgt gggtccctgt gctggctgtc      60
cttttgctgg aagcttgcca ggcacaccct atccctgact ccagccccct cctccaattc     120
ggaggccaag ttcgacagcg gtacctctac acggacgatg cccaggagac agaggcccac     180
ctagcgatca gggctgatgg cacagtggtg ggggctgcca gccggagccc agaaagtctc     240
ttggagctga aagccctgaa accgggggtc attcaaatcc tgggagtgaa acatctagg      300 ttcctgtgcc agggcccaga tgggacactg tacggatcgg tccgcttcga ccccgtagcc     360
tgcagcttcc gggaactgct cctggaggat gggtacaaca tctaccactc tgagaccctc     420
ggcctcccac ttcgcctgcc cgcccacaac tctccatacc gggactcggc gccccggggg     480
cctgcccgct tcctgcccct gccaggcctg cttccggtcc ccccggaccc cccagggatc     540
ctgggccccg agcctcccga cgtgggctcc tcggaccccc tgagcatggt ggggccttca      600
cagggccgaa gtcccagcta cgcttcctga                                       630
```

`<210> SEQ ID NO 292`
`<211> LENGTH: 630`
`<212> TYPE: DNA`
`<213> ORGANISM: Oryctolagus cuniculus`

`<400> SEQUENCE: 292`

```
atggactggg gcaaggccaa gtgccggccc ccggggctgt gggtccccgc gctcgctgcc      60
ctgctgctgg gggcctgcca ggcacacccc atccccgact ccagccccct cctccagttt     120
ggggaccaag tgcggcagca gcacctgtac acggacgatg cgcaggaaac agaagcccac     180
ctggagatca gggcggatgg cacggtggtg ggggctgccc ggaggagccc agaaagtctc     240
ttgcagatga aagccttaca accggggatc attcagatct gggggtcca gacgtccagg      300 ttcctctgcc agaggccgga tgcacgctc tacggctcgc tccacttcga ccgcgaggcc     360
tgcagcttcc gggagctgct gcgtgaggat gggtacaacg tttacctctc ggaggccctg     420
ggcctgcccc tgcgcctgtc ccccggcagc tccccacgca gggcgccggc ccccggggga    480
ccagcccgct tcctgccgct gcccggcctg ccgccagacc ttccggaacc gccaggcctc     540
ctggccgccg cgcccccccga tgtcgactcc ccggaccccc tgagcatggt gcagcctgcg    600
ctggaccaga gccccagcta cacctcctga                                       630
```

`<210> SEQ ID NO 293`
`<211> LENGTH: 630`
`<212> TYPE: DNA`
`<213> ORGANISM: Gorilla gorilla`

`<400> SEQUENCE: 293`

```
atggactcgg acgagaccgg gttcgagcac tcaggactgt gggtttctgt gctggctggt     60
cttctgctgg agcctgcca ggcacacccc atccctgact ccagtcctct cctgcaattc    120
gggggccaag tccggcagcg gtacctctac acagatgatg cccagcagac agaagcccac    180
ctggagatca ggaggatgg gacggtgggg ggtgctgctg accagagccc tgaaagtctc    240
ctgcagctga agccttgaa gccgggagtt attcaaatct tgggagtcaa gacatccagg    300
ttcctgtgcc agaggccaga tggggccctg tatggatcgc tccactttga ccctgaggcc    360
tgcagcttcc gggagctgct tcttgaggac ggatacaatg tttaccagtc cgaggcccac    420
ggcctcccgc tgcacctgcc ggggaacaag tccccacacc gggaccctgc accccgagga    480
ccagctcgct tcctgccact accaggcctg ccccccgcac ccccggagcc acccggaatc    540
ctggccccc agccccccga tgtgggctcc tcggaccctc tgagcatggt gggaccttcc    600
cagggccgaa gccccagcta cgcttcctga                                    630
```

<210> SEQ ID NO 294
<211> LENGTH: 630
<212> TYPE: DNA
<213> ORGANISM: Nomascus leucogenys

<400> SEQUENCE: 294

```
atggactcgg acgagaccgg gttcgagcac tcaggactgt gggttcctgt gctggctggt     60
cttctgctgg agcctgcca ggcacacccc atccctgact ccagtcctct cctgcaattc    120
gggggccaag tccggcagcg gtacctctac acagatgatg cccagcagac agaagcccac    180
ctggagatca ggaggatgg gacggtgggg ggcgctgctg accagagccc tgaaagtctc    240
ctgcagctga agccttgaa gccgggagtt attcaaatct tgggagtcaa gacatccagg    300
ttcctatgcc agaggccaga tggggccctg tatggatcgc tccactttga ccctgaggcc    360
tgcagcttcc gggagctgct tcttgaggac ggatacaatg tttaccagtc cgaggcccat    420
ggcctcccgc tgcacctgcc ggggaacaag tccccacacc gggaccctgc accccgagga    480
ccagctcgct tcctgccact accaggcctg ccccctgcac cccagagcc gcccggaatc    540
ctggccccc agccccccga tgtgggctcc tcggaccctc tgagcatggt gggaccttcc    600
cagggccgaa gccccagcta cgcttcctga                                    630
```

<210> SEQ ID NO 295
<211> LENGTH: 630
<212> TYPE: DNA
<213> ORGANISM: Procavia capensis

<400> SEQUENCE: 295

```
atggactggg ccaagtttgg gatcgagcac ccgggactgt gggtcccggt gatggcagta     60
cttctgctgg agcctgcca aggataccct attcctgact ccagcccct tctccaattc    120
ggaggccagg tccggcaacg ttacctctac acagatgacg cgcaggagac cgaggcccac    180
ctggagatcc gagcagacgg cacggtggtg ggggctgccc accggagccc cgagagtctc    240
ttggagctga agctttgaa gcccggcata attcagatct tgggagtcaa gacatccaga    300
ttcctctgcc agggtcctga tggggtgctg tatggatcgc tccgttttga cccagtggcc    360
tgcagcttcc gggagctgct tcttgaagat ggatacaatg tttaccagtc tgaggcccac    420
ggcctcccgc ttcgcctacc atcccacaat tccccacaga gggacctggc gtcccgggtg    480
ccagcccgct tcctgccact gccaggcggg ctcacggtgc tccagaaacc ttcggggtc    540
ctgggccctg agccccccga tgtggactcc tcagaccccc tgagcatggt ggggccttcg    600
```

```
cagggccgaa gccccagtta cgcctcctga                                   630
```

<210> SEQ ID NO 296
<211> LENGTH: 630
<212> TYPE: DNA
<213> ORGANISM: Cavia porcellus

<400> SEQUENCE: 296

```
atggactggg cccggactga gtgtgagcgc ccaaggctgt gggtctccat gctggccatc    60
cttctggtgg gagcctgcca ggcacaccct atccctgact ccagcccct  cctccagttt   120
gggggccagg tccggcagcg gtacctctac acagatgatg ctcaggacac tgaagtgcac   180
ctggagatca gggccgatgg ctcagtacgg ggcattgccc acaggagccc tgaaagtctc   240
ctggagctga aagccttgaa gccaggagtc attcagatct gggaatcag  gacttccagg   300
ttcctgtgcc agaggcccga tgggagtctg tatggatcac tccactttga tcctgaggcc   360
tgcagcttcc gggagctgct gcttgctgat ggctacaatg tctacaagtc tgaagcccac   420
ggcctccctc tgcacctgct gcgcggtgac tctctatcgc aggaaccagc acccccagga   480
ccagcccgat ttctgccact accaggcctg cccgcaacac cccggagcc  acccaggatg   540
ctgcccccag ggccccagag tgtgggctcc tcggacccct tgagcatggt ggggcctta    600
tgggaccgaa gccccagcta tacttcctga                                   630
```

<210> SEQ ID NO 297
<211> LENGTH: 583
<212> TYPE: DNA
<213> ORGANISM: Tupaia belangeri

<400> SEQUENCE: 297

```
atgggctggg acaaggcccg gttcgagcac ctggagcgt  gggctcctgt gctggctgtc    60
ctcctcctgg gagcctgcca ggcataccccc atccctgact ccagcccct  cctacaattc   120
gggggccagg tccggcagcg gtacctctac acggacgaca cgcaggacac agaagcccac   180
cttgagatca gggccgacgg caccgtggtg ggggccgccc accaaagccc ggaaagtctc   240
ctggagctga aagccttgaa gccggggtgtc attcaaatcc tggagtcaa  gacctccagg   300
ttcctgtgcc agaggccaga cggggccctg tacgggtcgc ttcacttcga ccccgaggcc   360
tgcagcttcc gggagctgct tctcgaggat ggatacaaca tttaccagtc tgaggctcgt   420
ggcctccccc tgcgcctgcc gccccacgac tccccacatc gggaccggac ccctcgggga   480
ccagctcgtt tcctgccgct gcctggcctg ccctggttc  ctccagagct gccagggtc   540
ctggcccttg agccccccga cgtgggctcc tcagacccgc tga                    583
```

<210> SEQ ID NO 298
<211> LENGTH: 586
<212> TYPE: DNA
<213> ORGANISM: Sorex araneus

<400> SEQUENCE: 298

```
atggtctggg acaaggccag ggggcagcag ttgggactgt gggcccccat gctgctgggc    60
ttgctgctgt gtgcctgcca ggcacaccccc ctccctgact ccagcccct  cctccaattt   120
gggggccaag tccgactgag gttcctgtac accgacgatg cccagaggac aggggcgcac   180
ctggagatca gggccgacgg cacagtgcag ggtgcggccc acaggacccc agaatgtctc   240
ctggagctga aagccttgaa gccaggcgta attcaaatcc ttggggtcag cacatccaga   300
```

```
ttcctgtgcc agcggcccga tggggtcctg tatggatcgc ttcgctttga cccagaggcc      360
tgcagtttcc gggaacttct tctccaggat ggatataacg tttaccagtc tgaggccctg      420
ggtctcccgc tctacctaca cccgcccagt gccccagtgt cccaggaacc agcctcacgg      480
ggcgccgtcc gcttcctgcc actgccagga ctgccacctg cctccctgga gccccccagg      540 cccccgccc cggtgcctcc agacgtgggt tcctcagacc ccctga                      586

<210> SEQ ID NO 299
<211> LENGTH: 546
<212> TYPE: DNA
<213> ORGANISM: Ictidomys tridecemlineatus

<400> SEQUENCE: 299
atgtacccca tccctgactc aagccccctc ctccaatttg ggggccaagt ccggcagcgg       60
tacctgtaca cagatgatgc ccaggagact gaggcccacc tggagatcag ggctgatggc      120
accgtggtgg gggctgccca tcaaagcccg gaaagtctct tggaactgaa agccttgaag      180
cctggggtca ttcaaatctt gggggtcaaa acatccaggt tcctgtgcca gaggccagat      240
ggagtgctgt atggatcgct ccactttgac cctgaggcct gcagcttccg ggagcagctt      300
ctggaggacg gtacaacgt ttaccagtca gaatcccacg gcctcccgt gcgcctgccc       360 cctaactcac ataccgggga cccagcgccg ccaggaccag cccgcttcct tccactgcca      420
ggcctgcccc cagcagccct ggagccgcca gggatcctgg gccctgagcc cctgatgtg      480 ggctcctccg acccactcag catggtgggg cctttgcagg gccgaagccc cagttacgct      540
tcctga                                                                 546

<210> SEQ ID NO 300
<211> LENGTH: 627
<212> TYPE: DNA
<213> ORGANISM: Loxodonta Africana

<400> SEQUENCE: 300
atggactggg ccaagtttgg gttggagcac ccaggactgt gggtccctgt gatggctgtc       60
cttctgctgg gagcctgcca gggacacccc atccctgact ccagccccct cctccaattc      120 ggggggccagg tccggcaacg ttacctctac acagatgatc aggagaccga ggcccacctg      180
gagatcagag cagatggcac agtggcggga gccgctcacc ggagctctga gagtctcttg      240
gagctgaaag ctttgaagcc tggaataatt cagatcttgg gggtcaagac atcccggttc      300
ctgtgccagg ggcctgatgg ggtgctgtac ggatcgctcc atttcgaccc agccgcctgc      360
agcttccggg agctgcttct tgaagatgga tacaatgttt actggtccga ggcccatgga      420
ctcccaatcc gcctgccctc ccacaactcc ccatataggg acccagcatc ccgggtacca      480
gcccgcttcc tgccactgcc aggcctgctc ccaatgctcc aagaacctcc aggggtcctg      540
gcccctgagc ccctgatgtg ggactcctca ccccctga gcatggtggg gccttcacag      600
ggccgaagcc ccagctatgc ctcctga                                          627

<210> SEQ ID NO 301
<211> LENGTH: 627
<212> TYPE: DNA
<213> ORGANISM: Sus scrofa

<400> SEQUENCE: 301
atgggctggg ccgaggccaa gttcgagcgc ttgggactgt gggtccctgt gctggctgtc       60
ctgctgggag cctgccaggc acgtcccatt cctgactcca gccccctcct ccaatttggg      120
```

```
ggccaagtgc gccaacgata cctctacacg gatgatgccc aggaaactga agcccacctg    180
gagatcagag ctgatggcac cgtggcaggg gtagcccgcc agagccctga aagtctcttg    240
gagctgaaag ccctgaagcc aggggtcatt caaattttgg gagtccagac atcccggttc    300
ctgtgccagg ggccagacgg gagactgtac ggatcgctcc acttcgaccc tgaggcctgc    360
agcttccggg agctgcttct tgaggatggc tacaacgttt accagtctga ggcccttggc    420
ctcccactcc ggctgcctcc gcaccgctcc tccaaccggg acctggcccc cggggacct    480 gctcgcttcc tgccactgcc aggcctgccc ccggcacccc cggagccgcc agggatcttg    540
gcccctgaac ctcccgacgt gggctcctcg gaccccctga gcatggtggg gccttcacac    600
ggccggagcc ccagctacac ttcttga                                       627
```

<210> SEQ ID NO 302
<211> LENGTH: 627
<212> TYPE: DNA
<213> ORGANISM: Felis catus

<400> SEQUENCE: 302

```
atgggctggg acgaggccgg gtcccagcgc ctgggactgt gggtcgtgct ggggggtcctt    60 ttgccggaag cctgccaggc acaccctatc cctgactcca gcccctcct ccaattcggg    120 ggccaagttc gacagcggtt cctctacacg gacgacgccc aggagacaga ggtccacctc    180
gagatcaagg ctgatggcac agtggtgggg accgctcgcc ggagccctga gagtctcttg    240
gagctaaaag ccctgaagcc gggggtaatt caaatcttgg gggtcaaaac gtccaggttc    300
ctgtgccagg gccagatgg gacactgtat ggatcgctcc gctttgaccc cgcagcctgc    360
agcttccggg aactgctcct ggaggacgga tacaacatct accatcgga gaccctcggg    420 ctcccactcc ggctgccccc cacaactcc ccataccggg acttggcccc ccgggcacct    480
gcccgcttcc tgccgctgcc aggcctgctt ccggcacccc cggagcctcc agggatcctg    540
gcccccgagc ccccggacgt gggctcctcg gaccctctga gcatggtggg gccttcccag    600
ggccgaagtc ccagctacgc ttcctga                                       627
```

<210> SEQ ID NO 303
<211> LENGTH: 627
<212> TYPE: DNA
<213> ORGANISM: Otolemur garnettii

<400> SEQUENCE: 303

```
gacaaggcca ggactgggtt caagcaccca ggaccatggt tccccctgct ggctgtactt    60
ttgttgggag cctgccaggc acaccctatc cctgactcca gcccctact ccagtttggt    120 ggccaagtcc ggcagcggta cctctacaca gatgatgccc aggagacaga agcccacctg    180
gagatcaggg aagatggcac agtggtgggg gctgcacaac agagccctga aagtctcttg    240
gagctgaaag ctttaaagcc aggggtcatt caaatcttgg gagtcaagac atccaggttc    300
ctgtgccaga ggccagatgg gggcctatat ggatcgctct actttgaccc caaggcctgc    360
agtttccggg agctgcttct tgaggatgga tacaacgttt actggtctga gacctatggc    420
ctcccactgc acctgcctcc tgccaattcc ccatactggg gccatccct tcggagccca    480 gcccgcttcc tgccactgcc aggccctcct gcagcatccc cagagctgcc ggggatcttg    540
gccctggaac ccccgatgt gggctcctcg gaccctctga gcatggtggg gccttcgcag    600
ggccgaagcc ccagctatgc ttcctga                                       627
```

<210> SEQ ID NO 304
<211> LENGTH: 627
<212> TYPE: DNA
<213> ORGANISM: Rattus norvegicus

<400> SEQUENCE: 304

```
atggactgga tgaaatctag agttggggcc ccgggactgt gggtctgtct cctgctgcct      60
gtcttcctgc tggggggtgtg cgaggcatac cccatctctg actccagccc cctcctccag    120
tttgggggtc aagtccgaca gaggtatctc tacacagatg acgaccagga caccgaagcc    180
cacctggaga tcagggagga cggaacagtg gtgggcacag cacaccgcag tccagaaagt    240
ctcctggagc tcaaagcctt gaagccaggg gtcattcaaa tcctgggtgt caaagcctct    300
aggtttcttt gccaacaacc agatggaact ctctatggat cgcctcactt tgatcctgag    360
gcctgcagtt tcagagagct gctgcttaag gacggataca atgtgtacca gtctgaggcc    420
catggcctgc cctgcgtctg ccccagaaag gactcccagg atccagcaac ccggggacct    480
gtgcgcttcc tgcccatgcc aggcctgccc acgagcccc aagagcaacc aggagtcctt    540
cccccagagc cccagatgt gggttcctcc gaccccctga gcatggtaga gcctttgcaa    600
ggccgaagcc ccagctatgc atcttga                                         627
```

<210> SEQ ID NO 305
<211> LENGTH: 633
<212> TYPE: DNA
<213> ORGANISM: Mus musculus

<400> SEQUENCE: 305

```
atggaatgga tgagatctag agttgggacc ctgggactgt gggtccgact gctgctggct      60
gtcttcctgc tggggggtcta ccaagcatac cccatccctg actccagccc cctcctccag    120
tttgggggtc aagtccggca gaggtacctc tacacagatg acgaccaaga cactgaagcc    180
cacctggaga tcagggagga tggaacagtg gtaggcgcag cacaccgcag tccagaaagt    240
ctcctggagc tcaaagcctt gaagccaggg gtcattcaaa tcctgggtgt caaagcctct    300
aggtttcttt gccaacagcc agatggagct ctctatggat cgcctcactt tgatcctgag    360
gcctgcagct tcagagaact gctgctggag gacggttaca atgtgtacca gtctgaagcc    420
catggcctgc cctgcgtctg cctcagaaag gactccccaa accaggatgc aacatcctgg    480
ggacctgtgc gcttcctgcc catgccaggc ctgctccacg agcccaaga ccaagcagga    540
ttcctgcccc cagagccccc agatgtgggc tcctctgacc cctgagcat ggtagagcct    600
ttacagggcc gaagccccag ctatgcgtcc tga                                   633
```

<210> SEQ ID NO 306
<211> LENGTH: 324
<212> TYPE: DNA
<213> ORGANISM: Vicugna pacos

<400> SEQUENCE: 306

```
atggactggg acgaggccaa gttcgagcat cggggactgt gggtcccagt gctcactgtc      60
cttctgctgg agcctgcca ggcacgcccc attcctgact ccagcccct cctccaattc     120
gggggccaag tccggcagcg gtacctctac acggatgacg cccaggagac agaagcccac    180
ctggagatca gggctgatgg cacagtggtg ggggtggccc gccagccga aggaattcct    240
cccgagcctc ctgacgtggg ctcctcagac cccctgagca tggtggggcc ttcatacagc    300
agaagcccca gctacacttc ctga                                             324
```

<210> SEQ ID NO 307
<211> LENGTH: 633
<212> TYPE: DNA
<213> ORGANISM: Anolis carolinensis

<400> SEQUENCE: 307

| | | | | | |
|---|---|---|---|---|---|
| tgtaaaagca | agggaggagg | gaaggggga | gagaggatgt | gggtagacct | agttttctgg | 60 |
| gctgccttgc | tccgcacagc | tcctgctctt | cccttgcgga | attccaaccc | catctaccaa | 120 |
| tttgatgggc | aggtccggct | tcggcacctc | tacacagcag | atgaacagac | gcacctccac | 180 |
| ttggagatct | tgccagacgg | taccgtgggt | ggatccaggt | ttcagaatcc | cttcagtttg | 240 |
| atggagatca | aagctgtgaa | gccaggagtc | attcgcatgc | aggccaagaa | gacctctaga | 300 |
| tttctctgta | tgaaacccaa | tggacgactg | tatggctcgc | tgttctactc | tgaggaggca | 360 |
| tgcaacttcc | atgagaaggt | tctcagcgat | ggctacaacc | tctactattc | tgaaaactac | 420 |
| aacatacctg | tcagcctcag | ctcggcaggg | aacctgggtc | agagccgtca | gttgcctccc | 480 |
| ttctcccaat | tcctgccgtt | agtcaacaaa | attcctcttg | agcctgtgct | tgaagacttt | 540 |
| gacttctatg | gacatcaatt | ggatgttgaa | tcagctgatc | cttttgagcat | tttaggacaa | 600 |
| aaccctggtt | tcatgagtcc | gagctatgtc | ttc | | | 633 |

<210> SEQ ID NO 308
<211> LENGTH: 564
<212> TYPE: DNA
<213> ORGANISM: Gadus morhua

<400> SEQUENCE: 308

| | | | | | |
|---|---|---|---|---|---|
| ctcctcctcg | ccaccctcct | ccacatcggc | ctctccttct | acgtccccga | ctccggcccc | 60 |
| ctgctgtggc | tgggcgacca | ggtcagggag | agacacctct | acacagcaga | gagccaccgg | 120 |
| aggggggctgt | tcctggagat | gagcccggac | ggtcaggtga | caggaagtgc | tgctcagacg | 180 |
| ccgctcagtg | ttctggagct | gaggtcggtc | agagcaggag | atacggtcat | cagagcgcgc | 240 |
| ctctcctctc | tctacctgtg | tgtggacagg | gcaggtcacc | tgacaggaca | gagacagtac | 300 |
| acagagtccg | actgcacctt | cagagaggtc | atccttgagg | acggctacac | ccacttcctg | 360 |
| tccgtgcacc | acggacttcc | tatttcgctg | gcgccgagac | actccccagg | gagacagggg | 420 |
| ctgcgcttca | gcaggttcct | cccgctgagg | agcagtctgt | cagaggatag | ggtcgccgag | 480 |
| cccccagaca | gcccactgaa | cctggactct | gaagaccccc | tggggatggg | tctgggttcg | 540 |
| ctcctcagcc | cggccttctc | catg | | | | 564 |

<210> SEQ ID NO 309
<211> LENGTH: 648
<212> TYPE: DNA
<213> ORGANISM: Latimeria chalumnae

<400> SEQUENCE: 309

| | | | | | |
|---|---|---|---|---|---|
| atgttatgcc | agagttttgt | gatattaagt | cagaaattca | ttttttgggct | cttttttgact | 60 |
| ggattgggggc | taacaggatt | ggcttggaca | aggcccttcc | aggattccaa | tcccatcctg | 120 |
| cagtattccg | attccatccg | gctccgacat | ctgtacactg | ccagtgagag | tcggcacctt | 180 |
| cacctacaaa | tcaactcgga | tggacaggtg | ggagggacaa | ccaagcaaag | cccttacagt | 240 |
| ctgttggaga | tgaaggcggt | gaagacaggt | tttgtggtca | tcaggggcaa | gaaaagcgcc | 300 |
| cgttacctct | gtatggaacg | tagtggacgg | ctctatggat | cgctgcagta | tacagaaaaa | 360 |

```
gactgcacct tcaaagaggt tgtgttggca gatggataca acctgtatgt ctcagaggaa    420
caccaggcca cagtgacgct gagcccatg agggcgagga tagcgcaagg gaaaaagatc    480 ccacccttt cccatttcct tccaatggtg aacaaggtgc ctgtggagga tgttgccgct    540
gagatggagt ttgtccaggt gctgcgggaa atgacggccg acgtggactc tccggatccc    600
tttggaatga cctgggaaga atcggttcac agtccgagct tttttgcc                648

<210> SEQ ID NO 310
<211> LENGTH: 579
<212> TYPE: DNA
<213> ORGANISM: Tursiops truncates

<400> SEQUENCE: 310
atgggctggg acaagaccaa actcgagcac ctgggactgt gggtccctgt gctagctgtc     60
ctgctgggac cctgccaggc acatcccatt cctgactcca gcccctcct ccaatttggg    120 ggccaagtcc gccagcgata cctctacacg gatgacgccc aggagacgga ggcccacctg    180
gagatcaggg ctgatggcac agtggtgggg acggcccgcc ggagcccga aggagttaaa    240 acatccaggt tcctgtgcca ggggccagag gggaggctgt atggatcgct ccacttcaac    300
ccccaggcct gcagcttccg ggagctgctt cttgaggatg gatacaacgt ttaccagtct    360
gaggctcttg gcattcccct ccgcctgccc ccgcaccgct cctccaactg ggacctggcc    420
ccccggggac ctgctcgctt cctgcgcctg ccaggcttcc tcccgccacc cctggagcct    480
ccagggatct tggcccccga gcctcccaac gtaggttcct cggacccctt gagcatggtg    540
ggaccttcac atggccgaag ccccagctac acttcctga                          579

<210> SEQ ID NO 311
<211> LENGTH: 630
<212> TYPE: DNA
<213> ORGANISM: Mustela putorius furo

<400> SEQUENCE: 311
atgggctggg aagaggccag gtccgagcac ctggggctgt gggtccctgt gctggcggtc     60
cttttgctgg gagcctgcca ggcataccct attcctgact ccagcccct cctccaattt    120 ggaggccaag ttcgacagcg gtacctctac acagacgacg ctcaggagac ggaggcccac    180
ctagagatca gggctgatgg cacggtggtg gggctgcccc gccggagccc cgaaagtctc    240
ttggagctga aagccctgaa gccaggggtc attcagatct gggagtgaa acatccagg    300 ttcctgtgcc agggcccgaa tgggacactg tacggatcgt tccacttcga ccccgtagcc    360
tgcagcttcc gggaagtgct tctggaagat ggatacaaca tctaccactc tgagaccctg    420
ggcctcccac tgcgcctgcc ccccacaac tccccacaca gggacctggc gcccgggg    480 cctgcccgct tcctgcccct gccaggcctg cttccggcca ccccggagtc ccgggggatc    540
ccagcccccg agcctcccaa cgtgggctcc tcagaccccc tgagcatggt ggggccttg    600 cagggtcaaa gtcccagcta cacttcctga                                    630

<210> SEQ ID NO 312
<211> LENGTH: 597
<212> TYPE: DNA
<213> ORGANISM: Takifugu rubripes

<400> SEQUENCE: 312
tttatttatt tatttattca aactgcactt ttttcccctt ccaaatggtt caactttat     60 ctccctgact ccaacccgct cttatccttt gacagtcatg gcagaggcat ccacctctac    120
```

```
acagataatc aaaggcgagg gatgtatctg cagatgagca cagatggaag cgtttccggg      180
agtgatgtcc agacggcgaa cagtgtgctg gaactgaagt cagtcagaaa cggccacgtc      240
gtcatccgag gaaaatcgtc ttctctgttt ctctgtatgg acagcagagg ccgtttatgg      300
gggcagaggc accccactga ggccgactgc actttcaggg aagtgttgct ggcagatgga      360
tacactcgct tcctgtccct gcacaacgga actcctgtgt ctctggcacc taaacaatct      420
ccagaccagc acacagtccc cttcactcgt ttcctgccgc tcaggaatac actggcagag      480
gagagcatgt ctgaaccacc atcaaaccaa cagagatatt ttaacattga ctctgatgat      540
cttcttggaa tggatttaaa tgcgatggtc agtcctcagt tttcaggggga caagtga      597
```

<210> SEQ ID NO 313  
<211> LENGTH: 612  
<212> TYPE: DNA  
<213> ORGANISM: Dipodomys ordii
<400> SEQUENCE: 313

```
atggaccagg caaagaccag ggttggggcc cggggctgg ggggccttgt gctggctgtc       60
ataattctgg gagcatgcaa ggcacggcct atccctgact ccagccccct cctccaattt     120
gggggtcaag ttcggcttcg gcacctctac acagatgaca ctcaggagac ggaagcccat     180
ctggagatca gggcagatgg cacggtagtg gggactgccc accggagccc tgaaagtctc     240
ttggagctga aagccttgaa gccaggagtc attcaaatct tagggatcaa gacatccaga     300
ttcttatgcc agagaccaga cggacactg tatggatcac tccactttga ccctgaggtt     360
tgcagcttcc aggagctgct tctggaagat ggatacaaca tttaccgttc tgaagccctg     420
ggtctccccc tgcgcctgtc cccagatcca gcacctgggg gccagcccg cttcctgccc     480 ctgcctggtg tgcccccgc accgccggag ccccccggga tcctggctcc cgaacccct     540 gatgtcggct cctccgaccc tctgagtatg gtgggactgt tgcagggccg aagcccagc     600 tatgcatcct ga                                                         612
```

<210> SEQ ID NO 314  
<211> LENGTH: 555  
<212> TYPE: DNA  
<213> ORGANISM: Echinops telfairi
<400> SEQUENCE: 314

```
atgggttgca ccaaatctgg gtggaagtcc ccgggactgt gggtccctgt gctggccagc      60
cttctgctgg gaggctgcgg agcacacccc atccctgact ccagccccct cctccaattc     120
gggggccaag tccggcagcg atacctctat acggatgacg cccagaccac cgaggcccac     180
ctggagatca gagcggatgg cacagtgggg ggcgtcgccc accagagccc agagaagttc     240
ctgagtcaat ggcgtgaaaa gcccctgaga tcactccatt tcgacccagc cgcctgcagc     300
ttccgggaga agcttctaga agacggatac aacttgtacc actctgagac ccacggcctc     360
cccctccgcc tcccacccg tggggggcgac ccctcttctc agcctggggc ccgcttccca     420
ccgctgccgg gccagctccc acaactccaa gagacgccag gggtcctcgc ccccgaaccc     480
cccgacgtgg gctcttcaga ccccctgagc atggtggggc cttggcgagg gcaaagtccc     540
agttatgcct cctga                                                      555
```

<210> SEQ ID NO 315  
<211> LENGTH: 633  
<212> TYPE: DNA

<213> ORGANISM: Macaca mulatta

<400> SEQUENCE: 315

| | | | | | | |
|---|---|---|---|---|---|---|
| atggactcgg | acgagaccgg | gttcgagcac | tcaggactgt | gggttcctgt | gctggctggt | 60 |
| cttctgctgg | gagcctgcca | ggcacacccc | atccctgact | ccagtcctct | cctgcaattc | 120 |
| gggggccaag | tccggcaacg | gtacctctac | acagatgatg | cccagcagac | agaagcccac | 180 |
| ctggagatca | ggaggatgg | gacagtgggg | ggcgctgctc | accagagccc | cgaaagtgag | 240 |
| tgtgggccag | agcctgggtc | tgagggagga | ggggctgtgg | gaggtgctga | gggacctgga | 300 |
| ctcctgggtc | tgagggaggc | agggctgggg | cctggatcct | ggctccactt | tgaccctgag | 360 |
| gcctgcagct | tccgggagct | gcttcttgag | aacggataca | atgtttacca | gtccgaggcc | 420 |
| cacggcctcc | cactgcacct | gccgggaaac | aagtccccac | accgggaccc | tgcatcccaa | 480 |
| ggaccagctc | gcttcctgcc | actaccaggc | ctgcccccg | caccccgga | gccgccagga | 540 |
| atcctcgccc | ccagccccc | cgatgtgggc | tcctcggacc | ctctgagcat | ggtgggacct | 600 |
| tcccaggccc | gaagccccag | ctatgcttcc | tga | | | 633 |

<210> SEQ ID NO 316
<211> LENGTH: 582
<212> TYPE: DNA
<213> ORGANISM: Microcebus murinus

<400> SEQUENCE: 316

| | | | | | | |
|---|---|---|---|---|---|---|
| atgggctggg | acgaggccgg | cgccgggttc | gagcacccag | gactgtggtt | tcccatgctg | 60 |
| ggtgtcctgc | tgctgggagc | ctgccaggcg | taccccatcc | tgactccag | ccccctcctc | 120 |
| caatttggcg | gccaagtccg | gcagcggcac | ctctacacag | acgatatcca | ggagacagaa | 180 |
| gcccacctgg | agatcaggc | ggacggcaca | gtggtggggg | ccgcccgaca | gagccctgag | 240 |
| ttggagctga | aagccttaaa | gccagggtc | attcaaatct | tgggagtcaa | gacctccagg | 300 |
| ttcctgtgcc | agaggccaga | cggggccctg | tacggatcgc | tccactttga | ccccgagtgc | 360 |
| agcttccggg | agctgcttct | tgaggatgga | tacaacgtct | actgtcccta | cctcccgctg | 420 |
| cacctgtccc | cacgcatcga | actggccgga | tcacgctctg | cgctgccact | gccccagca | 480 |
| cctgaacgca | ggatttttggc | cccggagccc | ccggatggct | cctcggaccc | tctgagcatg | 540 |
| gtggggcctt | cgcagggccg | aagtcccagc | tatgcttcct | ga | | 582 |

<210> SEQ ID NO 317
<211> LENGTH: 615
<212> TYPE: DNA
<213> ORGANISM: Ochotona princeps

<400> SEQUENCE: 317

| | | | | | | |
|---|---|---|---|---|---|---|
| aaagacatgg | acgggctcca | gcctccgggg | ctgcgggttc | ctgtgctggc | tgccctgctt | 60 |
| ttgggagttg | gccaggcacg | ccccatccct | gattctagcc | ctctcctcca | attcggggc | 120 |
| caggtccggc | agaggcacct | ctacacggat | gacgcccagg | aatcggaagt | acacctggag | 180 |
| atccgggcag | acggcaccgt | ggcagggact | gcccgccgga | gccctgaaag | tctcttagaa | 240 |
| atgaaagcgt | tgaagccagg | cgtcattcag | atcctgggg | tccacacatc | caggttcctg | 300 |
| tgccagagac | cagacgggac | gctgtacggc | tcgctccact | tcgaccacaa | ggcctgcagc | 360 |
| ttccgggagc | agctgctgga | ggatgggtac | aacgtgtacc | actcagagac | acacggcctc | 420 |
| ccgctgcgcc | tgtctccaga | ccgagccccc | cggggcccag | cccgcttcct | gccactgcca | 480 |
| ggccctcctc | ctgacctcct | ggtgccaccc | ctgccaccgg | acgtcctagc | ccctgagccc | 540 |

```
cccgacgtgg actccccaga cccctgagc atggtggggc ccttgcaggg ccaaagcccc    600
agctacactt cctga                                                    615
```

<210> SEQ ID NO 318
<211> LENGTH: 546
<212> TYPE: DNA
<213> ORGANISM: Xiphophorus maculates

<400> SEQUENCE: 318

```
tgcccgttcc ccttcctttt cttaatcctc tctcttccct ttttctcttc ctcgttttac     60
atcccagaat ccaacccaat ctttgccttc aggaatcagc tcagagaggt gcatctctac    120
acagaaaatc acagacgggg tttgtatgtg agatacatc tggatgggag agtgactgga    180
agtgatgctc agagtcctta tagtgtgttg cagataaagt ctgttaaacc gggtcatgtg    240
gtcataaagg gacagacatc gtccctgttc ctctgcatgg acgactccgg gaatctaaga    300
ggacagacaa cctatgacga ggctgactgc tccttcaggg aactgctgct ggccgatggc    360
tacacccgtt tcctgaactc acaacatggc gttcctttat cactggcatc cagaaactct    420
ccagatcgac actccgttcc tttcacaaga ttttacctc tcaggaatac tttaacggtt    480
tcagaagaat caacaaaaac tcagagggac ttcaacctgg actcggacga ccttctcggg    540
atggga                                                              546
```

<210> SEQ ID NO 319
<211> LENGTH: 576
<212> TYPE: DNA
<213> ORGANISM: Gasterosteus aculeatus

<400> SEQUENCE: 319

```
tctctcctcc tcatggtccc acttcctttc tgttcatcct tttatctcac tgactccagc     60
ccacttctac ccttcaataa tcaagtcaaa gaggtgcacc tctacacagc agagaatcac    120
agaagagcga tgtacctgca gatcgctctg gacgggagcg tgtcgggaag cgacgctcgg    180
tccacttaca gtgtgctgca gctgaaatct atccagccgg ccacgtggt catcagaggg    240 aaggcctcct ccatgttcct ctgcgtggac agcgggggcc gtttgagagg acaggggccg    300
tactcagagg ccgactgcag cttcaggag ctgctgctgg gggatggcta cacccggttc    360
ctgtcctcgc agcacgggtc cccgctgtct ctggcgtcga ggccttcccc ggatcccaac    420
tcggtgccct tcactcgatt cctacccatc cggaccgccc ccgaggctga gagcgtgatc    480
gaagagccac cgagcaatca gagatacgtc aacgtggact ccgaggatct tcttggaatg    540
ggcctgaaca ctgtggtcag tcctcagttc tcggcg                             576
```

<210> SEQ ID NO 320
<211> LENGTH: 495
<212> TYPE: DNA
<213> ORGANISM: Sarcophilus harrisii

<400> SEQUENCE: 320

```
gtgtctgcca tgggcctgag ggagcgagct cccaggtacc tggccccgct gctgtccttg     60
ctcttggcct gcagggcctc gggtcacccc ctccggatt ccagcccat gctcctgttt    120 gggggggcagg tccgcctccg gcacctctac acggatgtgg gccaggaggc cgaggcccac    180
gtggaactgg cgtccgacgg cacagtccgg cggcagcgc ggaggagtcc caacagtctc    240
ctggagctga aggctgtgaa gccgggcatc gtccgaatcc tggccgtcca cagctctcgg    300
```

```
tttctgtgta tgaggcccaa cggggagctg tacggagcga tacactacga cccttccgcc      360
tgcaactttc gggagcgcct gctggggac ggctacaacg tgtacgagtc cgaggctcac       420
gggaggaccc tccgcctgcc ccccaaggcc gcaccgggac ccgccggacc ttctcgcttc      480
ctgccgctcc ccggc                                                      495

<210> SEQ ID NO 321
<211> LENGTH: 627
<212> TYPE: DNA
<213> ORGANISM: Macropus eugenii

<400> SEQUENCE: 321
acagaggagc cttctactgg gtccaggcac ctgggacaat gggctcccgg gctgcctggt       60
cctctgctgt ccttgctcct ggcctacagg ggctggggct cccccatccc tgattccagc     120
cccatgctcc tgtttggtgg ccaggtccgc ctccgacacc tgtacacaga tgatggccag     180
gacacggagg cccatgtgga gctggggcca gatggagtgg ttcgagctgt ggctgagagg     240
agccccaaca gtcttctgga actgaaggcg gtgaagcctg gagtcatccg aatcctcgct     300
gtccagagct ctcggtttct gtgtatgagg cccaacgggg aactgtatgg agcggtacac     360
tatgaccctt ctgcctgcaa cttccgggaa catctgctgg gggatggtta taatgtgtat     420
gaatcagaga ctcacagaag gaccctccgt ctgtccccat ccctgggtca ggctggcccc     480
tctcgcttcc tgccacttcc aggcgactgg ctgcccggcc tgatccacc ttgggcacag      540 ggccctgagc cccagacgt gggctctgca gacccctga gcatggtggg ggccgtgcag       600
ggcctcagcc ccagctactc ctcctga                                         627

<210> SEQ ID NO 322
<211> LENGTH: 480
<212> TYPE: DNA
<213> ORGANISM: Xenopus tropicalis

<400> SEQUENCE: 322 agaggggta ggaccaaaaa aaagacgtta ctcaggaaat ggctttgcct tttagccatt        60
atgttgagta ggtcaaggtt ttctttagca aatcctatcc agaattcgaa cccaatctta     120
tccaacgaca accaagtacg gactcagtat ttatacacag ataacaataa catgcacctg     180
tatcttcaga tcacccacaa tggagtagta actggtaccg aagaaaagaa tgactatggt     240
gtgctggaaa taaaggcagt aaaagctggg gttgtagtta taaaggaat tcgaagcaat     300 ctctacctat gcatggattc tagacaccaa tttgtatgcgt cggcatatga taaagatgac     360 tgccattttcc atgaaaagat cacaccagat aattacaaca tgtatagctc agagaagcat     420
tcagaatacg tgtccttagc tccattaaaa ggaagccaga tggctcgttt tctacctata     480

<210> SEQ ID NO 323
<211> LENGTH: 585
<212> TYPE: DNA
<213> ORGANISM: Danio rerio

<400> SEQUENCE: 323
atgcttcttg cctgcttttt tatatttttt gctctttttc ctcatcttcg gtggtgtatg       60
tatgttcctg cacagaacgt gcttctgcag tttggcacac aagtcaggga acgcctgctt     120
tacacagatg ggttgtttct tgaaatgaat ccagatggct ccgtcaaagg ctctcctgaa     180
aagaatctaa attgtgtgct ggagctgcgt tcagtcaaag cgggtgaaac cgtcatccag     240
agtgcagcta catctctcta cctctgcgtc gatgatcaag acaagctgaa aggacagcat     300
```

```
cattactctg cactagactg caccttttcag gaattgctac tggatggata ttcgttttc      360 cttttctccac acactaatct tcccgtatcg ctcctctcga acgtcagaa acacggcaat      420 cctctttctc gcttcctccc tgttagcaga gcagaggaca gccggacaca ggaggtgaaa      480
cagtatattc aggatataaa cctggactct gacgacccac taggaatggg acatcggtca      540
cacttacaga ccgtcttcag tcccagtctg catactaaaa aatga                     585
```

<210> SEQ ID NO 324
<211> LENGTH: 630
<212> TYPE: DNA
<213> ORGANISM: Bos grunniens mutus

<400> SEQUENCE: 324

```
atgggctggg atgaagcgaa atttaaacat ctgggcctgt gggtgccggt gctggcggtg       60
ctgctgctgg gcacctgccg cgcgcatccg attccggata gcagcccgct gctgcagttt      120
ggcggccagg tgcgccagcg ctatctgtat accgatgatg cgcaggaaac cgaagcgcat      180
ctggaaattc gcgcggatgg caccgtggtg ggcgcggcgc gccagagccc ggaaagcctg      240
ctggaactga aagcgctgaa accgggcgtg attcagattc tgggcgtgaa aaccagccgc      300
tttctgtgcc agggcccgga tgcaaactg tatggcagcc tgcattttga tccgaaagcg      360
tgcagctttc gcgaactgct gctggaagat ggctataacg tgtatcagag cgaaaccctg      420
ggcctgccgc tgcgcctgcc gccgcagcgc agcagcaacc gcgatccggc cgcgcgggc      480 ccggcgcgct ttctgccgct gccgggcctg ccggcggaac cgccggatcc gccgggcatt      540
ctggcgccgg aaccgccgga tgtgggcagc agcgatccgc tgagcatggt gggcccgagc      600
tatggccgca gcccgagcta taccagctaa                                      630
```

<210> SEQ ID NO 325
<211> LENGTH: 630
<212> TYPE: DNA
<213> ORGANISM: Saimiri boliviensis boliviensis

<400> SEQUENCE: 325

```
atgggctcgg aggaggtcgc gttggagcgc cctgcactgt gggtctctgt gttggctggt       60
ctcctgctgg gaacctgcca ggcataccc atccctgact ctagtcccct cctgcaattt      120
ggaggccaag tccggcagcg gtacctctac acagatgacg ctcagcagac agaagcccac      180
ctggagatca gggaagatgg cacggtggcg ggggctgccc accagagccc gaaagtctc      240 ttgcagctga aagcctttaaa gccagggggtt attcaaatct tgggagtcaa gacctccagg      300
ttcctgtgcc agaggccgga cggggccctg tacggatcgc tctactttga ccccgaggcc      360
tgcagcttcc gggagctgct tcttgaggac ggatacaatg tgtaccagtc cgtgcccac      420 agcctcccgc tgcacctgcc aggggggcagg tccccaccct gggaccctgc acctcgagga      480
ccagctcgct tcctgccgct accaggcctg ccccccgaac cccccgaggc gccaggaatc      540
ctggcccccg agccccccga tgtgggctcc tcagaccctc tgagcatggt ggggccttcc      600
caaggccaaa gccccagcta cacttcctga                                      630
```

<210> SEQ ID NO 326
<211> LENGTH: 633
<212> TYPE: DNA
<213> ORGANISM: Callithrix jacchus
<220> FEATURE:
<221> NAME/KEY: misc_feature
<222> LOCATION: (190)..(190)

<223> OTHER INFORMATION: n is a, c, g, or t

<400> SEQUENCE: 326

| | |
|---|---|
| atgggctcgg aggaggtcgg gttggagcac cctgcactgt gggtttctgt gctggctggt | 60 |
| ctcctgctgg gaacctgcca ggcgcacccc atccctgact ccagtcccct cctgcaattt | 120 |
| ggaggccaag tccggcagcg gtacctctac acagatgacg cccagcagaa agaagcccac | 180 |
| ctggagatcn aggaagatgg cacagtggcc ggggctgcca ccaaagtccc gaaagtgagt | 240 |
| ctcttgcagc tgaaagcctt aaagccaggg gttattcaaa tcttgggagt caagacatcc | 300 |
| aggttcctgt gccagaggcc agacggggcg ctgtatggat cgctccactt tgaccccgag | 360 |
| gcctgcagct tccgggagct gcttcttgag gacggataca atgtgtacca gtctgtggcc | 420 |
| cacggcctcc cgctgcacct gccagagagc aggtcaccac cccgggaccc tgcaccccga | 480 |
| ggaccagctc gcttcctgcc actaccaggc ctgcccctg aaccccaga gccgccagga | 540 |
| atcctggccc ctgagccccc cgacgtgggc tcctcagacc ctctgagcat ggtggggcct | 600 |
| tcccaaggcc aaagccccag ctacgcttcc tga | 633 |

<210> SEQ ID NO 327
<211> LENGTH: 630
<212> TYPE: DNA
<213> ORGANISM: Tupaia chinensis

<400> SEQUENCE: 327

| | |
|---|---|
| atgggctggg ataaagcgcg ctttgaacat ctgggcgcgt gggcgccggt gctggcggtg | 60 |
| ctgctgctgg gcgcgtgcca ggcgtatccg attccggata gcagcccgct gctgcagttt | 120 |
| ggcggccagg tgcgccagcg ctatctgtat accgatgata cccaggatac cgaagcgcat | 180 |
| ctggaaattc gcgcggatgg caccgtggtg ggcgcggcgc atcagagccc ggaaagcctg | 240 |
| ctggaactga aagcgctgaa accgggcgtg attcagattc tgggcgtgaa aaccagccgc | 300 |
| tttctgtgcc agcgcccgga tggcgcgctg tatggcagcc tgcattttga tccggaagcg | 360 |
| tgcagctttc gcgaactgct gctggaagat ggctataaca tttatcagag cgaagcgcgc | 420 |
| ggcctgccgc tgcgcctgcc gccgcatgat agcccgcatc gcgatcgcac cccgcagggc | 480 |
| ccggcgcgct ttctgccgct gccgggcctg ccgctggtgc cgccggaact gccgggcgtg | 540 |
| ctggcgctgg aaccgccgga tgtgggcagc agcgatccgc tgagcatgat gggcccgagc | 600 |
| cagggccaga gcccgagcta tgcgagctaa | 630 |

<210> SEQ ID NO 328
<211> LENGTH: 567
<212> TYPE: DNA
<213> ORGANISM: Papio anubis

<400> SEQUENCE: 328

| | |
|---|---|
| atggactcgg acgagaccgg gttcgagcac tcaggactgt gggttcctgt gctggctggt | 60 |
| cttctgctgg gagcctgcca ggcacacccc atccctgact ccagtcctct cctgcaattc | 120 |
| gggggccaag tccggcaacg gtacctctac acagatgatg cccagcagac agaagcccac | 180 |
| ctggagatca ggaggatgg gacagtgggg ggcgctgctc accagagccc cgaaagtaag | 240 |
| tgtgggccag agcctgggtc tgagggagga ggggctctcc actttgaccc tgaggcctgc | 300 |
| agcttccgcg agctgcttct tgagaacgga tacaatgttt accagtccga ggcccacggc | 360 |
| ctcccactgc acctgccggg aaacaagtcc ccacaccggg accctgcatc ccgaggacca | 420 |
| gctcgcttcc tgccactacc aggcctgccc ccgcaccccc cagagccacc aggaatcctc | 480 |

```
gcccccagc cccccgatgt gggctcctcg gaccctctga gcatggtggg accttcccag    540
gcccgaagcc ctagctacgc ttcctga                                      567

<210> SEQ ID NO 329
<211> LENGTH: 627
<212> TYPE: DNA
<213> ORGANISM: Pteropus alecto

<400> SEQUENCE: 329
atgggctggg gcaaagcgcg cctgcagcat ccgggcctgt ggggcccggt gctggcggtg     60
ctgctgggcg cgtgccaggc gcatccgatt ctggatagca gcccgctgtt tcagtttggc    120
agccaggtgc gccgccgcta tctgtatacc gatgatgcgc aggataccga agcgcatctg    180
gaaattcgcg cggatggcac cgtggcgggc gcggcgcgcc gcagcccgga aagcctgctg    240
gaactgaaag cgctgaaacc gggcgtgatt caggtgctgg gcgtgaaaac cagccgcttt    300
ctgtgccagc gcccggatgg caccctgtat ggcagcctgc attttgatcc ggcggcgtgc    360
agctttcgcg aactgctgct gaaagatggc tataacgtgt atcagagcga agcgctggcg    420
cgcccgctgc gcctgccgcc gtatagcagc ccgagcagcg atccggcgcg ccgcggcccg    480
gcgcgctttc tgccgctgcc gggcccgccg ccggaaccgc cgcagccgcc gggccgcctg    540
gcgccggaac cgccggatgt gggcagcagc gatccgctga gcatggtgtg gccgagccgc    600
ggccgcagcc cgagctatac cagctaa                                      627

<210> SEQ ID NO 330
<211> LENGTH: 633
<212> TYPE: DNA
<213> ORGANISM: Heterocephalus glaber

<400> SEQUENCE: 330
atggattggg cgcgcgcgga aagcgaacgc ccgggcctgt gggtgccggc ggtgctggcg     60
gtgctgctgc tgggcgcgtg ccaggcgcat ccgattccgg atagcagccc gctgctgcag    120
tttggcggcc aggtgcgcca gcgccatctg tataccgatg atgcgcagga taccgaagtg    180
catctggaaa ttcgcgcgga tggcagcgtg ggcggcgcgc gcatcgcag cccggaaagc    240 ctgctggaac tgaaagcgct gaaaccgggc gtgattcaga ttctgggcgt gcgcaccagc    300
cgctttctgt gccagcgccc ggatggcacc ctgtatggca gcctgcattt tgatccggaa    360
gcgtgcagct ttcgcgaact gctgctggcg gatggctata acatttatca gagcgaagcg    420 tatgcctgc cgctgcgcat gctgccgagc gatagcgcga gcgcgatcc ggtgccgccg    480 ggcccggcgc gctttctgcc gctgccgggc ctgcatccgc cgccgctgga accgccgggc    540
atgctgccgc cggaaccgcc ggatgtgggc agcagcgatc cgctgagcat ggtgggcccg    600
ctgcagggcc gcagcccgag ctatgcgttt taa                               633

<210> SEQ ID NO 331
<211> LENGTH: 630
<212> TYPE: DNA
<213> ORGANISM: Cricetulus griseus

<400> SEQUENCE: 331
atggactgga tgaaatctgg agttgggggtc ccggactgt gggtccctct gctgcctatc     60
ttcctgctgg ggtctcccca ggcacacccc atccctgact ccagccccct cctccagttt    120
gggggtcaag tccggcacag gcacctctac acagatgaca accaggaaac tgaagtccac    180
```

```
ctggagatta ggcaggatgg cacggtgata gggaccacac accgcagccc agaaagtctc    240
ctggagctca aagccttgaa gccagaggtc atcccagtgc tgggtgtcaa ggcctccagg    300
tttctttgcc aacaaccaga cggaaccctg tatggatcgc ctcactttga tcctgaggcc    360
tgcagtttca gggagctctt gcttgaggat ggatacaatg tgtaccaatc tgaagtccat    420
ggcctgcccc tgcgcctgcc ccagagggac tctccaaacc aggcccagc atcctgggga     480 cctgtgcccc cctgccagt gccaggactg ctccaccagc cccaggagct accagggttc      540
ctggccccag aacctccaga tgtgggctcc tctgacccac tgagcatggt gggacctttg    600
cagggccgaa gccccagcta tgcttcctga                                      630
```

```
<210> SEQ ID NO 332
<211> LENGTH: 579
<212> TYPE: DNA
<213> ORGANISM: Ovis aries

<400> SEQUENCE: 332
atgggctggg acgaggccaa gttcaagcac ttgggactgt gggtccctgt gctggctgtc     60
ctcctgctag gaacctgccg ggcgcatcca attccagact ccagccccct cctccagttt   120
gggggccaag tccgccagcg gtacctctac acggatgatg cccaggagac agaggccac    180 ctggagatca gggccgatgg cacagtggtg ggggcggccc gccagagtcc cgaaagtctc   240
ttggagctga aagccctgaa gccaggagtc attcagatct tggagttaa acatccagg     300 ttcctgtgcc aggggccaga tgggaagctg tatggatcgc tgcactttga ccccaaagcc   360
tgcagcttcc gggagctgct tcttgaagat gggtacaatg tctaccagtc ggagaccctg    420
ggccttccac tccgcctgcc gccgcagcgc tcatccaacc gggacccggc ccgcggggga   480
cctccgaagc cccagctaca cttcttgaag acgtccgctg tgcagtactg gccacgttat    540
gagaaggtcc cagcttttct gcacccttc cccggctga                            579
```

```
<210> SEQ ID NO 333
<211> LENGTH: 405
<212> TYPE: DNA
<213> ORGANISM: Pan paniscus

<400> SEQUENCE: 333
atggactcgg acgagaccgg gttcgagcac tcaggactgt gggttctgt gctggctggt     60 cttctgctgg gagcctgcca ggcacacccc atccctgact ccagtcctct cctgcaattc   120
gggggccaag tccggcagcg gtacctctac acagatgatg cccagcagac agaagcccac    180
ctggagatca gggaggatgg gacggtgggg ggcgctgctg accagagccc cgaaagtctc    240
ctgcagctga aagccttgaa gccgggagtt attcaaatct tgggagtcaa gacatccagg    300
ttcctgtgcc agaggccaga tggggccctg tatggatcgg tgagtttcca ggaccctcct    360
caccacccac catgctcctc ctatatgtcg ccctcacagc ctggg                    405
```

```
<210> SEQ ID NO 334
<211> LENGTH: 351
<212> TYPE: DNA
<213> ORGANISM: Macaca fascicularis

<400> SEQUENCE: 334
atggatagcg atgaaaccgg cttttgaacat agcggcctgt gggtgccggt gctggcgggc     60
ctgctgctgg gcgcgtgcca ggcgcatccg attccggata gcagcccgct gctgcagttt   120
ggcggccagg tgcgccagcg ctatctgtat accgatgatg cgcagcagac cgaagcgcat    180
```
ctggaaattc gcgaagatgg caccgtgggc ggcgcggcgc atcagagccc ggaaagcctg    240
ctgcagctga aagcgctgaa accgggcgtg attcagattc tgggcgtgaa aaccagccgc    300
tttctgtgcc agaaaccgga tggcgcgctg tatggcagcg tgagctttta a            351

<210> SEQ ID NO 335
<211> LENGTH: 314
<212> TYPE: DNA
<213> ORGANISM: Mesocricetus auratus

<400> SEQUENCE: 335
ggtcatccaa atcctgggtg tcaaggctgc taggtttcct tgccagcaac cagacggaag     60
cctgtacgga tcgcctcact tcgatcccga ggcctgcagt ttccgggagc tcctgcttga    120
ggatggatac aatgtgtacc agtcggaagc ccacggcctg cccctgcgcc tgccccagag    180
ggacgctccg agccagcccc cagcatcctg ggaccggtg cgcttcctgc agtgcccgg     240 actgttccag ccgccccacg acctcccagg gcgcccggcc ccagagcctc cggacgtggg    300
ctcctccgac ccac                                                     314

<210> SEQ ID NO 336
<211> LENGTH: 456
<212> TYPE: DNA
<213> ORGANISM: Nile tilapia

<400> SEQUENCE: 336
atgtatttgc agatgaacat ggatgggaga gtcacaggaa gtgatgctca gacaccttac     60
agtttgatgc agctgaaatc agttaaacca ggccatgtaa tcattaaagg accatcatca    120
tctctttttc tctgtgtgga cagcgaaggc aatctgagag gcagagtca ctactcagaa    180 accagctgca ccttcagaga aatgctgctg gctgacggat acacccgttt catttcctca    240
caatatggat ttcccatgtc actggcatca agacattccc cagatcgaca cgcgcttccc    300
tttacgcggt tcctaccact gaggaataac ttgaaaacgg atagcgtatc agagcagctg    360
ccaaacaatc agagactctt caacgtggac tctgatgacc ttcttggaat gggtctaaat    420
tctatgggca gtcctcagtt ttctatggac aaataa                             456

<210> SEQ ID NO 337
<211> LENGTH: 216
<212> TYPE: PRT
<213> ORGANISM: Homo sapiens

<400> SEQUENCE: 337

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

```
Leu Gln Tyr Ser Glu Glu Asp Cys Ala Phe Glu Glu Ile Arg Pro
            115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
            195                 200                 205

Val Arg Ser Pro Ser Phe Glu Lys
    210                 215
```

<210> SEQ ID NO 338
<211> LENGTH: 651
<212> TYPE: DNA
<213> ORGANISM: Homo sapiens

<400> SEQUENCE: 338

```
atgcggagcg ggtgtgtggt ggtccacgta tggatcctgg ccggcctctg gctggccgtg      60
gccgggcgcc ccctcgcctt tcggacgcg gggccccacg tgcactacgg ctggggcgac     120
cccatccgcc tgcggcacct gtacacctcc ggcccccacg ggctctccag ctgcttcctg     180
cgcatccgtg ccgacggcgt cgtggactgc gcgcggggcc agagcgcgca cagtttgctg     240
gagatcaagg cagtcgctct gcggaccgtg gccatcaagg gcgtgcacag cgtgcggtac     300
ctctgcatgg gcgccgacgg caagatgcag gggctgcttc agtactcgga ggaagactgt     360
gctttcgagg aggagatccg cccagatggc tacaatgtgt accgatccga aagcaccgc     420 ctcccggtct ccctgagcag tgccaaacag cggcagctgt acaagaacag aggcttttctt     480 ccactctctc atttcctgcc catgctgccc atggtcccag aggagcctga ggacctcagg     540
ggccacttgg aatctgacat gttctctttcg cccctggaga ccgacagcat ggacccattt     600
gggcttgtca ccggactgga ggccgtgagg agtcccagct ttgagaagta a            651
```

<210> SEQ ID NO 339
<211> LENGTH: 192
<212> TYPE: PRT
<213> ORGANISM: Artificial
<220> FEATURE:
<223> OTHER INFORMATION: Chimeric protein

<400> SEQUENCE: 339

```
Met Ala Glu Gly Glu Ile Thr Thr Phe Thr Ala Leu Thr Glu Lys Phe
1               5                  10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95
```

```
Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Asp Gln
        115                 120                 125

Asn Gly Ser Cys Val Arg Gly Pro Arg Thr His Tyr Gly Gln Lys Ala
    130                 135                 140

Ile Leu Phe Leu Pro Leu Pro Gly Leu Pro Ala Leu Pro Glu Pro
145                 150                 155                 160

Pro Gly Ile Leu Ala Pro Gln Pro Pro Asp Val Gly Ser Ser Asp Pro
                165                 170                 175

Leu Ser Met Val Gly Pro Ser Gln Gly Arg Ser Pro Ser Tyr Ala Ser
            180                 185                 190

<210> SEQ ID NO 340
<211> LENGTH: 168
<212> TYPE: PRT
<213> ORGANISM: Artificial
<220> FEATURE:
<223> OTHER INFORMATION: Chimeric protein

<400> SEQUENCE: 340

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Asp Gln Asn Gly Ser Cys Val Arg Gly Pro
            100                 105                 110

Arg Thr His Tyr Gly Gln Lys Ala Ile Leu Phe Leu Pro Leu Pro Gly
        115                 120                 125

Leu Pro Pro Ala Leu Pro Glu Pro Pro Gly Ile Leu Ala Pro Gln Pro
    130                 135                 140

Pro Asp Val Gly Ser Ser Asp Pro Leu Ser Met Val Gly Pro Ser Gln
145                 150                 155                 160

Gly Arg Ser Pro Ser Tyr Ala Ser
                165

<210> SEQ ID NO 341
<211> LENGTH: 193
<212> TYPE: PRT
<213> ORGANISM: Artificial
<220> FEATURE:
<223> OTHER INFORMATION: Chimeric protein

<400> SEQUENCE: 341

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
```

```
                35                  40                  45
Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Asp
        115                 120                 125

Gln Thr Gly Gln Tyr Val Leu Gly Ser Lys Thr Gly Pro Gly Gln Lys
    130                 135                 140

Ala Ile Leu Phe Leu Pro Met Pro Gly Leu Pro Pro Ala Leu Pro Glu
145                 150                 155                 160

Pro Pro Gly Ile Leu Ala Pro Gln Pro Pro Asp Val Gly Ser Ser Asp
                165                 170                 175

Pro Leu Ser Met Val Gly Pro Ser Gln Gly Arg Ser Pro Ser Tyr Ala
            180                 185                 190

Ser
```

<210> SEQ ID NO 342
<211> LENGTH: 169
<212> TYPE: PRT
<213> ORGANISM: Artificial
<220> FEATURE:
<223> OTHER INFORMATION: Chimeric protein

<400> SEQUENCE: 342

```
His Phe Lys Asp Pro Lys Arg Leu Tyr Cys Lys Asn Gly Gly Phe Phe
 1               5                  10                  15

Leu Arg Ile His Pro Asp Gly Arg Val Asp Gly Val Arg Glu Lys Ser
                 20                  25                  30

Asp Pro His Ile Lys Leu Gln Leu Gln Ala Glu Glu Arg Gly Val Val
             35                  40                  45

Ser Ile Lys Gly Val Cys Ala Asn Arg Tyr Leu Ala Met Lys Glu Asp
 50                  55                  60

Gly Arg Leu Leu Ala Ser Lys Cys Val Thr Asp Glu Cys Phe Phe Phe
 65                  70                  75                  80

Glu Arg Leu Glu Ser Asn Asn Tyr Asn Thr Tyr Arg Ser Arg Lys Tyr
                 85                  90                  95

Thr Ser Trp Tyr Val Ala Leu Asp Gln Thr Gly Gln Tyr Val Leu Gly
            100                 105                 110

Ser Lys Thr Gly Pro Gly Gln Lys Ala Ile Leu Phe Leu Pro Met Pro
        115                 120                 125

Gly Leu Pro Pro Ala Leu Pro Glu Pro Pro Gly Ile Leu Ala Pro Gln
    130                 135                 140

Pro Pro Asp Val Gly Ser Ser Asp Pro Leu Ser Met Val Gly Pro Ser
145                 150                 155                 160

Gln Gly Arg Ser Pro Ser Tyr Ala Ser
                165
```

<210> SEQ ID NO 343
<211> LENGTH: 576
<212> TYPE: DNA
<213> ORGANISM: Artificial
<220> FEATURE:
<223> OTHER INFORMATION: Nucleic acid sequence encoding chimeric protein

<400> SEQUENCE: 343

| | | | | | |
|---|---|---|---|---|---|
| atggctgaag | ggaaatcac | caccttcaca | gccctgaccg | agaagtttaa | tctgcctcca | 60 |
| gggaattaca | agaagcccaa | actcctctac | tgtagcaacg | ggggccactt | cctgaggatc | 120 |
| cttccggatg | gcacagtgga | tgggacaagg | gacaggagcg | accagcacat | tcagctgcag | 180 |
| ctcagtgcgg | aaagcgtggg | ggaggtgtat | ataaagagta | ccgagactgg | ccagtacttg | 240 |
| gccatggaca | ccgacgggct | tttatacggc | tcacagacac | caaatgagga | atgtttgttc | 300 |
| ctggaaaggc | tggaggagaa | ccattacaac | acctatatat | ccaagaagca | tgcagagaag | 360 |
| aattggtttg | ttggcctcga | tcagaatggg | agctgcgttc | gcggtcctcg | gactcactat | 420 |
| ggccagaaag | caatcttgtt | tctcccctg | ccaggcctgc | ccccgcact | cccggagcca | 480 |
| cccggaatcc | tggcccccca | gcccccgat | gtgggctcct | cggaccctct | gagcatggtg | 540 |
| ggaccttccc | agggccgaag | ccccagctac | gcttcc | | | 576 |

<210> SEQ ID NO 344
<211> LENGTH: 504
<212> TYPE: DNA
<213> ORGANISM: Artificial
<220> FEATURE:
<223> OTHER INFORMATION: Nucleic acid sequence encoding chimeric protein

<400> SEQUENCE: 344

| | | | | | |
|---|---|---|---|---|---|
| aagcccaaac | tcctctactg | tagcaacggg | ggccacttcc | tgaggatcct | tccggatggc | 60 |
| acagtggatg | ggacaaggga | caggagcgac | cagcacattc | agctgcagct | cagtgcggaa | 120 |
| agcgtggggg | aggtgtatat | aaagagtacc | gagactggcc | agtacttggc | catggacacc | 180 |
| gacgggcttt | tatacggctc | acagacacca | aatgaggaat | gtttgttcct | ggaaaggctg | 240 |
| gaggagaacc | attacaacac | ctatatatcc | aagaagcatg | cagagaagaa | ttggtttgtt | 300 |
| ggcctcgatc | agaatgggag | ctgcgttcgc | ggtcctcgga | ctcactatgg | ccagaaagca | 360 |
| atcttgtttc | tccccctgcc | aggcctgccc | ccgcactcc | ggagccacc | cggaatcctg | 420 |
| gcccccagc | ccccgatgt | gggctcctcg | accctctga | gcatggtggg | accttcccag | 480 |
| ggccgaagcc | ccagctacgc | ttcc | | | | 504 |

<210> SEQ ID NO 345
<211> LENGTH: 579
<212> TYPE: DNA
<213> ORGANISM: Artificial
<220> FEATURE:
<223> OTHER INFORMATION: Nucleic acid sequence encoding chimeric protein

<400> SEQUENCE: 345

| | | | | | |
|---|---|---|---|---|---|
| atggcagccg | ggagcatcac | cacgctgccc | gccttgcccg | aggatggcgg | cagcggcgcc | 60 |
| ttcccgcccg | gccacttcaa | ggaccccaag | cggctgtact | gcaaaaacgg | ggcttcttc | 120 |
| ctgcgcatcc | accccgacgg | ccgagttgac | ggggtccggg | agaagagcga | ccctcacatc | 180 |
| aagctacaac | ttcaagcaga | gagagaggag | gttgtgtcta | tcaaaggagt | gtgtgctaac | 240 |
| cgttacctgg | ctatgaagga | agatggaaga | ttactggctt | ctaaatgtgt | acgatgagtg | 300 |
| tgtttctttt | ttgaacgatt | ggaatctaat | aactacaata | cttaccggtc | aaggaaatac | 360 |
| accagttggt | atgtggcact | ggatcagact | gggcagtatg | ttcttggatc | caaaacagga | 420 |
| cctgggcaga | aagctatact | ttttcttcca | atgccaggcc | tgcccccgc | actcccggag | 480 |

```
ccacccggaa tcctggcccc ccagcccccc gatgtgggct cctcggaccc tctgagcatg    540
gtgggacctt cccagggccg aagccccagc tacgcttcc                           579
```

<210> SEQ ID NO 346
<211> LENGTH: 507
<212> TYPE: DNA
<213> ORGANISM: Artificial
<220> FEATURE:
<223> OTHER INFORMATION: Nucleic acid sequence encoding chimeric protein

<400> SEQUENCE: 346

```
cacttcaagg accccaagcg gctgtactgc aaaaacgggg gcttcttcct gcgcatccac     60
cccgacggcc gagttgacgg ggtccgggag aagagcgacc ctcacatcaa gctacaactt    120
caagcagaag agagaggagt tgtgtctatc aaaggagtgt gtgctaaccg ttacctggct    180
atgaaggaag atggaagatt actggcttct aaatgtgtta cggatgagtg tttcttttt     240 gaacgattgg aatctaataa ctacaatact taccggtcaa ggaaatacac cagttggtat    300
gtggcactgg atcagactgg gcagtatgtt cttggatcca aaacaggacc tgggcagaaa    360
gctatacttt ttcttccaat gccaggcctg cccccgcac tcccggagcc acccggaatc     420
ctggcccccc agcccccga tgtgggctcc tcggaccctc tgagcatggt gggaccttcc     480
cagggccgaa gccccagcta cgcttcc                                         507
```

<210> SEQ ID NO 347
<211> LENGTH: 1044
<212> TYPE: PRT
<213> ORGANISM: Homo sapiens

<400> SEQUENCE: 347

```
Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly Phe Ser Gly Asp Gly Arg Ala Ile Trp Ser Lys Asn
    50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205
```

```
Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
        355                 360                 365

Phe Phe Ala Phe Ser Phe Gly Pro Asn Asn Phe Lys Pro Leu Asn Thr
370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser Arg Val Lys Thr Glu Asp Thr Thr Ala
            420                 425                 430

Ile Tyr Met Met Lys Asn Phe Leu Ser Gln Val Leu Gln Ala Ile Arg
        435                 440                 445

Leu Asp Glu Ile Arg Val Phe Gly Tyr Thr Ala Trp Ser Leu Leu Asp
450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
            500                 505                 510

Ser Thr Pro Asp Val Gln Gly Gln Phe Pro Cys Asp Phe Ser Trp Gly
        515                 520                 525

Val Thr Glu Ser Val Leu Lys Pro Glu Ser Val Ala Ser Ser Pro Gln
530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
        595                 600                 605

Thr Gly Asn Leu Ser Ala Val Asn Arg Gln Ala Leu Arg Tyr Tyr Arg
610                 615                 620

Cys Val Val Ser Glu Gly Leu Lys Leu Gly Ile Ser Ala Met Val Thr
```

-continued

```
             625                 630                 635                 640
Leu Tyr Tyr Pro Thr His Ala His Leu Gly Leu Pro Glu Pro Leu Leu
                 645                 650                 655
His Ala Asp Gly Trp Leu Asn Pro Ser Thr Ala Glu Ala Phe Gln Ala
                 660                 665                 670
Tyr Ala Gly Leu Cys Phe Gln Glu Leu Gly Asp Leu Val Lys Leu Trp
                 675                 680                 685
Ile Thr Ile Asn Glu Pro Asn Arg Leu Ser Asp Ile Tyr Asn Arg Ser
                 690                 695                 700
Gly Asn Asp Thr Tyr Gly Ala Ala His Asn Leu Leu Val Ala His Ala
705                 710                 715                 720
Leu Ala Trp Arg Leu Tyr Asp Arg Gln Phe Arg Pro Ser Gln Arg Gly
                 725                 730                 735
Ala Val Ser Leu Ser Leu His Ala Asp Trp Ala Glu Pro Ala Asn Pro
                 740                 745                 750
Tyr Ala Asp Ser His Trp Arg Ala Ala Glu Arg Phe Leu Gln Phe Glu
                 755                 760                 765
Ile Ala Trp Phe Ala Glu Pro Leu Phe Lys Thr Gly Asp Tyr Pro Ala
                 770                 775                 780
Ala Met Arg Glu Tyr Ile Ala Ser Lys His Arg Arg Gly Leu Ser Ser
785                 790                 795                 800
Ser Ala Leu Pro Arg Leu Thr Glu Ala Glu Arg Leu Leu Lys Gly
                 805                 810                 815
Thr Val Asp Phe Cys Ala Leu Asn His Phe Thr Thr Arg Phe Val Met
                 820                 825                 830
His Glu Gln Leu Ala Gly Ser Arg Tyr Asp Ser Asp Arg Asp Ile Gln
                 835                 840                 845
Phe Leu Gln Asp Ile Thr Arg Leu Ser Ser Pro Thr Arg Leu Ala Val
                 850                 855                 860
Ile Pro Trp Gly Val Arg Lys Leu Leu Arg Trp Val Arg Arg Asn Tyr
865                 870                 875                 880
Gly Asp Met Asp Ile Tyr Ile Thr Ala Ser Gly Ile Asp Asp Gln Ala
                 885                 890                 895
Leu Glu Asp Asp Arg Leu Arg Lys Tyr Tyr Leu Gly Lys Tyr Leu Gln
                 900                 905                 910
Glu Val Leu Lys Ala Tyr Leu Ile Asp Lys Val Arg Ile Lys Gly Tyr
                 915                 920                 925
Tyr Ala Phe Lys Leu Ala Glu Glu Lys Ser Lys Pro Arg Phe Gly Phe
                 930                 935                 940
Phe Thr Ser Asp Phe Lys Ala Lys Ser Ser Ile Gln Phe Tyr Asn Lys
945                 950                 955                 960
Val Ile Ser Ser Arg Gly Phe Pro Phe Glu Asn Ser Ser Arg Cys
                 965                 970                 975
Ser Gln Thr Gln Glu Asn Thr Glu Cys Thr Val Cys Leu Phe Leu Val
                 980                 985                 990
Gln Lys Lys Pro Leu Ile Phe Leu Gly Cys Cys Phe Phe Ser Thr Leu
                 995                 1000                1005
Val Leu Leu Leu Ser Ile Ala Ile Phe Gln Arg Gln Lys Arg Arg
                 1010                1015                1020
Lys Phe Trp Lys Ala Lys Asn Leu Gln His Ile Pro Leu Lys Lys
                 1025                1030                1035
Gly Lys Arg Val Val Ser
                 1040
```

<210> SEQ ID NO 348
<211> LENGTH: 1043
<212> TYPE: PRT
<213> ORGANISM: Mus musculus

<400> SEQUENCE: 348

```
Met Lys Thr Gly Cys Ala Ala Gly Ser Pro Gly Asn Glu Trp Ile Phe
1               5                   10                  15

Phe Ser Ser Asp Glu Arg Asn Thr Arg Ser Arg Lys Thr Met Ser Asn
            20                  25                  30

Arg Ala Leu Gln Arg Ser Ala Val Leu Ser Ala Phe Val Leu Leu Arg
        35                  40                  45

Ala Val Thr Gly Phe Ser Gly Asp Gly Lys Ala Ile Trp Asp Lys Lys
    50                  55                  60

Gln Tyr Val Ser Pro Val Asn Pro Ser Gln Leu Phe Leu Tyr Asp Thr
65                  70                  75                  80

Phe Pro Lys Asn Phe Ser Trp Gly Val Gly Thr Gly Ala Phe Gln Val
                85                  90                  95

Glu Gly Ser Trp Lys Thr Asp Gly Arg Gly Pro Ser Ile Trp Asp Arg
            100                 105                 110

Tyr Val Tyr Ser His Leu Arg Gly Val Asn Gly Thr Asp Arg Ser Thr
        115                 120                 125

Asp Ser Tyr Ile Phe Leu Glu Lys Asp Leu Leu Ala Leu Asp Phe Leu
    130                 135                 140

Gly Val Ser Phe Tyr Gln Phe Ser Ile Ser Trp Pro Arg Leu Phe Pro
145                 150                 155                 160

Asn Gly Thr Val Ala Ala Val Asn Ala Gln Gly Leu Arg Tyr Tyr Arg
                165                 170                 175

Ala Leu Leu Asp Ser Leu Val Leu Arg Asn Ile Glu Pro Ile Val Thr
            180                 185                 190

Leu Tyr His Trp Asp Leu Pro Leu Thr Leu Gln Glu Glu Tyr Gly Gly
        195                 200                 205

Trp Lys Asn Ala Thr Met Ile Asp Leu Phe Asn Asp Tyr Ala Thr Tyr
    210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Phe Gly Thr Gly Met His Ala
                245                 250                 255

Pro Gly Glu Lys Gly Asn Leu Thr Ala Val Tyr Thr Val Gly His Asn
            260                 265                 270

Leu Ile Lys Ala His Ser Lys Val Trp His Asn Tyr Asp Lys Asn Phe
        275                 280                 285

Arg Pro His Gln Lys Gly Trp Leu Ser Ile Thr Leu Gly Ser His Trp
    290                 295                 300

Ile Glu Pro Asn Arg Thr Asp Asn Met Glu Asp Val Ile Asn Cys Gln
305                 310                 315                 320

His Ser Met Ser Ser Val Leu Gly Trp Phe Ala Asn Pro Ile His Gly
                325                 330                 335

Asp Gly Asp Tyr Pro Glu Phe Met Lys Thr Gly Ala Met Ile Pro Glu
            340                 345                 350

Phe Ser Glu Ala Glu Lys Glu Glu Val Arg Gly Thr Ala Asp Phe Phe
        355                 360                 365

Ala Phe Ser Phe Gly Pro Asn Asn Phe Arg Pro Ser Asn Thr Val Val
```

```
              370                 375                 380
Lys Met Gly Gln Asn Val Ser Leu Asn Leu Arg Gln Val Leu Asn Trp
385                 390                 395                 400

Ile Lys Leu Glu Tyr Asp Asp Pro Gln Ile Leu Ile Ser Glu Asn Gly
                405                 410                 415

Trp Phe Thr Asp Ser Tyr Ile Lys Thr Glu Asp Thr Thr Ala Ile Tyr
                420                 425                 430

Met Met Lys Asn Phe Leu Asn Gln Val Leu Gln Ala Ile Lys Phe Asp
                435                 440                 445

Glu Ile Arg Val Phe Gly Tyr Thr Ala Trp Thr Leu Leu Asp Gly Phe
            450                 455                 460

Glu Trp Gln Asp Ala Tyr Thr Thr Arg Arg Gly Leu Phe Tyr Val Asp
465                 470                 475                 480

Phe Asn Ser Glu Gln Lys Glu Arg Lys Pro Lys Ser Ser Ala His Tyr
                485                 490                 495

Tyr Lys Gln Ile Ile Gln Asp Asn Gly Phe Pro Leu Lys Glu Ser Thr
                500                 505                 510

Pro Asp Met Lys Gly Arg Phe Pro Cys Asp Phe Ser Trp Gly Val Thr
                515                 520                 525

Glu Ser Val Leu Lys Pro Glu Phe Thr Val Ser Ser Pro Gln Phe Thr
            530                 535                 540

Asp Pro His Leu Tyr Val Trp Asn Val Thr Gly Asn Arg Leu Leu Tyr
545                 550                 555                 560

Arg Val Glu Gly Val Arg Leu Lys Thr Arg Pro Ser Gln Cys Thr Asp
                565                 570                 575

Tyr Val Ser Ile Lys Lys Arg Val Glu Met Leu Ala Lys Met Lys Val
                580                 585                 590

Thr His Tyr Gln Phe Ala Leu Asp Trp Thr Ser Ile Leu Pro Thr Gly
            595                 600                 605

Asn Leu Ser Lys Val Asn Arg Gln Val Leu Arg Tyr Tyr Arg Cys Val
610                 615                 620

Val Ser Glu Gly Leu Lys Leu Gly Val Phe Pro Met Val Thr Leu Tyr
625                 630                 635                 640

His Pro Thr His Ser His Leu Gly Leu Pro Leu Pro Leu Leu Ser Ser
                645                 650                 655

Gly Gly Trp Leu Asn Met Asn Thr Ala Lys Ala Phe Gln Asp Tyr Ala
                660                 665                 670

Glu Leu Cys Phe Arg Glu Leu Gly Asp Leu Val Lys Leu Trp Ile Thr
            675                 680                 685

Ile Asn Glu Pro Asn Arg Leu Ser Asp Met Tyr Asn Arg Thr Ser Asn
690                 695                 700

Asp Thr Tyr Arg Ala Ala His Asn Leu Met Ile Ala His Ala Gln Val
705                 710                 715                 720

Trp His Leu Tyr Asp Arg Gln Tyr Arg Pro Val Gln His Gly Ala Val
                725                 730                 735

Ser Leu Ser Leu His Cys Asp Trp Ala Glu Pro Ala Asn Pro Phe Val
                740                 745                 750

Asp Ser His Trp Lys Ala Ala Glu Arg Phe Leu Gln Phe Glu Ile Ala
            755                 760                 765

Trp Phe Ala Asp Pro Leu Phe Lys Thr Gly Asp Tyr Pro Ser Val Met
770                 775                 780

Lys Glu Tyr Ile Ala Ser Lys Asn Gln Arg Gly Leu Ser Ser Ser Val
785                 790                 795                 800
```

Leu Pro Arg Phe Thr Ala Lys Glu Ser Arg Leu Val Lys Gly Thr Val
            805                 810                 815

Asp Phe Tyr Ala Leu Asn His Phe Thr Thr Arg Phe Val Ile His Lys
            820                 825                 830

Gln Leu Asn Thr Asn Arg Ser Val Ala Asp Arg Asp Val Gln Phe Leu
            835                 840                 845

Gln Asp Ile Thr Arg Leu Ser Ser Pro Ser Arg Leu Ala Val Thr Pro
850                 855                 860

Trp Gly Val Arg Lys Leu Leu Ala Trp Ile Arg Arg Asn Tyr Arg Asp
865                 870                 875                 880

Arg Asp Ile Tyr Ile Thr Ala Asn Gly Ile Asp Leu Ala Leu Glu
            885                 890                 895

Asp Asp Gln Ile Arg Lys Tyr Tyr Leu Glu Lys Tyr Val Gln Glu Ala
            900                 905                 910

Leu Lys Ala Tyr Leu Ile Asp Lys Val Lys Ile Lys Gly Tyr Tyr Ala
            915                 920                 925

Phe Lys Leu Thr Glu Glu Lys Ser Lys Pro Arg Phe Gly Phe Phe Thr
    930                 935                 940

Ser Asp Phe Arg Ala Lys Ser Ser Val Gln Phe Tyr Ser Lys Leu Ile
945                 950                 955                 960

Ser Ser Ser Gly Leu Pro Ala Glu Asn Arg Ser Pro Ala Cys Gly Gln
            965                 970                 975

Pro Ala Glu Asp Thr Asp Cys Thr Ile Cys Ser Phe Leu Val Glu Lys
            980                 985                 990

Lys Pro Leu Ile Phe Phe Gly Cys Cys Phe Ile Ser Thr Leu Ala Val
    995                 1000                1005

Leu Leu Ser Ile Thr Val Phe His His Gln Lys Arg Arg Lys Phe
    1010                1015                1020

Gln Lys Ala Arg Asn Leu Gln Asn Ile Pro Leu Lys Lys Gly His
    1025                1030                1035

Ser Arg Val Phe Ser
    1040

<210> SEQ ID NO 349
<211> LENGTH: 3135
<212> TYPE: DNA
<213> ORGANISM: Homo sapiens

<400> SEQUENCE: 349
atgaagccag gctgtgcggc aggatctcca gggaatgaat ggattttctt cagcactgat     60
gaaataacca cacgctatag gaatacaatg tccaacgggg gattgcaaag atctgtcatc    120
ctgtcagcac ttattctgct acgagctgtt actggattct ctggagatgg aagagctata    180
tggtctaaaa atcctaattt tactccggta atgaaagtc agctgtttct ctatgacact    240
ttccctaaaa acttttttctg ggtattggga actggagcat tgcaagtgga agggagttgg    300
aagaaggatg gaaaaggacc ttctatatgg gatcatttca tccacacaca ccttaaaaat    360
gtcagcagca cgaatggttc cagtgacagt tatattttttc tggaaaaaga cttatcagcc    420
ctggatttta taggagtttc ttttttatcaa ttttcaattt cctggccaag gcttttcccc    480
gatggaatag taacagttgc caacgcaaaa ggtctgcagt actacagtac tcttctggac    540
gctctagtgc ttagaaacat tgaacctata gttactttat accactggga ttgcctttg    600 gcactacaag aaaaatatgg gggtggaaa atgatacca taatagatat cttcaatgac    660

```
tatgccacat actgtttcca gatgtttggg gaccgtgtca aatattggat tacaattcac    720
aacccatatc tagtggcttg gcatgggtat gggacaggta tgcatgcccc tggagagaag    780
ggaaatttag cagctgtcta cactgtggga cacaacttga tcaaggctca ctcgaaagtt    840
tggcataact acaacacaca tttccgccca catcagaagg gttggttatc gatcacgttg    900
ggatctcatt ggatcgagcc aaaccggtcg aaaacacga tggatatatt caaatgtcaa    960
caatccatgg tttctgtgct tggatggttt gccaacccta tccatgggga tggcgactat   1020
ccagagggga tgagaaagaa gttgttctcc gttctaccca ttttctctga agcagagaag   1080
catgagatga gaggcacagc tgatttcttt gccttttctt ttggacccaa caacttcaag   1140
cccctaaaca ccatggctaa aatgggacaa aatgtttcac ttaatttaag agaagcgctg   1200
aactggatta aactggaata caacaaccct cgaatcttga ttgctgagaa tggctggttc   1260
acagacagtc gtgtgaaaac agaagacacc acggccatct acatgatgaa gaatttcctc   1320
agccaggtgc ttcaagcaat aaggttagat gaaatacgag tgtttggtta tactgcctgg   1380
tctctcctgg atggctttga atggcaggat gcttacacca tccgccgagg attattttat   1440
gtggatttta acagtaaaca gaaagagcgg aaacctaagt cttcagcaca ctactacaaa   1500
cagatcatac gagaaaatgg ttttttcttta aaagagtcca cgccagatgt gcagggccag   1560
tttccctgtg acttctcctg gggtgtcact gaatctgttc ttaagcccga gtctgtggct   1620
tcgtccccac agttcagcga tcctcatctg tacgtgtgga acgccactgg caacagactg   1680
ttgcaccgag tggaagggggt gaggctgaaa acacgacccg ctcaatgcac agattttgta   1740
aacatcaaaa acaacttgaa gatgttggca agaatgaaag tcacccacta ccggtttgct   1800
ctggattggg cctcggtcct tcccactggc aacctgtccg cggtgaaccg acaggccctg   1860
aggtactaca ggtgcgtggt cagtgagggg ctgaagcttg gcatctccgc gatggtcacc   1920
ctgtattatc cgacccacgc ccacctaggc ctccccgagc ctctgttgca tgccgacggg   1980
tggctgaacc catcgacggc cgaggccttc caggcctacg ctgggctgtg cttccaggag   2040
ctgggggacc tggtgaagct ctggatcacc atcaacgagc ctaaccggct aagtgacatc   2100
tacaaccgct ctggcaacga cacctacggg gcggcgcaca acctgctggt ggcccacgcc   2160
ctggcctggc gcctctacga ccggcagttc aggccctcac agcgcggggc cgtgtcgctg   2220
tcgctgcacg cggactgggc ggaacccgcc aaccccatg ctgactcgca ctggagggcg   2280
gccgagcgct tcctgcagtt cgagatcgcc tggttcgccg agccgctctt caagaccggg   2340
gactaccccg cggccatgag ggaatacatt gcctccaagc accgacgggg gctttccagc   2400
tcggccctgc cgcgcctcac cgaggccgaa aggaggctgc tcaagggcac ggtcgacttc   2460
tgcgcgctca accacttcac cactaggttc gtgatgcacg agcagctggc cggcagccgc   2520
tacgactcgg acagggacat ccagtttctg caggacatca cccgcctgag ctcccccacg   2580
cgcctggctg tgattccctg gggggtgcgc aagctgctgc ggtgggtccg gaggaactac   2640
ggcgacatgg acatttacat caccgccagt ggcatcgacg accaggctct ggaggatgac   2700
cggctccgga gtactacct agggaagtac cttcaggagg tgctgaaagc atacctgatt   2760
gataaagtca gaatcaaagg ctattatgca ttcaaactgg ctgaagagaa atctaaaccc   2820
agatttggat tcttcacatc tgattttaaa gctaaatcct caatacaatt ttacaacaaa   2880
gtgatcagca gcaggggctt ccccttttgag aacagtagtt ctagatgcag tcagacccaa   2940
gaaaatacag agtgcactgt ctgcttattc cttgtgcaga agaaaccact gatattcctg   3000
ggttgttgct tcttctccac cctggttcta ctcttatcaa ttgccatttt tcaaaggcag   3060
```
aagagaagaa agttttggaa agcaaaaaac ttacaacaca taccattaaa gaaaggcaag    3120
agagttgtta gctaa    3135

<210> SEQ ID NO 350
<211> LENGTH: 3132
<212> TYPE: DNA
<213> ORGANISM: House mouse

<400> SEQUENCE: 350
atgaagacag ctgtgcagc agggtctccg gggaatgaat ggattttctt cagctctgat      60
gaaagaaaca cacgctctag gaaaacaatg tccaacaggg cactgcaaag atctgccgtg     120
ctgtctgcgt tgttctgct gcgagctgtt accggcttct ccggagacgg gaaagcaata     180
tgggataaaa aacagtacgt gagtccggta aacccaagtc agctgttcct ctatgacact     240
ttccctaaaa acttttcctg gggcgttggg accggagcat tcaagtggaa agggagttgg     300
aagacagatg gaagaggacc ctcgatctgg gatcggtacg tctactcaca cctgagaggt     360
gtcaacggca cagacagatc cactgacagt tacatctttc tggaaaaaga cttgttggct     420
ctggattttt taggagtttc tttttatcag ttctcaatct cctggccacg gttgtttccc     480
aatggaacag tagcagcagt gaatgcgcaa ggtctccggt actaccgtgc acttctggac     540
tcgctggtac ttaggaatat cgagcccatt gttaccttgt accattggga tttgcctctg     600
acgctccagg aagaatatgg gggctggaaa aatgcaacta tgatagatct cttcaacgac     660
tatgccacat actgcttcca gacctttgga gaccgtgtca atattggat tacaattcac     720 aacccttacc ttgttgcttg gcatgggttt ggcacaggta tgcatgcacc aggagagaag     780
ggaaatttaa cagctgtcta cactgtggga cacaacctga tcaaggcaca ttcgaaagtg     840
tggcataact acgacaaaaa cttccgccct catcagaagg gttggctctc catcaccttg     900
gggtcccatt ggatagagcc aaacagaaca gacaacatgg aggacgtgat caactgccag     960
cactccatgt cctctgtgct tggatggttc gccaaccca tccacgggga cggcgactac    1020
cctgagttca tgaagacggg cgccatgatc cccgagttct ctgaggcaga aaggaggag    1080 gtgaggggca cggctgattt ctttgccttt tccttcgggc caacaacttt caggccctca    1140
aacaccgtgg tgaaaatggg acaaaatgta tcactcaact taaggcaggt gctgaactgg    1200
attaaactgg aatacgatga ccctcaaatc ttgatttcgg agaacggctg gttcacagat    1260
agctatataa agacagagga caccacggcc atctacatga tgaagaattt cctaaaccag    1320
gttcttcaag caataaaatt tgatgaaatc cgcgtgtttg ttatacggc ctggactctc    1380 ctggatggct ttgagtggca ggatgcctat acgacccgac gagggctgtt ttatgtggac    1440
tttaacagtg agcagaaaga gaggaaaccc aagtcctcgg ctcattacta caagcagatc    1500
atacaagaca acggcttccc tttgaaagag tccacgccag acatgaaggg tcggttcccc    1560
tgtgatttct cttggggagt cactgagtct gttcttaagc ccgagtttac ggtctcctcc    1620
ccgcagttta ccgatcctca cctgtatgtg tggaatgtca ctggcaacag attgctctac    1680
cgagtggaag gggtaaggct gaaaacaaga ccatcccagt gcacagatta tgtgagcatc    1740
aaaaaacgag ttgaaatgtt ggcaaaaatg aaagtcaccc actaccagtt tgctctggac    1800
tggacctcta tccttcccac tggcaatctg tccaaagtta acagacaagt gttaaggtac    1860
tataggtgtg tggtgagcga aggactgaag ctgggcgtct tccccatggt gacgttgtac    1920
cacccaaccc actcccatct cggcctcccc ctgccacttc tgagcagtgg ggggtggcta    1980

```
aacatgaaca cagccaaggc cttccaggac tacgctgagc tgtgcttccg ggagttgggg    2040
gacttggtga agctctggat caccatcaat gagcctaaca ggctgagtga catgtacaac    2100
cgcacgagta atgacaccta ccgtgcagcc cacaacctga tgatcgccca tgcccaggtc    2160
tggcacctct atgataggca gtataggccg gtccagcatg gggctgtgtc gctgtcctta    2220
cattgcgact gggcagaacc tgccaacccc tttgtggatt cacactggaa ggcagccgag    2280
cgcttcctcc agtttgagat cgcctggttt gcagatccgc tcttcaagac tggcgactat    2340
ccatcggtta tgaaggaata catcgcctcc aagaaccagc gagggctgtc tagctcagtc    2400
ctgccgcgct tcaccgcgaa ggagagcagg ctggtgaagg gtaccgtcga cttctacgca    2460
ctgaaccact tcactacgag gttcgtgata cacaagcagc tgaacaccaa ccgctcagtt    2520
gcagacaggg acgtccagtt cctgcaggac atcacccgcc taagctcgcc cagccgcctg    2580
gctgtaacac cctggggagt gcgcaagctc cttgcgtgga tccggaggaa ctacagagac    2640
agggatatct acatcacagc caatggcatc gatgacctgg ctctagagga tgatcagatc    2700
cgaaagtact acttggagaa gtatgtccag gaggctctga agcatatctc cattgacaag    2760
gtcaaaatca aaggctacta tgcattcaaa ctgactgaag agaaatctaa gcctagattt    2820
ggatttttca cctctgactt cagagctaag tcctctgtcc agttttacag caagctgatc    2880
agcagcagtg gcctccccgc tgagaacaga agtcctgcgt gtggtcagcc tgcggaagac    2940
acagactgca ccatttgctc atttctcgtg gagaagaaac cactcatctt cttcggttgc    3000
tgcttcatct ccactctggc tgtactgcta tccatcaccg tttttcatca tcaaaagaga    3060
agaaaattcc agaaagcaag gaacttacaa aatataccat tgaagaaagg ccacagcaga    3120
gttttcagct aa                                                       3132
```

<210> SEQ ID NO 351
<211> LENGTH: 251
<212> TYPE: PRT
<213> ORGANISM: Homo sapiens

<400> SEQUENCE: 351

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
        50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
```

165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 352
<211> LENGTH: 42
<212> TYPE: PRT
<213> ORGANISM: Artificial
<220> FEATURE:
<223> OTHER INFORMATION: FGF21 variant

<400> SEQUENCE: 352

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Lys
        35                  40

<210> SEQ ID NO 353
<211> LENGTH: 42
<212> TYPE: PRT
<213> ORGANISM: Artificial
<220> FEATURE:
<223> OTHER INFORMATION: FGF21 variant

<400> SEQUENCE: 353

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Glu Ser
        35                  40

<210> SEQ ID NO 354
<211> LENGTH: 42
<212> TYPE: PRT
<213> ORGANISM: Artificial
<220> FEATURE:
<223> OTHER INFORMATION: FGF21 variant

<400> SEQUENCE: 354

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Phe Ala Ser
        35                  40

<210> SEQ ID NO 355
<211> LENGTH: 42
<212> TYPE: PRT
<213> ORGANISM: Artificial

<220> FEATURE:
<223> OTHER INFORMATION: FGF21 variant

<400> SEQUENCE: 355

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Val Arg Ser Pro Ser Tyr Ala Ser
        35                  40

<210> SEQ ID NO 356
<211> LENGTH: 42
<212> TYPE: PRT
<213> ORGANISM: Artificial
<220> FEATURE:
<223> OTHER INFORMATION: FGF21 variant

<400> SEQUENCE: 356

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Ala Gly Arg Ser Pro Ser Tyr Ala Ser
        35                  40

<210> SEQ ID NO 357
<211> LENGTH: 42
<212> TYPE: PRT
<213> ORGANISM: Artificial
<220> FEATURE:
<223> OTHER INFORMATION: FGF21 variant

<400> SEQUENCE: 357

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Glu Gln Gly Arg Ser Pro Ser Tyr Ala Ser
        35                  40

<210> SEQ ID NO 358
<211> LENGTH: 42
<212> TYPE: PRT
<213> ORGANISM: Artificial
<220> FEATURE:
<223> OTHER INFORMATION: FGF21 variant

<400> SEQUENCE: 358

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Leu
            20                  25                  30

Ser Gln Gly Arg Ser Pro Ser Tyr Ala Ser
        35                  40

<210> SEQ ID NO 359
<211> LENGTH: 43
<212> TYPE: PRT
<213> ORGANISM: Artificial
<220> FEATURE:
<223> OTHER INFORMATION: FGF21 variant

```
<400> SEQUENCE: 359

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Thr Gly
            20                  25                  30

Pro Ser Gln Gly Arg Ser Pro Ser Tyr Ala Ser
        35                  40

<210> SEQ ID NO 360
<211> LENGTH: 42
<212> TYPE: PRT
<213> ORGANISM: Artificial
<220> FEATURE:
<223> OTHER INFORMATION: FGF21 variant

<400> SEQUENCE: 360

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Leu Val Gly Pro
            20                  25                  30

Ser Gln Gly Arg Ser Pro Ser Tyr Ala Ser
        35                  40

<210> SEQ ID NO 361
<211> LENGTH: 42
<212> TYPE: PRT
<213> ORGANISM: Artificial
<220> FEATURE:
<223> OTHER INFORMATION: FGF21 variant

<400> SEQUENCE: 361

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Gly Met Val Gly Pro
            20                  25                  30

Ser Gln Gly Arg Ser Pro Ser Tyr Ala Ser
        35                  40

<210> SEQ ID NO 362
<211> LENGTH: 42
<212> TYPE: PRT
<213> ORGANISM: Artificial
<220> FEATURE:
<223> OTHER INFORMATION: FGF21 variant

<400> SEQUENCE: 362

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Phe Ser Met Val Gly Pro
            20                  25                  30

Ser Gln Gly Arg Ser Pro Ser Tyr Ala Ser
        35                  40

<210> SEQ ID NO 363
<211> LENGTH: 42
<212> TYPE: PRT
<213> ORGANISM: Artificial
<220> FEATURE:
<223> OTHER INFORMATION: FGF21 variant

<400> SEQUENCE: 363

Pro Gly Leu Pro Pro Ala Leu Pro Glu Pro Pro Gly Ile Leu Ala Pro
```

```
1               5                   10                  15
Gln Pro Pro Asp Val Gly Ser Met Asp Pro Leu Ser Met Val Gly Pro
            20                  25                  30

Ser Gln Gly Arg Ser Pro Ser Tyr Ala Ser
            35                  40

<210> SEQ ID NO 364
<211> LENGTH: 42
<212> TYPE: PRT
<213> ORGANISM: Artificial
<220> FEATURE:
<223> OTHER INFORMATION: FGF21 variant

<400> SEQUENCE: 364

Pro Gly Leu Pro Pro Ala Leu Pro Glu Pro Pro Gly Ile Leu Ala Pro
1               5                   10                  15

Gln Pro Pro Asp Val Asp Ser Ser Asp Pro Leu Ser Met Val Gly Pro
            20                  25                  30

Ser Gln Gly Arg Ser Pro Ser Tyr Ala Ser
            35                  40

<210> SEQ ID NO 365
<211> LENGTH: 42
<212> TYPE: PRT
<213> ORGANISM: Artificial
<220> FEATURE:
<223> OTHER INFORMATION: FGF21 variant

<400> SEQUENCE: 365

Pro Gly Leu Pro Pro Ala Leu Pro Glu Pro Pro Gly Ile Leu Ala Pro
1               5                   10                  15

Gln Pro Pro Asp Thr Gly Ser Ser Asp Pro Leu Ser Met Val Gly Pro
            20                  25                  30

Ser Gln Gly Arg Ser Pro Ser Tyr Ala Ser
            35                  40

<210> SEQ ID NO 366
<211> LENGTH: 42
<212> TYPE: PRT
<213> ORGANISM: Artificial
<220> FEATURE:
<223> OTHER INFORMATION: FGF21 variant

<400> SEQUENCE: 366

Pro Gly Leu Pro Pro Ala Leu Pro Glu Pro Pro Gly Ile Leu Ala Pro
1               5                   10                  15

Gln Pro Pro Glu Val Gly Ser Ser Asp Pro Leu Ser Met Val Gly Pro
            20                  25                  30

Ser Gln Gly Arg Ser Pro Ser Tyr Ala Ser
            35                  40

<210> SEQ ID NO 367
<211> LENGTH: 42
<212> TYPE: PRT
<213> ORGANISM: Artificial
<220> FEATURE:
<223> OTHER INFORMATION: FGF21 variant

<400> SEQUENCE: 367

Pro Gly Leu Pro Pro Ala Leu Pro Glu Pro Pro Gly Ile Leu Ala Pro
1               5                   10                  15

Gln Pro Leu Asp Val Gly Ser Ser Asp Pro Leu Ser Met Val Gly Pro
```

-continued 20                  25                  30

Ser Gln Gly Arg Ser Pro Ser Tyr Ala Ser
        35                  40

<210> SEQ ID NO 368
<211> LENGTH: 42
<212> TYPE: PRT
<213> ORGANISM: Artificial
<220> FEATURE:
<223> OTHER INFORMATION: FGF21 variant

<400> SEQUENCE: 368

Pro Gly Leu Pro Pro Ala Leu Pro Glu Pro Pro Gly Ile Leu Ala Pro
1               5                   10                  15

Ser Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 369
<211> LENGTH: 42
<212> TYPE: PRT
<213> ORGANISM: Artificial
<220> FEATURE:
<223> OTHER INFORMATION: FGF21 variant

<400> SEQUENCE: 369

Pro Gly Leu Pro Pro Ala Leu Pro Glu Pro Pro Gly Ile Leu Ala Ser
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 370
<211> LENGTH: 42
<212> TYPE: PRT
<213> ORGANISM: Artificial
<220> FEATURE:
<223> OTHER INFORMATION: FGF21 variant

<400> SEQUENCE: 370

Pro Gly Leu Pro Pro Ala Leu Pro Glu Pro Pro Gly Ile Leu Phe Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 371
<211> LENGTH: 42
<212> TYPE: PRT
<213> ORGANISM: Artificial
<220> FEATURE:
<223> OTHER INFORMATION: FGF21 variant

<400> SEQUENCE: 371

Pro Gly Leu Pro Pro Ala Leu Pro Glu Pro Pro Gly Ile Met Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser

```
                35                  40

<210> SEQ ID NO 372
<211> LENGTH: 42
<212> TYPE: PRT
<213> ORGANISM: Artificial
<220> FEATURE:
<223> OTHER INFORMATION: FGF21 variant

<400> SEQUENCE: 372

Pro Gly Leu Pro Pro Ala Leu Pro Glu Pro Pro Gly Asp Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 373
<211> LENGTH: 42
<212> TYPE: PRT
<213> ORGANISM: Artificial
<220> FEATURE:
<223> OTHER INFORMATION: FGF21 variant

<400> SEQUENCE: 373

Pro Gly Leu Pro Pro Ala Leu Pro Glu Pro Pro Ser Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 374
<211> LENGTH: 42
<212> TYPE: PRT
<213> ORGANISM: Artificial
<220> FEATURE:
<223> OTHER INFORMATION: FGF21 variant

<400> SEQUENCE: 374

Pro Gly Leu Pro Pro Ala Leu Pro Glu Pro Glu Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 375
<211> LENGTH: 42
<212> TYPE: PRT
<213> ORGANISM: Artificial
<220> FEATURE:
<223> OTHER INFORMATION: FGF21 variant

<400> SEQUENCE: 375

Pro Gly Leu Pro Pro Ala Leu Pro Glu Leu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40
```

-continued

```
<210> SEQ ID NO 376
<211> LENGTH: 43
<212> TYPE: PRT
<213> ORGANISM: Artificial
<220> FEATURE:
<223> OTHER INFORMATION: FGF21 variant

<400> SEQUENCE: 376

Pro Gly Leu Pro Pro Ala Leu Pro Glu His Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40

<210> SEQ ID NO 377
<211> LENGTH: 43
<212> TYPE: PRT
<213> ORGANISM: Artificial
<220> FEATURE:
<223> OTHER INFORMATION: FGF21 variant

<400> SEQUENCE: 377

Pro Gly Leu Pro Pro Ala Leu Pro Glu Gly Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40

<210> SEQ ID NO 378
<211> LENGTH: 43
<212> TYPE: PRT
<213> ORGANISM: Artificial
<220> FEATURE:
<223> OTHER INFORMATION: FGF21 variant

<400> SEQUENCE: 378

Pro Gly Leu Pro Pro Ala Leu Pro Glu Arg Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40

<210> SEQ ID NO 379
<211> LENGTH: 43
<212> TYPE: PRT
<213> ORGANISM: Artificial
<220> FEATURE:
<223> OTHER INFORMATION: FGF21 variant

<400> SEQUENCE: 379

Pro Gly Leu Pro Pro Ala Leu Pro Glu Leu Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40

<210> SEQ ID NO 380
<211> LENGTH: 43
<212> TYPE: PRT
```

<213> ORGANISM: Artificial
<220> FEATURE:
<223> OTHER INFORMATION: FGF21 variant

<400> SEQUENCE: 380

Pro Gly Leu Pro Pro Ala Leu Pro Glu Asp Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40

<210> SEQ ID NO 381
<211> LENGTH: 42
<212> TYPE: PRT
<213> ORGANISM: Artificial
<220> FEATURE:
<223> OTHER INFORMATION: FGF21 variant

<400> SEQUENCE: 381

Pro Gly Leu Pro Pro Ala Glu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 382
<211> LENGTH: 42
<212> TYPE: PRT
<213> ORGANISM: Artificial
<220> FEATURE:
<223> OTHER INFORMATION: FGF21 variant

<400> SEQUENCE: 382

Pro Gly Leu Pro Pro Glu Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 383
<211> LENGTH: 42
<212> TYPE: PRT
<213> ORGANISM: Artificial
<220> FEATURE:
<223> OTHER INFORMATION: FGF21 variant

<400> SEQUENCE: 383

Pro Gly Leu Val Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 384
<211> LENGTH: 42
<212> TYPE: PRT
<213> ORGANISM: Artificial
<220> FEATURE:
<223> OTHER INFORMATION: FGF21 variant

<400> SEQUENCE: 384

Pro Gly Met Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 385
<211> LENGTH: 42
<212> TYPE: PRT
<213> ORGANISM: Artificial
<220> FEATURE:
<223> OTHER INFORMATION: FGF21 variant

<400> SEQUENCE: 385

Pro Pro Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 386
<211> LENGTH: 42
<212> TYPE: PRT
<213> ORGANISM: Artificial
<220> FEATURE:
<223> OTHER INFORMATION: FGF21 variant

<400> SEQUENCE: 386

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Glu Lys
        35                  40

<210> SEQ ID NO 387
<211> LENGTH: 42
<212> TYPE: PRT
<213> ORGANISM: Artificial
<220> FEATURE:
<223> OTHER INFORMATION: FGF21 variant

<400> SEQUENCE: 387

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Phe Glu Lys
        35                  40

<210> SEQ ID NO 388
<211> LENGTH: 42
<212> TYPE: PRT
<213> ORGANISM: Artificial
<220> FEATURE:
<223> OTHER INFORMATION: FGF21 variant

<400> SEQUENCE: 388

-continued

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Val Arg Ser Pro Ser Phe Glu Lys
        35                  40

<210> SEQ ID NO 389
<211> LENGTH: 42
<212> TYPE: PRT
<213> ORGANISM: Artificial
<220> FEATURE:
<223> OTHER INFORMATION: FGF21 variant

<400> SEQUENCE: 389

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Ala Val Arg Ser Pro Ser Phe Glu Lys
        35                  40

<210> SEQ ID NO 390
<211> LENGTH: 42
<212> TYPE: PRT
<213> ORGANISM: Artificial
<220> FEATURE:
<223> OTHER INFORMATION: FGF21 variant

<400> SEQUENCE: 390

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Glu Ala Val Arg Ser Pro Ser Phe Glu Lys
        35                  40

<210> SEQ ID NO 391
<211> LENGTH: 42
<212> TYPE: PRT
<213> ORGANISM: Artificial
<220> FEATURE:
<223> OTHER INFORMATION: FGF21 variant

<400> SEQUENCE: 391

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Leu
            20                  25                  30

Glu Ala Val Arg Ser Pro Ser Phe Glu Lys
        35                  40

<210> SEQ ID NO 392
<211> LENGTH: 42
<212> TYPE: PRT
<213> ORGANISM: Artificial
<220> FEATURE:
<223> OTHER INFORMATION: FGF21 variant

<400> SEQUENCE: 392

Pro Gly Leu Pro Pro Ala Leu Pro Glu Pro Pro Gly Ile Leu Ala Pro
1               5                   10                  15

-continued

```
Gln Pro Pro Asp Val Gly Ser Ser Asp Pro Leu Ser Met Val Thr Gly
            20                  25                  30

Leu Glu Ala Val Arg Ser Pro Phe Glu Lys
        35                  40

<210> SEQ ID NO 393
<211> LENGTH: 43
<212> TYPE: PRT
<213> ORGANISM: Artificial
<220> FEATURE:
<223> OTHER INFORMATION: FGF21 variant

<400> SEQUENCE: 393

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Leu Val Thr Gly
            20                  25                  30

Leu Glu Ala Val Arg Ser Pro Ser Phe Glu Lys
        35                  40

<210> SEQ ID NO 394
<211> LENGTH: 43
<212> TYPE: PRT
<213> ORGANISM: Artificial
<220> FEATURE:
<223> OTHER INFORMATION: FGF21 variant

<400> SEQUENCE: 394

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Gly Leu Val Thr Gly
            20                  25                  30

Leu Glu Ala Val Arg Ser Pro Ser Phe Glu Lys
        35                  40

<210> SEQ ID NO 395
<211> LENGTH: 43
<212> TYPE: PRT
<213> ORGANISM: Artificial
<220> FEATURE:
<223> OTHER INFORMATION: FGF21 variant

<400> SEQUENCE: 395

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Phe Gly Leu Val Thr Gly
            20                  25                  30

Leu Glu Ala Val Arg Ser Pro Ser Phe Glu Lys
        35                  40

<210> SEQ ID NO 396
<211> LENGTH: 43
<212> TYPE: PRT
<213> ORGANISM: Artificial
<220> FEATURE:
<223> OTHER INFORMATION: FGF21 variant

<400> SEQUENCE: 396

Pro Gly Leu Pro Pro Ala Leu Pro Glu Pro Pro Gly Ile Leu Ala Pro
1               5                   10                  15

Gln Pro Pro Asp Val Gly Ser Met Asp Pro Phe Gly Leu Val Thr Gly
            20                  25                  30
```

Leu Glu Ala Val Arg Ser Pro Ser Phe Glu Lys
        35                  40

<210> SEQ ID NO 397
<211> LENGTH: 43
<212> TYPE: PRT
<213> ORGANISM: Artificial
<220> FEATURE:
<223> OTHER INFORMATION: FGF21 variant

<400> SEQUENCE: 397

Pro Gly Leu Pro Pro Ala Leu Pro Glu Pro Pro Gly Ile Leu Ala Pro
1               5                   10                  15

Gln Pro Pro Asp Val Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 398
<211> LENGTH: 43
<212> TYPE: PRT
<213> ORGANISM: Artificial
<220> FEATURE:
<223> OTHER INFORMATION: FGF21 variant

<400> SEQUENCE: 398

Pro Gly Leu Pro Pro Ala Leu Pro Glu Pro Pro Gly Ile Leu Ala Pro
1               5                   10                  15

Gln Pro Pro Asp Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 399
<211> LENGTH: 43
<212> TYPE: PRT
<213> ORGANISM: Artificial
<220> FEATURE:
<223> OTHER INFORMATION: FGF21 variant

<400> SEQUENCE: 399

Pro Gly Leu Pro Pro Ala Leu Pro Glu Pro Pro Gly Ile Leu Ala Pro
1               5                   10                  15

Gln Pro Pro Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 400
<211> LENGTH: 43
<212> TYPE: PRT
<213> ORGANISM: Artificial
<220> FEATURE:
<223> OTHER INFORMATION: FGF21 variant

<400> SEQUENCE: 400

Pro Gly Leu Pro Pro Ala Leu Pro Glu Pro Pro Gly Ile Leu Ala Pro
1               5                   10                  15

Gln Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 401
<211> LENGTH: 43
<212> TYPE: PRT
<213> ORGANISM: Artificial
<220> FEATURE:
<223> OTHER INFORMATION: FGF21 variant

<400> SEQUENCE: 401

Pro Gly Leu Pro Pro Ala Leu Pro Glu Pro Pro Gly Ile Leu Ala Pro
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 402
<211> LENGTH: 43
<212> TYPE: PRT
<213> ORGANISM: Artificial
<220> FEATURE:
<223> OTHER INFORMATION: FGF21 variant

<400> SEQUENCE: 402

Pro Gly Leu Pro Pro Ala Leu Pro Glu Pro Pro Gly Ile Leu Ala Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 403
<211> LENGTH: 43
<212> TYPE: PRT
<213> ORGANISM: Artificial
<220> FEATURE:
<223> OTHER INFORMATION: FGF21 variant

<400> SEQUENCE: 403

Pro Gly Leu Pro Pro Ala Leu Pro Glu Pro Pro Gly Ile Leu Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 404
<211> LENGTH: 43
<212> TYPE: PRT
<213> ORGANISM: Artificial
<220> FEATURE:
<223> OTHER INFORMATION: FGF21 variant

<400> SEQUENCE: 404

Pro Gly Leu Pro Pro Ala Leu Pro Glu Pro Pro Gly Ile Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 405
<211> LENGTH: 43

```
<212> TYPE: PRT
<213> ORGANISM: Artificial
<220> FEATURE:
<223> OTHER INFORMATION: FGF21 variant

<400> SEQUENCE: 405

Pro Gly Leu Pro Pro Ala Leu Pro Glu Pro Pro Gly Asp Met Phe Ser
1               5                   10                  15

Ser Pro Leu Glu Thr Asp Ser Met Asp Pro Phe Gly Leu Val Thr Gly
                20                  25                  30

Leu Glu Ala Val Arg Ser Pro Ser Phe Glu Lys
            35                  40

<210> SEQ ID NO 406
<211> LENGTH: 43
<212> TYPE: PRT
<213> ORGANISM: Artificial
<220> FEATURE:
<223> OTHER INFORMATION: FGF21 variant

<400> SEQUENCE: 406

Pro Gly Leu Pro Pro Ala Leu Pro Glu Pro Pro Ser Asp Met Phe Ser
1               5                   10                  15

Ser Pro Leu Glu Thr Asp Ser Met Asp Pro Phe Gly Leu Val Thr Gly
                20                  25                  30

Leu Glu Ala Val Arg Ser Pro Ser Phe Glu Lys
            35                  40

<210> SEQ ID NO 407
<211> LENGTH: 43
<212> TYPE: PRT
<213> ORGANISM: Artificial
<220> FEATURE:
<223> OTHER INFORMATION: FGF21 variant

<400> SEQUENCE: 407

Pro Gly Leu Pro Pro Ala Leu Pro Glu Pro Ser Asp Met Phe Ser
1               5                   10                  15

Ser Pro Leu Glu Thr Asp Ser Met Asp Pro Phe Gly Leu Val Thr Gly
                20                  25                  30

Leu Glu Ala Val Arg Ser Pro Ser Phe Glu Lys
            35                  40

<210> SEQ ID NO 408
<211> LENGTH: 43
<212> TYPE: PRT
<213> ORGANISM: Artificial
<220> FEATURE:
<223> OTHER INFORMATION: FGF21 variant

<400> SEQUENCE: 408

Pro Gly Leu Pro Pro Ala Leu Pro Glu Leu Glu Ser Asp Met Phe Ser
1               5                   10                  15

Ser Pro Leu Glu Thr Asp Ser Met Asp Pro Phe Gly Leu Val Thr Gly
                20                  25                  30

Leu Glu Ala Val Arg Ser Pro Ser Phe Glu Lys
            35                  40

<210> SEQ ID NO 409
<211> LENGTH: 44
<212> TYPE: PRT
<213> ORGANISM: Artificial
<220> FEATURE:
```

<223> OTHER INFORMATION: FGF21 variant

<400> SEQUENCE: 409

Pro Gly Leu Pro Pro Ala Leu Pro Glu His Leu Glu Ser Asp Met Phe
1               5                   10                  15

Ser Ser Pro Leu Glu Thr Asp Ser Met Asp Pro Phe Gly Leu Val Thr
            20                  25                  30

Gly Leu Glu Ala Val Arg Ser Pro Ser Phe Glu Lys
        35                  40

<210> SEQ ID NO 410
<211> LENGTH: 45
<212> TYPE: PRT
<213> ORGANISM: Artificial
<220> FEATURE:
<223> OTHER INFORMATION: FGF21 variant

<400> SEQUENCE: 410

Pro Gly Leu Pro Pro Ala Leu Pro Glu Gly His Leu Glu Ser Asp Met
1               5                   10                  15

Phe Ser Ser Pro Leu Glu Thr Asp Ser Met Asp Pro Phe Gly Leu Val
            20                  25                  30

Thr Gly Leu Glu Ala Val Arg Ser Pro Ser Phe Glu Lys
        35                  40                  45

<210> SEQ ID NO 411
<211> LENGTH: 46
<212> TYPE: PRT
<213> ORGANISM: Artificial
<220> FEATURE:
<223> OTHER INFORMATION: FGF21 variant

<400> SEQUENCE: 411

Pro Gly Leu Pro Pro Ala Leu Pro Glu Arg Gly His Leu Glu Ser Asp
1               5                   10                  15

Met Phe Ser Ser Pro Leu Glu Thr Asp Ser Met Asp Pro Phe Gly Leu
            20                  25                  30

Val Thr Gly Leu Glu Ala Val Arg Ser Pro Ser Phe Glu Lys
        35                  40                  45

<210> SEQ ID NO 412
<211> LENGTH: 47
<212> TYPE: PRT
<213> ORGANISM: Artificial
<220> FEATURE:
<223> OTHER INFORMATION: FGF21 variant

<400> SEQUENCE: 412

Pro Gly Leu Pro Pro Ala Leu Pro Glu Leu Arg Gly His Leu Glu Ser
1               5                   10                  15

Asp Met Phe Ser Ser Pro Leu Glu Thr Asp Ser Met Asp Pro Phe Gly
            20                  25                  30

Leu Val Thr Gly Leu Glu Ala Val Arg Ser Pro Ser Phe Glu Lys
        35                  40                  45

<210> SEQ ID NO 413
<211> LENGTH: 48
<212> TYPE: PRT
<213> ORGANISM: Artificial
<220> FEATURE:
<223> OTHER INFORMATION: FGF21 variant

<400> SEQUENCE: 413

-continued

Pro Gly Leu Pro Pro Ala Leu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 414
<211> LENGTH: 48
<212> TYPE: PRT
<213> ORGANISM: Artificial
<220> FEATURE:
<223> OTHER INFORMATION: FGF21 variant

<400> SEQUENCE: 414

Pro Gly Leu Pro Pro Ala Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 415
<211> LENGTH: 48
<212> TYPE: PRT
<213> ORGANISM: Artificial
<220> FEATURE:
<223> OTHER INFORMATION: FGF21 variant

<400> SEQUENCE: 415

Pro Gly Leu Pro Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 416
<211> LENGTH: 48
<212> TYPE: PRT
<213> ORGANISM: Artificial
<220> FEATURE:
<223> OTHER INFORMATION: FGF21 variant

<400> SEQUENCE: 416

Pro Gly Leu Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 417
<211> LENGTH: 48
<212> TYPE: PRT
<213> ORGANISM: Artificial
<220> FEATURE:
<223> OTHER INFORMATION: FGF21 variant

<400> SEQUENCE: 417

Pro Gly Met Val Pro Glu Glu Pro Glu Asp Leu Arg Gly His Leu Glu
1               5                   10                  15

```
Ser Asp Met Phe Ser Ser Pro Leu Glu Thr Asp Ser Met Asp Pro Phe
             20                  25                  30

Gly Leu Val Thr Gly Leu Glu Ala Val Arg Ser Pro Ser Phe Glu Lys
         35                  40                  45

<210> SEQ ID NO 418
<211> LENGTH: 48
<212> TYPE: PRT
<213> ORGANISM: Artificial
<220> FEATURE:
<223> OTHER INFORMATION: FGF21 variant

<400> SEQUENCE: 418

Pro Pro Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
             20                  25                  30

Gly Leu Val Thr Gly Leu Glu Ala Val Arg Ser Pro Ser Phe Glu Lys
         35                  40                  45
```

UNITED STATES PATENT AND TRADEMARK OFFICE
CERTIFICATE OF CORRECTION

PATENT NO. : 9,926,355 B2
APPLICATION NO. : 15/289447
DATED : March 27, 2018
INVENTOR(S) : Mohammadi et al.

Page 1 of 1

It is certified that error appears in the above-identified patent and that said Letters Patent is hereby corrected as shown below:

In the Specification

Column 1 at Lines 11-15, delete "This invention was made with government support under grant numbers DE13686, DK077276, AG019712, DK091392, and DK067158 awarded by the U.S. National Institutes of Health. The government has certain rights in this invention." and insert in its place --This invention was made with government support under DE13686 awarded by National Institutes of Health. The government has certain rights in the invention.--

Signed and Sealed this
Twenty-first Day of January, 2020

Andrei Iancu
*Director of the United States Patent and Trademark Office*